US011840695B2

(12) United States Patent
Leveau et al.

(10) Patent No.: US 11,840,695 B2
(45) Date of Patent: Dec. 12, 2023

(54) **RECOMBINANT *C. ACNES* PHAGES COMPRISING TRANSGENES**

(71) Applicant: Eligo Bioscience, Paris (FR)

(72) Inventors: Aymeric Leveau, Paris (FR); Inès Canadas Blasco, Paris (FR); Aurélie Mathieu, Paris (FR); Antoine Decrulle, Paris (FR)

(73) Assignee: Eligo Bioscience, Paris (FR)

( * ) Notice: Subject to any disclaimer, the term of this patent is extended or adjusted under 35 U.S.C. 154(b) by 0 days.

(21) Appl. No.: 17/821,940

(22) Filed: Aug. 24, 2022

(65) Prior Publication Data

US 2023/0073747 A1 Mar. 9, 2023

Related U.S. Application Data

(62) Division of application No. 17/518,960, filed on Nov. 4, 2021, now Pat. No. 11,473,093.

(60) Provisional application No. 63/145,969, filed on Feb. 4, 2021, provisional application No. 63/145,967, filed on Feb. 4, 2021, provisional application No. 63/109,834, filed on Nov. 4, 2020, provisional application No. 63/109,832, filed on Nov. 4, 2020.

(51) Int. Cl.
| | |
|---|---|
| *C12N 15/76* | (2006.01) |
| *A61P 17/10* | (2006.01) |
| *C12N 9/64* | (2006.01) |
| *A61K 39/02* | (2006.01) |
| *A61K 39/05* | (2006.01) |
| *C12N 9/22* | (2006.01) |
| *C12N 15/11* | (2006.01) |
| *C12N 15/01* | (2006.01) |
| *A61K 39/00* | (2006.01) |

(52) U.S. Cl.
CPC ............. *C12N 15/76* (2013.01); *A61K 39/02* (2013.01); *A61K 39/05* (2013.01); *A61P 17/10* (2018.01); *C12N 9/22* (2013.01); *C12N 15/11* (2013.01); *A61K 2039/53* (2013.01); *C12N 9/64* (2013.01); *C12N 2310/20* (2017.05); *C12N 2795/10343* (2013.01); *C12N 2800/101* (2013.01); *C12N 2800/80* (2013.01)

(58) Field of Classification Search
None
See application file for complete search history.

(56) References Cited

U.S. PATENT DOCUMENTS

| 2021/0252081 A1* | 8/2021 | Feron ............... C12N 15/86 |
|---|---|---|
| 2022/0135987 A1 | 5/2022 | Bioscience | |

FOREIGN PATENT DOCUMENTS

| WO | 2007/007055 A1 | 1/2007 | |
|---|---|---|---|
| WO | WO-2007007055 A1 * | 1/2007 | ............ A61K 35/76 |
| WO | 2017/114979 A1 | 7/2017 | |
| WO | 2019/243307 A1 | 12/2019 | |
| WO | 2020181178 A1 | 9/2020 | |
| WO | 2020181180 A1 | 9/2020 | |
| WO | 2020181193 A1 | 9/2020 | |
| WO | 2020181195 A1 | 9/2020 | |
| WO | 2020181202 A1 | 9/2020 | |

OTHER PUBLICATIONS

Rahman et al., Pak J Med Sci, 2012, 28(1):31-35. (Year: 2012).*
Vojdani et al., Journal of Immunology Research, vol. 2020, Article ID 1438957, 16 pages. (Year: 2020).*
Farrar et al., Journal of Bacteriology, 2007, 189(11):4161-4167. (Year: 2007).*
Mason et al., Molecules, 2015, 20:2229-2271. (Year: 2015).*
Castillo et al. (2019). Propionibacterium (Cutibacterium) acnes Bacteriophage Therapy in Acne: Current Evidence and Future Perspectives. Dermatology and Therapy. 9, 19-31.
Chen et al. (2019). Genetic Engineering of Bacteriophages Against Infectious Diseases. Frontiers in Microbiology. 10, 1-12.
Federici et al. (2020). Phages and their potential to modulate the microbiome and immunity. Cellular and Molecular Immunology. 18. 889-204.
Marinelli et al. (2012). Propionibacterium acnes Bacteriophages Display Limited Genetic Diversity and Broad Killing Activity against Bacterial Skin Isolates. mBio. 3(5). 1-13.
Abudayyeh et al. RNA targeting with CRISPR-Cas13a. Nature. Oct. 12, 2017; 550(7675): 280-284.
Adachi et al. Hair follicle-derived IL-7 and IL-15 mediate skin-resident memory T cell homeostasis and lymphoma. Nat Med. Nov. 2015 ; 21(11): 1272-1279.
Allhorn, M. et al. A novel enzyme with antioxidant capacity produced by the ubiquitous skin colonizer Propionibacterium acnes. Sci. Rep. 6, 36412, (2016).
Anzalone, A. et al. Search-and-replace genome editing without double-strand breaks or donor DNA. Nature. Dec. 2019 ; 576(7785): 149-157.
Aoki et al., Journal of Medical Microbiology 2019;68:26-30.
Aoki et al., Transferable Multidrug-Resistance Plasmid Carrying a Novel Macrolide-Clindamycin Resistance Gene, erm (50), in Cutibacterium acnes. Antimicrob Agents Chemother. Feb. 21, 2020;64(3):e01810-19.
Arazoe et al. Site-specific DNA double-strand break generated by I-SceI endonuclease enhances ectopic homologous recombination in Pyricularia oryzae. FEMS Microbiol Lett 352 (2014) 221-229.

(Continued)

*Primary Examiner* — Nicole Kinsey White
(74) *Attorney, Agent, or Firm* — Arrigo, Lee, Guttman & Mouta-Bellum LLP

(57) ABSTRACT

The invention relates to *C. acnes* strains carrying DNA vectors for the production of recombinant *C. acnes* phages. The invention encompasses a *C. acnes* producer cell carrying DNA vectors, with a template for recombination with *C. acnes* phage genome leading to the insertion of a gene of interest, for the production of recombinant phages that can lead to the transgene expression into *C. acnes* infected by the recombinant phage. The invention encompasses, *C. acnes* strains containing these vectors, *C. acnes* recombinant phages and methods of using these recombinant phages.

5 Claims, 19 Drawing Sheets

Specification includes a Sequence Listing.

(56) References Cited

OTHER PUBLICATIONS

Armenteros, et al. SignalP 5.0 improves signal peptide predictions using deep neural networks. Nat Biotechnol 37, 420-423 (2019).
Barnard, E. et al. Strains of the Propionibacterium acnes type III lineage are associated with the skin condition progressive macular hypomelanosis. Sci. Rep. 6, 31968, (2016).
Barnard, E. et al. The balance of metagenomic elements shapes the skin microbiome in acne and health. Sci. Rep. 6, 39491, (2016).
Bay L, et al. 2020. Universal dermal microbiome in human skin. mBio 11:e02945-19.
Brown et al. (2016) The Formulation of Bacteriophage in a Semi Solid Preparation for Control of Propionibacterium acnes Growth. PLoS One 11(3): e0151184.
Chen et al. Skin microbiota-host interactions. Nature. Jan. 24, 2018; 553(7689): 427-436.
Chen et al. Decoding commensal-host communication through genetic engineering of *Staphylococcus* 5 epidermidis. Jun. 10, 2019. bioRxiv 664656.
Chen et al. Precise and programmable C:G to G:C base editing in genomic DNA. bioRxiv 2020.07.21.213827.
Davidsson S, et al. (2017) Prevalence of Flp Pili-Encoding Plasmids in Cutibacterium acnes Isolates Obtained from Prostatic Tissue. Front. Microbiol. 8:2241.
Dréno, et al. (2018), Cutibacterium acnes (*Propionibacterium acnes*) and acne vulgaris: a brief look at the latest updates. J Eur Acad Dermatol Venereol, 32: 5-14.
Fitz-Gibbon et al. Propionibacterium acnes Strain Populations in the Human Skin Microbiome Associated with Acne. Journal of Investigative Dermatology (2013) 133, 2152-2160.
Fonfara et al. Phylogeny of Cas9 determines functional exchangeability of dual-RNA and Cas9 among orthologous type II CRISPR-Cas systems .Nucleic Acids Research, 2014, vol. 42, No. 4 2577-2590.
Gaudelli et al. Programmable base editing of A•T to G•C in genomic DNA without DNA cleavage. Nature. Nov. 23, 2017; 551(7681): 464-471.
Di Girolamo, et al. Characterization of the housekeeping sortase from the human pathogen Propionibacterium acnes: first investigation of a class F sortase. Biochem J Feb. 28, 2019; 476 (4): 665-682.
Grünewald et al. A dual-deaminase CRISPR base editor enables concurrent adenine and cytosine editing. Nat Biotechnol. Jul. 2020 ; 38(7): 861-864.
Karberg, et al. Group II introns as controllable gene targeting vectors for genetic manipulation of bacteria. Nat Biotechnol 19, 1162-1167 (2001).
Kasimatis et al. Analysis of Complete Genomes of Propionibacterium acnes Reveals a Novel Plasmid and Increased Pseudogenes in an Acne Associated Strain. Hindawi Publishing Corporation: BioMed Research International. 2013. 1-11.
Komor et al. Programmable editing of a target base in genomic DNA without double-stranded DNA cleavage. Nature. ; 533(7603): 420-424, (2016).
Koonin, et al. Diversity, classification and evolution of CRISPR-Cas systems. Current Opinion in Microbiology. vol. 37,2017, pp. 67-78.
Kurt et al. CRISPR C-to-G base editors for inducing targeted DNA transversions in human cells. Nat Biotechnol. Jan. 2021 ; 39(1): 41-46.
Li et al. Targeted, random mutagenesis of plant genes with dual cytosine and adenine base editors. Nature Biotechnology 38, 875-882 (2020).
Liu et al. The diversity and host interactions of Propionibacterium acnes bacteriophages on human skin. The ISME Journal (2015) 9, 2078-2093.
Lood et al. Characterization and genome sequencing of two Propionibacterium acnes phages displaying pseudolysogeny. BMC Genomics 2011, 12:198.
McDowell, et al. (2021), Is Cutibacterium (previously Propionibacterium) acnes a potential pathogenic factor in the aetiology of the skin disease progressive macular hypomelanosis ?. J Eur Acad Dermatol Venereol, 35: 338-344.
McLaughlin et al. Propionibacterium acnes and Acne Vulgaris: New Insights from the Integration of Population Genetic, Multi-Omic, Biochemical and Host-Microbe Studies. Microorganisms 2019, 7(5), 128.
Nagao et al. Stress-induced production of chemokines by hair follicles regulates the trafficking of dendritic cells in skin. Nat Immunol. ; 13(8): 744-752, (2014).
Naik et al. Commensal-dendritic-cell interaction specifies a unique protective skin immune signature. Nature. Apr. 2, 2015; 520(7545): 104-108.
Nakatsuji et al. The microbiome extends to subepidermal compartments of normal skin. Nat Commun. 2013 ; 4: 1431.
Nazipi et al. The Skin Bacterium Propionibacterium acnes Employs Two Variants of Hyaluronate Lyase with Distinct Properties. Microorganisms 2017, 5, 57.
Oh et al. Biogeography and individuality shape function in the human skin metagenome. Nature. Oct. 2, 2014; 514 (7520): 59-64.
Pasparakis et al. Mechanisms regulating skin immunity and inflammation. Nature Reviews: Immunology. vol. 14. 289-301, (2014).
Paus et al. The Hair Follicle and Immune Privilege. JID Symposium Proceedings. 2003. 1087-0024.
Petersen et al. Propionibacterium Acnes Phylogenetic Type III is Associated with Progressive Macular Hypomelanosis. Eur J Microbiol Immunol (Bp). Feb. 27, 2017;7(1):37-45.
Rouet et al. Expression of a site-specific endonuclease stimulates homologous recombination in mammalian cells. Jun. 1994. Proc. Nati. Acad. Sci. USA. Vol. 91, pp. 6064-6068.
Scharschmidt et al. A Wave of Regulatory T Cells into Neonatal Skin Mediates Tolerance to Commensal Microbes. Immunity, vol. 43, Issue 5, 1011-1021, (2015).
Scholz et al. The natural history of cutaneous propionibacteria, and reclassification of selected species within the genus *Propionibacterium* to the proposed novel genera *Acidipropionibacterium* gen. nov., *Cutibacterium* gen. nov. and *Pseudopropionibacterium* gen. nov. International Journal of Systematic and Evolutionary Microbiology (2016), 66, 4422-4432.
Sharon et al. Functional genetic variants revealed by massively parallel precise genome editing. Cell. Oct. 4, 2018; 175(2): 544-557.e16.
Sievers et al. Fast, scalable generation of high-quality protein multiple sequence alignments using Clustal Omega. Molecular Systems Biology 7; 539, (2011).
Sörensen et al. Mutagenesis of Propionibacterium acnes and analysis of two CAMP factor knock-out mutants. Journal of Microbiological Methods 83 (2010) 211-216.
Wannier et al. Improved bacterial recombineering by parallelized protein discovery. PNAS. Jun. 16, 2020. 117: 24. 13689-13698.
Yu. Different Propionibacterium acnes Phylotypes Induce Distinct Immune Responses and Express Unique Surface and Secreted Proteomes. Society for Investigative Dermatology. 2016. 2221-2228.
Zhao et al. New base editors change C to A in bacteria and C to G in mammalian cells. Nature Biotechnology. Jul. 20, 2020.
Simon et al., Retrons and their applications in genome engineering, Nucleic Acids Research, 2019, vol. 47, No. 21 11007-11019.

* cited by examiner

| Bacteriophage titer (PFU/µL) | 19 | 26 | 2 | 22 | 9 | 13 | 10 | 20 | 4 | 7 | ATCC29399 | 1 |
|---|---|---|---|---|---|---|---|---|---|---|---|---|
| | ? | 4.00E+06 | 2.20E+07 | 2.00E+07 | 1.60E+07 | 4.00E+06 | 1.00E+07 | 4.00E+04 | 1.60E+07 | 4.00E+06 | 2.00E+06 | 8.00E+06 |
| Ca0s2345-001 | 1 | 1 | 1 | 1 | 1 | 1 | 1 | 1 | 1 | 1 | 1 | 1 |
| Ca0s2341-001 | 1 | 1 | 1 | 1 | 1 | 1 | 1 | 1 | 1 | 1 | 1 | 1 |
| Ca0s2343-001 | 1 | 1 | 1 | 1 | 1 | 1 | 1 | 1 | 1 | 1 | 1 | 1 |
| Ca0s2329-001 | 1 | 1 | 1 | 1 | 1 | 1 | 1 | 1 | 1 | 1 | 1 | 1 |
| Ca0s2334-001 | 1 | 1 | 1 | 1 | 1 | 1 | 1 | 1 | 1 | 1 | 1 | 1 |
| Ca0s2328-001 | 1 | 1 | 1 | 1 | 1 | 1 | 1 | 1 | 1 | 1 | 1 | 1 |
| Ca0s2306-001 | 1 | 1 | 1 | 1 | 1 | 1 | 1 | 1 | 1 | 1 | 1 | 1 |
| Ca0s2277-001 | 1 | 1 | 1 | 1 | 1 | 1 | 1 | 1 | 1 | 1 | 1 | 1 |
| Ca0s2272-001 | 1 | 1 | 1 | 1 | 1 | 1 | 1 | 1 | 1 | 1 | 1 | 1 |
| Ca0s2391-001 | 1 | 1 | 1 | 1 | 1 | 1 | 1 | 1 | 1 | 1 | 1 | 1 |
| Ca0s2373-001 | 1 | 1 | 1 | 1 | 1 | 1 | 1 | 1 | 1 | 1 | 1 | 1 |
| Ca0s2327-001 | 1 | 1 | 1 | 1 | 1 | 1 | 1 | 1 | 1 | 1 | 1 | 1 |
| Ca0s2312-001 | 1 | 1 | 1 | 1 | 1 | 1 | 1 | 1 | 1 | 1 | 1 | 1 |
| Ca0s2289-001 | 1 | 1 | 1 | 1 | 1 | 1 | 1 | 1 | 1 | 1 | 1 | 1 |
| Ca0s2333-001 | 1 | 1 | 1 | 0.5 | 1 | 1 | 1 | 1 | 1 | 1 | 1 | 1 |
| Ca0s2262-001 | 1 | 1 | 1 | 1 | 0.5 | 1 | 0.5 | 1 | 1 | 1 | 1 | 1 |
| Ca0s2258-001 | 1 | 1 | 1 | 0.5 | 1 | 0.5 | 0.5 | 1 | 1 | 1 | 1 | 1 |
| Ca0s2260-001 | 1 | 1 | 1 | 0.5 | 1 | 1 | 0.5 | 0.5 | 1 | 1 | 1 | 1 |
| Ca0s2261-001 | 1 | 0.5 | 0.5 | 1 | 1 | 1 | 1 | 1 | 1 | 1 | 1 | 1 |
| Ca0s2265-001 | 0.5 | 0.5 | 0.5 | 1 | 1 | 1 | 1 | 1 | 1 | 1 | 1 | 1 |
| Ca0s2259-001 | 0.5 | 0.5 | 1 | 1 | 1 | 1 | 1 | 0.5 | 1 | 1 | 1 | 1 |
| Ca0s2263-001 | 0.5 | 0.5 | 1 | 1 | 1 | 1 | 1 | 1 | 1 | 1 | 1 | 1 |
| Ca0s2264-001 | 1 | 1 | 1 | 1 | 1 | 1 | 1 | 1 | 1 | 1 | 1 | 1 |
| Ca0s2550-002 | 1 | 1 | 1 | 1 | 1 | 1 | 1 | 1 | 1 | 1 | 1 | 1 |
| Ca0s2549-002 | 1 | 1 | 1 | 1 | 1 | 1 | 1 | 1 | 1 | 1 | 1 | 1 |
| Ca0s2552-002 | 1 | 1 | 1 | 1 | 1 | 1 | 1 | 1 | 1 | 1 | 1 | 1 |
| Ca0s2508-002 | 1 | 1 | 1 | 1 | 1 | 1 | 1 | 1 | 1 | 1 | 1 | 1 |
| Ca0s2548-002 | 1 | 1 | 1 | 1 | 1 | 1 | 1 | 1 | 1 | 1 | 1 | 1 |
| Ca0s2504-002 | 1 | 1 | 1 | 1 | 1 | 1 | 1 | 1 | 1 | 1 | 1 | 1 |
| Ca0s2506-002 | 1 | 1 | 1 | 1 | 1 | 1 | 1 | 1 | 1 | 1 | 1 | 1 |
| Ca0s2553-002 | 1 | 1 | 1 | 1 | 1 | 1 | 1 | 1 | 1 | 1 | 1 | 1 |
| Ca0s2507-002 | 1 | 1 | 1 | 1 | 1 | 1 | 1 | 1 | 1 | 1 | 1 | 1 |
| Ca0s2509-002 | 1 | 1 | 1 | 1 | 1 | 1 | 1 | 1 | 1 | 1 | 1 | 1 |

(Rows = C. acnes strains; Columns = C. acnes bacteriophage)

FIGURE 2A

| C. acnes strains | 19 | 26 | 2 | 22 | 9 | 13 | 10 | 20 | 4 | 7 | ATCC29399 | 1 |
|---|---|---|---|---|---|---|---|---|---|---|---|---|
| Ca0s2247-002 | 1 | 1 | 1 | 1 | 1 | 1 | 1 | 1 | 1 | 1 | 1 | 1 |
| Ca0s2243-002 | 1 | 1 | 1 | 1 | 1 | 1 | 1 | 1 | 1 | 1 | 1 | 1 |
| Ca0s2228-002 | 1 | 1 | 1 | 1 | 1 | 1 | 1 | 1 | 1 | 1 | 1 | 1 |
| Ca0s2225-002 | 1 | 1 | 1 | 1 | 1 | 1 | 1 | 1 | 1 | 1 | 1 | 1 |
| Ca0s2220-002 | 1 | 1 | 1 | 1 | 1 | 1 | 1 | 1 | 1 | 1 | 1 | 1 |
| Ca0s2218-002 | 1 | 1 | 1 | 1 | 1 | 1 | 1 | 1 | 1 | 1 | 1 | 1 |
| Ca0s2255-002 | 1 | 1 | 1 | 1 | 1 | 1 | 1 | 1 | 1 | 1 | 1 | 1 |
| Ca0s2227-002 | 1 | 1 | 1 | 1 | 1 | 1 | 1 | 1 | 1 | 1 | 1 | 1 |
| Ca0s2211-002 | 1 | 1 | 1 | 1 | 1 | 1 | 1 | 1 | 1 | 1 | 1 | 1 |
| Ca0s2219-002 | 1 | 1 | 1 | 1 | 1 | 1 | 1 | 1 | 1 | 1 | 1 | 1 |
| Ca0s2209-002 | 1 | 1 | 1 | 1 | 1 | 1 | 1 | 1 | 1 | 1 | 1 | 1 |
| Ca0s2208-002 | 1 | 1 | 1 | 1 | 1 | 1 | 1 | 1 | 1 | 1 | 1 | 1 |
| Ca0s2233-002 | 1 | 1 | 1 | 1 | 1 | 1 | 1 | 1 | 1 | 1 | 1 | 1 |
| Ca0s2232-002 | 1 | 1 | 1 | 1 | 1 | 1 | 1 | 1 | 1 | 1 | 1 | 1 |
| Ca0s2239-002 | 1 | 1 | 1 | 1 | 1 | 1 | 1 | 1 | 1 | 1 | 1 | 1 |
| Ca0s2235-002 | 1 | 1 | 1 | 1 | 1 | 1 | 1 | 1 | 1 | 1 | 1 | 1 |

C. acnes bacteriophage

FIGURE 2B

```
                         595                                                        654
PAC7 wt                  tagtggagaaaacaaccaccccggaacgtttaagacaccccctcaaacgaacaaaacagg
PAC7-m28-gp45 plaque n°1 TAGTGGAGAAAACAACCACCCCGGAACGTTTAAGACACCCCCTCAAACGAACAAAACAGG
PAC7-m28-gp45 plaque n°2 TAGTGGAGAAAACAACCACCCCGGAACGTTTAAGACACCCCCTCAAACGAACAAAACAGG
PAC7-m28-gp45 plaque n°3 TAGTGGAGAAAACAACCACCCCGGAACGTTTAAGACACCCCCTCAAACGAACAAAACAGG 655                                                        714
PAC7 wt                  gcctagaatcgatcagcagggcaccggtagggtattcctaccccagacgattcaaggcc
PAC7-m28-gp45 plaque n°1 GCCTAGAATCGATCAGCAGGGCACCGGTAGGGTATTCCTACCCCAGACGATTCAAGG***
PAC7-m28-gp45 plaque n°2 GCCTAGAATCGATCAGCAGGGCACCGGTAGGGTATTCCTACCCCAGACGATTCAAGG***
PAC7-m28-gp45 plaque n°3 GCCTAGAATCGATCAGCAGGGCACCGGTAGGGTATTCCTACCCCAGACGATTCAAGG***

715                                                        774
PAC7 wt                  attacaggagcaatgagaggctcacaggggccatgggagattgggggcgtgatggcaca
PAC7-m28-gp45 plaque n°1 ************************************************************
PAC7-m28-gp45 plaque n°2 ************************************************************
PAC7-m28-gp45 plaque n°3 ************************************************************

775                                                        834
PAC7 wt                  caccaaccgcacagccagccaagcccacggcgctggcgggcaaggctcatcacccaagc
PAC7-m28-gp45 plaque n°1 ************************************************************
PAC7-m28-gp45 plaque n°2 ************************************************************
PAC7-m28-gp45 plaque n°3 ************************************************************

835                                                        894
PAC7 wt                  ccgacaacaaggccaaaccgaatgcccactctgcggagtcaccatcacctggaacaccca
PAC7-m28-gp45 plaque n°1 *********************CCAAACCGAATGCCCACTCTGCGGAGTCACCATCACCTGGAACACCCA
PAC7-m28-gp45 plaque n°2 *********************CCAAACCGAATGCCCACTCTGCGGAGTCACCATCACCTGGAACACCCA
PAC7-m28-gp45 plaque n°3 *********************CCAAACCGAATGCCCACTCTGCGGAGTCACCATCACCTGGAACACCCA 895                                                        954
PAC7 wt                  cgacctgccaaccagccccgaagccgaccacatcacacccgtcagccggggaggactcaa
PAC7-m28-gp45 plaque n°1 CGACCTGCCAACCAGCCCCGAAGCCGACCACATCACACCCGTCAGCCGGGGAGGACTCAA
PAC7-m28-gp45 plaque n°2 CGACCTGCCAACCAGCCCCGAAGCCGACCACATCACACCCGTCAGCCGGGGAGGACTCAA
PAC7-m28-gp45 plaque n°3 CGACCTGCCAACCAGCCCCGAAGCCGACCACATCACACCCGTCAGCCGGGGAGGACTCAA 955        977
PAC7 wt                  caccctcgacaacgggcaaatca (SEQ ID NO: 113)
PAC7-m28-gp45 plaque n°1 CACCCTCGACAACGGGCAAATCA (SEQ ID NO: 78)
PAC7-m28-gp45 plaque n°2 CACCCTCGACAACGGGCAAATCA (SEQ ID NO: 85)
PAC7-m28-gp45 plaque n°3 CACCCTCGACAACGGGCAAATCA (SEQ ID NO: 114)
```

FIGURE 18

RECOMBINANT C. ACNES PHAGES COMPRISING TRANSGENES

CROSS REFERENCE TO RELATED APPLICATIONS

This application is a divisional of U.S. application Ser. No. 17/518,960, which claims the benefit of U.S. application 63/109,832 filed Nov. 4, 2020, U.S. application 63/145,967 filed Feb. 4, 2021, U.S. application 63/109,834 filed Nov. 4, 2020, and U.S. application 63/145,969 filed Feb. 4, 2021, all of which are herein incorporated by reference in their entirety.

REFERENCE TO SEQUENCE LISTING SUBMITTED ELECTRONICALLY

The instant application contains a Sequence Listing which has been submitted electronically in XML format and is hereby incorporated by reference in its entirety. Said Sequence Listing XML, created on Aug. 24, 2022, is named EB2020-04c-sequence.xml and is 537,898 bytes in size.

FIELD OF THE INVENTION

The present invention concerns *Cutibacterium acnes* recombinant phages and production method thereof.

BACKGROUND OF THE INVENTION

The skin is the largest organ of the human body and the biggest interface between our body and our environment. As such it also acts as a barrier protecting us from physical (e.g., UV, wounds), chemical (e.g., acid, base) and microbial (virus, bacteria, fungi) threats. This protection is not only the result of its passive physical isolating nature made from successive layers of dense and interconnected dead cells (stratum corneum) surrounded by a lipidic matrix. It is also thanks to active mechanisms orchestrated by diverse types of skin and immune cells that secrete antimicrobial peptides (AMP), produce cytokines and chemokines to recruit lymphoid immune cells, sense skin injuries and trigger wound healing mechanisms among other processes[1].

Skin is the first organ in contact with microorganisms after our birth, it is populated with a vast amount of immune cells in close contact with a great diversity of microorganisms and thus, the skin immune system needs to develop abilities to recognize beneficial microorganisms from pathogenic ones to avoid constant immune responses and inflammation. Part of this education is happening early in life when specific bacterial species are colonizing the skin and modulate immune responses in order for them to be tolerated[2]. These specific bacterial species are then able to stably colonize the skin establishing communities and becoming commensal strains.

Skin is not physiologically and spatially homogeneous throughout the body: oily (e.g cheek, back), moist (e.g., inguinal crease, interdigital web space, antecubital crease) and dry skin (e.g, volar forearm, hypothenar palm) exist depending on the body sites[3]. These different body sites are associated with different physiological conditions and carry distinct microbiomes, with oily sites being mostly colonized with *Cutibacterium acnes* (formerly known as *Propionibacterium acnes*), whereas *Staphylococcus* and *Corynebacterium* species are more abundant in moist sites[4]. In addition to these physiological characteristics, skin is also heterogeneous in spaces with different appendages: the sweat glands, the hair follicle, the sebaceous gland. The colonization of these appendages is only recently studied but shows differences compared to skin surface (stratum corneum)[4-6].

These skin appendages are specific anatomical places because they do not have stratum corneum. As a consequence, microorganisms inside these appendages are in contact with living keratinocytes and have access to a higher diversity of immune cells due to the dermis proximity. The hair follicle has specific immunological properties. It is able to recruit specific immune cells such as monocyte-derived Langerhans Cells precursors[7] and actively maintain resident memory T cells (TRM)[8] making it a potential essential place for antigen presentation. The hair follicle is also deprived of effector T cells and has a strong immunosuppressive environment making it an immune privileged area[9].

Examples in the published literature indicate that skin-resident bacteria actively engage host immunity through an intact skin barrier, and activate specific immune cells in a species- and strain-dependent manner (Chen et al, Nature 2018; 555(7697):543). For instance, some but not all strains of *S. epidermidis* induce activation of *S. epidermidis*-specific IL-17$^+$CD8$^+$ T cells that protect against cutaneous infection (Naik et al, Nature 2015, 520(7545):104-108).

Due to the absence of stratum corneum, the skin appendages are also more permeable to chemicals as these will only need to cross the tight-junction barrier and not the stratum corneum which normally prevents water exchange, and as a result all water-soluble substances are able to diffuse.

The pilosebaceous subunit comprising the hair follicle and the sebaceous gland is mostly colonized by *C. acnes* that thrive in this sebum rich and anaerobic environment. *Cutibacterium acnes* (formerly *Propionibacterium acnes*) is a gram-positive rod-shaped aerotolerant bacteria, first isolated from skin in 1897. It belongs to the order Actinomycetales, it is part of the Propionibacteriaceae family and it belongs to the genus *Cutibacterium*. This genus includes other human skin species such as *Cutibacterium avidum*, *Cutibacterium granulosum* and *Cutibacterium humerusii*[10]. *C. acnes* is one of the most prevalent and abundant bacteria on human skin where it can be found both on the skin surface (stratum corneum) and in the hair follicle. Inside the hair follicle, it is in direct contact with a large diversity of living cells such as keratinocytes, stem cells, sebaceous cells and immune cells, unlike on the stratum corneum where it is mostly in contact with the dead corneocyte. *C. acnes* is a commensal bacterium but has also been associated with several skin diseases such as acne vulgaris[11] or progressive macular hypomelanosis[12-14].

In particular, new findings on *C. acnes* reveal that specific phylotypes might play a critical role in acne development[11]. Precisely, the role of *C. acnes* phylotype IA1 in acne is being widely underscored. Fitz-Gibbon and colleagues demonstrated that chromosomal regions, loci 1, 2 and 3, characteristic of ribotypes RT4 and RT5 (classified within the phylogroup IA1), are strongly associated with acne[15]. Since these chromosomal regions are absent in ribotypes that are associated with healthy skin (i.e., RT6), they represent a potential target to eliminate acne-associated *C. acnes* strains.

Being able to edit *Cutibacterium acnes* population by removing specific proinflammatory strains to prevent or cure disease such as acne vulgaris or leverage their privilege location into the pilosebaceous unit to modulate host immune responses or improve wound healing are attractive therapeutic approaches. To implement such approaches, one can either genetically modify *C. acnes* strains in situ or provide in vitro genetically modified *C. acnes*. Because of the large intra-individual and inter-individual microbiome diversity both at the species and at the strain level, it appears difficult to provide a single or cocktail of engineered *C. acnes* strains able to colonize the skin of most patients.

Delivery of DNA in situ to the *C. acnes* population offers a way to circumvent such difficulties by allowing to leverage pre-established strains potentially without disturbing the local microbiome. However, in situ delivery of genetic material to *C. acnes* is a challenging task for several reasons. First, there are so far no genetic elements such as plasmid able to robustly and autonomously replicate inside *C. acnes*. The few described genetic modifications consist in genomic insertion of synthetic DNA through homologous recombination[16-18]. This in vitro process has been shown to be of very low efficiency and rely on the use of an antibiotic selection marker to select such events. Moreover, these genetic modifications have been restricted to a few specific strains (KPA17202, one RT6 *C. acnes*) and might not be generalizable to all *C. acnes* strains. Second, in order to perform in situ genetic modification of *C. acnes* delivery of DNA into *C. acnes* is needed. The only described method for introducing DNA into *C. acnes* is the use of electroporation[19,20], a method that can only be performed in vitro.

The present invention solves both the lack of replicative and stable DNA vectors and their delivery into *C. acnes* using phage-derived particles. The present invention also provides unique and robust tools for *C. acnes* phage genome engineering.

BRIEF SUMMARY OF INVENTION

The invention encompasses *Cutibacterium acnes* phagemids, bacterial cells comprising these phagemids, *Cutibacterium acnes* recombinant phages, methods for making phage-derived particles comprising these phagemids, phage-derived particles comprising these phagemids, and methods for using these phagemids, particles, and cells, particularly in treatments of *Cutibacterium acnes* related disorders and/or diseases.

The invention encompasses a recombinant DNA phagemid vector, phage-derived particles comprising these vectors, and *Cutibacterium acnes* carrying the vector, wherein the vector comprises:
a phage packaging signal allowing packaging of the DNA vector in a *Cutibacterium acnes* phage capsid; and
a gene of interest.

In one embodiment, the DNA vector comprises:
a phage packaging signal allowing packaging of the DNA vector in a *Cutibacterium acnes* phage capsid; wherein the phage packaging signal sequence is at least 80, 83, 85, 87, 90, 93, 95, 97, 98, 99, or 100% identical to the sequence SEQ ID NO: 76; and a gene of interest.

In one embodiment, the DNA vector comprises:
a phage packaging signal allowing packaging of the DNA vector in a *Cutibacterium acnes* phage capsid;
a gene of interest; and
a selection marker allowing for selection of the DNA vector in *Cutibacterium acnes*.

In one embodiment, the DNA vector comprises:
a phage packaging signal allowing packaging of the DNA vector in a *Cutibacterium acnes* phage capsid; wherein the phage packaging signal sequence is at least 80, 83, 85, 87, 90, 93, 95, 97, 98, 99, or 100% identical to the sequence SEQ ID NO: 76;
a gene of interest; and
a selection marker allowing for selection of the DNA vector in *Cutibacterium acnes*.

In one embodiment, the DNA vector comprises:
a phage packaging signal allowing packaging of the DNA vector in a *Cutibacterium acnes* phage capsid;
a gene of interest;
an origin of replication allowing replication in *Cutibacterium acnes*; and
optionally a selection marker allowing for selection of the DNA vector in *Cutibacterium acnes*.

In one embodiment, the DNA vector comprises:
a phage packaging signal allowing packaging of the DNA vector in a *Cutibacterium acnes* phage capsid; wherein the phage packaging signal sequence is at least 80, 83, 85, 87, 90, 93, 95, 97, 98, 99, or 100% identical to the sequence SEQ ID NO: 76;
a gene of interest;
an origin of replication allowing replication in *Cutibacterium acnes*; and
optionally a selection marker allowing for selection of the DNA vector in *Cutibacterium acnes*.

In one embodiment, the phage packaging signal sequence is at least 80, 83, 85, 87, 90, 93, 95, 97, 98, 99, or 100% identical to a phage packaging signal sequence selected from the group consisting of the sequences SEQ ID NO: 76, SEQ ID NO: 86, SEQ ID NO: 87, SEQ ID NO: 88, SEQ ID NO: 89 and SEQ ID NO: 90.

In one embodiment, the DNA vector further comprises a *C. acnes* phage origin of replication.

In one embodiment, the DNA vector further comprises a *C. acnes* phage origin of replication, wherein the phage origin of replication sequence is at least 75, 77, 80, 83, 85, 87, 90, 93, 95, 97, 98, 99 or 100% identical to the sequence SEQ ID NO: 67.

In one embodiment, the gene of interest is a DNA encoding an antigen.

The invention encompasses a *Cutibacterium acnes* producer cell carrying a recombinant DNA vector for the production of *Cutibacterium acnes* phage-derived particles that contain the recombinant DNA vector.

The DNA vector is typically packaged into proteins produced from a *Cutibacterium acnes* phage genome or a helper phage. The *C. acnes* phage genome can be introduced into the *C. acnes* producer cell, for instance, by transformation or transduction with a *C. acnes* phage whereas the helper phage can be introduced into the *C. acnes* producer cell, for instance, by transformation or conjugation before or after introduction of the DNA vector into the *C. acnes* producer cell (FIG. 1).

The *Cutibacterium acnes* producer cell carrying a recombinant DNA vector typically comprises a *Cutibacterium acnes* phage genome leading to the production of phage-derived particles carrying the DNA vector.

In one embodiment, the *Cutibacterium acnes* phage genome is a non-engineered/wild-type genome.

In another embodiment, the *Cutibacterium acnes* phage genome is engineered.

In one embodiment, the DNA vector comprises an origin of replication able to replicate only in the *Cutibacterium acnes* producer cell and not in the *Cutibacterium acnes* receiver cell.

In one embodiment, the DNA vector comprises:
a phage packaging signal allowing packaging of the DNA vector in a *Cutibacterium acnes* phage capsid;
at least one gene of interest;
an origin of replication allowing replication only in *Cutibacterium acnes* producer cell; and
optionally a selection marker allowing for selection of the DNA vector in *Cutibacterium acnes*.

In one embodiment, the selection marker is an auxotrophic marker and the *Cutibacterium acnes* producer cell growth is dependent on this auxotrophic marker.

In one embodiment, the selection marker is an antibiotic resistance marker.

In one embodiment, the DNA vector further comprises a CRISPR-Cas system.

In one embodiment, the CRISPR-Cas system targets a *C. acnes* chromosome locus. Preferably, the targeted locus is not present in the *C. acnes* producer cell. Preferably, the CRISPR array from the CRISPR-Cas system is expressing one or several crRNA targeting the chromosome locus.

In one embodiment, the CRISPR-Cas system targets several *C. acnes* chromosome loci. Preferably, the targeted loci are not present in the *C. acnes* producer cell. Preferably, the CRISPR array from the CRISPR-Cas system is expressing one or several crRNA targeting the chromosome loci.

In one embodiment, the CRISPR-Cas system targets a *C. acnes* plasmid locus.

Preferably, the targeted locus is not present in the *C. acnes* producer cell. Preferably, the CRISPR array from the CRISPR-Cas system is expressing one or several crRNA targeting the plasmid locus.

In one embodiment, the CRISPR-Cas system targets several *C. acnes* plasmid loci. Preferably, the targeted loci are not present in the *C. acnes* producer cell. Preferably, the CRISPR array from the CRISPR-Cas system is expressing one or several crRNA targeting the plasmid loci.

In one embodiment, the CRISPR-Cas system is not expressed in the *C. acnes* producer cell. Preferably the CRISPR-Cas system is repressed in the *C. acnes* producer cell.

In one embodiment, the CRISPR-Cas system targets a proinflammatory sequence related to a host disease.

In one embodiment, the CRISPR-Cas system targets a proinflammatory sequence related to acne vulgaris.

In one embodiment, the DNA vector comprises a CRISPR-Cas system targeting the DNA vector itself.

In one embodiment, the DNA vector comprises a template for homologous recombination in *C. acnes* phages.

In one embodiment, the DNA vector comprises a template for homologous recombination in *C. acnes* chromosome.

In one embodiment, the DNA vector comprises a template for homologous recombination in *C. acnes* endogenous plasmids.

In one embodiment, the DNA vector comprises a template for homologous recombination and a CRISPR-Cas system targeting the DNA vector itself outside of the template region.

In one embodiment, the DNA vector comprises a template for homologous recombination and a CRISPR-Cas system targeting the DNA vector itself outside of the template region wherein the RNA guide (crRNA or sgRNA) from the CRISPR-Cas system is not perfectly matching the DNA target.

In one embodiment, the DNA vector comprises an integrase gene expression cassette and a site specific recombination site allowing for the integration of the DNA vector inside the chromosome.

In one embodiment, the DNA vector comprises a prime editor gene expression cassette and one or multiple pegRNAs.

In one embodiment, the DNA vector comprises a base editor gene expression cassette and one or multiple crRNAs or sgRNAs.

In one embodiment, the selection marker is catA.
In one embodiment, the selection marker is ermE.
In one embodiment, the selection marker is hygB.

The invention encompasses a *C. acnes* phage-derived particle comprising any of the DNA vectors of the invention.

The invention encompasses a *C. acnes*, in particular an engineered *C. acnes*, comprising any of the DNA vectors of the invention.

In a particular embodiment, the engineered *C. acnes* comprises at least one, two, three or more DNA vectors, in particular DNA vectors of the invention.

In a particular embodiment, the engineered *C. acnes* comprises a DNA vector of the invention which comprises a DNA encoding an antigen.

The invention encompasses a *C. acnes* engineered following transduction of any of the vectors of the invention by phage-derived particles.

The invention encompasses an engineered *C. acnes* whose genome is altered following the transduction by a phage-derived particle containing any of the vectors of the invention.

The invention encompasses an engineered *C. acnes* produced by transducing *C. acnes* with any of the vectors of the invention, modifying the *C. acnes* with a gene of interest carried by the vector, and selecting for the modification.

The invention encompasses an engineered *C. acnes* produced by transducing *C. acnes* with any of the vectors of the invention, modifying the *C. acnes* with a gene of interest carried by the vector, selecting for the modification, and curing the engineered *C. acnes* of the vector.

In one embodiment, the engineered *C. acnes* has been modified by a CRISPR-Cas system carried by the vector and transduced by a phage-derived particle containing any vectors from the invention.

In one embodiment, the engineered *C. acnes* has been modified by insertion of an exogenous gene into the *C. acnes* chromosome In one embodiment, the engineered *C. acnes* has been modified by insertion of an exogenous gene into the *C. acnes* plasmid.

In one embodiment, the engineered *C. acnes* has been modified by deletion or mutation of an endogenous genetic sequence in the *C. acnes* chromosome.

In one embodiment, the engineered *C. acnes* has been modified by deletion, insertion or substitution of one or several nucleotides into the *C. acnes* chromosome.

In one embodiment, the engineered *C. acnes* has been modified by deletion, insertion or substitution of one or several nucleotides into the *C. acnes* plasmid.

The invention encompasses a method for producing *C. acnes* phage-derived particles that contain any vectors of the invention, comprising the introduction of any of the DNA vectors of the invention into a *C. acnes* producer cell and contacting the producer cell with *C. acnes* phage genome.

The invention encompasses a method for engineering *C. acnes* comprising the introduction of any of the DNA vectors of the invention into a *C. acnes*. The method can further comprise selecting a modified *C. acnes*. The method can further comprise selecting a modified *C. acnes* that has an insertion of an exogenous gene into the *C. acnes* chromosome or into an endogenous plasmid. The method can further comprise selecting a modified *C. acnes* that has one or several deletions, insertions or substitutions of one or several nucleotides into *C. acnes* chromosome or endogenous plasmids.

The invention encompasses a phage-derived particle produced by any of the methods of the invention.

The invention encompasses methods for treating a *C. acnes*-related disorder or disease. In one embodiment, the method comprises administering a phage-derived particle of the invention or a bacterium producing such a phage-derived particle to a subject. The invention further concerns a phage-derived particle of the invention or a bacterium producing such a phage derived particle for use in a method for treating a *C. acnes*-related disorder or disease.

The invention encompasses methods for modifying *C. acnes* to treat a disorder or disease or skin condition or for cosmetic applications. In one embodiment, the method comprises administering a phage-derived particle of the invention or a bacterium producing such a phage-derived particle to a subject. The invention further concerns a phage-derived particle of the invention or a bacterium producing such a phage-derived particle for use in a method for treating a disorder or disease or skin condition.

In one embodiment, the method is performed ex-situ.

In one embodiment, the method is performed in-situ.

In one embodiment, the method is performed ex-situ with a *C. acnes* strain isolated from the subject.

BRIEF DESCRIPTION OF DRAWINGS

In order to better understand the subject matter that is disclosed herein and to exemplify how it may be carried out in practice, embodiments will be described, by way of non-limiting example, with reference to the accompanying drawings. With specific reference to the drawings, it is stressed that the particulars shown are by way of example and for purposes of illustrative discussion of embodiments of the invention.

FIG. 2A-B depicts host range determination of isolated *C. acnes* bacteriophages. 1 indicates strain infection with full spot lysis; 0.5 indicates lower efficiency in strain infection with single plaques observed instead of full spot lysis.

FIG. 4A depicts a vector (pEB_HR01) containing a single homology arm (HA) to *C. acnes* chromosome which is conjugated into *C. acnes*. Because the vector is not replicative in *C. acnes*, only *C. acnes* cells that perform a single recombination event stably maintain the antibiotic marker and are able to grow on antibiotic plate. Cells that do not perform the first recombination event or cells that perform the first and the second recombination events are not able to grow on antibiotic plates (erythromycin). FIG. 4B depicts a vector (pEB_HR02) containing two homology arms to *C. acnes* chromosome which is conjugated into *C. acnes*. Selection of the final recombinant is performed using an antibiotic selection (ErmE) and a counter selection (SacB).

FIG. 6A depicts a vector, containing an antibiotic selection marker flanked by two homology arms and a CRISPR-Cas system targeting the vector outside the homology regions, which is conjugated into *C. acnes*. The CRISPR-Cas system cuts the vector leading to linearization of the template and plasmid loss. Thus, only recombinant cells are able to grow in the presence of an antibiotic. FIG. 6B depicts a vector, containing a mutant allele flanked by two homology arms and a CRISPR-Cas system targeting the vector outside the homology regions as well as the non mutated allele of *C. acnes* chromosome, which is conjugated into *C. acnes*. The CRISPR-Cas system cuts the vector leading to linearization of the template and plasmid loss as well as the *C. acnes* chromosome. Thus, only recombinant cells are able to grow in the presence of erythromycin.

FIG. 7A depicts the first step of the method. The first step consists in generating mutant phages (mt PAC7) by having a first phage (wt PAC7) infect a strain containing a plasmid with a recombination template (*C. acnes* pEB-PRECOMB). The recombination template contains a left homology arm (LHA) and a right homology arm (RHA) that are flanking a mutant allele. The two homology arms drive the in vivo recombination between the plasmid (pEB-PRE-COMB) and the phage genome. Suspension obtained from infection contains a mix of initial phage (wt PAC7) and the new mutated phage (mt PAC7). FIG. 7B depicts the second step of the method. To select between both phage particles, the suspension is put in contact with a *C. acnes* strain (*C. acnes* pEB-PSCREEN) containing a plasmid expressing CRISPR-Cas system targeting only the wt PAC7 phage and not the mt PAC7. Therefore infection of the *C. acnes* pEB-PSCREEN leads to selective replication of mt PAC7.

(Ca0s18234). Strain *C. acnes* ATCC 11828 is susceptible to both wild-type phage PAC7 and any mutant phage obtained by homologous recombination. Strain Ca0s18233 is resistant to wild-type phage PAC7 and susceptible to mutant phage obtained by homologous recombination with pIC253 template. Strain Ca0s18234 is resistant to wild-type phage PAC7 and resistant to mutant phage obtained by homologous recombination with pIC253.

Figure 10:
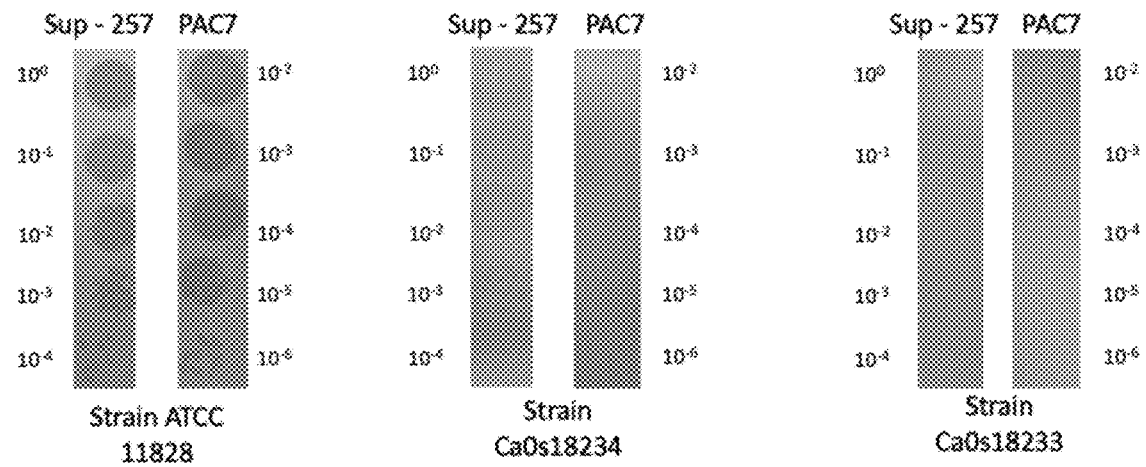

FIG. 10 depicts titration of supernatant obtained after infecting *C. acnes* harbouring editing/targeting vectors pIC257 (Ca0s18208), referred as Sup-257, on *C. acnes* ATCC 11828 wt, *C. acnes* ATCC 11828 harbouring pIC240 (Ca0s18234) and *C. acnes* ATCC 11828 harbouring pIC238 (Ca0s18233). Strain *C. acnes* ATCC 11828 is susceptible to both wild-type phage PAC7 and any mutant phage obtained by homologous recombination. Strain Ca0s18234 is resistant to wild-type phage PAC7 and susceptible to mutant phage obtained by homologous recombination with pIC257. Strain Ca0s18233 is resistant to wild-type phage PAC7 and resistant to mutant phage obtained by homologous recombination with pIC257.

Figure 11:
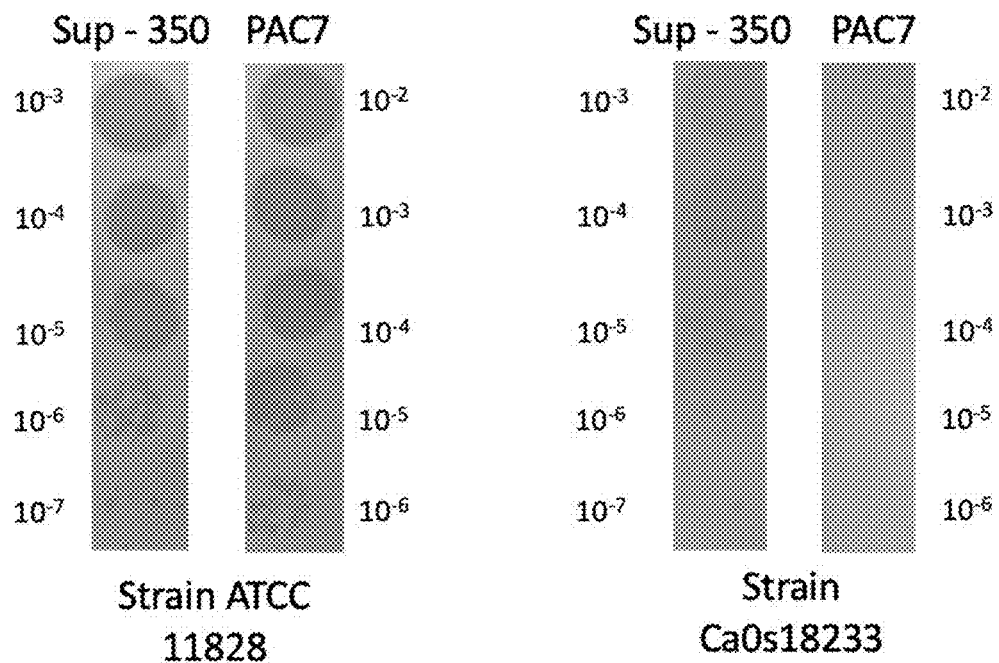

FIG. 11 depicts titration of supernatant obtained after infecting *C. acnes* harbouring editing pIC350 (Ca0s18379), referred as Sup-350, on *C. acnes* ATCC 11828 wt and *C. acnes* ATCC 11828 harbouring pIC238 (Ca0s18233). Strain *C. acnes* ATCC 11828 is susceptible to both wild-type phage PAC7 and mutant phage obtained by homologous recombination with pIC350. Strain Ca0s18233 is resistant to wild-type phage PAC7 and susceptible to mutant phage obtained by homologous recombination with pIC350.

Figure 12:
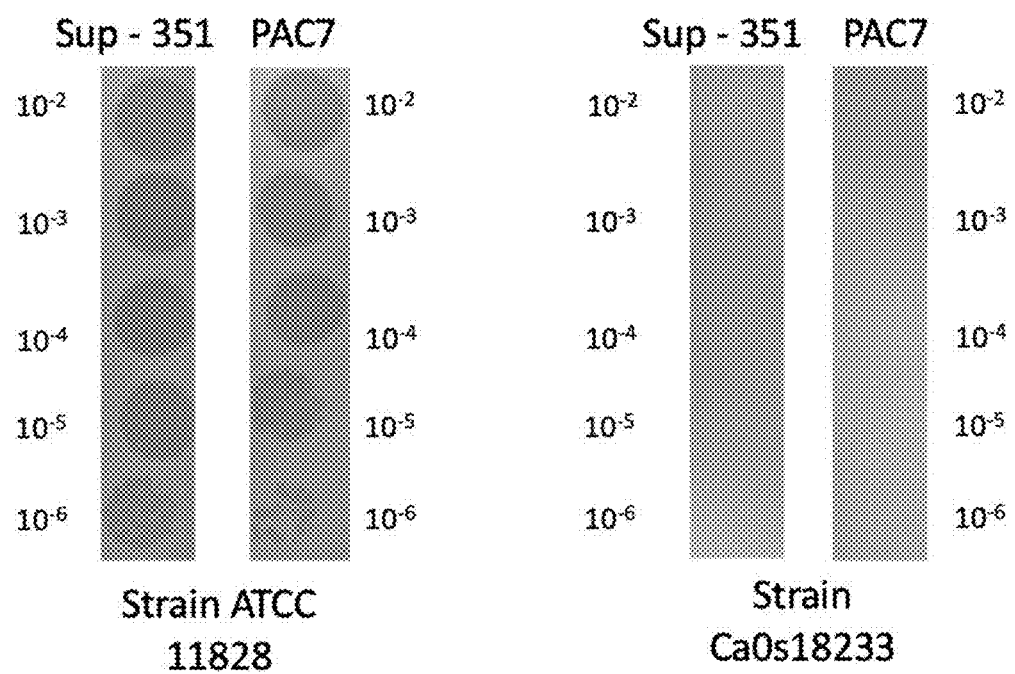

FIG. 12 depicts titration of supernatant obtained after infecting *C. acnes* harbouring editing pIC351 (Ca0s18381), referred as Sup-351, on *C. acnes* ATCC 11828 wt and *C. acnes* ATCC 11828 harbouring pIC238 (Ca0s18233). Strain *C. acnes* ATCC 11828 is susceptible to both wild-type phage PAC7 and mutant phage obtained by homologous recombination with pIC351. Strain Ca0s18233 is resistant to both wild-type phage PAC7 and mutant phage obtained by homologous recombination with pIC351.

Figure 13:
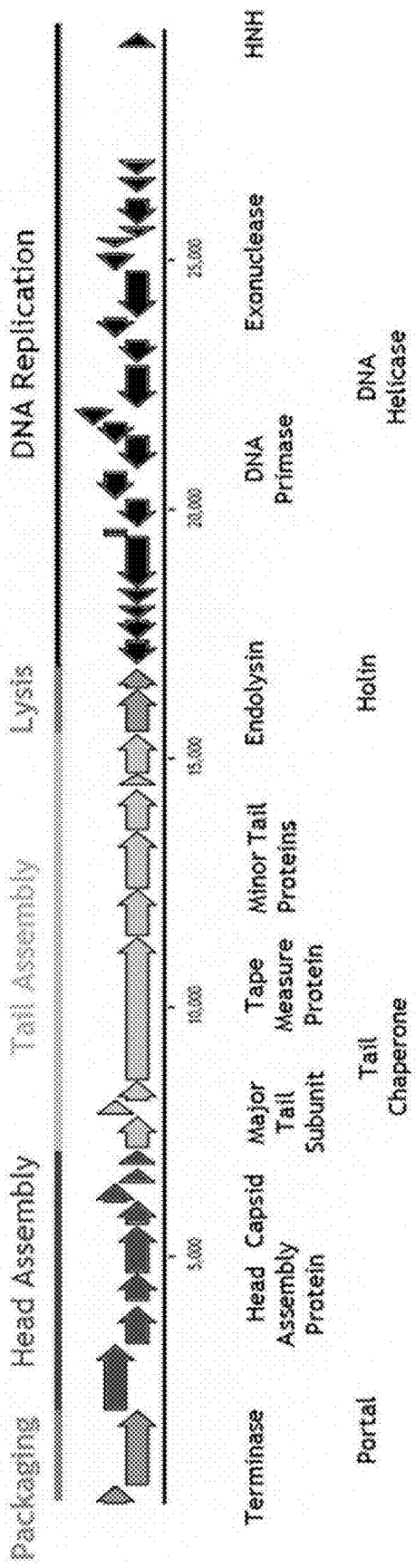

FIG. 13 depicts *C. acnes* phage genome organization. 5 different regions encode different proteins involved in various functions: packaging, head assembly, tail assembly, lysis, DNA replication (Brown et al[28]).

Figure 14A:
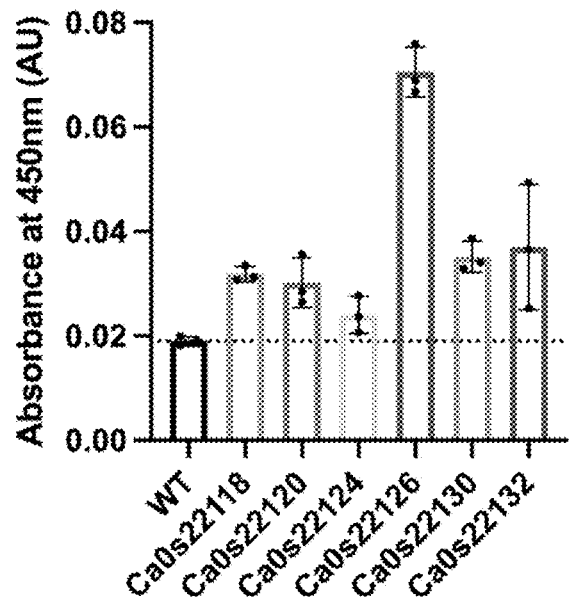
Figure 14B:
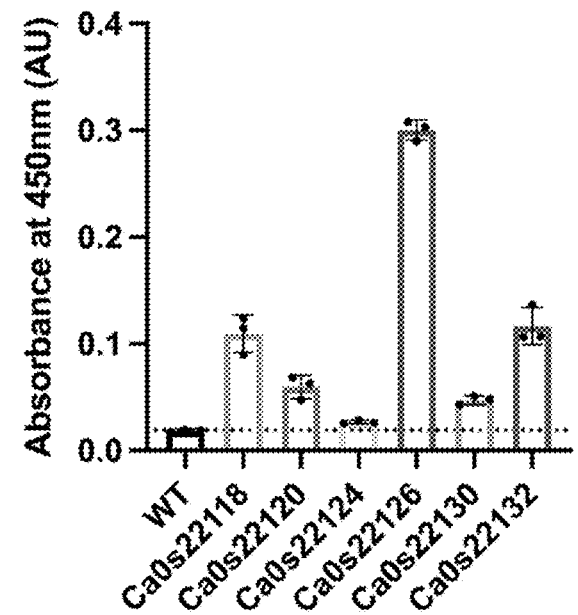

FIG. 14 (A and B) depicts absorbance values from ELISAs for the presence of chicken ovalbumin (OVA) protein in different *C. acnes* culture supernatant diluted 1/10. FIG. 14A and FIG. 14B represent two independent replicas. Bar graphs represent the mean of three technical replicates of the same supernatant culture. *C. acnes* strains ATCC 11828 (WT) was used as negative control.

Figure 15:
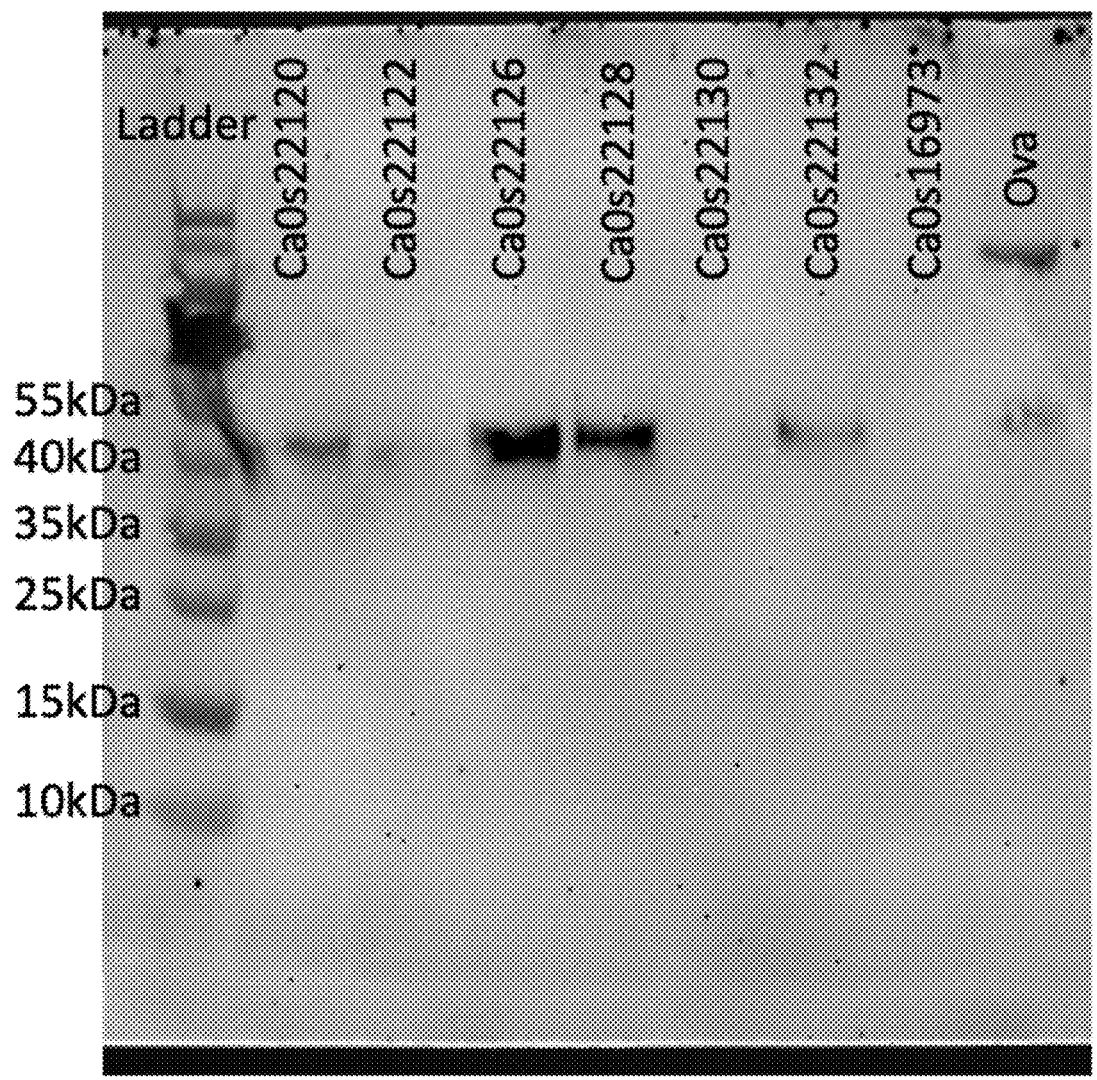

FIG. 15 depicts an ovalbumin specific western blot on culture supernatant from different *C. acnes* strains engineered to secrete ovalbumin. From left to right: (1) Pageruler ladder, (2) supernatant from strain Ca0s22120, (3) supernatant from strain Ca0s22122, (4) supernatant from strain Ca0s22126, (5) supernatant from strain Ca0s22128, (6) supernatant from strain Ca0s22130, (7) supernatant from strain Ca0s22132, (8) supernatant from strain Ca0s16973, (9) ovalbumin.

Figure 16:
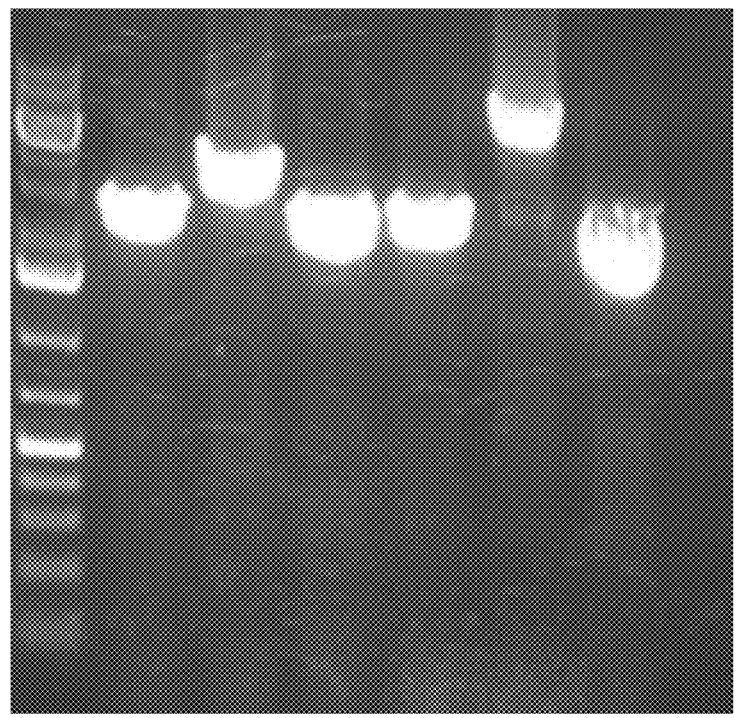

FIG. 16 depicts a gel. First well in the left (1) corresponds to GeneRuler 1 kb DNA Ladder. Other wells correspond to PCR with primers IC443/1C290 performed on plaques. From left to right: (2) Plaque no 5 from a lawn of the strain Ca0s20472+suspension of infected Ca0s20855, (3) Plaque no 7 from a lawn of the strain Ca0s20472+suspension of infected Ca0s20855, (4) Plaque no 1 from a lawn of the strain Ca0s20472+suspension of PAC7, (5) Plaque no 2 from a lawn of the strain Ca0s20472+suspension of PAC7, (6) Plaque no 3 from a lawn of the strain Ca0s20472+suspension of infected Ca0s20857, (7) Plaque no 3 from a lawn of the strain Ca0s20472+suspension of PAC7.

Figure 17:
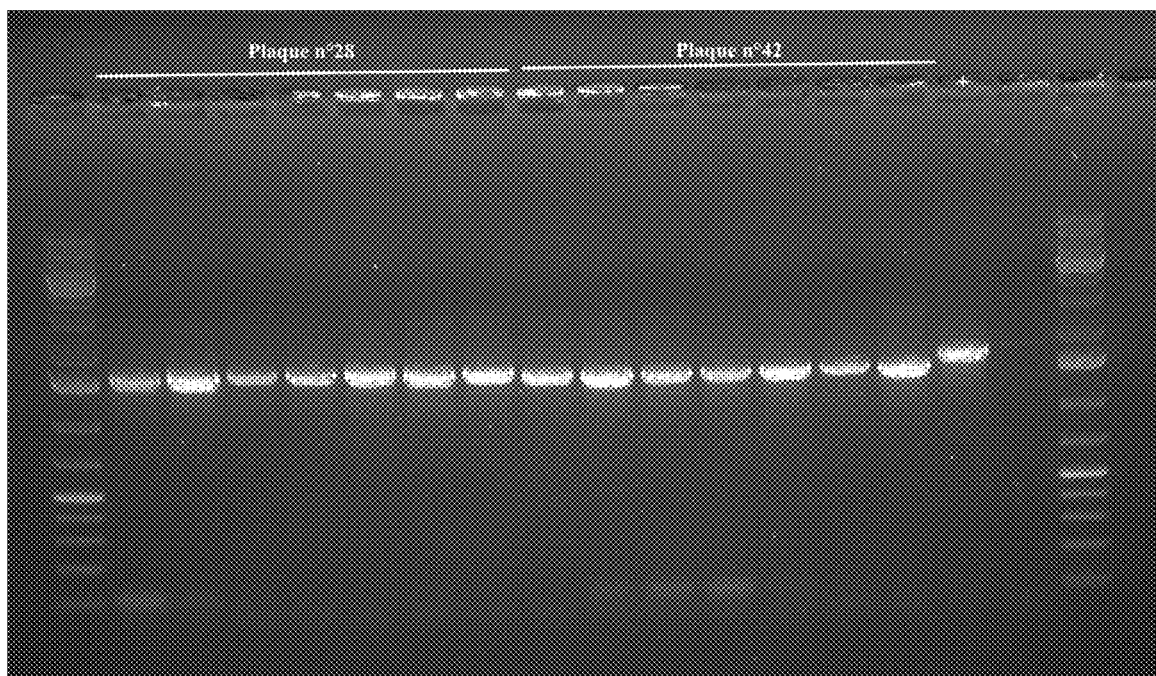

FIG. 17 depicts a gel. First well (1) in the left corresponds to GeneRuler 1 kb DNA Ladder. Other wells correspond to PCR with primers IC619/AL219. From left to right: (well 2-8) 7 plaques isolated from plaque no 28, (well 9-15) 7 plaques isolated from plaque no 28, (well 16) PCR on wt PAC7 (positive control), (well 17) negative control on lawn of Ca0s22235.

FIG. 18 depicts a DNA alignment between the PAC7 wt genome (SEQ ID NO: 113) and the sequencing of three different isolated plaques from PAC7-m28-gp45 using primer IC619 (SEQ ID NO: 78; SEQ ID NO: 85; SEQ ID NO: 114). Alignments performed using Clustal Omega (Sievers, F. et al. *Mol Syst Biol* 7, 539-539 (2011)).

DETAILED DESCRIPTION OF INVENTION

The inventors demonstrated, for the first time, the introduction of a recombinant replicative DNA in *C. acnes* by transduction by a phage-derived particle.

The inventors also demonstrated, for the first time, the production of *C. acnes* phage-derived particles from a *C. acnes* strain, carrying a recombinant self-replicative DNA vector.

The invention relates to a *C. acnes* strain carrying a DNA vector comprising a phage packaging signal and a gene of interest, the production of phage-derived particles containing the DNA vector and the use of this phage-derived particles to transduce *C. acnes* in vitro or in situ and the subsequent expression of the gene of interest in the transduced *C. acnes* cell. The invention also relates to the modified *C. acnes* strains obtained by transduction of a DNA vector by the phage-derived particle, the modified *C. acnes* strains containing or not the DNA vector.

*C. acnes* phages are naturally present in the human skin and have been isolated numerous times since the first isolation in 1964. More recently, sequencing of *C. acnes* phages has revealed an unusual high level of nucleotide conservation with ~85% identity. All *C. acnes* phages described so far are siphoviridae with a genome size constraint around 30 kb and a similar genome architecture. Despite their small genetic diversity, most *C. acnes* phages have the capacity to infect several *C. acnes* phylotypes and thus are considered as broad-host range. Their in-situ infectivity and their broad host range make them a relevant platform to be engineered for transgene delivery into the *C. acnes* population.

The inventors show for the first time that phage-derived particles can be produced from the co-occurrence of a wild-type or engineered *C. acnes* phage genome and a recombinant DNA vector with a packaging signal in a *C. acnes* cell ("producer cell"). The phage-derived particles are able to transduce the DNA vector into a "receiver" *C. acnes* cell and express a transgene such as an antibiotic resistance gene allowing the selection of the transductants. This widely expands the possibility to engineer *C. acnes* population directly on the skin, paving the way for many applications (industrial, therapeutic, cosmetic, environmental). The invention encompasses a *C. acnes* "producer" cell carrying DNA vectors, particularly phagemids, and methods for generating phage-derived particles and their use to modify or kill *C. acnes*.

DNA Vectors

The invention encompasses recombinant DNA vectors for use in *Cutibacterium acnes*. Preferably, the DNA vector is a recombinant DNA vector, which is not integrated into the *C. acnes* chromosome. The vector allows transfer to progeny cells. The vector is preferably a phagemid. The DNA vector preferably comprises an origin of replication allowing replication in *C. acnes* and a phage packaging signal.

In various embodiments, the DNA vector comprises any combination of a phage packaging signal, an origin of replication allowing replication in *C. acnes*, a selection marker allowing for selection of the DNA vector in *C. acnes*, a gene of interest, and an origin of replication allowing replication in *C. acnes* producer cell but no replication in *C. acnes* receiver cell.

In one embodiment, the DNA vector comprises a phage packaging signal, an origin of replication allowing replication in *C. acnes*, a first selection marker allowing for selection of the DNA vector in *C. acnes* and a gene of interest.

In one embodiment, the DNA vector comprises a phage packaging signal, an origin of replication allowing replication in *C. acnes* producer cell but no replication in *C. acnes* receiver cell, a first selection marker allowing for selection of the DNA vector in *C. acnes* and a gene of interest.

Preferably, the gene of interest is exogenous to *C. acnes*, that is, one that is not found naturally in *C. acnes*.

In one embodiment, the DNA vector comprises a phage packaging signal, wherein the phage packaging signal sequence is at least 80, 83, 85, 87, 90, 93, 95, 97, 98, 99, or 100% identical to the sequence SEQ ID NO: 76; an origin of replication allowing replication in *C. acnes*; a selection marker allowing for selection of the DNA vector in *C. acnes*; and a gene of interest.

In one embodiment, the DNA vector comprises a phage packaging signal, wherein the phage packaging signal sequence is at least 80, 83, 85, 87, 90, 93, 95, 97, 98, 99, or 100% identical to the sequence SEQ ID NO: 76; an origin of replication allowing replication in *C. acnes* or closely related species; a selection marker allowing for selection of the DNA vector in *C. acnes*; and a gene of interest.

In one embodiment, the DNA vector comprises a phage packaging signal, wherein the phage packaging signal sequence is at least 80, 83, 85, 87, 90, 93, 95, 97, 98, 99, or 100% identical to the sequence SEQ ID NO: 76; an origin of replication allowing replication in *C. acnes* or closely related species; a selection marker allowing for selection of the DNA vector in *C. acnes*; a selection marker allowing for selection in a first bacteria wherein the first bacteria is *E. coli*; an origin of replication allowing replication in a first bacteria wherein the first bacteria is *E. coli*; and a gene of interest.

In one embodiment, the DNA vector can be efficiently introduced into and stably replicated in *C. acnes* producer cell using electroporation, using protoplast electroporation, using chemical transformation, using conjugation, using natural competency or using transduction.

In one embodiment, the DNA vector can be efficiently transformed into and stably replicated in *C. acnes* producer cell using physical methods such as electroporation of *C. acnes* cells or electroporation of *C. acnes* protoplast.

In one embodiment, the *C. acnes* protoplasts are generated using Mutanolysin treatment or Lysozyme treatment, Mutanolysin and Lysozyme treatment, or Mutanolysin and Lysozyme and bead-beating treatment followed by resuspension into hypotonique media.

In one embodiment, the DNA vector can be efficiently transformed into and stably replicated in *C. acnes* producer cell using *C. acnes* protoplast mix with DNA vector or DNA vector+glass beads.

In one embodiment, delivery of the DNA vector into *C. acnes* is by transduction. In one embodiment, the DNA vector comprises one packaging signal selected from the group consisting of the packaging signals of the following *C. acnes* phages: PAC7 (typically of sequence SEQ ID NO: 68); PAC1 (typically of sequence SEQ ID NO: 69); PAC9 (typically of sequence SEQ ID NO: 70); PAC2 (typically of sequence SEQ ID NO: 71); PAC10 (typically of sequence SEQ ID NO: 72); PAC22 (typically of sequence SEQ ID NO: 73); PAC13 (typically of sequence SEQ ID NO: 74); and PAC263 (typically of sequence SEQ ID NO: 75), and is packaged into proteins expressed from the genome of a *C. acnes* phage selected from the group consisting of the phages PAC7 (typically of sequence SEQ ID NO: 68); PAC1 (typically of sequence SEQ ID NO: 69); PAC9 (typically of sequence SEQ ID NO: 70); PAC2 (typically of sequence SEQ ID NO: 71); PAC10 (typically of sequence SEQ ID NO: 72); PAC22 (typically of sequence SEQ ID NO: 73); PAC13 (typically of sequence SEQ ID NO: 74); and PAC263 (typically of sequence SEQ ID NO: 75), allowing transduction of the DNA vector into *C. acnes*.

In one embodiment, the DNA vector comprises a packaging signal, the sequence of which is at least 80, 83, 85, 87, 90, 93, 95, 97, 98, 99, or 100% identical to the sequence of any of the above packaging signals.

In one embodiment, the phage packaging signal is of sequence at least 80, 83, 85, 87, 90, 93, 95, 97, 98, 99, or 100% identical to a phage packaging signal sequence selected from the group consisting of: SEQ ID NO: 76, SEQ ID NO: 86, SEQ ID NO: 87, SEQ ID NO: 88, SEQ ID NO: 89 and SEQ ID NO: 90.

In one embodiment, delivery of the DNA vector into *C. acnes* is by conjugation.

In one embodiment, the DNA vector comprises an origin of transfer selected from the group consisting of: oriT_pMRC01 (typically of sequence SEQ ID NO: 1); oriT_RSF1010 (typically of sequence SEQ ID NO: 2); oriT_pRS01 (typically of sequence SEQ ID NO: 3); oriT_pMV158 (typically of sequence SEQ ID NO: 4); oriT_pTF1 (typically of sequence SEQ ID NO: 5); oriT_pSC101 (typically of sequence SEQ ID NO: 6); oriT_pBTK445 (typically of sequence SEQ ID NO: 7); oriT_pBBR1 (typically of sequence SEQ ID NO: 8); oriT_R721 (typically of sequence SEQ ID NO: 9); oriT_pRmeGR4a (typically of sequence SEQ ID NO: 10); oriT_ColE1 (typically of sequence SEQ ID NO: 11); oriT_pTiC58 (typically of sequence SEQ ID NO: 12); oriT_pMdT1 (typically of sequence SEQ ID NO: 13); oriT_R1 (typically of sequence SEQ ID NO: 14); oriT_Tn5520 (typically of sequence SEQ ID NO: 15); oriT_QKH54 (typically of sequence SEQ ID NO: 16); oriT_R64 (typically of sequence SEQ ID NO: 17); oriT_R751 (typically of sequence SEQ ID NO: 18); oriT_RP4 (typically of sequence SEQ ID NO: 19); oriT_pKL1 (typically of sequence SEQ ID NO: 20); oriT_RK2 (typically of sequence SEQ ID NO: 21); oriT_R1162 (typically of sequence SEQ ID NO: 22); oriT_Tn4555 (typically of sequence SEQ ID NO: 23); oriT_pHT (typically of sequence SEQ ID NO: 24); oriT_Tn4399 (typically of sequence SEQ ID NO: 25); oriT_Tn916 (typically of sequence SEQ ID NO: 26); oriT_pST12 (typically of sequence SEQ ID NO: 27); oriT_pCU1 (typically of sequence SEQ ID NO: 28); oriT_pSU233 (typically of sequence SEQ ID NO: 29);

oriT_F (typically of sequence SEQ ID NO: 30); oriT_pMAB01 (typically of sequence SEQ ID NO: 31); oriT_R388 (typically of sequence SEQ ID NO: 32); oriT_pS7a (typically of sequence SEQ ID NO: 33); oriT_pS7b (typically of sequence SEQ ID NO: 34); oriT_R702 (typically of sequence SEQ ID NO: 35); oriT_pMUR274 (typically of sequence SEQ ID NO: 36); oriT_R100 (typically of sequence SEQ ID NO: 37); oriT_pVCR94deltaX (typically of sequence SEQ ID NO: 38); oriT_R46 (typically of sequence SEQ ID NO: 39); oriT_pGO1 (typically of sequence SEQ ID NO: 40); and oriT_pIP501 (typically of sequence SEQ ID NO: 41).

In one embodiment, the DNA vector comprises the origin of transfer oriT_pMRC01 (typically of sequence SEQ ID NO: 1). In one embodiment, the DNA vector comprises the origin of transfer oriT_RSF1010 (typically of sequence SEQ ID NO: 2). In one embodiment, the DNA vector comprises the origin of transfer oriT_pRS01 (typically of sequence SEQ ID NO: 3). In one embodiment, the DNA vector comprises the origin of transfer oriT_pMV158 (typically of sequence SEQ ID NO: 4). In one embodiment, the DNA vector comprises the origin of transfer oriT_pTF1 (typically of sequence SEQ ID NO: 5). In one embodiment, the DNA vector comprises the origin of transfer oriT_pSC101 (typically of sequence SEQ ID NO: 6). In one embodiment, the DNA vector comprises the origin of transfer oriT_pBTK445 (typically of sequence SEQ ID NO: 7). In one embodiment, the DNA vector comprises the origin of transfer oriT_pBBR1 (typically of sequence SEQ ID NO: 8). In one embodiment, the DNA vector comprises the origin of transfer oriT_R721 (typically of sequence SEQ ID NO: 9). In one embodiment, the DNA vector comprises the origin of transfer oriT_pRmeGR4a (typically of sequence SEQ ID NO: 10). In one embodiment, the DNA vector comprises the origin of transfer oriT_ColE1 (typically of sequence SEQ ID NO: 11). In one embodiment, the DNA vector comprises the origin of transfer oriT_pTiC58 (typically of sequence SEQ ID NO: 12). In one embodiment, the DNA vector comprises the origin of transfer oriT_pMdT1 (typically of sequence SEQ ID NO: 13). In one embodiment, the DNA vector comprises the origin of transfer oriT_R1 (typically of sequence SEQ ID NO: 14). In one embodiment, the DNA vector comprises the origin of transfer oriT_Tn5520 (typically of sequence SEQ ID NO: 15). In one embodiment, the DNA vector comprises the origin of transfer oriT_QKH54 (typically of sequence SEQ ID NO: 16). In one embodiment, the DNA vector comprises the origin of transfer oriT_R64 (typically of sequence SEQ ID NO: 17). In one embodiment, the DNA vector comprises the origin of transfer oriT_R751 (typically of sequence SEQ ID NO: 18). In one embodiment, the DNA vector comprises the origin of transfer oriT_RP4 (typically of sequence SEQ ID NO: 19). In one embodiment, the DNA vector comprises the origin of transfer oriT_pKL1 (typically of sequence SEQ ID NO: 20). In one embodiment, the DNA vector comprises the origin of transfer oriT_RK2 (typically of sequence SEQ ID NO: 21). In one embodiment, the DNA vector comprises the origin of transfer oriT_R1162 (typically of sequence SEQ ID NO: 22). In one embodiment, the DNA vector comprises the origin of transfer oriT_Tn4555 (typically of sequence SEQ ID NO: 23). In one embodiment, the DNA vector comprises the origin of transfer oriT_pHT (typically of sequence SEQ ID NO: 24). In one embodiment, the DNA vector comprises the origin of transfer oriT_Tn4399 (typically of sequence SEQ ID NO: 25). In one embodiment, the DNA vector comprises the origin of transfer oriT_Tn916 (typically of sequence SEQ ID NO: 26). In one embodiment, the DNA vector comprises the origin of transfer oriT_pST12 (typically of sequence SEQ ID NO: 27). In one embodiment, the DNA vector comprises the origin of transfer oriT_pCU1 (typically of sequence SEQ ID NO: 28). In one embodiment, the DNA vector comprises the origin of transfer oriT_pSU233 (typically of sequence SEQ ID NO: 29). In one embodiment, the DNA vector comprises the origin of transfer oriT_F (typically of sequence SEQ ID NO: 30). In one embodiment, the DNA vector comprises the origin of transfer oriT_pMAB01 (typically of sequence SEQ ID NO: 31). In one embodiment, the DNA vector comprises the origin of transfer oriT_R388 (typically of sequence SEQ ID NO: 32). In one embodiment, the DNA vector comprises the origin of transfer oriT_pS7a (typically of sequence SEQ ID NO: 33). In one embodiment, the DNA vector comprises the origin of transfer oriT_pS7b (typically of sequence SEQ ID NO: 34). In one embodiment, the DNA vector comprises the origin of transfer oriT_R702 (typically of sequence SEQ ID NO: 35). In one embodiment, the DNA vector comprises the origin of transfer oriT_pMUR274 (typically of sequence SEQ ID NO: 36). In one embodiment, the DNA vector comprises the origin of transfer oriT_R100 (typically of sequence SEQ ID NO: 37). In one embodiment, the DNA vector comprises the origin of transfer oriT_pVCR94deltaX (typically of sequence SEQ ID NO: 38). In one embodiment, the DNA vector comprises the origin of transfer oriT_R46 (typically of sequence SEQ ID NO: 39). In one embodiment, the DNA vector comprises the origin of transfer oriT_pGO1 (typically of sequence SEQ ID NO: 40). In one embodiment, the DNA vector comprises the origin of transfer oriT_pIP501 (typically of sequence SEQ ID NO: 41).

In one embodiment, the DNA vector comprises an origin of transfer (oriT), the sequence of which is at least 80, 83, 85, 87, 90, 93, 95, 97, 98, 99, or 100% identical to the sequence of any of the above oriT.

In one embodiment, a donor bacterium, such as *E. coli*, carry a conjugative plasmid, a conjugative transposon, or an integrative and conjugative element (ICE) selected from the group consisting of pMRC01, RSF1010, pRS01, pMV158, pTF1, pSC101, pBTK445, pBBR1, R721, pRmeGR4a, ColE1, pTiC58, pMdT1, R1, Tn5520, QKH54, R64, R751, RP4, pKL1, RK2, R1162, Tn4555, pHT, Tn4399, Tn916, pST12, pCU1, pSU233, F, pMAB01, R388, pS7a, pS7b, R702, pMUR274, R100, pVCR94deltaX, R46, pGO1 and pIP501; and is used to efficiently transfer the DNA vector into *C. acnes* recipient cells. In one embodiment the DNA vector contains an origin of transfer and the associated relaxase of the conjugative plasmid, conjugative transposon, and integrative and conjugative element (ICE) selected from the group consisting of pMRC01; RSF1010; pRS01; pMV158; pTF1; pSC101; pBTK445; pBBR1; R721; pRmeGR4a; ColE1; pTiC58; pMdT1; R1; Tn5520; QKH54; R64; R751; RP4; pKL1; RK2; R1162; Tn4555; pHT; Tn4399; Tn916; pST12; pCU1; pSU233; F; pMAB01; R388; pS7a; pS7b; R702; pMUR274; R100; pVCR94deltaX; R46; pGO1 and pIP501.

In a preferred embodiment, the DNA vector comprises an origin of transfer and the relaxase of the following conjugative plasmid, conjugative transposon, and integrative and conjugative element (ICE) selected from the group consisting of pMRC01; RSF1010; pRS01; pMV158; pTF1; pSC101; pBTK445; pBBR1; R721; pRmeGR4a; ColE1; pTiC58; pMdT1; R1; Tn5520; QKH54; R64; R751; RP4; pKL1; RK2; R1162; Tn4555; pHT; Tn4399; Tn916; pST12; pCU1; pSU233; F; pMAB01; R388; pS7a; pS7b; R702; pMUR274; R100; pVCR94deltaX; R46; pGO1 and pIP501.

In a preferred embodiment the DNA vector comprises an origin of transfer selected from the group consisting of: oriT_pMRC01 (SEQ ID NO: 1); oriT_RSF1010 (SEQ ID NO: 2); oriT_pRS01 (SEQ ID NO: 3); oriT_pMV158 (SEQ ID NO: 4); oriT_pTF1 (SEQ ID NO: 5); oriT_pSC101 (SEQ ID NO: 6); oriT_pBTK445 (SEQ ID NO: 7); oriT_pBBR1 (SEQ ID NO: 8); oriT_R721 (SEQ ID NO: 9); oriT_pRmeGR4a (SEQ ID NO: 10); oriT_ColE1 (SEQ ID NO: 11); oriT_pTiC58 (SEQ ID NO: 12); oriT_pMdT1 (SEQ ID NO: 13); oriT_R1 (SEQ ID NO: 14); oriT_Tn5520 (SEQ ID NO: 15); oriT_QKH54 (SEQ ID NO: 16); oriT_R64 (SEQ ID NO: 17); oriT_R751 (SEQ ID NO: 18); oriT_RP4 (SEQ ID NO: 19); oriT_pKL1 (SEQ ID NO: 20); oriT_RK2 (SEQ ID NO: 21); oriT_R1162 (SEQ ID NO: 22); oriT_Tn4555 (SEQ ID NO: 23); oriT_pHT (SEQ ID NO: 24); oriT_Tn4399 (SEQ ID NO: 25); oriT_Tn916 (SEQ ID NO: 26); oriT_pST12 (SEQ ID NO: 27); oriT_pCU1 (SEQ ID NO: 28); oriT_pSU233 (SEQ ID NO: 29); oriT_F (SEQ ID NO: 30); oriT_pMAB01 (SEQ ID NO: 31); oriT_R388 (SEQ ID NO: 32); oriT_pS7a (SEQ ID NO: 33); oriT_pS7b (SEQ ID NO: 34); oriT_R702 (SEQ ID NO: 35); oriT_pMUR274 (SEQ ID NO: 36); oriT_R100 (SEQ ID NO: 37); oriT_pVCR94deltaX (SEQ ID NO: 38); oriT_R46 (SEQ ID NO: 39); oriT_pGO1 (SEQ ID NO: 40) and oriT_pIP501 (SEQ ID NO: 41).

In one embodiment, the DNA vector comprises an origin of transfer (oriT) that is at least 80, 83, 85, 87, 90, 93, 95, 97, 98, 99, or 100% identical to any of these ICE.

In one embodiment, the invention encompasses a DNA vector comprising an origin of replication allowing replication in *C. acnes*, an oriT allowing conjugation into *C. acnes*, a selection marker allowing for selection in the transconjugant *C. acnes*, and a selection marker allowing for selection in the donor bacteria. In another embodiment, the invention encompasses a DNA vector comprising an origin of replication allowing replication in *C. acnes* and an oriT allowing conjugation into *C. acnes* as defined above.

In one embodiment, the origin of replication allowing replication in *C. acnes* is selected from the group consisting of: R6K (typically of sequence SEQ ID NO: 42); RK2 (typically of sequence SEQ ID NO: 43); pBBR1 (typically of sequence SEQ ID NO: 44); pRO1600 (typically of sequence SEQ ID NO: 45); RSF1010 (typically of sequence SEQ ID NO: 46); pAMβ1 (typically of sequence SEQ ID NO: 47); pLME106 (typically of sequence SEQ ID NO: 48); pTZC1 (typically of sequence SEQ ID NO: 49); pBC1 (typically of sequence SEQ ID NO: 50); pEP2 (typically of sequence SEQ ID NO: 51); pWVO1 (typically of sequence SEQ ID NO: 52); pAP1 (typically of sequence SEQ ID NO: 53); pWKS1 (typically of sequence SEQ ID NO: 54); pLME108 (typically of sequence SEQ ID NO: 55); pLS1 (typically of sequence SEQ ID NO: 56); pUB6060 (typically of sequence SEQ ID NO: 57); p545 (typically of sequence SEQ ID NO: 58); pJD4 (typically of sequence SEQ ID NO: 59); pIJ101 (typically of sequence SEQ ID NO: 60); pSN22 (typically of sequence SEQ ID NO: 61); pGP01 (typically of sequence SEQ ID NO: 62); pIP501 (typically of sequence SEQ ID NO: 63); pCU1 (typically of sequence SEQ ID NO: 64); and pBAV1K-T5 (typically of sequence SEQ ID NO: 65). In one embodiment, the origin of replication allowing replication in *C. acnes* is R6K (typically of sequence SEQ ID NO: 42). In one embodiment, the origin of replication allowing replication in *C. acnes* is RK2 (typically of sequence SEQ ID NO: 43). In one embodiment, the origin of replication allowing replication in *C. acnes* is pBBR1 (typically of sequence SEQ ID NO: 44). In one embodiment, the origin of replication allowing replication in *C. acnes* is pRO1600 (typically of sequence SEQ ID NO: 45). In one embodiment, the origin of replication allowing replication in *C. acnes* is RSF1010 (typically of sequence SEQ ID NO: 46). In one embodiment, the origin of replication allowing replication in *C. acnes* is pAMβ1 (typically of sequence SEQ ID NO: 47). In one embodiment, the origin of replication allowing replication in *C. acnes* is pLME106 (typically of sequence SEQ ID NO: 48). In one embodiment, the origin of replication allowing replication in *C. acnes* is pTZC1 (typically of sequence SEQ ID NO: 49). In one embodiment, the origin of replication allowing replication in *C. acnes* is pBC1 (typically of sequence SEQ ID NO: 50). In one embodiment, the origin of replication allowing replication in *C. acnes* is pEP2 (typically of sequence SEQ ID NO: 51). In one embodiment, the origin of replication allowing replication in *C. acnes* is pWVO1 (typically of sequence SEQ ID NO: 52). In one embodiment, the origin of replication allowing replication in *C. acnes* is pAP1 (typically of sequence SEQ ID NO: 53). In one embodiment, the origin of replication allowing replication in *C. acnes* is pWKS1 (typically of sequence SEQ ID NO: 54). In one embodiment, the origin of replication allowing replication in *C. acnes* is pLME108 (typically of sequence SEQ ID NO: 55). In one embodiment, the origin of replication allowing replication in *C. acnes* is pLS1 (typically of sequence SEQ ID NO: 56). In one embodiment, the origin of replication allowing replication in *C. acnes* is pUB6060 (typically of sequence SEQ ID NO: 57). In one embodiment, the origin of replication allowing replication in *C. acnes* is p545 (typically of sequence SEQ ID NO: 58). In one embodiment, the origin of replication allowing replication in *C. acnes* is pJD4 (typically of sequence SEQ ID NO: 59). In one embodiment, the origin of replication allowing replication in *C. acnes* is pIJ101 (typically of sequence SEQ ID NO: 60). In one embodiment, the origin of replication allowing replication in *C. acnes* is pSN22 (typically of sequence SEQ ID NO: 61). In one embodiment, the origin of replication allowing replication in *C. acnes* is pGP01 (typically of sequence SEQ ID NO: 62). In one embodiment, the origin of replication allowing replication in *C. acnes* is pIP501 (typically of sequence SEQ ID NO: 63). In one embodiment, the origin of replication allowing replication in *C. acnes* is pCU1 (typically of sequence SEQ ID NO: 64). In one embodiment, the origin of replication allowing replication in *C. acnes* is pBAV1K-T5 (typically of sequence SEQ ID NO: 65).

In one embodiment, the DNA vector comprises an origin of replication allowing replication in *C. acnes*. In one embodiment, the DNA vector comprises an origin of replication selected from the group consisting of: R6K (SEQ ID NO: 42); RK2 (SEQ ID NO: 43); pBBR1 (SEQ ID NO: 44); pRO1600 (SEQ ID NO: 45); RSF1010 (SEQ ID NO: 46); pAMβ1 (SEQ ID NO: 47); pLME106 (SEQ ID NO: 48); pTZC1 (SEQ ID NO: 49); pBC1 (SEQ ID NO: 50); pEP2 (SEQ ID NO: 51); pWVO1 (SEQ ID NO: 52); pAP1 (SEQ ID NO: 53); pWKS1 (SEQ ID NO: 54); pLME108 (SEQ ID NO: 55); pLS1 (SEQ ID NO: 56); pUB6060 (SEQ ID NO: 57); p545 (SEQ ID NO: 58); pJD4 (SEQ ID NO: 59); pIJ101 (SEQ ID NO: 60); pSN22 (SEQ ID NO: 61); pGP01 (SEQ ID NO: 62); pIP501 (SEQ ID NO: 63); pCU1 (SEQ ID NO: 64); and pBAV1K-T5 (SEQ ID NO: 65).

Preferably, the origin of replication is of a sequence at least 80, 83, 85, 87, 90, 93, 95, 97, 98, 99, or 100% identical to the sequence of any of the above origins of replication.

In various embodiments, the selection marker is selected from ermE, catA, hygB, ermX, tetW, erm(50) and other high GC antibiotic resistance genes. In one embodiment, the selection marker is not ermE. In one embodiment, the selection marker is catA. In one embodiment, the selection marker is hygB.

In one embodiment, the DNA vector further comprises a CRISPR-Cas system. Typically, the CRISPR-Cas system comprises a CRISPR array. Typically, the CRISPR-Cas system comprises a RNA guide (crRNA or sgRNA).

In one embodiment, the CRISPR-Cas system targets a *C. acnes* chromosome locus. Preferably, the targeted locus is not present in the *C. acnes* producer cell. Preferably, the CRISPR array from the CRISPR-Cas system is expressing one or several crRNA targeting the chromosome locus.

In one embodiment, the CRISPR-Cas system targets several *C. acnes* chromosome loci. Preferably, the targeted loci are not present in the *C. acnes* producer cell. Preferably, the CRISPR array from the CRISPR-Cas system is expressing one or several crRNA targeting the chromosome loci.

In one embodiment, the CRISPR-Cas system targets a *C. acnes* plasmid locus. Preferably, the targeted locus is not present in the *C. acnes* producer cell. Preferably, the CRISPR array from the CRISPR-Cas system is expressing one or several crRNA targeting the plasmid locus.

In one embodiment, the CRISPR-Cas system targets several *C. acnes* plasmid loci. Preferably, the targeted loci are not present in the *C. acnes* producer cell. Preferably, the CRISPR array from the CRISPR-Cas system is expressing one or several crRNA targeting the plasmid loci.

In one embodiment, the CRISPR-Cas system is not expressed in *C. acnes* producer cell. Preferably the CRISPR-Cas system is repressed in *C. acnes* producer cell.

In one embodiment, the CRISPR-Cas system targets a proinflammatory sequence related to a host disease.

In one embodiment, the CRISPR-Cas system targets a proinflammatory sequence related to acne vulgaris.

In one embodiment, the DNA vector comprises a template for homologous recombination and the CRISPR-Cas system is targeting the DNA vector itself.

In one embodiment, the DNA vector comprises a template for homologous recombination in *C. acnes* phages.

In one embodiment, the DNA vector comprises a template for homologous recombination in *C. acnes* chromosome.

In one embodiment, the DNA vector comprises a template for homologous recombination in *C. acnes* endogenous plasmids.

In one embodiment, the DNA vector comprises a template for homologous recombination and a CRISPR-Cas system targeting the DNA vector itself outside of the template region.

In one embodiment, the DNA vector comprises a template for homologous recombination and a CRISPR-Cas system targeting the DNA vector itself outside of the template region wherein the RNA guide (crRNA or sgRNA) from the CRISPR-Cas system is not perfectly matching the DNA target.

In one embodiment, the DNA vector comprises an integrase gene expression cassette and a site specific recombination site allowing for the integration of the DNA vector inside the chromosome.

In one embodiment, the DNA vector comprises a base editor gene expression cassette and one or multiple crRNAs or sgRNAs.

In one embodiment, the base editor is used to inactivate the expression of a gene by editing one or several nucleotides involved in transcription or translation of said gene. More specifically the base editor is targeting one or several nucleotides of a promoter, a RBS or a start codon.

In one embodiment, the base editor is used to introduce a premature stop codon.

In one embodiment, the base editor is used to introduce one or several rare codons.

In another embodiment, the base editor is used to modulate the expression of genes by editing one or several nucleotides involved in transcription or translation of said genes. More specifically the base editor is targeting one or several nucleotides of a promoter, a RBS or a start codon, leading to an increase or decrease in gene expression.

In another embodiment, the base editor is used to revert a mutation that leads to the inactivation, decrease or increase in activity of a gene or pathway.

In another embodiment, the base editor is used to revert a mutation that leads to an increase of pathogenicity.

In one embodiment, the base editor is used to modify the regulation of a gene by editing one or several nucleotides involved in its regulation such as nucleotides of operator sequence, transcription factor binding site, riboswitch, RNAse recognition site, protease cleavage site, methylation site or post translational modification site (phosphorylation, glycosylation, acetylation, pupylation . . . ).

In one embodiment, the DNA vector comprises a prime editor gene expression cassette and one or multiple pegRNAs.

In one embodiment, the prime editor is used to introduce one or several premature stop codon.

In one embodiment, the prime editor is used to introduce one or several rare codons.

In one embodiment, the prime editor is used to introduce or delete a nucleotide inducing a frameshift in the reading frame.

In another embodiment, the prime editor is used to modulate the expression of genes by replacing, deleting or inserting one or several nucleotides involved in transcription or translation of said genes. More specifically the prime editor is replacing, deleting or inserting one or several nucleotides in a promoter, a RBS or a start codon, leading to an increase or decrease in gene expression.

In another embodiment, the prime editor is used to revert a mutation that leads to the inactivation or decrease in activity of a gene or pathway.

In another embodiment, the prime editor is used to revert a mutation that leads to an increase of pathogenicity.

In one embodiment, the vector is a plasmid which comprises an *E. coli* replicon and an *E. coli* resistance marker allowing extraction of the plasmid from *C. acnes* and transformation and replication in *E. coli*.

In one embodiment, the vector is a plasmid which comprises an *E. coli* replicon and an *E. coli* resistance marker allowing extraction of the plasmid from *E. coli* and transformation and replication in *C. acnes*.

In one embodiment, the vector comprises 2 origins or replication, one allowing replication in *C. acnes* or *C. acnes* producer cell only, the second origin of replication allowing replication in another bacteria.

In one embodiment, the vector comprising the template DNA for homologous recombination allows expression of genes increasing recombination rate.

In one embodiment, the template for homologous recombination contains homology arms upstream and downstream of recombination points. These homology arms can be at least 50, 100, 500 or at least 1000 bp in size.

In one embodiment, the gene of interest comprised by the DNA vector can be a transgene that is exogenous to the *C. acnes*. Transgenes include but are not limited to:

a DNA encoding a fluorescent protein (e.g., UnaG) that leads to fluorescent *C. acnes* cells once a specific substrate is added;

a DNA encoding an enzymatic reporter (e.g., LacZ) that leads to the production of a chromogenic compound by *C. acnes* colonies;

a DNA encoding a human protein (e.g., an interleukin);

a DNA encoding an antigen (e.g. a tumor antigen, a viral antigen, a bacterial antigen, a fungal antigen, a self-antigen, an allergen or a graft-specific antigen);

a CRISPR-Cas system;

a prime-editing system; or a base-editor system.

In a particular embodiment, the gene of interest encoded by the DNA vector is a DNA encoding an antigen, more particularly a DNA encoding an antigen selected from the group consisting of tumor antigens, viral antigens, bacterial antigens, fungal antigens, self-antigens, allergens and graft-specific antigens, as defined below.

*C. acnes* Strains Comprising DNA Vectors, Engineered *C. acnes* Strains

The invention encompasses *C. acnes* comprising any of the DNA vectors of the invention. The invention further encompasses *C. acnes* produced by any of the methods of the invention. Thus, the invention encompasses *C. acnes* that have been modified following transduction of any of the DNA vectors of the invention by a phage-derived particle, whether retaining the DNA vector or subsequently having that DNA vector removed (i.e., cured) from *C. acnes*.

Thus, the invention encompasses *C. acnes* produced by a method comprising: producing a phage-derived particle from a *C. acnes* producer cell containing a DNA vector of the invention; contacting these phage-derived particles with *C. acnes* receiver cells, leading to transduction of the DNA vector into the *C. acnes* receiver cell and modification of the *C. acnes* receiver cell with a gene of interest carried by the vector (e.g., a CRISPR-Cas system) and/or an exogenous gene inserted into the *C. acnes* chromosome; selecting for the modification; and curing *C. acnes* of the vector.

The invention encompasses an engineered *C. acnes* that has been modified by a CRISPR-Cas system transduced by a phage-derived particle carrying a vector of the invention.

The invention encompasses an engineered *C. acnes* that has been modified by transduction of DNA vector and subsequent insertion of an exogenous gene into the *C. acnes* chromosome.

The invention encompasses an engineered *C. acnes* that has been modified by transduction of DNA vector and subsequent deletion or mutation of an endogenous gene into the *C. acnes* chromosome or *C. acnes* endogenous plasmid.

The invention encompasses *C. acnes* produced by transduction of a DNA vector of the invention.

The invention encompasses an engineered *C. acnes* that has been modified by delivery of a plasmid, in particular by conjugation. In a particular embodiment, said plasmid comprises a CRISPR-Cas system. In another particular embodiment, said plasmid comprises an exogenous gene. In another particular embodiment, said plasmid enables the insertion of an exogenous gene into the *C. acnes* chromosome. In another particular embodiment, said plasmid enables the deletion or mutation of an endogenous gene into the *C. acnes* chromosome or *C. acnes* endogenous plasmid. In a particular embodiment, said plasmid comprises an origin of replication allowing replication in *C. acnes*, as defined above and/or an origin of transfer as defined above.

*Cutibacterium acnes*, previously named *Propionibacterium acnes*, has been historically classified in three major phylotypes based on recA and tly sequencing: IA, IB, II and III. These phylotypes have been further subdivided using different multi-locus sequence typing (MLST) schemes into IA1, IA2, IB, II and III. More recently, Fitz-Gibbon et al (Fitz-Gibbon, S. et al. (2013) *J Invest Dermatol* 133, 2152-2160) have introduced a new classification based on sequence diversity of 16S rRNA gene (ribotyping) as well as a refined classification of phylotypes: IA-1, IA-2, IB-1, IB-2, IB-3, IC, II, III. The present disclosure refers to this classification but concordance between this classification and others is well-known from the skilled person and can be obtained from the following review (Dréno, B. et al. (2018). *Journal of the European Academy of Dermatology and Venereology* 32, 5-14). In a particular embodiment, *C. acnes* may thus be from a phylotype selected from the group consisting of phylotypes IA-1, IA-2, IB-1, IB-2, IB-3, IC, II and III.

By comparing whole genome sequences of strains isolated from acne and healthy volunteers, Fitz-Gibbon and colleagues could identify acne-associated strains (IA-2 and IB-1) and healthy-associated strains (II) in accordance with previous studies. More interestingly, they found specific loci (locus1, locus 2 and locus 3) present in acne associated strains and absent of neutral and healthy strains. Similar loci were found in a subsequent metagenomic analysis confirming the association between the presence of these loci and acne vulgaris (Barnard, E. et al. (2016) *Scientific Reports* 6, srep39491).

The ability of specific strain phylotypes to induce immune response has been recently investigated (Yu et al. (2016) Journal of Investigative Dermatology 136:2221-2228). Yu et al. demonstrated that the different *C. acnes* phylotypes induced different cytokine profiles when incubated with peripheral blood mononuclear cells (PBMC). More particularly, they showed that acne-associated phylotypes IA-2 p+ (i.e. with a large plasmid associated with acne), IB-1, and IC induced high levels of inflammatory IFN-γ and IL-17 but low levels of IL-10, suggesting that these specific phylotypes could induce both Th1 and Th17 responses. They also showed that phylotypes IB-3, II and III induced lower levels of IL-17 (and of IFN-γ for phylotype III) but higher levels of IL-10, suggesting induction of Treg responses. They further showed that phylotypes IA-1, IA-2 p– (i.e. without the large plasmid associated with acne) and IB-2 induced lower levels of IFN-γ and IL-10 and higher levels of IL-17, suggesting induction of mainly Th17 responses.

Therefore, depending on the particular immune response that is desired when using the engineered *C. acnes* of the invention for a particular indication, the use of a given *C. acnes* phylotype or strain may be advantageous. Accordingly, in a particular embodiment, *C. acnes* is from a phylotype selected from the group consisting of phylotypes IA-2 p+, IB-1 and IC. In another embodiment, *C. acnes* is from a phylotype selected from the group consisting of phylotypes IA-1, IA-2 p– and IB-2. In still another embodiment, *C. acnes* is from a phylotype selected from the group consisting of phylotypes IB-3, II and III.

Furthermore, a previous study showed that it was possible, in *S. epidermidis*, to induce different T cell responses with different strains within the same species by engineering said strains (Chen et al. (2019) "Decoding commensal-host communication through genetic engineering of *Staphylococcus epidermidis*" bioRxiv doi. org/10.1101/664656).

Therefore, in a particular embodiment, the *C. acnes* is a strain inducing, or engineered to induce, a given T cell response. In a particular embodiment, more particularly when the *C. acnes* cell is intended to be used in the prevention and/or treatment of cancer, said *C. acnes* is a strain inducing, or engineered to induce, increased levels of IFN-γ and/or IL-17a. In a particular embodiment, more particularly when the *C. acnes* cell is intended to be used in the prevention and/or treatment of an infection, said *C. acnes* is a strain inducing, or engineered to induce, increased levels of IFN-γ and/or IL-17. In a particular embodiment, more particularly when the *C. acnes* cell is intended to be used in the prevention and/or treatment of an autoimmune disease, said *C. acnes* is a strain inducing, or engineered to induce, increased levels of IL-10. In a particular embodiment, more particularly when the *C. acnes* cell is intended to be used in the prevention and/or treatment of an allergy, such as asthma, said *C. acnes* is a strain inducing, or engineered to induce, increased levels of IFN-g and/or IL-10. In a particular embodiment, more particularly when the *C. acnes* cell is intended to be used in the prevention and/or treatment of a graft rejection, said *C. acnes* is a strain inducing, or engineered to induce, increased levels of IL-10.

*C. acnes* comprising a recombinant self-replicative DNA vector of the invention (or comprising a plasmid, in particular a conjugative plasmid as defined above) can be generated for the expression of molecules of interest and modulation of *C. acnes*-host interaction. The molecule of interest can be carried on a self-replicative DNA vector in the *C. acnes* (or on a plasmid, in particular a conjugative plasmid) or can be inserted into the chromosome of the *C. acnes* through the action of the self-replicative DNA vector (or of the plasmid, in particular the conjugative plasmid, as defined above).

In one embodiment, the DNA vector is used for *C. acnes* chromosome engineering.

In one embodiment, the DNA vector is used for *C. acnes* plasmid engineering.

In one embodiment, the DNA vector is used for *C. acnes* phage engineering.

In one embodiment, the DNA vector (or the plasmid, in particular the conjugative plasmid, as defined above) is used for the expression of molecules of interest and modulation of *C. acnes*-host interaction. In one embodiment, the DNA vector (or the plasmid, in particular the conjugative plasmid, as defined above) is used for the expression of transgenes in *C. acnes*. A transgene can be cloned into the recombinant autonomously-replicating DNA vector (or in the plasmid, in particular the conjugative plasmid) under the control of a given promoter (constitutive or inducible) and followed by a given terminator. The transfer of this vector into *C. acnes* allows the expression of the transgene. The transgene can be, for example, a CRISPR-Cas system or can encode a human protein, such as an interleukin. In one embodiment the DNA vector (or the plasmid, in particular the conjugative plasmid) encodes several transgenes under the control of a single promoter or under the control of different promoters. The promoters can be endogenous or exogenous, inducible or constitutive.

In one embodiment, the DNA vector (or the plasmid, in particular the conjugative plasmid) is used for the modification of *C. acnes* genome. In one embodiment, the transfer of the vector (or of the plasmid, in particular the conjugative plasmid) into *C. acnes* allows the expression of a CRISPR/Cas system that cleaves the *C. acnes* genome (plasmid or chromosome) at a specific site, leading to modification of the *C. acnes* genome. In one embodiment, the vector (or the plasmid, in particular the conjugative plasmid) further comprises a gene of interest and homology with the site of cleavage to facilitate integration of the gene of interest into the *C. acnes* genome.

Delivery of DNA Vectors into *C. acnes* Strains

In one embodiment, delivery of any DNA vector of the invention into *C. acnes* producer cell is performed by contacting *C. acnes* with any DNA vector of the invention.

In one embodiment, delivery of any DNA vector of the invention into *C. acnes* producer cell is performed by transfection (e.g., electroporation) into *C. acnes* cells, where it stably replicates. In one embodiment the DNA vector transfected is purified from dam(–) *E. coli* cells such as ET12567 and electroporated into *C. acnes* cells made competent at 24° C.

In one embodiment, delivery of any DNA vector of the invention into *C. acnes* producer cell is performed by transfection (e.g., electroporation) into *C. acnes* protoplasts. In one embodiment *C. acnes* protoplasts are generated using Mutanolysin treatment or Lysozyme treatment, Mutanolysin and Lysozyme treatment, or Mutanolysin and Lysozyme and bead-beating treatment followed by resuspension into hypotonique media.

In one embodiment, delivery of any DNA vector of the invention into a *C. acnes* producer cell is performed by mixing *C. acnes* protoplasts with the DNA vector. In one embodiment glass beads are added with the DNA vector and bead beating is performed to introduce the DNA into *C. acnes* protoplasts.

In one embodiment, delivery of DNA vectors of the invention into *C. acnes* is by transduction. In one embodiment, the DNA vector comprises one packaging signal of a *C. acnes* phage selected from the group consisting of the phages PAC7 (typically of sequence SEQ ID NO: 68); PAC1 (typically of sequence SEQ ID NO: 69); PAC9 (typically of sequence SEQ ID NO: 70); PAC2 (typically of sequence SEQ ID NO: 71); PAC10 (typically of sequence SEQ ID NO: 72); PAC22 (typically of sequence SEQ ID NO: 73); PAC13 (typically of sequence SEQ ID NO: 74) and PAC263 (typically of sequence SEQ ID NO: 75); and is packaged into proteins expressed from the genome of a *C. acnes* phage selected from the group consisting of the phages PAC7 (typically of sequence SEQ ID NO: 68); PAC1 (typically of sequence SEQ ID NO: 69); PAC9 (typically of sequence SEQ ID NO: 70); PAC2 (typically of sequence SEQ ID NO: 71); PAC10 (typically of sequence SEQ ID NO: 72); PAC22 (typically of sequence SEQ ID NO: 73); PAC13 (typically of sequence SEQ ID NO: 74) and PAC263 (typically of sequence SEQ ID NO: 75), allowing transduction of the DNA vector into *C. acnes*.

In one embodiment, delivery of any DNA vector of the invention into a *C. acnes* producer cell is by conjugation. In one embodiment, the DNA vector comprises an origin of transfer. In one embodiment, a donor bacterium, such as *E. coli*, is used to efficiently transfer the DNA vector into *C. acnes* recipient cells, where it stably replicates. In one embodiment, the DNA vector comprises an origin of transfer selected from the group consisting of: oriT_pMRC01 (typically of sequence SEQ ID NO: 1); oriT_RSF1010 (typically of sequence SEQ ID NO: 2); oriT_pRS01 (typically of sequence SEQ ID NO: 3); oriT_pMV158 (typically of sequence SEQ ID NO: 4); oriT_pTF1 (typically of sequence SEQ ID NO: 5); oriT_pSC101 (typically of sequence SEQ ID NO: 6); oriT_pBTK445 (typically of sequence SEQ ID NO: 7); oriT_pBBR1 (typically of sequence SEQ ID NO: 8); oriT_R721 (typically of sequence SEQ ID NO: 9); oriT_pRmeGR4a (typically of sequence SEQ ID NO: 10); oriT_ColE1 (typically of sequence SEQ ID NO: 11); oriT_pTiC58 (typically of sequence SEQ ID NO: 12); oriT_pMdT1 (typically of sequence SEQ ID NO: 13); oriT_R1 (typically of sequence SEQ ID NO: 14); oriT_Tn5520 (typically of sequence SEQ ID NO: 15); oriT_QKH54 (typically of sequence SEQ ID NO: 16); oriT_R64 (typically of sequence SEQ ID NO: 17); oriT_R751 (typically of sequence SEQ ID NO: 18); oriT_RP4 (typically of sequence SEQ ID NO: 19); oriT_pKL1 (typically of sequence SEQ ID NO: 20); oriT_RK2 (typically of sequence SEQ ID NO: 21); oriT_R1162 (typically of sequence SEQ ID NO: 22); oriT_Tn4555 (typically of sequence SEQ ID NO: 23); oriT_pHT (typically of sequence SEQ ID NO: 24); oriT_Tn4399 (typically of sequence SEQ ID NO: 25); oriT_Tn916 (typically of sequence SEQ ID NO: 26); oriT_pST12 (typically of sequence SEQ ID NO: 27); oriT_pCU1 (typically of sequence SEQ ID NO: 28); oriT_pSU233 (typically of sequence SEQ ID NO: 29); oriT_F (typically of sequence SEQ ID NO: 30); oriT_pMAB01 (typically of sequence SEQ ID NO: 31); oriT_R388 (typically of sequence SEQ ID NO: 32); oriT_pS7a (typically of sequence SEQ ID NO: 33); oriT_pS7b (typically of sequence SEQ ID NO: 34); oriT_R702 (typically of sequence SEQ ID NO: 35); oriT_pMUR274 (typically of sequence SEQ ID NO: 36); oriT_R100 (typically of sequence SEQ ID NO: 37); oriT_pVCR94deltaX (typically of sequence SEQ ID NO: 38); oriT_R46 (typically of sequence SEQ ID NO: 39); oriT_pGO1 (typically of sequence SEQ ID NO: 40) and oriT_pIP501 (typically of sequence SEQ ID NO: 41). In one embodiment, a donor bacterium, such as *E. coli*, carries a conjugative plasmid, a conjugative transposon or an integrative and conjugative element (ICE) selected from the group consisting of: pMRC01; RSF1010; pRS01; pMV158; pTF1; pSC101; pBTK445; pBBR1; R721; pRmeGR4a; ColE1; pTiC58; pMdT1; R1; Tn5520; QKH54; R64; R751; RP4; pKL1; RK2; R1162; Tn4555; pHT; Tn4399; Tn916; pST12; pCU1; pSU233; F; pMAB01; R388; pS7a; pS7b; R702; pMUR274; R100; pVCR94deltaX; R46; pGO1 and pIP501, and is used to efficiently transfer the DNA vector into *C. acnes* recipient cells. In one embodiment the DNA vector contains an origin of transfer and the associated relaxase of a conjugative plasmid, conjugative transposon or integrative and conjugative element (ICE) selected from the group consisting of: pMRC01; RSF1010; pRS01; pMV158; pTF1; pSC101; pBTK445; pBBR1; R721; pRmeGR4a; ColE1; pTiC58; pMdT1; R1; Tn5520; QKH54; R64; R751; RP4; pKL1; RK2; R1162; Tn4555; pHT; Tn4399; Tn916; pST12; pCU1; pSU233; F; pMAB01; R388; pS7a; pS7b; R702; pMUR274; R100; pVCR94deltaX; R46; pGO1 and pIP501.

In a preferred embodiment the DNA vector comprises the origin of transfer oriT_pMRC01 (typically of sequence SEQ ID NO: 1). In a preferred embodiment, the DNA vector comprises the origin of transfer oriT_RSF1010 (typically of sequence SEQ ID NO: 2). In a preferred embodiment, the DNA vector comprises the origin of transfer oriT_pRS01 (typically of sequence SEQ ID NO: 3). In a preferred embodiment, the DNA vector comprises the origin of transfer oriT_pMV158 (typically of sequence SEQ ID NO: 4). In a preferred embodiment, the DNA vector comprises the origin of transfer oriT_pTF1 (typically of sequence SEQ ID NO: 5). In a preferred embodiment, the DNA vector comprises the origin of transfer oriT_pSC101 (typically of sequence SEQ ID NO: 6). In a preferred embodiment, the DNA vector comprises the origin of transfer oriT_pBTK445 (typically of sequence SEQ ID NO: 7). In a preferred embodiment, the DNA vector comprises the origin of transfer oriT_pBBR1 (typically of sequence SEQ ID NO: 8). In a preferred embodiment, the DNA vector comprises the origin of transfer oriT_R721 (typically of sequence SEQ ID NO: 9). In a preferred embodiment, the DNA vector comprises the origin of transfer oriT_pRmeGR4a (typically of sequence SEQ ID NO: 10). In a preferred embodiment, the DNA vector comprises the origin of transfer oriT_ColE1 (typically of sequence SEQ ID NO: 11). In a preferred embodiment, the DNA vector comprises the origin of transfer oriT_pTiC58 (typically of sequence SEQ ID NO: 12). In a preferred embodiment, the DNA vector comprises the origin of transfer oriT_pMdT1 (typically of sequence SEQ ID NO: 13). In a preferred embodiment, the DNA vector comprises the origin of transfer oriT_R1 (typically of sequence SEQ ID NO: 14). In a preferred embodiment, the DNA vector comprises the origin of transfer oriT_Tn5520 (typically of sequence SEQ ID NO: 15). In a preferred embodiment, the DNA vector comprises the origin of transfer oriT_QKH54 (typically of sequence SEQ ID NO: 16). In a preferred embodiment, the DNA vector comprises the origin of transfer oriT_R64 (typically of sequence SEQ ID NO: 17). In a preferred embodiment, the DNA vector comprises the origin of transfer oriT_R751 (typically of sequence SEQ ID NO: 18). In a preferred embodiment, the DNA vector comprises the origin of transfer oriT_RP4 (typically of sequence SEQ ID NO: 19). In a preferred embodiment, the DNA vector comprises the origin of transfer oriT_pKL1 (typically of sequence SEQ ID NO: 20). In a preferred embodiment, the DNA vector comprises the origin of transfer oriT_RK2 (typically of sequence SEQ ID NO: 21). In a preferred embodiment, the DNA vector comprises the origin of transfer oriT_R1162 (typically of sequence SEQ ID NO: 22). In a preferred embodiment, the DNA vector comprises the origin of transfer oriT_Tn4555 (typically of sequence SEQ ID NO: 23). In a preferred embodiment, the DNA vector comprises the origin of transfer oriT_pHT (typically of sequence SEQ ID NO: 24). In a preferred embodiment, the DNA vector comprises the origin of transfer oriT_Tn4399 (typically of sequence SEQ ID NO: 25). In a preferred embodiment, the DNA vector comprises the origin of transfer oriT_Tn916 (typically of sequence SEQ ID NO: 26). In a preferred embodiment, the DNA vector comprises the origin of transfer oriT_pST12 (typically of sequence SEQ ID NO: 27). In a preferred embodiment, the DNA vector comprises the origin of transfer oriT_pCU1 (typically of sequence SEQ ID NO: 28). In a preferred embodiment, the DNA vector comprises the origin of transfer oriT_pSU233 (typically of sequence SEQ ID NO: 29). In a preferred embodiment, the DNA vector comprises the origin of transfer oriT_F (typically of sequence SEQ ID NO: 30). In a preferred embodiment, the DNA vector comprises the origin of transfer oriT_pMAB01 (typically of sequence SEQ ID NO: 31). In a preferred embodiment, the DNA vector comprises the origin of transfer oriT_R388 (typically of sequence SEQ ID NO: 32). In a preferred embodiment, the DNA vector comprises the origin of transfer oriT_pS7a (typically of sequence SEQ ID NO: 33). In a preferred embodiment, the DNA vector comprises the origin of transfer oriT_pS7b (typically of sequence SEQ ID NO: 34). In a preferred embodiment, the DNA vector comprises the origin of transfer oriT_R702 (typically of sequence SEQ ID NO: 35). In a preferred embodiment, the DNA vector comprises the origin of transfer oriT_pMUR274 (typically of sequence SEQ ID NO: 36). In a preferred embodiment, the DNA vector comprises the origin of transfer oriT_R100 (typically of sequence SEQ ID NO: 37). In a preferred embodiment, the DNA vector comprises the origin of transfer oriT_pVCR94deltaX (typically of sequence SEQ ID NO: 38). In a preferred embodiment, the DNA vector comprises the origin of transfer oriT_R46 (typically of sequence SEQ ID NO: 39). In a preferred embodiment, the DNA vector comprises the origin of transfer oriT_pGO1 (typically of sequence SEQ ID NO: 40). In a preferred embodiment, the DNA vector comprises the origin of transfer oriT_pIP501 (typically of sequence SEQ ID NO: 41).

In one embodiment, a donor bacterium is selected from selected from the group consisting of: *Escherichia coli, Pseudomonas aeruginosa, Lactococcus lactis, Lactobacillus casei, Lactobacillus fermentum, Lactobacillus rhamnosus, Propionibacterium freudenreichii, Lactobacillus brevis, Staphylococcus epidermidis, Staphylococcus aureus, Cutibacterium* granulosum, *Cutibacterium humerusii, Enterococcus faecalis* and *Bacillus subtilis*, carrying a conjugative plasmid, a conjugative transposon or an integrative and conjugative element (ICE).

In one embodiment the conjugation is performed growing at high density the donor bacteria, such as *E. coli*, harboring the mobilizable DNA vector and the conjugative machinery (ICE, plasmid, conjugative transposon). Donor cells are pelleted by centrifugation, and washed to remove antibiotics added during growth to maintain mobilizable and conjugative DNA vectors. Donor cells are then mixed in presence of *C. acnes* cells. The mixture donor cells-*C. acnes* is spotted onto *Brucella agar* plates and allowed to mate at 37° C. under anaerobic conditions. After mating, cells are harvested from the mating plate, re-suspended in BHI broth and plated onto *Brucella agar* plates that are supplemented with:

a compound killing donor cells but not *C. acnes*, or
an antibiotic selecting the mobilizable DNA vector.

After several days of incubation, *C. acnes* colonies are streaked on *Brucella agar* plates supplemented with the appropriate selection and the presence of the conjugated plasmid is confirmed via specific PCRs. The identity of *C. acnes* as well as the absence of donor cells is also confirmed by PCR analyses.

In one embodiment the conjugation is performed according to the following protocol: 2 mL of overnight cultures of *E. coli* donor cells harboring a mobilizable DNA vector and a conjugative machinery (ICE, plasmid, conjugative transposon) is grown in LB broth and pelleted at 6,000×g for 1 min. Supernatants are discarded and pellets are washed with 500 µL of pre-sterilized LB medium, centrifuged again using the same conditions. Pellet is then re-suspended in 200 µL of exponentially growing (OD600=0.5) *C. acnes* receptor BHI culture concentrated 10×. The mixture *E. coli*-*C. acnes* is spotted (50 µL/spot) onto *Brucella agar* plates and allowed to mate at 37° C. under anaerobic conditions for 24 hours. After that time, cells are harvested from the mating plate, re-suspended in 300 µL of BHI broth and plated onto *Brucella agar* plates that had been supplemented with 50 µg/mL polymyxin B and 5 µg/mL erythromycin or 3.5 µg/mL chloramphenicol depending on the selection marker present in the mobilizable DNA vector. After 7 days, *C. acnes* cells that grow in the presence of selection are streaked on *Brucella agar* plates supplemented with the appropriate selection and the presence of the conjugated plasmid confirmed via specific PCRs. The identity of *C. acnes* as well as the absence of *E. coli* donor strain are also confirmed by PCR analyses.

Methods to Modify Endogenous *C. acnes* Plasmids

Naturally occurring *C. acnes* plasmids have been described[21,22] and some of them are able to be transferred from one *C. acnes* to another by conjugation[20]. Being able to modify such plasmids is of interest to study their effect notably their pro-inflammatory role in acne vulgaris or to use them for further genetic manipulation of *C. acnes*. The inventors have developed methods to modify *C. acnes* plasmids.

In one embodiment, the method comprises, in a first step, introducing into *C. acnes* a replicative vector comprising:
a selection marker for *C. acnes* as defined above,
an origin of replication for *C. acnes* as defined above,
a phage packaging signal as defined above, and
a template for homologous recombination with the *C. acnes* endogenous plasmid.

In one embodiment, the method comprises, in a first step, introducing into *C. acnes* a replicative vector comprising:
a selection marker for *C. acnes* as defined above,
an origin of replication for *C. acnes* as defined above,
a phage packaging signal as defined above,
a CRISPR-Cas system, and
a template for homologous recombination in the *C. acnes* endogenous plasmid.

Introduction can be achieved with electroporation, electroporation of protoplast, conjugation, chemical transformation, or transduction. *C. acnes* recombinants are then preferably grown in presence of an antibiotic.

Recombinants are then typically infected with *C. acnes* phage to produce phage-derived particles carrying the DNA vectors.

Phage-derived particles are then typically mixed with *C. acnes* receiver cells containing an endogenous plasmid such as pIMPLE-HL096PA1. *C. acnes* transductants are then typically selected on the appropriate antibiotic.

In a second step, *C. acnes* transductants are grown in the presence of an antibiotic A to a high density to increase chances of a homologous recombination event occurring. Homologous recombination typically leads to introduction of a selection marker, giving resistance to an antibiotic B. In the dense culture, *C. acnes* strains carrying wild-type endogenous plasmid and recombinant endogenous plasmid carrying a resistance marker are typically present. The high-density culture is then preferably washed and typically put in the presence of a receiver *C. acnes* strain that is resistant to a third antibiotic C. Selection of transconjugant with antibiotics C and B typically leads to selection of receiver cells with the recombinant plasmid.

Other modifications enabled by the methods of the invention include the insertion of an *E. coli* replicon and an *E. coli* resistant marker on the plasmid allowing extraction of the plasmid from *C. acnes* and transformation and replication in *E. coli*.

Additionally, the plasmid carrying the template DNA for homologous recombination preferably allows the expression of genes that increase recombination rate.

The template for homologous recombination typically contains homology arms upstream and downstream recombination points. These homology arms are preferably 50, 100, 500, 1000 bp long or more.

*C. acnes* Genome Engineering and Engineered *C. acnes* Strains

The invention encompasses methods of *C. acnes* genome engineering and engineered *C. acnes* strains that have been engineered by any of the methods of the invention. An "engineered strain" is a strain that has been obtained by any of the methods of the invention to contain an alteration either found or not found in nature. For example, the engineered *C. acnes* strain can comprise any of the vectors or DNAs of the invention.

The invention encompasses methods for delivering DNA of interest into *C. acnes* strains by conjugation. The invention also encompasses methods for delivering DNA of interest into *C. acnes* strains via phage-derived particles.

The invention encompasses methods to engineer the *C. acnes* chromosome with replicative and non-replicative vector methods.

In one embodiment, delivery of the DNA vector into *C. acnes* is by transduction. In one embodiment, the DNA vector comprises a phage packaging signal (cos) originating from *C. acnes* phages. In one embodiment, phage-derived particles containing the DNA vector can be generated and can allow the DNA vector to be transduced into *C. acnes* cells.

In one embodiment, the invention encompasses replicative and non-replicative vector methods using a vector comprising at least a recombination template with one or two homology arms.

To engineer the *C. acnes* genome, the inventors have developed methods using replicative and non-replicative vectors.

Non-Replicative Vector Methods

In one embodiment, non replicative vector methods use a vector comprising at least:
- a phage packaging signal, as defined above;
- a selection marker for *C. acnes*, as defined above;
- a recombination template with one or two homology arms;
- an origin of replication allowing replication only in *Cutibacterium acnes* producer cell; and
- optionally a counter selection marker such as SacB.

Non-replicative vector methods use vectors that carry a *C. acnes* replicon that replicate only in a *C. acnes* producer cell but not in other *C. acnes* cells. Thus, such vectors are able to replicate in *C. acnes* producer cell, get packaged into phage capsid upon contacting with phage genome leading to a phage-derived particle, and get transduced by the phage-derived particle into *C. acnes* receiver cell where they do not replicate.

Figure 4A:
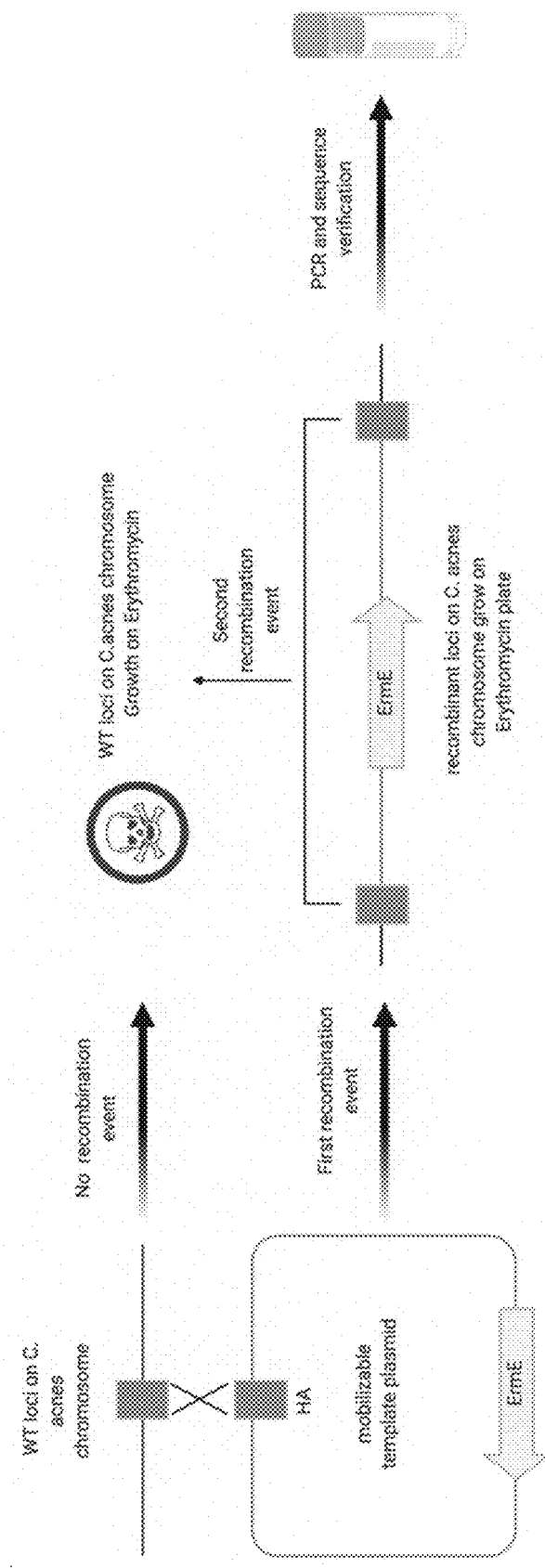
FIGS. 4A and 4B depict a method for *C. acnes* genome engineering using non-replicative vector carrying recombination template.
Figure 4B:
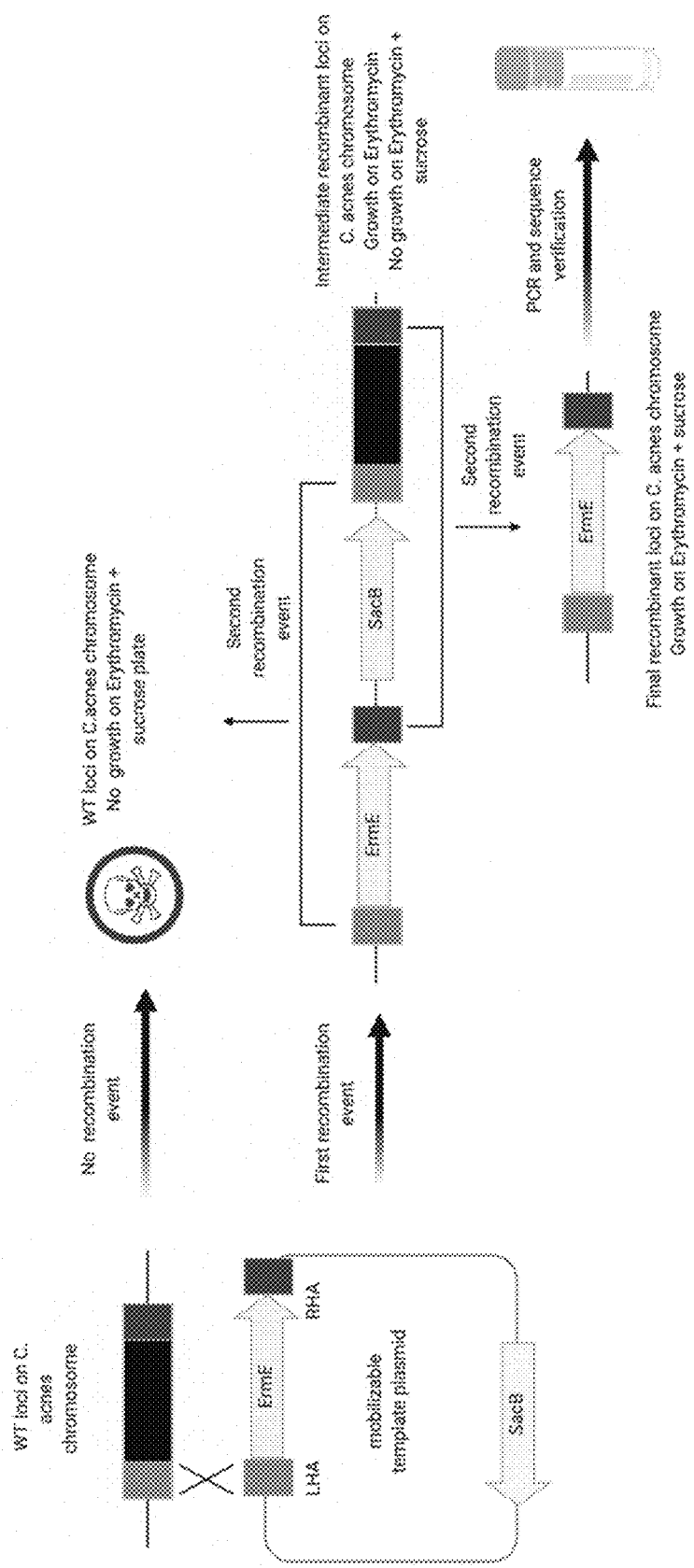

The methods comprise introducing into a *C. acnes* producer cell a plasmid containing a template for homologous DNA recombination inside the genome. The template can contain one (FIG. 4A) or two homologous regions (FIG. 4B) leading to homologous recombination.

In one embodiment, the method comprises a *C. acnes* producer cell, carrying a plasmid containing a template for homologous DNA recombination inside the chromosome where the homologous DNA is not present in the *C. acnes* producer cell, a phage packaging signal (cos) originating from *C. acnes* phages, a selection marker for *C. acnes*, as defined above, and an origin of replication for *C. acnes* producer cell but not replicating in *C. acnes* receiver cell. The template can contain one (FIG. 4A) or two homologous regions (FIG. 4B), leading to homologous recombination. The producer cell is typically infected by a *C. acnes* phage leading to production of phage-derived particles containing the DNA vector with homology arm(s). Phage-derived particles are preferably mixed with *C. acnes* receiver cells (e.g., ATCC 11828). Transductants can be selected on antibiotic plates, streaked on antibiotic plates and plasmid integration screened by PCR. Because the plasmid is not replicative in *C. acnes*, only recombinant cells that stably maintain the antibiotic marker are able to grow on antibiotic plates.

In the case where there are two homology arms present on the template DNA, a first recombination event (also called cross-over) typically leads to the full integration of the plasmid. This is typically followed by a second recombination event that removes the plasmid backbone and leads to either the modification of the chromosome or to the reconstitution of the wild-type locus.

In one embodiment, the *C. acnes* producer cell carries a vector containing a left homology arm (LHA) and a right homology arm (RHA) flanking a *C. acnes* selection marker, for example, ermE (pEB_HR02). The two homology arms typically do not match the *C. acnes* producer cell chromosome. In one embodiment, the vector also contains a phage packaging signal (cos) originating from *C. acnes* phages, a selection marker for *C. acnes* and an origin of replication for *C. acnes* producer cell but not replicating in *C. acnes* receiver cell. In one embodiment the DNA vector also contains a *C. acnes* counter-selection marker, such as sacB, on the plasmid backbone allowing selection of the second recombination event. The *C. acnes* producer cell carrying pEB_HR02 is typically infected by a phage leading to production of phage-derived particles comprising pEB_HR02. The phage-derived particles are typically put in presence of *C. acnes* receiver cells (e.g., ATCC 11828). Transductants are typically selected on plates supplemented with the antibiotic (e.g., erythromycin), streaked onto plates supplemented with the antibiotic (e.g., erythromycin) and integration of the plasmid confirmed by PCR. Because the plasmid is not replicative in *C. acnes* receiver cell, *C. acnes* clones able to grow in the presence of the antibiotic (e.g., erythromycin), have undergone a single homologous recombination event, which has led to the integration of the full plasmid. To select for final recombinant loci, cells are typically exposed to the counter-selection (e.g., sucrose) and the antibiotic (e.g., erythromycin), which leads to cell death due to sacB activity (the full plasmid remains integrated in the chromosome). Survivors are typically screened by PCR for successful final recombinant loci presence. In one embodiment the DNA vector contains only one homology arm (pEB_HR01). In one embodiment, both pEB_HR01 and pEB_HR02 phage-derived particles are applied on the skin and no antibiotic selection is applied.

In one embodiment, the *C. acnes* producer cell carries a plasmid (vector) containing a left homology arm (LHA) and a right homology arm (RHA) flanking *C. acnes* selection marker ErmE (pEB_HR02). The vector also preferably contains an *E. coli* origin of replication, an *E. coli* selection marker, an oriT and relaxase from a conjugative plasmid and a *C. acnes* counter-selection marker, such as sacB. pEB_HR02 can be transformed into an *E. coli* donor strain (e.g. Ec0s2862). Transformants are typically selected, grown and mixed with *C. acnes* receiver cells (e.g., ATCC 11828). Transconjugants are typically selected on plates supplemented with the antibiotic (e.g., erythromycin), streaked onto plates supplemented with the antibiotic (e.g., erythromycin) and integration of the plasmid confirmed by PCR. Because the plasmid is not replicative in *C. acnes* receiver cell, *C. acnes* clones able to grow in the presence of the antibiotic (e.g., erythromycin), have undergone a single homologous recombination event, which has led to the integration of the full plasmid. To select for final recombinant loci, cells are typically exposed to the counter-selection (e.g., sucrose) and the antibiotic (e.g., erythromycin), which leads to cell death due to sacB activity (the full plasmid remains integrated in the chromosome). Survivors are typically screened by PCR for successful final recombinant loci presence Replicative CRISPR-Cas System Selection Vector Methods The invention encompasses replicative vectors comprising an origin of replication for *C. acnes*.

In one embodiment, a replicative CRISPR-Cas selection vector method uses vector comprising at least:
- a phage packaging signal (cos) originating from *C. acnes* phages, as defined above;

a selection marker for *C. acnes*, as defined above;
an origin of replication for *C. acnes*;
a recombination template with two homology arms; and
a CRISPR-Cas system for expression in *C. acnes*.

In one embodiment, a replicative CRISPR-Cas selection vector method uses a vector comprising at least:
a selection marker for *E. coli*, as defined above;
an origin of replication for *E. coli*;
a selection marker for *C. acnes*, as defined above;
a recombination template with two homology arms;
an origin of replication for *C. acnes*; and
a CRISPR-Cas system that is expressed in *C. acnes*.

Thus, such vectors are able to replicate in *E. coli* and are able to replicate in *C. acnes*. They also carry a CRISPR-Cas system able to induce double stranded breaks at the wild-type loci where recombination is wanted, leading to death of *C. acnes* receiver cell.

Figure 5:
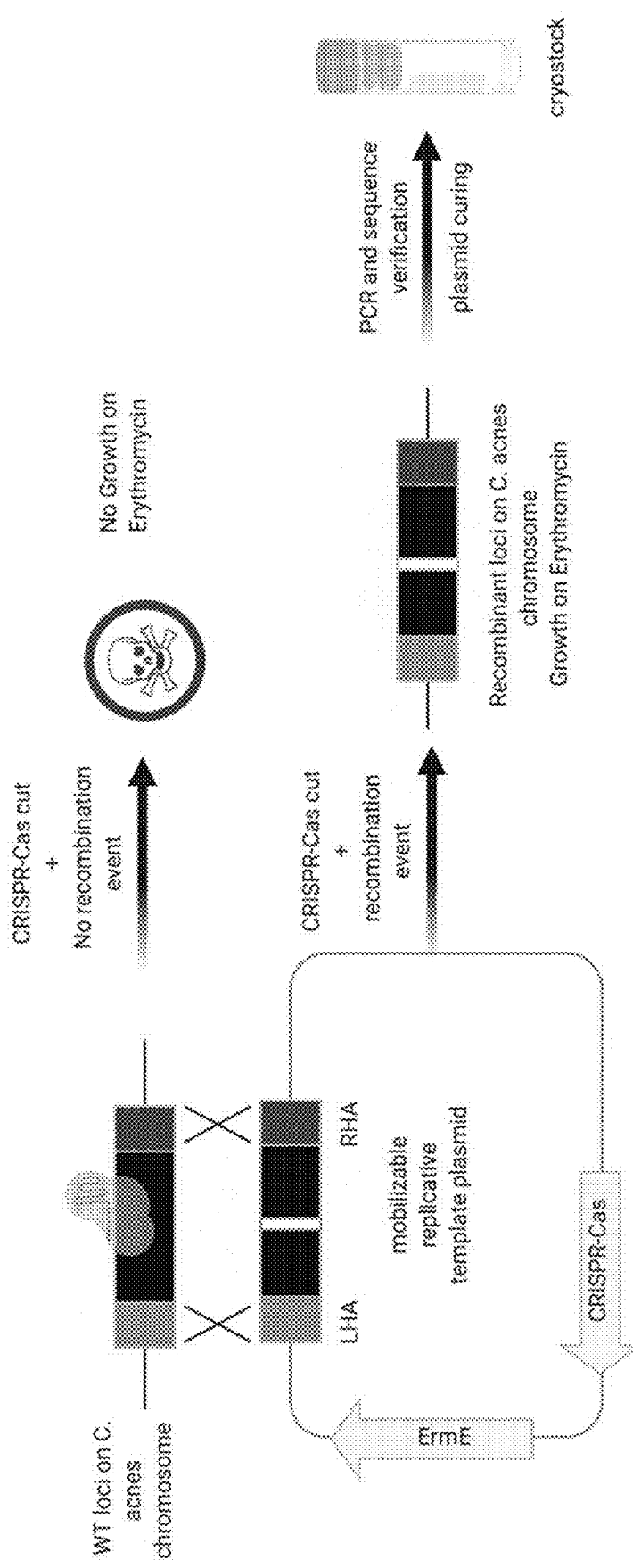
FIG. 5 depicts a method for *C. acnes* genome engineering using a replicative CRISPR-Cas system selection vector carrying a recombination template. A replicative CRISPR-Cas system selection vector containing a template for homologous DNA recombination with the chromosome is conjugated into *C. acnes*. The template contains two homology arms (LHA and RHA) leading to homologous recombination in *C. acnes* chromosome and removal of the target sequence of the CRISPR-Cas system. Thus, only recombinants *C. acnes* are able to grow in the presence of erythromycin when selected for the presence of the vector expressing CRISPR-Cas system.

In one embodiment, the method comprises the use of a *C. acnes* producer cell, for example strain ATCC 6919, carrying a replicative CRISPR-Cas system selection vector containing a template for homologous DNA recombination inside the chromosome and a phage packaging signal (cos) originating from *C. acnes* phages. In one embodiment, the template contains two homologous regions (FIG. 5), leading to homologous recombination. The producer cell preferably does not contain the wild-type loci targeted by the CRISPR-Cas system. The *C. acnes* producer cell is typically infected by a *C. acnes* phage leading to production of phage-derived particles carrying the DNA vector. Phage-derived particles are typically put in contact with *C. acnes* receiver cell. After transduction into *C. acnes* receiver cell, cells that have recombined with the DNA template vector are not targeted by the CRISPR-Cas system because, for example, they do not have the associated PAM sequence anymore. Plating on antibiotic-containing media, e.g. erythromycin plates, typically ensures that the cells that survive have been transduced and still carry the DNA vector (e.g. plasmid) expressing the CRISPR-Cas system. Single colonies are typically streaked on antibiotic-containing media, e.g. erythromycin plates, and recombinant loci are typically confirmed by PCR and sequencing.

In one embodiment, a step of plasmid curing is performed to eliminate the plasmid.

In one embodiment, the *C. acnes* producer cell contains the DNA target of the CRISPR-Cas system, but the CRISPR-Cas system is not expressed in the *C. acnes* producer cell but is expressed in *C. acnes* receiver cell. More preferably the CRISPR-Cas system is repressed in the *C. acnes* producer cell but not in *C. acnes* receiver cell.

Such methods can be used for scarless editing such as substitution, deletion or insertion because there is no need to introduce a selection marker to select for recombinants, the selection being done by CRISPR-Cas killing.

Self-Targeted Replicative Vector Methods

In one embodiment, the invention encompasses self-targeted replicative vector methods. In one embodiment, the invention encompasses the use of a CRISPR-Cas system to program cutting of the DNA vector (e.g. plasmid) in one or several target sequences, leading to linearization of the recombination template that have been shown to increase recombination efficiency[9]. To be able to clone a self-targeting vector, an inducible CRISPR-Cas system can be used, for example, using an inducible promoter upstream of the gene encoding the Cas nuclease. By combining this inducible promoter with a riboswitch, even tighter inhibition of CRISPR-Cas system expression can be assured. Another strategy to generate self-targeting CRISPR-Cas system relies on promoters that are repressed in the *C. acnes* producer cell and not in *C. acnes* receiver cell. In this way, the CRISPR-Cas system will only be active once transduced in a *C. acnes* receiver cell.

Figure 6A:
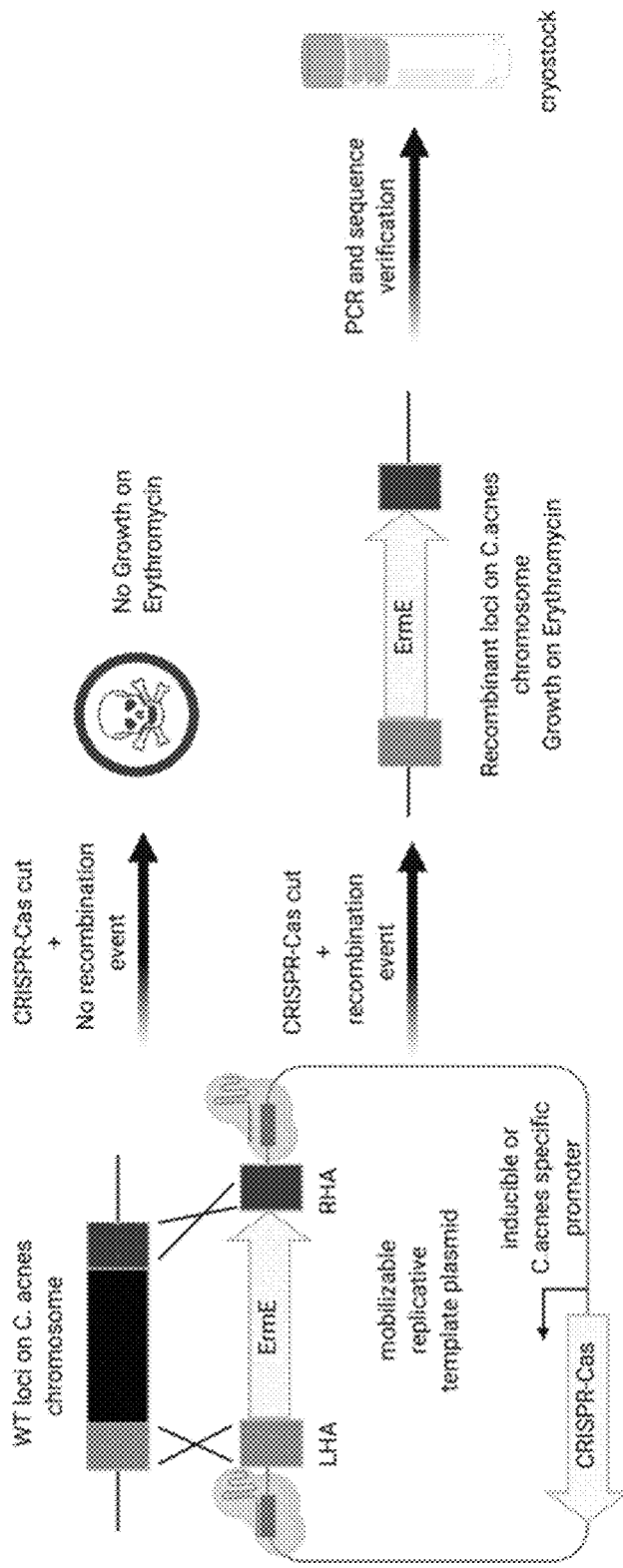
FIGS. 6A and 6B depict a method for *C. acnes* genome engineering using self-targeted replicative vector carrying a CRISPR-Cas system and a recombination template.
Figure 6B:
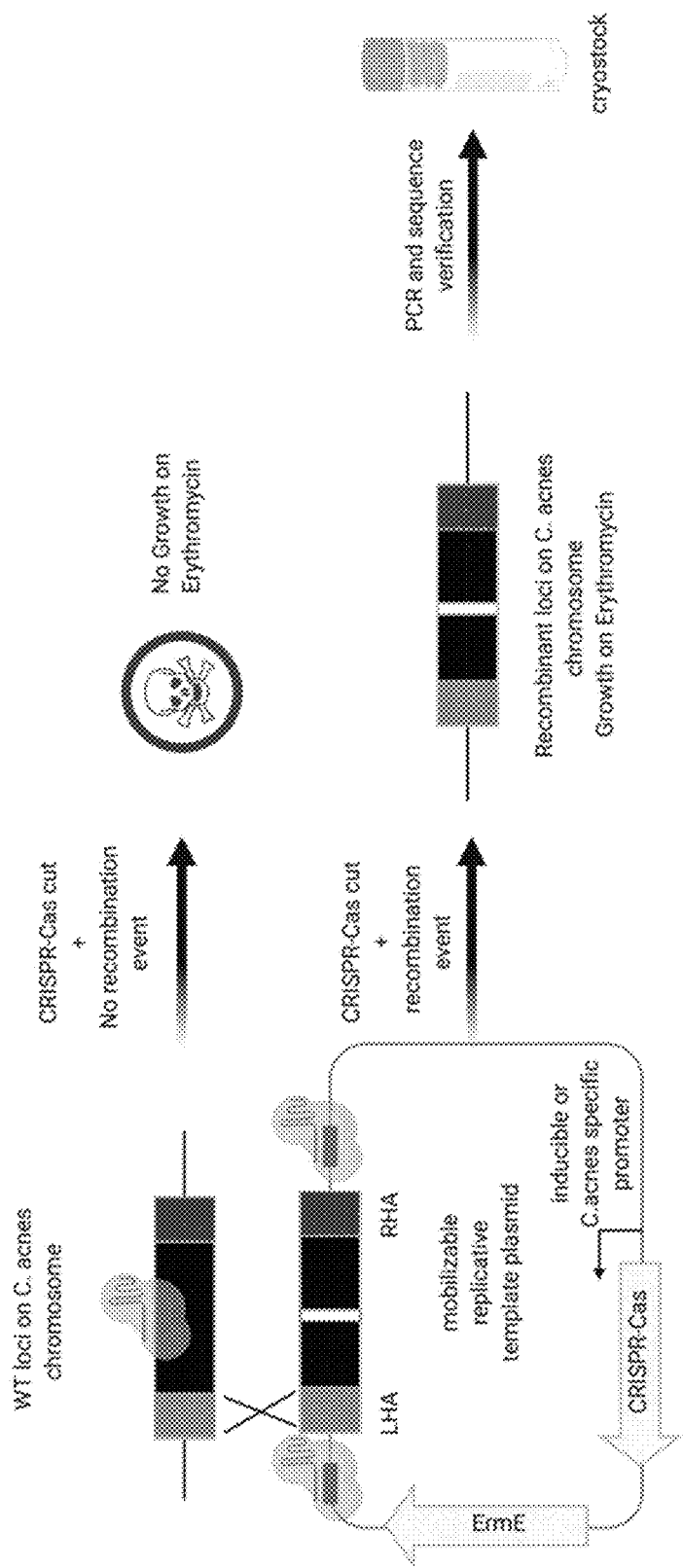

Using such strategy, for example, a gene replacement can be performed using an antibiotic marker flanked by homology arms (FIG. 6A) or by performing scarless recombination using the CRISPR-Cas system ability to kill the bacteria when targeting *C. acnes* chromosome (FIG. 6B).

After introduction and selection of the DNA vector (e.g. plasmid), a homologous event typically takes place leading to removal of a PAM sequence.

Additionally, the DNA vector (e.g. plasmid) carrying the template DNA for homologous recombination typically allows expression of genes increasing recombination rate.

In one embodiment, the DNA vector comprises a template for homologous recombination and a CRISPR-Cas system targeting the DNA vector itself outside of the template region wherein the RNA guide (crRNA or sgRNA) from the CRISPR-Cas system is not perfectly matching the DNA target.

In one embodiment, the invention encompasses replicative vector methods using a vector comprising at least:
a phage packaging signal (cos) originating from *C. acnes* phages, as defined above;
a selection marker for *C. acnes*, as defined above;
an origin of replication for *C. acnes*, as defined above; and
a CRISPR-Cas system for expression in *C. acnes*.

In one embodiment, vectors carry a CRISPR-Cas system able to induce double stranded break leading to death of most *C. acnes* receiver cells except *C. acnes* receiver cells that by spontaneous mutation or recombination do not carry anymore the CRISPR-Cas system target sequence.

*C. acnes* Phage Genome Engineering

The invention encompasses methods for *C. acnes* phage genome engineering and engineered *C. acnes* phage that have been engineered by any of the methods of the invention. An "engineered or recombinant phage" is a phage that has been obtained by any of the methods of the invention to contain an alteration either found or not found in nature. For example, an engineered *C. acnes* phage genome carries a substitution, a deletion or an insertion of one or several nucleotides. In another example the *C. acnes* phage genome carries one or several transgenes expressed upon phage infection.

In one embodiment, the *C. acnes* phage contains one or several genetic modifications into the *C. acnes* phage genome.

In one embodiment, the *C. acnes* phage genome modifications are insertion, deletion or substitution of one or several nucleotides into the *C. acnes* phage genome.

In one embodiment, the *C. acnes* phage genome modification is silent.

In one embodiment, the *C. acnes* phage genome modification is not silent.

In one embodiment, the *C. acnes* phage genome modifications do not impair *C. acnes* phage production.

In one embodiment, the *C. acnes* phage genome modification modifies the phage host range.

In one embodiment, the *C. acnes* phage genome modification leads to inhibition of its packaging into the phage capsid without interfering with the production of the capsid itself. More preferably the genome modification is a modification of the phage packaging sequence. Even more preferably the modification is a deletion of the phage packaging sequence.

In one embodiment, the deleted phage packaging sequence is a cos site from a *C. acnes* phage wherein the cos site sequence is at least 80, 83, 85, 87, 90, 93, 95, 96, 97, 98, 99 or 100% identical to the sequence SEQ ID NO: 66.

In one embodiment, the deleted phage packaging sequence is a cos site from a *C. acnes* phage wherein the cos site sequence is at least 80, 83, 85, 87, 90, 93, 95, 96, 97, 98, 99 or 100% identical to one or more sequence(s) selected from the group consisting of the sequences SEQ ID NO: 76, SEQ ID NO: 86, SEQ ID NO: 87, SEQ ID NO: 88, SEQ ID NO: 89 and SEQ ID NO: 90.

In one embodiment, the *C. acnes* phage modifications are inside coding sequences.

In one embodiment, the *C. acnes* phage modifications are inside regulatory elements such as promoters, transcriptional terminators, origins of replication, RBSs, riboswitch.

In one embodiment, the *C. acnes* phage modifications are inside non-coding sequences and non-regulatory sequences.

In one embodiment, the *C. acnes* phage modifications are insertion of one or several transgenes into the *C. acnes* phage genome.

In one embodiment, the *C. acnes* phage modifications are insertion of one or several transgenes into the *C. acnes* phage genome wherein the insertion does not remove any nucleotide originally present in the phage genome.

In one embodiment, the *C. acnes* phage modifications are insertion of one or several transgenes into the *C. acnes* phage genome wherein the insertion are in intergenic regions.

In one embodiment, the *C. acnes* phage modifications are insertion of one or several transgenes into the *C. acnes* phage genome wherein the insertion replaces one or several nucleotides.

In one embodiment, the *C. acnes* phage modifications are insertion of one or several transgenes into the *C. acnes* phage genome wherein the transgene replaces one or several genes inside a transcriptional unit containing one or several genes without perturbating upstream and downstream genes.

In one embodiment, the *C. acnes* phage modifications are insertion of one or several transgenes into the *C. acnes* phage genome wherein the transgene replaces the holin gene.

In one embodiment, the *C. acnes* phage modifications are insertion of one or several transgenes into the *C. acnes* phage genome wherein the transgene replaces the endolysin gene.

In one embodiment, the *C. acnes* phage modifications are insertion of one or several transgenes into the *C. acnes* phage genome wherein the transgene replaces the holin and the endolysin genes.

In one embodiment, the *C. acnes* phage modifications are insertion of one or several transgenes into the *C. acnes* phage genome wherein the holin and endolysin genes are previously modified to be inactive.

In one embodiment, the *C. acnes* phage modifications are insertion of one or several transgenes into the *C. acnes* phage genome wherein the transgene is a selection marker in *C. acnes*, as defined above.

In one embodiment, the *C. acnes* phage modifications are insertion of an origin of replication allowing replication in *C. acnes*.

In one embodiment, the *C. acnes* phage modifications are insertion of:
an origin of replication allowing replication in *C. acnes*, as defined above, and
a selection marker in *C. acnes*, as defined above.

In one embodiment, the *C. acnes* phage modifications are insertion of one or several transgenes into the *C. acnes* phage genome wherein each transgene contains a promoter, one or several coding sequence and a transcriptional terminator.

In one embodiment, the *C. acnes* phage modifications are insertion of one or several transgenes into the *C. acnes* phage genome wherein each transgene contain a promoter, one or several coding sequence with their ribosome binding sites and a transcriptional terminator and where the promoter is inducible.

In one embodiment, the *C. acnes* phage modifications are insertion of one or several transgenes into the *C. acnes* phage genome wherein each transgene contain a promoter, one or several coding sequence with their ribosome binding sites and a transcriptional terminator and where the promoter is active in specific *C. acnes* strains and inactive or less active in other *C. acnes* strains.

To engineer the *C. acnes* phage genome, the inventors have developed methods to generate recombinant *C. acnes* phages:
  using in vitro or in vivo DNA assembly of the recombinant phage genome, and introduction of the recombinant phage genome into rebooting bacteria such as, but not limited to, *C. acnes*, allowing production of recombinant phage; and/or
  using recombination in *C. acnes* and selection of recombinant phage using replicative CRISPR-Cas system selection vector.

Recombinant *C. acnes* Phage Engineering by Genome Assembly and Rebooting Methods The invention encompasses methods for producing engineered phages using DNA assembly to generate a modified phage genome and subsequent generation of phage containing the assembled modified phage genome.

In one embodiment, DNA fragments are assembled into a recombinant *C. acnes* phage genome and introduced into rebooting bacteria to produce recombinant *C. acnes* phages.

In one embodiment, DNA fragments are assembled into a recombinant *C. acnes* phage genome and transformed into rebooting bacteria to produce recombinant *C. acnes* phages.

In one embodiment, the rebooting bacteria is from the family Propionibacteriaceae. Preferably the rebooting bacteria is *P. freudenreichii*, even more preferably the rebooting bacteria is *C. acnes*.

In one embodiment, DNA fragments are assembled into a recombinant *C. acnes* phage genome inside a vector and introduced into rebooting bacteria to produce recombinant *C. acnes* phages.

In one embodiment, DNA fragments are assembled into a recombinant *C. acnes* phage genome inside a vector and introduced into a bacteria such as *E. coli* that conjugate the vector carrying the recombinant *C. acnes* phage genome into *C. acnes* into which recombinant phages are produced and then amplified on *C. acnes*.

In one embodiment, DNA fragments are assembled into a recombinant *C. acnes* phage genome inside a vector and transformed into a bacteria such as *E. coli* that conjugate the vector carrying the recombinant *C. acnes* phage genome into *C. acnes* into which recombinant phages are produced and then amplified on *C. acnes*.

In one embodiment, DNA fragments are assembled into a recombinant *C. acnes* phage genome inside a vector, wherein the vector contains:
  An origin of replication allowing replication in *E. coli*, as defined above;
  A selection marker for *E. coli*, as defined above;

An oriT from conjugative plasmid, as defined above;
optionally a relaxase from conjugative plasmid; and
optionally an origin of replication allowing replication in
    *C. acnes*, as defined above,
and transformed into an *E. coli* carrying a conjugative vector. The vector containing the recombinant *C. acnes* phage genome is then typically conjugated into *C. acnes*.

In one embodiment, the vector into which the DNA fragments are assembled into a recombinant *C. acnes* phage genome is a Bacterial Artificial Chromosome (BAC).

In one embodiment, DNA fragments are assembled into a recombinant *C. acnes* phage genome in vitro using one or a combination of the following techniques:
    Gibson assembly,
    PCR assembly,
    Golden Gate assembly and derivatives (MOCLO, GoldenBraid . . . ),
    GeneArt® Seamless assembly,
    SLIC assembly,
    CPEC assembly,
    SLiCE assembly.

In one embodiment, DNA fragments are generated by one of the following methods or a combination of the following methods:
    PCR on *C. acnes* phage genome,
    Digestion of *C. acnes* phage genome,
    DNA synthesis (chemical or enzymatic),
    Oligo assembly.

In one embodiment, DNA fragments are assembled into a recombinant *C. acnes* phage genome in vivo using Transformation Associated Recombination (TAR) in yeast.

In one embodiment, the DNA fragments are assembled, in vitro or in vivo, into a recombinant phage genome inside a cloning vector such as a Bacterial Artificial Chromosome (BAC), a Yeast Artificial Chromosome (YAC), a P1-derived artificial chromosome, a plasmid or any combination. The recombinant phage genome is then typically extracted from the cloning vector, optionally circularized and introduced into a rebooting bacterial strain.

In one embodiment, the recombinant *C. acnes* phage genome is introduced into *C. acnes* by transformation. More preferably the recombinant *C. acnes* phage genome is introduced into *C. acnes* by electroporation.

In one embodiment the recombinant *C. acnes* phage genome is introduced into *C. acnes* L-form or *C. acnes* protoplast.

*C. acnes* Phage Engineering by Recombination Methods

The invention encompasses methods for producing engineered phages comprising introducing modification into *C. acnes* phage genome using recombination between a DNA template and a *C. acnes* phage genome, and generation of phages containing the modified phage genome.

In one embodiment a *C. acnes* phage genome is introduced into a *C. acnes* strain containing a DNA template, and recombination events between the phage genome and the DNA template lead to modification of some of the phage genomes that are then packaged into *C. acnes* phages.

In one embodiment an engineered *C. acnes* phage is produced after introduction of a *C. acnes* phage genome into a *C. acnes* cell which comprises a replicative vector containing:
    a selection marker for *C. acnes*, as defined above,
    an origin of replication for *C. acnes*, as defined above,
    a recombination template with one or two homology arms, and
    optionally a recombination machinery.

In one embodiment an engineered *C. acnes* phage is produced after introduction of a *C. acnes* phage genome into a *C. acnes* with a replicative vector containing:
    a selection marker for a donor bacteria such as *E. coli*, as defined above,
    an origin of replication for a donor bacteria such as *E. coli*, as defined above,
    a selection marker for *C. acnes*, as defined above,
    an oriT from conjugative plasmid, as defined above,
    optionally a relaxase from conjugative plasmid,
    an origin of replication for *C. acnes*, as defined above,
    a recombination template with one or two homology arms, and
    optionally a recombination machinery.

In one embodiment the *C. acnes* phage genome is introduced into *C. acnes* by electroporation.

In one embodiment the *C. acnes* phage genome is introduced into *C. acnes* through infection by the phage.

In one embodiment the DNA templates for homologous recombination are linear double stranded DNA (dsDNA) or single stranded DNA (ssDNA) introduced by electroporation.

In one embodiment the DNA templates for homologous recombination are oligonucleotides.

In one embodiment both the phage genome and the DNA template are transformed into *C. acnes*. Preferably the transformation method is electroporation.

Recombinant Phage CRISPR-Cas System Selection Methods

The invention encompasses recombinant phage CRISPR-Cas system selection methods. The invention encompasses a *C. acnes* cell, carrying a CRISPR-Cas system expressed in *C. acnes* and engineered to target a wild-type phage or a previously modified phage genome but not the newly generated recombinant *C. acnes* phage.

In one embodiment, the engineered CRISPR-Cas system is an endogenous CRISPR-Cas system.

In another embodiment, the CRISPR-Cas system is an exogenous CRISPR-Cas system.

In one embodiment the CRISPR-Cas system is an exogenous CRISPR-Cas system integrated on the *C. acnes* chromosome.

In one embodiment the CRISPR-Cas system is an exogenous CRISPR-Cas system on a replicative vector.

In one embodiment, the invention encompasses replicative CRISPR-Cas system selection vector comprising at least:
    a selection marker for *C. acnes*, as defined above,
    an origin of replication for *C. acnes*, as defined above, and
    an exogenous CRISPR-Cas system that is expressed in *C. acnes* and targets the wild-type *C. acnes* phage genome or a previously modified phage genome but not the newly generated recombinant *C. acnes* phage genome.

In one embodiment, the invention encompasses replicative CRISPR-Cas system selection vector comprising at least:
    a selection marker for a donor bacteria such as *E. coli*, as defined above,
    an origin of replication for a donor bacteria such as *E. coli*, as defined above,
    a selection marker for *C. acnes*, as defined above,
    an oriT from conjugative plasmid, as defined above,
    optionally a relaxase from conjugative plasmid,
    an origin of replication for *C. acnes*, as defined above, and
    an exogenous CRISPR-Cas system that is expressed in *C. acnes* and targets the wild-type *C. acnes* phage genome or a previously modified phage genome but not the newly generated recombinant *C. acnes* phage genome.

In one embodiment, the method comprises conjugating into *C. acnes*, for example strain ATCC 6919, a replicative CRISPR-Cas system selection vector containing:
- a selection marker for a donor bacteria such as *E. coli*, as defined above,
- an origin of replication for a donor bacteria such as *E. coli*, as defined above,
- a selection marker for *C. acnes*, as defined above,
- an oriT from conjugative plasmid, as defined above,
- optionally a relaxase from conjugative plasmid,
- an origin of replication for *C. acnes*, as defined above, and
- an exogenous CRISPR-Cas system that is expressed in *C. acnes* and targets the wild-type *C. acnes* phage genome or a previously modified phage genome but not the newly generated recombinant *C. acnes* phage genome.

After conjugation into *C. acnes*, transconjugants are typically selected on appropriate antibiotic. After optional confirmation by PCR of the presence of the replicative CRISPR-Cas system selection vector in *C. acnes*, single colony is typically grown in a dense culture in presence of the appropriate antibiotic, is preferably mixed with a *C. acnes* phage suspension containing a mix of wild-type phage, or previously produced recombinant phage, and newly produced recombinant phage, and is typically poured as a top agar lawn. Optionally a first amplification of the recombinant *C. acnes* phage can be performed on the *C. acnes* carrying the replicative CRISPR-Cas system selection vector, phage suspension can typically be obtained and mixed with a new culture of *C. acnes* carrying the replicative CRISPR-Cas system selection vector for a top agar.

Newly generated recombinant phages typically bind, inject their recombinant phage genome, replicate and generate new recombinant particles leading to plaque formation, whereas wild-type or previously generated recombinant phages inject their phage genome which is recognized and cut by the CRISPR-Cas system leading to abortion of the phage replication cycle, thus leading to no plaques being produced. Single plaques are typically picked, isolated, and confirmed to be recombinant and carrying the expected genetic modification. Finally, the isolated plaque is typically reamplified into a *C. acnes* indicator strain or into the *C. acnes* carrying the replicative CRISPR-Cas system selection vector and the pure phage suspension is preferably stored.

In one embodiment, the recombinant DNA phage is not targeted by the CRISPR-Cas system because, for example, it does not have the associated PAM sequence.

Methods to produce recombinant phages in *C. acnes*

The invention encompasses methods to produce phage-derived particles in *C. acnes*. *C. acnes* phages that have been described so far are all genetically extremely conserved and are not able to stably replicate as a plasmid state, nor integrate in the chromosome of their host[1]. As a consequence, they are difficult to engineer because they lead to the death of the cell they infect. To address this issue, the inventors have developed a two-step method to engineer *C. acnes* phages.

In the first step, an *E. coli* donor strain carrying a conjugative vector is transformed with a mobilizable replicative vector (e.g., pEB-PRECOMB) comprising:
- a selection marker for *E. coli*, as defined above,
- an origin of replication for *E. coli*, as defined above,
- a selection marker for *C. acnes*, as defined above,
- a relaxase and oriT from conjugative plasmid, and
- a recombination template with one or two homology arms.

Figure 7A:
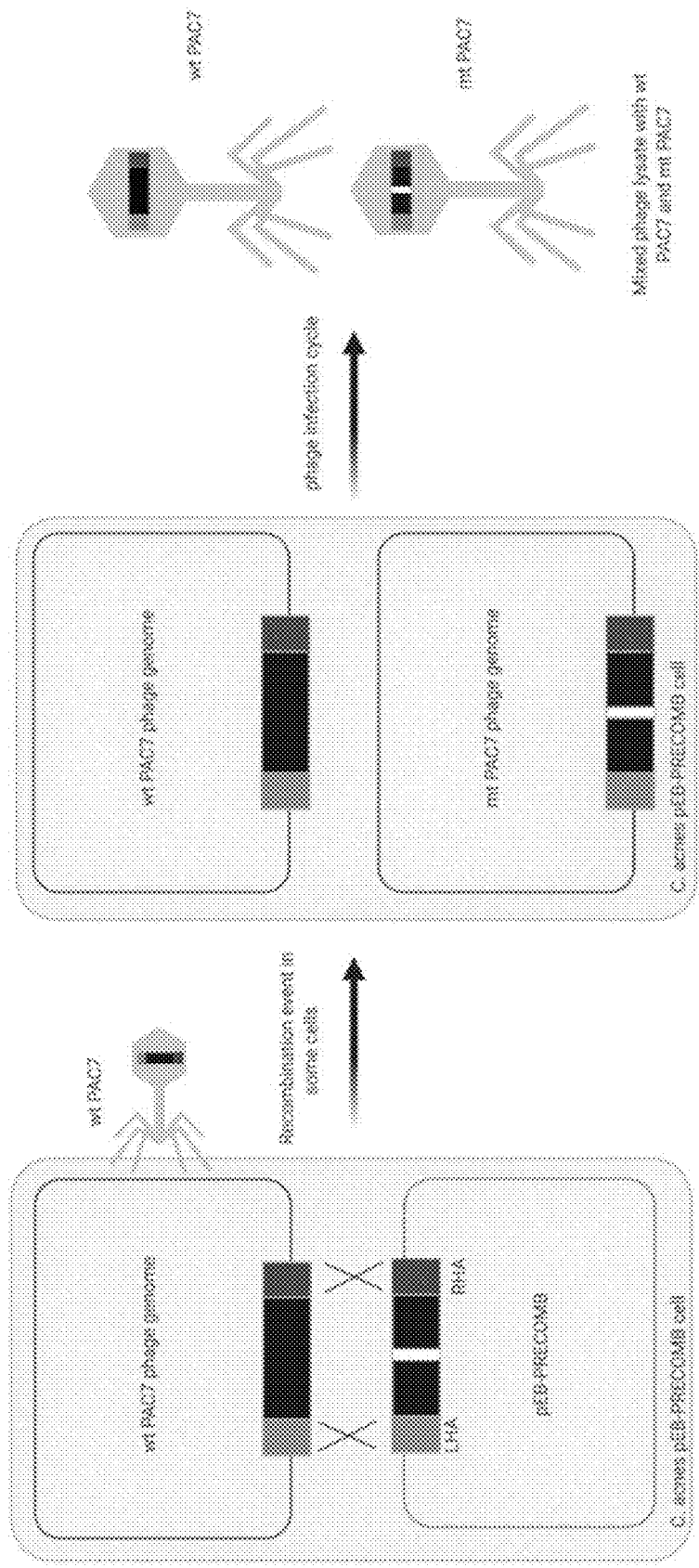
FIGS. 7A and 7B depict a two-step method for engineering and selection of *C. acnes* phages using CRISPR-Cas system.

Conjugation between *E. coli* donor cells (*E. coli* pEB-PRECOMB) and *C. acnes* receiver cells (for example *C. acnes* ATCC 6919) is performed. *C. acnes* transconjugants (*C. acnes* pEB-PRECOMB) are typically selected on the appropriate antibiotic, grown and infected by *C. acnes* phages (e.g., PAC7). After phage infection, a recombination event takes place, which leads to a phage lysate containing both wild-type *C. acnes* phage (e.g., wt PAC7) or parent *C. acnes* phage (i.e. a phage from which the desired recombinant phage originates) and recombinant phages (e.g., mt PAC7) (FIG. 7A).

In the second step, a replicative plasmid (e.g., pEB-PSCREEN) is used, comprising:
- a selection marker for *E. coli*, as defined above,
- an origin of replication for *E. coli*, as defined above,
- a selection marker for *C. acnes*, as defined above, and
- a relaxase and oriT from a conjugative vector, as defined above, and
- a CRISPR-Cas system for expression in *C. acnes* and targeting the wild-type phage (e.g., PAC7).

Figure 7B:
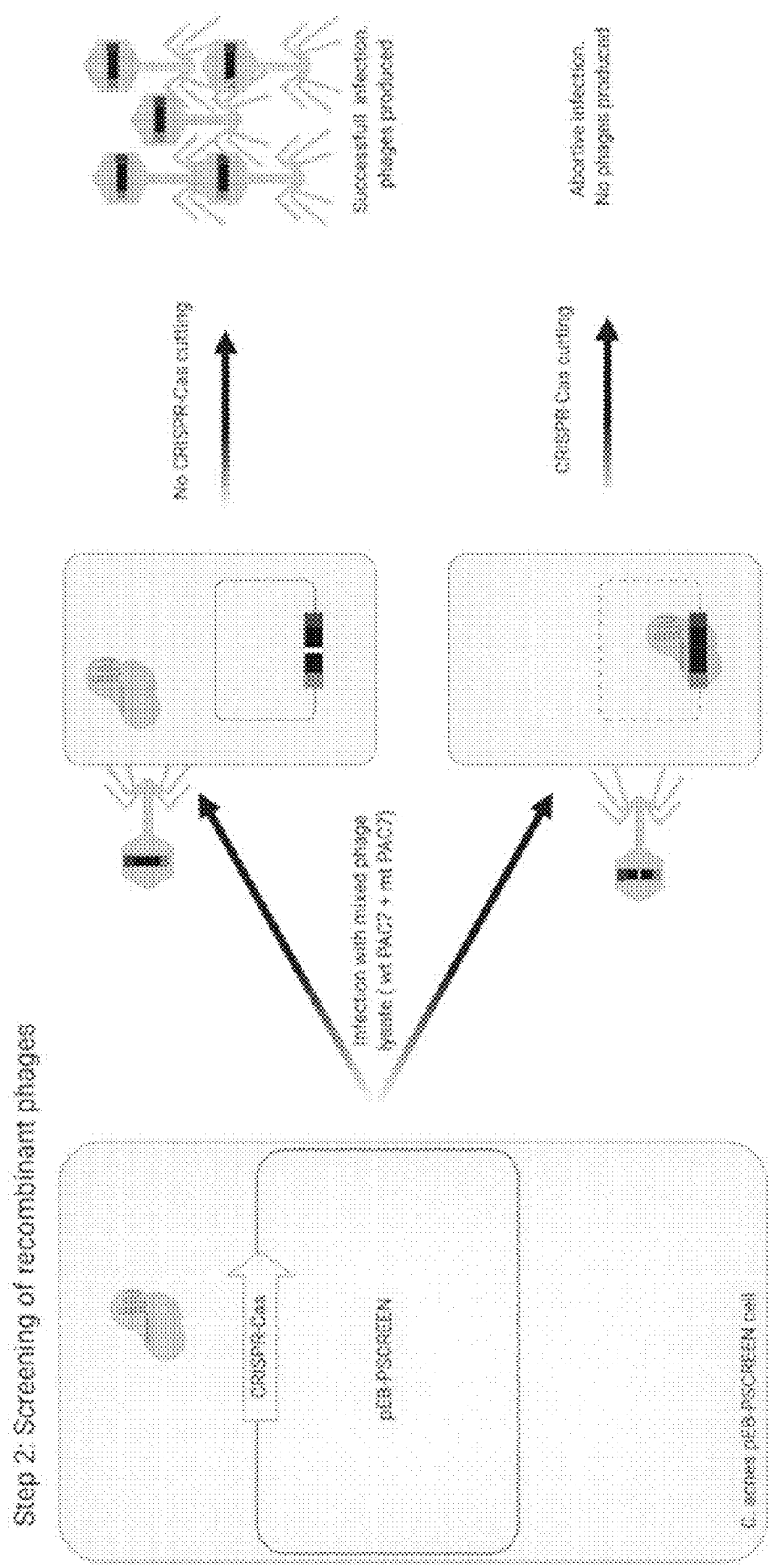

In one embodiment, said replicative plasmid is transformed into an *E. coli* donor strain carrying a conjugative plasmid (e.g. leading to the production of *E. coli* donor strain pEB-PSCREEN). Conjugation is performed between the *E. coli* donor strain pEB-PSCREEN and *C. acnes* receiver cells (for example *C. acnes* ATCC 6919). Transconjugant *C. acnes* pEB-PSCREEN cells are typically selected on antibiotic plates, grown to a dense culture and mixed with the phage lysate containing both wild-type phage (e.g., wt PAC7) and mutant phage (e.g., mt PAC7) (FIG. 7B). Wild-type phage genomes are typically cut by the CRISPR-Cas nuclease and are not able to replicate and form plaques, whereas recombinant mt phage genomes are not recognized by the CRISPR-Cas system and successfully replicate, which leads to plaque formation. Single plaques are typically isolated, screened by PCR and sequence verified. If confirmed by sequencing, the recombinant phages are typically amplified on wild-type *C. acnes* strain or on *C. acnes* strain with the CRISPR-Cas system vector targeting wild-type phage.

The recombination event can lead to substitution, deletion, or insertion that leads, therefore, to the removal of the PAM sequence or any part of the sequence necessary for CRISPR-Cas targeting. Insertion can lead to the introduction of a fluorescent or enzymatic reporter that helps to isolate recombinant plaques.

The template for homologous recombination typically contains homology arms upstream and downstream recombination points. These homology arms are typically at least 50, 100, 500, 1000 or at least 5000 bp in size.

Examples of applications of the engineering of *C. acnes* phages include, but are not limited to:
- expression of therapeutic proteins that are produced during phage infection and released when cells are lysed,
- expression of therapeutic proteins that are produced, secreted or exported to surface during phage infection,
- display of specific proteins, such as antigens, on the capsid of the phage,
- modification of the host range of the phage, and
- obtaining of a strictly lytic phage variant.

Additionally, the vector (e.g. plasmid) carrying the template DNA for homologous recombination typically allows expression of genes that increase recombination rate.

Additionally, the vector (e.g. plasmid) carrying the template DNA for homologous recombination is typically carrying an inducible endonuclease, such as but not limited to CRISPR-Cas, that leads to the linearization of the vector during infection of the phage. This linearization of the template vector typically leads to an increase in recombination rate.

Expression of Proteins by Engineered *C. acnes* Phage

The invention encompasses the expression of proteins by engineered *C. acnes* phage. By incorporating an expression cassette into the phage, the protein can be expressed by the infected *C. acnes*. The promoter within the expression cassette can be inducible or constitutive, allowing inducible or constitutive expression of proteins by engineered *C. acnes* phage.

In one embodiment, the phage is used for the expression of molecules of interest and/or modulation of *C. acnes*-host interaction. In one embodiment, the phage genome is used for the expression of transgenes in *C. acnes*. A transgene can be cloned into the recombinant autonomously-replicating phage vector under the control of a given promoter (constitutive or inducible) and followed by a given terminator. The injection of this phage genome into *C. acnes* allows the expression of the transgene. The transgene can be, for example, a CRISPR-Cas system, a base editing or prime editing expression cassette, or can encode a human protein, such as an interleukin, or can encode an antigen, such as a tumor antigen, a viral antigen, a bacterial antigen, a fungal antigen, a self-antigen, an allergen or a graft-specific antigen, as defined below.

Expression of Proteins by Engineered *C. acnes* Strains

The invention encompasses the expression of proteins by engineered *C. acnes* strains. By incorporating an expression cassette into the DNA vector, the protein can be expressed by the transduced *C. acnes*. The promoter within the expression cassette can be inducible or constitutive, allowing inducible or constitutive expression of proteins by engineered *C. acnes* strains. Expression of several proteins can be performed as single transcriptional unit (operon) or as separated transcriptional units. In a particular embodiment, said protein is an antigen, such as a tumor antigen, a viral antigen, a bacterial antigen, a fungal antigen, a self-antigen, an allergen or a graft-specific antigen, as defined below.

*C. acnes* Phage

The invention encompasses the *C. acnes* phage and related engineered phages, methods for producing these phages, and methods for using these phages to transduce *C. acnes*.

In a particular embodiment, the engineered *C. acnes* phage of the invention is incapable of self-reproduction.

In the context of the present invention, the terms "self-reproduction" and "self-replication" are used indifferently, and refer to the capability of having a progeny, in particular of producing new phages.

By "phage incapable of self-reproduction" is meant herein that at least one, several or all functional gene(s) necessary to produce said phage (also called herein "essential gene(s)") is(are) absent from said engineered phage (and from said phage genome included in said engineered phage).

In a preferred embodiment, said at least one, several or all functional gene(s) necessary to produce said engineered phage is(are) present in a producer cell, preferably in a plasmid, in a phagemid, in the chromosome or in a helper phage present in the producer cell, enabling the production of said engineered phage in said producer cell. In such an embodiment, said engineered *C. acnes* phage incapable of self-reproduction is also called conditionally replicative *C. acnes* phage.

In the context of the invention, said functional gene necessary to produce an engineered phage may be absent through (i) the absence of the corresponding gene or (ii) the presence of the corresponding gene but in a non-functional form.

In an embodiment, the sequence of said gene necessary to produce said engineered phage is absent from said engineered phage. In a preferred embodiment, the sequence of said gene necessary to produce said engineered phage has been replaced by a nucleic acid sequence of interest.

Alternatively, said gene necessary to produce said engineered phage is present in said engineered phage in a non-functional form, for example in a mutant non-functional form, or in a non-expressible form, for example with deleted or mutated non-functional regulators. In a preferred embodiment, said gene necessary to produce said engineered phage is present in said engineered phage in a mutated form which renders it non-functional in the receiver cell, while remaining functional in the producer cell.

In the context of the invention, genes necessary to produce said engineered phage encompass any coding or non-coding nucleic acid required for the production of said engineered phage.

Examples of genes necessary to produce said engineered phage include genes encoding phage structural proteins; phage genes involved in the control of genetic expression; phage genes involved in transcription and/or translation regulation; phage genes involved in phage DNA replication; phage genes involved in production of phage proteins; phage genes involved in phage proteins folding; phage genes involved in phage DNA packaging; and phage genes encoding proteins involved in bacterial cell lysis.

In one embodiment, the engineered *C. acnes* phage comprises an essential gene, as defined above, the expression of which is controlled by a *C. acnes* phage promoter. It can be expressed constitutively or under an inducible system, such as an inducible promoter or a riboswitch. When said essential gene is under an inducible system, said engineered *C. acnes* phage is also considered as a conditionally replicative phage.

In one embodiment the conditionally replicative phage does not or cannot kill a non-engineered *C. acnes* production strain, in particular which does not comprise said essential gene(s) absent from said conditionally replicative phage.

In one embodiment the conditionally replicative phage is carrying a CRISPR-Cas system.

In one embodiment the conditionally replicative phage comprises a transgene.

Phage-Derived Particles in *C. acnes*

The invention encompasses phage-derived particles comprising any DNA vector of the invention and the methods for the production of these phage-derived particles.

In one embodiment a *C. acnes* strain carrying any DNA vector of the invention is contacted with a *C. acnes* phage leading to introduction of the phage genome into the *C. acnes* strain and the expression of the phage proteins necessary for the assembly of a phage capsid and the packaging of the DNA vector inside the phage capsid.

In one embodiment a *C. acnes* strain carrying any DNA vector comprising a selection marker for *C. acnes* as defined above, a *C. acnes* phage packaging signal (cos site) as defined above and an origin of replication for *C. acnes*, as defined above, is contacted with a *C. acnes* phage leading to introduction of the phage genome into the *C. acnes* strain and the expression of the phage proteins necessary for the assembly of a phage capsid and the packaging of the DNA vector inside the phage capsid.

In one embodiment, the phage genome is a wild type phage genome.

In one embodiment, the *C. acnes* phage is PAC7 (typically of sequence SEQ ID NO: 68).

In one embodiment, the phage genome is an engineered phage genome.

The phage-derived particles can be purified by methods known in the art. The invention encompasses purified phage-derived particles comprising a DNA vector of the invention. In one embodiment, the purified phage-derived particles are in an isolated composition or pharmaceutical composition. The composition can comprise at least $10^4$, $10^5$, $10^6$, $10^7$, $10^8$, $10^9$, $10^{10}$, $10^{11}$, $10^{12}$, $10^{13}$, $10^{14}$, or more purified phage-derived particles.

Sequence Specific Killing of *C. acnes* by Phage-Derived Particles

In one embodiment, the invention comprises specific killing of *C. acnes* by phage-derived particles carrying CRISPR-Cas system.

Phage-derived particles carrying a vector (e.g. plasmid) encoding CRISPR-Cas system have been recently used to perform in situ sequence specific killing of bacterial[10,11]. The inventors have developed a method to produce such phage-derived particles to target *C. acnes*, which is encompassed by the invention.

In said method, a *C. acnes* producer strain comprising a DNA vector of the invention is contacted with a *C. acnes* phage, such as PAC7 (typically of sequence SEQ ID NO: 68) to produce a high titer phage suspension.

In one embodiment, the *C. acnes* comprises a DNA vector comprising:
- a selection marker for *C. acnes*, as defined above,
- a *C. acnes* phage packaging signal (cos site), as defined above,
- an origin of replication for *C. acnes*, as defined above and
- a CRISPR-Cas system targeting a specific *C. acnes* receiver cell chromosomal locus (pTarget).

High titer *C. acnes* phage suspensions are typically added to *C. acnes*. The suspensions typically contain a mix of wild-type phages and phage-derived particles carrying the plasmid. Contacting of *C. acnes* cells carrying the locus targeted by the pTarget CRISPR-Cas system is typically performed with phage-derived particles containing pTarget. This can be performed in vivo or in vitro. Sequence specific killing is typically observed for lysate containing phage-derived particles comprising pTarget.

In one embodiment, the phage-derived particles comprising the pTarget vector (e.g. plasmid) are not mixed with phage and allow sequence specific killing of cells carrying the DNA targeted by the CRISPR-Cas system.

*C. acnes* Plasmid Curing

Naturally occurring *C. acnes* plasmids have been described and some of them have been associated with pro-inflammatory phenotypes[15,23] and acne vulgaris[16-18]. Being able to cure such plasmids is of interest to study their effect, notably, their pro-inflammatory role in acne vulgaris. The inventors have developed a method to cure *C. acnes* plasmid.

In a first step, a *C. acnes* producer cell carrying a DNA vector comprising:
- a *C. acnes* phage packaging signal as defined above,
- optionally a selection marker for *C. acnes*, as defined above,
- an origin of replication that allows replication only in *C. acnes* producer cell, as defined above, and
- a transgene, such as a CRISPR-Cas system targeting a genetic sequence of an endogenous plasmid to be cured in a target *C. acnes* receiver cell, the sequence being preferably in a conserved region such as the origin of replication or in loci associated with acne vulgaris, is infected by a *C. acnes* phage leading to production of phage-derived particles carrying the DNA vector.

Contacting *C. acnes* phage-derived particles with *C. acnes* receiver cell carrying the endogenous plasmid to be cured, such as pIMPLE-HL096PA1 is performed. This can be performed in vivo or in vitro.

In some embodiments, *C. acnes* transductants can be selected on the appropriate antibiotic. Single colonies are typically streaked on plates with media containing the antibiotic and the presence of the plasmid is typically screened by PCR. Single colonies where no positive PCR for the plasmid pIMPLE-HL096PA1 is obtained, are then cured from the vector (e.g. plasmid) comprising the CRISPR-Cas system, and typically cryostocked.

Treatment Methods

The invention encompasses methods to treat a *C. acnes* related disorder or disease.

The invention encompasses the use of engineered *C. acnes* strains as defined above, phage-derived particles as defined above and engineered phages as defined above, and/or bacteria producing them for the treatment and/or prevention of a wide range of skin diseases and disorders.

The invention encompasses methods to treat a decrease in sebum production, follicular hyperkeratinization, colonization of skin bacteria, and inflammation using engineered *C. acnes* strains as defined above, phage-derived particles as defined above and engineered phages as defined above, and/or bacteria producing them.

The invention encompasses the use of engineered *C. acnes* strains as defined above in cosmetics and other compositions.

In one embodiment, the invention encompasses expression of therapeutic molecules by engineered *C. acnes*.

In one embodiment, the invention encompasses expression of non-therapeutic molecules by engineered *C. acnes*.

*Cutibacterium acnes* is one of the most prevalent and abundant bacteria on human skin, where it can be found both on the skin surface (stratum corneum) and in the hair follicle[12]. Inside the hair follicle, it is in direct contact with a large diversity of living cells such as keratinocytes, stem cells, sebaceous cells and immune cells. This is not the case on the stratum corneum, where it is mostly in contact with the dead corneocyte[13]. Thus, it appears interesting to use *C. acnes* as a bacterial chassis for the production and delivery of therapeutic molecules in situ inside and outside the hair follicle.

Phage-derived particles as defined above and engineered phages as defined above, and/or bacteria producing them, can be delivered to the skin by dermal or other appropriate administration method to a subject.

The subject according to the invention is an animal, preferably a mammal, even more preferably a human. However, the term "subject" can also refer to non-human animals, in particular mammals such as dogs, cats, horses, cows, pigs, sheep, donkeys, rabbits, ferrets, gerbils, hamsters, chinchillas, rats, mice, guinea pigs and non-human primates, among others, or non-mammals such as poultry, that are in need of treatment.

The human subject according to the invention may be a human at the prenatal stage, a new-born, a child, an infant, an adolescent or an adult at any age.

Preferably, the treatment is administered regularly, preferably between every day and every month, more preferably between every day and every two weeks, more preferably between every day and every week, even more preferably the treatment is administered every day. In a particular embodiment, the treatment is administered several times a day, preferably 2 or 3 times a day, even more preferably 3 times a day.

The duration of treatment with engineered *C. acnes* strains as defined above, phage-derived particles as defined above, engineered phages as defined above, and/or bacteria producing them (e.g., *E. coli* or *C. acnes*) according to the invention, is preferably comprised between 1 day and 20 weeks, more preferably between 1 day and 10 weeks, still more preferably between 1 day and 4 weeks, even more preferably between 1 day and 2 weeks. In a particular embodiment, the duration of the treatment is of about 1 week. Alternatively, the treatment may last as long as the infection, disorder and/or disease persists.

The form of the pharmaceutical or veterinary compositions, the route of administration and the dose of administration of engineered *C. acnes* strains as defined above, phage-derived particles as defined above, engineered phages as defined above, and/or bacteria producing them (e.g., *E. coli* or *C. acnes*) according to the invention, can be adjusted by the man skilled in the art according to the type and severity of the disease, disorder and/or infection (e.g. depending on the bacteria species involved in the disease, disorder and/or infection and its localization in the patient's or subject's body), and to the patient or subject, in particular its age, weight, sex, and general physical condition.

Particularly, the amount of engineered *C. acnes* strains as defined above, phage-derived particles as defined above, engineered phages as defined above, and/or bacteria producing them (e.g., *E. coli* or *C. acnes*) according to the invention, to be administered has to be determined by standard procedure well known by those of ordinary skills in the art. Physiological data of the patient or subject (e.g. age, size, and weight) and the routes of administration have to be taken into account to determine the appropriate dosage, so as a therapeutically effective amount will be administered to the patient or subject.

For example, the total amount of phage-derived particles as defined above and/or engineered phages as defined above according to the invention, for each administration is comprised between $10^4$ and $10^{15}$ particles.

Preferably, total amount of an engineered bacteria producing phage-derived particles as defined above and/or engineered phages as defined above (e.g., *E. coli* or *C. acnes*) according to the invention, or engineered *C. acnes* strains as defined above, for each administration is comprised between $10^4$ and $10^{15}$ bacteria.

The invention encompasses plasmids for the expression of toxins such as nuclease, more preferably CRISPR-Cas systems to kill transduced *C. acnes* population.

The invention encompasses plasmids for the expression of CRISPR-Cas systems where the CRISPR-Cas system is targeted towards sequences present only in specific strains and not present in others allowing strain specific killing among the *C. acnes* population.

The invention encompasses modifications of *C. acnes* chromosome or *C. acnes* endogenous plasmid. Modifications such as deletion, substitution and/or insertion leading to alteration in the *C. acnes*-host relation are for example contemplated.

The invention encompasses vectors, e.g. plasmids, for the expression of therapeutic molecules containing one or several genes involved in the production of the therapeutic molecule.

In the case where the therapeutic molecule is not freely diffusing from *C. acnes* cells, such as in the case of a therapeutic protein, a fusion with a signal peptide allowing secretion or export on the cell membrane or wall of *C. acnes* cells is preferably encoded on the vector, e.g. plasmid. Examples of secretion systems or signal peptides include: TAT, SEC and type VII/WXG100 secretion systems. More specifically, the signal peptide can be extracted from proteins selected from the group consisting of the proteins PPA0532 (typically referenced as Q6AAD1 in the UniprotKB database as of Nov. 4, 2020); PPA0533 (typically referenced as Q6AAD0 in the UniprotKB database as of Nov. 4, 2020); PPA0534 (typically referenced as Q6AAC9 in the UniprotKB database as of Nov. 4, 2020); PPA0598 (typically referenced as Q6AA63 in the UniprotKB database as of Nov. 4, 2020); PPA0644 (typically referenced as Q6AA16 in the UniprotKB database as of Nov. 4, 2020); PPA0687 (typically referenced as Q6A9X2 in the UniprotKB database as of Nov. 4, 2020); PPA0721 (typically referenced as Q6A9T8 in the UniprotKB database as of Nov. 4, 2020); PPA0816 (typically referenced as Q6A9J4 in the UniprotKB database as of Nov. 4, 2020); PPA1310 (typically referenced as Q6A856 in the UniprotKB database as of Nov. 4, 2020); PPA1498 (typically referenced as Q6A7M0 in the UniprotKB database as of Nov. 4, 2020); PPA1662 (typically referenced as Q6A771 in the UniprotKB database as of Nov. 4, 2020); PPA1715 (typically referenced as Q6A720 in the UniprotKB database as of Nov. 4, 2020); PPA1939 (typically referenced as Q6A6F6 in the UniprotKB database as of Nov. 4, 2020); PPA2097 (typically referenced as Q6A608 in the UniprotKB database as of Nov. 4, 2020); PPA2105 (typically referenced as Q6A601 in the UniprotKB database as of Nov. 4, 2020); PPA2106 (typically referenced as Q6A600 in the UniprotKB database as of Nov. 4, 2020); PPA2142 (typically referenced as Q6A5W4 in the UniprotKB database as of Nov. 4, 2020); PPA2164 (typically referenced as Q6A5U3 in the UniprotKB database as of Nov. 4, 2020); PPA2175 (typically referenced as Q6A5T2 in the UniprotKB database as of Nov. 4, 2020); PPA2152 (typically referenced as Q6A5V4 in the UniprotKB database as of Nov. 4, 2020); PPA1340 (typically referenced as Q6A826 in the UniprotKB database as of Nov. 4, 2020) and PPA2239 (typically referenced as Q6A5M0 in the UniprotKB database as of Nov. 4, 2020).

In the case where secretion is not wanted or functional, a lysing module can be added to the vector, e.g. plasmid, in order to lyse the cell and release the therapeutic molecule.

In a particular embodiment, said therapeutic molecule may be displayed on the cell membrane or wall of *C. acnes* cells. To be displayed, a protein of interest typically requires a N-terminal secretion signal peptide such as the ones described above as well as a C-terminal LPXTG motif allowing the class F sortase from *C. acnes* (Girolamo, S. D. et al., *Biochem J* 476, 665-682 (2019) to covalently link the protein of interest to the cell wall. Additionally a PT rich region might be integrated upstream of the LPXTG motif. Alternatively a more classical cell wall sorting sequence (CWSS) combining a LPxTG motif followed by hydrophobic amino acids and a positively charged C-terminus can be used.

In order to control expression of the therapeutic molecule, one or several of the genes, as an operon or as single isolated genes, can be put under the control of an inducible system, such as an inducible promoter, a riboswitch, a RNA-based induction system or a combination thereof. Several promoters of several transcriptional strengths might be tested and combined with different RBS strengths to optimize for in situ production of the therapeutic molecule. An RBS library approach might be used to select the best RBS variant for in vitro or in situ expression.

Examples of therapeutic molecules include but are not limited to antibodies, antibody-based drugs, Fc fusion proteins, anticoagulants, blood factors, bone morphogenetic proteins, engineered protein scaffolds, enzymes, growth factors, hormones, interferons, interleukins, and thrombolytics. Other examples include those that bind non-covalently to target (e.g., monoclonal antibodies), those that affect covalent bonds (e.g., enzymes), and those that exert activity without specific interactions (e.g., serum albumin).

Also contemplated herein are therapeutic molecules (e.g., recombinant therapeutic proteins) used to treat, for example, cancers, immune disorders, infections and/or other diseases. Engineered proteins, including bispecific mAbs and multi-specific fusion proteins, and proteins with optimized pharmacokinetics are also contemplated by the present disclosure.

In some embodiments, the therapeutic protein is Etanercept, Bevacizumab, Rituximab, Adalimumab, Infliximab, Trastuzumab, Insulin glargine, Epoetin alfa, Pegfilgrastim, Ranibizumab, Darbepoetin alfa, Interferon beta-Ia, Interferon beta-Ia. Insulin aspart, Rhu insulin, Octocog alfa, Insulin lispro, Cetuximab, Peginterferon alfa-2a, Interferon beta-Ib, Eptacog alfa, Insulin aspart, OnabotulinumtoxinA, Epoetin beta, Rec antihemophilic factor, Filgrastin, Insulin detemir, Natalizumab, Insulin (humulin) or Palivizumab.

Examples of antibodies, antibody fragments, and/or Fc fusion proteins that may be expressed in the context of the present disclosure include, without limitation, Abagovomab, Abciximab, Actoxumab, Adalimumab, Adecatumumab, Afelimomab, Afutuzumab, Alacizumab pegol, ALD, Alemtuzumab, Alirocumab, Altumomab pentetate, Amatuximab, Anatumomab mafenatox, Anifrolumab, Anrukinzumab, Apolizumab, Arcitumomab, Aselizumab, Atinumab, Atlizumab (or tocilizumab), Atorolimumab, Bapineuzumab, Basiliximab, Bavituximab, Bectumomab, Belimumab, Benralizumab, Bertilimumab, Besilesomab, Bevacizumab, Bezlotoxumab, Biciromab, Bimagrumab, Bivatuzumab mertansine, Blinatumomab, Blosozumab, Brentuximab vedotin, Briakinumab, Brodalumab, Canakinumab, Cantuzumab mertansine, Cantuzumab ravtansine, Caplacizumab, Capromab pendetide, Carlumab, Catumaxomab, Cedelizumab, Certolizumab pegol, Cetuximab, Citatuzumab bogatox, Cixutumumab, Clazakizumab, Clenoliximab, Clivatuzumab tetraxetan, Conatumumab, Concizumab, Crenezumab, Dacetuzumab, Daclizumab, Dalotuzumab, Daratumumab, Demcizumab, Denosumab, Detumomab, Dorlimomab aritox, Drozitumab, Duligotumab, Dupilumab, Dusigitumab, Ecromeximab, Eculizumab, Edobacomab, Edrecolomab, Efalizumab, Efungumab, Eldelumab, Elotuzumab, Elsilimomab, Enavatuzumab, Enlimomab pegol, Enokizumab, Enoticumab, Ensituximab, Epitumomab cituxetan, Epratuzumab, Erlizumab, Ertumaxomab, Etaracizumab, Etrolizumab, Evolocumab, Exbivirumab, Fanolesomab, Faralimomab, Farletuzumab, Fasinumab, FBTA, Felvizumab, Fezakinumab, Ficlatuzumab, Figitumumab, Flanvotumab, Fontolizumab, Foralumab, Foravirumab, Fresolimumab, Fulranumab, Futuximab, Galiximab, Ganitumab, Gantenerumab, Gavilimomab, Gemtuzumab ozogamicin, Gevokizumab, Girentuximab, Glembatumumab vedotin, Golimumab, Gomiliximab, Guselkumab, Ibalizumab, Ibritumomab tiuxetan, Icrucumab, Igovomab, lmciromab, lmgatuzumab, Inclacumab, Indatuximab ravtansine, Infliximab, Intetumumab, Inolimomab, Inotuzumab ozogamicin, Ipilimumab, Iratumumab, Itolizumab, Ixekizumab, Keliximab, Labetuzumab, Lambrolizumab, Lampalizumab, Lebrikizumab, Lemalesomab, Lerdelimumab, Lexatumumab, Libivirumab, Ligelizumab, Lintuzumab, Lirilumab, Lodelcizumab, Lorvotuzumab mertansine, Lucatumumab, Lumiliximab, Mapatumumab, Margetuximab, Maslimomab, Mavrilimumab, Matuzumab, Mepolizumab, Metelimumab, Milatuzumab, Minretumomab, Mitumomab, Mogamulizumab, Morolimumab, Motavizumab, Moxetumomab pasudotox, Muromonab-CD3, Nacolomab tafenatox, Namilumab, Naptumomab estafenatox, Narnatumab, Natalizumab, Nebacumab, Necitumumab, Nerelimomab, Nesvacumab, Nimotuzumab, Nivolumab, Nofetumomab merpentan, Ocaratuzumab, Ocrelizumab, Odulimomab, Ofatumumab, Olaratumab, Olokizumab, Omalizumab, Onartuzumab, Oportuzumab monatox, Oregovomab, Orticumab, Otelixizumab, Oxelumab, Ozanezumab, Ozoralizumab, Pagibaximab, Palivizumab, Panitumumab, Panobacumab, Parsatuzumab, Pascolizumab, Pateclizumab, Patritumab, Pemtumomab, Perakizumab, Pertuzumab, Pexelizumab, Pidilizumab, Pinatuzumab vedotin, Pintumomab, Placulumab, Polatuzumab vedotin, Ponezumab, Priliximab, Pritoxaximab, Pritumumab, PRO, Quilizumab, Racotumomab, Radretumab, Rafivirumab, Ramucirumab, Ranibizumab, Raxibacumab, Regavirumab, Reslizumab, Rilotumumab, Rituximab, Robatumumab, Roledumab, Romosozumab, Rontalizumab, Rovelizumab, Ruplizumab, Samalizumab, Sarilumab, Satumomab pendetide, Secukinumab, Seribantumab, Setoxaximab, Sevirumab, Sibrotuzumab, Sifalimumab, Siltuximab, Simtuzumab, Siplizumab, Sirukumab, Solanezumab, Solitomab, Sonepcizumab, Sontuzumab, Stamulumab, Sulesomab, Suvizumab, Tabalumab, Tacatuzumab tetraxetan, Tadocizumab, Talizumab, Tanezumab, Taplitumomab paptox, Tefibazumab, Telimomab aritox, Tenatumomab, Teneliximab, Teplizumab, Teprotumumab, TGN, Ticilimumab (or tremelimumab), Tildrakizumab, Tigatuzumab, TNX-, Tocilizumab (or atlizumab), Toralizumab, Tositumomab, Tovetumab, Tralokinumab, Trastuzumab, TRBS, Tregalizumab, Tremelimumab, Tucotuzumab celmoleukin, Tuvirumab, Ublituximab, Urelumab, Urtoxazumab, Ustekinumab, Vantictumab, Vapaliximab, Vatelizumab, Vedolizumab, Veltuzumab, Vepalimomab, Vesencumab, Visilizumab, Volociximab, Vorsetuzumab mafodotin, Votumumab, Zalutumumab, Zanolimumab, Zatuximab, Ziralimumab and Zolimomab aritox.

Other examples of Fc fusion proteins that may be expressed in the context of the present disclosure include, without limitation, Etanercept, Alefacept, Abatacept, Rilonacept, Romiplostim, Belatacept and Aflibercept.

Examples of anticoagulants and/or blood factors that may be expressed in the context of the present disclosure include, without limitation, Protein C, Protein S, and antithrombin, Factors I-VIII, prothrombinase, prothrombin, thrombin von Willebrand Factor (vWF), fibrinogen, fibrin and fibrinopeptides.

Examples of bone morphogenetic proteins (BMPs) that may be expressed in the context of the present disclosure include, without limitation, BMP1-BMP7, BMP8a, BMP8b, BMP 10, and BMP15.

Examples of enzymes that may be expressed in the context of the present disclosure include, without limitation, any of the enzymes assigned an Enzyme Commission Number (EC) number (e.g., EC1-EC6) by the International Union of Biochemistry and Molecular Biology (IUBMB) (Webb, Edwin C. Enzyme nomenclature 1992: recommendations of the Nomenclature Committee of the International Union of Biochemistry and Molecular Biology on the nomenclature and classification of enzymes. San Diego: Published for the International Union of Biochemistry and Molecular Biology by Academic Press. ISBN 0-12-227164-5 (1992), incorporated by reference herein). Other examples include: styrene monooxygenase (StyAB), toluene dioxygenase (TODC1C2AB), luciferase and lactase. In some embodiments, the enzyme is toluene dioxygenase. In some embodiments, the enzyme is styrene monooxygenase.

Examples of growth factors that may be expressed in the context of the present disclosure include, without limitation, Adrenomedullin (AM), Angiopoietin (Ang), Autocrine motility factor, Bone morphogenetic proteins (BMPs), Brain-derived neurotrophic factor (BDNF), Epidermal growth factor (EGF), Erythropoietin (EPO), Fibroblast growth factor (FGF), Glial cell line-derived neurotrophic factor (GDNF), Granulocyte colony-stimulating factor (G-CSF), Granulocyte macrophage colony-stimulating factor (GM-CSF), Growth differentiation factor-9 (GDF9), Hepatocyte growth factor (HGF), Hepatoma-derived growth factor (HDGF), Insulin-like growth factor (IGF), Migration-stimulating factor, Myostatin (GDF-8), Nerve growth factor (NGF) and other neurotrophins, Platelet-derived growth factor (PDGF), Thrombopoietin (TPO), Transforming growth factor alpha (TGF-a), Transforming growth factor beta (TGF-P), Tumor necrosis factor-alpha (TNF-), Vascular endothelial growth factor (VEGF), placental growth factor (P1GF), Foetal Bovine Somatotrophin (FBS) and IL-1-IL7.

Examples of peptide hormones that may be expressed in the context of the present disclosure include, without limitation, Amylin (or Islet Amyloid Polypeptide), Antimullerian hormone (or Müllerian inhibiting factor or hormone), Adiponectin, Adrenocorticotropic hormone (or corticotropin), Angiotensinogen and angiotensin, Antidiuretic hormone (or vasopressin, arginine vasopressin), Atrial-natriuretic peptide (or atriopeptin), Brain natriuretic peptide, Calcitonin, Cholecystokinin, Corticotropin-releasing hormone, Enkephalin, Endothelin, Erythropoietin, Follicle-stimulating hormone, Galanin, Gastrin, Ghrelin, Glucagon, Gonadotropin-releasing hormone, Growth hormone-releasing hormone, Human chorionic gonadotropin, Human placental lactogen, Growth hormone, Inhibin, Insulin, Insulin-like growth factor (or somatomedin), Leptin, Lipotropin, Luteinizing hormone, Melanocyte stimulating hormone, Motilin, Orexin, Oxytocin, Pancreatic polypeptide, Parathyroid hormone, Prolactin, Prolactin releasing hormone, Relaxin, Renin, Secretin, Somatostatin, Thrombopoietin, Thyroid-stimulating hormone (or thyrotropin), and Thyrotropin-releasing hormone.

Examples of interferons (IFNs) that may be expressed in the context of the present disclosure include, without limitation, IFN-α, IFN-β, IFN-ω and IFN-γ.

Examples of interleukins that may be expressed in the context of the present disclosure include, without limitation, interleukin 1-17. In some embodiments, the interleukin is Interleukin-4, Interleukin-6, Interleukin-10, Interleukin-11 or Interleukin-13.

Other examples of therapeutic proteins that may be expressed in the context of the ipresent disclosure include, without limitation, Insulin (blood glucose regulator), Pramlintide acetate (glucose control), Growth hormone GH (growth failure), Pegvisoman (growth hormone receptor antagonist), Mecasermin (IGFI, growth failure), Factor VIII (coagulation factor), Factor IX (coagulation factor, Protein C concentrate (anti-coagulation), al-proteinase inhibitor (anti-trypsin inhibitor), Erythropoietin (stimulates erythropoiesis), Filgrastim (granulocyte colony-stimulating factor, G-CSF; stimulates neutrophil proliferation), Sargramostim[36,37] (granulocytemacrophage colony-stimulating factor, GM-CSF), Oprelvekin (interleukin II, IL11), Human follicle-stimulating hormone (FSH), Human chorionic gonadotropin (HCG), Lutropin-a (human luteinizing hormone), Interleukin 2 (IL2), Interleukin-1 Receptor Agonist, Denileukin diftitox (fusion of IL2 and Diphtheria toxin), Interferon alfacon 1 (consensus interferon), Interferon-2a (IFNa2a), Interferon-2b (IFNa2b), Interferon-n3 (IFNan3), Interferon-pia (rIFN-β), Interferon-β Ib (rIFN-β), Interferon-ylb (IFNy, Salmon calcitonin (32-amino acid linear polypeptide hormone), Teriparatide (part of human parathyroid hormone 1-34 residues), Exenatide (Incretin mimetic with actions similar to glucagon-like peptide 1), Octreotide (octapeptide that mimics natural somatostatin), Dibotermin-a (recombinant human bone morphogenic protein 2), Recombinant human bone morphogenic protein 7, Histrelin acetate (gonadotropin-releasing hormone; GnRH), Palifermin (Keratinocyte growth factor, KGF), Becaplermin (platelet-derived growth factor, PDGF), Nesiritide (recombinant human B-type natriuretic peptide), Lepirudin (recombinant variant of hirudin, another variant is Bivalirudin), Anakinra (interleukin 1 (IL1) receptor antagonist), Enfuviritide (an HIV-1 gp41-derived peptide), β-Glucocerebrosidase (hydrolyzes to glucose and ceramide), Alglucosidase-a (degrades glycogen), Laronidase (digests glycosaminoglycans within lysosomes), Idursulfase (cleaves O-sulfate preventing GAGs accumulation), Galsulfase (cleave terminal sulphate from GAGs), Agalsidase-β (human α-galactosidase A, hydrolyzes glycosphingolipids), Lactase (digest lactose), Pancreatic enzymes (lipase, amylase, protease; digest food), Adenosine deaminase (metabolizes adenosine), Tissue plasminogen activator (tPA, serine protease involved in the breakdown of blood clots), Factor Vila (serine protease, causes blood to clot), Drotrecogin-a (serine protease, human activated protein C), Trypsin (serine protease, hydrolyzes proteins), Botulinum toxin type A (protease, inactivates SNAP-25 which is involved in synaptic vesicle fusion), Botulinum toxin type B (protease that inactivates SNAP-25 which is involved in synaptic vesicle fusion), Collagenase (endopeptidase, digest native collagen), Human deoxyribonuclease I (endonuclease, DNase I, cleaves DNA), Hyaluronidase (hydrolyzes hyaluronan), Papain (cysteine protease, hydrolyzes proteins), L-Asparaginase (catalyzes the conversion of L-asparagine to aspartic acid and ammonia), Rasburicase (urate oxidase, catalyzes the conversion of uric acid to allantoin), Streptokinase (Anistreplase is anisoylated plasminogen streptokinase activator complex (APS AC)), and Antithrombin III (serine protease inhibitor).

Other examples of therapeutic proteins that may be expressed in the context of the present disclosure include antigens, as defined below.

The invention further encompasses engineered C. acnes comprising vectors (e.g. plasmids) for the expression of antigens, such as a tumor antigen, a viral antigen, a bacterial antigen, a fungal antigen, a self-antigen, an allergen or a graft-specific antigen.

As used herein, an "antigen" refers to a molecule containing one or more epitopes (e.g., linear, conformational or both) that elicit an immunological response. The antigen may be of any type. In particular, it can be a protein, a polypeptide or a peptide, a carbohydrate, a lipid, a nucleic acid, such as DNA or RNA. In a particular embodiment, it is a protein, a polypeptide or a peptide. As intended herein, "protein" will be understood to encompass protein, polypeptide and peptide. Furthermore, for purposes of the present invention, an "antigen" encompasses a protein which includes modifications, such as deletions, additions and substitutions (generally conservative in nature), to the native sequence, so long as the protein maintains the ability to elicit an immunological response. These modifications may be deliberate, as through site-directed mutagenesis, or may be accidental, such as through mutations of hosts which produce the antigens.

In a particular embodiment, said antigen induces the activation or enhancement of an immune response, in particular specific to said antigen. In an alternative embodiment, said antigen results in tolerization or suppression of an immune response, in particular towards said antigen.

In a particular embodiment, said antigen decreases the subject inflammatory response.

In a particular embodiment, said antigen is a tumor antigen.

By "tumor antigen" is meant herein an antigenic substance produced in tumor cells. Tumor antigens can be, for example, peptide-containing tumor antigens, such as a polypeptide tumor antigen or glycoprotein tumor antigens. A tumor antigen can also be, for example, a saccharide-containing tumor antigen, such as a glycolipid tumor antigen or a ganglioside tumor antigen.

Tumor antigens include, but are not limited to, (a) polypeptide-containing tumor antigens, including polypeptides (which can range, for example, from about 8 to about 20 amino acids in length, although lengths outside this range are also common), lipopolypeptides and glycoproteins, and (b) saccharide-containing tumor antigens, including polysaccharides, mucins, gangliosides, glycolipids and glycoproteins. Moreover, tumor antigens can be (a) full length molecules associated with cancer cells, (b) homologs and modified forms of the same, including molecules with deleted, added and/or substituted portions, and (c) fragments of the same. Tumor antigens include, for example, class I-restricted antigens recognized by CD8+ lymphocytes or class II-restricted antigens recognized by CD4+ lymphocytes.

Numerous tumor antigens are known in the art, including: (a) cancer-testis antigens such as NY-ESO-1, SSX2, SCP1 as well as RAGE, BAGE, GAGE and MAGE family polypeptides, for example, GAGE-1, GAGE-2, MAGE-1, MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumors), (b) mutated antigens, for example, p53 (associated with various solid tumors, e.g., colorectal, lung, head and neck cancer), p21/Ras (associated with, e.g., melanoma, pancreatic cancer and colorectal cancer), CD 4 (associated with, e.g., melanoma), MUM 1 (associated with, e.g., melanoma), caspase-8 (associated with, e.g., head and neck cancer), CIA 0205 (associated with, e.g., bladder cancer), HLA-A2-R1701, beta catenin (associated with, e.g., melanoma), TCR (associated with, e.g., T-cell non-Hodgkin's lymphoma), BCR-abl (associated with, e.g., chronic myelogenous leukemia), triosephosphate isomerase, IA 0205, CDC-27, and LDLR-FUT, (c) overexpressed antigens, for example, Galectin 4 (associated with, e.g., colorectal cancer), Galectin 9 (associated with, e.g., Hodgkin's disease), proteinase 3 (associated with, e.g., chronic myelogenous leukemia), WT 1 (associated with, e.g., various leukemias), carbonic anhydrase (associated with, e.g., renal cancer), aldolase A (associated with, e.g., lung cancer), PRAME (associated with, e.g., melanoma), HER-2/neu (associated with, e.g., breast, colon, lung and ovarian cancer), alpha-fetoprotein (associated with, e.g., hepatoma), SA (associated with, e.g., colorectal cancer), gastrin (associated with, e.g., pancreatic and gastric cancer), telomerase catalytic protein, MUC-1 (associated with, e.g., breast and ovarian cancer), G-250 (associated with, e.g., renal cell carcinoma), and carcinoembryonic antigen (associated with, e.g., breast cancer, lung cancer, and cancers of the gastrointestinal tract such as colorectal cancer), (d) shared antigens, for example, melanoma-melanocyte differentiation antigens such as MART-I/Melan A, gpIOO, MC1R, melanocyte-stimulating hormone receptor, tyrosinase, tyrosinase related protein-1/TRPI and tyrosinase related protein-2/TRP2 (associated with, e.g., melanoma), (e) prostate associated antigens such as PAP, PSA, PSMA, PSH-P1, PSM-P1, PSM-P2 (associated with e.g., prostate cancer), (f) immunoglobulin idiotypes (associated with myeloma and B cell lymphomas, for example), and (g) other tumor antigens, such as polypeptide- and saccharide-containing antigens including (i) glycoproteins such as sialyl Tn and sialyl Lex (associated with, e.g., breast and colorectal cancer) as well as various mucins; glycoproteins may be coupled to a carrier protein (e.g., MUC-1 may be coupled to LH); (ii) lipopolypeptides (e.g., MUC-1 linked to a lipid moiety); (iii) polysaccharides (e.g., Globo H synthetic hexasaccharide), which may be coupled to a carrier protein (e.g., to KLH), (iv) gangliosides such as GM2, GM 12, GD2, GD3 (associated with, e.g., brain, lung cancer, melanoma), which also may be coupled to carrier proteins (e.g., KLH).

Other tumor antigens include pi 5, Hom/Mel-40, H-Ras, E2A-PRL, H4-RET, IGH-IGK, MYL-RAR, Epstein Barr virus antigens, EBNA, human papillomavirus (HPV) antigens, including E6 and E7, hepatitis B and C virus antigens, human T-cell lymphotropic virus antigens, TSP-180, p185erbB2, p180erbB-3, c-met, mn-23H I, TAG-72-4, CA 19-9, CA 72-4, CAM 17.1, NuMa, K-ras, p 16, TAGE, PSCA, CT7, 43-9F, 5T4, 791 Tgp72, beta-HCG, BCA225, BTAA, CA 125, CA 15-3 (CA 27.29\BCAA), CA 195, CA 242, CA-50, CAM43, CD68\KP1, CO-029, FGF-5, Ga733 (EpCAM), HTgp-175, M344, MA-50, MG7-Ag, MOV 18, NB/70K, NY-CO-1, RCAS1, SDCCAG16, TA-90 (Mac-2 binding protein\cyclophilin C-associated protein), TAAL6, TAG72, TLP, TPS, and the like.

In another embodiment, said antigen is a viral antigen.

By "viral antigen" is meant herein a protein encoded by a viral genome.

In certain embodiments, viral antigens preferably include epitopes which are exposed on the surface of the virus during at least one stage of its life cycle. Viral antigens are preferably conserved across multiple serotypes or isolates. Viral antigens suitable for use in the context of the invention include, but are not limited to, antigens derived from one or more of the viruses set forth below as well as the specific antigens examples identified below.

Orthomyxovirus: Viral antigens include, but are not limited to, those derived from an Orthomyxovirus, such as Influenza A, B and C. In certain embodiments, orthomyxovirus antigens are selected from one or more of the viral proteins, including hemagglutinin (HA), neuraminidase (NA), nucleoprotein (NP), matrix protein (MI), membrane protein (M2), one or more of the transcriptase components (PB1, PB2 and PA). In certain embodiments the viral antigen include HA and NA. In certain embodiments, the influenza antigens are derived from interpandemic (annual) flu strains, while in other embodiments, the influenza antigens are derived from strains with the potential to cause a pandemic outbreak (i.e., influenza strains with new haemagglutinin compared to the haemagglutinin in currently circulating strains, or influenza strains which are pathogenic in avian subjects and have the potential to be transmitted horizontally in the human population, or influenza strains which are pathogenic to humans).

Paramyxoviridae viruses: Viral antigens include, but are not limited to, those derived from Paramyxoviridae viruses, such as Pneumoviruses (RSV), Paramyxoviruses (PIV), Metapneumovirus and Morbilliviruses (Measles).

Pneumovirus: Viral antigens include, but are not limited to, those derived from a Pneumovirus, such as Respiratory syncytial virus (RSV), Bovine respiratory syncytial virus, Pneumonia virus of mice, and Turkey rhinotracheitis virus. Preferably, the Pneumovirus is RSV. In certain embodiments, pneumovirus antigens are selected from one or more of the following proteins, including surface proteins Fusion (F), Glycoprotein (G) and Small Hydrophobic protein (SH), matrix proteins M and M2, nucleocapsid proteins N, P and L and nonstructural proteins NS1 and NS2. In other embodiments, pneumovirus antigens include F, G and M.

Paramyxovirus: Viral antigens include, but are not limited to, those derived from a Paramyxovirus, such as Parainfluenza virus types 1-4 (PIV), Mumps, Sendai viruses, Simian virus 5, Bovine parainfluenza virus, Nipahvirus, Henipavirus and Newcastle disease virus. In certain embodiments, the Paramyxovirus is PIV or Mumps. In certain embodiments, paramyxovirus antigens are selected from one or more of the following proteins: Hemagglutinin-Neuraminidase (HN), Fusion proteins F1 and F2, Nucleoprotein (NP), Phosphoprotein (P), Large protein (L), and Matrix protein (M). In other embodiments, paramyxovirus proteins include HN, F1 and F2. In other embodiments, the Paramyxovirus is Nipahvirus or Henipavirus and the antigens are selected from one or more of the following proteins: Fusion (F) protein, Glycoprotein (G) protein, Matrix (M) protein, Nucleocapsid (N) protein, Large (L) protein and Phosphoprotein (P).

Poxviridae: Viral antigens include, but are not limited to, those derived from Orthopoxvirus such as Variola vera, including but not limited to, Variola major and Variola minor.

Metapneumovirus: Viral antigens include, but are not limited to, Metapneumovirus, such as human metapneumovirus (hMPV) and avian metapneumoviruses (aMPV). In certain embodiments, metapneumovirus antigens are selected from one or more of the following proteins, including surface proteins Fusion (F), Glycoprotein (G) and Small Hydrophobic protein (SH), matrix proteins M and M2, nucleocapsid proteins N, P and L. In other embodiments, metapneumovirus antigens include F, G and M.

Morbillivirus: Viral antigens include, but are not limited to, those derived from a Morbillivirus, such as Measles. In certain embodiments, morbillivirus antigens are selected from one or more of the following proteins: hemagglutinin (H), Glycoprotein (G), Fusion factor (F), Large protein (L), Nucleoprotein (NP), Polymerase phosphoprotein (P), and Matrix (M).

Picornavirus: Viral antigens include, but are not limited to, those derived from Picornaviruses, such as Enteroviruses, Rhinoviruses, Heparnavirus, Cardioviruses and Aphthoviruses. In certain embodiments, the antigens are derived from Enteroviruses, while in other embodiments the enterovirus is Poliovirus. In still other embodiments, the antigens are derived from Rhinoviruses.

Enterovirus: Viral antigens include, but are not limited to, those derived from an Enterovirus, such as Poliovirus types 1, 2 or 3, Coxsackie A virus types 1 to 22 and 24, Coxsackie B virus types 1 to 6, Echovirus (ECHO) virus) types 1 to 9, 11 to 27 and 29 to 34 and Enterovirus 68 to 71. In certain embodiments, the antigens are derived from Enteroviruses, while in other embodiments the enterovirus is Poliovirus. In certain embodiments, the enterovirus antigens are selected from one or more of the following Capsid proteins VP0, VP1, VP2, VP3 and VP4.

Bunyavirus: Viral antigens include, but are not limited to, those derived from an Orthobunyavirus, such as California encephalitis virus, a Phlebovirus, such as Rift Valley Fever virus, or a Nairovirus, such as Crimean-Congo hemorrhagic fever virus. Rhinovirus: Viral antigens include, but are not limited to, those derived from rhinovirus. In certain embodiments, the rhinovirus antigens are selected from one or more of the following Capsid proteins: VP0, VP1, VP2, VP2 and VP4.

Heparnavirus: Viral antigens include, but are not limited to, those derived from a Heparnavirus, such as, by way of example only, Hepatitis A virus (HAV).

Togavirus: Viral antigens include, but are not limited to, those derived from a Togavirus, such as a Rubivirus, an Alphavirus, or an Arterivirus. In certain embodiments, the antigens are derived from Rubivirus, such as by way of example only, Rubella virus. In certain embodiments, the togavirus antigens are selected from E1, E2, E3, C, NSP-1, NSPO-2, NSP-3 or NSP-4. In certain embodiments, the togavirus antigens are selected from E1, E2 or E3.

Flavivirus: Viral antigens include, but are not limited to, those derived from a Flavivirus, such as Tick-borne encephalitis (TBE) virus, Dengue (types 1, 2, 3 or 4) virus, Yellow Fever virus, Japanese encephalitis virus, Kyasanur Forest Virus, West Nile encephalitis virus, St. Louis encephalitis virus, Russian spring-summer encephalitis virus, Powassan encephalitis virus. In certain embodiments, the flavivirus antigens are selected from PrM, M, C, E, NS-1, NS-2a, NS2b, NS3, NS4a, NS4b, and NS5. In certain embodiments, the flavivirus antigens are selected from PrM, M and E.

Pestivirus: Viral antigens include, but are not limited to, those derived from a Pestivirus, such as Bovine viral diarrhea (BVDV), Classical swine fever (CSFV) or Border disease (BDV).

Hepadnavirus: Viral antigens include, but are not limited to, those derived from a Hepadnavirus, such as Hepatitis B virus. In certain embodiments, the hepadnavirus antigens are selected from surface antigens (L, M and S), core antigens (HBc, HBe).

Hepatitis C virus: Viral antigens include, but are not limited to, those derived from a Hepatitis C virus (HCV). In certain embodiments, the HCV antigens are selected from one or more of E1, E2, E1/E2, NS345 polyprotein, NS 345-core polyprotein, core, and/or peptides from the non-structural regions. In certain embodiments, the Hepatitis C virus antigens include one or more of the following: HCV E1 and or E2 proteins, E1/E2 heterodimer complexes, core proteins and non-structural proteins, or fragments of these antigens, wherein the non-structural proteins can optionally be modified to remove enzymatic activity but retain immunogenicity.

Rhabdovirus: Viral antigens include, but are not limited to, those derived from a Rhabdovirus, such as a Lyssavirus (Rabies virus) and Vesiculovirus (VSV). Rhabdovirus antigens may be selected from glycoprotein (G), nucleoprotein (N), large protein (L), nonstructural proteins (NS).

Caliciviridae; Viral antigens include, but are not limited to, those derived from Caliciviridae, such as Norwalk virus, and Norwalk-like Viruses, such as Hawaii Virus and Snow Mountain Virus.

Coronavirus: Viral antigens include, but are not limited to, those derived from a Coronavirus, SARS, Human respiratory coronavirus, Avian infectious bronchitis (IBV), Mouse hepatitis virus (MHV), and Porcine transmissible gastroenteritis virus (TGEV). In certain embodiments, the coronavirus antigens are selected from spike (S), envelope (E), matrix (M), nucleocapsid (N), and Hemagglutinin-esterase glycoprotein (HE). In certain embodiments, the coronavirus antigen is derived from a SARS virus. In certain embodiments, the coronavirus is derived from a SARS viral antigen as described in WO 04/92360.

Retrovirus: Viral antigens include, but are not limited to, those derived from a Retrovirus, such as an Oncovirus, a Lentivirus or a Spumavirus. In certain embodiments, the oncovirus antigens are derived from HTLV-1, HTLV-2 or HTLV-5. In certain embodiments, the lentivirus antigens are derived from HIV-1 or HIV-2. In certain embodiments, the antigens are derived from HIV-1 subtypes (or clades), including, but not limited to, HIV-1 subtypes (or clades) A, B, C, D, F, G, H, J. K, O. In other embodiments, the antigens are derived from HIV-1 circulating recombinant forms (CRFs), including, but not limited to, A/B, A/E, A/G, A/G/I, etc. In certain embodiments, the retrovirus antigens are selected from gag, pol, env, tax, tat, rex, rev, nef, vif, vpu, and vpr. In certain embodiments, the HIV antigens are selected from gag (p24gag and p55gag), env (gp160 and gp41), pol, tat, nef, rev vpu, miniproteins, (preferably p55 gag and gp140v delete). In certain embodiments, the HIV antigens are derived from one or more of the following strains: HIVIIIb, HIVSF2, HIVLAV, HIVLAI, HIVMN, HIV-1CM235, HIV-1US4, HIV-1 SF162, HIV-1TV1, HIV-1MJ4. In certain embodiments, the antigens are derived from endogenous human retroviruses, including, but not limited to, HERV-K ("old" HERV-K and "new" HERV-K).

Reovirus: Viral antigens include, but are not limited to, those derived from a Reovirus, such as an Orthoreovirus, a Rotavirus, an Orbivirus, or a Coltivirus. In certain embodiments, the reovirus antigens are selected from structural proteins $\lambda 1$, $\lambda 2$, $\lambda 3$, $\mu 1$, $\mu 2$, $\sigma 1$, $\sigma 2$, or $\sigma 3$, or nonstructural proteins $\sigma NS$, $\mu NS$, or ols. In certain embodiments, the reovirus antigens are derived from a Rotavirus. In certain embodiments, the rotavirus antigens are selected from VP1, VP2, VP3, VP4 (or the cleaved product VP5 and VP8), NSP 1, VP6, NSP3, NSP2, VP7, NSP4, or NSP5. In certain embodiments, the rotavirus antigens include VP4 (or the cleaved product VP5 and VP8), and VP7.

Parvovirus: Viral antigens include, but are not limited to, those derived from a Parvovirus, such as Parvovirus B19. In certain embodiments, the Parvovirus antigens are selected from VP-1, VP-2, VP-3, NS-1 and NS-2. In certain embodiments, the Parvovirus antigen is capsid protein VP1 or VP-2.

Delta hepatitis virus (HDV): Viral antigens include, but are not limited to, those derived from HDV, particularly δ-antigen from HDV.

Hepatitis E virus (HEV): Viral antigens include, but are not limited to, those derived from HEV.

Hepatitis G virus (HGV): Viral antigens include, but are not limited to, those derived from HGV.

Human Herpesvirus: Viral antigens include, but are not limited to, those derived from a Human Herpesvirus, such as, by way of example only, Herpes Simplex Viruses (HSV), Varicella-zoster virus (VZV), Epstein-Barr virus (EBV), Cytomegalovirus (CMV), Human Herpesvirus 6 (HHV6), Human Herpesvirus 7 (HHV7), and Human Herpesvirus 8 (HHV8). In certain embodiments, the Human Herpesvirus antigens are selected from immediate early proteins (a), early proteins (β), and late proteins (γ). In certain embodiments, the HSV antigens are derived from HSV-1 or HSV-2 strains. In certain embodiments, the HSV antigens are selected from glycoproteins gB, gC, gD and gH, fusion protein (gB), or immune escape proteins (gC, gE, or gI). In certain embodiments, the VZV antigens are selected from core, nucleocapsid, tegument, or envelope proteins. A live attenuated VZV vaccine is commercially available. In certain embodiments, the EBV antigens are selected from early antigen (EA) proteins, viral capsid antigen (VCA), and glycoproteins of the membrane antigen (MA). In certain embodiments, the CMV antigens are selected from capsid proteins, envelope glycoproteins (such as gB and gH), and tegument proteins. In other embodiments, CMV antigens may be selected from one or more of the following proteins: pp65, IE1, gB, gD, gH, gL, gM, gN, gO, UL128, UL129, gUL130, UL150, UL131, UL33, UL78, US27, US28, RL5A, RL6, RL10, RL11, RL12, RL13, UL1, UL2, UL4, UL5, UL6, UL7, UL8, UL9, UL10, UL11, UL14, UL15A, UL16, UL17, UL18, UL22A, UL38, UL40, UL41A, UL42, UL116, UL119, UL120, UL121, UL124, UL132, UL147A, UL148, UL142, UL144, UL141, UL140, UL135, UL136, UL138, UL139, UL133, UL135, UL148A, UL148B, UL148C, UL148D, US2, US3, US6, US7, USB, US9, US10, US11, US12, US13, US14, US15, US16, US17, US18, US19, US20, US21, US29, US30 and US34A. CMV antigens may also be fusions of one or more CMV proteins, such as, by way of example only, pp65/IEI (Reap et al., Vaccine (2007) 25:7441-7449).

Papovaviruses: Antigens include, but are not limited to, those derived from Papovaviruses, such as Papillomaviruses and Polyomaviruses. In certain embodiments, the Papillomaviruses include HPV serotypes 1, 2, 4, 5, 6, 8, 11, 13, 16, 18, 31, 33, 35, 39, 41, 42, 47, 51, 57, 58, 63 and 65. In certain embodiments, the HPV antigens are derived from serotypes 6, 11, 16 or 18. In certain embodiments, the HPV antigens are selected from capsid proteins (L1) and (L2), or E1-E7, or fusions thereof. In certain embodiments, the HPV antigens are formulated into virus-like particles (VLPs). In certain embodiments, the Polyomavirus viruses include BK virus and JK virus. In certain embodiments, the Polyomavirus antigens are selected from VP1, VP2 or VP3.

Adenovirus: Antigens include those derived from Adenovirus. In certain embodiments, the Adenovirus antigens are derived from Adenovirus serotype 36 (Ad-36). In certain embodiments, the antigen is derived from a protein or peptide sequence encoding an Ad-36 coat protein or fragment thereof (WO 2007/120362).

In another embodiment, said antigen is a bacterial antigen.

Examples of bacterial antigens suitable for use in the context of the invention include, but are not limited to, proteins, polysaccharides and lipopolysaccharides, which are derived from a bacteria. In certain embodiments, the bacterial antigens include epitopes which are exposed on the surface of the bacteria during at least one stage of its life cycle. Bacterial antigens are preferably conserved across multiple serotypes. In certain embodiments, the bacterial antigens include antigens derived from one or more of the bacteria set forth below as well as the specific antigens examples identified below:

*Neisseria meningitidis:* N. *meningitidis* antigens include, but are not limited to, proteins, saccharides (including a polysaccharide, or lipooligosaccharide), derived from N. *meningitidis* serogroup such as A, C, W135, Y, X or B. A useful combination of N. *meningitidis* protein antigens includes one, two or three of a NHBA, a fHbp, and/or a NadA immunogen.

*Streptococcus pneumoniae:* Streptococcus pneumoniae antigens include, but are not limited to, a saccharide (including a polysaccharide or an oligosaccharide) and/or protein from *Streptococcus pneumoniae*. In certain embodiments saccharide antigens are selected from one or more of the following pneumococcal serotypes 1, 2, 3, 4, 5, 6A, 6B, 7F, 8, 9N, 9V, 10A, 11A, 12F, 14, 15B, 17F, 18C, 19A, 19F, 20, 22F, 23F, and/or 33F. A vaccine or immunogenic composition may include multiple serotypes e.g. 2, 3, 4, 5, 6, 7, 8, 9, 10, 11, 12, 13, 14, 15, 16, 17, 18, 19, 20, 21, 22, 23 or more serotypes. 7-valent, 9-valent, 10-valent, 11-valent and 13-valent conjugate combinations are already known in the art, as is a 23-valent unconjugated combination. For example, an 10-valent combination may include saccharide from serotypes 1, 4, 5, 6B, 7F, 9V, 14, 18C, 19F and 23F. An 11-valent combination may further include saccharide from serotype 3. A 12-valent combination may add to the 10-valent mixture: serotypes 6A and 19A; 6A and 22F; 19A and 22F; 6A and 15B; 19A and 15B; r 22F and 15B; A 13-valent combination may add to the 11-valent mixture: serotypes 19A and 22F; 8 and 12F; 8 and 15B; 8 and 19A; 8 and 22F; 12F and 15B; 12F and 19A; 12F and 22F; 15B and 19A; 15B and 22F. etc. In certain embodiments, protein antigens may be selected from a protein identified in WO98/18931, WO98/18930, U.S. Pat. Nos. 6,699,703, 6,800,744, WO97/43303, WO97/37026, WO 02/079241, WO 02/34773, WO 00/06737, WO 00/06738, WO 00/58475, WO 2003/082183, WO 00/37105, WO 02/22167, WO 02/22168, WO 2003/104272, WO 02/08426, WO 01/12219, WO 99/53940, WO 01/81380, WO 2004/092209, WO 00/76540, WO 2007/116322, LeMieux et al., Infect. Imm. (2006) 74:2453-2456, Hoskins et al., J. Bacteriol. (2001) 183:5709-5717, Adamou et al., Infect. Immun. (2001) 69(2):949-958, Briles et al., J. Infect. Dis. (2000) 182:1694-1701, Talkington et al., Microb. Pathog. (1996) 21(1):17-22, Bethe et al., FEMS Microbiol. Lett. (2001) 205(1):99-104, Brown et al., Infect. Immun. (2001) 69:6702-6706, Whalen et al., FEMS Immunol. Med. Microbiol. (2005) 43:73-80, Jomaa et al., Vaccine (2006) 24(24):5133-5139. In other embodiments, *Streptococcus pneumoniae* proteins may be selected from the Poly Histidine Triad family (PhtX), the Choline Binding Protein family (CbpX), CbpX truncates, LytX family, LytX truncates, CbpX truncate-LytX truncate chimeric proteins, pneumolysin (Ply), PspA, PsaA, Sp128, SpIOI, Sp130, Sp125, Sp133, pneumococcal pilus subunits.

*Streptococcus pyogenes* (Group A *Streptococcus*): Group A *Streptococcus* antigens include, but are not limited to, a protein identified in WO 02/34771 or WO 2005/032582 (including GAS 40), fusions of fragments of GAS M proteins (including those described in WO 02/094851, and Dale, Vaccine (1999) 17:193-200, and Dale, Vaccine 14(10): 944-948), fibronectin binding protein (Sfbl), Streptococcal heme-associated protein (Shp), and Streptolysin S (SagA).

*Moraxella catarrhalis*: Moraxella antigens include, but are not limited to, antigens identified in WO 02/18595 and WO 99/58562, outer membrane protein antigens (HMW-OMP), C-antigen, and/or LPS.

*Bordetella pertussis*: Pertussis antigens include, but are not limited to, pertussis toxoid (PT) and filamentous haemagglutinin (FHA) from *B. pertussis*, optionally also combination with pertactin and/or agglutinogens 2 and 3.

*Burkholderia*: Burkholderia antigens include, but are not limited to *Burkholderia mallei, Burkholderia pseudomallei* and *Burkholderia cepacia*.

*Staphylococcus aureus*: *S. aureus* antigens include, but are not limited to, a polysaccharide and/or protein from *S. aureus*. *S. aureus* polysaccharides include, but are not limited to, type 5 and type 8 capsular polysaccharides (CP5 and CP8) optionally conjugated to nontoxic recombinant *Pseudomonas aeruginosa* exotoxin A, such as StaphVAX™, type 336 polysaccharides (336PS), polysaccharide intercellular adhesions (PIA, also known as PNAG). *S. aureus* proteins include, but are not limited to, antigens derived from surface proteins, invasins (leukocidin, kinases, hyaluronidase), surface factors that inhibit phagocytic engulfment (capsule, Protein A), carotenoids, catalase production, Protein A, coagulase, clotting factor, and/or membrane-damaging toxins (optionally detoxified) that lyse eukaryotic cell membranes (hemolysins, leukotoxin, leukocidin). In certain embodiments, *S. aureus* antigens may be selected from a protein identified in WO 02/094868, WO 2008/019162, WO 02/059148, WO 02/102829, WO 03/011899, WO 2005/079315, WO 02/077183, WO 99/27109, WO 01/70955, WO 00/12689, WO 00/12131, WO 2006/032475, WO 2006/032472, WO 2006/032500, WO 2007/113222, WO 2007/113223, WO 2007/113224. In other embodiments, *S. aureus* antigens may be selected from IsdA, IsdB, IsdC, SdrC, SdrD, SdrE, ClfA, ClfB, SasF, SasD, SasH (AdsA), Spa, EsaC, EsxA, EsxB, Emp, HlaH35L, CP5, CP8, PNAG, 336PS.

*Staphylococcus epidermis*: *S. epidermidis* antigens include, but are not limited to, slime-associated antigen (SAA).

*Clostridium tetani* (Tetanus): Tetanus antigens include, but are not limited to, tetanus toxoid (TT).

*Clostridium perfringens*: Antigens include, but are not limited to, Epsilon toxin from *Clostridium perfringens*.

*Clostridium botulinum* (Botulism): Botulism antigens include, but are not limited to, those derived from *C. botulinum*.

*Corynebacterium diphtheriae* (Diphtheria): Diphtheria antigens include, but are not limited to, diphtheria toxin, preferably detoxified, such as CRM 197. In certain embodiments, the diphtheria toxoids are used as carrier proteins.

*Haemophilus influenzae* B (Hib): Hib antigens include, but are not limited to, a Hib saccharide antigen. The Hib antigens may be conjugated.

*Pseudomonas aeruginosa*: Pseudomonas antigens include, but are not limited to, endotoxin A, Wzz protein, *P. aeruginosa* LPS, LPS isolated from PAO1 (O5 serotype), and/or Outer Membrane Proteins, including Outer Membrane Proteins F (OprF).

*Brucella*: Bacterial antigens derived from *Brucella*, including but not limited to, *B. abortus, B. canis, B. melitensis, B. neotomae, B. ovis, B. suis* and *B. pinnipediae*.

*Francisella*: Bacterial antigens derived from *Francisella*, including but not limited to, *F. novicida, F. philomiragia* and *F. tularensis*.

*Streptococcus agalactiae* (Group B *Streptococcus*): Group B *Streptococcus* antigens include, but are not limited to, a protein or saccharide antigen identified in WO 02/34771, WO 03/093306, WO 04/041157, or WO 2005/002619 (including proteins GBS 80, GBS 104, GBS 276 and GBS 322, and including saccharide antigens derived from serotypes Ia, Ib, Ia/c, II, III, IV, V, VI, VII and VIII).

*Neisseria gonorrhoeae*: Gonorrhoeae antigens include, but are not limited to, Por (or porin) protein, such as PorB (see Zhu et al., Vaccine (2004) 22:660-669), a transferrin binding protein, such as TbpA and TbpB (See Price et al., Infection and Immunity (2004) 71(1):277-283), a opacity protein (such as Opa), a reduction-modifiable protein (Rmp), and outer membrane vesicle (OMV) preparations (see Plante et al, J Infectious Disease (2000) 182:848-855), also see, e.g., WO99/24578, WO99/36544, WO99/57280, WO02/079243).

*Chlamydia trachomatis*: Chlamydia trachomatis antigens include, but are not limited to, antigens derived from serotypes A, B, Ba and C (agents of trachoma, a cause of blindness), serotypes L1, L2 & L3 (associated with Lymphogranuloma venereum), and serotypes, D-K. In certain embodiments, *Chlamydia trachomatis* antigens include, but are not limited to, an antigen identified in WO 00/37494, WO 03/049762, WO 03/068811, or WO 05/002619, including PepA (CT045), LcrE (CT089), ArtJ (CT381), DnaK (CT396), CT398, OmpH-like (CT242), L7/L12 (CT316), OmcA (CT444), AtoSS (CT467), CT547, Eno (CT587), HrtA (CT823), and MurG (CT761).

*Treponema pallidum* (Syphilis): Syphilis antigens include, but are not limited to, TmpA antigen.

*Haemophilus ducreyi* (causing chancroid): *Ducreyi* antigens include, but are not limited to, outer membrane protein (DsrA).

*Enterococcus faecalis* or *Enterococcus faecium*: Antigens include, but are not limited to, a trisaccharide repeat or other *Enterococcus* derived antigens.

*Helicobacter pylori*: *H. pylori* antigens include, but are not limited to, CagA, VacA, NAP, HopX, HopY and/or urease antigen.

*Staphylococcus saprophyticus*: Antigens include, but are not limited to, the 160 kDa hemagglutinin of *S. saprophyticus* antigen.

*Yersinia enterocolitica*: Antigens include, but are not limited to, LPS.

*E. coli*: *E. coli* antigens may be derived from enterotoxigenic *E. coli* (ETEC), enteroaggregative *E. coli* (EAggEC), diffusely adhering *E. coli* (DAEC), enteropathogenic *E. coli* (EPEC), extraintestinal pathogenic *E. coli* (ExPEC) and/or enterohemorrhagic *E. coli* (EHEC). ExPEC antigens include, but are not limited to, accessory colonization factor (orf3526), orf353, bacterial Ig-like domain (group 1) protein (orf405), orf1364, NodT-family outer-membrane-factor-lipoprotein efflux transporter (orf1767), gspK (orf3515), gspJ (orf3516), tonB-dependent siderophore receptor (orf3597), fimbrial protein (orf3613), upec-948, upec-1232, A chain precursor of the type-1 fimbrial protein (upec-1875), yap H homolog (upec-2820), and hemolysin A (recp-3768).

*Bacillus anthracis* (anthrax): *B. anthracis* antigens include, but are not limited to, A-components (lethal factor (LF) and edema factor (EF)), both of which can share a common B-component known as protective antigen (PA). In certain embodiments, *B. anthracis* antigens are optionally detoxified.

*Yersinia pestis* (plague): Plague antigens include, but are not limited to, F1 capsular antigen, LPS, *Yersinia pestis* V antigen.

*Mycobacterium tuberculosis*: Tuberculosis antigens include, but are not limited to, lipoproteins, LPS, BCG antigens, a fusion protein of antigen 85B (Ag85B), ESAT-6, *Mycobacterium tuberculosis* (Mtb) isocitrate dehydrogenase associated antigens, and MPT51 antigens.

*Rickettsia*: Antigens include, but are not limited to, outer membrane proteins, including the outer membrane protein A and/or B (OmpB), LPS, and surface protein antigen (SPA).

*Listeria monocytogenes*: Bacterial antigens include, but are not limited to, those derived from *Listeria monocytogenes*.

*Chlamydia pneumoniae*: Antigens include, but are not limited to, those identified in WO 02/02606.

*Vibrio cholerae*: Antigens include, but are not limited to, proteinase antigens, LPS, particularly lipopolysaccharides of *Vibrio cholerae* II, O1 Inaba O-specific polysaccharides, *V. cholera* O139, antigens of IEM108 vaccine and Zonula occludens toxin (Zot).

*Salmonella typhi* (typhoid fever): Antigens include, but are not limited to, capsular polysaccharides preferably conjugates (Vi, i.e. vax-TyVi).

*Borrelia burgdorferi* (Lyme disease): Antigens include, but are not limited to, lipoproteins (such as OspA, OspB, Osp C and Osp D), other surface proteins such as OspE-related proteins (Erps), decorin-binding proteins (such as DbpA), and antigenically variable VI proteins, such as antigens associated with P39 and P13 (an integral membrane protein), VIsE Antigenic Variation Protein.

*Porphyromonas gingivalis*: Antigens include, but are not limited to, *P. gingivalis* outer membrane protein (OMP).

*Klebsiella*: Antigens include, but are not limited to, an OMP, including OMP A, or a polysaccharide optionally conjugated to tetanus toxoid.

Other bacterial antigens used in the context of the invention include, but are not limited to, capsular antigens, polysaccharide antigens, or protein antigens of any of the above. In certain embodiments, the bacterial antigens used in the context of the invention are derived from gram-negative bacteria, while in other embodiments they are derived from gram-positive bacteria. In certain embodiments, the bacterial antigens used in the context of the invention are derived from aerobic bacteria, while in other embodiments they are derived from anaerobic bacteria.

In another embodiment, said antigen is a fungal antigen.

Examples of fungal antigens used in the context of the invention include, but are not limited to, those derived from one or more of the fungi set forth below.

Fungal antigens may be derived from Dermatophytes, including: *Epidermophyton floccosum, Microsporum audouini, Microsporum canis, Microsporum distortum, Microsporum equinum, Microsporum gypsum, Microsporum nanum, Trichophyton concentricum, Trichophyton equinum, Trichophyton gallinae, Trichophyton gypseum, Trichophyton megnini, Trichophyton mentagrophytes, Trichophyton quinckeanum, Trichophyton rubrum, Trichophyton schoenleinii, Trichophyton tonsurans, Trichophyton verrucosum, T. verrucosum* var. *album,* var. *discoides,* var. *ochraceum, Trichophyton violaceum,* and/or *Trichophyton faviforme*.

Fungal antigens may also be derived from *Aspergillus fumigatus, Aspergillus flavus, Aspergillus niger, Aspergillus nidulans, Aspergillus terreus, Aspergillus sydowii, Aspergillus flavarus, Aspergillus glaucus, Blastoschizomyces capitatus, Candida albicans, Candida enolase, Candida tropicalis, Candida glabrata, Candida krusei, Candida parapsilosis, Candida stellatoidea, Candida krusei, Candida parakwsei, Candida lusitaniae, Candida pseudotropicalis, Candida guilliermondii, Cladosporium carrionii, Coccidioides immitis, Blastomyces dermatitidis, Cryptococcus neoformans, Geotrichum clavatum, Histoplasma capsulatum, Klebsiella pneumoniae, Microsporidia, Encephalitozoon* spp., *Septata intestinalis* and *Enterocytozoon bieneusi;* the less common are *Brachiola* spp, Microsporidium spp., *Nosema* spp., *Pleistophora* spp., *Trachipleistophora* spp., *Vittaforma* spp *Paracoccidioides brasiliensis, Pneumocystis Pythium insidiosum, Pityrosporum ovale, Saccharomyces cerevisiae, Saccharomyces boulardii, Saccharomyces pombe, Scedosporium apiospermum, Sporothrix schenckii, Trichosporon beigelii, Toxoplasma gondii, Penicillium mameffei, Malassezia* spp., *Fonsecaea* spp., *Wangiella* spp., *Sporothrix* spp., *Basidiobolus* spp., *Conidiobolus* spp., *Rhizopus* spp, *Mucor* spp, *Absidia* spp, *Mortierella* spp, *Cunninghamella* spp, *Saksenaea* spp., *Alternaria* spp, *Curvularia* spp, *Helminthosporium* spp, *Fusarium* spp, *Aspergillus* spp, *Penicillium* spp, *Monilinia* spp, *Rhizoctonia* spp, *Paecilomyces* spp, *Pithomyces* spp, and *Cladosporium* spp.

For example, the fungal antigen may elicit an immune response against a *Candida* fungus such as *C. albicans*.

In another embodiment, said antigen is a self-antigen.

In the context of the invention, the term "self-antigen" refers to an immunogenic antigen or epitope which is native to the subject and which may be involved in the pathogenesis of an autoimmune disease.

In some embodiments, the self-antigen is a central nervous system (CNS) antigen. In some embodiments, the self-antigen is a multiple sclerosis-associated antigen, a diabetes mellitus-associated antigen, a rheumatoid arthritis associated antigen, a myocarditis associated self-antigen, or a thyroiditis associated antigen.

Exemplary self-antigens are disclosed, for example, in US Patent Application Publication 2016/0022788, which is incorporated herein by reference in its entirety.

In some embodiments, the self-antigen is a multiple sclerosis-associated antigen. In some embodiments, the self-antigen is an antigenic peptide of or derived from myelin oligodendrocyte glycoprotein (MOG), myelin basic protein (MBP), myelin associated glycoprotein (MAG), alphaB-crystallin, S100beta, or proteolipid protein (PLP).

In some embodiments, the self-antigen is a diabetes mellitus-associated antigen. In some embodiments, the self-antigen is selected from insulin, chromogranin A, glutamic acid decarboxylase (GAD1; GAD67), glutamate decarboxylase 2 (GAD2; GAD65) and islet-specific glucose-6-phosphatase catalytic subunit-related protein and combinations thereof. Antigenic fragments and antigenic derivatives of these antigens are also contemplated. In some embodiments, the antigen can be proinsulin.

In some embodiments, the self-antigen is a rheumatoid arthritis associated antigen. In some embodiments, the rheumatoid arthritis associated self-antigen can be the peptide (Q/R)(K/R)RAA. In some embodiments, the arthritis associated self-antigen can be type II collagen or a fragment thereof.

In some embodiments, the self-antigen is a myocarditis associated self-antigen. In some embodiments, the myocarditis associated self-antigen is myosin or an antigenic fragment or antigenic derivative. In some embodiments, the antigen can be a peptide contained in human myosin. In some embodiments, the antigen can be a peptide contained within a-myosin.

In some embodiments, the self-antigen is a thyroiditis associated antigen. In some embodiments, the self-antigen is selected from thyroid peroxidase (TPO), thyroglobulin, or Pendrin.

In another embodiment, said antigen is an allergen.

An "allergen" is defined as a substance, usually a protein, which elicits the production of IgE antibodies in predisposed individuals. Similar definitions are presented in the following references: Clin. Exp. Allergy, No. 26, pp. 494-516 (1996); Mol. Biol. of Allergy and Immunology, ed. R. Bush, Immunology and Allergy Clinics of North American Series (August 1996). In a particular embodiment, the antigen is a protein allergen, i.e. any amino acid chain likely to trigger an allergic response, including short peptides of about 6 to 20 amino acids, polypeptides, or full proteins.

Non limitative examples of allergens include pollen allergens (such as tree-, herb, weed-, and grass pollen allergens), insect allergens (such as inhalant, saliva and venom allergens, e.g., cockroach and midges allergens, hymenoptera venom allergens), mite allergens, animal hair and dandruff allergens (from e.g. dog, cat, horse, rat, mouse etc.), and food allergens.

For instance, the protein allergen may be selected from the group consisting of a protein allergen of the genus *Dermatophagoides*; a protein allergen of the genus Fells; a protein allergen of the genus *Ambrosia*; a protein allergen of the genus *Lolium*; a protein allergen of the genus *Cryptomeria*; a protein allergen of the genus *Alternaria*; a protein allergen of the genus *Alder*, a protein allergen of the genus *Betula*; a protein allergen of the genus of *Blomia*; a protein allergen of the genus *Quercus*; a protein allergen of the genus *Olea*; a protein allergen of the genus *Artemisia*; a protein allergen of the genus *Plantago*; a protein allergen of the genus *Parietaria*; a protein allergen of the genus *Canine*; a protein allergen of the genus *Blattella*; a protein allergen of the genus *Apis*; a protein allergen of the genus *Cupressus*; a protein allergen of the genus *Thuya*; a protein allergen of the genus *Chamaecyparis*; a protein allergen of the genus *Periplaneta*; a protein allergen of the genus *Agropyron*; a protein allergen of the genus *Secale*; a protein allergen of the genus *Triticum*; a protein allergen of the genus *Cynorhodon*; a protein allergen of the genus *Juniperus*; a protein allergen of the genus *Dactylis*; a protein allergen of the genus *Festuca*; a protein allergen of the genus *Poa*; a protein allergen of the genus *Avena*; a protein allergen of the genus *Holcus*; a protein allergen of the genus *Anthoxanthum*; a protein allergen of the genus *Arrhenatherum*; a protein allergen of the genus *Agrostis*; a protein allergen of the genus *Phleum*; a protein allergen of the genus *Phalaris*; a protein allergen of the genus *Paspalum*; and a protein allergen of the genus *Sorghum*.

Examples of various known protein allergens derived from some of the above-identified genus include: *Betula* (*verrucosa*) Bet v I; Bet v II; *Blomia* Blo t I; Blo t III; Blo t V; Blo t XII; *Cynorhodon* Cyn d I; *Dermatophagoides* (*pteronyssinus* or *farinae*) Der p I; Der p II; Der p III; Der p VII; Der f I; Der f II; Der f III; Der f VII; *Felis* (*domesticus*) Fel d I; *Ambrosia* (*artemiisfolia*) Amb a I.1; Amb a I.2; Amb a I.3; Amb a I.4; Amb a II; *Lollium* (*perenne*) Lol p I; Lot p II; Lol p III; Lot p IV; Lol p IX (Lol p V or Lol p Ib); *Cryptomeria* (*japonica*) Cry j I; Cry j II; *Canis* (*familiaris*) Can f I; Can f II; *Juniperus* (*sabinoides* or *virginiana*) Jun s I; Jun v I; *Juniperus* (ashes) Jun a I; Jun a II; *Dactylis* (*glomerata*) Dac g I; Dac g V; *Poa* (*pretensis*) Poa p I; PhI p I; PhI p V; PhI p VI and *Sorghum* (*halepensis*) Sor h I.

Food allergens may originate from milk and milk products, eggs, legumes (peanuts and soy), tree nuts, cereals (such as wheat), brassicaceae (such as mustard), crustaceans, fish, and mollusks. In particular, food allergens may be ovalbumin or gluten.

The invention also encompasses vaccine and/or immunogenic and/or immunotherapeutic compositions comprising a DNA vector, as defined above, comprising a nucleic acid encoding an antigen, such as a tumor antigen, a viral antigen, a bacterial antigen, a fungal antigen, a self-antigen, an allergen or a graft-specific antigen, as defined above, or an engineered *C. acnes* comprising said DNA vector; and optionally an adjuvant.

Any conventional or exploratory, synthetic or biological adjuvant for vaccination, including heat-labile enterotoxin (LT), cholera-toxin (CT), cholera toxin B subunit (CTB), polymerised liposomes, mutant toxins, probiotic bacteria, oligonucleotides, RNA, siRNA, DNA, lipids can be used.

The invention also encompasses methods to prevent and/or a treat cancer in a subject in need thereof, comprising administering to said subject a therapeutically or prophylactically efficient amount of a DNA vector comprising a nucleic acid encoding a tumor antigen, as defined above, or of an engineered *C. acnes* comprising said DNA vector. The invention also concerns a DNA vector comprising a nucleic acid encoding a tumor antigen, as defined above, or an engineered *C. acnes* comprising said DNA vector for use in a method to prevent and/or treat cancer in a subject.

As used herein, the term "cancer" means a type of hyperproliferative disease that includes a malignancy characterized by deregulated or uncontrolled cell growth. Cancers of virtually every tissue are known. Examples of cancer include, but are not limited to, carcinoma, lymphoma, blastema, sarcoma, and leukemia or lymphoid malignancies. More particular examples of such cancers are noted below and include squamous cell cancer (e.g., epithelial squamous cell cancer), lung cancer (including small-cell lung cancer, non-small cell lung cancer, adenocarcinoma of the lung and squamous carcinoma of the lung), cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial cancer, uterine carcinoma, salivary gland carcinoma, kidney or renal cancer, prostate cancer, thyroid cancer, hepatic carcinoma, as well as head and neck cancer. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor).

The term "cancer," is encompassed within the scope of the broader term "abnormal cellular proliferation", which can also be referred to as "excessive cellular proliferation or "cellular proliferative disease". Examples of diseases associated abnormal cellular proliferation include metastatic tumors, malignant tumors, benign tumors, cancers, precancers, hyperplasias, warts, and polyps, as well as non-cancerous conditions such as benign melanomas, benign chondroma, benign prostatic hyperplasia, moles, dysplastic nevi, dysplasia, hyperplasias, and other cellular growths occurring within the epidermal layers. Classes of precancers include acquired small or microscopic precancers, acquired large lesions with nuclear atypia, precursor lesions occurring with inherited hyperplastic syndromes that progress to cancer, and acquired diffuse hyperplasias and diffuse metaplasias. Examples of small or microscopic precancers include HGSIL (high grade squamous intraepithelial lesion of uterine cervix), AIN (anal intraepithelial neoplasia), dysplasia of vocal cord, aberrant crypts (of colon), PIN (prostatic intraepithelial neoplasia). Examples of acquired large lesions with nuclear atypia include tubular adenoma, AILD (angioimmunoblastic lymphadenopathy with dysproteinemia), atypical meningioma, gastric polyp, large plaque parapsoriasis, myelodysplasia, papillary transitional cell carcinoma in-situ, refractory anemia with excess blasts, and Schneiderian papilloma.

The invention also encompasses methods to prevent and/or treat a viral infection in a subject in need thereof, comprising administering to said subject a therapeutically or prophylactically efficient amount of a DNA vector comprising a nucleic acid encoding a viral antigen, as defined above, or of an engineered *C. acnes* comprising said DNA vector. The invention also concerns a DNA vector comprising a nucleic acid encoding a viral antigen, as defined above, or an engineered *C. acnes* comprising said DNA vector for use in a method to prevent and/or treat a viral infection in a subject.

In said embodiment, said antigen preferably induces the activation or enhancement of an immune response, in particular specific to said antigen.

Particular examples of viral infections include, but are not limited to, cytomegalovirus (CMV) pneumonia, enteritis and retinitis; Epstein-Barr virus (EBV) lymphoproliferative disease; chicken pox/shingles (caused by varicella zoster virus, VZV); HSV-1 and -2 mucositis; HSV-6 encephalitis, BK-virus hemorrhagic cystitis; viral influenza; pneumonia from respiratory syncytial virus (RSV); AIDS (caused by HIV); and hepatitis A, B or C. Additional examples of viral infections include infections caused by Retroviridae; Picornaviridae (for example, polio viruses, hepatitis A virus; enteroviruses, human coxsackie viruses, rhinoviruses, echoviruses); Calciviridae (such as strains that cause gastroenteritis); Togaviridae (for example, equine encephalitis viruses, rubella viruses); Flaviviridae (for example, dengue viruses, encephalitis viruses, yellow fever viruses); Coronaviridae (for example, coronaviruses); Rhabdoviridae (for example, vesicular stomatitis viruses, rabies viruses); Filoviridae (for example, ebola viruses); Paramyxoviridae (for example, parainfluenza viruses, mumps virus, measles virus, respiratory syncytial virus); Orthomyxoviridae (for example, influenza viruses); Bungaviridae (for example, Hantaan viruses, bunga viruses, phleboviruses and Nairo viruses); Arenaviridae (hemorrhagic fever viruses); Reoviridae (e.g., reoviruses, orbiviruses and rotaviruses); Bimaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and HSV-2, varicella zoster virus, cytomegalovirus (CMV), herpes viruses); Poxviridae (variola viruses, vaccinia viruses, pox viruses); and Iridoviridae (such as African swine fever virus); and unclassified viruses (for example, the etiological agents of Spongiform encephalopathies, the agent of delta hepatitis (thought to be a defective satellite of hepatitis B virus), the agents of non-A, non-B hepatitis (class I=internally transmitted; class 2=parenterally transmitted (i.e., Hepatitis C)); Norwalk and related viruses, and astroviruses.

The invention also encompasses methods to prevent and/or treat a bacterial infection in a subject in need thereof, comprising administering to said subject a therapeutically or prophylactically efficient amount of a DNA vector comprising a nucleic acid encoding a bacterial antigen, as defined above, or of an engineered *C. acnes* comprising said DNA vector. The invention also concerns a DNA vector comprising a nucleic acid encoding a bacterial antigen, as defined above, or an engineered *C. acnes* comprising said DNA vector for use in a method to prevent and/or treat a bacterial infection in a subject.

In said embodiment, said antigen preferably induces the activation or enhancement of an immune response, in particular specific to said antigen.

Examples of bacterial infections include, but are not limited to, infections caused by *Helicobacter pylori, Borrelia burgdorferi, Legionella pneumophila,* Mycobacteria sp. (such as *M. tuberculosis, M. avium, M. intracellulare, M. kansasii, M. gordonae), Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (anaerobic sps.), *Streptococcus pneumoniae,* pathogenic *Campylobacter* sp., *Enterococcus* sp., *Haemophilus influenzae, Bacillus anthracis, Corynebacterium diphtheriae, Corynebacterium* sp., *Erysipelothrix rhusiopathiae, Clostridium perfringens, Clostridium tetani, Enterobacter aerogenes, Klebsiella pneumoniae, Pasteurella multocida, Bacteroides* sp., *Fusobacterium nucleatum,*

*Streptobacillus moniliformis, Treponema pallidum, Treponema pertenue, Leptospira*, and *Actinomyces israelii*.

The invention also encompasses methods to prevent and/or treat a fungal infection in a subject in need thereof, comprising administering to said subject a therapeutically or prophylactically efficient amount of a DNA vector comprising a nucleic acid encoding a fungal antigen, as defined above, or of an engineered *C. acnes* comprising said DNA vector. The invention also concerns a DNA vector comprising a nucleic acid encoding a fungal antigen, as defined above, or an engineered *C. acnes* comprising said DNA vector for use in a method to prevent and/or treat a fungal infection in a subject.

In said embodiment, said antigen preferably induces the activation or enhancement of an immune response, in particular specific to said antigen.

Examples of fungal infections include but are not limited to: aspergillosis; thrush (caused by *Candida albicans*); cryptococcosis (caused by *Cryptococcus*); and histoplasmosis. Thus, examples of fungal infections include, but are not limited to, infections caused by *Cryptococcus neoformans, Histoplasma capsulatum, Coccidioides immitis, Blastomyces dermatitidis, Chlamydia trachomatis*, or *Candida albicans*.

The invention also encompasses methods to prevent and/or treat an auto-immune disease in a subject in need thereof, comprising administering to said subject a therapeutically or prophylactically efficient amount of a DNA vector comprising a nucleic acid encoding a self-antigen, as defined above, or of an engineered *C. acnes* comprising said DNA vector. The invention also concerns a DNA vector comprising a nucleic acid encoding a self-antigen, as defined above, or an engineered *C. acnes* comprising said DNA vector for use in a method to prevent and/or treat an auto-immune disease in a subject.

In said embodiment, said antigen preferably results in tolerization or suppression of an immune response, in particular towards said antigen.

Autoimmune diseases include, but are not limited to, multiple sclerosis, rheumatoid arthritis, myasthenia gravis, psoriasis, systemic lupus erythematosus, autoimmune thyroiditis (Hashimoto's thyroiditis), Graves' disease, inflammatory bowel disease, autoimmune uveoretinitis, myocarditis, polymyositis, and certain types of diabetes, including Type 1 diabetes.

The invention also encompasses methods to prevent and/or treat allergy, such as asthma in a subject in need thereof, comprising administering to said subject a therapeutically or prophylactically efficient amount of a DNA vector comprising a nucleic acid encoding an allergen, as defined above, or of an engineered *C. acnes* comprising said DNA vector. The invention also concerns a DNA vector comprising a nucleic acid encoding an allergen, as defined above, or an engineered *C. acnes* comprising said DNA vector for use in a method to prevent and/or treat allergy, such as asthma in a subject.

In said embodiment, said antigen preferably results in tolerization or suppression of an immune response, in particular towards said antigen.

In the context of the disclosure allergy relates to asthma or to the allergies due to the above-defined allergens.

The invention also encompasses methods to prevent and/or treat graft rejection in a subject in need thereof, comprising administering to said subject a therapeutically or prophylactically efficient amount of a DNA vector comprising a nucleic acid encoding a graft-specific antigen, as defined above, or of an engineered *C. acnes* comprising said DNA vector. The invention also concerns a DNA vector comprising a nucleic acid encoding a graft-specific antigen, as defined above, or an engineered *C. acnes* comprising said DNA vector for use in a method to prevent and/or treat graft rejection in a subject.

In said embodiment, said antigen preferably results in tolerization or suppression of an immune response, in particular towards said antigen.

Unless defined otherwise, all technical and scientific terms used herein have the same meaning as commonly understood by one of ordinary skill in the art to which this invention belongs.

All publications mentioned herein are incorporated herein by reference. It is understood that the present disclosure supersedes any disclosure of an incorporated publication to the extent there is a contradiction.

It must be noted that, as used in this specification and the appended claims, the singular forms "a", "an" and "the" include plural referents unless the content clearly dictates otherwise. Thus, for example, reference to "an antigen" includes a mixture of two or more antigens, and the like.

Definitions

«Delivery Vehicle»

As used herein, the term «delivery vehicle» refers to any mean that allows the transfer of a payload into a bacterium.

There are several types of delivery vehicle encompassed by the present invention including, without limitation, bacteriophage scaffold, virus scaffold, chemical based delivery vehicle (e.g., cyclodextrin, calcium phosphate, cationic polymers, cationic liposomes), protein-based or peptide-based delivery vehicle, lipid-based delivery vehicle, nanoparticle-based delivery vehicles, non-chemical-based delivery vehicles (e.g., transformation, electroporation, sonoporation, optical transfection), particle-based delivery vehicles (e.g., gene gun, magnetofection, impalefection, particle bombardment, cell-penetrating peptides) or donor bacteria (conjugation).

Any combination of delivery vehicles is also encompassed by the present invention.

The delivery vehicle can refer to a bacteriophage derived scaffold and can be obtained from a natural, evolved or engineered capsid.

In some embodiment, the delivery vehicle is the payload as bacteria are naturally competent to take up a payload from the environment on their own.

«Conjugation»

Conjugation is a process by which a donor bacteria actively transfers DNA to a recipient bacteria. DNA transfer involves recognition of an origin of transfer (oriT) by a protein known as the relaxase which nicks and covalently binds to the oriT DNA. The relaxase and single stranded DNA are then typically injected into a recipient cell through a type IV secretion system. During conjugation of a plasmid or ICE (Integrative and Conjugative Elements), transfer of the relaxase is coupled with rolling circle replication of the plasmid or ICE. Once in the recipient, the relaxase will recircularize the transferred strand at the oriT. —Smillie et al, Microbiology and Molecular Biology Rev, 2010, P. 434-452.

Examples of conjugative plasmids are F, R388, RP4, RK2, R6K. Plasmids of the following groups are frequently conjugative and carry a type IV secretion system: IncA, IncB/O (Ind O), IncC, IncD, IncE, IncFI, IncF2, IncG, IncHM, IncHI2, Inch, IncI2, IncJ, IncK, IncUM, IncN, IncP, IncQI, IncQ2, IncR, IncS, IncT, IncU, IncV, IncW, IncXI, IncX2, IncY, IncZ, ColE1, ColE2, ColE3, p15A, pSC101, IncP-2, IncP-5, IncP-7, IncP-8, IncP-9, Ind, Inc4, Inc7, Inc8, Inc9, Inc11, Inc13, Ind 4 or Ind 8.

List of type IV secretion systems can be found in public databases such as AtlasT4SS.

Conjugation is not limited to plasmids but can also occur from the chromosome of bacteria when an oriT is present. This can happen naturally through the recombination of conjugative plasmids in the chromosome or artificially by introducing an oriT at a position of interest in the chromosome. A particular class of conjugative elements are known as Integrative and Conjugative Elements (ICEs). These are not maintained in a circular plasmidic form but integrate in the host chromosome. Upon transfer, the ICE excises from the chromosome and is then transferred in a manner akin to a conjugative plasmid. Once in a recipient cell, the ICE integrates in the recipient's chromosome. Lists of ICE elements can be found in public databases such as ICEberg.

ICEs or plasmids which carry both an origin of transfer and the type IV secretion system genes are commonly referred to as mobile elements, while ICEs or plasmids that only carry the oriT can be referred to as mobilisable plasmids. Mobilisable elements can only be transferred from the donor cell to a recipient cell if a type IV secretion system is expressed in trans, either by another plasmid or from the chromosome of the host cell.

«Payload»

As used herein, the term «payload» refers to any nucleic acid sequence or amino acid sequence, or a combination of both (such as, without limitation, peptide nucleic acid or peptide-oligonucleotide conjugate) transferred into a bacterium with a delivery vehicle.

The term «payload» may also refer to a plasmid, a vector or a cargo.

The payload can be a phagemid or phasmid obtained from natural, evolved or engineered bacteriophage genome. The payload can also be composed only in part of phagemid or phasmid obtained from natural, evolved or engineered bacteriophage genome.

In some embodiment, the payload is the delivery vehicle as bacteria are naturally competent to take up a payload from the environment on their own.

«Nucleic Acid»

As used herein, the term "nucleic acid" refers to a sequence of at least two nucleotides covalently linked together which can be single-stranded or double-stranded or contains portion of both single-stranded and double-stranded sequence. Nucleic acids of the present invention can be naturally occurring, recombinant or synthetic. The nucleic acid can be in the form of a circular sequence or a linear sequence or a combination of both forms. The nucleic acid can be DNA, both genomic or cDNA, or RNA or a combination of both. The nucleic acid may contain any combination of deoxyribonucleotides and ribonucleotides, and any combination of bases, including uracil, adenine, thymine, cytosine, guanine, inosine, xanthine, hypoxanthine, isocytosine, 5-hydroxymethylcytosine and isoguanine. Other examples of modified bases that can be used in the present invention are detailed in Chemical Reviews 2016, 116 (20) 12655-12687. The term "nucleic acid" also encompasses any nucleic acid analogs which may contain other backbones comprising, without limitation, phosphoramide, phosphorothioate, phosphorodithioate, O-methylphophoroamidite linkage and/or deoxyribonucleotides and ribonucleotides nucleic acids. Any combination of the above features of a nucleic acid is also encompassed by the present invention.

«Vector»

As used herein, the term "vector" refers to any construct of sequences that are capable of expression of a polypeptide in a given host cell. If a vector is used then the choice of vector is dependent upon the method that will be used to transform host bacteria as is well known to those skilled in the art. Vectors can include, without limitation, plasmid vectors and recombinant phage vectors, or any other vector known in that art suitable for delivering a polypeptide of the invention to target bacteria. The skilled artisan is well aware of the genetic elements that must be present on the vector in order to successfully transform, select and propagate host cells comprising any of the isolated nucleotides or nucleic acid sequences of the invention.

«Phagemid»

As used herein the term "phagemid" or "phasmid" are equivalent and refer to a recombinant DNA vector comprising at least one sequence of a bacteriophage genome. A phagemid of the disclosure comprises a phage packaging site and optionally an origin of replication (ori), in particular a bacterial and/or phage origin of replication. In one embodiment, the phagemid of the disclosure does not comprise a bacterial origin of replication and thus cannot replicate by itself once injected into a bacterium. Alternatively, the phagemid comprises a plasmid origin of replication, in particular a bacterial and/or phage origin of replication.

«Packaged Phagemid»

As used herein, the term "packaged phagemid" or "phage-derived particle" refers to a phagemid which is encapsidated in a bacteriophage scaffold, bacterial virus particle or capsid. Particularly, it refers to a bacteriophage scaffold, bacterial virus particle or capsid devoid of a bacteriophage genome. The packaged phagemid or phage-derived particle may be produced with a helper phage strategy, well known from the man skilled in the art. The helper phage comprises all the genes coding for the structural and functional proteins that are indispensable for the phagemid according to the invention to be encapsidated. The packaged phagemid or phage-derived particle may be produced with a satellite virus strategy, also known from the man skilled in the art. Satellite virus are subviral agent and are composed of nucleic acid that depends on the co-infection of a host cell with a helper virus for all the morphogenetic functions, whereas for all its episomal functions (integration and immunity, multicopy plasmid replication) the satellite is completely autonomous from the helper. In one embodiment, the satellite genes can encode proteins that promote capsid size reduction of the helper phage, as described for the P4 Sid protein that controls the P2 capsid size to fit its smaller genome.

«Peptide»

As used herein, the term "peptide" refers both to a short chain of at least 2 amino acids linked between each other and to a part of, a subset of, or a fragment of a protein which part, subset or fragment being not expressed independently from the rest of the protein. In some instances, a peptide is a protein. In some other instances, a peptide is not a protein and peptide only refers to a part, a subset or a fragment of a protein. Preferably, the peptide is from 4, 5, 6, 7, 8, 9, 10, 11, 12, 13, 14, 15 amino acids to 4, 5, 6, 7, 8, 9, 10, 11, 12, 13, 14, 15, 20, 25, 30, 40, 50, 100, 200 amino acids in size.

"Engineered"

As used herein, the term "engineered" means that the bacterial cells, phages, phage-derived particles, phagemids or vectors of the invention have been modified by molecular biology techniques. As will be understood by the skilled person, engineering of bacterial cells, phages, phage-derived particles, phagemids or vectors implies a deliberate action to introduce or modify a nucleic acid sequence and does not cover introduction or modification of a nucleic acid sequence through natural evolution of the bacterial cell, phage, phage-derived particle, phagemid or vector.

"Percent of Identity"

As used herein, the percent identity is calculated in relation to polymers (e.g., polynucleotide or polypeptide) whose sequences have been aligned. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (Comput. Appl. Biosci., 4: 11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. 48:444-453 (1970)) algorithm which has been incorporated into the GAP program in the GCG software package (available at www.gcg.com), using a BLOSUM62 matrix, a BLOSUM30 matrix or a PAM250 matrix, and a gap weight of 16, 14, 12, 10, 8, 6, or 4 and a length weight of 1, 2, 3, 4, 5, or 6. In a specific embodiment the BLOSUM30 matrix is used with gap open penalty of 12 and gap extension penalty of 4.

CRISPR-Cas System

A CRISPR-Cas system refers to DNA encoding two distinct elements, i.e. i) an endonuclease, in this case the CRISPR associated nuclease (Cas or "CRISPR associated protein") and ii) a guide RNA. Depending on the type of CRISPR system, the guide RNA may be in the form of a chimeric RNA which consists of the combination of a CRISPR (crRNA) bacterial RNA and a tracrRNA (trans-activating RNA CRISPR) (Jinek et al., Science 2012). The guide RNA combines the targeting specificity of the crRNA corresponding to the "spacing sequences" that serve as guides to the Cas proteins, and the conformational properties of the tracrRNA in a single transcript. When the guide RNA and the Cas protein are expressed simultaneously in the cell, the target genomic sequence can be permanently interrupted (and causing disappearance of the targeted and surrounding sequences and/or cell death, depending on the location) or modified. The modification may be guided by a repair matrix.

The CRISPR-Cas system includes two main classes depending on the nuclease mechanism of action:
Class 1 is made of multi-subunit effector complexes and includes type I, III and IV
Class 2 is made of single-unit effector modules, like Cas9 nuclease, and includes type II (II-A, II-B, II-C, II-C variant), V (V-A, V-B, V-C, V-D, V-E, V-U1, V-U2, V-U3, V-U4, V-U5) and VI (VI-A, VI-B1, VI-B2, VI-C, VI-D)

The sequence of interest according to the present invention comprises a nucleic acid sequence encoding Cas protein. A variety of CRISPR enzymes are available for use as a sequence of interest on the plasmid according to the present invention. In some embodiments, the CRISPR enzyme is a Type II CRISPR enzyme, a Type II-A or Type II-B CRISPR enzyme. In another embodiment, the CRISPR enzyme is a Type I CRISPR enzyme or a Type III CRISPR enzyme. In some embodiments, the CRISPR enzyme catalyzes DNA cleavage. In some other embodiments, the CRISPR enzyme catalyzes RNA cleavage. In one embodiment, the CRISPR enzymes may be coupled to a guide RNA or single guide RNA (sgRNA). In certain embodiments, the guide RNA or sgRNA targets a gene selected from the group consisting of an antibiotic resistance gene, virulence protein or factor gene, toxin protein or factor gene, a bacterial receptor gene, a membrane protein gene, a structural protein gene, a secreted protein gene, a gene expressing resistance to a drug in general and a gene causing a deleterious effect to the host.

The sequence of interest may comprise a nucleic acid sequence encoding a guide RNA or sgRNA to guide the Cas protein endogenous to the targeted bacteria, alone or in combination with a Cas protein and/or a guide RNA encoded by the payload.

Non-limiting examples of Cas proteins as part of a multi-subunit effector or as a single-unit effector include Cas1, Cas1B, Cas2, Cas3, Cas4, Cas5, Cas6, Cas7, Cas8, Cas9 (also known as Csn1 and Csx12), Cas10, Cas11 (SS), Cas12a (Cpf1), Cas12b (C2c1), Cas12c (C2c3), Cas12d (CasY), Cas12e (CasX), C2c4, C2c8, C2c5, C2c10, C2c9, Cas13a (C2c2), Cas13b (C2c6), Cas13c (C2c7), Cas13d, Csa5, Csc1, Csc2, Cse1, Cse2, Csy1, Csy2, Csy3, Csf1, Csf2, Csf3, Csf4, Csm1, Csm2, Csm3, Csm4, Csm5, Csm6, Cmr1, Cmr3, Cmr4, Cmr5, Cmr6, Csn2, Csb1, Csb2, Csb3, Csx17, Csx14, Csx10, Csx16, CsaX, Csx13, Csx1, Csx15, SdCpf1, CmtCpf1, TsCpf1, CmaCpf1, PcCpf1, ErCpf1, FbCpf1, UbcCpf1, AsCpf1, LbCpf1, homologues thereof, orthologues thereof, variants thereof, or modified versions thereof. In some embodiments, the CRISPR enzyme cleaves both strands of the target nucleic acid at the Protospacer Adjacent Motif (PAM) site.

In a particular embodiment, the CRISPR enzyme is any Cas9 protein, for instance any naturally-occurring bacterial Cas9 as well as any variants, homologs or orthologs thereof.

By "Cas9" is meant a protein Cas9 (also called Csn1 or Csx12) or a functional protein, peptide or polypeptide fragment thereof, i.e. capable of interacting with the guide RNA(s) and of exerting the enzymatic activity (nuclease) which allows it to perform the double-strand cleavage of the DNA of the target genome. "Cas9" can thus denote a modified protein, for example truncated to remove domains of the protein that are not essential for the predefined functions of the protein, in particular the domains that are not necessary for interaction with the gRNA (s).

The sequence encoding Cas9 (the entire protein or a fragment thereof) as used in the context of the invention can be obtained from any known Cas9 protein (Fonfara et al., 2014; Koonin et al., 2017). Examples of Cas9 proteins useful in the present invention include, but are not limited to, Cas9 proteins of *Streptococcus pyogenes* (SpCas9), *Streptococcus thermophiles* (St1Cas9, St3Cas9), *Streptococcus mutans, Staphylococcus aureus* (SaCas9), *Campylobacter jejuni* (CjCas9), *Francisella novicida* (FnCas9) and *Neisseria meningitides* (NmCas9).

The sequence encoding Cpf1 (Cas12a) (the entire protein or a fragment thereof) as used in the context of the invention can be obtained from any known Cpf1 (Cas12a) protein (Koonin et al., 2017). Examples of Cpf1(Cas12a) proteins useful in the present invention include, but are not limited to, Cpf1(Cas12a) proteins of *Acidaminococcus sp*, *Lachnospiraceae bacteriu* and *Francisella novicida*.

The sequence encoding Cas13a (the entire protein or a fragment thereof) as used in the context of the invention can be obtained from any known Cas13a (C2c2) protein (Abudayyeh et al., 2017). Examples of Cas13a (C2c2) proteins useful in the present invention include, but are not limited to, Cas13a (C2c2) proteins of Leptotrichia *wadei* (LwaCas13a).

The sequence encoding Cas13d (the entire protein or a fragment thereof) as used in the context of the invention can be obtained from any known Cas13d protein (Yan et al., 2018). Examples of Cas13d proteins useful in the present invention include, but are not limited to, Cas13d proteins of *Eubacterium* siraeum and Ruminococcus sp.

In a particular embodiment, the nucleic sequence of interest is a CRISPR/Cas9 system for the reduction of gene expression or inactivation a gene selected from the group consisting of an antibiotic resistance gene, virulence factor or protein gene, toxin factor or protein gene, a gene expressing a bacterial receptor, a membrane protein, a structural protein, a secreted protein, a gene expressing resistance to a drug in general and a gene causing a deleterious effect to the host.

In one embodiment, the CRISPR-Cas system is used to target and inactivate a virulence factor. A virulence factor can be any substance produced by a pathogen that alters host-pathogen interaction by increasing the degree of damage done to the host. Virulence factors are used by pathogens in many ways, including, for example, in cell adhesion or colonization of a niche in the host, to evade the host's immune response, to facilitate entry to and egress from host cells, to obtain nutrition from the host, or to inhibit other physiological processes in the host. Virulence factors can include enzymes, endotoxins, adhesion factors, motility factors, factors involved in complement evasion, scavenging factors and factors that promote biofilm formation. For example, such targeted virulence factor gene can be *E. coli* virulence factor gene such as, without limitation, EHEC-HlyA, Stx1 (VT1), Stx2 (VT2), Stx2a (VT2a), Stx2b (VT2b), Stx2c (VT2c), Stx2d (VT2d), Stx2e (VT2e) and Stx2f (VT2f), Stx2h (VT2h), stx2k, fimA, fimF, fimH, neuC, kpsE, sfa, foc, iroN, aer, iha, papC, papGI, papGII, papGIII, hlyC, cnf1, hra, sat, ireA, usp ompT, ibeA, malX, fyuA, irp2, traT, afaD, ipaH, eltB, estA, bfpA, eaeA, espA, aaiC, aatA, TEM, CTX, SHV, csgA, csgB, csgC, csgD, csgE, csgF, csgG, csgH, T1SS, T2SS, T3SS, T4SS, T5SS, T6SS (secretion systems). For example, such targeted virulence factor gene can be *Shigella dysenteriae* virulence factor gene such as, without limitation, stx1 and stx2. For example, such targeted virulence factor gene can be *Yersinia pestis* virulence factor gene such as, without limitation, yscF (plasmid-borne (pCDI) T3SS external needle subunit). For example, such targeted virulence factor gene can be *Francisella tularensis* virulence factor gene such as, without limitation, fslA. For example, such targeted virulence factor gene can be *Bacillus anthracis* virulence factor gene such as, without limitation, pag (Anthrax toxin, cell-binding protective antigen). For example, such targeted virulence factor gene can be *Vibrio cholera* virulence factor gene such as, without limitation, ctxA and ctxB (cholera toxin), tcpA (toxin co-regulated pilus), and toxT (master virulence regulator). For example, such targeted virulence factor gene can be *Pseudomonas aeruginosa* virulence factor genes such as, without limitation, pyoverdine (e.g., sigma factor pvdS, biosynthetic genes pvdL, pvdI, pvdJ, pvdH, pvdA, pvdF, pvdQ, pvdN, pvdM, pvdO, pvdP, transporter genes pvdE, pvdR, pvdT, opmQ), siderophore pyochelin (e.g., pchD, pchC, pchB, pchA, pchE, pchF and pchG, and toxins (e.g., exoU, exoS and exoT). For example, such targeted virulence factor gene can be *Klebsiella pneumoniae* virulence factor genes such as, without limitation, fimA (adherence, type I fimbriae major subunit), and cps (capsular polysaccharide). For example, such targeted virulence factor gene can be *Acinetobacter baumannii* virulence factor genes such as, without limitation, ptk (capsule polymerization) and epsA (assembly). For example, such targeted virulence factor gene can be *Salmonella enterica Typhi* virulence factor genes such as, without limitation, MIA (invasion, SPI-1 regulator), ssrB (SPI-2 regulator), and those associated with bile tolerance, including efflux pump genes acrA, acrB and tolC. For example, such targeted virulence factor gene can be *Fusobacterium nucleatum* virulence factor genes such as, without limitation, FadA and TIGIT. For example, such targeted virulence factor gene can be *Bacteroides fragilis* virulence factor genes such as, without limitation, bft. For example, such targeted virulence factor gene can be *Cutibacterium acnes* porphyrins genes, CAMP-factors (CAM P1, CAMP2, CAM P3, CAMP4), Hyaluronate lyase (HYL-IB/II, HYL-IA), Lipases (GehA, GehB), Haemolysins, Sialidases, Endoglycoceramidases, Endo-ß-N-acetylglucosaminidase, Dermatan sulphate adhesin (DsA1, DsA2), Proline-Threonine Repeats (PTRs) or any virulence factors included on the acne associated genomic loci 1, 2, 3 (plasmid), 4 such as a tight adhesion locus (tad), Streptolysin S-associated genes (sag), nonribosomal peptide synthetases (NRPS) as described in Tomida et al.

In another embodiment, the CRISPR/Cas9 system is used to target and inactivate an antibiotic resistance gene such as, without limitation, GyrB, ParE, ParY, AAC(1), AAC(2'), AAC(3), AAC(6'), ANT(2"), ANT(3"), ANT(4'), ANT(6), ANT(9), APH(2"), APH(3"), APH(3'), APH(4), APH(6), APH(7"), APH(9), ArmA, RmtA, RmtB, RmtC, Sgm, AER, BLA1, CTX-M, KPC, SHV, TEM, BlaB, CcrA, IMP, NDM, VIM, ACT, AmpC, CMY, LAT, PDC, OXA β-lactamase, mecA, Omp36, OmpF, PIB, bla (blaI, blaR1) and mec (mecI, mecR1) operons, Chloramphenicol acetyltransferase (CAT), Chloramphenicol phosphotransferase, Ethambutol-resistant arabinosyltransferase (EmbB), MupA, MupB, Integral membrane protein MprF, Cfr 23S rRNA methyltransferase, Rifampin ADP-ribosyltransferase (Arr), Rifampin glycosyltransferase, Rifampin monooxygenase, Rifampin phosphotransferase, DnaA, RbpA, Rifampin-resistant beta-subunit of RNA polymerase (RpoB), Erm 23S rRNA methyltransferases, Lsa, MsrA, Vga, VgaB, Streptogramin Vgb lyase, Vat acetyltransferase, Fluoroquinolone acetyltransferase, Fluoroquinolone-resistant DNA topoisomerases, Fluoroquinolone-resistant GyrA, GyrB, ParC, Quinolone resistance protein (Qnr), FomA, FomB, FosC, FosA, FosB, FosX, VanA, VanB, VanD, VanR, VanS, Lincosamide nucleotidyltransferase (Lin), EreA, EreB, GimA, Mgt, Ole, Macrolide phosphotransferases (MPH), MefA, MefE, Mel, Streptothricin acetyltransferase (sat), Sul1, Sul2, Sul3, sulfonamide-resistant FolP, Tetracycline inactivation enzyme TetX, TetA, TetB, TetC, Tet30, Tet31, TetM, TetO, TetQ, Tet32, Tet36, MacAB-ToIC, MsbA, MsrA, VgaB, EmrD, EmrAB-ToIC, NorB, GepA, MepA, AdeABC, AcrD, MexAB-OprM, mtrCDE, EmrE, adeR, acrR, baeSR, mexR, phoPQ, mtrR, or any antibiotic resistance gene described in the Comprehensive Antibiotic Resistance Database (CARD card.mcmaster.cal).

In another embodiment, the CRISPR/Cas9 system is used to target and inactivate a bacterial toxin gene. Bacterial toxin can be classified as either exotoxins or endotoxins. Exotoxins are generated and actively secreted; endotoxins remain part of the bacteria. The response to a bacterial toxin can involve severe inflammation and can lead to sepsis. Such toxin can be for example Botulinum neurotoxin, Tetanus toxin, Staphylococus toxins, Diphteria toxin, Anthrax toxin, Alpha toxin, Pertussis toxin, Shiga toxin, Heat-stable enterotoxin (*E. coli* ST), colibactin, BFT (*B. fragilis* toxin) or any toxin described in Henkel et al., (Toxins from Bacteria in EXS. 2010; 100: 1-29).

Base Editing

Base editing (BE) refers to the ability to substitute a specific nucleotide base pair on a DNA or RNA molecule by another. Until recently, the only way to perform a specific substitution on DNA in vivo was using recombination of a template DNA, carrying the specific base pair change, with the locus of interest. Base editing technology relies on completely different strategies. There is no exchange of DNA, instead an enzymatic reaction converts a nucleotide to another one leading to a mismatch at the level of dsDNA that is then corrected by the cell machinery.

One of the main challenges for base editing is how to restrict activity of the enzyme performing the nucleotide conversion to the target nucleotide, for example a SNP involved in pathogenicity. This spatial restriction has been achieved recently repurposing the CRISPR-Cas system. Indeed, fusing catalytically impaired or inactive Cas nuclease to base modification enzymes that are active only on single stranded DNA, it's possible to achieve high efficiency base editing. This is possible thanks to the CRISPR-Cas ability to generate locally ssDNA bubble in an 'R loop' when the complex is annealed to its DNA target strand by RNA-DNA base pairing.

So far there are seven types of DNA base editors described:

Cytosine Base Editor (CBE) that convert C:G into T:A (Komor, A et al. Programmable editing of a target base in genomic DNA without double-stranded DNA cleavage. Nature 533:420-4. (2016).

Adenine Base Editor (ABE) that convert A:T into G:C (Programmable base editing of A•T to G•C in genomic DNA without DNA cleavage. Nature 551(7681) 464-471 (2017).

Cytosine Guanine Base Editor (CGBE) that convert C:G into G:C Chen, L et al. Precise and programmable C:G to G:C base editing in genomic DNA. Biorxiv (2020); Kurt, I et al. CRISPR C-to-G base editors for inducing targeted DNA transversions in human cells. Nature Biotechnology (2020).

Cytosine Adenine Base Editor (CABE) that convert C:G into A:T Zhao, D et al. New base editors change C to A in bacteria and C to G in mammalian cells. Nature Biotechnology (2020).

Adenine Cytosine Base Editor (ACBE) that convert A:T into C:G (Liu, D et al. A:T to C:G base editors and uses thereof. Patent application WO2020181180 (2020).

Adenine Thymine Base Editor (ATBE) that convert A:T into T:A (Liu, D et al. A:T to C:G base editors and uses thereof. Patent application WO2020181180 (2020).

Thymine Adenine Base Editor (TABE) that convert T:A into A:T (Liu, D et al. T:A TO A:T base editing through adenosine methylation. Patent application WO2020181193 (2020); Liu, D et al. T:A TO A:T base editing through thymine alkylation. Patent application WO2020181178 (2020); Liu, D et al. T:A TO A:T base editing through adenine excision. Patent application WO2020181195 (2020).

Base editors differ in the base modification enzymes. CBE rely on ssDNA cytidine deaminase among which: APOBEC1, rAPOBEC1, APOBEC1 mutant or evolved version (evoAPOBEC1), and APOBEC homologs (APOBEC3A (eA3A), Anc689), Cytidine deaminase 1 (CDA1), evoCDA1, FERNY, evoFERNY. ABE rely on deoxyadenosine deaminase activity of a tandem fusion TadA-TadA* where TadA* is an evolved version of TadA, an *E. coli* tRNA adenosine deaminase enzyme, able to convert adenosine into Inosine on ssDNA.TadA* include TadA-8a-e and TadA-7.10.

Except from base modification enzyme there has been also modifications implemented to base editor to increase editing efficacy, precision and modularity:

the addition of one or two uracil DNA glycosylase inhibitor domain (UGI) to prevent base excision repair mechanism to revert base edition the addition of Mu-GAM that decrease insertion-deletion rate by inhibiting Non-homologous end joining mechanism in the cell (NHEJ)

the use of nickase active Cas9 (nCas9 D10A) that, by creating nicks on the non-edited strand favor its repair and consequently the fixation of the edited base the use of divers Cas proteins from for example different organisms, mutants with different PAM motifs or different fidelity or different family (e.g. Cas12a)

Non-limiting examples of DNA based editor proteins include BE1, BE2, BE3, BE4, BE4-GAM, HF-BE3, Sniper-BE3, Target-AID, Target-AID-NG, ABE, EE-BE3, YE1-BE3, YE2-BE3, YEE-BE3, BE-PLUS, SaBE3, SaBE4, SaBE4-GAM, Sa(KKH)-BE3, VQR-BE3, VRER-BE3, EQR-BE3, xBE3, Cas12a-BE, Ea3A-BE3, A3A-BE3, TAM, CRISPR-X, ABE7.9, ABE7.10, ABE7.10*, xABE, ABESa, VQR-ABE, VRER-ABE, Sa(KKH)-ABE, ABE8e, SpRY-ABE, SpRY-CBE, SpG-CBE4, SpG-ABE, SpRY-CBE4, SpCas9-NG-ABE, SpCas9-NG-CBE4, enAsBE1.1, enAsBE1.2, enAsBE1.3, enAsBE1.4, AsBE1.1, AsBE1.4, CRISPR-Abest, CRISPR-Cbest, eA3A-BE3, AncBE4.

Cytosine Guanine Base Editors (CGBE) consist of a nickase CRISPR fused to:

A cytosine deaminase (rAPOBEC) and base excision repair proteins (e.g. rXRCC1). (Precise and programmable C:G to G:C base editing in genomic DNA. Biorxiv (2020).

A rat APOBEC1 variant (R33A) protein and an *E. coli*-derived uracil DNA N-glycosylase (eUNG). (Kurt, I et al. CRISPR C-to-G base editors for inducing targeted DNA transversions in human cells. Nature Biotechnology (2020).

Cytosine Adenine Base Editors (CABE) consist of a Cas9 nickase, a cytidine deaminase (e.g. AID), and a uracil-DNA glycosylase (Ung). Zhao, D et al. New base editors change C to A in bacteria and C to G in mammalian cells. Nature Biotechnology (2020).

ACBE include a nucleic acid programmable DNA-binding protein and an adenine oxidase. Liu, D et al. A:T to C:G base editors and uses thereof. Patent application WO2020181180 (2020).

ATBE consist of a Cas9 nickase and one or more adenosine deaminase or an oxidase domain. Liu, D et al. A:T to T:A base editing through adenine deamination and oxidation. Patent application WO2020181202 (2020).

TABE consist of a Cas9 nickase and an adenosine methyltransferase, a thymine alkyltransferase, or an adenosine deaminase domain. (Liu, D et al. T:A TO A:T base editing through adenosine methylation. Patent application WO2020181193 (2020); Liu, D et al. T:A TO A:T base editing through thymine alkylation. Patent application WO2020181178 (2020); Liu, D et al. T:A TO A:T base editing through adenine excision. Patent application WO2020181195 (2020).

Base editor molecules can also consist of two or more of the above listed editor enzymes fused to a Cas protein (e.g.

combination of an ABE and CBE). These biomolecules are named dual base editors and enable the editing of two different bases. (Grunewald, J et al. A dual-deaminase CRISPR base editor enables concurrent adenine and cytosine editing, Nature Biotechnology (2020); Li, C et al. Targeted, random mutagenesis of plant genes with dual cytosine and adenine base editors, Nature Biotechnology (2020).

In one embodiment, the base editor is used to inactivate the expression of a gene by editing one or several nucleotides involved in transcription or translation. More specifically the base editor is targeting one or several nucleotides of a promoter, a RBS, a start codon.

In one embodiment, the base editor is used to introduce a premature stop codon.

In one embodiment, the base editor is used to introduce one or several rare codons.

In another embodiment, the base editor is used to modulate the expression of genes by editing one or several nucleotides involved in transcription or translation. More specifically the base editor is targeting one or several nucleotides of a promoter, a RBS, a start codon. leading to an increase or decrease of gene expression.

In another embodiment, the base editor is used to revert a mutation that leads to the inactivation, decrease or increase in activity of a gene or pathway.

In another embodiment, the base editor is used to revert a mutation that leads to an increase of pathogenicity.

In one embodiment, the base editor is used to modify the regulation of a gene by editing one or several nucleotides involved in its regulation such as nucleotides of operator sequence, transcription factor binding site, riboswitch, RNAse recognition site, protease cleavage site, methylation site, post translational modification site (phosphorylation, glycosylation, acetylation, pupylation . . . ).

RNA Based Editing

RNA base editing is based on the same principle as DNA base editing: an enzyme catalysing the conversion of a RNA base into another has to be brought close to the target base to perform its conversion locally. So far the only enzyme used for RNA editing is an adenosine deaminase from ADAR family that converts Adenosine into Inosine in dsRNA structure. Several seminal studies used this specificity for dsRNA and fused the ADAR deaminase domain (ADARDD) to an antisense oligo in order to program local RNA base editing. More recently the ability of some CRISPR-Cas systems to bind RNA molecules was repurposed into RNA editing. Using catalytically dead Cas13b enzyme (dPspCas13b) fused to an hyperactive mutant of ADAR2 deaminase domain (ADAR2DD-E488Q for REPAIRv1 and ADAR2DD-E488Q-T375G for REPAIRv2) Cox et al improved specificity and efficiency compare to previous RNA editing strategies.

Non-limiting examples of RNA based editor proteins include REPAIRv1, REPAIRv2

In one embodiment, the RNA base editor is used to inactivate the expression of a gene by editing one or several nucleotides involved in translation. More specifically the base editor is targeting one or several nucleotides of a 5'UTR, a RBS, a start codon.

In one embodiment, the RNA base editor is used to introduce a premature stop codon.

In one embodiment, the RNA base editor is used to introduce one or several rare codons.

In another embodiment, the RNA base editor is used to modulate the expression of genes by editing one or several nucleotides involved in translation. More specifically the base editor is targeting one or several nucleotides of a 5'UTR, a RBS, a start codon leading to an increase or decrease of gene expression.

In another embodiment, the RNA base editor is used to revert a mutation that leads to the inactivation or a decrease in activity of a gene or pathway.

In another embodiment, the base editor is used to revert a mutation that leads to an increase of pathogenicity.

Prime Editing

Prime editors (PE), as described in Anzalone et al. (Anzalone, A. V. et al. Search-and-replace genome editing without double-strand breaks or donor DNA. Nature 576, 149-157 (2019) which is hereby incorporated by reference, consist of a nCas9 fused to a reverse transcriptase used in combination with a prime editing RNA (pegRNA; a guide RNA that includes a template region for reverse transcription).

Prime Editing allows introduction of insertions, deletions (indels) and 12 base-to-base conversions. Prime editing relies on the ability of a reverse transcriptase (RT), fused to a Cas nickase variant, to convert RNA sequence brought by a prime editing guide RNA (pegRNA) into DNA at the nick site generated by the Cas protein. The DNA flap generated from this process is then included or not in the targeted DNA sequence.

Prime editing systems include:
  a Cas nickase variant such as Cas9-H840A fused to a reverse transcriptase domain such as M-MLV RT or its mutant version (M-MLV RT(D200N), M-MLV RT(D200N/L603W), M-MLV RT(D200N/L603W/T330P/T306K/W313F)
  a prime editing guide RNA (pegRNA)

To favor editing the prime editing system can include the expression of an additional sgRNA targeting the Cas nickase activity towards the non-edited DNA strand ideally only after the resolution of the edited strand flap by designing the sgRNA to anneal with the edited strand but not with the original strand.

Non-limiting examples of prime editing systems include PE1, PE1-M1, PE1-M2, PE1-M3, PE1-M6, PE1-M15, PE1-M3inv, PE2, PE3, PE3b, Cas9 Retron preciSe Parallel Editing via homologY ('CRISPEY'), a retron RNA fused to the sgRNA and expressed together with Cas9 and the retron proteins including at least the reverse transcriptase (Sharon, E. et al. Functional Genetic Variants Revealed by Massively Parallel Precise Genome Editing. Cell 175, 544-557.e16 (2018).), The SCRIBE strategy: a retron system expressed in combination with a recombinase promoting the recombination of single stranded DNA, also known as single stranded annealing proteins (SSAPs)12. Such recombinases include but are not limited to phage recombinases such as lambda red, recET, Sak, Sak4, and newly described SSAPs described in Wannier et al (Wannier, T. M. et al. Improved bacterial recombineering by parallelized protein discovery. Biorxiv 2020.01.14.906594 (2020) doi:10.1101/2020.01.14.906594.), the targetron system based on group II introns described in Karberg et al. (Karberg, M. et al. Group II introns as controllable gene targeting vectors for genetic manipulation of bacteria. Nat Biotechnol 19, 1162-7 (2001) and which has been adapted to many bacterial species, Other retron based gene targeting approaches, as described in Simon et al (Simon, A. J., Ellington, A. D. & Finkelstein, I. J. Retrons and their applications in genome engineering. Nucleic Acids Res 47, 11007-11019 (2019)).

In one embodiment, the prime editing system is used to inactivate the expression of a gene by replacing, deleting, inserting one or several nucleotides involved in transcription or translation. More specifically the prime editing system is replacing, deleting, inserting one or several nucleotides in a promoter, a RBS, a coding sequence.

In one embodiment, the prime editing system is used to introduce one or several premature stop codon.

In one embodiment, the prime editing system is used to introduce one or several rare codons.

In one embodiment, the prime editing system is used to introduce, delete a nucleotide inducing a frameshift in the reading frame.

In another embodiment, the prime editing system is used to modulate the expression of genes by replacing, deleting, inserting one or several nucleotides involved in transcription or translation. More specifically the prime editing system is replacing, deleting, inserting one or several nucleotides in a promoter, a RBS, a start codon. leading to an increase or decrease of gene expression.

In another embodiment, the prime editing system is used to revert a mutation that leads to the inactivation or a decrease in activity of a gene or pathway.

In another embodiment, the prime editing system is used to revert a mutation that leads to an increase of pathogenicity.

The invention encompasses the following embodiments:
1. A recombinant *C. acnes* phage.
2. The recombinant *C. acnes* phage of embodiment 1, comprising at least one transgene.
3. The recombinant *C. acnes* phage of embodiment 2, wherein said transgene is a CRISPR-Cas system or part of a CRISPR-Cas system.
4. The recombinant *C. acnes* phage of embodiment 1, wherein the host range is different from the host range of the corresponding wild type *C. acnes* phage.
5. The recombinant *C. acnes* phage of embodiment 1, comprising an engineered capsid.
6. The recombinant *C. acnes* phage of embodiment 5, wherein an antigen is displayed at the surface of the engineered capsid.
7. A *C. acnes* cell carrying a recombinant DNA vector comprising:
   a DNA template for homologous recombination with a *C. acnes* phage genome
   an origin of replication allowing replication in *C. acnes*; and
   optionally a first selection marker allowing for selection of the DNA vector in *C. acnes*;
8. The *C. acnes* cell of embodiment 7, wherein the *C. acnes* phage genome is introduced into said cell
9. The *C. acnes* cell of embodiment 7, wherein the *C. acnes* phage genome recombines with the DNA vector leading to production of recombinant phages.
10. A *C. acnes* cell carrying a DNA vector for the selective production of recombinant *C. acnes* phage comprising:
    an origin of replication allowing replication in *C. acnes*;
    a CRISPR-Cas system expressed in said *C. acnes* cell but not targeting the newly generated recombinant *C. acnes* phage genome, and
    optionally a first selection marker allowing for selection of the DNA vector in *C. acnes*.
11. A method for producing a phage lysate containing wild-type or parent *C. acnes* phages and recombinant *C. acnes* phages wherein a wild-type or parent *C. acnes* phage genome is introduced into *C. acnes* cell of embodiment 7.
12. A method for selecting recombinant *C. acnes* phages wherein a phage lysate containing wild-type or parent *C. acnes* phages and recombinant *C. acnes* phages is mixed with the *C. acnes* cell of embodiment 10, leading to selective production of recombinant *C. acnes* phages.
13. A method to treat *C. acnes* related disorder or disease comprising administering to a subject a recombinant *C. acnes* phage of anyone of embodiments 1-6 or a recombinant *C. acnes* phage obtained by the methods of embodiments 11-12.
14. A recombinant DNA vector comprising:
    an origin of replication allowing replication in *C. acnes*;
    optionally a first selection marker allowing for selection of the DNA vector in *C. acnes*; and
    a gene of interest.
15. The DNA vector of embodiment 14 further comprising an oriT allowing conjugation into *C. acnes*; an origin of replication allowing replication in a donor bacteria and a second selection marker allowing for selection in a donor bacteria.
16. The DNA vector of embodiment 14 or 15, wherein the origin of replication allowing replication in *C. acnes* is R6K (typically of sequence SEQ ID NO: 42).
17. The DNA vector of embodiment 14 or 15, wherein the origin of replication allowing replication in *C. acnes* is RK2 (typically of sequence SEQ ID NO: 43).
18. The DNA vector of embodiment 14 or 15, wherein the origin of replication allowing replication in *C. acnes* is pBBR1 (typically of sequence SEQ ID NO: 44).
19. The DNA vector of embodiment 14 or 15, wherein the origin of replication allowing replication in *C. acnes* is pRO1600 (typically of sequence SEQ ID NO: 45).
20. The DNA vector of embodiment 14 or 15, wherein the origin of replication allowing replication in *C. acnes* is RSF1010 (typically of sequence SEQ ID NO: 46).
21. The DNA vector of embodiment 14 or 15, wherein the origin of replication allowing replication in *C. acnes* is pAMβ1 (typically of sequence SEQ ID NO: 47).
22. The DNA vector of embodiment 14 or 15, wherein the origin of replication allowing replication in *C. acnes* is pLME106 (typically of sequence SEQ ID NO: 48).
23. The DNA vector of embodiment 14 or 15, wherein the origin of replication allowing replication in *C. acnes* is pTZC1 (typically of sequence SEQ ID NO: 49).
24. The DNA vector of embodiment 14 or 15, wherein the origin of replication allowing replication in *C. acnes* is pBC1 (typically of sequence SEQ ID NO: 50).
25. The DNA vector of embodiment 14 or 15, wherein the origin of replication allowing replication in *C. acnes* is pEP2 (typically of sequence SEQ ID NO: 51).
26. The DNA vector of embodiment 14 or 15, wherein the origin of replication allowing replication in *C. acnes* is pWVO1 (typically of sequence SEQ ID NO: 52).
27. The DNA vector of embodiment 14 or 15, wherein the origin of replication allowing replication in *C. acnes* is pAP1 (typically of sequence SEQ ID NO: 53).
28. The DNA vector of embodiment 14 or 15, wherein the origin of replication allowing replication in *C. acnes* is pWKS1 (typically of sequence SEQ ID NO: 54).
29. The DNA vector of embodiment 14 or 15, wherein the origin of replication allowing replication in *C. acnes* is pLME108 (typically of sequence SEQ ID NO: 55).
30. The DNA vector of embodiment 14 or 15, wherein the origin of replication allowing replication in *C. acnes* is pLS1 (typically of sequence SEQ ID NO: 56).

31. The DNA vector of embodiment 14 or 15, wherein the origin of replication allowing replication in *C. acnes* is pUB6060 (typically of sequence SEQ ID NO: 57).
32. The DNA vector of embodiment 14 or 15, wherein the origin of replication allowing replication in *C. acnes* is p545 (typically of sequence SEQ ID NO: 58).
33. The DNA vector of embodiment 14 or 15, wherein the origin of replication allowing replication in *C. acnes* is pJD4 (typically of sequence SEQ ID NO: 59).
34. The DNA vector of embodiment 14 or 15, wherein the origin of replication allowing replication in *C. acnes* is pIJ101 (typically of sequence SEQ ID NO: 60).
35. The DNA vector of embodiment 14 or 15, wherein the origin of replication allowing replication in *C. acnes* is pSN22 (typically of sequence SEQ ID NO: 61).
36. The DNA vector of embodiment 14 or 15, wherein the origin of replication allowing replication in *C. acnes* is pGP01 (typically of sequence SEQ ID NO: 62).
37. The DNA vector of embodiment 14 or 15, wherein the origin of replication allowing replication in *C. acnes* is pIP501 (typically of sequence SEQ ID NO: 63).
38. The DNA vector of embodiment 14 or 15, wherein the origin of replication allowing replication in *C. acnes* is pCU1 (typically of sequence SEQ ID NO: 64).
39. The DNA vector of embodiment 14 or 15, wherein the origin of replication allowing replication in *C. acnes* is pBAV1K-T5 (typically of sequence SEQ ID NO: 65).
40. The DNA vector of any one of embodiments 15 to 39, wherein the oriT is oriT_pMRC01 (typically of sequence SEQ ID NO: 1).
41. The DNA vector of any one of embodiments 15 to 39, wherein the oriT is oriT_RSF1010 (typically of sequence SEQ ID NO: 2).
42. The DNA vector of any one of embodiments 15 to 39, wherein the oriT is oriT_pRS01 (typically of sequence SEQ ID NO: 3).
43. The DNA vector of any one of embodiments 15 to 39, wherein the oriT is oriT_pMV158 (typically of sequence SEQ ID NO: 4).
44. The DNA vector of any one of embodiments 15 to 39, wherein the oriT is oriT_pTF1 (typically of sequence SEQ ID NO: 5).
45. The DNA vector of any one of embodiments 15 to 39, wherein the oriT is oriT_pSC101 (typically of sequence SEQ ID NO: 6).
46. The DNA vector of any one of embodiments 15 to 39, wherein the oriT is oriT_pBTK445 (typically of sequence SEQ ID NO: 7).
47. The DNA vector of any one of embodiments 15 to 39, wherein the oriT is oriT_pBBR1 (typically of sequence SEQ ID NO: 8).
48. The DNA vector of any one of embodiments 15 to 39, wherein the oriT is oriT_R721 (typically of sequence SEQ ID NO: 9).
49. The DNA vector of any one of embodiments 15 to 39, wherein the oriT is oriT_pRmeGR4a (typically of sequence SEQ ID NO: 10).
50. The DNA vector of any one of embodiments 15 to 39, wherein the oriT is oriT_ColE1 (typically of sequence SEQ ID NO: 11).
51. The DNA vector of any one of embodiments 15 to 39, wherein the oriT is oriT_pTiC58 (typically of sequence SEQ ID NO: 12).
52. The DNA vector of any one of embodiments 15 to 39, wherein the oriT is oriT_pMdT1 (typically of sequence SEQ ID NO: 13).
53. The DNA vector of any one of embodiments 15 to 39, wherein the oriT is oriT_R1 (typically of sequence SEQ ID NO: 14).
54. The DNA vector of any one of embodiments 15 to 39, wherein the oriT is oriT_Tn5520 (typically of sequence SEQ ID NO: 15).
55. The DNA vector of any one of embodiments 15 to 39, wherein the oriT is oriT_QKH54 (typically of sequence SEQ ID NO: 16).
56. The DNA vector of any one of embodiments 15 to 39, wherein the oriT is oriT_R64 (typically of sequence SEQ ID NO: 17).
57. The DNA vector of any one of embodiments 15 to 39, wherein the oriT is oriT_R751 (typically of sequence SEQ ID NO: 18).
58. The DNA vector of any one of embodiments 15 to 39, wherein the oriT is oriT_RP4 (typically of sequence SEQ ID NO: 19).
59. The DNA vector of any one of embodiments 15 to 39, wherein the oriT is oriT_pKL1 (typically of sequence SEQ ID NO: 20).
60. The DNA vector of any one of embodiments 15 to 39, wherein the oriT is oriT_RK2 (typically of sequence SEQ ID NO: 21).
61. The DNA vector of any one of embodiments 15 to 39, wherein the oriT is oriT_R1162 (typically of sequence SEQ ID NO: 22).
62. The DNA vector of any one of embodiments 15 to 39, wherein the oriT is oriT_Tn4555 (typically of sequence SEQ ID NO: 23).
63. The DNA vector of any one of embodiments 15 to 39, wherein the oriT is oriT_pHT (typically of sequence SEQ ID NO: 24).
64. The DNA vector of any one of embodiments 15 to 39, wherein the oriT is oriT_Tn4399 (typically of sequence SEQ ID NO: 25).
65. The DNA vector of any one of embodiments 15 to 39, wherein the oriT is oriT_Tn916 (typically of sequence SEQ ID NO: 26).
66. The DNA vector of any one of embodiments 15 to 39, wherein the oriT is oriT_pST12 (typically of sequence SEQ ID NO: 27).
67. The DNA vector of any one of embodiments 15 to 39, wherein the oriT is oriT_pCU1 (typically of sequence SEQ ID NO: 28).
68. The DNA vector of any one of embodiments 15 to 39, wherein the oriT is oriT_pSU233 (typically of sequence SEQ ID NO: 29).
69. The DNA vector of any one of embodiments 15 to 39, wherein the oriT is oriT_F (typically of sequence SEQ ID NO: 30).
70. The DNA vector of any one of embodiments 15 to 39, wherein the oriT is oriT_pMAB01 (typically of sequence SEQ ID NO: 31).
71. The DNA vector of any one of embodiments 15 to 39, wherein the oriT is oriT_R388 (typically of sequence SEQ ID NO: 32).
72. The DNA vector of any one of embodiments 15 to 39, wherein the oriT is oriT_pS7a (typically of sequence SEQ ID NO: 33).
73. The DNA vector of any one of embodiments 15 to 39, wherein the oriT is oriT_pS7b (typically of sequence SEQ ID NO: 34).
74. The DNA vector of any one of embodiments 15 to 39, wherein the oriT is oriT_R702 (typically of sequence SEQ ID NO: 35).

75. The DNA vector of any one of embodiments 15 to 39, wherein the oriT is oriT_pMUR274 (typically of sequence SEQ ID NO: 36).
76. The DNA vector of any one of embodiments 15 to 39, wherein the oriT is oriT_R100 (typically of sequence SEQ ID NO: 37).
77. The DNA vector of any one of embodiments 15 to 39, wherein the oriT is oriT_pVCR94deltaX (typically of sequence SEQ ID NO: 38).
78. The DNA vector of any one of embodiments 15 to 39, wherein the oriT is oriT_R46 (typically of sequence SEQ ID NO: 39).
79. The DNA vector of any one of embodiments 15 to 39, wherein the oriT is oriT_pGO1 (typically of sequence SEQ ID NO: 40).
80. The DNA vector of any one of embodiments 15 to 39, wherein the oriT is oriT_pIP501 (typically of sequence SEQ ID NO: 41).
81. The DNA vector of any one of embodiments 14 to 80, further comprising:
a relaxase gene;
a selection marker allowing for selection in the transconjugant *C. acnes*; and
a selection marker allowing for selection in the donor bacteria wherein the donor bacteria is an *E. coli* strain carrying a conjugative plasmid, conjugative transposon, or integrative and conjugative element (ICE), expressing a conjugative machinery.
82. The DNA vector of embodiment 81, wherein the donor bacteria is an *E. coli* strain carrying the conjugative plasmid, conjugative transposon or ICE pMRC01.
83. The DNA vector of embodiment 81, wherein the donor bacteria is an *E. coli* strain carrying the conjugative plasmid, conjugative transposon or ICE RSF1010.
84. The DNA vector of embodiment 81, wherein the donor bacteria is an *E. coli* strain carrying the conjugative plasmid, conjugative transposon or ICE pRS01.
85. The DNA vector of embodiment 81, wherein the donor bacteria is an *E. coli* strain carrying the conjugative plasmid, conjugative transposon or ICE pMV158.
86. The DNA vector of embodiment 81, wherein the donor bacteria is an *E. coli* strain carrying the conjugative plasmid, conjugative transposon or ICE pTF1.
87. The DNA vector of embodiment 81, wherein the donor bacteria is an *E. coli* strain carrying the conjugative plasmid, conjugative transposon or ICE pSC101.
88. The DNA vector of embodiment 81, wherein the donor bacteria is an *E. coli* strain carrying the conjugative plasmid, conjugative transposon or ICE pBTK445.
89. The DNA vector of embodiment 81, wherein the donor bacteria is an *E. coli* strain carrying the conjugative plasmid, conjugative transposon or ICE pBBR1.
90. The DNA vector of embodiment 81, wherein the donor bacteria is an *E. coli* strain carrying the conjugative plasmid, conjugative transposon or ICE R721.
91. The DNA vector of embodiment 81, wherein the donor bacteria is an *E. coli* strain carrying the conjugative plasmid, conjugative transposon or ICE pRmeGR4a.
92. The DNA vector of embodiment 81, wherein the donor bacteria is an *E. coli* strain carrying the conjugative plasmid, conjugative transposon or ICE ColE1.
93. The DNA vector of embodiment 81, wherein the donor bacteria is an *E. coli* strain carrying the conjugative plasmid, conjugative transposon or ICE pTiC58.
94. The DNA vector of embodiment 81, wherein the donor bacteria is an *E. coli* strain carrying the conjugative plasmid, conjugative transposon or ICE pMdT1.
95. The DNA vector of embodiment 81, wherein the donor bacteria is an *E. coli* strain carrying the conjugative plasmid, conjugative transposon or ICE R1.
96. The DNA vector of embodiment 81, wherein the donor bacteria is an *E. coli* strain carrying the conjugative plasmid, conjugative transposon or ICE Tn5520.
97. The DNA vector of embodiment 81, wherein the donor bacteria is an *E. coli* strain carrying the conjugative plasmid, conjugative transposon or ICE QKH54.
98. The DNA vector of embodiment 81, wherein the donor bacteria is an *E. coli* strain carrying the conjugative plasmid, conjugative transposon or ICE R64.
99. The DNA vector of embodiment 81, wherein the donor bacteria is an *E. coli* strain carrying the conjugative plasmid, conjugative transposon or ICE R751.
100. The DNA vector of embodiment 81, wherein the donor bacteria is an *E. coli* strain carrying the conjugative plasmid, conjugative transposon or ICE RP4.
101. The DNA vector of embodiment 81, wherein the donor bacteria is an *E. coli* strain carrying the conjugative plasmid, conjugative transposon or ICE pKL1.
102. The DNA vector of embodiment 81, wherein the donor bacteria is an *E. coli* strain carrying the conjugative plasmid, conjugative transposon or ICE RK2.
103. The DNA vector of embodiment 81, wherein the donor bacteria is an *E. coli* strain carrying the conjugative plasmid, conjugative transposon or ICE R1162.
104. The DNA vector of embodiment 81, wherein the donor bacteria is an *E. coli* strain carrying the conjugative plasmid, conjugative transposon or ICE Tn4555.
105. The DNA vector of embodiment 81, wherein the donor bacteria is an *E. coli* strain carrying the conjugative plasmid, conjugative transposon or ICE pHT.
106. The DNA vector of embodiment 81, wherein the donor bacteria is an *E. coli* strain carrying the conjugative plasmid, conjugative transposon or ICE Tn4399.
107. The DNA vector of embodiment 81, wherein the donor bacteria is an *E. coli* strain carrying the conjugative plasmid, conjugative transposon or ICE Tn916.
108. The DNA vector of embodiment 81, wherein the donor bacteria is an *E. coli* strain carrying the conjugative plasmid, conjugative transposon or ICE pST12.
109. The DNA vector of embodiment 81, wherein the donor bacteria is an *E. coli* strain carrying the conjugative plasmid, conjugative transposon or ICE pCU1.
110. The DNA vector of embodiment 81, wherein the donor bacteria is an *E. coli* strain carrying the conjugative plasmid, conjugative transposon or ICE pSU233.
111. The DNA vector of embodiment 81, wherein the donor bacteria is an *E. coli* strain carrying the conjugative plasmid, conjugative transposon or ICE F.
112. The DNA vector of embodiment 81, wherein the donor bacteria is an *E. coli* strain carrying the conjugative plasmid, conjugative transposon or ICE pMAB01.
113. The DNA vector of embodiment 81, wherein the donor bacteria is an *E. coli* strain carrying the conjugative plasmid, conjugative transposon or ICE R388.

114. The DNA vector of embodiment 81, wherein the donor bacteria is an *E. coli* strain carrying the conjugative plasmid, conjugative transposon or ICE pS7a.

115. The DNA vector of embodiment 81, wherein the donor bacteria is an *E. coli* strain carrying the conjugative plasmid, conjugative transposon or ICE pS7b.

116. The DNA vector of embodiment 81, wherein the donor bacteria is an *E. coli* strain carrying the conjugative plasmid, conjugative transposon or ICE R702.

117. The DNA vector of embodiment 81, wherein the donor bacteria is an *E. coli* strain carrying the conjugative plasmid, conjugative transposon or ICE pMUR274.

118. The DNA vector of embodiment 81, wherein the donor bacteria is an *E. coli* strain carrying the conjugative plasmid, conjugative transposon or ICE R100.

119. The DNA vector of embodiment 81, wherein the donor bacteria is an *E. coli* strain carrying the conjugative plasmid, conjugative transposon or ICE pVCR94deltaX.

120. The DNA vector of embodiment 81, wherein the donor bacteria is an *E. coli* strain carrying the conjugative plasmid, conjugative transposon or ICE R46.

121. The DNA vector of embodiment 81, wherein the donor bacteria is an *E. coli* strain carrying the conjugative plasmid, conjugative transposon or ICE pGO1.

122. The DNA vector of embodiment 81, wherein the donor bacteria is an *E. coli* strain carrying the conjugative plasmid, conjugative transposon or ICE pIP501.

123. An engineered *C. acnes* comprising any of the DNA vectors of any one of embodiments 14 to 122.

124. An engineered *C. acnes* produced by contacting *C. acnes* with any of the vectors of any one of embodiments 14 to 122.

125. A method for engineering a *C. acnes* comprising introducing the DNA vector of any one of embodiments 14 to 122 into a *C. acnes*.

126. A recombinant *C. acnes* phage.

127. The recombinant *C. acnes* phage according to embodiment 126 comprising at least one transgene.

128. The recombinant *C. acnes* phage according to embodiment 127 wherein said transgene is a CRISPR-Cas system or part of a CRISPR-Cas system.

129. The recombinant *C. acnes* phage according to embodiment 127 wherein said transgene is a DNA encoding an antigen.

130. The recombinant *C. acnes* phage according to any one of embodiments 126 to 129, wherein the host range of the recombinant phage is different from the host range of the corresponding wild type *C. acnes* phage.

131. The recombinant *C. acnes* phage according to any one of embodiments 126 to 130 comprising an engineered capsid.

132. The recombinant *C. acnes* phage according to embodiment 131 wherein an antigen is displayed at the surface of the engineered capsid.

133. A *C. acnes* cell carrying a recombinant DNA vector comprising:
a DNA template for homologous recombination with a *C. acnes* phage genome,
an origin of replication allowing replication in *C. acnes*, and
optionally a first selection marker allowing for selection of the DNA vector in *C. acnes*.

134. The *C. acnes* cell according to embodiment 133, wherein the *C. acnes* phage genome is introduced into said cell.

135. The *C. acnes* cell according to embodiment 133, wherein the *C. acnes* phage genome recombines with the DNA vector leading to production of recombinant phages.

136. A *C. acnes* cell comprising a recombinant DNA vector which comprises a DNA encoding an antigen.

137. A *C. acnes* cell carrying a DNA vector for the selective production of recombinant *C. acnes* phage comprising:
an origin of replication allowing replication in *C. acnes*,
a CRISPR-Cas system expressed in said *C. acnes* cell but not targeting the newly generated recombinant *C. acnes* phage genome, and
optionally a first selection marker allowing for selection of the DNA vector in *C. acnes*.

138. A method for producing a phage lysate containing wild-type or parent *C. acnes* phages and recombinant *C. acnes* phages wherein a wild-type or parent *C. acnes* phage genome is introduced into a *C. acnes* cell of embodiment 133.

139. A method for selecting recombinant *C. acnes* phages wherein a phage lysate containing wild-type or parent *C. acnes* phages and recombinant *C. acnes* phages is mixed with the *C. acnes* cell of embodiment 137, leading to selective production of recombinant *C. acnes* phages.

140. A method to treat *C. acnes* related disorder or disease comprising administering to a subject a recombinant *C. acnes* phage of anyone of embodiments 126 to 131 or a recombinant *C. acnes* phage obtained by the methods of embodiments 138 or 139.

141. A vaccine and/or immunogenic composition comprising a *C. acnes* cell of embodiment 136 comprising a DNA vector comprising a nucleic acid encoding an antigen.

142. A method to prevent and/or treat cancer in a subject in need thereof, comprising administering to said subject a therapeutically or prophylactically efficient amount of a *C. acnes* cell of embodiment 136 comprising a DNA vector comprising a nucleic acid encoding a tumor antigen.

143. A method to prevent and/or treat a viral infection in a subject in need thereof, comprising administering to said subject a therapeutically or prophylactically efficient amount of a *C. acnes* cell of embodiment 136 comprising a DNA vector comprising a nucleic acid encoding a viral antigen.

144. A method to prevent and/or treat a bacterial infection in a subject in need thereof, comprising administering to said subject a therapeutically or prophylactically efficient amount of a *C. acnes* cell of embodiment 136 comprising a DNA vector comprising a nucleic acid encoding a bacterial antigen.

145. A method to prevent and/or treat a fungal infection in a subject in need thereof, comprising administering to said subject a therapeutically or prophylactically efficient amount of a *C. acnes* cell of embodiment 136 comprising a DNA vector comprising a nucleic acid encoding a fungal antigen.

146. A method to prevent and/or treat an autoimmune disease in a subject in need thereof, comprising administering to said subject a therapeutically or prophylactically efficient amount of a *C. acnes* cell of embodiment 136 comprising a DNA vector comprising a nucleic acid encoding a self-antigen.

147. A method to prevent and/or treat allergy in a subject in need thereof, comprising administering to said subject a therapeutically or prophylactically efficient amount of a *C. acnes* cell of embodiment 136 comprising a DNA vector comprising a nucleic acid encoding an allergen.

148. A method to prevent and/or treat graft rejection in a subject in need thereof, comprising administering to said subject a therapeutically or prophylactically efficient amount of *C. acnes* cell of embodiment 136 comprising a DNA vector comprising a nucleic acid encoding a graft-specific antigen.

149. A recombinant *C. acnes* phage of anyone of embodiments 126 to 131 or a recombinant *C. acnes* phage obtained by the methods of embodiment 138 or 139 for use in a method to treat *C. acnes* related disorder or disease.

150. A *C. acnes* cell of embodiment 136 comprising a DNA vector comprising a nucleic acid encoding a tumor antigen for use in a method to prevent and/or treat cancer in a subject.

151. A *C. acnes* cell of embodiment 136 comprising a DNA vector comprising a nucleic acid encoding a viral antigen for use in a method to prevent and/or treat a viral infection in a subject.

152. A *C. acnes* cell of embodiment 136 comprising a DNA vector comprising a nucleic acid encoding a bacterial antigen for use in a method to prevent and/or treat a bacterial infection in a subject.

153. A *C. acnes* cell of embodiment 136 comprising a DNA vector comprising a nucleic acid encoding a fungal antigen for use in a method to prevent and/or treat a fungal infection in a subject.

154. A *C. acnes* cell of embodiment 136 comprising a DNA vector comprising a nucleic acid encoding a self-antigen for use in a method to prevent and/or treat an autoimmune disease in a subject.

155. A *C. acnes* cell of embodiment 136 comprising a DNA vector comprising a nucleic acid encoding an allergen for use in a method to prevent and/or treat allergy in a subject.

156. A *C. acnes* cell of embodiment 136 comprising a DNA vector comprising a nucleic acid encoding a graft-specific antigen for use in a method to prevent and/or treat graft rejection in a subject.

EXAMPLES

Example 1. Phage-Derived Particles for Delivery of DNA Payload into *C. acnes*

*C. acnes* phage-derived particles containing a synthetic DNA payload and able to inject it inside *C. acnes* were developed. It is demonstrated for the first time the stable and autonomous replication of a recombinant DNA vector that allows for transgene expression. These phage-derived particles are produced upon the co-occurrence of a *C. acnes* phage genome and a DNA payload inside a *C. acnes* producer cell. The DNA payload is introduced into the *C. acnes* producer cell by different methods such as electroporation, electroporation of protoplast, conjugation, chemical transformation, transduction into the *C. acnes* producer cell. Such phage-derived particles open possibilities to deliver DNA encoding a therapeutic molecule into all *C. acnes* strains in situ with high efficiency and specificity, allowing, for example, sequence specific killing due to CRISPR-Cas expression or modulation of the immune system by secretion of immunomodulators.

Being able to edit *Cutibacterium acnes* population by removing specific proinflammatory strains to prevent or cure disease such as acne vulgaris or leverage their privilege location into the pilosebaceous unit to modulate the immune system or improve wound healing are attractive therapeutic approaches. To implement such approaches, one can either genetically modify *C. acnes* strains in situ or provide in vitro genetically modified *C. acnes*. Because of the large intra and inter-individual microbiome diversity both at the species and strain level, it appears difficult to provide a single or cocktail of engineered *C. acnes* strains able to colonize the skin of most patients.

Delivery of DNA in situ to the *C. acnes* population offers a way to circumvent such difficulties by allowing to leverage pre-establish strains potentially without disturbing the local microbiome. However, in situ delivery of genetic material to *C. acnes* is a challenging task for several reasons. First, there are so far no genetic elements such as plasmid able to robustly and autonomously replicate inside *C. acnes*. The few described genetic modifications consist in genomic insertion of synthetic DNA through homologous recombination[26]. This in vitro process has been shown to be very low efficiency and rely on the use of an antibiotic selection marker to select such events. Moreover, these genetic modifications have been restricted to a few specific strains (KPA17202) and might not be generalizable to all *C. acnes* strains. Second, in order to perform in situ genetic modification of *C. acnes* delivery of DNA is needed. The only described method for introducing DNA into *C. acnes* is the use of electroporation[26,27], a method that can only be performed in vitro.

The present invention solves both delivery and maintenance of synthetic DNA inside *C. acnes* population in situ. Phage-derived particles composed of a synthetic DNA vector/payload packaged inside the phage capsid at the expense of the phage genome are used. By hijacking the phage-capsid, it was taken advantage of the ability of the phage to transduce DNA into the bacterial host. These phage-derived particles, when put in the presence of the natural bacterial host of the phage, are able to bind to the bacteria and inject the DNA vector/payload inside the bacterial cytoplasm where it can replicate and lead to expression of a protein of interest.

*C. acnes* phage are naturally present on the skin where they infect and replicate using *C. acnes* as a host. *C. acnes* phages have a broad host range, meaning that they can infect most of the *C. acnes* strain diversity isolated so far. This makes the capsid of these phages a really efficient vehicle to deliver DNA in situ into all *C. acnes* strains regardless of their genetic diversity. To develop phage-derived particles from *C. acnes* phages, several phages from the skin of volunteer individuals were first isolated by sampling nose microcomedones using Biore Deep Cleansing Pore Strips (Kao Brands Company), following manufacturer's instructions. After being removed from the nose, microcomedones were collected, homogenized in sterile water and spread onto an RCM *agar* plate. After incubation under anaerobic conditions at 37° C. for 7 days, plaques could be observed on the lawn of *C. acnes* growth. Plaques were then isolated and the phages amplified on an indicator strain. Phage DNA was extracted using the Promega wizard DNA clean-up System and sent for library preparation by mechanical random fragmentation and sequenced with an Illumina MiSeq platform. Sequencing reads were assembled using Spades. As expected from previous publications, isolated phages were genetically similar to other sequenced phages.

A host-range determination was performed with the different isolated phages against a collection of *C. acnes* strains, covering the known phylogenetic diversity. All phages were able to infect most of the *C. acnes* strains showing, as previously reported, a broad host-range (FIG. 2). PAC7 phage was selected for further experiments.

Genome of phage PAC7 was purified, mechanically sheared to allow for random DNA fragmentation and a PCR-free library preparation was performed prior to paired-end sequencing using illumina Mi-seq. DNA reads were assembled using Spades, a single contig was obtained and annotated. After annotation, cohesive-ends were identified and DNA fragments of different sizes, containing cohesive ends, were cloned in order to identify the packaging sequence (called cos site for phages with cohesive ends) that allow recognition by the small terminase and packaging of the phage genome into the phage capsid. Potential packaging signals from PAC7 were cloned into the pIC086 vector in two different orientations. The pIC086 vector contains:
- an origin of replication allowing replication into *C. acnes*, and
- a selection marker functional in *C. acnes* (here giving resistance to erythromycin).

Cos containing vectors (cosmids) were cloned into the *E. coli* DH10B cloning strain, sequence verified. The DNA vectors (Table 1) were introduced into the *C. acnes* strain ATCC 11828, and recombinants were selected on *agar* plates with erythromycin.

To produce phage-derived particles, a liquid culture of the different *C. acnes* strains carrying the DNA vector (Table 2) were grown and infected by PAC7. A strain containing a plasmid without cos PAC7 (Ca0s16973) was used as control. After infection, the supernatant was filtered and collected. Because both phage genomes and DNA vectors contain a packaging signal, they compete for packaging into the capsid, giving rise to a phage/phage-derived particle mixture.

Figure 8:
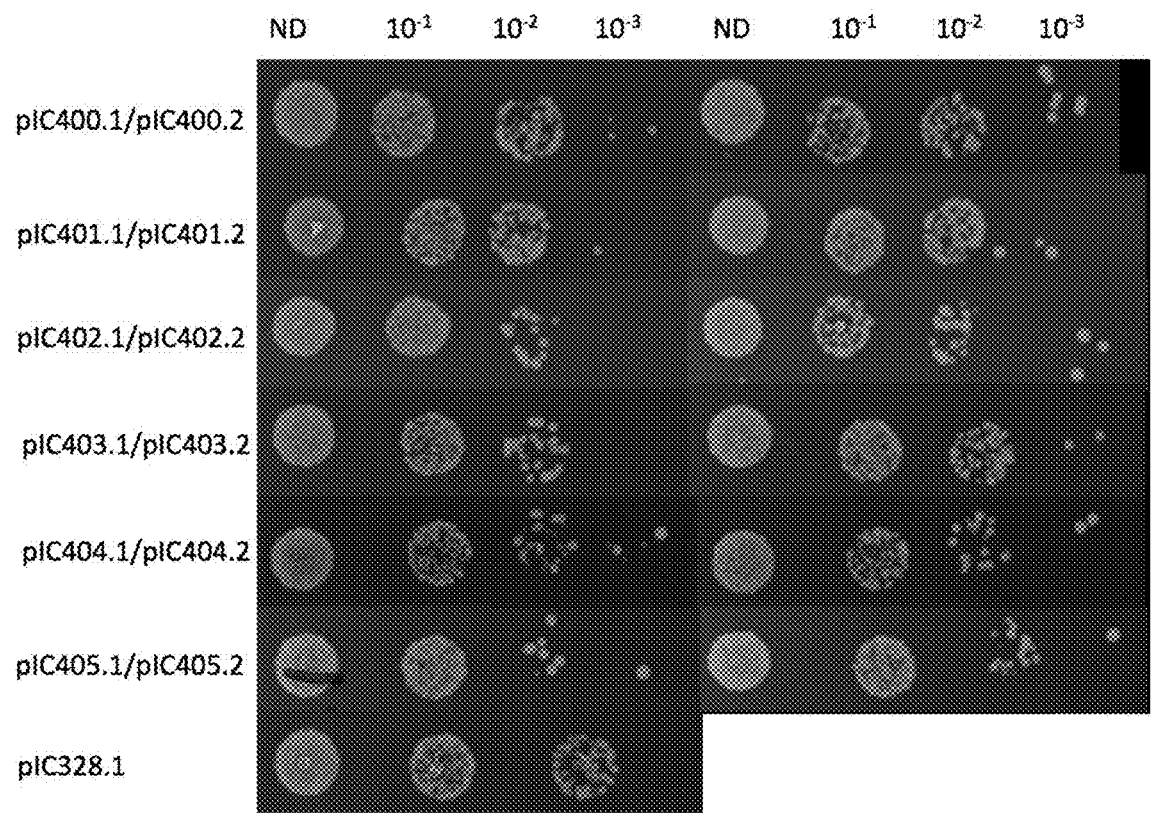
FIG. 8 depicts *C. acnes* transductants of phage-derived particles carrying DNA vector with phage packaging signal (cos) of different sizes. Each suspension of phage-derived particles, also containing phages, was mixed with *C. acnes* ATCC 11828 pseudolysogene, the mixture was incubated for 1 hour at room temperature, diluted and 4 µL of each dilution was plated on *Brucella* plates in presence of erythromycin (5 µg/mL). For each phage-derived particle containing a same DNA vector, two suspensions from independent productions were used (e.g. pIC400.1 and pIC400.2).

To quantify the number of phages and phage-derived particles in the suspension, phage and phage-derived particles titration was performed. Titration of phage-derived particles was first performed with *C. acnes* ATCC 6919, showing high efficiency killing due to phage infection but no transductants could be observed. In these conditions, transductants are co-infected with the phage, leading to death of transduced cells and to the underestimation of phage-derived particle titers. To circumvent this, it was decided to perform titration with a *C. acnes* ATCC 11828 pseudolysogene strain. Indeed, *C. acnes* phages are not strictly temperate nor strictly lytic phages in laboratory conditions. They are able to inject their genome into cells and stay dormant in the cell without integrating into the genome. These cells carrying the phage in pseudolysogeny state are immune to phage killing. Using a pseudolysogene culture for phage/phage-derived particles titration, a higher amount of transductants were observed. However due to some residual killing of *C. acnes* by phages, a large variability in phage-derived particle titers can be observed in different productions from infection of the same producer cell (FIG. 8). The concentration of phage was determined by plaque assay and showed a high concentration of phage for all phage/phage-derived particle suspension with a titer of approximately $10^7$ PFU/µL for each suspension (Table 3). Several colonies were confirmed to be *C. acnes* harbouring the cosmid by PCR. Phage suspension from infection of Ca0s16973 carrying pIC086 plasmid without cos did not show any transductant, confirming that packaging, and thus, the production of phagemid particles, was specific to cos carrying plasmids.

Titration of the phage-derived particles carrying the DNA vectors comprising phage packaging signal of different sizes shows (FIG. 8) no significant difference in number of transductants. The phage-derived particles titer was similar between all the different cosmids indicating that they are all functional and allow packaging of the DNA vector inside the phage capsid to produce phage-derived particles.

The results show, for the first time:
- transduction by a phage-derived particle of a synthetic DNA vector in *C. acnes*
- replication of the DNA vector in *C. acnes*
- expression of a transgene (erythromycin resistance gene) carried by the replicative DNA vector.

This is a key milestone for the development of in situ DNA delivery, genetic modification and transgene expression in *C. acnes*.

Materials and Methods:

Cosmids construction: Cos fragments were extracted by PCR on diluted phage PAC7 suspension, gel purified and cloned using SapI golden gate reaction and the pIC086 vector.

Introduction of cosmids in *C. acnes* can be performed by methods such as electroporation, protoplast electroporation, chemical transformation, using conjugation, natural competency, transduction.

*C. acnes* conjugation: 2 mL of overnight cultures of *E. coli* donor harboring the different mobilizable shuttle plasmids, grown in LB broth (Fisher Scientific), were pelleted in a benchtop centrifuged at 6,000×g for 1 min. Supernatants were discarded and pellets were washed with 500 µL of pre-sterilized LB medium and centrifuged again using the same conditions. Each pellet was then re-suspended in 200 µL of exponentially growing ($OD_{600}$=0.5) *C. acnes* receptor BHI culture concentrated 10× (BHI broth, Oxoid). The mixture *E. coli-C. acnes* was spotted (50 µL/spot) onto *Brucella agar* plates (Sigma-Aldrich) and allowed to mate at 37° C. under anaerobic conditions for 24 hours. After that time, cells were harvested from the mating plate, re-suspended in 300 µL of BHI broth and plated onto *Brucella agar* plates that had been supplemented with 50 µg/mL polymyxin B (Sigma-Aldrich) and 5 µg/mL erythromycin (Sigma-Aldrich) or 5 µg/mL chloramphenicol (Sigma-Aldrich). After 7 days, *C. acnes* cells that grew in the presence of selection were streaked on *Brucella agar* plates supplemented with the appropriate selection and the presence of the conjugated plasmid was confirmed via specific PCRs. The identity of *C. acnes* as well as the absence of *E. coli* donor strain were also confirmed by PCR analyses.

Phage/phage-derived particles production: Overnight cultures of *C. acnes* ATCC 11828 harbouring the different vectors (two clones per construct) were set in 10 mL BHI cultures supplemented with 5 µg/mL erythromycin. Production from phagemid pIC328 was used as a positive control. After overnight culture, once the OD600 had reached 0.8-1, 15 mL of each culture were taken and spin down at 3,000×g for 5 min. The supernatant was discarded and the pellet was re-suspended in 200 µL of PAC7 phage suspension and left on the bench at room temperature for 30 min so phages infect the cells. After one hour, 15 mL of BHI medium were added to each culture and allowed to grow/infect overnight under anaerobic conditions at 37° C. After overnight incubation, cultures were very clear, indicating that infection had taken place. Cultures were spun down at 3,000×g for 5 min, and the supernatant was filtered through a 0.45 µm filter.

Phage titration: Serial dilutions of the phage/packaged phagemid mixture were made in MgSO$_4$ 5 mM and 4 µL of each dilution were spotted onto *Brucella* plates containing a top layer of agarose 4.5 g/L and the strain ATCC 11828. After overnight incubation under anaerobic conditions at 37° C., lysis plaques were counted.

Phage-derived particles titration: 90 µL of an overnight culture (OD$_{600}$ approx 0.8-1, concentrated ×10) of *C. acnes* ATCC 11828 pseudolysogene cells were mixed with 10 uL of Phage/Phage-derived particles from non-diluted to dilution $10^{-4}$ (dilution in MgSO$_4$ 5 mM). A control of cells with no phage was included in the assay. The cultures were incubated at room temperature for 1 hour. After this first incubation period, the cultures (bacteria+phages/phage-derived particles at different dilutions) were serially diluted up to $10^{-7}$ in BHI and incubated for 3-4 hours under anaerobic conditions at 37° C. After incubation, 4 µL of each dilution were spotted onto *Brucella* plates in the presence and absence of erythromycin (5 µg/mL). After 5 days of incubation at 37° C. under anaerobic conditions, colonies on BHI plates and BHI+erythromycin 5 µg/mL plates were scanned (FIG. 8).

Pseudolysogene production: strains were freshly made prior to the transduction test. PAC7 phage was added to a suspension of *C. acnes* ATCC 11828 cells and plated onto BHI *agar* plates. After 3 to 4 incubation days, cells growing on plates were recovered and either plated again to have more cells or used for titration. If successive growth on plates is needed, *C. acnes* phages are added to the culture in order to maintain strains in the pseudolysogene state.

Figure 1:
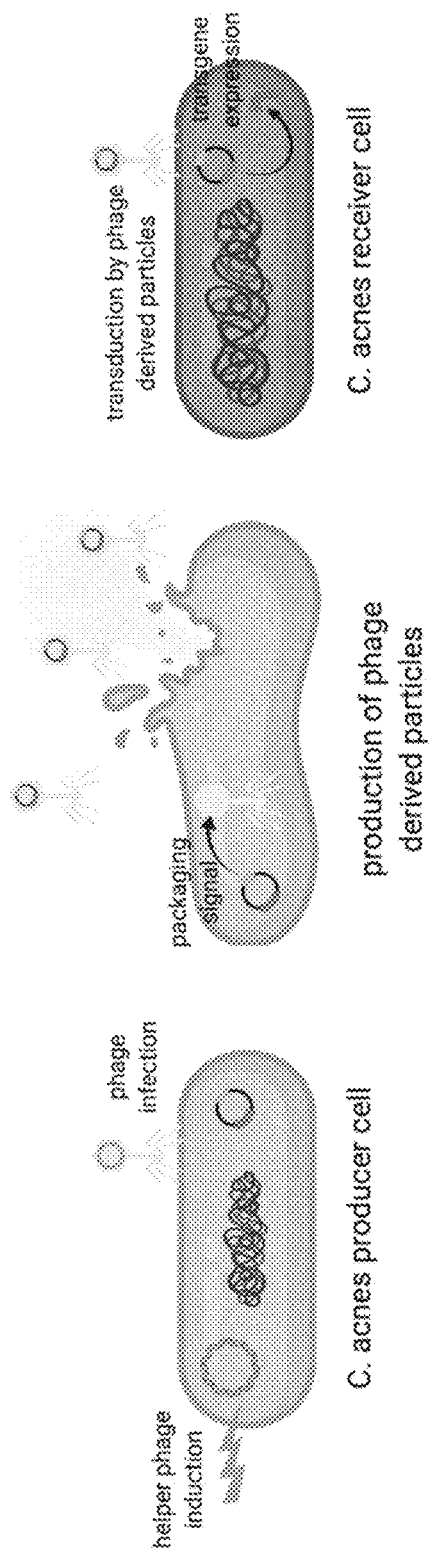
FIG. 1 depicts a *C. acnes* producer cell carrying a DNA vector with a packaging signal and a transgene which is infected by a *C. acnes* phage; phage-derived particles carrying the DNA vector are then produced and upon binding to *C. acnes* receiver cell transduce the DNA vector that replicates and leads to transgene expression. Alternatively, the *C. acnes* producer is not infected by a phage but carries also a helper phage that is induced to trigger phage-derived particle production.
Figure 3:
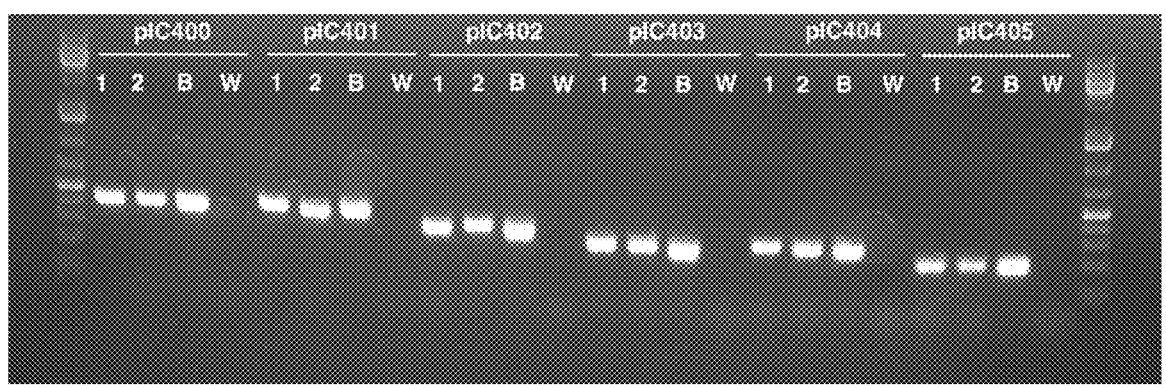
FIG. 3 depicts a gel. Individual colonies from phage-derived particles titration were streaked and a PCR on an individual colony was performed with primers IC208 (SEQ ID NO: 99)/IC310 (SEQ ID NO: 100) to confirm the presence of the phagemid. 1 and 2 refer to transductants coming from the independent production and titration of phage-derived particles carrying the same phagemid. B and W are respectively PCR on the phagemid extraction (positive control) and the ATCC 11828 strain (negative control). Presence of the plasmid after restreak confirms that transductants carry the replicative phagemid.

Confirmation of the phagemid transduction into *C. acnes* cells: colonies observed on BHI plates supplemented with erythromycin were re-isolated on BHI+erythromycin plates. Individual erythromycin resistant colonies obtained after streaking were then tested by PCR to confirm the presence of the phagemid (FIG. 3).

PCR verification of the transductant: colony PCR to check the presence of the phagemid was performed with primers IC208/1C310. A PCR performed with primers AD1261/AD1262 was also included to confirm *C. acnes* identity.

TABLE 1

Mobilizable DNA vectors including packaging signal of PAC7 phage

| DNA vector Name | Cos region | Primers for cloning | Mobilisable vector |
|---|---|---|---|
| plC328 | PAC7 Cos region 1 in orientation 1 (383 bp) | AD1542/ AD1541 | plC086 |
| plC400 | PAC7 Cos region 1 in orientation 1 (317 bp) | IC511/ AD1542 | plC086 |
| plC401 | PAC7 Cos region 1 in orientation 2 (317 bp) | AD1541/ IC512 | plC086 |
| plC402 | PAC7 Cos region 2 in orientation 1 (217 bp) | IC511/ IC512 | plC086 |
| plC403 | PAC7 Cos region 2 in orientation 2 (167 bp) | IC513/ IC512 | plC086 |
| plC404 | PAC7 Cos region 3 in orientation 1 (167 bp) | IC511/ IC514 | plC086 |
| plC405 | PAC7 Cos region 3 in orientation 2 (83 bp) | IC513/ IC514 | plC086 |

TABLE 2

List of *C. acnes* strains generated

| name | Strain description | plasmid |
|---|---|---|
| Ca0s16973 | *Cutibacterium acnes* ATCC 11828 | plC086 |
| Ca0s18253 | *Cutibacterium acnes* ATCC 11828 | plC328 |
| Ca0s19443 | *Cutibacterium acnes* ATCC 11828 | plC400 |
| Ca0s19444 | *Cutibacterium acnes* ATCC 11828 | plC401 |
| Ca0s19445 | *Cutibacterium acnes* ATCC 11828 | plC402 |
| Ca0s19446 | *Cutibacterium acnes* ATCC 11828 | plC403 |
| Ca0s19447 | *Cutibacterium acnes* ATCC 11828 | plC404 |
| Ca0s19448 | *Cutibacterium acnes* ATCC 11828 | plC405 |

TABLE 3

Results of phage titration

| strain infected | DNA payload | Phage used for infection | Phage titer (PFU/µL) on *C. acnes* ATCC 11828 indicator strain |
|---|---|---|---|
| Ca0s16973 | plC086 | PAC7 | ~1E+8 |
| Ca0s18253 | plC328 | PAC7 | ~1E+7 |
| Ca0s19443 | plC400 | PAC7 | ~1E+7 |
| Ca0s19444 | plC401 | PAC7 | ~1E+7 |
| Ca0s19445 | plC402 | PAC7 | ~1E+7 |
| Ca0s19446 | plC403 | PAC7 | ~1E+7 |
| Ca0s19447 | plC404 | PAC7 | ~1E+7 |
| Ca0s19448 | plC405 | PAC7 | ~1E+7 |

TABLE 4

Primers sequences

| Primers name | Primers sequence |
|---|---|
| AD1541 | GTTCCAGCTCTTCCGAGGACCACATCACACCCGTC (SEQ ID NO: 91) |
| AD1542 | GTTCCAGCTCTTCCTGCCCACTCCTCATCAGACAC (SEQ ID NO: 92) |
| IC511 | GTTCCAGCTCTTCCGAGAGGCAACAGAACACAACCAAA (SEQ ID NO: 93) |
| IC512 | GTTCCAGCTCTTCCTGCGACTATCAGGAAGCTCAGGC (SEQ ID NO: 94) |

TABLE 4-continued

Primers sequences

| Primers name | Primers sequence |
|---|---|
| IC513 | GTTCCAGCTCTTCCGAGAAAACCCGCCAACCCCCACC (SEQ ID NO: 95) |
| IC514 | GTTCCAGCTCTTCCTGCACAAAAGGGAGGTATTTCACT (SEQ ID NO: 96) |
| AD1261 | CAGCGGCGCTGCTAAGAACTT (SEQ ID NO: 97) |
| AD1262 | CCGGCTGGCAAATGAGGCAT (SEQ ID NO: 98) |
| IC208 | GCTTCCTTAGCTTGCGAAATCTCGA (SEQ ID NO: 99) |
| IC310 | GTTCGGCTAAACCCAAAAGTAAAAAC (SEQ ID NO: 100) |

Example 2. Engineering and Selection of C. acnes Phages Using CRISPR-Cas System

Single nucleotide modifications (SNM) were performed at various loci of the C. acnes phage PAC7 using CRISPR via two different strategies. In one strategy, a single vector containing both the editing template and the CRISPR system targeting the unmodified (not engineered or wt phage), allows to generate and amplify selectively the recombinant phage compared to the WT. However a step of isolation of the mutant phages is necessary. In the second strategy, two vectors, one harbouring the editing template and another harbouring the CRISPR system targeting the wt phage, are necessary to obtain and select mutant phages. In this document, both examples are included and explained separately:

Single Vector Strategy:

Using DNA sequences and associated annotations, the putative endolysin gene (SEQ ID NO: 77) and cos sequences (SEQ ID NO: 66) were identified and it was decided to attempt a SNM in such loci. In the case of the endolysin locus, the single base change leads to the same protein as the original or wt sequence after translation—a so-called synonymous mutation. In both cases, the editing template was designed so that after a second homologous recombination event, which results in the intended modification of the phage genome, the PAM sequence necessary for the CRISPR system to perform a double strand break, is removed. In such scenario, only the unmodified phage—and not the mutant phage—is targeted by the CRISPR system, providing the selection necessary for mutant-wt discrimination.

A CRISPR vector, named pIC104, was selected to further introduce the elements necessary to engineer PAC 7. pIC104 is an E. coli-C. acnes shuttle plasmid that includes:
- an origin of replication allowing replication into C. acnes
- a selection marker functional in C. acnes (here giving resistance to erythromycin)
- a relaxase and associated origin of transfer (oriT) to conjugate the DNA payload into C. acnes
- an origin and selection marker allowing replication in E. coli.
- the elements necessary for CRISPR targeting, including the gene encoding SpCas9, previously codon-optimised for C. acnes expression and the sgRNA.

Introduction of the target/seed sequences into pIC104 led to the vectors pIC238 and pIC240 in the case in which the endolysin (SEQ ID NO: 79) and the cos site (SEQ ID NO: 80) are targeted, respectively. Introduction of the editing template (SEQ ID NO: 81 for endolysin, SEQ ID NO: 82 for cos) into pIC238 and pIC240 led to vectors pIC253 and pIC257, respectively. Vectors (editing/targeting vectors) were cloned into the E. coli DH10B cloning strain, sequence verified and transformed into the E. coli donor strain harbouring conjugation machinery. These vectors were finally conjugated into C. acnes strain ATCC 11828 and transformants were selected on agar plates supplemented with erythromycin. The following strains were generated Ca0s18233 (C. acnes ATCC 11828 harbouring pIC238); Ca0s240 (C. acnes ATCC 11828 harbouring pIC240); Ca0s18206 (C. acnes ATCC 11828 harbouring pIC253), and; Ca0s18208 (C. acnes ATCC 11828 harbouring pIC257).

To produce engineered phages, a liquid culture of the different C. acnes strains carrying the DNA vector pIC253 (Ca0s18206) or pIC257 (Ca0s18208) were grown and infected by phage PAC7. After infection, the supernatant was filtered and collected. Here, it is referred to these supernatants as Sup-253 and Sup-257 to those obtained after infecting with phage PAC7 the strains Ca0s18206 and Ca0s18208, respectively. Theoretically, the unmodified phage has been targeted by the CRISPR system and the supernatant contains a high fraction of the engineered phage, the efficiency of the wt phage targeting being dependent on the efficiency of the CRISPR system and seed sequence used.

Figure 9:
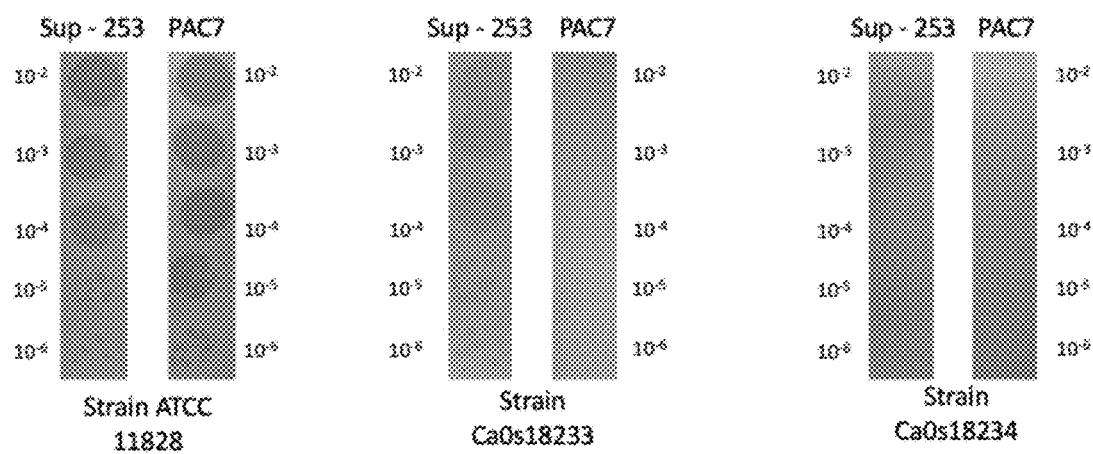
FIG. 9 depicts titration of supernatants obtained after infecting *C. acnes* harbouring editing/targeting vectors pIC253 (Ca0s18206), referred as Sup-253, on *C. acnes* ATCC 11828 wt, *C. acnes* ATCC 11828 harbouring pIC238 (Ca0s18233) and *C. acnes* ATCC 11828 harbouring pIC240

To demonstrate and quantify the presence of mutant and wt phage in the suspension, a phage titration was performed. Titration was performed with C. acnes ATCC 11828 and C. acnes ATCC 11828 harbouring pIC238 (Ca0s18233) and pIC240 (Ca0s18234) in the case of the phage modified in the endolysin or cos loci, respectively (FIG. 9 and FIG. 10). As mentioned above, these vectors contain the CRISPR system that selects for the intended modifications for each locus. If the mutant phage has been obtained and replicate, plaques corresponding to recombinant phage when titrating on C. acnes ATCC 11828 harbouring the targeting vectors should be observed. Titration of the supernatant obtained after infecting the strain containing the editing template for the endolysin locus in the strain harbouring the targeting vector for the cos locus—and vice versa—serves as a control in this experiment (any phage obtained in this supernatant should be targeted by C. acnes harbouring a vector that targets the wt cos locus in the same manner as a wt phage is targeted).

Individual plaques obtained after titration of supernatants on C. acnes ATCC 11828 were screened by PCR using primers IC443/1C444 and IC446/AD1289 in the case of Sup-253 and Sup-257, respectively, and the identity of the phage mutant confirmed by genome sequencing. Sequencing results of isolated plaques obtained after re-infection of C.

*acnes* ATCC 11828 with previously isolated and sequenced plaques further confirmed the identity of the engineered phage.

Two-Vector Strategy:

Using DNA sequences and associated annotations, the putative endolysin gene (SEQ ID NO: 77) was identified and it was decided to attempt a SNM in such loci. The single base change leads to the same protein as the original or wt sequence after translation—a so-called synonymous mutation. The editing template or homology arms were designed so that after a second homologous recombination event, which results in the intended modification of the phage genome, the PAM sequence necessary for the CRISPR system to perform a double strand break, is removed. In such scenario, only the unmodified phage—and not the mutant phage—is targeted by the CRISPR system, providing the selection necessary for mutant-wt discrimination.

A shuttle mobilisable vector, named pIC086, was selected to further introduce the editing template. pIC086 is an *E. coli-C. acnes* shuttle plasmid that includes:
- an origin of replication allowing replication into *C. acnes*
- a selection marker functional in *C. acnes* (here giving resistance to erythromycin)
- a relaxase and associated origin of transfer (oriT) to conjugate the DNA payload into *C. acnes*
- an origin and selection marker allowing replication in *E. coli*.

A CRISPR vector, named pIC104, was selected to further introduce the elements necessary to engineer PAC 7. pIC104 is an *E. coli-C. acnes* shuttle plasmid that includes:
- An origin of replication allowing replication into *C. acnes*
- a selection marker functional in *C. acnes* (here giving resistance to erythromycin)
- a relaxase and associated origin of transfer (oriT) to conjugate the DNA payload into *C. acnes*
- an origin and selection marker allowing replication in *E. coli*.
- the elements necessary for CRISPR targeting, including the gene encoding SpCas9, previously codon-optimised for *C. acnes* expression and the sgRNA.

Introduction of the editing template into pIC086 led to the vector pIC350. Introduction of the target/seed sequence into pIC104 led to the vector pIC238. A vector containing the editing template for a different locus (vector pIC351) was also included as control. Targeting and editing vectors were cloned into the *E. coli* DH10B cloning strain, sequence verified and transformed into the *E. coli* donor strain harbouring a conjugation machinery. These vectors were finally conjugated into *C. acnes* strain ATCC 11828 and transformants were selected on *agar* plates supplemented with erythromycin. The following strains were generated Ca0s18233 (*C. acnes* ATCC 11828 harbouring pIC238); Ca0s18379 (*C. acnes* ATCC 11828 harbouring pIC350), and; Ca0s18381 (*C. acnes* ATCC 11828 harbouring pIC351).

To produce engineered phages, a liquid culture of the different *C. acnes* strains carrying the DNA vectors pIC350 (Ca0s18379) and pIC351 (control for editing template; strain Ca0s18381) were grown and infected by phage PAC7. After infection, the supernatant was filtered and collected. Here, it is referred to these supernatants as Sup-350 and Sup-351 to those obtained after infecting with phage PAC7 the strains Ca0s18379 and Ca0s18381, respectively. Theoretically, if homologous recombination has taken place, the suspension contains a mixture of wt and engineered phage.

To select and quantify the presence of mutant and wt phage in the suspension, a phage titration was performed. Titration was performed with *C. acnes* ATCC 11828 and *C. acnes* ATCC 11828 harbouring pIC238 (Ca0s18233) (FIG. 11). The vector pIC238 contains the CRISPR system that selects for the intended modifications. If the mutant phage has been obtained, phage titer on Sup-350 should differ when titrated on *C. acnes* ATCC 11828 and *C. acnes* ATCC 11828 harbouring the targeting vector pIC238 (Ca0s18233). *C. acnes* ATCC 11828 is susceptible to both wt phage PAC7 and the engineered phage, whereas *C. acnes* harbouring pIC238 is only susceptible to the engineered phage. Titration of Sup-351 (control for editing template) on *C. acnes* ATCC 11828 and *C. acnes* harbouring pIC238 (Ca0s18233) should be the same, since both strains are susceptible to both, the wt phage PAC7 and the engineered phage (FIG. 12).

Individual plaques obtained after titration of supernatants on *C. acnes* ATCC 11828 were screened by PCR using primers 10443/10444 and IC446/AD1289 and the identity of the phage mutant confirmed by genome sequencing. Sequencing results of isolated plaques obtained after re-infection of *C. acnes* ATCC 11828 with previously isolated and sequenced plaques further confirmed the identity of the engineered phage.

It has been demonstrated, for the first time, that recombinant *C. acnes* phages could be efficiently produced, using in vivo recombination (recombineering) in *C. acnes* between a DNA template carried by a DNA vector and a *C. acnes* phage genome. These recombinant particles can be directly amplified selectively compared to wt particles if the DNA vector contains a CRISPR-Cas system targeting the wt phage genome but not the recombinant phage genome (1 vector strategy). Otherwise the few recombinant particles, obtained using a DNA vector that do not contain CRISPR-Cas system targeting wt phage genome, can be selected using a second infection with a *C. acnes* strain carrying a CRISPR-Cas system targeting wt phage genome but not recombinant phage genome (2 vector strategy). This demonstration was performed using single nucleotide modifications however insertion, deletion, replacement of one or several nucleotides including introduction of transgene without perturbing the phage production open the possibility to use *C. acnes* recombinant phage has a tool to for example express therapeutic proteins in vivo or to modify *C. acnes* phage host range.

Materials and Methods:

*C. acnes* conjugation: 2 mL of overnight cultures of *E. coli* harboring the different mobilizable shuttle plasmids, grown in LB broth (Fisher Scientific), were pelleted in a benchtop centrifuged at 6,000×g for 1 min. Supernatants were discarded and pellets were washed with 500 µL of pre-sterilized LB medium and centrifuged again using the same conditions. Each pellet was then re-suspended in 200 µL of exponentially growing ($OD_{600}$=0.5) *C. acnes* receptor BHI culture concentrated 10× (BHI broth, Oxoid). The mixture *E. coli-C. acnes* was spotted (50 µL/spot) onto *Brucella agar* plates (Sigma-Aldrich) and allowed to mate at 37° C. under anaerobic conditions for 24 hours. After that time, cells were harvested from the mating plate, re-suspended in 300 µL of BHI broth and plated onto *Brucella agar* plates that had been supplemented with 50 µg/mL polymyxin B (Sigma-Aldrich) and 5 µg/mL erythromycin (Sigma-Aldrich) or 5 µg/mL chloramphenicol (Sigma-Aldrich). After 7 days, *C. acnes* cells that grew in the presence of selection were streaked on *Brucella agar* plates supplemented with the appropriate selection and the presence of the conjugated plasmid was confirmed via specific PCRs. The identity of *C. acnes* as well as the absence of *E. coli* donor strain were also confirmed by PCR analyses.

Phage production: a liquid culture (BHI+erythromycin 5 µg/mL) of *C. acnes* ATCC 11828 or *C. acnes* carrying a DNA vector were grown to the exponential phase, centrifuged and resuspended (approx. $10^8$-$10^9$ cells) in 100 µL of *C. acnes* phage PAC7 suspension (approx. $10^5$ PFU/µL). The mixture was then incubated for 30-60 min at RT so that infection took place. After incubation, the mixture was diluted in 5 mL BHI supplemented with 5 µg/mL erythromycin and incubated overnight at 37° C. under anaerobic conditions. After overnight incubation, cultures were centrifuged and filtered through a 0.2 µm membrane filter.

Phage titration: phage suspensions were serially diluted in MgSO4 5 mM and spotted (4 µl/spot) on a BHI double-layer plates containing *C. acnes* ATCC 11828 wt or *C. acnes* ATCC 11828 harbouring a targeting vector (Ca0s18233 and Ca0s18234). After 2 days of incubation under anaerobic conditions at 37° C., lysis plaques were counted.

PCR screening of phage mutants: PCR on individual plaques was performed with primers IC443/1C444 and IC446/AD1289 for SNM obtained in the endolysin and cos loci, respectively.

TABLE 5

Mobilizable targeting, editing and targeting/editing DNA vectors:

| DNA vector Name | Description | Target/ seed sequences | Editing template sequence |
|---|---|---|---|
| pIC238 | Mobilisable targeting vector with CRISPR system targeting the endolysin gene | SEQ ID NO: 79 | — |
| pIC240 | Mobilisable targeting vector with CRISPR system targeting the cos locus | SEQ ID NO: 80 | — |
| pIC253 | Mobilisable targeting and editing vector with CRISPR system targeting the endolysin gene and editing template to introduce a SNM in the endolysin gene | SEQ ID NO: 79 | SEQ ID NO: 81 |
| pIC257 | Mobilisable targeting and editing vector with CRISPR system targeting the cos locus and editing template to introduce a SNM in the cos locus | SEQ ID NO: 80 | SEQ ID NO: 82 |
| pIC350 | Mobilisable editing vector to introduce a SNM in the endolysin gene | — | SEQ ID NO: 81 |
| pIC351 | Mobilisable editing vector to introduce a SNM in the endonuclease locus. Used as control. | — | SEQ ID NO: 83 |

TABLE 6

List of *C. acnes* strains generated:

| Name | Strain description | Plasmid |
|---|---|---|
| Ca0s18233 | *Cutibacterium acnes* ATCC 11828 | pIC238 |
| Ca0s18234 | *Cutibacterium acnes* ATCC 11828 | pIC240 |
| Ca0s18206 | *Cutibacterium acnes* ATCC 11828 | pIC253 |
| Ca0s18208 | *Cutibacterium acnes* ATCC 11828 | pIC257 |

TABLE 6-continued

List of *C. acnes* strains generated:

| Name | Strain description | Plasmid |
|---|---|---|
| Ca0s18379 | *Cutibacterium acnes* ATCC 11828 | pIC350 |
| Ca0s18381 | *Cutibacterium acnes* ATCC 11828 | pIC351 |

TABLE 7

Primer sequences

| Primers name | Primers sequence |
|---|---|
| IC443 | CCAGGGTGTGAAACCGTCGCCTCTA (SEQ ID NO: 101) |
| IC444 | CGCAAACACCCCGTTTACCGGCCTT (SEQ ID NO: 102) |
| IC446 | AGGGTATTCCTACCCCCAGACGATT (SEQ ID NO: 103) |
| AD1289 | CCAATCATCCAACACCTGCTGC (SEQ ID NO: 104) |

Example 3. Introduction and Expression of Transgene into *C. acnes* Phages Using CRISPR-Cas System Introduction of a transgene expression cassette is performed at various loci of the *C. acnes* phage using in vivo homologous recombination in a first *C. acnes* strain followed by selection of the *C. acnes* recombinant phage, containing the transgene expression cassette, in a second *C. acnes* strain carrying a vector expressing a CRISPR-Cas system targeting WT phage but not the recombinant phage. Upon infection transgene expression can be observed.

One of the challenges in engineering bacteriophage is being able to perform genetic modifications without affecting the production of functional particles. This appears to be particularly difficult because bacteriophage genomes have few non-coding regions and their genetic program is tightly regulated to maximize progeny production. As an example of such genetic constraints, most of the bacteriophages organize their genetic information as long operon whose transcription is dependent on anti-termination mechanism or the expression of specific RNA polymerase or sigma factor. Another example of the high compaction of genetic information is the presence of numerous overlapping coding sequences. Indeed a lot of genes have their ribosome binding site and their start codon inside the gene upstream. Finally because of their small size, typically only a small fraction of genes are not essential to the phage life-cycle.

For all these reasons it is difficult to introduce transgene without perturbing the production of phage thus only specific genes and specific intergenic region can be used to introduce transgenes.

The genetic architecture of *C. acnes* phages is highly conserved and five different regions with different functions have been identified: Packaging, head assembly, tail assembly, lysis, DNA replication (FIG. 13).

Several candidates loci for insertion of transgene (Table 8) were selected. These loci have been chosen for several reasons.

Locus 1 for example is at the end of a potential operon (table 8 locus 1) and thus introduction of the transgene will supposedly have no impact on upstream genes.

Locus 2 is between the end of the region encoding tail assembly and upstream the lysis region. Introduction of a transgene here should not impact the tail assembly and if it happens to impact downstream lysis gene, consisting of a holin and an endolysin, recombinant particles by lysing *C. acnes* cells using for example chloroform treatment could still be produced.

Locus 3 is downstream of the HNH endonuclease gene and no gene is present downstream limiting potential interference of the transgene insertion.

TABLE 8

| Locus number | Description | Location in PAC7 phage genome (SEQ ID NO: 105) |
|---|---|---|
| 1 | Downstream of holin (gp21) and upstream of gp22 | 16709-16793 |
| 2 | Downstream of tail protein (gp19) and upstream of amidase (gp20) | 15390-15478 |
| 3 | Downstream endonuclease (gp45) | 29705-29755 |

Transgene can be inserted or replace one or several genes. The transgene can be with its own promoter and terminator, as a translational unit (RBS-CDS) or as a single coding sequence.

To determine which loci in the *C. acnes* phage genome allow for transgene insertion, production of phage and the expression of the transgene during infection a transcriptional unit (promoter RBS CDS terminator) or a translational unit (RBS-CDS) driving the expression of a reporter gene, here the oxygen independent and bilirubin dependent fluorescent gene UnaG (SEQ ID NO: 84) codon optimized for *C. acnes* expression, is inserted.

Introduction of the transgene will be performed using in vivo recombination.

Plasmids with 1 kb homologies upstream and downstream to the phage genome insertion site and the transgene in-between is cloned into an *E. coli-C. acnes* shuttle mobilisable vector (table 9) that includes:

An origin of replication allowing replication into *C. acnes* a selection marker functional in *C. acnes* (here giving resistance to erythromycin)

a relaxase and associated origin of transfer (oriT) to conjugate the DNA payload into *C. acnes* an origin and selection marker allowing replication in *E. coli*.

TABLE 9

Plasmid containing DNA template for homologous recombination with phage genome at different loci

| Plasmid name | Description |
|---|---|
| pIC86-UnaGPAC7locus1 | Locus 1 upstream homology arm-UnaG transcriptional unit-Locus 1 downstream homology arm |
| pIC86-UnaGPAC7locus2 | Locus 2 upstream homology arm-UnaG transcriptional unit-Locus 2 downstream homology arm |
| pIC86-UnaGPAC7locus3 | Locus 3 upstream homology arm-UnaG transcriptional unit-Locus 3 downstream homology arm |

A CRISPR vector, will be constructed to select recombinant *C. acnes* phage with transgene. pIC104 is an *E. coli-C. acnes* shuttle plasmid that includes:

an origin of replication allowing replication into *C. acnes* a selection marker functional in *C. acnes* (here giving resistance to erythromycin)

a relaxase and associated origin of transfer (oriT) to conjugate the DNA payload into *C. acnes* an origin and selection marker allowing replication in *E. coli*.

the elements necessary for CRISPR targeting, including the gene encoding SpCas9, codon-optimised for *C. acnes* expression and the sgRNA scaffold.

Several sgRNA targets candidates targeting the WT phage at the locus of transgene insertion are cloned into pIC104 (Table 10).

TABLE 10

| Plasmid name | Description |
|---|---|
| pIC104-PAC7locus1 | pIC104 with sgRNA targeting locus 1 |
| pIC104-PAC7locus2 | pIC104 with sgRNA targeting locus 2 |
| pIC104-PAC7locus3 | pIC104 with sgRNA targeting locus 3 |

Targeting and editing vectors is cloned into the *E. coli* DH10B cloning strain, sequence verified and transformed into the *E. coli* donor strain harboring the conjugation machinery. These vectors are finally conjugated into *C. acnes* strain ATCC 11828 and transformants are selected on agar plates supplemented with erythromycin.

To produce engineered phages, a liquid culture of the different *C. acnes* strains carrying respectively pIC86-UnaGPAC7locus1, pIC86-UnaGPAC7locus2, pIC86-UnaGPAC7locus3 is grown and infected by phage PAC7. After infection, the supernatant is filtered and collected. Theoretically, if homologous recombination has taken place, the suspension contains a mixture of wt and engineered phage.

To select and quantify the presence of mutant and WT phage in the suspensions, a phage titration is performed. Titration is performed with *C. acnes* ATCC 11828 and *C. acnes* ATCC 11828 carrying respectively pIC104-PAC7locus1, pIC104-PAC7locus2, pIC104-PAC7locus3. *C. acnes* ATCC 11828 is susceptible to both wt phage PAC7 and the engineered phage, whereas *C. acnes* harbouring the corresponding pIC104 derivative is only susceptible to the phage engineered at the corresponding locus. A titration is also performed on a pIC104 derivative targeting a locus non engineered as a control for the CRISPR-Cas specificity. Titration is performed by spot assay on BHI erythromycin (5 µg/mL) supplemented with Bilirubin (20 µM). Bilirubin is necessary for UnaG fluorescence.

Individual plaques obtained after titration of supernatants on *C. acnes* ATCC 11828 and *C. acnes* carrying pIC104 derivatives are screened for fluorescence under blue light. Plaques that show fluorescence are screened by PCR to check the presence of the transgene. Finally sequencing of the insertion locus is performed.

Recombinant plaques are then isolated and reamplified on the *C. acnes* ATCC 11828 or *C. acnes* 11828 carrying the corresponding pIC104 derivative.

Expected number of total plaques and fluorescent plaques observed are summarized in the following table (Table 11).

TABLE 11

Expected outcome of phage titration of different suspension on different C. acnes strains

| Strain used for recombinant phage production | Phage plaques/fluorescent phage plaques on strain ATCC 11828 | Phage plaques/fluorescent phage plaques on strain ATCC 11828 pIC104-PAC7locus1 | Phage plaques/fluorescent phage plaques on strain ATCC 11828 pIC104-PAC7locus2 | Phage plaques/fluorescent phage plaques on strain ATCC 11828 pIC104-PAC7locus3 |
|---|---|---|---|---|
| pIC86-UnaGPAC7locus1 | $\sim 10^7$ plaques No fluorescent plaques | $<10^7$ plaques Only fluorescent plaques | No plaques or few plaques Not fluorescent | No plaques or few plaques Not fluorescent |
| pIC86-UnaGPAC7locus2 | $\sim 10^7$ plaques No or few fluorescent plaques Not fluorescent | No plaques or few plaques Not fluorescent | $<10^7$ plaques Only fluorescent plaques | No plaques or few plaques Not fluorescent |
| pIC86-UnaGPAC7locus3 | $\sim 10^7$ plaques No fluorescent plaques | No plaques or few plaques Not fluorescent | No plaques or few plaques Not fluorescent | $<10^7$ plaques Only fluorescent plaques |

Locus for which transgene is inserted and fluorescence can be observed are suitable for transgene expression.

Based on the screening of locus, several potential therapeutic proteins to be expressed by a recombinant phage are inserted among which IL-10 and anti-TNFalpha.

In conclusion, ability to engineer C. acnes phages allows the combination of two functions:
- transgene expression in situ
- killing of a fraction of the C. acnes population in situ.

This can offer beneficial outcome for disease or conditions were C. acnes colonization is to high and/or leading to inflammatory response by for example expressing an anti-inflammatory protein such as IL-10 while killing C. acnes cell leading to inflammation.

Materials and Methods:

C. acnes conjugation: 2 mL of overnight cultures of coli donor strain harboring the conjugation machinery and the different mobilizable shuttle plasmids and a conjugative plasmid or ICE, grown in LB broth (Fisher Scientific), were pelleted in a benchtop centrifuged at 6,000×g for 1 min. Supernatants were discarded and pellets were washed with 500 μL of pre-sterilized LB medium and centrifuged again using the same conditions. Each pellet was then re-suspended in 200 μL of exponentially growing ($OD_{600}$=0.5) C. acnes receptor BHI culture concentrated 10× (BHI broth, Oxoid). The mixture E. coli-C. acnes was spotted (50 μL/spot) onto Brucella agar plates (Sigma-Aldrich) and allowed to mate at 37° C. under anaerobic conditions for 24 hours. After that time, cells were harvested from the mating plate, re-suspended in 300 μL of BHI broth and plated onto Brucella agar plates that had been supplemented with 50 μg/mL polymyxin B (Sigma-Aldrich) and 5 μg/mL erythromycin (Sigma-Aldrich) or 3.5 μg/mL chloramphenicol (Sigma-Aldrich). After 7 days, C. acnes cells that grew in the presence of selection were streaked on Brucella agar plates supplemented with the appropriate selection and the presence of the conjugated plasmid was confirmed via specific PCRs. The identity of C. acnes as well as the absence of E. coli donor strain were also confirmed by PCR analyses.

Phage production: a liquid culture (BHI+erythromycin 5 μg/mL) of C. acnes ATCC 11828 or C. acnes carrying a DNA vector were grown to the exponential phase, centrifuged and resuspended (approx. $10^5$-$10^9$ cells) in 100 μL of C. acnes phage PAC7 suspension (approx. $10^5$ PFU/μL). The mixture was then incubated for 30-60 min at RT so that infection took place. After incubation, the mixture was diluted in 5 mL BHI supplemented with 5 μg/mL erythromycin and incubated overnight at 37° C. under anaerobic conditions. After overnight incubation, cultures were centrifuged and filtered through a 0.2 μm membrane filter.

Phage titration: phage suspensions were serially diluted in $MgSO_4$ 5 mM and spotted (4 μl/spot) on a BHI double-layer plates containing C. acnes ATCC 11828 wt or C. acnes ATCC 11828 harbouring a targeting vector. After 2 days of incubation under anaerobic conditions at 37° C., lysis plaques were counted.

PCR screening of phage mutants: PCR on individual plaques was performed with primers matching on one side the transgene and on the other side the WT phage.

Example 4

Effects of genetically modified C. acnes strains are tested in vitro for their effects on immune cells, in particular for their ability to induce specific cytokines or immune profiles, according to previously described protocols.

In particular, the protocol disclosed in Yu et al. (2016) Journal of Investigative Dermatology 136:2221-2228, with optional modifications and/or adaptations if needed, is implemented on said strains.

Example 5: Secretion of Antigens by Engineered C. acnes Strains

The pilosebaceous unit (PSU) is a complex skin appendage containing a diverse set of cells such as immune cells, sebaceous cells and stem cells. It's also a highly vascularized area making it an entry point for systemic delivery of molecules. The PSU microbiota is dominated by C. acnes, therefore the ability to engineer C. acnes to secrete recombinant proteins in situ is of great interest to both modulate the activity of the cells present as well as for the delivery of molecules in the blood. The present example demonstrates the use of DNA vectors that once introduced into C. acnes led to the secretion of recombinant proteins, here the chicken ovalbumin antigen protein. This invention opens possibilities to use engineered C. acnes strains secreting specific proteins of interest such as antigens as skin probiotics. Alternatively engineered phages or phage-derived particles can be used to deliver DNA vectors, encoding for the secretion of protein of interest, in the C. acnes population already present in the PSU.

C. acnes is one of the, if not the, most abundant and prevalent bacterial commensal of the human skin. It resides mostly in the PSU even if it can also be isolated from the skin surface. Specific strains belonging to specific phylotypes have been associated with acne vulgaris disease and are considered to be "pro-inflammatory". In order to characterize the difference between the different C. acnes phylotypes, a few studies have been characterizing the secretome in order to identify potential proteins specific to the pro-inflammatory phenotypes. Using a subset of the identified secreted proteins, the present inventors were able to identify putative secretion signal peptides (Table 12) using signalP (Armenteros, J. et al. SignalP 5.0 improves signal peptide predictions using deep neural networks. *Nat Biotechnol* 37, 420-423 (2019)).

To test ability of these secretion signal peptides to drive secretion of a recombinant protein in *C. acnes*, the present inventors built several replicative plasmids comprising:
- a promoter driving the expression of the recombinant protein,
- a signal peptides addressing the proteins to secretion systems fused to the N-terminal of a chicken ovalbumin CDS codon optimized for *C. acnes*,
- an erythromycin selection marker for *C. acnes*,
- an origin of replication functional in *C. acnes*.

The different DNA vectors (Table 13) were introduced into *C. acnes* ATCC 11828 (Table 14). Introduction into *C. acnes* cells can be performed by different methods such as electroporation, electroporation of protoplast, conjugation, chemical transformation, transduction into the *C. acnes*. Presence of the DNA vectors into *C. acnes* was confirmed, after streaking on selective plates, by colony PCR. Secretion of chicken ovalbumin protein in the different *C. acnes* culture supernatants was monitored using ELISA (FIG. 14) and Western Blot (FIG. 15). As shown in FIG. 14, both replicas of ELISA experiment show a significantly higher absorbance for most engineered *C. acnes* strains, except Ca0s22124, compared to wild-type *C. acnes* (*C. acnes* ATCC 11828). Strain Ca0s22126 was repeatedly giving the highest signal indicating higher level of secreted ovalbumin in culture supernatant. Secretion was further confirmed by Western blot (FIG. 15). A single band just above 40 kDa was observed for culture supernatant from strains Ca0s22120, Ca0s22122, Ca0s22126, Ca0s22128 and Ca0s22132. This band corresponds to ovalbumin size (43 kDa) and to the faint band from the ovalbumin control well. No band was observed for control strain Ca0s16973 that carries the empty plasmid used for cloning the different secretion plasmids. More intense band was found for Ca0s22126 confirming the results of the ELISA.

In conclusion, the present inventors describe for the first time the use of endogenous *C. acnes* secretion peptide for the secretion of recombinant protein by *C. acnes* using replicative DNA plasmids.

Materials and Methods:

Plasmids construction: Synthetic DNA fragments were ordered and assembled using SapI golden gate cloning in the pIC47 plasmid (pIC086).

Conjugation: As described in Materials and methods of Example 1.

ELISA: The different *C. acnes* strains were streaked from cryostock into BHI+erythromycin plate, except for the control strain without plasmid that was streaked on BHI without antibiotic, and plates were incubated at 37° C. in anaerobic conditions for 4-7 days. When fully grown, 10 mL cultures of BHI+5 µg/mL erythromycin were inoculated with an inoculum from the corresponding streak and incubated one overnight at 37° C. in anaerobic conditions. After incubation, $OD_{600\ nm}$ was measured to control for difference in growth. 1 mL of culture was dispensed into a 1.5 mL tube and centrifuged 6 min at 6000 g. 10 µL of the supernatant was transferred to a high-binding 96 well-plate (Greiner 655061) prefiled with 90 µL of 1×PBS. Incubation of the covered plate during 2 hours at 37° C. was performed. After incubation, samples were discarded from the plate, 100 µL of PBS+5% bovine serum albumin (BSA) was added and the covered plate was incubated for 1 hour at 37° C. Three consecutive washing steps with 100 µL of PBS+0.05% Tween 20 were performed prior to the addition of 100 µL of primary antibody solution (Anti-OVA innovagen PA-0323-100 diluted 1/1000 in PBS 1×+1% BSA+0.05% Tween 20). The covered plate was incubated at RT for 1 hour. Following incubation, three consecutive washing steps with 100 µL of PBS+0.05% Tween 20 were performed prior to the addition of 100 µL of secondary antibody solution (Anti-rabbit Invitrogen A16035 antibody diluted 1/5000 in PBS 1×+1% BSA+0.05% Tween 20) and incubation at RT for 1 hour. After incubation, samples were discarded from the plate and final three consecutive washing steps with 100 µL of PBS+0.05% Tween 20 were performed. 100 µL of TMB-ELISA substrate (Thermo Scientific 34028) was added to each well and incubation was performed under light protection for 10 to 12 min at RT. 100 µL of 1 M sulfuric acid was added to each well to stop the reaction. Absorbance measurement at 450 nm was performed using an infinite reader (Tecan).

Western blot: The different *C. acnes* strains were streaked from cryostock into BHI+erythromycin plate, except for the control strain without plasmid that was streaked on BHI without antibiotic, and plates were incubated at 37° C. in anaerobic conditions for 4-7 days. When fully grown, 10 mL cultures of BHI+5 µg/mL erythromycin were inoculated with an inoculum from the corresponding streak and incubated one overnight at 37° C. in anaerobic conditions. After incubation, $OD_{60}0$ was measured to control for difference in growth. 1 mL of culture was dispensed into a 1.5 mL tube and centrifuged 6 min at 6000 g. Filtration of the supernatant using 0.2 µm filter. 30 µL of the filtered supernatant was supplemented with 7.5 µL of LDS sample buffer (B0008 Invitrogen™) and 3 µL of Bolt™ antioxidant (BT0005 Invitrogen™) before boiling at 100° C. for 10 min. 30 µL of the mixture was loaded into a Bolt™ 4 to 12% Bis-Tris gel (NW04120 Invitrogen™). After migration, transfer on nitrocellulose membrane was performed. After the transfer, the membrane was: soaked first in 5% skim milk solution in PBS+0.05% Tween 20 for 1 h, then soaked in 20 mL 5% skim milk solution in PBS+0.05% Tween 20 containing the primary antibody (Anti-OVA innovagen PA-0323-100) diluted 1:1000 overnight at 4° C., washed three times with PBS+Tween 0.05%, soaked 1 h in 20 mL 5% skim milk solution in PBS+0.05% Tween 20 containing the secondary antibody (Anti-rabbit Invitrogen A16035 antibody) diluted 1:5000, washed three times with PBS+Tween 0.05%. Final step of revelation was performed using chemiluminescent substrate (34580 Thermofisher). Imaging was done using iBright CL1000 (Invitrogen™)

TABLE 12

Secreted proteins used to extract secretion signals

| Protein id | SignalP 5.0 prediction |
|---|---|
| YP_056615.1 | Prediction: Signal peptide (Sec/SPI) Cleavage site between pos. 23 and 24: GAA-TP. Probability: 0.4339 |
| YP_056817.1 | Prediction: Lipoprotein signal peptide (Sec/SPII) Cleavage site between pos. 20 and 21: LSA-CG. Probability: 0.9859 |
| YP_055402.1 | Prediction: Signal peptide (Sec/SPI) Cleavage site between pos. 28 and 29: AHA-VE. Probability: 0.9710 |
| YP_056047 | Prediction: Signal peptide (Sec/SPI) Cleavage site between pos. 28 and 29: AHA-AP. Probability: 0.8551 |

TABLE 13

DNA vectors encoding secretion of ovalbumin

| DNA vector Name | Promoter | signal peptide from | protein |
|---|---|---|---|
| p2152 | P138 | YP_056047 | chicken ovalbumin |
| p2154 | P138 | YP_055402.1 | chicken ovalbumin |
| p2156 | P138 | YP_056817.1 | chicken ovalbumin |
| p2158 | P138 | YP_056615.1 | chicken ovalbumin |
| p2160 | ProxP | YP_056047 | chicken ovalbumin |
| p2162 | ProxP | YP_055402.1 | chicken ovalbumin |
| p2164 | ProxP | YP_056817.1 | chicken ovalbumin |
| p2166 | ProxP | YP_056615.1 | chicken ovalbumin |

TABLE 14

List of C. acnes strains generated

| name | Strain description | plasmid |
|---|---|---|
| Ca0s22118 | Cutibacterium acnes ATCC 11828 | p2152 |
| Ca0s22120 | Cutibacterium acnes ATCC 11828 | p2154 |
| Ca0s22122 | Cutibacterium acnes ATCC 11828 | p2156 |
| Ca0s22124 | Cutibacterium acnes ATCC 11828 | p2158 |
| Ca0s22126 | Cutibacterium acnes ATCC 11828 | p2160 |
| Ca0s22128 | Cutibacterium acnes ATCC 11828 | p2162 |
| Ca0s22130 | Cutibacterium acnes ATCC 11828 | p2164 |
| Ca0s22132 | Cutibacterium acnes ATCC 11828 | p2166 |
| Ca0s16973 | Cutibacterium acnes ATCC 11828 | p1047 (pIC86) |

Example 6: Introduction of Recombinant DNA into C. acnes Phages Using CRISPR-Cas System Inventors demonstrated the successful introduction of several recombinant DNA fragments inside C. acnes phage genome. Introduction of fragments as large as 3.3 kb could be performed without abolishing the ability of the engineered C. acnes phage to produce plaques. Engineered C. acnes phages were produced by first infecting different C. acnes strains (Ca0s20855, Ca0s20857, Ca0s20859) with wild-type PAC7. Each of these strains (table 15) contains a DNA vector carrying a template for homologous recombination with the recombinant DNA to be inserted flanked by homology regions present upstream and downstream of the phage insertion locus (FIG. 7A). The selected locus was locus 1 as described in Table 8.

Once the first infection performed, the phage suspension, containing both WT phage (PAC7) and potential mutant phages, was mixed with the screening strain Ca0s20472 in a top assay. After incubation, plaques could be observed for all three suspensions. Mutant phage plaques were discriminated from wild-type phage plaques using PCR from each individual plaques. Once identified, putative mutant plaques were peaked and isolated by streaking on a new top with Ca0s20472. New PCR on isolated plaques, with primers IC443 (SEQ ID NO: 101)/10290 (SEQ ID NO: 106), were performed to confirm the presence of a recombinant insert in the phage locus 1 (FIG. 16). Plaques coming from infection with PAC7 gave a band at the size corresponding to wt PAC7 (2.4 kb) whereas plaques coming from the infection of Ca0s20855 and Ca0s20859 gave a band at higher size, respectively 3.3 kb and 5.4 kb. Sequencing of the PCR product was performed and confirmed the introduction of the recombinant DNA in the locus 1 of the phage genome. Therefore, inventors demonstrated for the first time the introduction of a recombinant DNA into C. acnes phage genome.

Materials and Methods:

Phage production: 20 mL of dense liquid culture (BHI+ erythromycin 5 µg/mL) of C. acnes carrying a DNA vector were grown to the exponential phase, centrifuged and resuspended (approx. $10^8$-$10^9$ cells) in 200 µL of C. acnes phage PAC7 suspension (approx. $10^7$ PFU/µL). The mixture was then incubated for 30-60 min at RT so that infection took place. After incubation, 20 mL of BHI was added to the mixture and incubated overnight at 37° C. under anaerobic conditions. After overnight incubation, cultures were centrifuged and filtered through a 0.2 µm membrane filter.

Top assay: 100 µL of phage suspension was mixed with dense culture of Ca0s20472 in a final mixture of 2 mL of 0.45% BHI agar. All mixture was poured on Brucella plates supplemented with 5 µg/mL erythromycin.

TABLE 15

List of C. acnes strains

| name | Strain description | plasmid |
|---|---|---|
| Ca0s20855 | Cutibacterium acnes ATCC 11828 with template for homologous recombination to introduce 908bp in locus 1 (SEQ ID NO: 112) | p1717 |
| Ca0s20857 | Cutibacterium acnes ATCC 11828 with template for homologous recombination to introduce 2863bp in locus 1 | p1719 |
| Ca0s20859 | Cutibacterium acnes ATCC 11828 with template for homologous recombination to introduce 3315bp in locus 1 | p1721 |
| Ca0s20472 | Cutibacterium acnes ATCC 11828 containing a CRISPR-Cas system targeting wt PAC7 phage genome at locus 1 | p1683 |

Example 7: Production/Generation of Conditionally-Replicative Phage

Phage therapy using cocktails of naturally occurring or engineered phages appears to be an attractive alternative to antibiotics for the killing of pathogenic bacteria or as a way to modulate microbiota by specific removal of strains or species. One peculiar feature of phages as a drug is their ability to replicate. Indeed after each infection of the target bacteria by one phage, as much as hundreds of particles might be produced. This replication implies that the activity of the phage drug substance is actually not controlled solely by the dose given but also by how much replication of the phage might happen. Amount of phage replication might depend on the accessibility and the load of the target bacterial population as well as the identity of the target population. Indeed different strains might lead to different burst size, meaning a different number of phage progeniture from the infection by one phage. These uncontrolled pharmacodynamics aspects might be a negligible drawback when phages are used to eradicate a population of pathogenic strains but this may be problematic if it is intended to use phages for precise regulation of a given bacterial population among a given microbiota.

Inventors herein demonstrate how to select conditionally replicative C. acnes phages; these phages are able to replicate in a specific engineered host production strain but not in the target bacterial population. This invention paves the way for the use of conditionally-replicative phages as an alternative to classical phage therapy.

For a phage to successfully produce more copies of itself it needs to go through several steps:
1) Binding to a bacterial host and injection of its genome into the cytoplasm,
2) Replication of its genome,
3) Expression of the different genes necessary for the production of the new capsids,
4) Packaging of the newly replicated genomes into the capsids, and
5) Release of the particles thanks to the active lysis of the host bacterial cell.

Completion of all these steps, in a manner that maximizes the number of phage particles produced, requires the coordinated expression of dozens of genes. For example, expression of genes involved in lysis such as holin and endolysin is programmed so that lysis occurs only once most of the phage particles assembly is done. In order to generate a conditionally-replicative phage, the inventors propose to delete or inactivate, in the phage genome, one or several genes that are essential for a complete phage replication cycle and to provide them in trans.

As a proof of concept, inventors were able to produce conditionally-replicative C. acnes phages with a deletion in an essential endonuclease gene (gp45, SEQ ID NO: 107).

First, a C. acnes strain (Ca0s22235) containing a plasmid (p2192) expressing spCas9, a sgRNA targeting the wt PAC7 phage in the region of the essential endonuclease gene (SEQ ID NO: 108), and a cassette expressing the essential endonuclease using P138 promoter was generated. A suspension of PAC7 phage was mixed with the strain Ca0s22235 in a top assay. After incubation plaques were obtained and screened by PCR for deletion using primers IC446 (SEQ ID NO: 103)/AL97 (SEQ ID NO: 109). 2 plaques (no 28 and no 42) showed shorter band size compared to wt PAC7 indicating potential deletion in the endonuclease locus. Plaques were peaked and re-isolated separately with selective strain Ca0s22235. After incubation, plaques were picked for PCR using IC619 (SEQ ID NO: 110)/AL219 (SEQ ID NO: 111). PCR confirmed the presence of a deletion in the essential endonuclease gene with smaller band size for plaques no 28 (PAC7-m28-gp45) and no 42 compared to wt PAC7 plaques (FIG. 17). Sequencing of the PCR product showed partial deletion of the first 25 amino acids of the endonuclease for phage PAC7-m28-gp45 (FIG. 18). Streaking of the isolated plaques in presence of C. acnes ATCC 11828 strain led to no plaques for phage PAC7-m28-gp45 whereas plaques could be observed for phage isolated from plaque no 42. This indicates that phage PAC7-m28-gp45 can produce plaques in strain Ca0s22235 that express in trans the essential endonuclease whereas it cannot produce plaques in the strain ATCC 11828 (which does not carry the essential endonuclease gene). Thus phage PAC7-m28-gp45 is a conditionally-replicative phage that can only replicate in a strain expressing in trans the endonuclease.

To conclude, inventors demonstrated production of the first C. acnes conditionally-replicative phage. This phage containing a deletion in the endonuclease gp45 was only able to replicate in an engineered strain expressing the endonuclease in trans.

TABLE 16

List of C. acnes strains

| name | Strain | plasmid | Description |
| --- | --- | --- | --- |
| Ca0s22235 | Cutibacterium acnes ATCC 11828 | p2192 | p2192 carry a CRISPR-Cas system targeting wt PAC7 phage genome in the endonuclease region |

Materials and Methods:
Phage production: 20 mL of dense liquid culture (BHI+ erythromycin 5 µg/mL) of C. acnes carrying a DNA vector were grown to the exponential phase, centrifuged and resuspended (approx. $10^8$-$10^9$ cells) in 200 µL of C. acnes phage PAC7 suspension (approx. $10^7$ PFU/µL). The mixture was then incubated for 30-60 min at RT so that infection took place. After incubation, 20 mL of BHI was added to the mixture and incubated overnight at 37° C. under anaerobic conditions. After overnight incubation, cultures were centrifuged and filtered through a 0.2 µm membrane filter.
Top assay: 50 µl of phage suspension was mixed with 50 µl of Ca0s22235 high cell density culture, in a final mixture of 2 ml of 0.45% BHI agar. Mixture was poured BHI agar plate supplemented with 5 ug/ml erythromycin. Top plate was incubated at 37° C. in anaerobic conditions.

REFERENCES

1. Pasparakis, M., Haase, I. & Nestle, F. O. Mechanisms regulating skin immunity and inflammation. Nature Reviews Immunology 14, 289-301 (2014).
2. Scharschmidt, T. C. et al. A Wave of Regulatory T Cells into Neonatal Skin Mediates Tolerance to Commensal Microbes. Immunity 43, 1011-1021 (2015).
3. Oh, J. et al. Biogeography and individuality shape function in the human skin metagenome. Nature 514, 59-64 (2014).
4. Oh, J. et al. Biogeography and individuality shape function in the human skin metagenome. Nature 514, 59-64 (2014).
5. Nakatsuji, T. et al. The microbiome extends to subepidermal compartments of normal skin. Nat Commun 4, 1431 (2013).
6. Bay, L. et al. Universal Dermal Microbiome in Human Skin. Mbio 11, (2020).
7. Nagao, K. et al. Stress-induced production of chemokines by hair follicles regulates the trafficking of dendritic cells in skin. Nat Immunol 13, 744-752 (2012).
8. Adachi, T. et al. Hair follicle-derived IL-7 and IL-15 mediate skin-resident memory T cell homeostasis and lymphoma. Nat Med 21, 1272-1279 (2015).
9. Paus, R., Ito, N., Takigawa, M. & Ito, T. The Hair Follicle and Immune Privilege. J Invest Derm Symp P 8, 188-194 (2003).
10. Scholz, C. F. & Kilian, M. The natural history of cutaneous propionibacteria, and reclassification of selected species within the genus Propionibacterium to the proposed novel genera Acidipropionibacterium gen. nov., Cutibacterium gen. nov. and Pseudopropionibacterium gen. nov. International Journal of Systematic and Evolutionary Microbiology 66, 4422-4432 (2016).
11. McLaughlin, J. et al. Propionibacterium acnes and Acne Vulgaris: New Insights from the Integration of Population 12. Barnard, E. et al. Strains of the *Propionibacterium acnes* type III lineage are associated with the skin condition progressive macular hypomelanosis. *Scientific reports* 6, 31968 (2016).
13. Petersen, R. L. W., Scholz, C. F. P., Jensen, A., Bruggemann, H. & Lomholt, H. B. *Propionibacterium acnes* phylogenetic type III is associated with progressive macular hypomelanosis. *European J Microbiol Immunol* 7, 37-45 (2017).
14. McDowell, A., McLaughlin, J. & Layton, A. M. Is *Cutibacterium* (previously *Propionibacterium*) *acnes* a potential pathogenic factor in the aetiology of the skin disease progressive macular hypomelanosis? *J European Acad Dermatology Venereol Jeadv* (2020) doi:10.1111/jdv.16789.
15. Fitz-Gibbon, S. et al. *Propionibacterium acnes* Strain Populations in the Human Skin Microbiome Associated with Acne. *J Invest Dermatol* 133, 2152-2160 (2013).
16. Sorensen, M. et al. Mutagenesis of *Propionibacterium acnes* and analysis of two CAMP factor knock-out mutants. *Journal of Microbiological Methods* 83, 211-216 (2010).
17. Allhorn, M., Arve, S., Bruggemann, H. & Lood, R. A novel enzyme with antioxidant capacity produced by the ubiquitous skin colonizer *Propionibacterium acnes*. *Sci Rep-uk* 6, 36412 (2016).
18. Nazipi, S., Stødkilde, K., Scavenius, C. & Bruggemann, H. The Skin Bacterium *Propionibacterium acnes* Employs Two Variants of Hyaluronate Lyase with Distinct Properties. Microorg 5, 57 (2017).
19. Kasimatis, G., Fitz-Gibbon, S., Tomida, S., Wong, M. & Li, H. Analysis of Complete Genomes of *Propionibacterium acnes* Reveals a Novel Plasmid and Increased Pseudogenes in an Acne Associated Strain. *BioMed Research International* 2013, 1-11 (2013).
20. Davidsson, S. et al. Prevalence of Flp Pili-Encoding Plasmids in *Cutibacterium acnes* Isolates Obtained from Prostatic Tissue. *Frontiers in microbiology* 8, 2241 (2017).
21. Aoki, S., Nakase, K., Hayashi, N. & Noguchi, N. Transconjugation of erm(X) conferring high-level resistance of clindamycin for *Cutibacterium acnes*. *Journal of Medical Microbiology* (2018) doi:10.1099/jmm.0.000875.
22. Aoki, S. et al. Transferable Multidrug-Resistance Plasmid Carrying a Novel Macrolide-Clindamycin Resistance Gene, erm (50), in *Cutibacterium acnes*. Antimicrob Agents Ch 64, (2019).
23. Barnard, E., Shi, B., Kang, D., Craft, N. & Li, H. The balance of metagenomic elements shapes the skin microbiome in acne and health. *Scientific Reports* 6, srep39491 (2016).
24. Rouet, P., Smih, F. & Jasin, M. Expression of a site-specific endonuclease stimulates homologous recombination in mammalian cells. *Proc National Acad Sci* 91, 6064-6068 (1994).
25. Arazoe, T. et al. Site-specific DNA double-strand break generated by I-Scel endonuclease enhances ectopic homologous recombination in Pyricularia *oryzae*. *Fems Microbiol Lett* 352, 221-229 (2014).
26. Liu, J. et al. The diversity and host interactions of *Propionibacterium acnes* bacteriophages on human skin. *The ISME Journal* 9, 2078 (2015).
27. Lood, R. & Collin, M. Characterization and genome sequencing of two *Propionibacterium acnes* phages displaying pseudolysogeny. *BMC Genomics* 12, 198 (2011).
28. Brown, T., Petrovski, S., Dyson, Z., Seviour, R., Tucci, J. The Formulation of Bacteriophage in a Semi Solid Preparation for Control of *Propionibacterium acnes* Growth. PloS one 11(3), e0151184. (2016)

We claim:

1. A recombinant *C. acnes* phage comprising at least one transgene, said transgene encoding an interleukin.

2. The recombinant *C. acnes* phage according to claim 1, wherein the recombinant *C. acnes* phage is further engineered so that its host range is different from the host range of the corresponding wild type *C. acnes* phage.

3. The recombinant *C. acnes* phage according to claim 1, comprising an engineered capsid.

4. The recombinant *C. acnes* phage according to claim 3, wherein an antigen is displayed at the surface of the engineered capsid.

5. A method comprising administering to a subject a recombinant *C. acnes* phage of claim 1.

SEQUENCE LISTING

```
Sequence total quantity: 114
SEQ ID NO: 1              moltype = DNA  length = 38
FEATURE                   Location/Qualifiers
misc_feature              1..38
                          note = oriT_pMRC01
source                    1..38
                          mol_type = other DNA
                          organism = synthetic construct
SEQUENCE: 1
acaccaccca attttggagt ggtgtgtaag tgcgcatt                            38

SEQ ID NO: 2              moltype = DNA  length = 38
FEATURE                   Location/Qualifiers
misc_feature              1..38
                          note = oriT_RSF1010
source                    1..38
                          mol_type = other DNA
                          organism = synthetic construct
SEQUENCE: 2
ccagtttctc gaagagaaac cggtaagtgc gccctcc                             38

SEQ ID NO: 3              moltype = DNA  length = 40
FEATURE                   Location/Qualifiers
misc_feature              1..40
                          note = oriT_pRS01
source                    1..40
                          mol_type = other DNA
                          organism = synthetic construct
SEQUENCE: 3
tccgtaagat gctatcatct tactatgctt gcaaaggtc                           40
```

```
SEQ ID NO: 4              moltype = DNA  length = 41
FEATURE                   Location/Qualifiers
misc_feature              1..41
                          note = oriT_pMV158
source                    1..41
                          mol_type = other DNA
                          organism = synthetic construct
SEQUENCE: 4
cactttatga atataaagta tagtgtgtta tactttacat g                    41

SEQ ID NO: 5              moltype = DNA  length = 42
FEATURE                   Location/Qualifiers
misc_feature              1..42
                          note = oriT_pTF1
source                    1..42
                          mol_type = other DNA
                          organism = synthetic construct
SEQUENCE: 5
gcacgggtaa tctcgaagag attactctaa gtgcgccctt gc                   42

SEQ ID NO: 6              moltype = DNA  length = 45
FEATURE                   Location/Qualifiers
misc_feature              1..45
                          note = oriT_pSC101
source                    1..45
                          mol_type = other DNA
                          organism = synthetic construct
SEQUENCE: 6
gggcgcacgt ttctgaacga agtgaagaaa gtctaagtgc gccct                45

SEQ ID NO: 7              moltype = DNA  length = 51
FEATURE                   Location/Qualifiers
misc_feature              1..51
                          note = oriT_pBTK445
source                    1..51
                          mol_type = other DNA
                          organism = synthetic construct
SEQUENCE: 7
agcctttaaa gcgaaaatag ggtactccat gctcgctata tcatcctgac a         51

SEQ ID NO: 8              moltype = DNA  length = 52
FEATURE                   Location/Qualifiers
misc_feature              1..52
                          note = oriT_pBBR1
source                    1..52
                          mol_type = other DNA
                          organism = synthetic construct
SEQUENCE: 8
ggtcacgact ttgcgaagca aagtctagtg agtatactca agcattgagt gg        52

SEQ ID NO: 9              moltype = DNA  length = 53
FEATURE                   Location/Qualifiers
misc_feature              1..53
                          note = oriT_R721
source                    1..53
                          mol_type = other DNA
                          organism = synthetic construct
SEQUENCE: 9
cacacgattg taacatgacc ggaacggtct tgtgtacaat cggtatcgtg cct       53

SEQ ID NO: 10             moltype = DNA  length = 59
FEATURE                   Location/Qualifiers
misc_feature              1..59
                          note = oriT_pRmeGR4a
source                    1..59
                          mol_type = other DNA
                          organism = synthetic construct
SEQUENCE: 10
gcaggaaaac ggcgtagcac attttttccgt atcctgcccc tccacattgt aagggatt  59

SEQ ID NO: 11             moltype = DNA  length = 60
FEATURE                   Location/Qualifiers
misc_feature              1..60
                          note = oriT_ColE1
source                    1..60
                          mol_type = other DNA
                          organism = synthetic construct
SEQUENCE: 11
```

```
gggtgtcggg gcgcagccct gacccagtca cgtagcgata gcggagtgta tactggctta    60

SEQ ID NO: 12          moltype = DNA   length = 61
FEATURE                Location/Qualifiers
misc_feature           1..61
                       note = oriT_pTiC58
source                 1..61
                       mol_type = other DNA
                       organism = synthetic construct
SEQUENCE: 12
ggatccaagg gcgcaattat acgtcgctga cgcgacgcct tgcgtagggg gccaaacagg    60
g                                                                   61

SEQ ID NO: 13          moltype = DNA   length = 64
FEATURE                Location/Qualifiers
misc_feature           1..64
                       note = oriT_pMdT1
source                 1..64
                       mol_type = other DNA
                       organism = synthetic construct
SEQUENCE: 13
aggtttcggg gcgcagccct gaaccagtca cctagcgcta gcggagtgta tactggctta    60
gtat                                                                64

SEQ ID NO: 14          moltype = DNA   length = 71
FEATURE                Location/Qualifiers
misc_feature           1..71
                       note = oriT_R1
source                 1..71
                       mol_type = other DNA
                       organism = synthetic construct
SEQUENCE: 14
agcaaatcag caaaaacttg tttttgcgtg gggtgtggtg cttttggtgg tgagaaccac    60
caacctgttg a                                                        71

SEQ ID NO: 15          moltype = DNA   length = 71
FEATURE                Location/Qualifiers
misc_feature           1..71
                       note = oriT_Tn5520
source                 1..71
                       mol_type = other DNA
                       organism = synthetic construct
SEQUENCE: 15
cttattgggg aattttcagc gatacggagt attgcggctc ggaaaattcc ctaataagct    60
acggtatttt c                                                        71

SEQ ID NO: 16          moltype = DNA   length = 90
FEATURE                Location/Qualifiers
misc_feature           1..90
                       note = oriT_QKH54
source                 1..90
                       mol_type = other DNA
                       organism = synthetic construct
SEQUENCE: 16
gtgaagatag ttaaccggct tgccggttag ctaacttcac ctatcttgcc cggctcttcg    60
agccgtttaa cgccaggtga gtatcgcata                                    90

SEQ ID NO: 17          moltype = DNA   length = 92
FEATURE                Location/Qualifiers
misc_feature           1..92
                       note = oriT_R64
source                 1..92
                       mol_type = other DNA
                       organism = synthetic construct
SEQUENCE: 17
ggggtgtcgg ggcgaagccc tgaccagatg gcaattgtaa tagcgtcgcg tgtgacggta    60
ttacaattgc acatcctgtc ccgttttttcg gg                                92

SEQ ID NO: 18          moltype = DNA   length = 99
FEATURE                Location/Qualifiers
misc_feature           1..99
                       note = oriT_R751
source                 1..99
                       mol_type = other DNA
                       organism = synthetic construct
SEQUENCE: 18
gaataaggga cagtgaagat agataaccgg ctcgccggtt agctaacttc acacatcctg    60
cccgccttac ggcgttaata acaccaagga aagtctaca                          99
```

```
SEQ ID NO: 19           moltype = DNA  length = 814
FEATURE                 Location/Qualifiers
misc_feature            1..814
                        note = oriT_RP4
source                  1..814
                        mol_type = other DNA
                        organism = synthetic construct
SEQUENCE: 19
cgacaggctc atgccggccg ccgccgcctt ttcctcaatc gctcttcgtt cgtctggaag    60
gcagtacacc ttgataggtg ggctgcccct cctggttggc ttggtttcat cagccatccg   120
cttgccctca tctgttacgc cggcggtagc cggccagcct cgcagagcag gattcccgtt   180
gagcaccgcc aggtgcgaat aagggacagt gaagaaggaa cacccgctcg cgggtgggcc   240
tacttcacct atcctgcccg gctgacgccg ttggatacac caaggaaagt ctacacgaac   300
cctttggcaa aatcctgtat atcgtgcgaa aaaggatgga taccgaaa aaatcgctat    360
aatgaccccg aagcagggtt atgcagcgga aaagcgctgc ttccctgctg ttttgtggaa   420
tatctaccga ctggaaacag gcaaatgcag gaaattactg aactgagggg acaggcgaga   480
gacgatgcca aagagctaca ccgacagct ggccgagtgg gttgaatccc gcgcggccaa    540
gaagcgccgg cgtgatgagg ctgcggttgc gttcctggcg gtgagggcgg atgtcgaggc   600
ggcgttagcg tccggctatg cgctcgtcac catttgggag cacatgcggg aaacggggaa   660
ggtcaagttc tcctacgaga cgttccgctc gcacgccagg cggcacatca aggcaagcc    720
cgccgatgtg cccgcaccgc aggccaaggc tgcggaaccc gcgccggcac ccaagacgcc   780
ggagccacgg cggccgaagc aggggggcaa ggct                              814

SEQ ID NO: 20           moltype = DNA  length = 100
FEATURE                 Location/Qualifiers
misc_feature            1..100
                        note = oriT_pKL1
source                  1..100
                        mol_type = other DNA
                        organism = synthetic construct
SEQUENCE: 20
cggggtgtcg gggtgaagcc ctgaccaagt ggtaatcgta tcggcgtgca tgcgcggtta    60
tacgattaca catcctgtcc cgatttctga ggcgttttaa                        100

SEQ ID NO: 21           moltype = DNA  length = 112
FEATURE                 Location/Qualifiers
misc_feature            1..112
                        note = oriT_RK2
source                  1..112
                        mol_type = other DNA
                        organism = synthetic construct
SEQUENCE: 21
ccggccagcc tcgcagagca ggattcccgt tgagcaccgc caggtgcgaa taagggacag    60
tgaagaagga acacccgctc gcgggtgggc ctacttcacc tatcctgccc gg          112

SEQ ID NO: 22           moltype = DNA  length = 160
FEATURE                 Location/Qualifiers
misc_feature            1..160
                        note = oriT_R1162
source                  1..160
                        mol_type = other DNA
                        organism = synthetic construct
SEQUENCE: 22
ggccagtttc tcgaagagaa accggtaaat gcgccctccc ctacaaagta gggtcgggat    60
tgccgccgct gtgcctccat gatagcctac gagacagcac attaacaatg gggtgtcaag   120
atggttaagg ggagcaacaa ggcggcggat cggctggcca                        160

SEQ ID NO: 23           moltype = DNA  length = 174
FEATURE                 Location/Qualifiers
misc_feature            1..174
                        note = oriT_Tn4555
source                  1..174
                        mol_type = other DNA
                        organism = synthetic construct
SEQUENCE: 23
ccctcgggag agcccacaac tacgtaagcg gagcgtgtag ttatagtggg ctatatcaat    60
ggcaagccat tgtctgcaaa ctccagccta cggcttccgc tctcctccgt cagggaggtt   120
tttcatcatc gttgccgatt ggagatgcac cgaccagcac aaggtctaaa tcgt        174

SEQ ID NO: 24           moltype = DNA  length = 192
FEATURE                 Location/Qualifiers
misc_feature            1..192
                        note = oriT_pHT
source                  1..192
                        mol_type = other DNA
                        organism = synthetic construct
SEQUENCE: 24
ccaaagaatt aatgcaaaga gcataaggga aaactaatag caccttccta aaggaaggtg    60
gctaagttgg ctgtgccaac tggttttctt tcaaaatcac ttcatatttt ttgctatcac   120
```

```
aaaaaaatcc attttcgacc tattttcggt cataatatag tacctacttt tggtcatagt    180
ttcgtccgta gt                                                        192

SEQ ID NO: 25          moltype = DNA   length = 199
FEATURE                Location/Qualifiers
misc_feature           1..199
                       note = oriT_Tn4399
source                 1..199
                       mol_type = other DNA
                       organism = synthetic construct
SEQUENCE: 25
taaggtgatt atgttgtttt tcttcatctg ttctatctgt tttttagtga ataatccgat    60
tgatgtaatc tgaaaagtcc gtgaccatcg ggagccgttc ccctcatctt tttgaggggc   120
aagtggtcgg ggaatgtaat acgccgacat taacttgcta tcctaaaaaa gatgtgattt   180
acggcttaga tgccgaatc                                                 199

SEQ ID NO: 26          moltype = DNA   length = 216
FEATURE                Location/Qualifiers
misc_feature           1..216
                       note = oriT_Tn916
source                 1..216
                       mol_type = other DNA
                       organism = synthetic construct
SEQUENCE: 26
aagcggaagt cgcaggtgtg gactgatctt gctggctggt gtggcaatag ccacgccagc    60
acttaacccc ccgtatctaa caggggggta caaatcgaca ggaaacagtc aaaaaaacat   120
tagaaaatcc tttggttaca agggatttac aaaaatttcag cgtatgtcaa atgggcttta   180
aaagttgaca tacggccttt ttgattggag ggattt                              216

SEQ ID NO: 27          moltype = DNA   length = 242
FEATURE                Location/Qualifiers
misc_feature           1..242
                       note = oriT_pST12
source                 1..242
                       mol_type = other DNA
                       organism = synthetic construct
SEQUENCE: 27
ttgtgtgatt atatcgcgta ccacttttcg actgttttac cgccggtatt ctgccgtctg    60
acgctttgac gggtatttct gcctgacaat actgtcactg ccaaaaaact gccgtgcctt   120
tgtcggtaat tcgagcttgc tgacaggaca ggatgtgcaa ttgttatacc gcgcatacat   180
gcacgctatt acaattaccc tggtcagggc ttcgccccga caccccatgt cagatacgga   240
gc                                                                   242

SEQ ID NO: 28          moltype = DNA   length = 268
FEATURE                Location/Qualifiers
misc_feature           1..268
                       note = oriT_pCU1
source                 1..268
                       mol_type = other DNA
                       organism = synthetic construct
SEQUENCE: 28
gtattaccaa agtaataaag caaactcatt ataaacaat gagttattag gtgttttaa      60
tacctaatta ttaccgaata ttgacgctat ttatttttt atttttaaa tcagtgtgat     120
agcgtgattt atgccgctgc gttaggtgta tagcaggtta agggataaaa aatcatcttt   180
tttggtagga gcgatctacg taggttaagg actaactgac taaaaagcgt tcaatattcc   240
gtattcatgc ttgcatgaat accagtac                                       268

SEQ ID NO: 29          moltype = DNA   length = 279
FEATURE                Location/Qualifiers
misc_feature           1..279
                       note = oriT_pSU233
misc_feature           199
                       note = n is a, c, g, or t
source                 1..279
                       mol_type = other DNA
                       organism = synthetic construct
SEQUENCE: 29
cgctagcagc gccctgacg gtatcctata aaaaaacaca ccgcgccgct agcagcaccc    60
ctaatataaa ataatgtttt ttataaaaat agtcagtacc acccctacaa agcggtgtcg   120
gcgcgttgct gtagctgcgt taacgacgct gctttaaata aatcagattt aaacaatata   180
aatccacaaa tacaactcna tgatattaaa gataaatcag caaaaactg ttttttgcgtg   240
gggtgtggtg cttttggtgg tgagaaccac caacctgtt                           279

SEQ ID NO: 30          moltype = DNA   length = 290
FEATURE                Location/Qualifiers
misc_feature           1..290
                       note = oriT_F
source                 1..290
                       mol_type = other DNA
```

```
                        organism = synthetic construct
SEQUENCE: 30
cgcaccgcta gcagcgcccc tagcggtatc ctataaaaaa acacaccgcg ccgctagcag    60
caccccctaat ataaaataat gttttttata aaaatagtca gtaccacccc tacaaaacgg   120
tgtcggcgcg ttgttgtagc cgcgccgaca ccgctttttt aaatatcata aagagagtaa   180
gagaaactaa ttttttcataa cactctattt ataagaaaaa atcagcaaaa acttgttttt   240
gcgtggggtg tggtgcttttt ggtggtgaga accaccaacc tgttgagcct             290

SEQ ID NO: 31           moltype = DNA    length = 304
FEATURE                 Location/Qualifiers
misc_feature            1..304
                        note = oriT_pMAB01
source                  1..304
                        mol_type = other DNA
                        organism = synthetic construct
SEQUENCE: 31
tgcctcgcag agcaggatga cccgttgagc gcccccggcg cgaataaggg acagtgaaga    60
tagataaccg gctcgccggt tagctaactt cacacatcct gcccgcctta cggcgttaat   120
aacaccaagg aaagtctaca ccagccatta cgatttatcc gcaactatcg cgctatcagg   180
ccgcaaaagc agcaacggat atagcgaaaa ccgccacaat ggcccataat gccgctatcg   240
aagcgtgcca atgcacgccg atagcggact ttttgcgttt ccgtagcgcc gcttagtagc   300
gtta                                                                304

SEQ ID NO: 32           moltype = DNA    length = 402
FEATURE                 Location/Qualifiers
misc_feature            1..402
                        note = oriT_R388
source                  1..402
                        mol_type = other DNA
                        organism = synthetic construct
SEQUENCE: 32
ccgcctcgtc ctccaaaagt gcctgctttt ccgggcttag ccgtacttgg atggggtcgc    60
ctagtgccat gtcctctccc gtagtgttac tgtagtggtt caatcctagc atttacaagg   120
ggttgcggca atattgtagt ggcataacac tacacaggtt ttcgtccttg gcgtggaagt   180
cattgtaaat caatgactta cgcgcaccga aaggtgcgta ttgtctatag cccagattta   240
aggataccaa cccggctttt aaggacggaa accatgcgat aacgccagcg tgaccctaaa   300
gagggtcaaa actgctccca atgcgctatg cgcattgggt tatcgtgcag caatgatgca   360
actataatgc tatgatggtg ctacaatgat gcagaaaatg ag                      402

SEQ ID NO: 33           moltype = DNA    length = 456
FEATURE                 Location/Qualifiers
misc_feature            1..456
                        note = oriT_pS7a
source                  1..456
                        mol_type = other DNA
                        organism = synthetic construct
SEQUENCE: 33
ggatgatcaa acaaaatacg agagattttt tgttcgttca tccatggttt tagaaaaaag    60
agggacgatt tcggaagaag aaaatcgtct cttttttttc ttcttttttgt atgacaaaaa   120
gaaagatctt ttgcccattt ttatttttta taaaatgggc aggtggcgtt tgcgtaaagc   180
aaatcgacac aatccaaagg ggataaaagg ggaaagtgaa acttcccct tttcaagcca   240
cattgtaata caagaacgaa gtgctttgta ttacaatgtg atagcttgca gtatttatgg   300
ttttatatgg tctatttttgt tgtgaggatt gtaaccgaat agggcgcaat acttattaca   360
aaatcaatga caaagggcga ttgagaaatg agcgctgggg cattttatct ttgaggaagt   420
tcttgatgga tcagaaaaat gtatcacaaa tttaaa                             456

SEQ ID NO: 34           moltype = DNA    length = 456
FEATURE                 Location/Qualifiers
misc_feature            1..456
                        note = oriT_pS7b
source                  1..456
                        mol_type = other DNA
                        organism = synthetic construct
SEQUENCE: 34
tggatgatca acaaaatac gagagatttt tgttcgttc atccatggtt ttagaaaaaa     60
gagggacgat ttcggaagaa gaaaatcgtc tcttttttttt cttcttttg tatgacaaaa   120
agaaagatct tttgcccatt tttattttt ataaaatggg caggtggcgt ttgcgtaaag   180
caaatcgaca caatccaaag gggataaaag gggaaagtga acttcccccc ttttcaagcc   240
acattgtaat acaagaacga agtgctttgt attacaatgt gatagcttgc agtatttatg   300
gttttatatt tcctattttg ttgtgaggat tgtaaccgaa tagggcgcaa tgcttattac   360
aaaatcaatg acaaagggcg agtgaggaat gagcgctgag gcattttatc tttgaggaag   420
ttcttgatgg atcagaaaaa tgtatcacaa atttaa                             456

SEQ ID NO: 35           moltype = DNA    length = 697
FEATURE                 Location/Qualifiers
misc_feature            1..697
                        note = oriT_R702
source                  1..697
                        mol_type = other DNA
```

```
                         organism = synthetic construct
SEQUENCE: 35
ccctgcttcg gggtcattat agcgattttt tcggtatatc catccttttt cgcacgatat  60
acaggatttt gccaaagggt tcgtgtagac tttccttggt gtatccaacg gcgtcagccg 120
ggcaggatag gtgaagtagg cccacccgcg agcgggtgtt ccttcttcac tgtcccttat 180
tcgcacctgg cggtgctcaa cgggaatcct gctctgcgag gctggccggc taccgccggc 240
gtaacagatg agggcaagcg gatggctgat gaaaccaagc caaccaggaa gggcagccca 300
cctatcaagg tgtactgcct tccagacgaa cgacgagcga ttgaggaaaa ggcggcggcg 360
gccggcatga gcctgtcggc ctacctgctg gccgtcggcc agggctacaa aatcacgggc 420
gtcgtggact atgagcacgt ccgcgagctg gcccgcatca atggcgacct gggccgcctg 480
ggcggcctgc tgaaactctg gctcaccgac gacccgcgca cggcgcggtt cggtgatgcc 540
acgatcctcg ccctgctggc gaagatcgaa gagaagcagg acgagcttgg caaggtcatg 600
atgggcgtgt tccgcccgag ggcagagcca tgacttttt agccgctaaa acggccgggg 660
ggtgcgcgtg attgccaagc acgtccccat gcgctcc                         697

SEQ ID NO: 36          moltype = DNA   length = 475
FEATURE                Location/Qualifiers
misc_feature           1..475
                       note = oriT_pMUR274
source                 1..475
                       mol_type = other DNA
                       organism = synthetic construct
SEQUENCE: 36
actccgatac gttgccctcc gaacggtatt caaggtcgat tttttgcgct tcggtcactc  60
ttaaactgat agatggcata ggtttccttt gtgtaatacc gatgtaatac atacaaatct 120
agcatagatg cggcttaatt ccacatatgt aatacgttgt gtattacata ttaaaacaca 180
aattagaata atttgttttg ttttcaagca tttacgatga aaatcgtaat tgcgtatggt 240
gtatagccgt taagggatac catccacgc cttttttaag ggagaaaccg gtgttacgtg 300
caagtgaatc gctcaaaaag cgttcacatt cacacctttc atgcttgcat gaaaggaaac 360
ggacgggaat tagacaaaaa taagacacga tgagtaagtt attgagacaa gaaaaggaca 420
caaataagac attttttaga aaaaaacatt gacttgagac tagaaatgga caata       475

SEQ ID NO: 37          moltype = DNA   length = 550
FEATURE                Location/Qualifiers
misc_feature           1..550
                       note = oriT_R100
source                 1..550
                       mol_type = other DNA
                       organism = synthetic construct
SEQUENCE: 37
ttactctggc cataagataa aacctttcat tattaagcaa cgaacttttc actataaata  60
tgcatatagt gtttacaagt aagaaagaca ctcctagcag cgcctctagg atcatcctat 120
aaaaaaatgc gatccggcgc taggggcgtc cctaatatca atcaatgttt ttcgtgaaaa 180
ttgtcagtac tgatcctaat aagagtcgct atagggtcgt aacaggatcg ccaacgactc 240
tctatttaat aattcagaat tattaaatat aaatagcgtt tgttaattac atgatttaaa 300
acgtaaatca gcaaaaactt gttttgtgcgt agtgtgtggt gcttttggtg gtgagaacca 360
ccaacctgtt gagccttttt gtggagtggg ttaaattatt tacggataaa gtcaccagag 420
gtggaaaaat gaaaaaatgg atgttagcaa tctgcctgat gtttataaat gggatctgcg 480
aagccgccga ttgctttgat cttgcaggtc gggattacaa aatagacccg gatttactaa 540
gaatgatatc                                                        550

SEQ ID NO: 38          moltype = DNA   length = 551
FEATURE                Location/Qualifiers
misc_feature           1..551
                       note = oriT_pVCR94deltaX
source                 1..551
                       mol_type = other DNA
                       organism = synthetic construct
SEQUENCE: 38
gagcagagct atgtgtgaca agaagtatag agattacgag gtagccatca tggtcgatgt  60
gaacccttc gacagggtta tgaatgaatt gaaaagtcgt ggccgcaaga acgctcacat 120
cctgagcatc ctccaattcg actggcctgc atcggaggcc atcatcgaga agctgagctg 180
ctacatcaca gacgggatta aggctaatca ggagcctgtg atttacccga tcattgaaga 240
agctctgcat cgctacagcc agctcgtgtt tcatgagcag agagaaat atgaagaccc 300
ggccagaatt ggggcatttc tggaaaccct gatcaccgaa acctgccggg cgttggaagt 360
gcaaattgtc gatagtggcg gtgattcatg gtctgtcgat tcaggagagt cgttctcact 420
gtggctttc tcccatccag gagaactatc cattaacccg cagccccatg aggatgagac 480
ctctttgcgt ggcttgctgt atgagctcat cacctgtgag agcgtgaaaa ctgttttaag 540
gagaaccgac t                                                      551

SEQ ID NO: 39          moltype = DNA   length = 650
FEATURE                Location/Qualifiers
misc_feature           1..650
                       note = oriT_R46
source                 1..650
                       mol_type = other DNA
                       organism = synthetic construct
SEQUENCE: 39
agcgccgcag ataatctgac cgattacctc ctgaaaccag gtctatatag gccaaaaagt  60
```

```
tcatctgata cttttgcggt tattattggc attcagtcct cacattgtgc atttcttaaa    120
caaaagattg ggatctaaca agctgaaatc ttagtattac caaagtaata aagcaaactc    180
attataaaac aatgagttat taggtgtttt taatacctaa ttattaccga atattgacgc    240
tatttatttt tttattttt aaatcagtgt gatagcgtga tttatgccgc tgcgttaggt    300
gtatagcagg ttaagggata aaaaatcatc tttttgatg ggagcgatct acgtaggtta    360
aggactaact gactaaaaag cgttcaatat tccgtattca tgcttgcatg aataccagta    420
caacactatt acaacaaaag tacatcaaaa ttacatcaaa agtacatcac ttgaaggttg    480
acagtacaac agaattacat cattatctgg tactgaggta gccagtacaa caaagtaca    540
tcaaaaatac atcataaata catcagaaat acatcaaaat tacatcattc taaatgaggg    600
tactatgaag cccaaaagta tcagggcggc acttcagttg atgttgccgg                650

SEQ ID NO: 40              moltype = DNA   length = 36
FEATURE                    Location/Qualifiers
misc_feature               1..36
                           note = oriT_pGO1
source                     1..36
                           mol_type = other DNA
                           organism = synthetic construct
SEQUENCE: 40
cacgcgaacg gaacgttcgc ataagtgcgc ccttac                                36

SEQ ID NO: 41              moltype = DNA   length = 38
FEATURE                    Location/Qualifiers
misc_feature               1..38
                           note = oriT_pIP501
source                     1..38
                           mol_type = other DNA
                           organism = synthetic construct
SEQUENCE: 41
atacgaagta acgaagttac tgcgtataag tgcgccct                              38

SEQ ID NO: 42              moltype = DNA   length = 392
FEATURE                    Location/Qualifiers
misc_feature               1..392
                           note = R6K
source                     1..392
                           mol_type = other DNA
                           organism = synthetic construct
SEQUENCE: 42
gatctgaaga tcagcagttc aacctgttga tagtacgtac taagctctca tgtttcacgt     60
actaagctct catgtttaac gtactaagct ctcatgttta acgaactaaa ccctcatggc    120
taacgtacta agctctcatg gctaacgtac taagctctca tgtttcacgt actaagctct    180
catgtttgaa caataaaatt aatataaatc agcaacttaa atagcctcta aggttttaag    240
ttttataaga aaaaaagaa tatataaggc ttttaaagcc tttaaggttt aacggttgtg    300
gacaacaagc cagggatgta acgcactgag aagcccttag agcctctcaa agcaattttg    360
agtgacacag gaacacttaa cggctgacat gg                                   392

SEQ ID NO: 43              moltype = DNA   length = 2222
FEATURE                    Location/Qualifiers
misc_feature               1..2222
                           note = RK2
source                     1..2222
                           mol_type = other DNA
                           organism = synthetic construct
SEQUENCE: 43
gcgatgcagg tggctgctga accccagcc ggaactgacc ccacaaggcc ctagcgtttg      60
caatgcacca ggtcatcatt gacccaggcg tgttccacca ggccgctgcc tcgcaactct    120
tcgcaggctt cgccgacctg ctcgcgccac ttcttcacgc gggtgaatc cgatccgcac    180
atgaggcgga aggtttccag cttgagcggg tacggctcc ggtgcgagct gaaatagtcg    240
aacatccgtc gggccgtcgg cgacacgcttg cggtacttcc cccatatgaa tttcgtgtag    300
tggtcgccag caaacagcac gacgatttcc tcgtcgatca ggacctggca acgggacgtt    360
ttcttgccac ggtccaggac gcggaagcgg tgcagcagcg acaccgattc caggtgccca    420
acgcggtcgg acgtgaagcc catcgccgtc gcctgtaggc gcgacaggca ttcctcggcc    480
ttcgtgtaat accggccatt gatcgaccag cccaggtcgt gaaagctc gtagaacgtg    540
aaggtgatcg gctcgccgat aggggtgcgc ttcgcgtact ccaacacctg ctgccacacc    600
agttcgtcat cgtcggcccg cagctcgacg ccggtgtagg tgatcttcac gtccttgttg    660
acgtggaaaa tgaccttgtt ttgcagcgcc tcgcgcggga ttttcttgtt gcgcgtggtg    720
aacagggcag agcgggccgt gtcgtttggc atcgctcgca tcgtgtccgg ccacggcgca    780
atatcgaaca aggaaagctg catttccttg atctgctgct tcgtgtgttt cagcaacgcg    840
gcctgcttgg cttcgctgac ctgtttgcc aggtcctcgc cggcggtttt tcgcttcttg    900
gtcgtcatag ttcctcgcgt gtcgatggtc atcgacttcg ccaaacctgc cgcctcctgt    960
tcgagacgac gcgaacgctc cacggcggcc gatggcgcgg gcagggcagg gggagccagt   1020
tgcacgctgt cgcgctcgat cttggccgta gcttgctgga ctatcgagcc gacggactgg   1080
aaggtttcgc ggggcgcacg catgacggtg tggtttcgc atcctcggca                1140
gaaaccccg cgtcgatcag ttcttgcctg tatgccttcc ggtcaaacgt ccgattcatt    1200
caccctcctt gcgggattgc cccggaatta ttccccgga tcgatccgtc gatcttgatc    1260
ccctgcgcca tcagatcctt ggcggcaaga aagccatcca gttacttgg cagggcttcc    1320
caaccttacc agagggcgcc ccagctggca attccggttc gcttgctgtc cataaaaccg    1380
cccagtctag ctatcgccat gtaagcccac tgcaagctac ctgctttctc tttgcgcttg   1440
```

```
cgttttccct tgtccagata gcccagtagc tgacattcat ccggggtcag caccgtttct  1500
gcggactggc tttctacgtg gctgccattt ttggggtgag gccgttcgcg gccgaggggc  1560
gcagcccctg gggggatggg aggcccgcgt tagcgggccg ggagggttcg agaaggggg   1620
gcaccccct  tcggcgtgcg cggtcacgcg cacagggcgc agccctggtt aaaaacaagg  1680
tttataaata ttggtttaaa agcaggttaa aagacaggtt ggcggtggcc gaaaaacggg  1740
cggaaaccct tgcaaatgct ggattttctg cctgtggaca gcccctcaaa tgtcaatagg  1800
tgcgcccctc atctgtcagc actctgcccc tcaagtgtca aggatcgcgc ccctcatctg  1860
tcagtagtcg cgcccctcaa gtgtcaatac cgcagggcac ttatcccag  gcttgtccac  1920
atcatctgtg ggaaactcgc gtaaaatcag gcgttttcgc cgatttgcga ggctggccag  1980
ctccacgtcg ccggccgaaa tcgagcctgc ccctcatctg tcaacgccgc gccgggtgag  2040
tcggcccctc aagtgtcaac gtccgcccct catctgtcag tgagggccaa gttttccgcg  2100
aggtatccac aacgccggcg gccctacatg gctctgctgt agtgagtggg ttgcgctccg  2160
gcagcggtcc tgatccccg  cagaaaaaaa ggatctcaag aagatccttt gatcttttct  2220
ac                                                                 2222

SEQ ID NO: 44          moltype = DNA  length = 1522
FEATURE                Location/Qualifiers
misc_feature           1..1522
                       note = pBBR1
source                 1..1522
                       mol_type = other DNA
                       organism = synthetic construct
SEQUENCE: 44
ctaccggcgc ggcagcgtta cccgtgtcgg cggctccaac ggctcgccat cgtccagaaa  60
acacggctca tcgggcatcg gcaggcgctg ctgcccgcgc cgttcccatt cctccgtttc  120
ggtcaaggct ggcaggtctg gttccatgcc cggaatgccg ggctggctgg gcggctcctc  180
gccggggccg gtcggtagtt gctgctcgcg cggatacagg gtcgggatgc ggcgcaggtc  240
gccatgcccc aacagcgatt cgtcctggtc gtcgtgatca accaccacgg cggcactgaa  300
caccgacagg cgcaactggt cgcggggctg gccccacgcc acgcggtcat tgaccacgta  360
ggccgacacg gtgccgggc  cgttgagctt cacgacggag atccagcgct cggccaccaa  420
gtccttgact gcgtattgga ccgtccgcaa agaacgtccg atgagcttgg aaagtgtctt  480
ctggctgacc accacggcgt tctggtggca catctgcgcc acgaggtgat gcagcagcat  540
tgccgccgtg ggtttcctcg caataagccc ggcccacgcc tcatgcgctt gcgttccgt   600
ttgcacccag tgacccgggct tgttcttggc ttgaatgccg atttctctgg actgcgtggc  660
catgcttatc tccatgcgtt aggggtgccg cacggttgcg caccatgcca caatcagctg  720
caacttttcg gcagcgcgac aacaattatg cgttgcgtaa aagtggcagt caattacaga  780
ttttctttaa cctacgcaat gagctattgc gggggggtgcc gcaatgagct gttgcgtacc  840
cccctttttt aagttgttga tttttaagtc tttcgcattt cgccctatat ctagttcttt  900
ggtgcccaaa gaagggcacc cctgcgggt  tccccccacg cttcgtgcgg gctcccctc   960
cggcaaaaag tggcccctcc ggggcttgtt gatcgactgc gcggccttcg gccttgccca  1020
aggtggcgct gccccttgg aacccccgca ctcgccgccg tgaggctcgg ggggcaggcg  1080
ggcgggcttc gcccttcgac tgcccccact cgcataggct gggtcgttc  caggcgcgtc  1140
aaggccaagc cgctgccgcg gtcgctgcgcg agccttgacc cgccttccac ttggtgtcca  1200
accggcaagc gaagcgcgca ggccgcaggc cggaggcttt tccccagaga aaattaaaaa  1260
aattgatggg gcaaggccgc aggccgcgca gttggagccg gtgggtatgt ggtcgaaggc  1320
tgggtagccg gtgggcaatc cctgtggtca agctcgtggg caggcgcagc ctgtccatca  1380
gcttgtccag caggggttgtc cacgggccga gcgaagcgag ccagccggtg gccgctcgcg  1440
gccatcgtcc acatatccac gggctggcaa gggagcgcag cgaccgcgca gggcgaagcc  1500
cggagagcaa gcccgtaggg gg                                           1522

SEQ ID NO: 45          moltype = DNA  length = 1969
FEATURE                Location/Qualifiers
misc_feature           1..1969
                       note = pRO1600
source                 1..1969
                       mol_type = other DNA
                       organism = synthetic construct
SEQUENCE: 45
gataatctca tgaccaaaat cccttaacgt gagttttcgt tccactgagc gtcagacccc  60
gtagaaaaga tcaaaggatc ttcttgagat cctttttttc tgcgcgtaat ctgctgcttg  120
caaacaaaaa aaccaccgct accagcggtg gtttgtttgc cggatcaaga gctaccaact  180
cttttccga  aggtaactgg cttcagcaga gcgcagatac caaatactgt tcttctagtg  240
tagccgtagt taggccacca cttcaagaac tctgtagcac cgcctacata cctcgctctg  300
ctaatcctgt taccagtggc tgctgccagt ggcgataagt cgtgtcttac cgggttggac  360
tcaagacgat agttaccgga taaggcgcag cggtcgggct gaacgggggg ttcgtgcaca  420
cagcccagct tggagcgaac gacctacacc gaactgagat acctacagcg tgagctatga  480
gaaagcgcca cgcttcccga agggagaaag gcggacaggt atccggtaag cggcagggtc  540
ggaacaggag agcgcacgag ggagcttcca gggggaaacg cctggtatct ttatagtcct  600
gtcgggtttc gccacctctg acttgagcgt cgatttttgt gatgctcgtc aggggggcgg  660
agcctatgga aaaacgccag caacgcggcc gtgaaaggca ggccggtccg tggtggccac  720
ggcctctagg ccagatccag cggcatctgg gttagtcgag cgcgggccgc ttcccatgtc  780
tcaccagggc gagcctgttt cgcgatctca gcatctgaaa tcttcccggc cttgcgcttc  840
gctgggcct  tacccaccgc cttggcgggc ttcttcggtc caaaactgaa caacagatgt  900
gtgaccttgc gcccggtctt tcgctgcgcc cactccatcg cagttgaggt tgctctcgttg  960
atctgcgtca cggctggatc aagcactcgc aacttgaagt ccttgatcga gggataccgg  1020
ccttccagtt gaaaccactt tcgcagctgg tcaatttcta tttcgcgctg gccgatgctg  1080
tcccattgca tgagcagctc gtaaagcctg atcgcgtggg tgctgtccat cttggccacg  1140
tcagccaagg cgtatttggt gaactgtttg gtgagttccg tcaggtacgg cagcatgtct  1200
ttggtgaacc tgagttctac acggccctca ccctcccggt agatgattgt ttgcacccag  1260
```

```
ccggtaatca tcacactcgg tcttttcccc ttgccattgg gctcttgggt taaccggact  1320
tcccgccgtt tcaggcgcag ggccgcttct ttgagctggt tgtaggaaga ttcgataggg  1380
acacccgcca tcgtcgctat gtcctccgcc gtcactgaat acatcacttc atcggtgaca  1440
ggctcgctcc tcttcacctg gctaatacag gccagaacga tccgctgttc ctgaacactg  1500
aggcgatacg cggcctcgac cagggcattg cttttgtaaa ccattggggg tgaggccacg  1560
ttcgacattc cttgtgtata aggggacact gtatctgcgt cccacaatac aacaaatccg  1620
tcccttttaca acaacaaatc cgtcccttct taacaacaaa tccgtccctt aatggcaaca  1680
aatccgtccc tttttaaact ctacaggcca cggattacgt ggcctgtaga cgtcctaaaa  1740
ggtttaaaag ggaaaaggaa gaaaagggtg gaaacgcaaa aaacgcacca ctacgtggcc  1800
ccgttggggc cgcatttgtg cccctgaagg ggcggggggag gcgtctgggc aatccccgtt  1860
ttaccagtcc cctatcgccg cctgagaggg cgcaggaagc gagtaatcag ggtatcgagg  1920
cggattcacc cttggcgtcc aaccagcggc accagcggcg cctgagagg             1969

SEQ ID NO: 46           moltype = DNA    length = 3674
FEATURE                 Location/Qualifiers
misc_feature            1..3674
                        note = RSF1010
source                  1..3674
                        mol_type = other DNA
                        organism = synthetic construct
SEQUENCE: 46
tcagcctgcc gccttgggcc gggtgatgtc gtacttgccc gccgcgaact cggttaccgt    60
ccagcccagc gcgaccagct ccggcaacgc ctcgcgcacc cgctggcggc gcttgcgcat   120
ggtcgaacca ctggcctctg acggccgaca atagccgcac aaggtatcta tggaagcctt   180
gccggttttg ccggggtcga tccagccaca cagccgctgg tgcagcaggc gggcggtttc   240
gctgtccagc gcccgcacct cgtccatgct gatgcgcaca tgctgccatg tcaccacatg   300
ggcctgcgcg atcaagggg tcagggccac gtacaggcgc ccgtccgcct cgtcgctggc   360
gtactccgac agcagccgaa acccctgccg cttgcgcca ttctgggcga tgatggatac   420
cttccaaagg cgctcgatgc agtcctgtat gtgcttgagc gccccaccac tatcgacctc   480
tgccccgatt tccttttgcca gcgcccgata gctacctttg accacatgc attcagcggt   540
gacggcctcc cacttgggtt ccaggaacag ccggagctgc cgtccgcctt cggtcttggg   600
ttccgggcca agcactaggc cattaggccc agccatggcc accagccctt gcaggatgcg   660
cagatcatca gcgcccagcg gctccgggcc gctgaactcg atccgcttgc cgtcgccgta   720
gtcatacgtc acgtccagct tgctgcgctt gcgctcgccc cgctctgaggg cacggaacag   780
gccgggggcc agacagtgcg ccgggtcgtg ccggacgtgg ctgaggctgt gcttgttctt   840
aggcttcacc acgggcacc cccttgctct tgcgctgcct ctccagcacg gcgggcttga   900
gcaccccgcc gtcatgccgc ctgaaccacc gatcagcgaa cggtgcgcca tagttggcct   960
tgctcacacc gaagcggacg aagaaccggc gctggtcgtc gtccacaccc cattcctcgg  1020
cctcggcgct ggtcatgctc gacaggtagg actgccagcg gatgttatcg accagtaccg  1080
agctgccccg gctggcctgc tgctggtcgc ctgcgcccat catggccgcg cccttgctgg  1140
catggtgcag gaacacgata gagcaccgg tatcggcggc gatggcctcc atgcgaccga  1200
tgacctgggc catgggccg ctggcgttt cttcctcgat gtggaaccgg cgcagcgtgt  1260
ccagcaccat caggcggcgg ccctcggccg gcgcttgag cactccggca              1320
ccatgatgtt gggcaggctg ccgatcagcg gctggatcag caggccgtca gccacgggtt  1380
gccgttcctc ggcgctgagg tgcgccccaa gggcgtgcag gcggtgatga atggcggtgg  1440
gcgggtcttc ggcgggcagg tagatcaccg ggccggtggg cagttcgccc acctccagca  1500
gatccggccc gcctgcaatc tgtgcggcca gttgcaggc cagcatggat ttaccggcac   1560
caccgggcga caccagcgcc ccgaccgtac cggccaccat gttgggcaaa acgtagtcca  1620
gcggtggcgg cgctgctgcg aacgcctcca gaatattgat aggcttatgg gtagccattg  1680
attgcctcct ttgcaggcag ttggtggtta ggcgctggcg gggtcactac ccccgccctg  1740
cgccgctctg agttcttcca ggcactcgcg cagccctcg tattcgtcgt cggtcagcca  1800
gaacttgcgc tgacgcatcc ctttggcctt catgcgctcg gcatatcgcg cttggcgtac  1860
agcgtcaggg ctgccagca ggtcgccggt ctgcttgtcc ttttggtctt tcatatcagt  1920
caccgagaaa cttgccgggg ccgaaaggct tgtcttcgcg gaacaaggac aaggtgcagc  1980
cgtcaaggtt aaggctggcc atatcagcga ctgaaaagcg gccagcctcg gccttgtttg  2040
acgtataacc aaaagccaccg ggcaaccaat agcccttgtc acttttgatc aggtagaccg  2100
accctgaagc gcttttttcg tattccataa aaccccttc tgtgcgtgag tactcatagt  2160
ataacaggcg tgagtaccaa cgcaagcact acatgctgaa atctggcccg cccctgtcca  2220
tgcctcgctg gcgggtgccg gtgcccgtg ccagctcggc ccgcgcaage tggacgctgg  2280
gcagacccat gaccttgctg acggtgcgct cgatgtaatc cgcttcgtgg ccggggcttgc  2340
gctctgccag cgctgggctg gcctcggcca tggccttgcc gatttcctcg gcactgcggg  2400
cccggctggc cagcttctgc gcggcgataa agtcgcactt gctgaggtca tcaccgaagc  2460
gcttgaccag cccggccatc tcgctgcggt actcgtccga cgccgtgcgc cggtggcggc  2520
taagctgccg ctcgggcagt tcgaggctgg ccagcctgcg ggcttctcc tgctgccgct  2580
gggcctgctc gatctgctgg ccagcctgct gcaccagcgc cggggccagcg gtggcggtct  2640
tgcccttgga ttcacgcagc agcacccacg gctgataacc ggcgcgggtg gtgtgcttgt  2700
ccttgcggtt ggtgaagccc gccaagcggc catagtggcg gctgtcggcg ctggccgggt  2760
cggcgtcgta tcgctggcc agcgtccggg caatctgccc ccgaagttca ccgcctgcgg  2820
cgtcggccat cttgacccat gcctgatagt tcttcgcggt gtttccact accagggcag  2880
gctcccggcc ctcggctttc atgtcatcca ggtcaaactc gctgaggtcg tccaccagca  2940
ccagaccatg ccgctcctgc tcggcggcc tgatatacac gtcattgccc tgggcattca  3000
tccgcttgag ccatgcgtg ttctggagca cttcggcggc tgaccattcc cggttcatca  3060
tctggccggt ggtggcgtcc ctgacgccga tatcgaagcg ctcacagccc atggccttga  3120
gctgtccgc tatgtccgtgc aaagtcctgt cgttcttcat cgggccacca agcgattccc  3180
acacattata cgagcggaa gcataaagtg taaagcctag atccgaagga tgagccgggc  3240
tgaatgatcg accgagacag gccctgcggg gctgcacacg cgccccacc cttcgggtag  3300
ggggaaaggc cgctaaagcg gctaaaagcg ctccagcgta tttctgcggg gtttggtgtg  3360
gggtttagcg ggctttgccc gcctttcccc ctgccgcgca gcgtggggc ggtgtgtagc  3420
ctagcgcagc gaatagacca gctatccggc ctctggccgg gcatattggg caagggcagc  3480
```

```
agcgccccac aagggcgctg ataaccgcgc ctagtggatt attcttagat aatcatggat    3540
ggattttttcc aacaccccgc cagccccgc ccctgctggg tttgcaggtt tgggggcgtg    3600
acagttattg caggggttcg tgacagttat tgcaggggggg cgtgacagtt attgcagggg    3660
ttcgtgacag ttag                                                       3674

SEQ ID NO: 47           moltype = DNA  length = 2982
FEATURE                 Location/Qualifiers
misc_feature            1..2982
                        note = pAMbeta1
source                  1..2982
                        mol_type = other DNA
                        organism = synthetic construct
SEQUENCE: 47
attctcccaa gaattagaaa tgagtagatc aaattattca cgaatagaat caggaaaatc    60
agatccaacc ataaaaacac tagaacaaat tgcaaagtta actaactcaa cgctagtagt    120
ggattttaat cccaaatgag ccaacagaac cagagccaga aacagaatca gaacaagtaa    180
cattggatttt agaaatggaa gaagaaaaaa gcaatgactt cgtgtgaata atgcacgaaa    240
tcgttgctta ttttttttaa aagcggtata ctagatataa cgaaacaacg aactgaatag    300
aaacgaaaaa agagccatga cacatttata aaatgtttga cgacatttta taaatgcata    360
gcccgataag attgccaaac caacgcttat cagttagtca gatgaactct tccctcgtaa    420
gaagttattt aattaacttt gtttgaagac ggtatataac cgtactatca ttatataggg    480
aaatcagaga gttttcaagt atctaagcta ctgaatttaa gaattgttaa gcaatcaatc    540
ggaaatcgtt tgattgcttt ttttgtattc atttatagaa ggtggagttt gtatgaatca    600
tgatgaatgt aaaacttata taaaaaatag tttattggag ataagaaaat tagcaaatat    660
ctatacacta gaaacgttta agaaagagtt agaaaagaga aatatctact tagaaacaaa    720
atcagataag tattttttctt cggagggggga agattatata tataagttaa tagaaaataa    780
caaaataatt tattcgatta gtggaaaaaa attgacttat aaaggaaaaa aatctttttc    840
aaaacatgca atattgaaac agttgaatga aaaagcaaac caagttaatt aaacaaccta    900
ttttatagga tttataggaa aggagaacag ctgaatgaat atcccttttg ttgtagaaac    960
tgtgcttcat gacggcttgt taaagtacaa atttaaaaat agtaaaattc gctcaatcac    1020
taccaagcca ggtaaaagca aaggggctat ttttgcgtat cgctcaaaat caagcatgat    1080
tggcggtcgt ggtgttgttc tgacttccga ggaagcgatt caagaaaatc aagatacatt    1140
tacacattgg acacccaacg tttatcgtta tggaacgtat gcagacgaaa accgttcata    1200
cacgaaaggga cattctgaaa acaatttaag acaaatcaat accttcttta ttgattttga    1260
tattcacacg gcaaaagaaa ctatttcagc aagcgatatt ttaacaaccg ctattgattt    1320
aggttttatg cctactatga ttatcaaaatc tgataaaggt tatcaagcat attttgtttt    1380
agaaacgcca gtctatgtga cttcaaaatc agaatttaaaa tctgtcaaag cagccaaaat    1440
aatttcgcaa aatatccgag aatatttttgg aaagtctttg ccagttgatc taacgtgtaa    1500
tcattttggt attgctcgca taccaagaac ggacaatgta gaatttttttg atcctaatta    1560
ccgttattct ttcaaagaat ggcaagattg gtctttcaaa caaacagata taagggctt    1620
tactcgttca agtctaacgg ttttaagcgg tacagaaggc aaaaaaacaag tagatgaacc    1680
ctggttttaat ctcttattgc acgaaacgaa attttcagga gaaaagggtt taatagggcg    1740
taataacgtc atgttttaccc tctctttagc ctactttagt tcaggctatt caatcgaaac    1800
gtgcgaatat aatatgtttg agtttaataa tcgattagat caaccttag aagaaaaaga    1860
agtaatcaaa attgttagaa gtgcctattc agaaaactat caaggggcta atagggaata    1920
cattaccatt ctttgcaaag cttgggtatc aagtgattta accagtaaag atttatttgt    1980
ccgtcaaggg tggtttaaat tcaagaaaaa aagaagcgaa cgtcaacgtg ttcatttgtc    2040
agaatggaaa gaagatttaa tggcttatat tagcgaaaaa agcgatgtat acaagccta    2100
tttagtgacg accaaaaaag agattagaga agtgctaggc attcctgaac ggacattaga    2160
taaattgctg aaggtactga aggcgaatca ggaaatttttc tttaagatta aaccaggaag    2220
aaatgtggc attcaacttg ctagtgttaa atcattgttg ctatcgatca ttaaagtaaa    2280
aaaagaagaa aaaagaagct atataaaggc gctgacaaat tcttttgact tagagcatac    2340
attcattcaa gagactttaa acaagctagc agaacgccct aaaacggaca cacaactcga    2400
tttgtttagc tatgatacag gctgaaaata aaacccgcac tatgccatta catttatatc    2460
tatgatacgt gttttgtttt tctttgctgt ttagcgaatg attagcagaa atatacagag    2520
taagatttta attaattatt aggggggagaa ggagagagta gcccgaaaac ttttagttga    2580
cttggactga acgaagtgag ggaaaggcta ctaaaacgtc gaggggcagt gagagcgaag    2640
cgaacacttg attttttaat tttctatctt ttataggtca ttagagtata cttatttgtc    2700
ctataaacta tttagcagca taatagattt attgaatagg tcatttaagt tgacatatt    2760
agaggaggaa aatcttggag aaatatttga agaacccgat tacatggatt ggattagttc    2820
ttgtggttac gtggttttta actaaaagta gtgaatttttt gatttttggt gtgtgtgtct    2880
tgttgttagt atttgctagt caaagtgatt aaatagaatt ctcatgtttg acagcttatc    2940
atcggagctc gatgataag ctgtcaaaca tgagaattcc cg                        2982

SEQ ID NO: 48           moltype = DNA  length = 4154
FEATURE                 Location/Qualifiers
misc_feature            1..4154
                        note = pLME106
source                  1..4154
                        mol_type = other DNA
                        organism = synthetic construct
SEQUENCE: 48
gatccggcgg aacttcacgt cctggcggtg gagttggcgg gcgcgttcca gccgttcctc    60
cagcacggtg atccgggcct ccagacgctc acgctcaccc tgctccaggt gccgggtcac    120
cgtcaccgtc cgcaccggcc gggcctcggc ctgggcggcc cggcgttcct cactgggcccg    180
cttccggcaa tcgtcggaac accacaccccg gggccgaccc cgcccaccgt gggcctccac    240
cggcgccccg cagtgggggac acgcccgcag cgccgacgca tcctcatcca aggccatcac    300
cgggtcggaa tccatacccg aaaccatatc gtccggacga tgaactgcgc cagacagcta    360
agaatgcacg aggtgtgtct ccgattctca ggaaacgctc agcattttcc gagacgttcg    420
```

```
gcgcacgcac  acaccccccac  aagaaccgac   ccgcccagca  tccgccgaca   cgtcgatccg   480
caccccgcgat  gggctggccg   aggccgacta   cgaccgctag  tcagcacctg   cgctgatcta   540
ccgtcgccct  gaccgactct   cccgtcggga   ttgtcgccgg  ccgctgccag   catggacctg   600
cggccccgcc  ccctcgccct   gcaactcgag   ggaggcgggg  ccgtccaccc   cccacaccac   660
cccgacaccg  tgatgcgccc   atgtcgccta   acgggttgcc  cgactctccc   gacatcaaga   720
aaacctgaca  ccgtcgccgc   aagcgctaca   ctgactacta  gtagtcagga   ggtgcgtgat   780
gaccatcgcc  acatcggtga   aactctccga   agagaccggc  cgcaaactcg   atgaactagc   840
ccggggccacc  gggcgatcca   agtcctacta   cctgcgcgag  gccatcgagg   accacatcga   900
ccagatggtc  cacgactacg   ccatcgcccg   actcgccgac  gacgtgcgag   ccggccgggc   960
cgccacctac  agcgccgacg   aagtggacca   gatccttggc  ctggacgatt   gagtacaccg  1020
accccgccgt  caaagcactg   cgcaaactga   accgagccca  ggcccgccgc   atcaccgcct  1080
acatacgtga  gctcaccggc   ctggacgatc   cccaccaacg  cgggaaaggc   ctcaccgggc  1140
ccctggccgg  actctggcgc   taccgcgtcg   gggactaccg  gatcatctgc   gacctgaacg  1200
ccgaccgcct  ggccatcatc   gccctgacca   tcgagcccga  cacctggccc   taccgctgac  1260
acgcaaccccc  gcaccctcgg   ccaagacgtc   acacaccacc  cgcccaccg   agcactgagg  1320
atgtcaactc  gcccgagccg   gcctgccggc   cgtcttacgg  gttgtcttgg   cgggcggggt  1380
gtctttgccc  tggcccagca   gccccacgat   ctcccgcagc  gtgtcggcgg   tggcggcgtc  1440
ccggggcgcc  tgacgctccg   attccgcccct  ggcctgctcg  gctgcctgcg   cccgatcctc  1500
cgcggcggcg  gcctgctccc   tcgcctcggc   cagctcgccg  gtcagggcct   cgacccgggc  1560
ctgcacctgc  ccaggcgcg   cctccgcctc   ctgctgcacc  tgctcggccc   gggcctccgc  1620
ctggtccccgg  gccgctcgg   cctcggcccg   gtgctgatcc  gccagggccg   cctcggccac  1680
cgcttcggcc  tgcccatcca   ccgcctgctc   ggcccgacgc  ccgaactcgt   cgcgggccgg  1740
atcactcgcc  tgacgccacg   ccgccgccca   caccagaccc  aacggctccg   acagatccgg  1800
cggggccggc  gtctgaccg   acgccgagac   gtcgcgcagg  aaccccgccg   cagcgtcggt  1860
ggagcaccccc  gcctccgcct   tcaacgaccg   caccgtcacc  cgccgacccg   caccgctcaa  1920
ccgcgcatag  gccgccgcca   accttgaccc   attcgactcc  atgacccacc   ctcccattct  1980
gtaccctgta  cctgttccta   ggtacgttcc   taatgtacct  caccggatgc   agaaccccga  2040
accccccctca  cactccccct   gcacgggggcc   cgccccctgc  accccccgctg   ccgcgcccgc  2100
tcctgcgtcg  cggccttgcc   cctgcccaac   gccgggccgg  cgggcagccc   accagaggct  2160
ctgtgagacg  tcggcgcccc   cgtccaccta   ccctaaagac  caaccccaa   tggaaacgtc  2220
tgtgaggagc  cttgtaggag   ttcccaggac   aagccagcaa  ggccgggcct   gacggcccgg  2280
aaaggaagtc  gctgcgctcc   tacgaagaag   cccctctggg  gaccccccaga   ccccggaact  2340
atctgatttg  gttagcggc   gtacttccgt   cataccggaa  tttatggcat   gctgtggtca  2400
tggcgacgac  gacggtcgat   gagcagtggg   agcaggtgtg  gctgccccgc   tggccctgg   2460
cctccgacga  cctggcccggg   ggcatctacc   ggatggcccg  cccctcggcg   ctggggggtcc  2520
gatacatcga  ggtcaacccc   caagccatca   gcaacctcct  cgtggtcgac   tgcgaccacc  2580
ccgacgctgc  catgcgcgcc   gtctgggacc   gccacgactg  gctgcccaac   gccatcgtcg  2640
agaacccgaa  caacggccac   gcccacgccg   tgtgggccct  ggaagcagcc   atcccgcgca  2700
ccgagtacgc  ccaccgcaag   cccatcgcct   acgccgccgc  cgtcaccgag   ggcctgccgc  2760
gatccgtcga  cggagacgcc   tcctacgccg   gcctgatcac  caagaacccc   gaacaccccg  2820
cctgaaacac  cacctggtgc   accgaccacc   tctaccgggt  ggccgagctc   gacacccacc  2880
tggatgccgc  cggcctcatg   cccgccccct   cctggcgacg  cacccgccgg   cgcaacccg   2940
tcggcctggg  ccgcaactgc   gccatcttcg   agaccgccgc  cacctgggcc   taccgcgacg  3000
cccgccgcat  ccgacaacgc   cacgaatacc   cgaccgccga  ggactcggcc   gacctgcacg  3060
ccgtcatcgc  ctccaccgtc   gaggcgctca   acgccggcta  cagcgaaccc   ctgccggccc  3120
gcgaggccgc  cggcatcgcc   gccagcatcc   accgatggat  cacccaccgt   ttctacggct  3180
ggatcgactc  ccacaccgtc   aacgaggcca   cttctctccac  catccagagc   tacagaggac  3240
acaagggagc  cggcaaggct   cgtcctcgtg   cccgccgtgc  tgcttctatc   accgattggg  3300
aggcatgatg  gctgacgtcc   agcaccgcgt   gaagcgtcgg  ggcacggccc   gcgaggccgc  3360
agaacgtgta  ggggcctcca   tccgaaccgc   ccagcggtgg  acctccatcc   ccgtgaggca  3420
atggatcact  cagaaggccg   tcgagcgtga   ggagatccgg  gcctacaagt   acgacgaggg  3480
gcacacgtgg  ggcgagacct   cgcgccactt   cgggatcgcg  aagaccaccg   cccaggagcg  3540
ggcccggcgg  gctcgaaggg   agcgggcgg   cgaagcggag  aaggctgccg   aggaggccga  3600
ggccgcgctg  cgtccgacac   tcttcgaggg   ccaggagcaa  ggttctgcat   gagcaaccccc  3660
gagtcctcgg  gtagaccgtc   tggcccgacg   ttaagcatgg  ctgaagcggc   ccgtgcctgt  3720
ggggttttcag  tgtccacggt   gaggcgtcac   cgtgatgcgc  tggtggccca   cggtgctacc  3780
cgtcatgacg  cgtcatgggt   gatacccccta   tcagcgttga  tttcatgcgg   tttgatgccc  3840
cgggtgacac  cccctgatgc   cccgtcaccc   aataacgtgg  cgcctgccat   gacgtccac   3900
ggtgacgcc  ccctgacggg   ggaagtccaa   gagctgcgcg  agcgactggc   caacgctgag  3960
catcgagcccg  agctagcagt   agaggttggg   gacgacgtct  cggccgactcc   ggagaacacc  4020
aagtcagggt  ctcatgagtg   tgcgatagct   tgagctgtct  accaatctgg   atatagctat  4080
atcggtcgtt  tgtgtctgat   tcgccagtga   gccaacggcg  ggggcgacac   gcggtggcga  4140
aaccccctgg  caga                                                            4154
```

| SEQ ID NO: 49 | moltype = DNA   length = 22046 |
|---|---|
| FEATURE | Location/Qualifiers |
| misc_feature | 1..22046 |
| | note = pTZC1 |
| source | 1..22046 |
| | mol_type = other DNA |
| | organism = synthetic construct |

SEQUENCE: 49

```
gcgagcacac  ttccctcacg   ctgactcgtc   actccgacac  gctcgctcgt   gtccgtgaac   60
tggcgggcga  cggcccgcca   gtcacccgga   tcgatgaccg  tcgcattagt   cgaaacccac  120
acgccatcct  gggtcgcatc   gggccgcgtg   atgtacccaa  cgcgccttcg   cggcgtcgtc  180
ttgatctgcc  ccatcttcac   aacagccatc   actccgcccc  cgcttccgtt   gcggcgtcga  240
tggcccgttg  gacttgtccc   agcagctccc   gcgtggcacg  catctgctca   accgtcacca  300
catcatcagt  gttcacctgc   cgagcgatct   ggttgatgtt  gttcccgatc   ctcgacaact  360
cggcgcgcag  cggagccgga   tcgaacgcca   cgcgacgcac  gacgatcttc   ccctcagtga  420
```

```
gagcgcgccg cgcatagtcg gcgaacgtcc tcgcctccgc aagttccata cgccgttcca  480
cccgcttcca ttcagcatca ctgagccaca agcccttgaa gacccctcgc gaccgcttcg  540
cgccctgctc agccatgcat ccactcctac cgggtttggg cagagcccat agtgcccagg  600
gggccacgca actgtgtaac agttgctatg cttgctaccc cgtcagggtc agtctacaac  660
ctacggtcta catggcgcta gaatgagaaa cggatcgtcc ggctaaccgg acgatccgag  720
atcggaaggg ccgccagggg gcggccacg atgatccttg tacggggtgt cccgcgctgc  780
ccgcgcggga caccctaggg gtcgccgtcg gcggccccgc accaagatga aggagggcgt  840
atggccacca agtccgaccc cgatctaatc gacgacctgc tgcgccaaga cgaggcggag  900
ctgcgggcga agaagaagcg gctgcgcgcc tttcagacgg ctctgatga gcttcggcac  960
gccagcgagg cagtggccac ggccggtgcc gccctcatcg ctgccggcga tgtctccgcc 1020
gccgaggcga gcaaggtctt caagctctcc aaggggagaac gcgccgccgc gttccctacc 1080
cggcctcgct cagagtcgag cgtcgcggat gcggtcgatg agccgccgaa ccccgtagac 1140
gatccatccg atgagtcgga tgaacagcac accgatctgg tcagtagcc acaccgcgac 1200
gtggaagatc gcgctcagtc cgtacatcgc gatgatgagg atgagcgcga gcacggcgat 1260
cacgccggcg atcatcaacc acgcgagccc catcgctcat cctcccttca actctcggtg 1320
tctccatggt gccacttcgg gatgactctt gtcccgatgc catcaggatg gtgcgctcca 1380
ggtcgccgtc aagggcgctg cgcgtcgctg cgcgatgccg caagcggcac ccttgaccgc 1440
gaccctccac acaccgattg gcagttatcg gaacgaaggg gcgctctggg ctccggacgag 1500
ggctcggcgt accgacgacg tgctcacacc gagcacggtg gcgatatgcg cgttgctctg 1560
accctgcgcc ttcatgcgca aggcggcgtc ggtccgctcc ggacccatga cggtgggacg 1620
gccaccgact ctgccctggg cccgcgcgta ggccaggccc cgccgggtgt tctcccggat 1680
cgtgtccacg cgcagctggg cgaacacggc catgatcccc aaatggcct ggcccatcgg 1740
gctcgacgtg tcgatgctca acgccggctc cgtcaggctc ctgatactca ctccctgccc 1800
gatcaggtca tggacgatct cgatggccat gacctcgctt ccggcagcc ggtccagcgc 1860
ccggaacacc agcgtgtcgc ccggacgcag atagtcgcgg cacgccaacc actgcggccg 1920
gtccggccgca cggctggact cgccgtggtc cacgaacaca cgctcggccc cggccgcgag 1980
cagctcggcc tcctgcgcgg ccgggttctg ctcgcgcgtg gacacgcgcg cgtaccgac 2040
gatggtcatc ttctcccccg ccccacaggg ccgcctcggt gcggtcgtc gtcgccgcgc 2100
tccgctcgac gacgttccac ctcccgctcg atgcgctcgt gcaggccgct gcgggtactc 2160
tcccgccggg ctaggccgcg aatgctcgcc gcccacgcct tggtgcgcgt cttcacgtcg 2220
tcgagctgac tggccgtcag accgtagacg cgcacctctt cgggctggat gcgctccacg 2280
ttgtcgaggt tctgggcgaa ccgtcctagg tcgaagccgg catcagcgtt gcgggccaag 2340
ttcagcagtt ccttgtcgct gtacctgccg gaacgccgga tcgcgtccac atcgagatag 2400
tcgcgggtct cggcccgcga gaacagggca cccaccttgt tccctaccgc gtcctcgatg 2460
gcaagcacgg gcccgacctc cagccgcacg ggcgggtgag cccgccagtc cacgcccagg 2520
tccatgtcgg tactgcgccc ttgcgcactg acgatggtga gctgggcgaa cgtgtcctgg 2580
cggcggcggg tctccacggt gtagccggcc gcacgcagcg cggcgataat ccggtcgagc 2640
gacgtgccga atcgggcctg gcctgctgg acggtgaaca ggtccacgtc ctctgtgggc 2700
cggtcgatca gcccatgctc acggatgcg cccggaccgc gcagggcgaa gccggcatcg 2760
tcgccgacgg cctccagggc caggcgcgtg atgcgccgct gctcctcctg gtcaccgctc 2820
acacgggcac ccgaagccgg gggaaccgtc cctcccacaa gacgcggacg tgcgggtcca 2880
tgttcaggat cggccacgtc tcgatgagcc gatctcggtt catcaagcgg ccctgctcgt 2940
caaccgtccc ctcggcgagc agcgcctggt aggccatacg acgccaaccc aggttcgaca 3000
cgtccacacc gagccgatca gcctgccagc gcacagagtg aggcaggtcg atgggccgt 3060
catagggccc acgcagctcg tcgagcgaag cgggcgcgtc ataggcttg acatcgcgga 3120
accgcacacg agtcgctgcc acctcagcca tggcccgcct ccttccatct catcccagtt 3180
tacccggcca ggtcgaaaac ggtctatcac tggtttcggt ttcggtgggg gtttgaccg 3240
cccttccacc gccaacctac gcggattgtg aatgtgatcg ctatatgtcg tggattcttg 3300
atcactctat ggcgtgctgg tctggtggac cgggaagaca ttgctcttcg catggcaaac 3360
ggtgccgtct ttaggatttc tctgcgccag gatccggaag ggatggcact tcttctcctg 3420
ccgacatcgg tcggagcggc tgatggtatc gcgatcagct tgccttttagc accccacggg 3480
cgtaaacagt gtggcccact gccccgcgtc caactgtttc ggcagtgcgt gtgccggaac 3540
accggcctca cgcaagacct gggcacaccg tcgcgcacgc cgacgcccca caacccggga 3600
cacgatgtcg gcgacgccac ggcccttgcc ggtgaacacg tcatggacga aggacgcgta 3660
ccgcgcacgc tccgaccagt ccacgagagg ttcctcccgg cgacgtatca ccaggacacc 3720
ggcgtcgacg gtggggcggg gacgaaatg cgtggacggc acccgcccgt actgttcgaa 3780
gtcgacccac ggccaccact gggcagtcat catcgtggca ccaccgacac cggcgcggcg 3840
gcgcgcgacc tcccactgca ccaggagcac cgcgtgggtc caccccggtg agtgaaggac 3900
gtccgcagg atcgcggtgg tcaggtggaa cggcaggttc cccaccagga cgtgcgggcc 3960
gtccggaagc acaaaatcaa ggacatcctg ctcgtacagg tggacctccg ggcgcagccg 4020
cttctccaac caccggacag aggccgggtc gatctcgacg gcggtcaacg atccaccggc 4080
agccaagaca cgatcctgaa ggggaaaggt cagcgccccg tgtcccgggc cgatctcgat 4140
gaccgggacg gaggcgttga cggggacgag gtcgacgatc cgtctgatcg tcgcctcatt 4200
gacgaggtag ttctgccgt tctcgtgacg gcccttgttc ggtcgtgatgg taggcatgga 4260
aagacactcc gcagcagata tcgtgctccg gcatgccga aaaggccgcc cggctggaca 4320
agctgagcgg tgggtgtctc tacctccgtg gaacgtcccc cgttagcgca cacacccacc 4380
ggcggctccg gggttccgga gccgaccgaa ggtggtgaaa attgcattca ttgcacccat 4440
ggggtgaacc ataccacagc acgcggatgc ctgacctgcc ctgtcccggt catccaaaac 4500
tgtcatgtgg acctgacccg gtcggtctgc cgactggtga tgatacgcc gccggggtca 4560
gattggtggg tgagtaccta cgcctccacg gaggtacggc agcaagcaac gtgcatgcgc 4620
tggcagaaac aattctgtct gatgttctcc ctcggctcgg gctaggtaat gagtagtagt 4680
acaaaactgt actgcccgtt ctctcttgta ttgaaatgct aaaggtttac aagacatcta 4740
cggcgaacgc actgaaacag ggcgctcctg cgagaatcga cccgaaaact gtctcgtata 4800
cctgtctcac cgtaatgtgt tccaccttct tccaatctgg ggtttggtga ggcatgatgg 4860
tggtcatgag actgttgggc tacacccggg tgtccaccgt cggtcaggat ccgactcttc 4920
aacacgacgc cttggtcacc gccggggttc aggaccgtga tgtcttcagc gatgtcacct 4980
ccggggcgaa aaacgccact gagcgtccgg ggatgaagaa gctcctcgcc tacgctcaac 5040
ccggtgacac ggtggtggtg tggcgcatcg accggctggg ccggtcccta ctcgatgtac 5100
tcaacacggt gaacctgtta cgcgaacgag acgtgaaaat caagtccgtc tccgacggca 5160
```

```
tcgacccgga gacctcctcg ggccggttga tgctcggcat gctgggcacc ctggctgagt    5220
acgaacgaga actgatcacc gaacgcgtca acgccggcat cgccgcagca aagtccaacg    5280
gcacccgctt cggccgacca cctgtggatc cagaggtggt cgaccgcaaa ctcgccatcg    5340
tcgccgagga acgagccaaa ggccgcagtg ccgaagacgc cgcgagcatg gtcggctggt    5400
cacgggcgac actgtaccgc catctgcagg gcgccaaacg acgacagtca gcactgcccg    5460
cctgacacgg acacaatgac cagcgcgtga ggtgacggtg atggacgaga tgcaacgctg    5520
ggagatcctc cggctccaca tcgaagacga catcaccctg accgacctgg cacaggccac    5580
cgacatcagc acccgaaccc tatcccggtg ggtagcccga taccgcgccg acggaatccg    5640
cgggctacgc aacaccacac gatccgacgc cggagcccat cgcatatccg cggaactcgt    5700
cgcctacatc gaacaccttg gtctcaccaa gccacgccca tcgatcgccg ccctgcatcg    5760
cctcgtgagc tgtcgagcac aacaactatc gctgaaacca cccagctacg ccaccgtgcg    5820
cagcatcatc aagcccttg acccggcgat ggtcaccctc gcattggagg gcccgacgtc    5880
ctaccgagat cgacacgaac tggtctaccg gcacccgggc gaacacccca acgccatctg    5940
gcaggccgat cacacccaac tcgacatcct catccagaac ccggacggca ccccgactcg    6000
cccctggctc accatcatca tcgacgacta ctcccgggca gtgtgcgggct acatggtcac    6060
caccaccgca ccctcggcaa tgaacaccgc cctggcacta cgccaggcga tctggcgaaa    6120
aacagacccc acctgggcga tgtgcggtat tcccgacgtc ctctacgtcg atcacggctc    6180
cgacttcacc agtggccata tcacgtacac cacgacagca ctgaagatcc ggatcatcca    6240
ctcgaccatc gcccgtccgc agggccgcgg caagatcgac cggttcttca gcaccgtcaa    6300
caccgaactt ctcaccaccc tgcccggcca cctcgcccc ggcgtccgca acccacaccc    6360
cgtactagac ctgacgagcc tggataccgc cgtcggcgag ttcatcagca gctacaacca    6420
gcgcacgcat tcttcaatca acaccagccc gaaagccgcg tggactgggc aggggtggat    6480
ccccagaatg ccggagaacc ttgaagaact cgacggactc ctgctgcggg tctccaccca    6540
ccgccgagtc cagcgagacg gcatccactt ccaaggccag cgctacatca gcccgaccct    6600
ggcacctttt gtcggccatg acgtcaccat ccgctacgac ccgcgggatc tctccgagat    6660
ccgggtctac gaccacgaca cgttgctgtg cgtcgctgtc gatgaagacc accccaacca    6720
gcgctacagc ctggccgata tccaggccgc tcgtcgacgc cgacggcgtc aactacgtgc    6780
cgggatcaac gagcgcatcc ccatccacga gccacgccca tcagaccttg ccctgtgaa    6840
ccccgatgtg agcgccgaag cgccacggcc gcgtggtcgt acgtctcgcc tgcggaccta    6900
tgaagaggac ctgtcaccat gaaccgcgac ttcatcgtca ccaaagagca ccgccgcttc    6960
gtcgagttcg ccaacgcgat ccgcaaagac gccaccatcg gcatctgcca cggtgatgca    7020
ggagtcggca aaacacagtc cgccagacgc tatgcccact gggatgctct gggctcgttc    7080
attgacgact ggggtccacg cagtgaatct gacctggcca tctacgcgac ggctcatcgg    7140
gcgcgcaccg tgttctacac ccctgaggtg caaccgaagt acggacgtt gatccgtgac    7200
atcgaatttt accggggcaa actcgacgtc tgcatcatgg agcatctgat ggccaccgga    7260
cagcgggaca ggctccacat gcgcagatcc agtggcgaga agctcaccca actgatcatt    7320
attgatgagg cagaacgtct gcctcccacc gccctggaga tgctgcgcga catccacgat    7380
cgtgacggtg tggcgatcat gttcatcggc atgcccggta ttgaccagcg cttccggcac    7440
taccctcagt tgttcagccg gctggggttc tcgcatcgct accgtgccct gggcaaagac    7500
gagctgctgt tcgtgctgaa ccggcactgg aggcgcctgg gtagagaatt gaacccggag    7560
gatttcacgg atgcgcaggc catcgccgcg atcgagcggc tgacccgcgg caatttccgt    7620
gtggtggagc gattgttccc acagatcaag cgagtgttga agatcaacga gttggagacc    7680
atcaccgacg atgtgattga agctgccgcc agcaccctgg tactcggccg ctgaccaggt    7740
cagtacgaca catagtgatc aaaaagcag gccacatagc gatcacattc acagcggatc    7800
acacgacata ccgccaaccg gtgcaaaaac gatcgttttt gagacgcacc gcgagagcgg    7860
agccgttagc cgctcccgga gcgtccacaa cgcgtctcaa aaccggtcgt gtcgcaccct    7920
ggttttacgc ccggggcagtc tgcttatgtg tgataaagaa gcaatagaag tgcaaaaaat    7980
tttgccgttc ctatccgaca cttggccatt gtgtcggata ggtcgggcgg ttattcgggc    8040
aagtcaatct tgccgacaaa gctgtaataa atctcaatgt cctgcctgcg ggtgccgttc    8100
tcatcatagc tgcactcatg caccacaatt ttctcgatca tttccgcaa gagagtgggg    8160
gtcagttctt caaaggcaag gtgcttgcgg acaatgccca taaatttctc ggcgttgacg    8220
gtagttgcct gtgacttgtc cagttcggct tgcagggcgg cggctctctt tttcagctcc    8280
gcttgctcgg cttcgtagtc agccgacagt tccatgaaac gctcatcgct gattttgccg    8340
tttacattgt cctcatacag ccgcttgata atgcggctga tttcagaaat gcgttcctgc    8400
gcctgttcaa gctgcttgat ggctgcggcg gtctttcgct tgccgccgat ctcgttctgc    8460
tggacaaaat gtaatccgca ggattaggag ataagaagttc cgttactttg ggacgcacta    8520
cctctctgtg aaattcatta gattcgtcac ccattgcatt atcccaaaat tgtgcgttct    8580
cctcccagat tttttactt tcctctgttc ccatgttctc tcccactccc caaatttgct    8640
tttttgcttc cattaaatct tccttactat attccattgt tacctccat aacttctgat    8700
tgttgccgtc ttgacgatta tgtatcttta cattaccttc tgaaacatat ggcgcacctt    8760
gtccaggcgg ctgtttggac ggcggggctg atgaccggc tgaccgacag cggcctgata    8820
tcctttcagc tctgtaaggc atacgctccg cccgttggtg taaaaggcca gatcagtacg    8880
gtatgcctgt atacagcggg cgggaatctc gccagtaaag acaacttcat cctttttac    8940
ctgggccgtt tcgatggtgg cacagtattt cggtgcatca tgataagcc tggaaaggta    9000
ttcctggggc gcatagagga tgaaggagag ataaggttcc agcagctgcg tccccgattc    9060
cttcaatgcc tgttccaata caatcggggc caatgagcgg aagtccgccg gcgtgctgac    9120
cggactgtaa taaagcccgt attcaaagca aatcttacag tccgttacgt tccagccgaa    9180
caagccctgc tccagccgt aacggatacc atccctgaca gcgttttgaa aactctggtt    9240
caagtatccc agcgctctcgta ttgtacaccg gagccaagcg agagtggttg    9300
aacagacagt cctatggatg cccaaaacgg gttgggcggc acctcgatat ggatggtgtg    9360
gctggctgct ttgagcggcc gctccatata aatgacggag ggttcccttta ccactgtttc    9420
aagcttgtat ttttccgaca gcaaagcgga aacaacctcc aactgcaccc ggcccaaaaa    9480
agaaagaatg atctcatggg tgatggaatc cacttcgcaa cgcaaaagcg ggtcagtatc    9540
tcgcaagttgc gtaagacgt ccagcagcgt ttctcttttgc gctgccgttt tcggcgcaat    9600
cgtcgtccgc agcatgggga gggggtcctc gcgccacctt ttacgaggga gccgggtttg    9660
gtccctaat acatcgttta acctcacgct gtcgctggga aggataacaa tttcaccctg    9720
ataagcggtg tctgtccgaa caatttcccc tttggatgga atacgcatct ctgtgatttt    9780
cagcttttct ctcccggcca gggccaccgt atcccgcagg cgcagcgttc cgctgtataa    9840
ccgtagatag acacgccgct ggccgcaatc ggtgtactca accttgaaaa cgctgccgca    9900
```

```
tagggcggcg ccccccctgtt ccccaatcgg ttggaacagc cctgtcaccg catccatcaa   9960
cggttgaatg ccaaggccat ttttggcgct gccatgatag actgggaaca gggaggcgtc  10020
ttgaacccgc tgctgttcct cccgcgcaag ttttcccgg ctgattggtt ctcctgcgat   10080
atacttttcc aataattcat cgttattttc gatgaccgca tcccatgctt ctatgtcggt  10140
attttcctcc aggactattt ccggggacag cgacaccgtc tgcttgatga taatatcggc  10200
ggagagctta tcccgaacag actgaaccac gctctgcaaa tcaacgccag cctggtcgat  10260
cttgttgata aagataacgg tgggaatgtt cattttccgc agggcatgga acagaatacg  10320
ggtctgggcc tgcacgccat ctttagcgga gatcaccaag atggcccat  ctaaaacagc   10380
caaagagcgg tacacctccg ccaaaaaatc catgtggccg ggcgtatcca caatgttaac  10440
tttacatctg tgccactgga aggaagtgac tgccgcttga atggtaatcc cacgctgccg  10500
ctccaaaaac atggtgtccg tcctcgttgt ccctttttcg acgctccccg gttctgaaat  10560
ggctccgctg gcatatagca ggctctccgt caaggtcgtc tttccagcgt ctacatgggc  10620
aagaattcca atattgatta ttttcatgtg attgtcctcc ctttacagcc caaagggca   10680
taaaaatccc cagcagtaaa atactttac cactgggagt tataagttgc ggacatacac  10740
atatacagca tacacctgtt tgtgattgct gttttttgggg atatgtcaaa attgataagg  10800
caaaagtatt cttaaattgg gtacaaaaaa ctaagcccct acaaaaggag ctatcataat  10860
cctttgttcc cactatttga ttatagttttt atttaagaat accttgccgc atattttta   10920
ctccttttct ggattaaatc attgtatcac atcagtttta ggaaagcaag tacctaaaag  10980
aaatttttct tccccttata tgtaacaatc ataccggctt cctagcgttc agaatgtttt  11040
ctgctgtctg ctgtggtgtt tggttggaat tgtccaacca aaagccgatc cgtggtgttg  11100
tctgcatttt actaaataca aattcaatgt atacagaaag atataaggag tgggagggat  11160
tccgccgtag ttggcattgt aggaaaatcc aaaagtttag attttcccac aatgcttatc  11220
ttttggtctt tggttcggaa tagtgtagtg ctgccggtct atctcttgtt ttcgttgct   11280
tgcttcctta ccgtacatga gcattcgcgc agtgcattcc cgaccacgtc cggcacggca  11340
cctcgaccgt ctgcgccgcg ctgaacattg cgaccgctt  cgacaaactc gccatcacgt  11400
accgcgccgg cgtcaccctc tgcgccatcc tcacctggct ccgactattg ggagacacga  11460
cctaggagaa gaccggctcc cacatccgct accgcttcgt ggggaggccgt ggccggctc   11520
ccgccgggca tgaagaaggg tccgctgaag gtttggttga cctcctacgg cagcagctca  11580
gccagttctc gcagctgctc aaggatccgc tcggcctggt cgggagcgac attcttgtcc  11640
agctgcttga gctgacgctg catcttctcg atgactgcgt cggaaccagc ggactcgctg  11700
tggagcttca ggaagtgtac ccaagcacgc gtctcgatac cgaggatggg cacacgcatc  11760
gtcgactcaa cgaacgaatc catgaggggg cgacaccgag gcagtcgtcc gaagttgcca  11820
ccgccatcgt tcaccggatg caccgtcacg cggtcagcct tcgacgggta cggcgtcgcg  11880
tcggccgggt actccagctc cgcactgcca tcggtctcct tgatgttggt ccaccagtag  11940
tgcgccact  cggcggcgta cttggcggac tcgacccacg gctcggccac caccggcacg  12000
ccgctgacgg cgctgtcgag gtgccacggc acgcagcaca ccaggtccca gtcggtgcag  12060
gcatcggggg agacctggta ccgcagcgaa gggaccttct ccttggccag catccaccag  12120
cccttgagct cgatgccgat cgcgatgggc tcaccctcgg ttccacgatt caccagacgc  12180
acgtcgggaa aggcctcgc  cgaccgctcg aaccggtagg tcgaccactc ggagtccggg  12240
tcccagatct gccgaaggct gttcagcgtg cgcacgacct ccagctcgat gcccgagccc  12300
aagaagctgt tgaggctgaa caggtcgtg  gcgttgaccc cgctgatctc gttcttcgac  12360
tcgaactcgc ccggaagggc ttggagggcc gcggagaccc ccttctggag cttggtatgc  12420
ggatcgttgg gatccagcac cgggcgggca ggacccgac  ccacctgggc gctcgtcgc   12480
actgcatcaa ccgacattgc tctcctcctc ggggttggcg tcgaagaggg ccacgagctc  12540
gtcgttggtc tcggcctcct cggcggcgac gtcaagccgc tcgtgcgcaa gctccgcgaa  12600
gtaggggtca cgctcggcaa ggaaagcctg ccgacgcagg gccaccgcag ccacggagcc  12660
cgtgccaagc ccgccgaagg gctcccctac gacgtcgccc tccttcgtga cggcgtgcac  12720
caggcgctcc atgagctcca gtggcttctg gttcagatgg gtcgtgctgg ccttcgtggg  12780
cttgtacacg cgccggcgccg accgacgcat cgagcccttc atacgctcgc cgtcgtgcag  12840
cggggggcgg ctccacacgt tggtcaggcc atggacgtgg tgccactggt ggcgcatccg  12900
gtcccaagc  ttcgcggtga ccgacgtcac accgtcgagc gagaagtacg ggcggccgct  12960
ctccaggccg tgctgattgc agtacgcggc catggcggcc acggcgactc ccggcggcca  13020
gtaccagagc cagtcgttcg tcaggtactt cgcgtggcg  gcgttcttca cgccgcaggc  13080
ctcattggcc aggtacatcg gcagaccaga gcggcgccac tcgtgccgca gccactgctg  13140
ggcatcgaga atgcccgcgt cggtcgccgc ctcgaagcgg cgctggtaga ggacgcagac  13200
ctccgtgacg acggggaagc ggcggatggt gttgccgttg acgttgcccg cgatgtggct  13260
cagacccttg tccagacca  cggtctggac gtagtcccag ccctgacgct tcaactcagg  13320
atgcaccgtg gcccagccca cctccgtacc ccagaaccac agcgccgtgc ccggggcggc  13380
agccttcgtc cactgctcga tgtgcggggc gtaccagtca ggagccctt  cctcgtcggt  13440
ggtgtccccg taaaaaccgc ggacgccgta ggcgccgtcg ctgatgatgc acgtcggcga  13500
cggccaggac gcgtaggcgt ccgccacatc ccccacgtgc aggtcgtagg gcctcttctt  13560
ctcggccatg ctcccagcct tcataatcg  atggttactg gtcattcgcc cggtccaggt  13620
acgtcaggcc ggcgcggcgt agcgcgtcgg ccggcgtgcc gccgctccag tcgggggcgg  13680
tcccggtcat cggcagggc  gtggccgacc gggctgttgtt ctccagctcg tcggccagtt  13740
cgtcccactc gggcacgtcg aggacctggt tgaccgagac ctcgacgacg acgctcaccc  13800
cgcgctcggc cagcagccgg cccacggtct ccttgtacgac ctcggcgtag tcggcctggt  13860
cctgctccca ccgggcctct acagcgtcag cggcgcgccg cgcctcgatg agggtggccg  13920
ccagcggatg ggcactctcg gctgctcgct cctccacgtc cttgatgatc tttccggcct  13980
cctcatacat cgccggtcac ccggtcgggt cactgtccca cactgtccca ccgagctggg  14040
gcatgtcggc ctgagcgcg  gccagccggt cgcgctcctc ggccgtggcc acggcctccc  14100
agagtgcatc ggccgccgcg tcgacgcggc ggccgagttc ttcggccgcg tcctcgtaga  14160
gctggtagag cccgaagtcc tcgaagacgg cctccacgtc gagcgcgagg cgcaccggct  14220
cggtgcgcca ggcagcagg  tccgatcat cggtgccggc tgtccctcg acgacctggc  14280
ggatgagggc ggctcccac gatccggcgcc ggccggccga ggcggccgca cggccggcga  14340
tgttcgcggc cacggccgtg agcacgtggc acgcgatccc cgcgaagtcg tccggctccg  14400
tgtgctcgct tggggtgccc gctccgacga cgcgacgccg gcgcgccgcg tcggtcaggg  14460
ccgtgatcgc ctgggcgatc gggtccggga ctgtctcggt catgtctggc ccttcagtg   14520
ggtggtgatg ccgggcttgg ggcctggcgt cacggcgtcg aggtcgggga acgggcggcc  14580
gtcgttgtac tcggcttcca gccgggcgac tttctcgttg acggcttctt ggacgaactg  14640
```

```
ccagtagggg cggatgccga gcttcgcctg cgtgtagaac cacgctcccc tggcacgccg   14700
gccttcctcg atggtgtgct tgaagctggt gcgcgtccat ccttcgccgg tcccggtctt   14760
tttcgcggcc tcgtgccggg cctcgtcaac gttgggcggc tgcgccgcct cgacggcctg   14820
gggcacgagg gggttgctca ggttggtggt gcgccgctcg ggccgcttgc tcatttgatc   14880
gctcctttag tgatggtgtc gaggtgctgg cggtagaggt cggccagctc ggcggcgtcc   14940
ttgccgcccc actggtccag gccggtggca gcctccagcg cgtcggcgat gacggcgcgc   15000
ttcgggatgg gcggatcaag gatggtcagg ccctcgatct tctccaggtc ttccagagcg   15060
cttcgcgcgc cgatggtttg cgcctcgtac tggttgacga tcaccccggc cacggccaac   15120
tgcgggttgt agtacttgcg cacgatggcg atcgtctgaa gcagccgacc gagcccggcg   15180
atcgagtaga ccttggcctg ggtgacgatg gccacccgct cggcggccac taggccgttg   15240
agggtgaggt gatccagcga tggcgggcag tcgatgagca ccaggtcgta gcggtccgcg   15300
acgctggcca cggcctcgct cagccggtgc tcgacgccgg gggtctgcgt ggtcagcagt   15360
tcgttgcgaa cgctggtcag cgcctcgttg gcggcgtcg gggccacgtc gaggccatcc   15420
cacacgccgg ggacgatgac gctctccagc gtctcggtac tgcgttcact cagcgcgtcg   15480
gccacgccga cgtcctcggg cgtgggcgtg tctttcgcgg ccgacatgct ggcgttaccc   15540
tgcgggtcga ggtcgatcag gagggtccgc cggccctcgg tgacggcggc gcgcgcgaag   15600
ttgacggcgg tggtcgtctt cccgacaccg cccttctggt tgctgattgc gagggtcatg   15660
ctcatgctgt tggttccgtt cgtcgattg gtgcggttcg tggtgttagt gccattcgtt   15720
ctgttcgcac taactagtgt agtcgcttcc cgcctcgctg tcacggcgtc gaggacagtc   15780
gggagatcaa gtccgccgg aggccggcgc accgtggggg ctccggccgg acttgttctc   15840
actgttcatt ctattcgttc ctttcgttct aatggtgcga atcgcaccat tagaactagt   15900
cggtgatggc ttcgatgatc cggtgcgcgg cggccagcac ggcgtgggcg ctcttgcgga   15960
tgaggtcggc gtctcccttg gaccatccgg cgacgtagcc gacgctgtag cgcgtggtgt   16020
cgagtccaac gatgccggcg accacgtggg cgacgctttc ggcctcgacc tcgcattgtc   16080
cccggtgctc gtggtactcg gtgggggtga tgtcggcgtg catgagcgcg tgggcggcct   16140
cgtgaagggt cgtcttggcg gcttgggcgg gggagatatc ggccgcgatc acgattcgct   16200
tgtcgtcgtg gctggtgtag ccgttgagtc cggccccgag ctggtcgtgc tcgatggtcc   16260
agccctggcc ggtgagccag tcggtcacgg cctcggcgat gccggcgggg tcgtcgccgc   16320
tgagctggtg ggcgtcggcg gggttctcgg ggatcggctc ggctccctcg atggggtcgg   16380
tctggggcgag gtcgaaagacg gacacgggga agaatcggct gcggcgtcgc tcggtctcct   16440
ctccggtggt ctcgtcctcg atcgtttcgg tgacctcgcg gccgccaag attctgattc   16500
cgcgctcacc tttgcggacc tgccggccga gcttctgcca ggtgcggtac cccgcgacct   16560
gcgtcgcgtt ctcgcgctgg gcgaggatca ggagcaagtt gttcaggctg tagcggtgga   16620
acttcccggc gaaggcgagg aactgggccc atgcttccga ggtggccagg gcctcaacct   16680
gctgggcgat ggtctcgtgc agttcggtcg gcgcgtgctcg gcggtcttgt   16740
gggtcttgat cttccgggcc atgatgttgg ttccttcgt gtgattggtg cggttcgtgc   16800
gaactgcctg tcttccctca cgttttttttg ccattgaagg cactgaagt gccgccaggg   16860
agggagcccg gagtgcaagg gaccgtgaa taccggactg agcgcagcga gggaggatat   16920
gccgcgaaag cccttgcgcg tagggcggac gaccgtatgc tgccgaaggc ttcaatggca   16980
aaaacgtgcg ccgtaggcgc atgctgccgg ccgcgcagcg gccgtccta tgatgacggt   17040
ccgccagggc cgcctgggga gggtcggcct ggggggccggc tcgttgtggt cggctgtcca   17100
cctgtgggcg ggccagccgg tcgggagctg ggccgtccac aggtgcgtca ggcggtcccc   17160
tctacggagc ggccctgtgg ggcgttctgc gggcgtatgc ccccttccgc gtcgtggttg   17220
ctgggtgggg ttgagttcgg ccgtttcggg gcgttgtatg gcgtcgtttt tcgtggtcga   17280
tcatggctgc cgcctgtgga cggcccttcg gcccgcccac agttgccttc gaaaccgggt   17340
ggccgggttc cggcgtggtt gggacgaggg ttgcccccgg cggtcaggcg gcagtgacga   17400
ggctcgatgg aaggtggtcg agtgctccgg cggcgatcgc ttcgcgggcg gctcgatggt   17460
cagcgcggcc gtctggtcgg cgcgggtagg gggggtagat gtcccagggt cggccgaacg   17520
tgagcgcaat ctgtcccgtg ggctggtggc gtcgtttgtg gcggcctggt gtggtcatcc   17580
attccagttc ggcctgccac cattcccaca gatcgcgctc ggccttgtag cggccttctc   17640
gtgcgtcgag acgcccctcg acgccgagcc gtcgggccgc gaggtcgcgc agctcgggg   17700
gggttcgccg ccagccggtg ggcgtggcca cgatgagacc ggcgtaggcg agtcggtcga   17760
gtagggggt gatctccgta gtggtggacct gggggtgatt gagcctggcg tagaggtttc   17820
ctgccggcgag gcccagggcg tgggggttgg tgaaggtgtc gtggcgggcg aggtctaggc   17880
ggtgggtgag ttcgtccagg aggaggtttc tccatccggct gcccgccct gcggggcgtg   17940
cagcccccttg tgaccgggca tggtctgcat ccatgtggat agcggtctgg ggctcgattg   18000
tccaggtggt ggcgtgcctg ccggtgcccg cctgggcctg gctgatccac ccgtcgccgg   18060
ccaggcgcag gagggcggtg cggcggtct tcggccgat gccggcgagc agggcgaggc   18120
ggcgcacgtc tgcttcgacg gctgcgctga cggcttggag ggcgagcagg cacagggcgt   18180
cgagcacgcg ccggtcggcc ggcctcctc cgcgtgtcca ggcccctggt gccgcatcgg   18240
cgcggcgctg cacctggtcg acggtggcgg cgatcgcttc ggctcggggg tcgaaggtgg   18300
gatcgtcgcc tgcctggcgc gcgtgggtgg ccacgaacct gacggcggcc tgccacactc   18360
ggccgagcgc ggcttcgctg ctttgggctc cgtgtgtggg gcgcgcctgg cgtgcacggc   18420
ctccgtgcg tgccgcgtag tgcggggcgt gctccatgcc gggtgccgtg gacacgaggg   18480
cggccgcgtc gcggtagtgc cagtgggcgg cggctgcacc gagcaggatc acgtagagga   18540
cgcgggaggc gtcctcactg gcggcggcgt tttgtcgac ggcagcgcgg ctcttggcgg   18600
gcatggcacg gcgggggtccg ggcagccacg gccgcccgtc ctcgtcgacg gcacgcgca   18660
gctcggctgc gtggggagc gaggtcaccg tggccacgtc gccgaactcc tcattgagtc   18720
gggtcgccag ggccacgagc tgggctggtg tggtggtgag gtggcgagat   18780
ttccggcgat cacgcgggat gctccaccgt ggcggtgggg cgtgccgggg gggcgcaagc   18840
atccggtggt cgggttgagc aggggagtgg ggtccaggct ggtggcgaga ccctggaggg   18900
agtgcgtcag gtggtgcacg agctgcgggt cggccgtctc ggccagggcg atccacacgt   18960
ggcggccgcc ggtggggccg gactcgcaga tgacgtgctc gatgccggcc tggtcgagca   19020
ccgatcgcgat cgccgtggca tcccgctctg cttgggcggc ggcggggcgg   19080
ggtcgaggcg gatgtagcgg tagcggcgct gcgcgtccgt caggtacatg gcccacgggc   19140
cggccgggc cggcccgcg acgggcacct cgtcgggta ggcgttcacc tggtcgccgc   19200
tggcggcgcg cacctgcggg cgcgggctca acgtgcgtgt gagacgccac gccgcgccga   19260
tatgcgtagc gtcacggtta tcggcatctg ttgctatcat gtacgtgttc cttccgggga   19320
aagacgcaac gatccctcct tcggttggtg ggcccctgcc aagggcccta ggtgtttggg   19380
```

-continued

```
tgttgcatcg ggtgccgact gccaaaccgg cttccgtact tggttcgctt gatctggttg    19440
tgttggggaa ctcagcagat caggcgctta ctcttctgac ccccgccctg ccaagggcgg    19500
gggtctgttc atgtctatgc ggtgcccgta gggtcctcct cgatgctcag ttccggttgg    19560
gtgctatctg gggttggaag ctcccatccc tgtggccagc cgtccgggcc tgggacacca    19620
gagcggatcg cagcttcaag gactgcccac tgggggcgca ccttggcgcg cgcgtaggcg    19680
tcgagcttgg ccttgacgtc cggcgcaacg aagatgtgaa gcgctacggt aggcgctcca    19740
cggtcgcgac ggaatcggct ggtcatgaca gtcatcatat aagggcggct gtacatgtac    19800
acgggccgac acgccggcgt gtcgcgactt cttttcagat atcagagtcc tcgggcgacg    19860
gcggcggctg cgcgcagcca tgcgcgttgt gtgctggggc gcaggctgtc ccattggagg    19920
atgccgtcca cgatggcggg gtcgtggggg atcgtgacga cttcgcgggc gaggtcctgg    19980
tagccggtga cgatgttggt gatgtcggtc ttgctggcgc gcgggtcggc ttgggtgacc    20040
acggcgacgg cgttgtccgc gagctggcgt gagtgttggt cgcggccgcg cagcgcgtcg    20100
aggaggagcg cgccggcttc ggcgtggtct gcgcgggtgg tggtgggcac gacgatctgg    20160
tcggcgtgtt cgatggcttc cagccacaca ggatcggatt cgtcgttgcc ggtgtcgatg    20220
aagatgaggc ggtagtactt gccgacgacg ttccagatga ggtcgacgtc gtgagggtg    20280
acgcgctggt cggcggcgag ctggatgggc tggctgcgca gcacgtcgaa ccggtcggcg    20340
gtctggtggt gaacgtagtg cgccagatcg gccgactggg ctccggtgcc caacagtcgt    20400
tcggtttggg gaaggaggtc gaggacggtg gcctcgtggg gtccctgttc ggtccgccat    20460
cccaggggtgc ccctggttgt gttggcgtcc caggcgacca cgcccgcgcc gccataacgc    20520
gcgaacacag cactgagtag caccgtggtg ggggttttgc ctgccccgcc cttcccgttg    20580
gccacgatga tcgtcctggg gccgggccag tgctgggaga cggcgtgcac gtcgtcccgt    20640
tccgcgcgct cctgctggct cgggttcatg cgcagcccga gccggtggc aacgccgcc    20700
cagccctgcg tggcgggctg ctcgatctcg gtgctttga ggaatgaatg gcggctctgg    20760
acctcgcgcc tgctgggcag gtgcgcgatg gggctgtcgg ccgagcgtgg gagagtgtgt    20820
gcctgggtgt gagggctgtc ctggcgtggg gttgggctgt catagaccgg ggccgccgtg    20880
gcggccgcgg cctcggcggg atcgtggagt tcgccgtggg gggtgacgat gacggtccac    20940
acgccgtcgg ggtcggaggc ggtgagcgtg gcgctttcgg cggcggtggc tgcgcgctcc    21000
tgggcgatcg cgacgacctg ggcgcgggcg tcttcgaggc tggtggcggt gatcttctgc    21060
ggcgtgccgt cgatcgtgac gatggcgctg ccgtcgcggg ctgtggtggc ctctatgtcc    21120
atgggggatgc tccttcgttc agctttgggt ggcctgggtc tgcatggcgtc tgatcgccca    21180
ctggccgttc tcttgggtcg cggtgaccca tgcgtcccag gccacgtcgt cggggcgtc    21240
tgagccgtct cggggcgtgg tcttgacgag gtagtggacg atccggtgcg cgtcgccgtc    21300
ttggtcgggg tcgagtcctt cctcgacaat ctcgcggatg tgacggtgg tgtaggagtc    21360
atgctgcgcg ggctgtgtga actgggcctg gcccttcgcg gtgtcggggt cgtagtcggc    21420
ggccgcttgg cgtagcgcgt cggttaggta gatcgcccgc cgttgggtcg gctaggcgct    21480
ggtcttgtcg accgtggtgt cccaggtggc ggccgtggcc acgtaggcgc ggatgacggc    21540
ctcggggtcg gtgcggtcga cggtgctggg gttgggcagg tcggcgagcc aggtgggctt    21600
gcccccgggg atgggtgtgc cgtcgggtgc ctgcccgatt gtggggctgg tcgtggccgg    21660
cgtgctgtg gcgctcgtct gatccggtgc cgggggtgtcg ttggctgtcg tgtggccgca    21720
gccggtgatg gcgggccagag tgatggtgcc gatgacgagg gcgcggcac gccggtgggt    21780
gcgcctcatt ggattctcct gtagttgctc ggtgagccgt agatgggctc gaagttgatg    21840
ccatcaatgt ggttgtcggc gctgaccatc cagccgttgc cggcgtagat ggcgacgtgg    21900
taggccggcg tgccgtagaa gatgaggtcg ccgaccctga gttcgccgcg ctcgatgccg    21960
gtgccgacct gctgctgctg ggcggctgtg cggggcaggc tgatgccgag gcggcggtag    22020
acggcgctgg tgagcccgga gcagtc                                          22046
```

```
SEQ ID NO: 50         moltype = DNA   length = 1615
FEATURE               Location/Qualifiers
misc_feature          1..1615
                      note = pBC1
source                1..1615
                      mol_type = other DNA
                      organism = synthetic construct
SEQUENCE: 50
ccccgatggt ttttcccccg acggctcgcc tttgggaagt ttgaagggcg caggttccac      60
acgaaaaacc acaaggcttt ttttgagtaa taaaaaagcg gacggcgagg gcgtgaaaaa     120
aacccgatga acccttgaaa ataaagggcg ggacggggttt tttcttatct tgataatata    180
tagaaacaat gagattttaa aaaaagcct caaacccttg ataatactgg gtttgtggcg     240
ttttttggg gtgataaat aaaaaccctc tgtgttatgg ttatgttgac tagacaaaac      300
catacagagg gctttacgcc tttctgtatc cagaaaggga ttattaaatt ttatgcacgt    360
taatcatagc attaaaacgt caaatctatc aaatatcgaa ttttttgcaag ataaaacgaa    420
aacaggaaaa gagagagatt ggaaaggcaa gaaacaacgg tctttgctga cagcggaaca    480
cttcgaggta gcagggctga ctagcaaagc ggaacagtgc gagagtgtgc tgacacgttg    540
gtgtttaagc gaactgccga agggttaaaa ctatatcaag catggttctg taaagtgagg    600
ttatgcccga tgtgcaattg gcgaagatcg ctgaaaatag cttaccagaa taaaagggtg    660
gtagaggcgg ttaatcaacg tgagaacgtt cagtggctat tcctaaccct taccgtccgc    720
aacacgagcc ctgagagcct tccagagacg atttcagcca tgtttgaggg gtttaatagg    780
ctgacgaagt acaaagcctt taaaacgtct gtaaaggggct attttagggc tttagaggtc    840
acaaagaata gagaccctca tagtgaatgg tttggcaggt atcaccctca ttttcacgtt    900
ctgctgtgtg ttccatccag ctatttcaag aaaaaagaat tatacataac cgaacaagaa    960
tggactgacc tttggaaaaa ggctatgaag ttggattaca cgccgattgt ccacgtgcaa   1020
agggtaaaac ccaagaaca gcttgaggac atggaaacct atgaagaaca gcttaaaaac   1080
gccattaggg aacaaaatgc gatttttgaa gtctctaaat atccggtcaa agatacggac   1140
gtcattaaag ggaataaggt cacggccgaa aatgtggaaa ccgtttttgc gttagacaac   1200
gccttggcaa ataagcggtt aatcgggtat ggcggtctttt tgaaacaggt tcacaaggaa   1260
ttaaaccttg gagatccgga agatggagat ttagttcatg tttcggaaga ggatgaaatc   1320
gctaatggtc catttgaggt catggcgaaa tggcatatcg gttttagaga ttattggatt   1380
caaaaatagc aggagagaaa actcctgctt ttttattttt tccgaagtta ttggcgaaag   1440
caaacttttt atcgagcgaa gcgaacccta ttgaatacct gcatggcaag gtatgtaaat   1500
```

```
gggcactctg tgattttttgg atacaaaata gactctagcg agccgatttt atgacgcagc    1560
aaaaaacgta gtcttttttgc gttggagagc ccttcaagta aactgaccaa ggtgg         1615
```

| SEQ ID NO: 51 | moltype = DNA   length = 1854 |
|---|---|
| FEATURE | Location/Qualifiers |
| misc_feature | 1..1854 |
| | note = pEP2 |
| source | 1..1854 |
| | mol_type = other DNA |
| | organism = synthetic construct |

SEQUENCE: 51
```
atggtaaatc tgcgcagaca gccctgtgca gctgaaacgc ggttacgtat agcttgccat      60
atgtctagcc atacgtaacc gcaggtaaaa ggcatatttt tcgcgtgtca tggctagtaa    120
ataacaccgg tgtcatttag agtcagggaa agacaatgaa agccaccggg agccaccggg    180
cggcaacccg atgactttcg cttatcaccc agcacacacc tgggagaaat cacggtcatg    240
agtttacaga ctcatgcgca gaatgcgcac actaaaacac ctacccgcgt cgagcgcgac    300
cgtggtggac tggacaacac cccagcatct gccagtgacc gcgaccttt  acgcgatcat    360
ctaggccgcg atgtactcca cggttcagtc acacgagact ttaaaaagcg ctatcgacgc    420
aacgctgacg gcacgaactc gccgcgtatg tatcgcttcg agactgatgc tttaggacgg    480
tgcgagtacg ccatgctcac caccaagcag tacgccgccg tcctggtcgt agacgttgac    540
caagtaggta ccgcaggcgg tgaccccgca gacttaaacc cgtacgtccg cgacgtggtg    600
cgctcactga ttactcatag cgtcgggcca gcctgggtgg gtattaaccc aactaacggc    660
aaagcccagt tcatatggct tattgaccct gtctacgctg accgtaacgg taaatctcgcg    720
cagatgaagc ttcttgcagc aaccacgcgt gtgctgggtg agcttttaga ccatgacccg    780
cacttttccc accgctttag ccgcaacccg ttctacacag gcaaagcccc taccgcttat    840
cgttggtata ggcagcacaa ccgggtgatg cgccttgaga acttgataaa gcaggtaagg    900
gatatggcag acacgaccca gttcaacccc accccacgcc agcaattcag ctctggccga    960
gaacttatca acgcggtcaa gacccgccgt gaagaagccc aagcattcaa agcactcgcc   1020
caggacgtag acgcggaaat cgccggtggt ctcgaccagt atgacccgga acttatcgac   1080
ggtgtgcgtg tgctctggat tgtccaagga accgacgacgc gcgacgaaac agccttttaga   1140
catgcgctta agactggcca ccgcttgcgc cagcaaggcc aacgcctgac agacgcagca   1200
atcatcgacg cctatgagca cgcctacaac gtcgcacaca cccacggcgg tgcaggccgc   1260
gacaacgaga tgccacccat gcgcgaccgc caaaccatgg caaggcgcgt gcgcgggtat   1320
gtcgcccaat ccaagagcga gacctacagc ggctctaacg aacaggtaa  agccaccagc   1380
agcgagcgga aagccttggc cacgatggga cgcagaggcg gacaaaaagc cgcacaacgc   1440
tggaaaacag accccgaggg caaatatgcg caagcacaaa ggtcgaagct tgaaaagacg   1500
caccgtaaga aaaaggctca aggacgatct acgaagtccc gtattagcca aatggtgaac   1560
gatcagtatt tccagacagg gacagttccc acgtgggctg aaataggggc agaggtagga   1620
gtctctcgcg ccacggttgc taggcatgtc gcggagctaa agaagacggg tgactatccg   1680
gacgtttaag gggtctcata ccgtaagcaa tatacggttc ccctgccgtt aggcagttag   1740
ataaaacctc acttgaagaa aaccttgagg ggcagggcag cttatatgct tcaaagcatg   1800
acttcctctg ttctcctaga cctcgcaacc ctccgccata acctcaccga attc          1854
```

| SEQ ID NO: 52 | moltype = DNA   length = 2178 |
|---|---|
| FEATURE | Location/Qualifiers |
| misc_feature | 1..2178 |
| | note = pWV01 |
| source | 1..2178 |
| | mol_type = other DNA |
| | organism = synthetic construct |

SEQUENCE: 52
```
cgatttttta ttaaaacgtc tcaaaatcgt ttctgagacg ttttagcgtt tatttcgttt      60
agttatcggc ataatcgtta aaacaggcgt tatcgtagcg taaaagccct tgagcgtagc    120
gtggctttgc agcgaagatg ttgtctgtta gattatgaaa gccgatgact gaatgaaata    180
ataagcgcag cgcccttcta tttcggttgg aggaggctca agggagtatg agggaatgaa    240
attccctcat gggtttgatt ttaaaaattg cttgcaattt tgccgagcgg tagcgctgga    300
aaatttttga aaaaaattg  gaatttggaa aaaaatgggg ggaaggaag  cgaattttgc    360
ttccgtacta cgaccccca  ttaagtgccg agtgccaatt tttgtgccaa aaacgctcta    420
tcccaactgg ctcaagggtt taagggggttt tcaatcgcc aacgaatcgc caacgttttc    480
gccaacgttt tttataaatc tatatttaag tagcttttatt gttgttttta tgattacaaa    540
gtgatacact aactttataa aattatttga ttggagtttt ttaaatggtg atttcagaat    600
cgaaaaaaag agttatgatt tctctgacaa aagagcaaga taaaaaatta acagatatgg    660
cgaaacaaaa aggttttttca aaatctgcgg ttgcggcgtt agctatagaa gaatatgcaa    720
gaaaggaatc agaacaaaaa aaataagcga agctcgcgtt tttagaagg  atacgagttt    780
tcgctacttg tttttgataa ggtaattata tcatggctat taaaaatact aaagctagaa    840
attttggatt tttattatat cctgactcaa ttccctaatga ttggaaagaa aaattagaga    900
gtttgggcgt atctatggct gtcagtcctt tacacgatat ggacgaaaaa aaagataaag    960
atacatggaa tagtagtgat gttatacgaa atggaaagca ctaaaaaaaa ccacactatc   1020
acgttatata tattgcacga aatcctgtaa caatagaaca cgttaggaac aagattaagc   1080
gaaaattggg gaatagttca gttgctcatg ttgagatact tgattatatc aaaggttcat   1140
atgaatatttt gactcatgaa tcaaaggacg ctattgctaa gaataaacat atatacgaca   1200
aaaaagatat tttgaacatt aatgattttg atattgaccg ctatataaca cttgatgaaa   1260
gccaaaaag  agaattgaag aatttacttt tagatatagt ggatgactat aatttggtaa   1320
ataacaaaaa tttaatggct tttattcgcc ttaggggagc ggagtttgga attttaaata   1380
cgaatgatgt aaaagatatt gttttcaacaa actctagcgc ctttagatta tggtttgagg   1440
gcaattatca gtgtggatat agagcaagtt atgcaaaggt tctgatgct  gaaacggggg   1500
aaataaaatg acaaacaaag aaaaagagtt atttgctgaa aatgaggaat aaaaaaaga   1560
aattaaggac ttaaaagagc gtattgaaag atacagagaa atggaagttg aattaagtac   1620
aacaatagat ttattgagag gagggattat tgaataaata aaagccccct gacgaaagtc   1680
```

```
gaaggggggtt tttattttgg tttgatgttg cgattaatag caatacaatt gcaataaaca   1740
aaatgatcga tgctgtttgg caaaaaaga aaaagtgatt aatttatatt ttatttatgg    1800
cgctaattta ttacggcttt ttttgttgtc ggctagccga ttctgataca tttttttaag   1860
cacaaaaacc acccaatttt ggagtggtgt gtaagtgcgc attgtcatga aaaaatggca   1920
cgcaatttca tcacttttta aagtgatgtg taagtgcgca ttgtcatgaa aaaatggcac   1980
gcaatttcat cacttttaa agtgatgtgt aagtgcgcat tgttcgaaaa atcgaactat   2040
gatttatttt tgctgttgta tttattttc atcttttggg ttttggtttt gtttttgtt   2100
gctatcgtag tttatttgct ttttaagggc tctattttc gttctacggc atttttataa   2160
tttgccaata taatttat                                                 2178
```

SEQ ID NO: 53        moltype = DNA   length = 2439
FEATURE              Location/Qualifiers
misc_feature         1..2439
                     note = pAP1
source               1..2439
                     mol_type = other DNA
                     organism = synthetic construct
SEQUENCE: 53
```
aacaagggtt gttcgcgggg acaaaactag ccccaagctc gcgtttccgc gaacaatccg    60
cgttagtacc ttgacgcggc tttacccagc gcgcctacgc gccgagattt cgcagttcct   120
gcatacttta accagacagt tttaacacta cgagacaaga aagcgccccc ggcagtccgg   180
caagactccg agggcaactg gaagattggt ccttcctcta atgaatagat tatctgaaag   240
aacggcgtta agccttccgg ctcgccagat tcaaaaagtt atccccgccg caggcggaag   300
gtcgctgaag tccttcgaag ggatgacggg acgtggtcg gcgcgaggag gagcctccag    360
cgacgaacgc agcagagaca agcgaagcca aatcccttcg aaccggaggg aaggacgctc   420
agcgacccat ccccttggca atacggtatt aacttttcga gtatcaaacg agagcaagaa   480
aacagctaaa tctcgccgtt ctgagagata cgaactcaga gacggattag ccgaaatctc   540
gaccattgag tccgtccgga agtgtggccg cgtgcccgtg gcacctctcg tctcgttgcg   600
agcaaaatct gacggtaaag gcgccggata tggtggtttg cacacttgtg gaagcgtctg   660
ggcgtgccca gtctgtagcg cgaaaatcgc cgctcgccga aaaaccgacc tccaacaggt   720
cgttgaccac gccgtaaaac acggaatgac cgtctcaatg cttacgctca cccagcgtca   780
ccacaaggga caagggctaa acacctctg ggacgccttg tcgacggcat ggaatcgcgt    840
taccctctggt cgtcgttgga ttgagttcaa ggagcaattt ggtttagtcg gttatgttcg   900
agccaatgaa attactcatg gaaagcacgg ctggcatgtg cattcccatg ttctgattat   960
tccgagaaa gacccgctga ccagcacgtt tgtctatcaa cgcaaacaag gacgccgccg   1020
ccttcccctac ccccagaga tttatatgtc atccgatttc attgctgaac ggtgggaagc   1080
tggccttgcg aagcacggcg ttgatttttct ccgcgattcc ggaggcttgg actgaccgt   1140
tgcgaaagac gcgcgagcca tcggcaacta tgtcagcaag atgcagacgt ccacagacgc   1200
gattagctcg gaagtcacgt tgggcggctt caaaaaagcc cgaaacggga acaggacgcc   1260
cttccagata ctcgcggata tccttttcgct cggcgatgtc gacgacctca agctctggaa   1320
agaatatgag aaagcttcgt tcggacgccg tgcacttaca tggtcgaaag ggctcagaga   1380
ttgggcaaat ctcggcgttg aacagtccga cgaagagatt gcctctgagg aaatcgggga   1440
cgaagcaata gcgctattta cgcatgacgc ttggcgtgac gtgcgacgtt tggagccgc   1500
tgaactactc gatgtgaccg aatccggagg tcgtgcggcc gcttaccgct ggttggattt   1560
tagggaaatt gattggtcat tgcctccgaa aatcgagtga agtcgtcaaa ccatactta   1620
agtagaggtc gagaagtccg tggaaaagtc gcggcgcctc tactgcgaaa gtaggtattt   1680
atcgatgttt ttcatcggaa aatatagaac taaattccag cccatcgcgc catgcaaacc   1740
ctccccgatt tttgacggca acggcaaacg cacaggtgaa ttttcttcgg agaagatgcg   1800
gactcaagca atcaccgaag acggccgcct cgtcgagctc acctcgattc ctccccagtt   1860
cgtccagttg attgatgacg ctgtgaagag tcggaacttt cttgaattcg agaaggtcaa   1920
tcttgccgta ttgccgcgca acggaggcgg aatttccacc tacctgacac tagggggaag   1980
cgtccacgtc cccgctccgg tcgtcgtgga ggtctcggaa tgatgagcga accctacgga   2040
atcagttcga acgctgaact gcaactcgtt tttagccgtc cagctaaacg agaagcccgt   2100
ctgtatatgt ctcggattct caagaaagaa ctggaatcag ggaagcactc gacgccgacg   2160
gaggccttgg aatcatgcga aaagctctac tggagcgttt ttgaaccgcg acttgttgat   2220
gttgtttgc acgaggtcgg agaatgccgg tgcgcgggta caattcgc ggttgcccgc    2280
tcgctctcct ctcgcgcatt cattcctgca aggttcgttc aatctcttga aaatggggga   2340
cgcaacccag cccagctcct gacccaagac caagttgcag gtatgcggaa aactttagga   2400
acaaggtgac cacagcgtca cctgaccacc cttttcgtt                          2439
```

SEQ ID NO: 54        moltype = DNA   length = 2697
FEATURE              Location/Qualifiers
misc_feature         1..2697
                     note = pWKS1
source               1..2697
                     mol_type = other DNA
                     organism = synthetic construct
SEQUENCE: 54
```
gaattcatgg tgttccagga tgatgacgag ttgcgtttcg ggcgcaccat cggcggcagg    60
gtccagaccg ccccaggccg acgctttgca atcctgcgct gcgccaagat caagaccctc   120
ggcaacatgg gcgccagcct tcaacacacc ttccgggaac gcgaaccccc gaacgccgat   180
cctgcccgcc ggaccgacaa cacgttctg atcggcggaa cagacagcgc tgcggtcctc   240
gatgcatggc gcgcccgtgc gccggaaaaa atccgcgcca atgccgtgca tgggctggaa   300
tacttcgttg gcggatcacc cgaggccctg aaggcgtga gcggggatca gcaggacgcc   360
tatttccgcg atgccctgaa ctggctcaag acccggcatg gagccgaaaa catcctctca   420
gccgtcatcc accgcgacga gaccacccg cacatgacgg ttatgaccat cccgctggac   480
caacagggca agctcaatgc ccgcgctttg gtcggcagcc gtcagcagct ctcggctatg   540
cagaccgact tcgcaaaggt tgtgggacag gcgcatggcc ttcagcgcgg tctggaaggc   600
tccagagcca cccacgagcg ggtgaagcgg gtctatgccc atatcagcga cccggaagcc   660
```

-continued

```
tctgtgagcc tcccagagcg ccgcagaggc ggtttcatgg gtcggggtgg ggaaacggag    720
gcagaatggc gggaaagggc cacagaagcc gtcacagagg cgctggcggg ggtccagcac    780
gccttgcggc gggaacgccg cgacagggct gcagagaccg aggcactgcg tcagcgcctt    840
cagggcagtc cagatcagca gcaggtgaac cagagactgg aacggcaggt tgcccggctg    900
aaggccgaaa cggcccgcct gcacgacagg ctggccaagg tcaaagacga agccgatgca    960
tatcacctca atgcgctcaa gctggacgcg gcccgcgagg ttatcctgac ccatgcgatt   1020
gccttcgtcc gcgatcacgg cctagacgag ccgacatgc tggcgcggat ggaggccggt    1080
ctgaacgaag ctctggcgga gtttaagccg gtgcagcagg agcaggtcgg gacagaacac   1140
gatgccgtgc aaaaaacccg ccagcgcgat gaggggctgg atcacggaga ctaagccgat   1200
ccgccgccag ttcaggccgt ccggccccgg attctgacca taatttcatc gaaaaaaggg   1260
gcgcagccct tcttgttcta atagttctat aagttcaggc gaaaatcgtg cagcaattac   1320
aaaaggttgc gcgtctataa gtggggaatc cagccgcaaa agtggggaat ccagccgcaa   1380
aagtggggaa tccagccgaa atcgcggatt gacgagtggg atttcccgcc caataaatcc   1440
accatgggaa agacactcga cgttgcccgc gaccgggcct ttgaccagac cgcgaccgtg   1500
ctgcccgccg aaatggcgcg gggggtctat atgcgcaacg cccccagcct cgcggccctg   1560
aagctgatgc atctgatgat cgccacggcg ggcgggcgca tggccgatga cgtgcgccac   1620
gaaatgcggc tggccgacat ccgcaagatc gacggtatgg ataaccacac ccgggccagc   1680
ctgaccccgc tctttgcgga actggccgcg gcggtgctga ccccacggca ccggaaaaag   1740
cgggtcgtga ccatcggtgg cctgctggac gaagcccgga tcgattaccg gcacgaggtc   1800
agcggcgatc ttctggtgtc gtggaccttc cgcagcatgt tccgccgcat ggcggcggaa   1860
tcgaaccatt gggcgattct cgaccggcag accgtgttcc acctcggcag caagtattcc   1920
gtgctgttgt tccagcacat cgccagcttc aaggaatacg accacattac cggcaagacc   1980
tttaccgtgc cggagttgcg ggctgtgttt ggtatcccg agggcaaaat caagcgtttc    2040
gcagacctca acagagacgt gctgacgccc gccattgccg aaatcaacca gctttcccgc   2100
ctgactctga ccgccacgcc gaacaagatc gggcgcaccg tggccagcgt gacgattgct   2160
tgggaagaaa agcccctcga aggcaagcgc tcgaccaagg ccgaactgga ccgcccgaag   2220
gtgggccgga aggcccggcg cgacggcacc gccgagacgg tggcacgggc cttcccggca   2280
tcgggcggga tcgagttcga ccagcattgg cgcgacctca gcgggcggc gggctgcaac    2340
atggacaaca ccatgatcgc cgacaaattc cgggcatggt gcgccgggaa gggcctcgct   2400
ctcgatgccc ggaacatcga acaggcgttc agcagcttct gacccaaggt gggccgggtc   2460
tgagacccgc cgcgccggtc gctcgatacc tgtggtctcg ctccctctgc ggctaccgtc   2520
agcgcctcgc ctgcatcgcc gcccttccg atcctcatcc cgccccagcc ttatggggg    2580
atgaggatcg ggccgggact gaaacccgaa gggtaatgaa tgtgtctttc cctgcttggc   2640
agggcgaacg acattcggca gaatgtctag tgagtacaca ttcattaccc ttcaggt     2697
```

| SEQ ID NO: 55 | moltype = DNA length = 1952 |
|---|---|
| FEATURE | Location/Qualifiers |
| misc_feature | 1..1952 |
| | note = pLME108 |
| source | 1..1952 |
| | mol_type = other DNA |
| | organism = synthetic construct |

SEQUENCE: 55
```
gcagctcaag cgcctggtcg atccgttctc gcacaacgat gaagcgctcg aaaacatctt    60
cttcttcccc cggttctgac atcgctcccc cagtcatcgt gccgtgctag tgctaccggt   120
tcgggtgtgt cgggcgggct gcgccacccc aaggggtccc cgcgcctccc gtccgccgca   180
cccgaaccca tcagcccgag catcgccgca acgtccgcga aagatcatc aggagtcggg    240
agaccgcaac agcacccacc cgacaaacag acctccacag ccacgagacg gcccccaggg   300
cggccagctg cccgacgatc agccctgttc atccgagacc ccctcagaag accgcagacg   360
cgccgcaacg tccgcacccc agacgtccac gtcctgcccg aacacccgcc gaaactcgtt   420
gacctggcg tacatcgtgc tctcagccat gaccccgcc cccagcaggc cggagcgtcc     480
gccgtagatg tgccacatca gccagaaccc aagcagccgt tgcaccgtgc tccgagcaac   540
accgaggag agcgccgaca caccggggat catgccgctg atcagcgcca gcacgtccca   600
cggacccaca ttcttttccg acttcttctt cgccatttta gtccacctcc accaattcgt   660
gttcgattcc gtgctcttgc agccaccgcg ccaagccgtc ttgaccgcc aattcgcaac     720
ttcgcagaca ctcgtagagc ttctgctgcc cgacgaggcg acgccatccg tcacccgtga   780
tcaaagcgac agtgtcagcg accgagccga cctcctcagc cgcgatcacg tcgtcagatt   840
cctcaaccat gaggccgagg cggtccctca ggcccgcaga ccagccaatc tgtctgcgtc   900
cccggctacc ctttctcccac tcgaaccaca ggccaacctc tttcgccaag ccgttggccg   960
cgtcgcccag cacctcccaa gtcgatcgag tcgagagcgc agaacgcgcc gtcttgctct  1020
gggagttcgt caactcgtgg ccgatcttac cttgaaattg tgctttgctc aggtagcgcg  1080
cgaggtggtc gaggccagtt gctgcgctca tctgctgaac gtcttgcgcg cgagcaaggg  1140
gagtcccgag gcccgccgcg agcacgccgc gttcccaacg gccaacatg gaccggtgca   1200
gcgccagagc gtcgccgaag tcgcccacga ggaacacgaa cacatgcaga tgcacatgcc  1260
acccattgcg cccgtgcgta acctcgacca cacgcacgaa gccctcgacc cgtgacgga    1320
gctggtccga ggtccagccc ttgcccgaag tgactgcccg ccacccgaa gcgacaccat    1380
cccaaacagc cgtcaaggaa tccttacgag agtgccgaac cgtgaacgtc atgaacgcca   1440
cacgaccacc gtgcttagtc cacgtttcga ccgccgcgc gagttcaagg ccacgccgag   1500
ccatgatctt cgcgttacac accgggcagg cccagaccga tccgcagctc tgcaacccag  1560
cgaaaccggc ccggccgtcg ctgcaccgca caccaaccga agcgaccgcc gaggcggcaa   1620
cacgaccgca gaacgcaacg cgcttgagcg acgtatgacg ccacaaccaa taacggaccg   1680
aaaaccggtg tttgcgcttg tcggcggcca cttcaccagc ggcgggcacg gccgaaggtg   1740
aaacattgtt cgcatgatta tctagggcgc ccctagcgg ggcaccgcc gggctgccgc     1800
ccccacccc ccggacgcca cgacttcggg cgcgggcatc gaccaccatt ggtcgcgtac    1860
tctgggacaa ggaagacccc ctgctagttg atgctggatc gacaccagac acgctagcag   1920
gggttctctc agttttggga gttctcagtt ct                                1952
```

| SEQ ID NO: 56 | moltype = DNA length = 4408 |
|---|---|
| FEATURE | Location/Qualifiers |

| | | |
|---|---|---|
| misc_feature | 1..4408 | |
| | note = pLS1 | |
| source | 1..4408 | |
| | mol_type = other DNA | |
| | organism = synthetic construct | |

SEQUENCE: 56

```
ctgcagaagt agtcgctgat tggctaattc agcgtatcaa agacaaaggc gaccaaaaat    60
agcttgagtt cttttagaac aaaaaagaaa gacagtagtt gcacctactg tctttctttt   120
gcgttgtgct tttagttcct cgaactttta gcgtcaagca tattatatca tggggcgaga   180
aattctgtca aaataatgct ataatgcttt tgaggcacct cagcgatacg gtcggtggtg   240
tgaatctcat ttacgtaggg cgactggaaa cggatagctc aaaggcgcg tttgagtgtc    300
gggtgtggga ctgccttcag cttcgggctg taaagacccc tgatactttt gaatgagatg   360
acccttttggg gtcttttttg ttttttttagg gagatgttgt gggggatttt ttctccgaaa   420
aaatctaaaa tatgggggg ctactacgac cccccctata gtgccgagtg ccaaaatcaa   480
aaaaaaaacg cctttagcct tagagctgca aggtttgag gctcgtcaaa tctcggcgac   540
ttttcggcga cttttcggcg acttttttaga gattttttggg gaaaaatacg aaaagattg    600
cattgagtgc acgttatgc tactatagtt ttataaaatt ttgagaggtg acgcatgaaa    660
aaaagattga cgataacatt aagtgaatcg gtacttgaaa atcttgaaaa aatggcaaga    720
gagatgggt tatcaaaatc tgcaatgatt tctgttgcct tggaaaatta caagaaaggt    780
caagaaaaat aaaaaaagcc gtgctggcag gcactggcta aagtcaaaca tttcttgggt    840
atattatact ttatggctaa agaaaagca agatacttca ctttttttact ttatcctgaa    900
tcaattccaa gcgactggga gctgaaactt gaaacgcttg gaagtgccgat ggcaattagt   960
ccattgcatg ataaggataa gagtagtatc aaaggacaaa aatataagaa agctcattat  1020
catgtgcttt atatagctaa aaatccagtt actgcagata gtgtacgtaa aaagattaaa  1080
ttattgcttg gtgaaaaaag tcttgcaatg gtgcaggtta ttctcaatgt cgaaaatatg  1140
tatttgtatt taacgcacga gagcaaggac gctattgcta agaagaaaca tgtttatgat  1200
aaggctgata taaagctaat caataatttt tgatattgacc gttatgtgac gttagatgtc  1260
gaggaaaaga ccgaactttt caatgtggtt gtatcgctta ttcgtgcgta cactctccaa  1320
aatatttttg atttgtatga tttcattgac gaaaatggag aaacttatgg gttgactata  1380
aatttggtta acgaagttat tgcagggaaa actggttta tgaaatttgtt gtttgacgga  1440
gcttatcaac gtagtaagcg tggaacaaag aacgaagaga gataaaagt tgatctttgt  1500
gaaaactaca gaaagtaaag aatgaaaaga gtaatgctaa catagcatta cggatttttat  1560
gaccgatgat gaagaaaaga atttgaaact tagttttatat gtggtaaaat gttttaatca  1620
agtttaggag gaattaatta tgaagtgtaa ttaatgtaac agggttcaat taaaagaggg  1680
aagcgtatca ttaaccctat aaactacgtc tgccctcatt attggagggt gaaatgtgaa  1740
tacatcctat tcacaatcga atttacgaca caaccaaatt ttaatttggc tttgcatttt  1800
atctttttttt agcgtattaa atgaaatggt tttgaacgtc tcattacctg atattgcaaa  1860
tgatttaat aaaccacctg cgagtacaaa ctgggtgaac acagccttta tgttaacctt  1920
ttccattgga acagctgtat atggaaagct atctgatcaa ttaggcatca aaaggttact  1980
cctatttgga attataataa attgtttcgg gtcggtaatt gggtttgttg gccattcttt  2040
cttttcctta cttattatgg ctcgttttat tcaaggggct ggtgcagctg catttccagc  2100
actcgtaatg gttgtagttg cgcgctatat tccaaaggaa aatagggggta aagcatttgg  2160
tctattgga tcgatagtag ccatgggaga aggagtcggg ccagcgattg gtggaatgat  2220
agcccattat attcattggt cctatcttct actcattcct atgataacaa ttatcactgt  2280
tccgtttctt atgaaattat aaagaaaga agtaaggata aaggtcatt ttgatatcaa  2340
aggaattata ctaatgtctg taggcattgt attttttatg ttgtttacaa catcatatag  2400
catttctttt cttatcgtta gcgtgctgtc atttcctaaa ttgtaaaac atatcaggaa  2460
agtaacagat cctttttgttg atcccggatt agggaaaaat atacctttta tgattggagt  2520
tctttgtggg ggaattatat ttgaacagt agcagggttt gtctctatgg ttcctttat  2580
gatgaaagat gttccaccagc taagtactgc cgaaatcgga agtgtaatta ttttccctgg  2640
aacaatgagt gtcattattt tcggctacat tggtgggaa cttgttgata gaaggtcc  2700
tttatacgtg ttaaacatcg gagttacatt tcttttctgtt agcttttaa ctgcttcctt  2760
tcttttagaa acaacatcat ggttcatgac aattataatc gtatttgtt taggtgggct  2820
ttcgttcacc aaaacagtta tatcaacaat tgtttcaagt agcttgaaac agcaggaagc  2880
tggtgctgga atgagtttgc ttaactttac cagctttttта tcagagggaa caggtattgc  2940
aattgtaggt ggtttattat ccatacccctt acttgatcaa aggttgttac ctatggaagt  3000
tgatcagtca acttatctgt atagtaattt gttattactt ttttcaggaa tcattgtcat  3060
tagttggctg gttaccttga atgtatataa acattctcaa agggattttct aaatcgttaa  3120
gggatcaact ttgggagaga gttcaaaatt gatcctttt ttataacagg aattcaagag  3180
ggcaatggct gatatgggaac tcaaaggagga acttcttga aaatatcatg caccgctttt  3240
tgttgatgag agaacaggcg agttgaacaa tgacacggaa gctttttggc atgaaaaaga  3300
gtttgctgat atgtttgaag ttcaatctcc gatacgtgaa acaactaacc aagaaaaaat  3360
ggactggtta agaaaacagt accaagaaga gctgaaaaaa ctagaatcgt ctaaaaagcc  3420
cctagaagac gatttaagcc atttagaaga gttgcttgat aaaagacca aggaatatat  3480
taaaatcgat tctgaggcct ctgagagggc ctcagagcta tctaaagccg agggatatat  3540
aaatacccta gaaatcatt cgaagagctt agagcgaaa atagagtgtt tagagagtga  3600
taatctacaa ttggaaaaac aaaaggcgac aaaactcgaa gcgaaagcgt tgaacgagag  3660
tgagttgcga gaactaaagc ctaagaagaa ttttctagga aaagacatt atgagttaag  3720
tcctgaacaa tttgaaggg tgaaggcaga agtttatcgt agtagaactc tattgcacca  3780
caaagatatt gaactggagg aagcaaaacg tcaagtatct ctgagagcct ctaaaaacta  3840
ttttacagct agtttagagc gagctaagga aaaagctaaa ggtgagagta tagaccgtct  3900
taaaagcgaa ataagcgac taaaaacga aattcaatt ttacgtcagc aaaatgacaa  3960
gatgctaggg aaattaagag agttaatgcc tgataaagcc tttaagaatt tgttatcaga  4020
acttaaggcg attaagccaa tcgtgaatat aattaaaaag gctattgaaa agagcttgtt  4080
ctgagcgatt tatgccgtga agctatttg acaataagac gtgacagagt acgctaggac  4140
gtgccgagcc gaaaggcttt agcgtttcgg acggacacgg acaaaggacg gcagtcactg  4200
gttactgtt gtcaaaataga ccatggaata aaaagcgtca aagtcttga gtggatgata  4260
ccctatggta ctctattcgc ctttgacttt tttgctata atttaagtgt cgccagttct  4320
tccgtcaggt aatgcgaact agactggag gtgagcgttg tgaagacatt cctcgagctt  4380
```

```
gtctttgtcc ctttttgtggt tggcgttg                                      4408

SEQ ID NO: 57          moltype = DNA   length = 5804
FEATURE                Location/Qualifiers
misc_feature           1..5804
                       note = pUB6060
source                 1..5804
                       mol_type = other DNA
                       organism = synthetic construct
SEQUENCE: 57
actgcgatgt acgatagatg ctgtattaag caagtacaca cagcgtcccc tctgcgaggt    60
gccgtctgtg actggttcag ggggctcgcc gccccccgaa accccctagca tccactgcga   120
aaattcgcac gtttgggtgcg aaactttctc agcggattct catggaaaag cgcaccaaag   180
agatcaaaat cagactcacc gaagcggagc atcagcggtt acttgaacgc tgtgaccgaa   240
cgcatttggc cgagtggtta cgtgccgttg gtttaggcga atcgcggaca gctcgtcgtc   300
gtccgctacc taccgtagac ccgatcttgt tacgtcaggt cagcgggatc ggtaataacc   360
tcaatcaaat agcccgttac ttgaatcagc atggcttacc gccgcaagaa cgggtgtcgt   420
tgttagatgt gctcaatagc attgaccaac atcttgccga actgctggag caacatcatg   480
atcgttaaga ttcatggtcg tggtgccggt ggcgggagtg gccctgtcga ttaccttctg   540
ggccctgatc gtcagcgtga acaagcgacg gttgttacggg gtaaccctga gcacgtcaaa   600
gagctgattg atggctgcga atttgcccga acctatacct ctggcgtgct ctcttttcag   660
gagagcgact tacccgcagg cgaaaaaaca gcgtttgatg gagaatggga gcagacattg   720
atgaccggtc tagataaaga ccagtatgcc tgcctctggg ttcaacatca ggacaaaggg   780
cgtcttgaat tgaattttgt tatcccgaac atcgaattgc agagcggaaa acggctgcaa   840
ccttactttg atcgggctga ccggcctcgc gttaacgcat ggcaaaccct caccaatgac   900
cggcttggat tacgcgaccc gaatgacccc gccaatcgcc gcattaac cccctcgaat   960
gaccttcctc gcaacaaaca caggcagcg gaagccatta ccaaagggct aatcagcttg  1020
attgagcagg gagaaattac ggatcgtaaa gggggtgatttt cccaccttac cgatgccgga  1080
ttgtcggtcg tacgggaaac caaatccagt atcagtattg ctgatccggc aggtggcccg  1140
aatattcgct taaaaggagt gctgtatgag cgagatttta aatttagcgc gggagttcga  1200
gagcaaatcg aagcagcaag ccaagactac cgcaacgagc gtcgcgagcg cattcgagaa  1260
gcacgagaaa cgtatcaccg aggccttgaa attaagctca gggaacatac agaccgctat  1320
ccaagaagag aacgacaacc agctaaaaca gatacaccgc ttagtcggaa tgacatggct  1380
gtacagcctg gcattaagcg cgatcctgtt tgcgacattg attggagtag cttggtatct  1440
cgggactatc gtggtcgaac gccagaacga aatcagcgaa cagagccaga tcctgcagga  1500
cttaaagagc cagaccggag ccggcgtatc gataattcac gattccaaga caagagcgt   1560
gtattacctg atccttccgc aggggcgaaa gcagatcgac gagtacaaga acgctcaaca  1620
tcgtcaggtc atcaagtaca cgccaaaata acctcatcag acgccacaga atcgattctg  1680
ggcggtttta tctatcaggg tgaagagatt catgccgaaa tggcagcagc agcttctgga  1740
cgcattagag agcttacaga ggcactacga acaacagcaa caagcgtggc aggacagcta  1800
cgccaactta cagcgcatgt tcgaggttac ctcgcaggag ttggcgaaaa acgacagggt  1860
ttgtcaggcc ttgagcatgc aagtcaccgg cttggcgcag caagtcgaga gcttaaacag  1920
aacagtgcgc cgcttgagca attagccaag cggcacgaac agcgcattc tcggcggtca  1980
cggcatgagt ttataagcgt ttatcggcag catcataagc ggcagaacgc tcgcgcttac  2040
cgaccgccac cacgaatacc gtaatggttt gatcgcgaac ctgatagacc aaacgataac  2100
cggatgctcg tagcttgatt ttgtagcaat ccggcagctc tcgcaggcga tttttatcga  2160
tccgcggtcg ctgtagaacc tgctcgagtt ttttcttgaa ctgcagacgg acatcatccc  2220
cgagcttgcg ccattccttc agggctcggg gatcaaactc aaggttatag ctcatccagt  2280
gacacccttta cgcccgcctg tgggttttcc agacgatccc gaacgatagc catcaaatcg  2340
gcatcatcct cggtcagcaa cacctgctgg aacggcaagc gtccgctttg ggccacatac  2400
tccagtgtt ggcgcagaac ctcggacggc gttacgccca gcttttccag tgcggcataa  2460
gagcggcttt tcagctcgtc atcgatccga atattaatcg tggccatcat ctcacctctt  2520
gatgtagtga caagtgtatc tacaagaagt agtatgagcg taaagccgtg cgagaacaag  2580
caggaataac ggattgtcgg ggatgacaaa aaccgttgtt gaggtgtaac ttagcggcag  2640
aaaaaacaaa gccccgaatt catgtgctca acttggcgga agactcatga aattcagggc  2700
taggtcgaaa cctagaaagg atattagcac atgcagcgtg caaaacaaca gccccgccat  2760
aaggctggga gccatggcta atcaggcttt aacgcttttt aacgaccggt taccccacaa  2820
gccgtacttc tccgatgatt tacagtttgg tgtccgcatt gccggtaaag agcgtgctct  2880
cctcgcaaaa tacatccagt ttaaccagcc ccacgccatg tactggcttt gctttgacgt  2940
ggacagggcc ggagccgcga ttgattgggc cgatctgggt gcacctgcgc cgacactcac  3000
catcaaaaac cccgataacg gacatgctca cctgttgtat gccttgaaca ttgcggtacg  3060
caccgcgccg gatggtcgag gccgcctcct caaatatgcc gccgcattg agaatgcgct  3120
gcgtaaaaaa ttgggcgccg atgcggggta ttcaggcta atttgcaaga atccgaacca  3180
cctgcactgg cagatcaccg tctggcagcc tgagctctac aaccctcgact ggctagccga  3240
ctatctcgac cttggcgctg ccaatgaccg agaaatcctg cccgactacg gtttaggccg  3300
taactgcacc ctattcgata aaaccgcaa gtgggcttac cgcgctatcc gccaaggctg  3360
gccggagtat agccaatggc tacaagcctg cattgaacgc gctaaagcct acaacctgca  3420
gttctccgca cctttagacg agaacgaagt catgggaatt gctaaaagca tttccaagtg  3480
gacaatggtc acttatcgca tgtcgggtc tgatgatgat gtgaagttaa ctcattcagc  3540
cgaggtacaa gcatatcgcg gtcggcgaag taaggcggt ggtagaccta gtattgggga  3600
accatggtta gctttaggta ttagtcgtcg aagttatttt agatgaaaaa gctaggtaa   3660
attatgaaaa taattagttt tatcaatatg aaaggtggtg ttggtaagtc tacgttgct   3720
attaatgttg ctcattgctt agcggagcga atcaaaaaaa aggtattgat aattgatatt  3780
gatcctcagt ttaatgcaac tcagtgcgtt atgaaggcag aggattacat agagcatatg  3840
cgtacgggta aggatactat ttgttctttg tttaactctg accgagttgc agctaaagc   3900
gttagtggac catcttttga aaaatgcaaa gatatcagta gcatatctcc tgttgaaatg  3960
tctgagtatt tgcatatttt acctggtgac cttggtttg atcgaattga ggttacagct   4020
gggagcgggc aggagttcaa gttaaaacga tacttggatt ctatcagtga caagtatgat  4080
tatgtgattg tggatactcc gccaacacca tcaatatgga tgtctagcgc attgatagct  4140
```

```
tctgactatt atataatacc ggttaaacca gatccgttat caaggacggg gattgattgc    4200
ttgatagtat aatagcagat aaaaaaggaa actttgattt aaaaataaaa tgtgctggag    4260
tggtgtttaa tatggttgaa gaaaactgtg tttagagaga ctaagagttt ttttaataac    4320
agtgatactt ggcgcaatta cattttttaga tctttcctgc ctaagaaagt tgcgatagct    4380
aaaaggcaga catcaggaga acatatatta aagacaaaag attcctcttt gcacatgaaa    4440
cttgtcagag tggtcgatga aatcgaagag agaatacagt aataggataa cgtatggata    4500
agttaacaac taaagaaata aagacgttat tgaatttcat tgaagagttc tcttggatttt   4560
caaataaata taaaaatttg gataccaata agttatatga ggctcttaat aattgcgagt    4620
ctcgtcgtca aaatgaatat aatgattata tttcgtactc aaaaagtgta ggtaagaata    4680
atcatgtgtc atataggaat agccttaaag ataagacatt tctaattggt aagctcccat    4740
ctcttttgat ggataaagaa ttgttctcta aaaataagga gctatctgac tttgctcgac    4800
tacttggtgt tgaggtcaga ttccctgaga acgttctag agatgagata atcggcacta     4860
ttatttgctc attacaagag gaaagtagtg ttaaaagaat tcatgagatt ggtgagttta    4920
tctatgcttt aactagcgat gaaaaactaa tgaataacat taaggttgag aagaaaatat   4980
ataatgatga gtatgattgg aataatgtaa ttagactttt atttatgggt aaatgatgtc    5040
tagattgata gggaaagact ttgatttatt tttaggcttc ttttttaaatt acagccttaa  5100
agatttggca tctaatggtg attttaaaaa gaagctgcgt gaggcacaca aaaaatacta    5160
tccgttactc actcttagcg ctgagcttga tctcatgttt aggggggatg tgggagagga   5220
ttgtgctgat agggttaaag aaacttgctc tgatataggt tcgtctattt ttttattagc   5280
ccatggaatg tataagcaat ccaacatgtc attgcgtagt tctattgaga acttttttaa    5340
atcaataggt tgcaatcatt gccctgacat attaacagat aagagtgttt tttctgtttt   5400
tgaaaaggct gggcaattag agttatttttt agatcctgtg ttcaaatgca agtttgatga    5460
gttgcaatct atttactcat cgttgtgctt atatactcat accgcaagtg ctgaacacat    5520
ggctaaaatt agtgctatgg gcagtattcc aaaaacatgat aaagcgaaaa gcgctattct   5580
tgttaatgac ctcactaggc ttgttcgaat ttatcttttc atttcacga agttgtttag    5640
gtgtgaattc ttcaaattta accatgacaa ccgagatgt attctcagcg cattaaccaa    5700
gtcgcaacga cgttcgttaa tggaaccatc ctgatgtggc actaaacaac ctatatcaga   5760
taacagcect gcttttgcgg ggcttttttgt ttgtgcgtga tgtg                    5804

SEQ ID NO: 58         moltype = DNA   length = 1711
FEATURE               Location/Qualifiers
misc_feature          1..1711
                      note = p545
source                1..1711
                      mol_type = other DNA
                      organism = synthetic construct
SEQUENCE: 58
ggtgccatga gggttctcac tgatacctga atgagtttga cggtggggcc gcatgcacga     60
ctgccatacc gtcaatccga gcgccgcaga ctgggcatgt cccctgagt aacacttgcc    120
caccgggttc aacgtccgtt gctgatgccc cccattggct gtagccacaa tggccgcagg    180
ataagaacgt ggcgcgcact gtgcaaccgc acgcgaacgt agtgccaagc ggtgcacgat    240
caagaaaatg ctcatcgtgc ggcgttacgg tcatgcgtca gttcgattct tgttcagcgc    300
gtagtgcacg gtgcccacgg aaaccccgac ctcggcacga atcgcacgca tgctctgacc    360
ctccgagcgg agctcacgaa tccgcgcgtg gcgtgcggca acgcgggcca cgaactcctc    420
gcgtggctcg gaagtccacc gcttgacggt ggactcggag acaccgagct tttcgcagc    480
agcggcgatg ctgtagccgt gcgggggag acgttcacgt gtggtcatga gagaccctcc    540
aagaactgtt gacgggtatg ggcgcgccgt gatgcgccac tgccaatgcc gccttttgtgg  600
ccgccttctt tgccgccttt ggatgctcca cggaggctga tcgctttctg gcgtgcgcgg   660
aaggtttcgg gggtgaagtt gcgccagacc catcgggaaa tggatcgaga taagtgctta    720
agttcgttca agccgagggg gcctgtgcg aattcgtcgg cgatgatcgt ctcgttcagt     780
aggtggatgt gctcgaatac ggtgtgctcc cattcggcga ccggggccgc caaggagtgc    840
cggacggccc ggtatgccca catgcgggtg tgtcgaaca gggtgacgtt gcggccgacc    900
gttgatcggg tgacgttgcg acgcgggttc cctgcctccg gcagtgcgtg gatctcgtcg    960
agggtgtgtg cgagggcgcg cagctcgtag agcgcgtctg cggggcccca gagggtcgca   1020
tgggcggtgc tgagcgggtt cttttgtgatc cggtgcccgt aggatgcatc gccgccgaga   1080
acgtcgcata ggccctgctc gacgcgggcg agcaggttga taggccgtcg ccgcgcggca   1140
tcggtcagac acacagggtt cttcaaggca tagacgatgt gtccggtggt cgtgacacgg   1200
ttcatggaca cgtaggacgg tgaaggcagc ccagcgaggt ctgcgcccca gtcagcatcc   1260
gaagcatctc gatcggtgat gaccaaggac tgcatgacca acgggttcgc ttcgatgtaa   1320
ggcagctcca gcgccctctg ccgagtcacg tgccggtacg ccccagactt ctcggctgac   1380
gccagcggct tgcgtggcag ccagctctca gggaacaacg tctcgaacga atccatacat    1440
gcagtcgaag catgcgagtca cgttcagcgt ggtccattcc tcggcgtgtt caaagtgggc   1500
gacgaagacc ccatatcagt tagttacccg gttgagccat gtgagcaaag cgaactctct   1560
ttccacatcc cctgccaaac atcccccgac tccctgacg ctgccacctg ctccaaggga   1620
tggctgggc gtgttcgggc attgcggcta gttcctcgcg cagctgtgcg atcttcgcct   1680
gaactgctcg ccggctgtca gggtcgacgg c                                  1711

SEQ ID NO: 59         moltype = DNA   length = 7426
FEATURE               Location/Qualifiers
misc_feature          1..7426
                      note = pJD4
source                1..7426
                      mol_type = other DNA
                      organism = synthetic construct
SEQUENCE: 59
ctgcagcaat ggcaacaacg ttgcgcaaac tattaactgg cgaactactt actctagctt     60
cccggcaaca attaatagac tggatggagg cggataaagt tgcaggacca cttctgcgct    120
cggcccttcc ggctggctgg tttattgctg ataaatctgg agccggtgag cgtgggtctc    180
gcggtatcat tgcagcactg gggccagatg gtaagccctc ccgtatcgta gttatctaca    240
```

-continued

```
cgacggggag tcaggcaact atggatgaac gaaatagaca gatcgctgag ataggtgcct    300
cactgattaa gcattggtaa ctgtcagacc aagtttactc atatatactt tagattgatt    360
taaaacttca ttttttaattt aaaaggatct aggtgaagat cctttttgat aatctcatga   420
ccaaaatccc ttaacgtgag ttttcgttcc actgagcgtc agaccccgtat ctataaactc   480
ttggcttggt tctaatccct ctaaacgatt attatcaata gccgctcgaa ccgcttttc    540
tcggcttaat ttttctgtct ctgttataaa attgctattc atcttgttct tcttcaaaaa    600
aaagttaagt aaaatacctca cctaaatttt tactagttcg caatctacga gcttataacc   660
tcgttttttc aattcattta aaaatcaga ttttgagcct aatttttgatc tattgctatc    720
gttacccgct agaaatacccc agtaattacg caaatcttca ttggtaactt tcgtaatatc   780
ggtgtaatga tcttcgagta ttttttaagca atctctagcc cataaaccgt actcgtgatt   840
gctcatctta gggttttgct tatcgagttt gacgaacttc ccatacttgt ttttatgtgg   900
aaatactggc cgttttgcaa cttcttcaat tttttgagct gttcgttttt tactaccaat   960
cacaaaattt aaagagtgaa tagtacgccc acgcttgatt tgttcaacct caacgactaa  1020
atcagatttc tcgttaatct cagttattgc aggttccaaa acacgttgat ttaatgaatt  1080
aaatctaggg tatttatttt caacctgaag ccattctttt agttttcta ctgtaatttc   1140
acgactacca acagagcgat attgtgtaat tagctcataa attcgaattg aatgtacact  1200
gttgaaataa gcgatatgtt tgagttgata ttgcgtgaat tgcccttaa gttgcgttag   1260
gtatggcata acttcatcag tcattgcaat tctaaaacgc ccctctttct tgaaatatgt  1320
tctagaggaa acccaacgaa attcagttac acggtcttta tcttcagttt taacacttcg  1380
gtcataaatc cgttttatag ccgcctgaat ttgcttatag gcgttatctt ggcttatttc  1440
tggaaactca cggacaaaat cagccaccgt aaaatcaaaa atcttttgat tagatttcgg  1500
atccatagtc ccaatagtta aagctaaaat tctgatttca tcaatactca atcggtaatt  1560
ggcttcaata aggctattag cctttacaac aactaaatca tttggcataa gacaacaaat  1620
ttcctgttta aaacaacaag caaaatatac ctgttgttta tatataaaac aacaagtatt  1680
ttcttaaaag ttgtctataa caggaaattt gttgtcttat aacaggaaat ttgttgtcgt  1740
ataacaggaa atttgttgtc gtataacagg aaatttggtc tcgtataagt ttgtaactta  1800
ttgattttac tggttttaaa aacgccgaaa acaagtaaaa aacaaaaata taaaaatata  1860
gggactttcg tcccttttttt gggctttcag ccctaatttt ttcttttttc aggattaaaa  1920
attacaaaac ccttacagag caagtaaact tgtttgcttg ttctgcaagg gttcagcaac  1980
cgaagccgtt aggcgtaggc ggtagcctat aaaagccatt taattttatc tttaaatttc  2040
cgtttaaatg ctttgagtgg gtgtcttttta tcgtactcat caatccttt ttgcattctt   2100
tcgtttgctt tgtgatcggc aaattttgaa taagattttt ccatctcatc taacattcta  2160
tcaatccgtt ttttatgttg ccatttcagg taaacataaa cacttatagc aataaaagac  2220
aatatcaata cattgtaaaa aatgattgtt acaatttcgc tcacagttat tttttacctt  2280
tttcaatttc ttcattgata aatgcactca attcatcaaa tttcttgtca tcattgataa  2340
atttacgcaa cttagggaag tttctatcta catctaaaag aggggttaaac gattattatc  2400
aatagccgct ctaaccgctt tttctcggct taattttct gtctctgtta taaaattgct   2460
attcatcttg ttcttctctc acacttttaac taattcacag ttcacaatct tatacccctcg 2520
attttgcaac tcgttttaaaa aatctgaccg cttaccaagt tttgatctaa aactagcatt  2580
gctagtcaaa aaaacccaat aatgccgtaa atcttctgtt gtaacatcgg caagatcaga  2640
ataaaaatct tcaaggattt ttaggcaatc tctcgcatag tttccatatt cagcattact  2700
cattttggga ttttgagtat ccaatttcac aaacttcccg tacttgtttt tatgcggaaa  2760
tgcagggcgt ttctgttcga tttttaccgc acttttctta ctcttgatcg tgaattttaa  2820
tgctacgatt gttcgcccac gcttgatagg ttcaacatca acaagcagat cggatttagc  2880
attaatttca tttatggatg gagttaatac tcgctttta aaatccttaa acagtgggta   2940
cttatcagag atacttaacc aacttttaat atcttctacg cttgtttgtc gccaacctgt   3000
atcacgatat tgagaacaca attcataaag gcgaatagcg tgcgtactac ccaaagcccc  3060
aatattgatc aatttatatt ttgtgtagtt atcgtgtaat tcagaaatgt aaggaattag  3120
ctcatcgtgg aactcgatat aaaatcgccc ttctttttta aaataggaac gcttatgaat  3180
taaagctact tctgttaatt cgtgttcgtt atcaaccagt gtaacccaac gctttgagat  3240
ttttaaaacg gcatttctaa cttgtgtgta agctatatca ggatttacat cggggaagct  3300
tttacaaaaa tctgccaccg tgaaatcaaa tccacgctta gacggatttt taggattaaa  3360
aacccccaaa gttaaagcca gaatccgcat ttcatcaagt gtcattgaat agctggcttg  3420
tacaaaattg ttagctttat ggactgttaa atcatttgtc atatcatcaa ggtggacata  3480
aaataaagat tgtcccatta taaccataca gttaaatggt ggtcaataaa aaacaaagac  3540
cactataaca ataaatttgt ccacctataa caataaattt gtccacctat aacaataaat  3600
ttgtccacct ataaatctcg caagccttgt gtaacaaggg gagccagagc ctacaaacaa  3660
gaatacaaac aagaatacaa aaaaatagag cctaaaggct ctttttgggg ctttcagccc  3720
taattttttc tttttttcag gatttaaaat tacaaaaccc ttacagagca agtaaacttg  3780
tttgcttgtt ctgcaagggt tcagcaaccg tagccgtcag gcgtagggcg gtagcctata  3840
aaagccattt aatttttatct ttaaacttcc ttttaaatgc tttgagtggg tgtcttttat  3900
cgtactcatc aatccttttt tgcattcttt cgtttgcttt gtgatcggca aattttgaat  3960
aagatttttc catctcatct aacattctat caatccgttt tttatgttgc catttcaggt  4020
aaacataaac acttatagca attaaagaca atatcaatac attgtaaaaa atgattgtta  4080
caatttcgct cacagttatt ttttaccttt tcaatttct tcattgataa atgcactcaa   4140
ttcatcaaat ttcttgtcat cattgataaa tttacgcaac ttagggaagt ttctatctac  4200
atctaaaaga gggttattta ttatttcatt tagccaaaaa gccctaata aaaccttgta   4260
atgcgtagct ttcttacgct ttttctgctt tctctttgac ttaatcgcac gaattttcgc  4320
tttgatttcg tcctgcttgc gttgtaaatc tgcttgttgc tgttccaatc ttgtaagttt  4380
ttcgcttgcc atactagccc ctttatatag ttagaaatta tcgttatttt attcagtagg  4440
tgctaggctt gcaagtgttc tgttcattac gttaaaataa cgtaatgccc acttatcagt  4500
ttctcttcga gaaactggtg ggcaagcgta ccgcttgacc gtttcgcaat actcaacact  4560
atggcaatct atcattaaa cgttcgtat tgcagtaaaa gcaagggca atcagctcaa    4620
gccaaaaacg actacatcaa ccgcaatgat aatattcaa agcggttaga tgatttacag  4680
ttttcaggct atggtaatat gccaaaattt gccgaagata tccgcaaga attttggcga   4740
ttgtcagata tttcgagcg agctaatgcc cgagtttgta ctgaaattga atttgcttta   4800
cctagagaat taaccctaga acaacagcaa aaattagtaa gttcgtttat agaaaatacg  4860
gttgatagcg gtagcaataa actaccctac tctttcgcta tccatccgcta aaaaataat    4920
cataatcccc attgtcattt gatattttca gaacgccaac ttgacggcat agaccgtaca   4980
```

```
gccgagcagt ttttaaacg tgctaatact aaatcccag aaagggcgg agcgatgaaa    5040
acggcagatt ttcgagatcg tgagtttatc caatctgtcc gaaaaacgtg gagagagcaa   5100
gctaatcaag cctagagca atacggatat gccgcacgaa ttgacgaacg tagctacaag    5160
gaacaaggca tagagcaagc cccaagagca agaattgaca gggtaacgtg caagaattg    5220
aaccgattag agcaagaaga acgccaaatc gtgcaagagc ttgcacttaa aggacaagaa   5280
attaacaaag aaaaatccta cttgcagaaa atcgaagaaa aacaggctca aggaatgggc   5340
aaatatgaat ccaaattcgc agctgcgttt tctaaattat cggaaagtgc cctaaaacac   5400
gatttaagca acgaaaaga aaagacagt aaaatacaca ctcaagaaga aaagtgcct     5460
caaaatcgca ttcaggggct ttctcaagca gattttgatc agttttaat tgatgaatgt   5520
ctacctcaaa tagaaaaata cgttaaagcc caagaaaagc gggacggaat ggaagtagag   5580
atcacgcaat acgacaagga tttacagcgt attcagggag actataacaa gctcacagat   5640
aaaatcagg gttttctcgg tttatgggaa actaaagagc aaaagcaaa gaaaaaagag    5700
cttgaagatg aatacaaaca tacagcagag caacggaacg ctaaaagcca agaattagcc   5760
gagtatagcc aaaaataaa agcatacgaa cagaaaacgc tagagccaat caacgagaag   5820
attgccaaat atcaagctga caaccctgaa ataaaatgc ggagcttagg attttgtgaaa   5880
aaaattaagg ctcaagggc atataaagcg gctcaagagc gaatggagcg agaaaaacag   5940
caccaacagg aaaaacaaca gagacattta gagcgagaga gtggtttgag cttgtagcta   6000
acgccctacg cctacggctt cggttgttca acccttaaag aactcgcaac aagttgcaaa   6060
ttctttaagg gttcgcaata aaaacaaccg ctaaacatt ctgcccagcg gttgaaaatt    6120
tacctattca ccattacaat gatcaagcag gaaatttttt tgattgccgt aaatgtccgt    6180
atatctagtt gaggcacaac ccgccaaagt cattgcccca accagaacgg cgataaaccg    6240
tatatttacc gataaggcat ccggcagttc aacagaccgg gaagggctgg atttgctgag   6300
gatgaaggtg gaggaaggtg atgtcattct ggttaagaag ctcgaccgtc ttggccgcga   6360
cactgccgat atgatccaac tgataaagga atttgacgct cagggcgtgg cagtccggtt   6420
cattgatgac gggatcagta ccgacggtga tatgggcaa atggtggtca ccatcctgtc   6480
ggctgtggca caggctgaac gccggaggat cctagaacgc acgaatggcg ccgacagga    6540
agcaaagctg aaaggaatca aatttggccg caggcgtacc gtggacagga acgtcgtgct   6600
gacgcttcat cagaagggca ctggtgcaac ggaaattgct catcagctca gtattgcccg   6660
ctccacggtt tataaaattc ttgaagacga aagggcctcg tgatacgctt atttttatag   6720
gttaatgtca tgataataat ggtttcttag acgtcaggtg gcactttcg gggaaatgtg   6780
cgcggaaccc ctatttgttt attttttctaa atacattcaa atatgtatcc gctcatgaga   6840
caataacccct ggtaaatgct tcaataatat tgaaaaagga agagtatgag tattcaacat   6900
tttcgtgtcg cccttattcc cttttttgcg gcatttttgcc ttcctgtttt tgctcaccca   6960
gaaacgctgg tgaaagtaaa agatgctgaa gatcagttgg gtgcacgagt gggttacatc   7020
gaactggatc tcaacagcgg taagatcctt gagagttttc gccccgaaga actttttcca   7080
atgatgagca ctttaaagt tctgctatgt ggtgcggtat tatcccgtgt tgacgccggg   7140
caagagcaac tcggtcgccg catacactat tctcagaatg acttggttga gtactcacca   7200
gtcacagaaa agcatcttac ggatggcatg acagtaagag aattatgcag tgctgccata   7260
accatgagtg ataacactgc tgccaactta cttctgacaa cgatcggagg accgaaggag   7320
ctaaccgctt ttttgcacaa catggggat catgtaactc gccttgatcg ttgggaaccg   7380
gagctgaatg aagccatacc aaacgacgag cgtgacacca cgatgc                 7426
```

SEQ ID NO: 60           moltype = DNA  length = 8830
FEATURE                 Location/Qualifiers
misc_feature            1..8830
                        note = pIJ101
source                  1..8830
                        mol_type = other DNA
                        organism = synthetic construct
SEQUENCE: 60

```
ggatcctcgt tgccgtcctt gccttcggcg gccggtcg cctcgaggtc gagggcgcgg     60
cgggtgaccg cgtgccatcc gtcctcggtc acgcgaccc cggccgcag ctccccgccg    120
tcggcgtcgg ccgccaggag cagatcgagg tcgtcggcct cggtgtcgcc gccgtcgagc   180
ccgagcatct gccgcaggta gcgggtccat tcgatggccc ggcgtccccg ggttgccgc   240
tcgtactcgt gccagcgcga gaggttccac tccagcgagc cgaccccggc ggcgtcgtc   300
tcggtcatgc cgccggtcag gtccccgatc cgtccgagga gttcgaacgg ggcgacgttc   360
ccgccggtcg ccgtcttgag gtcggcgcgg gcgagttcga gggcgggcgc cttcccgtcc   420
tgggtcttgg cgatgtactc ggcgaggtcg ttggcgtcgc gctcggtctc cagccgcttg   480
aagtcgacgc cgtgccggtc gtcgggcgtg aaggcggggt tgaccttgcg caggggcggcg   540
gtccacacgg accgcagtg ccctgccac tcgtcgaagg cgcgccggt cggctcgaag    600
gtggcgacga tctgcttcgc ggaccgctcc ccctcggtcc ggccgccgac caggacgatc   660
gcgtggatgt gcgggtgcca gccgttgatc tgccccacgg tgacttcggt cgcgcggatc   720
atgccgacgt acccgatccg gtctcggatg ccctcgcggt cggcggcccg gtgccgtcc   780
ttggccggc gtccggccca cgtgccgccc gtgatcagtc gctggtaggc ccccggccgc   840
cgggggctgt ccggcgtctt ccgggtgccc tggagggcgt ccatgaggtc cgcgagccgg   900
tccgtgtgcc catgcgggc cgtgaaggtg accaggtagg cggtcccccc gcgcttgatc   960
cactcgacca cggcggcgt gatcctcg gcccgcttgt gccggatcgt ggcggcgcag    1020
accgggcaga gccagatccg cccgcaccgc atcaggccca ggaccacgga cgttccggcc   1080
gccgtctggg cgacgatcac gccgaggca gggtccatca gggccgggcc gcagcccttc   1140
cacgcggcgt ccccgctgat ccgcacagc gtccggcggc gcctgtaccg ggcggctttc   1200
cgcagtcggg cagcctcgt ccgcgacgtg cttcctactt cccagaggct gtcgcctctc    1260
gggctctccc catccacccc gtccggagaa accgcaggtc ggagggtgc gggaaactct   1320
gttgtttctt tcccaaggtg ttcgcttttg cctcgggcgg catctcgcgt cacacgcgcg   1380
atcgcccgtc tcgctgccat ccggcagcgg tctgagcagt agatacgcgg ccgttgccc   1440
ggtgtgtggg caattccggt cccgcagtgg cagcggggcc cggcgggccg atctggcaat   1500
gcctcggcat cgctccgtac tctgggcacg agcaacgttc ctgtctcgcc cggctaaggg   1560
gcgcgagtct gggagcggac gggtcggagg tgcgaagtcc ggcccgttgc tctttggtct   1620
ggtgggaatc ctggcaccaa tcgggccaga ggttccctcc gccactcccg acgccccttg   1680
gggctggtgt gacttggagg gccgaagaga gccccgccgg gtatccggcg gggctttgac   1740
```

```
gtgcggtcag tgcgtgtgtc ggcgagcgat ggccacgagg ccctggaagc cgagcggtcc   1800
ggcgaagtcg gcccagtcgc aaccgggctc agccgcagtgg gcggaccagc caccgccgtt   1860
ggggtcctgg accaggttca cggtcccctc ggtcaggcgt ccgtcgaagt cggtcatggt   1920
cggtctcctg gtgggtgggg gcggggcgcc agcacgaagt gccggcgccc cgcgggggtt   1980
ggtcgggtca ggcgccgaac cggcgggcgg cggcggcgac caggccgtcg gcggcggcca   2040
tggcgcggtc gcggtcggtg gtgagggcgg tgccggtcggc ggcggccgc aggtcgtagg   2100
ccgcttgggc ggcggcggtc gctgcggggg cgagggcggg ggcgagcacc gacacggtgg   2160
tgaggggcgc ggtgatcgcg gagcgggtgg cgtgggactc ggtgcgggcc gcctcgtacg   2220
cctcggggga ggcgccggtc aggcgcaggt cctcgcgcac ccacatggcg cggcggtggt   2280
cggcgagggc ggcggacgg cctggacggc ccgtcgcgg cgggagtcgc   2340
cgcgggtggt gcgggcggtg cggtgctgga ggagtccggc gaggccggtc ccggcgagcg   2400
tgccgatcac ggcaatgagc gtggtcacca tgtgagcccc ctggcgtcgt gtccgtctgc   2460
ctacgtgtat cagtctgaca cgcacgtgtc aggttgcgca atgggtaggc cccgccggtt   2520
tccggcgggg ccatccgtca tgcggcggtg ctgagtcggg cggcgagctg gtgggtgcgg   2580
gcgaggatga cgcggatctc cgcgccgccg tcgaccgccg cgagggcggg ggcggggcg   2640
ggtgccggcg gattggtcgg ggtcgggcgg cggcggaggg cgacggccag gaccatggcg   2700
gcgatcgcca cggtggcgag gtaggcgagg gcgatcacgc ggccacctcc ctcgtgacgc   2760
ggcgccagga cgcctgcagc cgtgcctccc ggcggagta gcccatgtcc cggaagcgtc   2820
cggcggcgac ccggtacgac ccggagtcga ccaggccgga catgatcccg tcgatctcct   2880
cgttgctgag cgggaccacg tcggccgacc cctcgatggc ggcgggacg ggctccgtgg   2940
gtccccagac gggcaggcgc caggagggcg gagacgtggg cgtgacacga gaggtgacgc   3000
aggtcagagc gcgtgccgtg ccctcgccct cgcgggcgcc ctccagcgtc gaccaggccg   3060
acgccagctc cccggcgtc tcggcctgga ccgggcgac ccggcgcccg cgcccggtca   3120
cggcctccag ccgggtgacc tccgtaccgg cctcggcccg gagctgagcg cgggccacgg   3180
ccgccctgtc gcgggcgtcc tgctggatgt cgcggatctg gtccagggcg gtcggggtga   3240
gcgcggtccg ctcccagagc ccgtgcacga gccagagcgc cttggcggca aggggggagcc   3300
aggcgaccgc gagccaggcc cggccgact cctcacccag cgcgtgcgcg accaggacgc   3360
cggtcgccac ggcgccgaat ccccacccga cgccggtgat cgcgcggctg tggtcgcccc   3420
gcgcggcgag gcgccgctcg tacgcgaggg tggccagcca tccgccgtcg agcccgaggc   3480
cgacgaccaa ggcaaccgcc cacatgcatg cctccccgag ccacatcacg atcacgacca   3540
cggtcaggac catggacacc gccgtcatgg cgacggccgg ggcggcgtc atcgaacgct   3600
tcttctccat gatcacttcc ccttccgggc cttgagcgag atggacaggc cgaccccggc   3660
gggggcggcg gcggcgagcg cggtcgccgt ggtggcggcg gtctggagca ggaggcagag   3720
cgtcatgacg acgccgaccg agccgccagc ggcgaccagc gccaggagga tcgggccggt   3780
ccagtcgcgg gcctcggcct ggtggtggac gacgacgagc gtgcggggggt cggtgccgtc   3840
cgggatcagg tgggccggaa tgtgaccggc cctcatctgc gcgtcggggg tgcgcatcag   3900
gccgacacct ccccgacctg cgtcacgacg gacagggagc cgtcctcgga ccgcaggacc   3960
tcgcccgcgt cgagcagctg cttgaccgcc ttcgacacgg agcccttgtt gatgccggtc   4020
acggtgcgga cgtcggcgac ggctcgtagcg cccgtgccga tcgcggctgc gaccttctcc   4080
cggttggtcg gcgccttggt cggctggcc gggacctcag ccgcggggggc ggtctcttc   4140
accagcggga gcggggccgg ggcggaggcg ccggcacttc gtgcaggcga ctcctggcga   4200
cgccagaccg gccggtcggg gagcgcgatc acgtcggccg gggagaacgc gcgggtgttg   4260
atcgggtgag gctgcacctt cgggccggac cggagcatcg caaccccggc catgggcagc   4320
tcgtgcgcgt gccagcccctt ctccgtcgcg tcctcgccga acaccacgcg ggactccccg   4380
gaggtgctga gcgcgagggc ggccggtag tgatctgcg cgctgatctg cgggtcgatg   4440
ccgcccttgg cgtccatggt cggcttctgc gtgcccaga tcaggatgat ctcggccgcc   4500
cgtgccatcc gggccagcgt gctcaggttc tccatgatcc ggaccagtc cgggtcaccc   4560
ggctcttcct tcgacccctt cgcccgggtc ttcttggcca tggccgatgac ctcggcgccc   4620
tcgtcgatga acaccgtgat ccggggccgc tccgggctga tctggatcac gtcctggccg   4680
cgcgggatca gttcaagccg ctcgtgcatc tcctcgacca gctcgtcggt cacgtccagg   4740
acgtcttcga tcgagatggc cgtgcgagcc cggtgctgcc agttgatcgc ctcgaccgc   4800
ttggggtcga cgacgaccag gcggtgatcg gcgtactccg agccttccgc cagcagggcg   4860
cgggtggacc aggacttgcc cgagccggac gtaccggcga tcagcatccg gcgcccgagc   4920
ggcacctgca ccggctcgcc ggtcaccgtg tcgactcccc acggggcgcc gggcgtccag   4980
ccggtcaggt cgatcccgtc ggccgcgctg cgggtccgca cgtgatcac ggccggtcg   5040
ccgtgcgatc cggccttgat ctccatgcgg aggtcggtcc gggctccgag cagggcgcgg   5100
atctcctcgt gcttggcctt gaaggcggac ggcttcacc ggccgtccag gcgcaccgtg   5160
gtgaccagcc cggccggggt gacctgaacc ggcgtcgtca ccgtgcctac gaggccgcgc   5220
tcgtcggcgt gctcgagccca gtacgacggg tcgagccgct cgaccaggcg ccgctcctcc   5280
gctgacagtt cgtccgcgac cgcgaccgcg accttgggc tgagcgatcac cagccggcg   5340
acgttggccg cgatgagtgc gagcgagccc gcgaccggcc aggccccggc ctggtccag   5400
ccgagagcgg agatgccggc gcccggcacc gcgtgcatgg cgtgcgcctg aacgggctcgc   5460
gcccggaggg tcgccgggta gtccttgcgc gcggccttga gcttggtctt cgcctggtcg   5520
cggtcgctgc gggccgcctt gtccgccgtg cgagccgcgc gacgcacggt cgacacgcgg   5580
ttcttggacg ccgcccgcgc ggccgtccgc tggctcttgg ccgtggccgc cgtcgaccgc   5640
gcggagttgt agcccttctg ggcgtccatc agccgccttca ggtgctccgg ggtccggagc   5700
gccatgcggc ggtcggcctc ggcgtccag cgggccgcga acggcgcgag ggtcggggcc   5760
atggcgtcga gcgcgttcgt gatcgctccg gcggcgttct tggagccggt tgcgatcttc   5820
gtagagactg ccttcgggtc cacggtttgt ccttttcgggg aggacgtgga tctaggggcg   5880
gagaccgttc acgcggtctc cggtccgccc cgtttccggg gctgtgtgtg gcgtcgaaca   5940
aggtccatac tgtggtcgca cagttgctgt gtcaaggcat acactgtgct agacagctac   6000
acaccgcgca ccacactcga aggagtcgtc atgtccctgg agcgcacgcc cccgtacctc   6060
caagtcgtcg ccgcgctgaa ggcaaagatc gtcagcgggg agctgaagca cggggacacg   6120
ctgccgtccg tgcgggacct cgccgcgcag tacgaggagt cgaccgccac ggcccagaag   6180
gtccaccgga cgctgaaggc ggaagggctg gcgaggagcga agcaggcag cgcgaccacg   6240
gtcagcacgc gacggaccct gcaccggacc gcagccgacc ggctggagtc ggcgctcagc   6300
acgggccgga tctacgcgga cggggagtac gcggtcatca ccagccgcgc ccttgccgag   6360
ccgcccgagt gggtggccga tctcctcggc accgagagcg ccaggccgt gcgacgcgag   6420
cgcgtcaccc actcagccga cgaccagccg gtgagcgcca gcgtgagctg gttctccgca   6480
```

```
gacctcgcgg agaccgtgcc cgccctcctg gtccgcgacc ggatcatcgg cggcaccccg   6540
tccgcgatcg aggcagccac cggccgccgg gccgtcgcca ccgaggaagc caccacggcg   6600
gccgccgcga ccgaggacca ggccgcgctt ctgggcgtag ccgcaggcgc cccagtcctg   6660
ctctcacgca acgtctacgt ggacgctcag ggcgacacga tcgaggtcgg ggagtccgtc   6720
gctccggacg gccgctggcg cgtccaccgg gactgatcac tcgcccattg agaagcccg    6780
tcaggcaccg cccgacgggg cttcttcacg tccagacgac gtggtttccg ggggttgccc   6840
acccggttga gccgttgcac cccgttgac  cccccgcaac cgggtctgac ctgcgaagtt   6900
gcaaggttgc gacggtttcc aggagggggc cctacgcgtg cgcgcgcgag gaagccattt   6960
ttgatctagc ttccggagcc cttctcggcc tccgccttgg cccacgcccg ggccgtgttc   7020
ggagcgaccg ccgtcacctc gttgatgcgg cggtagggga cctccatccg gaccgcctcc   7080
gcgatcagcg ggcgcagctc cttctcaatc tcgtccagct ccgcgaggag cttgatccgc   7140
tgctgcccca acggcttcag cgccgcctct gcctcggccc ggatctcgcc cggtgtcttt   7200
tgcgtcatga agtcatcctg accgactgtg tcagtctgcg caactagttc aggctgcgtt   7260
ttttgcggta caactttccc tacgtcatca aggcggccgg cgagcgggcc gcgcggcccg   7320
gcccacggcc cggccgacgc tcctgtcttc gccccgctcc ggcccggccg ccgaccggcc   7380
cgcgcacacg acgggggcgg catcggtggg cggtttacgt ggcgcctgct ccgccgactg   7440
cgggcatcgc cgttgtgctc gccgacaggg cagcggggag gggtggggga ctcgcggccc   7500
tacgcggcg tctgagcgcc tgtcagcctc ccggagcgcc gtaccccgc cgtcgcggcg    7560
ctgagccgcg tgaggcgacc ctgagccccg tcgtgggttg ctggggagca cctgctgccg   7620
cgatgaggtg gcggccgtcg agctggtcag ccgtgcggct ccgtcgtggc cggtcatccg   7680
gctgcccgat cgtggtgggc aagatgccgg cggaaccggc ggacctcgac cgcgacggct   7740
atccggcggg ccgcggggcgg gcctccgtag agggcgaggg cgggcgccat ccgacccgcc   7800
acggcgggcc acaggcccag gagctcccgc acgatcagcg tcccgccgac caggagcagt   7860
gcggccagca ctgccgctaa cgcctggtcc tggtcccggt cctggtggtg catcagtcct   7920
ccccgtgatc acttcggcac ccaccgtagt gatcaccccc gacagcggat caaggggttt   7980
gcgggtcccg gtccggccg gggggtgcgg gcaggaccgc ccgacgctgc ctctgggacg    8040
ggccggacgg caggggggacc gcggccgggc cgagctgcag ccgggggtcc ggcagggccg   8100
gagcgggcgg aaccgtgctc tgacctgcgg cccgagtttc gtcacgtgac ggaatggaag   8160
gctgctgcat ttcgtcacgt gacgtatctc ggcgagcgac tgccgacgcc acggcggaca   8220
cgatcgcctc gcgctggcgc cgggccgtcgt acgcccgcgtc acgcaggag cggcggcagt   8280
agtcccggct ccggccgacg ccggattgct tgatctccga gccgcaccag gcgcagagct   8340
tcgcgccgtc ggcgtccctg ggggtggtgg tgctcatggc cgacgaccgt acgcggcacg   8400
tctcgtagcg aggcgagtcg ggcgcgaggt accgcctgca cgaagtgccg gcggggccga   8460
ccccgggcga gtaatcccag gattactccc gcggcttcga ccccggccgc cgtcgccgcg   8520
tacgtcaccg accccccgcg tacgtcaccg ggatgacgta cggcgggggg gagcgagtta   8580
gtgcgaagtg ggcccacttg cgagccggc gatgtgccgg gcgcccgct cctggccggtc    8640
gtcggcgtcg tcgtcctggt cgtcgtcctg ctctcgccgt cggcgtgcag ttgcttcctc   8700
gcggcgctgg gcgagggcgg cgagcatgtc ggcgtacgcc tcgccaccct cccccgccgt   8760
gagcaccacc actgtgtcgg ccgcgtcggc cagcgccagg acctcccgca cccgttcgcc   8820
cacggccgcc                                                         8830
```

SEQ ID NO: 61          moltype = DNA  length = 11046
FEATURE                Location/Qualifiers
misc_feature           1..11046
                       note = pSN22
source                 1..11046
                       mol_type = other DNA
                       organism = synthetic construct
SEQUENCE: 61

```
ctgcaggccg gtgactccag agaagggttg aagcggagtt gcggggctag cccccccgagc   60
ctccatcgtt ccgaccgccc ggcctgtccg ggacgggagg acttttcgag cacctggagg   120
agcacgtgac caaccagcag caggaccagg agcagccgca gcgcccggcg gaccgtggcc   180
gccgcgagtt cgcgaagaag ggagccgtga ccgtgctcgc cgctctcgtc tccgagctg    240
ctcgggcggg ggtagcccac ctcctcacgg gaggtggcga gtgacgcggc tcggcagccg   300
ggccggccgc cggacggagg caggagcggc ccggccgaa gccggccgc cgggcccgct    360
cgcgggccgc cttgatggag tagggaaagt tctaccgcgc ccactcgcca cgccacgaga   420
cgtgccgcgt acgtcgtcg gtcatgagca cagagacacc cacgaacggc gacggcgaga   480
cgctgtgcgc ctggtgcggc cgtggcccg tgccacccag ccggggaacc aagccgcggg    540
cctactgctc gcgcagctgc gtccagcgag cccacgagtc gcgaaagctc cgcaagaagc   600
tgctcacggt gtacatgaag ggcgggccg aggaggctga gctgcgcgga ggaaagtcac    660
gtgacgatgc aggaaagtca cgtgactttc ccgtcggca ggcccagca aagtcacgtg    720
actttccaaa accccaggtc aaccctgggg ttccgcgtcc cgcggtcccg gtgacgtccg   780
cgccccggtc gaaaggccgg cgcccgctgc tgccccccgc gccgggcgtg acgcgggaga   840
cgctccccgc t gttcggcgac gacgacacgc agcccggccc tcgatgcgg cgcgcgaaca    900
cggagtgacc acgacggccg tcaccccatc gcggcagcag cccgctcccc atcgacccga   960
gacgggcggt gcgtcgcct cacgcagccc agccccgcga cggcggggt acgggggtc      1020
cggcgactcc tggcccgcca gacggccgca cagagccgcc gaccccccac ccctcccgc    1080
cagccgtcgg cgacgcgcac aacgacgatg cccggcggcc gggtgacggc ccgccatgta   1140
aaccgctcag ggatgccgct cgtgggcagc agaaagcgct ccggggtgtct cggacggggga  1200
ctcaatgggg aggtagggcg ggggcctggg gtcactcgcc catgggcacc cgggcgccgg   1260
gggcgtagac gtcttcccag tagccgagcg cctgttcgtc gtcgtggaac gtgacggtgg   1320
tgaccatgac ggcgatgggct gagtgggccg ggggcgtcga tctcagagcg ttgagttcgt   1380
cctgggacgc ctgccgtgcg tgggcggccc gctgtccctt caccacttcg cgaccggtgc   1440
gtcgctgta gagcttgtcg aactgcttca ccatccgtac gtcctcccc agctcgggga    1500
cggcggccac cgtgtgggc gggtagacgg agacgccgac cgacgtcggc ttgtcgtcct    1560
ggcggaagac gcgaatgcgg atcacggctt cgtcgccggg ctcaggtgtg agagccgtgc   1620
agatctcggc gatcgtggacc gacccgggtca tcacgcggtg gccggaggag gtctcgccgg  1680
gcgcgtagcg catcccgttc ttctccatgc gcttcaagcg gtccgcgcca gtgatgacga   1740
tgggggttctt ctccacgacc gtaccagcg ccccgcgcga gctgaccagg ccctcgctct   1800
```

```
tcagcacggc caaggcccgg ctcacggtct tggccgccac gccgaactgg gcacggatgt 1860
cagcgacgga cggcagcgtg tcgcccggtg cgagttcccc gctcttgatc agcgtgcgga 1920
agtgggtggc cacgtcggca tagcccttcc cctccggtgc cttgtatggc atggcttctc 1980
cctgtttgtc ggagcgcggt acaccccga aggtacatca atgacccccc caaggtacat 2040
ccttgcttcg aatcggtgct tgatgtacct tcgtggccgc ggcaaggtac gttaagtacc 2100
tcccgctgac tgatgcgtac cttcggcaag agagggtctg tcgtggccac gaggaacgtt 2160
ccgcccccg gggcgaacaa cagcaggaac aacaagttcg ccgacatggg ggcggcggcc 2220
ggcggtttc tcggtgcgat gggcggctcg ttcgtcccgc ccgtgaacgt cacggtcaac 2280
cgcacgacca acaagggcgg tggcggacag cagtccggcg gccgccagtc gcatttcatc 2340
ctcggggagc cggagttcaa ctcggctgag gacgtgcgca actactgcaa ccacgtccgc 2400
gccctgatgc tccaggccgc gatcgagctg gccatggccg ccaagatcct ggaggcccgc 2460
ctcgcccagg cgcagacgct gcccggtgac aatccgatcc agggccggat gcgggcgcgg 2520
aaggtcggcc ggagcctcaa gaaggccgcc gacgcgcca cgtccgccgc gaagggcgcg 2580
gtcaccacct acggcgcctt caccgcgag tacgcccgacc tgatgcgccc ggccccccag 2640
cgtcaggcgc ccaccaaccc cttcaagttc tgagaggcgg taccgagatg ggcaaggacg 2700
ttcagcagca gcaggaagac cgcctcaact ccggcggcac gggaatggggt gcctggctgt 2760
ggcaccgggc caagccgtac accccgccgt ggatcgtcac gggcgcggtc ggcgcggcgg 2820
gcgccggcgc ccacgagctg tggggcaact cgcccctggc cggagtcggc ctcacccctcg 2880
cggggggtcgg cctgacggcc gcgacctggt gggcgggcaa gtccaccggg cagcagcgcc 2940
gcctccactc cgccatcacc gtggcggccg ggcgacctg gttcaccgcc tccgccctct 3000
ccggcccgct caccggcccg ctgcccgacc tgtacctgat gggcggcacg agcctcgccc 3060
tgacctggaa catccgccag gtcatcgcgt cgtcgacgcc cgagggcgcc ggatccgact 3120
cggacaaggg actcctggag aaggtcgggc tcgcccggac caagctcaag gacgtcaagg 3180
tcgagcccaa ccgcgtcacg gtccctacg agctgcctgc cggggagctg accaacgacg 3240
acatcaacaa ggccatcccg cgcatcgcgt cggctcgcga cgtgccgacc acggccatcc 3300
gtgtccagca cgaccccgac tccgcgagga agggccagt cgtgatcgtc gccgaggaca 3360
tgctgaagca gcccacgatc tggcccggcc cgttcgcgcc cggcgagtcc gtggccgtgc 3420
gctgcggatc gcgtctacga cgacgcagcg acctggttct cccgctcctc gacgcgatcc 3480
acctgctcgt catgggatg accggctcgg gcaagaccga gggcgccgtg gacctcctgc 3540
tggagatcct gacccgcaac gacgtgaccg tgtggctcgc ggccgcggcc aaggccggcg 3600
aggacttcca gcccctcgtg cccgccctcg actgggcagc cctggacacg gcgtcggccg 3660
gagcgatggt cgacgcggtc caggccgtca tccccgcccg caccgcctgg ctgcgggacc 3720
acagctaccg ggcctgggag cccgcggccg ccaagacgca gaccaacccc gcgcactcct 3780
gcgcgtcggc cggcgcctgc ggctgccccg ggatgccgta cctgctcacc tggttcgagg 3840
aggcggccaa gctcctgcgc gagctggcg acgacgtgtt caccggcatc gcccaggagg 3900
cccggtcggc gggcgtctcc ctggtcgtct ccatgcagcg cgcctccggc taccagctct 3960
cgacggacac gagggcctcg ctcccggccg ccatgtgctt cggcgtccgg ggcgacgacg 4020
ccgggttcgc cctccccgag gaggtcctgg acgcaggtgc caaccggcc gcgtgggca 4080
acaagcgcaa gggctacgtg tacctgctgt ccgccgaggc cgaggaggac cgtgtacgcca 4140
accccgcccg gacgttctgg acgggcccccc cggccgaggg cagctacgag cggatgccc 4200
gctacgtcgt cgagcacttc gcctcggttc gtgccgagct ggaccggtg accggcgccg 4260
ccgccgagca ggctgcggga ccgctgttca ccaaccgccg tgcccgcgcg ggcgccgcct 4320
ccgccccggc ccgcccggtc caggagcaga tgctcctcga caccgccgcc caggaggacg 4380
gcgacctcgt ggagatggag cacgacggca tcgacctgag cgccgacctc ccgcccgtgg 4440
agaacgacgc ggaactcccg ccggccaagc cgtcgaccga ggaggccgc gagctcctcg 4500
acgaaatggt cgccacgctc gcctcggtcg gccccgcac ggtcgctgtc cgcgacctca 4560
agccgtacct ggagcagatc ggccgtgacc gctcctggtt ctcccgcgag atgaagcgga 4620
tggccgagga gggccgcctg gccgccacgg gcgaggaggg cgtctaccgc ctcatcccca 4680
cgctcgccgg ggtctgagac ggcccgcaca gccgcacagc cgcacagcgc gaatccccac 4740
gtcacacggc gtgtgaagag ggccgcacac cgcctcgcac accgtgcgca cagccggacc 4800
gcacaccccc cgcacaccga acgacgacgg accgccccgc agcaaccggg gcggcccgcc 4860
cgatgaccac ggaggtagag cccgtgacca ccgaccgaa gcatctcacc gactccgagg 4920
cttccgccga agctgcccgc ctgatccgcg aggcgtacca gccgaccccg gagccgcgcc 4980
ccatgacctt ccgcgacacc acccggtcac agcgttcggc ccgacccgcc cgtgcccag 5040
cccgagaccc ggatcgtccc cgagtcggcc gccggggtcg ccgtcgcctc catcggcatc 5100
ggcgccggcg tcaccggcct cggctgcgga gcctggctca tcttccaggg cctgtcctcc 5160
gtgaccctgc tcggagtcat cgctatcgcc gccccgttcg tcggcgtcgc cacggtggcc 5220
acggccatcg gcgccgccat ctccaaggcc aagcgctcgt cgaccacgaa cgtctaccag 5280
gggaccgtga tcaagcggac cgacatcacg tcgaccgccc gcggcatcgg cgcccgtcc 5340
cggatcgagg gctgagcgcc atgcagatga acactcagga gcaggtcgag caggcggaga 5400
aggtgctccg gctgagctgg atcatcgtct tcggcgtgat cctgttctcc gtcttcacgg 5460
tgacgccct ggtagagcgg tccactccgg agggctggga gtggtcggcg ccgatcctgc 5520
cgctcgtggt cgacgtcgcc gtcgtcatct cgatccgggt cgacgcgatc gtgtcccggc 5580
tcggagggtc gaccaccggg tggccgctcg ccctgccggt gctcaccggc gcgcctccg 5640
tggcgctcaa cgtcgggcac tccgtactcc agggcgacct ggtgggcgcg ctcgtgcaca 5700
cggccgccc ggcggtgctc atcgtcgtcg ccgaagcgtc gctcaagtgg cgcaaggaga 5760
tcgccgccgc cacggcccgg atcgaggctg agcaccgtga gcgcgaggac gcccgccgcc 5820
gtgagcagcg tgagcgcgag gagaaggcgc gggccgaccg cgacgtgag caggaggccc 5880
ggcgcctgga gcgtgagcgg caggaggccg ccgccgccgc gaggaactcg 5940
ccgaccgtga gcgggagcgt gagcacgccg cccggctcgc caacaggag cgtgagacga 6000
ggcccggctg gaggccgagc gcgaggaccg gccgacgcc cgccgccgcg aggagcagga 6060
ccgccaggag cgtgaacgcg agaaggagcg ggagcgcagg agcaggagcg ccgtgagcag 6120
gaggctgccc gcaaggccaa ggaggccgtg cagaaggccg aacgggaccg gaaggcagcc 6180
gaggccgcga agccgcgcct cgcgccgctg agcgctgctg tgagcacccc gagccccgcc 6240
gtgagcgccc ccgtgagcac tccgctcac gagactgctc acgacgccaa gcccgtccag 6300
aagatgagcg aggccgacgc ccgccaggcc gtgccgacg cggtccgtga gggccgctca 6360
cagcgtcagg tggccacgct caccggctgg tcgaccggct gggtcgccgc ccgcttcaag 6420
gagcttgagg gggccgccgc atgagccgcg ccctgatgta cgcgctcatc ctgccgctgt 6480
tcgcggcgga gtgctgggcc cagttcgtgg tccatgacca gcgctggacg acgctcttcg 6540
```

```
cnctnntcgc cggggccgtg ctcgccgtcc gctacgccct cggtccgcgc acggacgacg  6600
aggaatgcct gcccgactgc ccgaagtgcc gcgaatccag gggggacctg tgagcaccac  6660
cgaccagcac ctgaccgcac agcacgccga agtgaaggcc gagatcaccc gcaccgacac  6720
gaagaccgcg ctcttgctcg ccttcgtcgg cgcggtcttg gccggcgcct ggtccctcgc  6780
ccgagacctc cacctcaacc ccgtcgcgta cctggtcggc gtcctcggac tcgccgccct  6840
cctcgccgcg gccggcctcc tgctccggtc ggtccgcccg aacctcaacg gcgggcacgg  6900
cttcccgctg tgggccaccc tcaccccgca gcagctcacc gccgccgccg agacccgcga  6960
cctggccgcc gacgtcgtcg cctgtcccgc ctcgccgttg ccaagttcac ctgcctgcgc  7020
ctggccgtcg acctgacctg cacagggacg gcgtcctcct cgtcctggcc gccgtgatcg  7080
ccctcggagg tgccgcatga cccgcaagcc cgccatccac gacgccgagg cccacgtcgt  7140
cacctcccac ggcagccgac ttcttcaggc gaggaccgcc acccgctcaa ccgggtcgcc  7200
tccctcgccg ggtacgccga gggctgcctg ccgtacgccg aacagccgcc cgctggtcct  7260
gctgctgacc aaccccggcg acggcgggac catgacgctg ctcaggccgg agagatggcc  7320
acgctcctgc ggaagctcgc ccgccaccgg ttcgtcaaga ccagcgccgc cgcccacgcc  7380
cgcgcactgg gcgacgccgc cgcccgcgcc gccgccgacg cgagccctgg gaatggcgga  7440
tcgaagccgc tgcctgaaca ccgaagcccc gccggctttt cggctggcgg ggcttccttc  7500
ggcccgtcaa atcacatctg ccccacgggc cgtgtcgcgt gccggggga acctccggca  7560
caaaaagtgc caggatcacc cccagcaaag cgaaacggcc agggattagg gccccctgac  7620
gcttctgacg tccgcccgga taccaaccaa gggactcgtc tgttgaacag ggtaagggac  7680
gctgaggcgt ccgcaagagc actcccggct cgcgccgtcc gtccgcgctg ccactgcggc  7740
actgcgatcg agcacacgcc cggcaaacgg ccgcgcgtgt actgctcgaa cgcctgcaag  7800
cagcgggcga agcgcgctct tgccaagatc gcccgggaag ccgccgacgc gcgtccgacc  7860
cccaaaacgt gtcgcgcctt gggaaagaaa caacagagtt tccgcacccc ctccgacctg  7920
cggaaacgtc ggcggggggca aaaccggtcg cggacagccg ggacgacgcc gcccgcgccc  7980
ggaaggctcg ccggtacgcg aaccgccgga cgctgtggcg gatcaccggg gacgccgcgt  8040
gcaaggcgtg cggccggggcc ctgatggacc cgcctccgg cgtgatcgtc gcccagacgg  8100
cggccggaac gtccgtggtc cttgggctga tgcggtccgg gcggatctgg ctctgcccgg  8160
tctgcgccgc cacgatccgg cacaagcggg ccgaggagat caccgccgcc gtggtcgagt  8220
ggatcaagcg cgggggggacc gcctacctgg tcaccttcac cgcccggcac gggcacacgg  8280
accggctcgc ggacctcatg gacgccttgc agggcacgcg gaagacggcc gacgctcccc  8340
ggcggccggg tgcctaccaa cggctgatca cggcggcac atgggccgga cgccgggcca  8400
aggacgggca ccgggccgct gaccgcgaag gcatccgcga ccgatcggc tacgtcggca  8460
tgatccgcgc gaccgaagtc accgtgggcc agatcaacgg ctggcacccg cacatccacg  8520
cgatcgtcct ggtcggcggc cggaccgagg gcgagaggtc cgcgaagcag atcgtcggca  8580
ccttcgagcc gtccgaggcc gcgctcgacg agtggcaagg ccagtggcga gccgtgtgga  8640
ccgctgcccct gcgcaaggtc aacccgcagt tcacgcccga cgaccggcac ggcgttgact  8700
tcaagcggct ggagaccgaa cgcgacgcca acgacctcgc cgagtacatc gccaagaccc  8760
aggacgggaa agcgccggca ctcgaactcg cccgcgccga cctcaagacg cgcaacggcg  8820
ggaacgtcgc cccgttcgaa ctcctcggac ggatcgggaa cctgaccggc gcatgaccg  8880
aggacgacgc cgccgggggtc ggctcgctgg aatggaacct ggcccgctgg cacgagtacg  8940
agcgggcgac caaggggcgc cggggccatcg aatggacccg ctacctgcgg cagatgctcg  9000
ggctcgacgg cggcgacacc gaggccgacg acctcgacct gctcctggcg gccgacgccg  9060
acggccgcga actccgcgcc ggggtcgccg tgaccgagga cggatggcac gcggtcaccc  9120
gtcgcgccct cgaccttgcc gccacgcagg ccgccgaggg aaccgacggc aacaccgatc  9180
cggccgccat gggcgagagg gtgcgcgagg tcctggcgca cgccgacgcc gccgacgccg  9240
tggtggtgct cacctccggc gaggtcgccg aggcgtacgc cgacatgctc gccgcccctg  9300
ccctgcgccg cgaggaagca gctgcacgcc gccgccggga gcaggacgac gaccaggacg  9360
acgacgccga cgaccgccag gagcggggccg cccggcacat cgcccgactg cggaactgat  9420
atcgatccgc actaactcgc tgcccgcccc tactccgcg ccgacctctc cgtgacccgc  9480
acggagaggt gtcggcggcg gtcggaggct tgcccacgag gcgcgacctg cgaggcagcc  9540
gcaggcttgc ccacgggccc tcccaccctc ggtcccaccc tcggtcccac cttcggtccg  9600
acggtggacg cgacggtggg agcaacggcc gagccccctg ctgaagcaac cccgcccggc  9660
gggcgtcact gatatcagtg acccacaact cgctctgcct gtggttactg cctccgaggc  9720
accgccatcg ggtccgccag cccaccgcca tacgcccgcc cacgaccgcc atccgaccgg  9780
aatgcatggc ggtcccatgg cggtcggatc ggaccccatg gcggacccctt ggcggtgcca  9840
tgcggaccc agcggagcga gcaagttatc gcgagagcaa tgctctcgcg ggcgctcgtt  9900
ggggcgagca agtatccgc ttggagactc cagcggtgcc ccgaccgagg gcggtcgggg  9960
ttccccgggg aggggaaccc cctttgtcct caccccggtt ttgatcacgt cggcctacgg  10020
cgacggaccc gcgcggcgcg agccgtgcgg aacggaaaac ccggctgccg atcccctcgc  10080
cgccgcccg cgttcccgcc ccacctccct ctcctcctgg tgctcgtgcc ggtcgtgggt  10140
ggcgtagagg ggatgtctgc ccaagcggaa gccccgacc atgcgcggtg acgtgggacg  10200
ccgcgaagcc cggaaccgga tccccgcaac acccagcgca acccatggcg caacccatgg  10260
cgcaacaccc agcgcaaccc cgaccaagga cggccgggaa cccgctacga caccccctcg  10320
acgggcacgc cgtcgactcc cggtccgagc gtccgccgtc cttccggtcc ggccacgtcc  10380
tggtgctcga tgtcccccag gagtgcgtcc ggctccactc gctcgacggg cagcagccgc  10440
ggactcgcgt ccgccgtcgg cgtgctcctg tggtgctcg ggccggtgcc gaggtgacgg  10500
cgcggggtgc tcatgacggg agtctcccgt gccgttcccg gagctcccgc agcggccctg  10560
atcgagccgt gcggcttgtg cgttcgtgaa tgcaagaggt gtgaccgttc ttcgcgtgca  10620
ccgtgtgct cgtgcacctg tgcacgcggt acggcttcgc cgcgacttc gtcgtgacgg  10680
gagcggtcac acctcaggca ttacgaatga cctcggctgg tcgcgccctg cgttgtgccc  10740
tgggtcgcgt cctggattcc ggcctgagtc acgtcctggg tcgcaccgga cgggtccccg  10800
gccgcgcccg gttcggcgcc gtgacctggt ggacaagggg gcggtcggct gccgttccgc  10860
gcgccgactt cttgctggga gcggtgtcgg cgggcgcctt cggatcggaa tgcaagggtg  10920
tgcggcttgc tgctgccgta cgtcatctcg aagacgtacg cgggccgtcg gtgacgtact  10980
cgaggaacga ggccgggctc ggctcggctt ggtcgacccc aggggctttt tcgtctgcgg  11040
tcctgt                                                             11046
```

SEQ ID NO: 62    moltype = DNA  length = 3539
FEATURE          Location/Qualifiers

| misc_feature | 1..3539 |
| | note = pGP01 |
| source | 1..3539 |
| | mol_type = other DNA |
| | organism = synthetic construct |

SEQUENCE: 62

```
ccacggtgtt ggatgacagt cctttgttgc cactgtcgca gttttctctt tcgcgaagtg    60
cttgagatcc ttgatgggtg gacagtacgg tatcctcaac cgtggattct acaacggaag   120
ccacaacgaa atcataggag gatatcccat gaaccggacga gtgattgttt ggcctgatcc   180
tgcgctcttg tctgccatgc ctttaagttc cggattttcc ccggtcatgt cgtggaaccg   240
cgagctgaag tgtttcaccg atgtgcagac cacgactgac gacggactgc ctgtctgggg   300
ggcagatgcg tggttgagga tgggatggca accgcacgct gacacagtcc aactgcgcat   360
cgctgcacct cgaaagcctg cggtccagcc tgatcctgcg agaatcgctg atttttttgc   420
gcctcgacgt agtgaggctg agcactgatg gcaggcgaac gaactgctgt tctgaccgcg   480
gtctactggt ggctccgtat cttgccggtc ttattactcg gcgttgcctt cgcgtgctgt   540
tgtttctcgg tgcatctggt ctacgtgatc ggcttgctg ttgcggcctt ggcggtggag    600
gcttttccgc cgtctgtatg gcaggtgccc aagaacatgc aggtgccagc acgatacgtc   660
tatcgctggt ggtggtcctt ggcgaaagcg ttcaagccga ttgaatccta tggcggcgac   720
agaatttact atcgacccgg cttgcagtgg atccgctctg accgacatgt actgcatctg   780
gtgcttcgcg ttcctgcagg tcttgccgac tcggcggcat atctggagaa aggtgcagca   840
gagatccaac gacagctacg tggcaagaag tcttggagga cctgcatcgt caaacctgcc   900
gagcatggcc tggacatcat tcctcgcgac gcgacagcgtg gtgatgagtt acttcctgctc  960
ccgtccacgt cgtcgtggaa cgtgccagtc ggggttaaac ctgacgggtc cgaggtcgtc  1020
ttggatctct cccatccatc ccacatcctc gtctccggaa agactcgttc cggcaagtca  1080
tcgttcgtct acggcctgct cgatcagatg cgtcatcttc ctgtcactgt ggctggtgtc  1140
gacccgaccg gaatcctctt taatgagctg ggcgacggct gggacggtga tgctctgcgt  1200
tccaagcgca tcacgaatga cgctgatgct gcagcagttg tccaggtcct ctccatgatc  1260
accgatgaaa tggatcggcg tatctatctt cttaactgtg agcatcgcga caagtggagc  1320
cgcaacgatt tcgagtccga cccgggacgt cgactcatca tcgtcatcct cgaggaatat  1380
ccgggcttga ttgagcggct gcagaacttc gattccgccg tggcgctcg ctccagtgag   1440
cgttttgcct cgaaggcagc tggcctcgtt ggccgcatcg cgtacgaagg cgccaaggtc  1500
ggggttgtcc tcctccttgt cacacagcga cctgacgcca aaattatcgg cggtccactg  1560
cgagcccagc tcactacgcg ggtgacgttc gcccaagact cagacggatt gcgtatgtcg  1620
catcctgagc tctcatctga gcaggtcaaa cagaattcat gggcctcagg tgtcgggttc  1680
atcgaagcag atggcgtgat tccgctcact cggttccggt cctatcgagc ggaactcacc  1740
gacctgcatc ggcccggggc gtcggtcggc cagatcgatc tgatccagtg aggagctgct  1800
gccgaccgat gccgcggaac tctgagatcg acacgaccac agatgccgta gtcacggaga  1860
cgctcgagga agagatagga ttcagtacca gataaaaat gcctccccac agcgccaact   1920
gcggggagcg gagtaagacc tttttctccc gggtcatgac cgccaaggag gcgatcggtc  1980
ttaaacatag taacactatc caaggcgcag ccacatgatc ggttgtgctc tgagcatgag  2040
ccgtgtgcgc ctcgccgcag cgagcgtcag cgagcggcgg gcgaccgcct ggtaccacg   2100
cgagcaactt ttccggtatc agattccccc tgtagaaagc cgaatgaggg ccgtcgccat  2160
cgctatgaa tgagggatgg tctacgaaat ccgcaggtca tgccgctgga gcgcgttcga   2220
aagtgcgggg cagtgccggt ttcgcaacgg atcgcgttga tggcgggtca tggtggtgcc  2280
ggttatgccg gttggcgac gtgcggaagt gtgtgggctt gccctgtctg tgcggcaaag   2340
atttccgcgc accgtcgtga tgagctggcc cgtgttgtcc aggttgcggt tggactcggc  2400
ttcaaggtgt cgatgctgac gcttactcaa cgtcatcatg ctggtcagga tctcgccgag  2460
ctgtgggcgt cgctccagtc gggttggaat gctgtcacga gtggtcgacg gtggcaggaa  2520
ttttgcgctc agctcggcgt ccagggatgg gtcaaggcag ttgaagtcac ccatgggtcg  2580
catgggtggc acgttcacgt gcacgtgctc gtcatctcta gcaggatcc gactagcgtt   2640
gacactaaga ttcggcatcg ccgcaaacaa ggtcggcgac ggaccccgta tccagaagag  2700
gtacagaggc ccgaagactt catcgctgaa cggtggtcgc gaggtttgag gaagcgcggc  2760
gtcgacttca tcgccggtag tggtggcctc gattggcaga ctgctgattc tggagacgag  2820
gaagctctcg gtcggtacgt cgcgaagatg aactcgtccg tcgatggcct agcgaacgag  2880
gccacgttgg gcgggttcaa gaaggctcgt agaggtaatc ggacgccgtt ccagatcctc  2940
gaagatttcc tggatacggg ctcggagact gacctgagac tctggcgtac ctatgttcct  3000
gcaagtcatg gccgtaaggc attgacgtgg tccaagggtt tgcgtgactg ggctggcatg  3060
gaatctgaga tgagcgatga gcaggtcgcc gcccaagacc agtgcgggga agcggtcgcc  3120
cttttgacc atgacgcgtg gcggcagatc cgcactgccg gtgccgcttt cctcctcgac  3180
gagctgagc tccacggatc cgagggcgtc tacgcctgc tgaagaagcg aagaatccat    3240
tatgagatac ctctagttcc ttggagtacg agtacctagg agccagtcgg ggtctgtcaa  3300
ttttttagct cctccatttc atcacactct ttctatgatg aagtcatcac aattcggtat  3360
tctttgactc ccctgagaag ccgataatca ggccagtaga gctatcttat gtgcctaggt  3420
ggatactatt tattcttcac ctatcaggga ctctggtcga tcacagcctc cgtcgacgat  3480
gacacatctg actaggtact atgatgactt catcatagac agaggtggag cacagacga   3539
```

| SEQ ID NO: 63 | moltype = DNA length = 8136 |
| FEATURE | Location/Qualifiers |
| misc_feature | 1..8136 |
| | note = pIP501 |
| source | 1..8136 |
| | mol_type = other DNA |
| | organism = synthetic construct |

SEQUENCE: 63

```
cctgctcggg accccccta gaatttcgtt attcaccaaa aaaatacgca tggtataaag     60
caccaagcga ttataaaaaa cgtagtcgaa aaaattatga tatggacaca ataagggaa   120
tgtatgaag ccaaaaaatt aaagaagaaa agcagaaaa aaatactta caagcccgat     180
agggtttgta agtttatcag aaaggaagtt ttaagtgga tattaaaata aaaaaaataa   240
attttgaagg taatatttta aaagttataa agcgacagt aacagaaatg agaggaataa   300
```

```
ataatcatca aaaatatgat tttgattttat atcaaataga agcacgttcg ccaatgtcaa    360
caagagaaat aactttaaca gttgacttta tagaaaaaaa gtatcaggtg atattatcgc    420
ttttggtgat tggtacgatt tggatataga atcagtaaat gaaatattaa agcaattaaa    480
aaaggaagaa caaacattaa gaacaatcaa ttttatttaa aaaagtatca aaaaaggaa    540
aattattttt cctttttttg atacttttta ggtttatttg cttaatata ttcagaaaaa    600
atttttaaaa attcttccgt ttcttctaca gttaaatagt caatttcaaa atactttct    660
aacaaagcac cttttcaat tagacgcttt gttcttcttt ttctgttaat attttgctcg    720
ctattcgctc gcaaaatatt ttttgaatt tttagttttt ctattctttt gttgatgtca    780
tttaaatcat tatttgccat aactatttaa gtaattcaga aaaatttga ctattcgcat    840
ttaataaagt ttctaattcg tcatagaata attctttgtt ttcttcaatt gattcaatag   900
aaatattatt ttttgaaagg gtagaaagaa caaagtcacc aatatctgct ttagacttta   960
gaattaattc ttctttttc ttttgtaatt ctttaatttg aagttcaata tcagaaacag  1020
ttttcttctt tcttttttt ggcttcgttt tagaattaaa attaccatta attgcattaa  1080
tattttgatc ttgattttcc atgaaatacg cctcctaata tattgtgtaa ctctatcata  1140
ttatattatt tttctaaaat caataaatat aaacgaaat gtcaggttaa acatatttac  1200
ttttataatg ataagtggta aaattaattt attaaggatt cccttagatt atttactaag  1260
ggcgcactta tacgcagtaa cttcgttact tcgtatttat gctataaaac ttaactgtta  1320
gttagttta tcgtcaagcg tgttttgttaa aattcgctac gctcatgttt gaaaagaaag  1380
agaggtgata caattggcaa tcttccattt atcaatgaca atagcaaaaa gagaaaacgg  1440
aaaaagaagt ttaatcgcaa tggcttctta tcgaagtggt gaaaaattgt atagtgaact  1500
atatgaaaaa actaatctat acaaccatag aactgttaaa ccagaagctt ttattttaaa  1560
acctgattat gtacctaatg agttttaga tagacagaca ttatgaata aaatggaatt  1620
agcagaaaaa agtccaaacg ctcaactttg tcgagaggta aatgtagcat tgccaattga  1680
attaaataat tcagaccaaa gaatgttgat tgaagatttt gttaaagata attttgtcaa  1740
tgaaggaatg attgcagacg tagccattca tagagatgat gaaaacaatc ctcatgctca  1800
cattatgcta acaatgagag aagtagatag tgaaggcaat atcttaaaca aaagtcatag  1860
aatacctaaa ctagatgaaa atggcaatca gatttttaat gaaaagggc aaagagtaac  1920
cgtttcaatt aaaacaaatg attggggtag aaaatctctt gtttctgaaa ttcgtaaaga  1980
ttgggcagac aaagttaatc aatatttaaa agatagaaat atcgatcaac aaataacaga  2040
aaaatcgcat gcggaacttg gaaaaaaaga actaccaaca attcatgaag gttttttactc  2100
aaaaaaatta gaagacaaag gagttataag cgagttaaaa agaaaaaatt tagaaattca  2160
aagttacaat gatattctag ccgaacttga taaacttgaa aatcaagaaa agtattaaa  2220
acaagaccaa aactttactt taaaatttga aaaaactttc tcacctttag aaaaaggaga  2280
actgaaaat ctttcaaaag aattgaaatt atttattaat gatgaaaaca ttgataaacg  2340
attaggtgaa ttaaaacgat gggaaaattc acttatcttt aataataaaa tggaaattca  2400
aaaacaacgt ttgatgttaa gtaaaattag tagtgaacga gatatgctta caaaggcaaa  2460
tgaaatttta gacaaacaag cagaaagatt cttcaaaaaa tcttatccaa gtttgaatat  2520
tgacaaattt tcaaatcacg aagttagagc aatggttaat gaaaccatat ttagaaaaca  2580
gttattgaat aagaccagt tagcagaggt catttacaat gaaagagtag tagaaaaaga  2640
agaaagtaaa aagattttta agaaaaaacc atttcaaact agccgttatc ttgattcaaa  2700
aattaaacaa attgaagata gtataacaaa agaaaataac cctgaaagaa aagaaattt  2760
atcaattaaa aaagaaaaac taataggaat aaaacaagga ttgatagaat atgttcaatc  2820
agaagttgaa agaaaatttg ataaaaatgt ttcaatagat tcagtcatag aaggtgaaat  2880
gttacttgca aaagctgact attacaaaac aactgattt tctaaagtcg aaggagttgc  2940
tagattcagc agtgaggaaa ttaattccat gttggaacaa tcaaaaggct tcttaactaa  3000
cattcagacg gtgaaaattc ctaatgattg tcaaggtgta tttttttgttc aagatagcat  3060
gaaacatatt gatgaactaa gcccattagc aaaacaaaat ctgaaaaagg ttgttaatcg  3120
caatgcttat ttacctgatt ctgataagat agaattaagt aaagaaattg aaaatccaa  3180
taaagatcaa tcccaagaat tggataaaga cgtaccagaa aaaaatgaag tgactgtaaa  3240
aatgttccaa tttgcgaagt caattaatcg tttgttgagt ggtaaccaac tacagaaaaa  3300
acgaaaccta gacaaattga ttaagcaaac aaaagcaaaa aaaaatcaat cattacaaag  3360
gaatattcct ttgcgataaa ataaaaacaa gaggtgtata aaatgaaaaa atttatcaaa  3420
gatacaaagt ttaagcttgg aagtgcggtt gttgcgttgg gtacattgtt tattactgat  3480
ccagtgtttg cagccactga tccacaagcg aaattagttc aagcgggtaa cactataaaa  3540
ggtgtttaa cagccttaat tgttgtagtt ggtgggattg cttgtgcgaa gattgttatt  3600
aaatacttgc cgtctattga tgacccacaa gaaaaaaata ccatgctataa agccttggga  3660
acagccttgc ttgttacggc attaggtggg gcgttggttt ggttagtacc ttgggcgtat  3720
ggcttacttg cttaatagag aagggagtta gttatgaata gcgatcaagt gaaacaagcc  3780
ctattagatt tgttaaatgc agacactgaa aaagggcgga cttggttttt tccgtctaat  3840
gtatctgatc ggtacacagt cattttaggg ctagatttaa aacaatcagc aaaagcgatc  3900
ggtacggcat taataagcgt gttattgaca attcttatt tccgtagcac agccgttttt  3960
cctttaatta tctatgtcat tgttggttg gtgtcatttg gtggtgtatg ggcgtttat  4020
acgattaaac caattacaga ccgacctaac atttctatat ctgattttat gaagcaaaga  4080
aaagacttt ctaaaaagacc aaaagtctat tacaaaaagc caaaagaacg agtgataaag  4140
agaggtgatt taattgtttg attttctaaa aaaaagttcc aaaagtaacg ataataaaa  4200
aagcgatacg atgaaagaaa tgatttattg ggaagatagt tcccgatttc aaggcgtttt  4260
taaagacttt tttgtcgttt atcagccaga aaaaagcaa ttcagccttg tgagtatgct  4320
aaaagttgac ggcttaaacg ttgataccttt gccagtatca gagcaagaag ggttaaacga  4380
agattttgat gtcttttctat ctcaaaacgt tctatatgca ccgcagatca cttctaagaa  4440
tgtaccagta gaaattgacg attttgtaga agcctgggg attacagtag aaaattatcg  4500
caaaatgcca gggcataacg aagctttat acaattaaag gctagttact attatcatta  4560
tagaaattta gcaagtaaca tggaaacttc aaagaaacaa cattttgtaa ttaattctga  4620
accaattca aaggaaacat atgatagttt agaattgtcc tatcaagtgt tacgtgataa  4680
gacaaggaca gtcaggacgg cttttaattgc taatgatgat gccaagttga  4740
aatgtgtacg attggcgaga tgaaaaggt tttgaatagt taggagcgtt aaaatggaga  4800
agataccaaa agagaaaatt gtcttgatac ccgaagttga tacggacgtt gtatctgatt  4860
tagcaccatt taacttaca gtagaacgtg acaaattatt gattgatgat tcatacgcag  4920
ttccctatgt cattacaaaa tacaacaata agccacgtgg gaattggttt aatcgtattc  4980
gtaaaatgag tggagatata accatatctc attactacac taaagcaaac ggtaactcat  5040
```

```
tgaatgatta ttacaacaga accattaaga acaagcaagc agagatcgat cgttcgcatg   5100
atccgttgac gattatccgt ttagaacgtg aaatgaaaat tgctcaaacg cagttagaac   5160
aagccgttga cgaaaacact tcttatcttt acttgtacac ctatgttttg attaaaagta   5220
agtcagaaga taaattaaaa aaattgtgtg aagattttga aacacgttgt atcgcaagtc   5280
gagtaaaagc gttaattcca tatactatga ttgataaggc gtattggagt tcattaccgt   5340
tacaatctaa tgaagtacct gaatacacct atacaatcgc taattcaatc agtgcaagca   5400
gtattttttcc ttttgatgat aatgaattaa gtgtatttac taaaaatatg attattgagg   5460
gaattaataa agatactgaa aatatcgtta gtattgatta caccaacaga aaattagtag   5520
tcaatcgtaa taaattcgtt tttggtttat ctggtggggg aaagaccact tacttaacgt   5580
cagactattt aaaaaaatat gcttttttctg ataactcaac agaattaagg cacagaattg   5640
tttttatttga tcccgaagat gaacaaacag agcgtgtacg ttctctaggg ggcgaaataa   5700
tcaatctatc gtctatgtca gatgttcgta tcaatccatt tcaaatttac tcacgcaata   5760
cgctagatgt tgatttaaaa gaatcattat ccgattttga agaggacgag cttgtagaaa   5820
atattgaaat aaagcataaa gattatgaaa tgactgacaa tgatattgat aaagaaatca   5880
gtaaacgaat gaatatttta acgccttatt tcctaatggt ggatcattct ttgactgata   5940
gtcaattatc cattattaaa atagaagcta aaaaatgcta taccactttta tacgagaaga   6000
aaaacttgtc aaaaatggaa aacaccgatt ttccaacatt ttcagactta gaaaatcgat   6060
tgaaagcctt agaagaaact gatccaaaaa gatcaaacg aattgaagat tttatttatt   6120
cattagaaga ttttacaatc ggaagtcgta ccattttttaa cggtcataca aatatagact   6180
taaacaatcc gttaatttgc ttttctttgc gagatttaca gaccgaagaa gggatcagag   6240
atttagcata ccctcaacagc tttagttatc tatttgaaga aataaccaac aatccgcaaa   6300
ttgtaacgtc tgtttatgca gatgaatttc acttttttatt ggagaataaa attagtgctg   6360
acttttttctt ccaagcatat aaacgcttta gaaaatacaa tgctgattgt accgtatcaa   6420
cccaacagat tgatgatgta ttaaaagcac ctgataatat cggtaaagca attattggga   6480
atagcttttac aaaagtattc ttcggacttg atgaaacgga agcacaaggt atttcaaatg   6540
agttgaaact taaactcaca aaaaaagaat tatcgttcat tacctcaaaa cgtcaagggg   6600
aagctttgct ttttcatggt acaaagcgag caaagataaa agtagattta acacaggaag   6660
aaatgcgttt gcttaaccca ggcgaatatg aagatattta cggcgttagt ccgaagaaag   6720
agatcaactg gttgttaaga tcgaaaattc aatagaaggg agaaaaaaat gaaatacaaa   6780
atcttgaaaa atttacaatt ctactatcaa gagaatgtca ttgtcgtcca ataaacgaa   6840
aaatatttga cgaatcgaga acatattttt gatgtagaaa aaagtgaaca atattttgtt   6900
gatgtcgagg agattttgac caaagacgga aagctagaaa ttgtttataa ccgacctaat   6960
ggctatacac cactactaga tttaaaagaa tatgctgatt tttataaatt ggatatagtg   7020
aatcgattac ttgaaatgaa tgtactagaa aaaacaacca cctatctagc aatgcaaaat   7080
atcctactca agatacacg tgacttgctt tttatttata aagcagatca ctttgataat   7140
ttgccttact caactaaaga agaattagag cagtggaaaa attttatttg tagttttttt   7200
ggtaaattca cacttgagaa gtatgagaag aatcgtattg aggttctaac aaaagaaaaa   7260
aattcatttt taaatgatgt agaagcagtt gaaagcttgg aatcattaag agatttaata   7320
aaaaatcgac taaccgaaga acaaaaagaat ttcttttctg ctgaattaca ggacaagaaa   7380
gcagacgtcc gaaaaattcg cagaaataaa agcttaaaaa ttgcgttagt tgtaggtgtt   7440
attgcgttat atgcggtac ggttttactt atgaaagtaa atgagaagaa acaagttacg   7500
gctacacagc aaagcgcaga aacagagatc actattttaa ataagattat tgataatgat   7560
agtgagaata tcgaagaaga tatgcaaaag ctcaattatc ctaagaaaac acaagttgat   7620
atttacgtga aacttggtga ttataccaag gcttatgaac ttgataaaaa gtcagataaa   7680
aaaattattc aaagtctgta caaacaagga gaaaccgaaa aaatagaagc ccttgattta   7740
ccaggaagcg actatttagc agacttcaaa aagattttag cgtatgacaa ttcaacagat   7800
attgagtatc tggttcaaac tagtaccgat acaacaattg ttgaagcttt aatcgataaa   7860
tcagtaaaag aaaaagacat tccaacagtg aaaaatattc gtcaagtatc aattacacaa   7920
aagaaattag caatcgatcc taaacgtcaa atcagtatga ttgacttatt gattgaaaat   7980
aacagtgaag aattagaaaa tatgtataag gataattctt taaatgagga cttgaagaaa   8040
aaacaaacca atgacttgtt agaagaaaac aacacgttgc ttagtgaaaa gattgaatta   8100
acaaacgctg aaaaagatta ggaaggttgg tgattt                             8136

SEQ ID NO: 64            moltype = DNA   length = 2053
FEATURE                  Location/Qualifiers
misc_feature             1..2053
                         note = pCU1
source                   1..2053
                         mol_type = other DNA
                         organism = synthetic construct
SEQUENCE: 64
ctgtttccat tctgtttctg aaattctgtt tttctgagcc atctgtgggc ctccgtagtt     60
ttggttacag aaaggatata tcagaataaa ataggggtca atacaagtac gattttttata   120
aactttattt tatttgaggg tgaggcccgg tgcggcacga gcgcggcgtt gatggtgccg    180
cgaaaggtgc ctggcgccat gcttggatta aaacatgaac cgtgaagaac tgcgaaactt    240
gttttcgcgg ttctgagggg ttgaccgagc cgcgaagtgg taagcgatga tatgcacata    300
tccacaggca tattttaaaa aggtattttta tagattttttt atctttttaa agtctttag    360
agctatataa ctcattgatt taaaatcata aataagtgtt atctctggga atccgccac     420
cttgttatgg gaattggccc acctatctat gggaaacacc ccacctttact atgggaatta    480
gcccaccttg ttatgggaat tggcccacct tagacgaaac tgtaaaaaat gtatttactt    540
gtttgaactt tgtggtagtg tggagagtaa tttttaaccc acaaaggcaa ggctcatgga    600
taagttgctg aacaaaaaga taaaagtaa gcagtctaac gagcttaccg aagctgctta    660
ctacctctcg ctaaaagcaa agcgcgttct ctggttatgt cttatgcaga cgtatttcac    720
agcttcagta agcgaagatg atgatgagat ggctgtactc ggtgactcta ctttcaaagt    780
aaaggtggct gactatcagc aaattttttca ggtaagccgt aaccaggcta tcaaggatgt    840
taaagaaggc gtgtttgagt taagccgttc tgcggtaatc ttttaccga agaagggagg    900
ttttgactgc gtcgcgcgcc cctggctaac agaggctggc agccgatcag ctcgtggtat    960
ctgggaaatc gaatttaacc ataaactcct gcggtacatt tacggcctga cgaaccagtt   1020
caccacctac tcgctccgcg attgtggcag tcttcgaaat ccacgacga tccgccttta   1080
```

```
tgaaagtctt gctcaattca aatcttcagg cttatgggtt actactcatg cttggttaaa   1140
tgaccgtttc cttttgccgg aatcccaaca gaagaacttg gcagagttga acgatctttt   1200
ccttgatcct gctctcaagc agataaatga gaaaacacct ttacttgcta agtatagtat   1260
tgatgattca ggaaaatttc tgttctcaat aattgataag caaatcccg tctgacataa    1320
atcacgcacac atgagcctgt catttgacaa attttttgtca tgaagatggg cgaatttcca  1380
cacagcaccg gcgccggca aggtgggcgg attcccacac ggcaccgacg cccggcaagg    1440
tgggcggatt cccacacggc accggcgccc ggcaacggtg gcggatttc cacacagcac    1500
cggcgcccgg caaggtgggc ggattcccac acggcaccgg cgcccggcaa ggtgggcgga   1560
ttcccacaca gcaccggcgc ccggcaaggt gggcggattt ccacacagca ccggcgcccg   1620
gcaaggtggg cggattccca cacggcaccg gcgcccggca aggtgggcgg attcccacac   1680
ggcaccggcg cccggcaagg tgggcggatt cccacacggc accggcgccc ggcaaggtgg   1740
gcggatttcc acacagcacc ggcgcccggc aaggtgggcg gatttccaca cagcaccggc   1800
gcccggcaag gtgggcggat tccacacgg caccggcgcc cggcaaggtg gcggatttc    1860
cataacttta attataccctt tgtgttattt gtggattgtg cagctcagtg ggcgctggc    1920
cgtgacggtg cggtgtcccc cgtaaccggc cgcgcggccg ctaactcgca gtacggcgcc   1980
gcgacccgca gcgggccgcc gtacccgcgc gcacggcgc ccactgcgca ccccgtgga     2040
ggacgtgcgg cag                                                      2053

SEQ ID NO: 65              moltype = DNA  length = 1540
FEATURE                    Location/Qualifiers
misc_feature               1..1540
                           note = pBAV1K-T5
source                     1..1540
                           mol_type = other DNA
                           organism = synthetic construct
SEQUENCE: 65
tccgccgccc tagacctagt gtcatttta ttccccgtt tcagcatcaa gaacctttgc      60
ataacttgct ctatatccac actgataatt gccctcaaac cataatctcaa aggcgctaga  120
gtttgttgaa acaatatctt ttacatcatt cgtatttaaa attccaaact ccgctccct    180
aaggcgaata aaagccatta aatctttgt atttaccaaa ttatagtcat ccactatatc    240
taagagtaaa ttcttcaatt ctcttttttg gctttcatca agtgttatat agcggtcaat   300
atcaaaatca ttaatgttca aaatatcttt tttgtcgtat atatgttat tcttagcaat    360
agcgtccttt gattcatgag tcaaatattc atatgaacct tgatataat caagtatctc    420
aacatgagca actgaactat tccccaattt tcgcttaatc ttgttcctaa cgcttttctat  480
tgttacagga tttcgtgcaa tatatataaaccc gtgatagtgt ggttttttat agtgctttcc 540
atttcgtata acatcactac tattccatgt atctttatct ttttttttcgt ccatatcgtg   600
taaaggactg acagccatag atacgcccaa actctctaat ttttccttcc aatcattagg    660
aattgagtca ggatataata aaaatccaaa atttctagct ttagtatttt taatagccat    720
gatataatta ccttatcaaa aacaagtagc gaaaactcgt atccttctaa aaacgcgagc    780
tttcgcttat ttttttttgtt ctgattcctt tcttgcatat tcttcatatag ctaacgccgc   840
aaccgcagat tttgaaaaac cttttgtttt cgccatatct gttaattttt tatcttgctc    900
ttttgtcaga gaaatcataa ctcttttttt cgattctgaa atcaccattt aaaaactcc    960
aatcaataa ttttataaag ttagtgtatc actttgtaat cataaaaaca acaataaagc     1020
tacttaaata tagattata aaaaacgttg gcgaaaacgt tggcgattcg ttggcgattg    1080
aaaaaccccct taaaccttg agccagttgg gatagagcgt ttttggcaca aaaattggca    1140
ctcggcactt aatggggggt cgtagtacgg aagcaaaatt cgcttccttt ccccccattt     1200
ttttccaaat tccaaatttt tttcaaaaat ttttccagcgc taccgctcgg caaaattgca   1260
agcaattttt aaaatcaaac ccatgaggga atttcattcc ctcatactcc cttgagcctc    1320
ctccaaccga aatagaaggg cgctgcgctt attatttcat tcagtcatcg gctttcataa    1380
tctaacagac aacatcttcg ctgcaaagcc acgtacgct caaggcgttt tacgctacga     1440
taacgcctgt tttaacgatt atgccgataa ctaaacgaaa taaacgctaa aacgtctcag    1500
aaacgattt gagacgtttt aataaaaaat cgcctagtgc                          1540

SEQ ID NO: 66              moltype = DNA  length = 383
FEATURE                    Location/Qualifiers
misc_feature               1..383
                           note = Cos PAC7 383
source                     1..383
                           mol_type = other DNA
                           organism = synthetic construct
SEQUENCE: 66
gaccacatca cacccgtcag ccggggagga ctcaacaccc tcgacaacgg gcaaatcatc     60
tgcagaacat gcaacagaag caaaggcaac agaaacacaa caaacatcaa attccaacaa   120
caaaccacaa aaacattgat tccatggtga aaaacccgcc aaccccacc gggccaccac    180
cctgcacacc cgtgcaagac ctcgtacggc ttagtgaaat acctccctt tgttgttta    240
tcgttttgtc gactttttgt ttggtggtgt gtgtggtgca gcctgagctt cctgatagtc    300
gtgattggtc tgggggagacg cgtcggtggt ggtgtgtgtg gggcgaggat ccgcgtgccg    360
ggttttgtgtc tgatgaggag tgg                                          383

SEQ ID NO: 67              moltype = DNA  length = 511
FEATURE                    Location/Qualifiers
misc_feature               1..511
                           note = phage PAC7 origin
source                     1..511
                           mol_type = other DNA
                           organism = synthetic construct
SEQUENCE: 67
cgacatcagt cttaaagtct taaacacttt aagtaactttt aaagcttcaa ggcttagccc     60
ttaaggatct aagttactat aaaagcttta aacacttaaa gtaactataa agcttttaaga   120
```

```
gcttaacatt taaggatata aataaacatt aaagctttaa agtcttaaag taaatatata    180
accttaacac ttaagttaag tataaaacct taaaggctta gcacttaagg atataaactt    240
aacatcagtg tttaagactt aaagagttaa agtaactatt aagacttaaa ggcttataag    300
ctttaatact ttaagtagct ataagacttt aaaaacctga agtacttaaa gttaaccatc    360
agtcttaaac tttaatatta taagtattaa agcttataag ttataaaagt ttttagaaga    420
gttaaagggt taacttcttt acttctcttc tctcttttgg tctttctctc ttctcttctt    480
ttcttcatca ggggagaaga ggaacccttta a                                  511

SEQ ID NO: 68          moltype = DNA    length = 29768
FEATURE                Location/Qualifiers
misc_feature           1..29768
                       note = PAC7
source                 1..29768
                       mol_type = other DNA
                       organism = synthetic construct
SEQUENCE: 68
tgcaggtgct gacggtgtga acggcgttga cggcgctgat ggtcgggatg gttctgccgg     60
tgagcgcggc ccgcaaggcc cttcaggtcc tgccggcccg caaggtgcac agggtgaacg    120
gggtgagcgt ggtcccgccg gtgcgaatgg atcggatggc catgatggta aggatgggcg    180
ctcggtggtg tctgtgtact gttccggggg ccgcctggtt gtgaaatata gtgacggtgt    240
ggcttccacg atatcgggtt cggcggcctg ccagggtgtg aaaccgtcgc ctctagtgac    300
tatatcatcc cacaaataga aaggagtggc tgtgatggtg gtgtttggtg gtggtgtgtt    360
gtgagatata ttcctgcggc gcatcattct gccggctcga atagtccggt gaataggggtt    420
gtgattcatg cgacgtgccc ggatgtgggg tttccgtccg cctcgcgtaa aggacgggct    480
gtgtccacgg caaactattt cgcttcccca tcgtctggtg gttcggcgca ttatgtgtgt    540
gatattgggg agacggtgca atgcttgtcg gagtctacga ttgggtggca tgccccgccg    600
aatccgcata gtttgggtat agagatttgc gcggatgggg gttcgcacgc ctcgttccgg    660
gtgccgggc atgcttacac tcgtgagcag tggctggatc ctcgcgtgtg gcctgcggtt    720
gagcgtgccg ccatcctgtg tagacgtttg tgtgacaagc atggtgttcc gaaaaggaaa    780
ctgtctgtgg ccgatttgaa ggccggtaaa cggggtgttt ggccgcatgt ggatgttaca    840
gatgcgtggc atcagtcgga tcatgacgat ccggggccgt ggtttccgtg ggacaaattt    900
atggctgtgg ttaatggcca cggcggcggt tcaagtagtg aggagttgag tatggctgat    960
gtacaagcgt tacataatca gattaaacag ttgtcggcac aggtggccca gtcggtgaat   1020
aagctgcatc acgatgttgg tgtggttcag gttcagaatg gtgatttggg taaacgtgtt   1080
gatgccttgt cgtgggtgaa gaatcctgtg acggggaagc tgtggcgcac taaggatgct   1140
ttgtggagtg tctggtatta cgtgttggag tgtcgtagcc gtcttgacag gctcgagtct   1200
gctgtcaacg atttgaaaaa gtgatggtgg tttgttgtgg gtaaacagtt ttggttaggt   1260
ttgctggagc gtgccctgaa aacttttgtt caaacgtttg ttgccgtgtt gggggttact   1320
gcgggtgtca cctatactgc ggagtcgttt cgtggtttgc cgtgggaatc cgcgctgatc   1380
acggcaacgg ttgctgctgt cctgtcggtt gctacctcgt ttggtagccc gtcgtttgtg   1440
gccggcaagc ccggcaagca gcccaggtg gatgcgggtt tggttccacc ggatgatggg   1500
ggcttggttg agccgcatat ggtggatgtg tcggatcctg gcatgatcga gccgacggat   1560
gatgcggtc ttgccggcta tgagcctcgg cgtgcagccg agtcggaggt tggcacggta   1620
gagtctactg ttgcataatt gaatatagat gtgtgcccca gcggtgctgc cacgattgtg   1680
tggtggcggc tgctggggca ctattttgt atatgcggtg tggctatgat tcgttgctgt   1740
cgatggtgtc ttcgagcatc tgatacaggt ggaggcaggt agagatagtt tcgctggcct   1800
gatcgagaac gttccggccg ataacgtttt tgtggttgtc gcggtggcgg atgatagccc   1860
acatgatctc gtcggctgcc gcctgtaata gtttggcctg gtatgcgatt ccggcgagcc   1920
agtctagtgc ttcctggctt gtataggggc tctggtcctc gctgttgccg cgggtgttgc   1980
tgttgtttgt ggggtgtcct gcactgtcgc atagccacag gatttcgctg cactcgtcta   2040
gcgtgtcttg gtcgatagcg agatcgtcga ggctgacatt gttgacggta aggttcgtta   2100
tgtcgaggga gatgggtaca ccgtactggt tttcgacact gtcaacaatg ttttccagct   2160
gttgcatgtt ggtgggctgt tgttggacga tacggtgtat cgctgtgttg agggtggtgt   2220
aggtgatgtt gtgtgtgttg tccatggttt ttatgccatt ccttcgttat cgtctggcat   2280
gtagtatgtg ctgtttgcgt actcggttaa cgtcatcagt gtttggtctg cccactgttt   2340
cacggtttgc cgggtgactc cgagtcgttg ggcggctgtg gcgtaggttt gatcataccc   2400
gtatacttcc cggaatgctg ccaacctagc taggtgtttc ctctgtttgg atggttcaca   2460
ggtgagggtg tagtcgtcga tggctagctg tagatcgatc atggagacga tgttgttgcc   2520
gtggtgttgt ggcgcggttg gtgggggtgg cattcctggc tccacggagg gtttccaggg   2580
gccgccgttc cagatccatt gggcagcttg gatgatgtcg ggatgtcggt aggttcggtt   2640
cactggtcac cccctgaaca ggtcgttggt gttgttggtg tcgaatcgtc cgacgcagtg   2700
gcagtagtcg tacatgagtt taataatgtg ttggtggtct cccaaatagg tgtttccgct   2760
gatgctgtat gtggctgtgc cgtctttcgc gatggtgtat ttggcggtga tggtttcggg   2820
gttttgggtg tcggtgatga ttgctgtggt ggtggcgtc actgtttgga gatggtggt    2880
ttggttccg tcgtcgatgg tggttttaac catggtgtgt gttttccctt ttgttagttg    2940
cttgttttggt tgtcggctag atgaataata tcggtaaag gttcggctg tctaggtgt     3000
tgtatgtttt tgttggctag ccgttggct acctgtaac acattttggt gtagtgtttg    3060
ttgtctaggt tgtggtattg ttcccgcacc gcaatatata aataagagtc ttgtacagg    3120
tcgtctgcac tgattgcggg tagtgtgcg gctgttttgg tgcatgcccg gttgagtgtg    3180
cgaagatgat ggtctgtggc ccacacccac gatgcggtgg tggccaggtc ggcttttgtt   3240
ggtcgtctgc tcatgcacact atttcatctc gctatctgat agttgtttgg tgttttgttg    3300
tggatagtgt agcacactag tcctgggtgg ccggtgtgtc ctgtgcggtg acggaaccat   3360
gtggattcgc cttccatgga tgggcattgg atgaaggtgc gttgtccttg ctcggagatt   3420
tctaggtggt gccggtgtc ggccatgaga atattagata ccggagttct gtgaattct     3480
tggccgcgcc accaatcata gtgtttaccg gtgcgccatt ggtgcccgtg ggcgtgcagt   3540
atccgtgtgc ctgccacatc aacggtggtg gtcatttcgt ctcggctggg gaagtggaag   3600
tgtaggttgg ggtattggtt attgagctgg taggcttctg cgatgcccg gcagcagtcc   3660
acgtcgaatg agtcatcgta ggtggtgact cctttaccga agcgcacggc ttcaccatgg   3720
ttgccgggga tggatgtgat ggtcacattt ttgcagtggt cgaattggtg gatgagttgc   3780
```

```
atcatggcca tgcgggtgag cctgatttgt tcggtgaggg gtgtttgtgt tcgccaggcg 3840
ttgttgcctc cttgtgacac gtatccttcg atcatgtcgc cgaggaaggc gatgtggact 3900
cgttcgggtt tgcctgcttg ttgccagcag tgttttgcga ctatgaggga gtgtaggtag 3960
ttgtcggcga agtgtgctgt ttctccgccg gggatgcctt tgccgatttg gaagtctcct 4020
gccccgatga cgaaggctgc ggtgctgtag tcggtgtggg tgtcttgttc gggttttggg 4080
ggtgtccatt cggctagttt atcgacgagt tcgtctaccg ggtagggggtt tgttgcgggt 4140
tggtggtcga tgattttttg tatgatcgg cctgtttctc cgttggggag tgtccattcg 4200
gagatgcgtg tgcggcgcac ggtgccgttg gctagattgt cgtcgatggt gtcgatggcg 4260
ttgtcgtggt tggctagctg tgtgagtagc cggtcaatat tgtctatcac tgggtatcct 4320
cctcttgcgg ggtggtgctg gcttgttttgc ggcgatagtc tttaataacg gtggcggaga 4380
tggggtatcc tgcctgggtg agctgttttg ctagccatga ggcggggata gacctgtcgg 4440
cgagcacgtc ggcggctttg ttgccgtagc gttgaataag ggtttcagtt ttggttgcca 4500
tgatgtccta tcggttgtgt ggtgggctgc catcctgtgc ggcagtcgcc gtcgtgtcct 4560
ggtttgcgtg tgcaccacga tacggttccg tctgtgtggt tgagtgtttt accgcacatg 4620
acgtttcgga gatgctccgg cagctggtca tcctggttgc tggtttgtgt gtcgaagagt 4680
gttttctggt tggtgaaatg ttctgacacg gtgccgttat gcacgggtag tatccatgtt 4740
ttccattgtt gttgtagcct ggtgttccag tggaattgtt tggcggcgtt ttcggcctgt 4800
tttaaggttt tgtggtagcc gactagtatg cgttgatgct gctggtctgg aggggttggg 4860
cctcgccagt attgtgccgc cacgcgtag cggttgctgt ctgtgaaggc gtcccagcag 4920
tattcgataa tgtgttgcaa catactgtct ggcaggctgt cagggttgat gttgatgttt 4980
tgggtgataa tgtcacggat ggcttgccgg ttttggtgg tgggtttgaa cgagatgctc 5040
acgatagtac cggctggtcg tcttgcatga actggttgaa gtgttgttc ccggcgtgtt 5100
gggcttgtgt tatttgttgg tcggtccagt ctgggtgttg ctgtttcaga tagtgccagt 5160
ggcacgcatt gtaggtttcg tcttgtagcc gtgtgagatg gttttcgtg atgatttgtt 5220
tccacatggc ccatgacacg tcgagccggt cgaggatttc gagggctggg atgttgaatt 5280
ggttcaggaa gaggatttcg tgggtgtagt agttttttctc gtaggcgtcc catccgcttc 5340
ggtgcctgtt gggctggttt ttggggtagg cttcccggca tactttgtgt aaacgcttgg 5400
ccatgtcgtc gggtagttta atgtcggggt tggcgcggat catggatcgc atcccatcat 5460
aggtggtgcc ccaggtgtgc atgatgtagg tggggtcttc tccgtcggcc catttttctg 5520
cacagatggc gaggcggata cgcctcctgg cagcttggct ggtgttgcgc cggttgggga 5580
ttgggcacgt gtcgagggga tccatgatgt tttagttgtac cttttctggtt tcgtgttgtt 5640
gacaggttttt actgtagcac agtgtctagt gcgtgtgtca accctgtttt tccggcttga 5700
aggtaggtgt ctgtgacatc ccctagggtg aggggcacgt gcacagcttg ggggagtgcc 5760
gcctggaggg tttgggccat ctggtcgcct gcggggtctg ggtctgacca gatgtagatg 5820
tggtcgtagc cttcaaaaaa tttgttccaa aaaatttgcc acgaggttgc gccgggtagg 5880
gcgacggccg accatccgca ttgttcgagg atcatggagt cgaattcgcc ttcgcaaatg 5940
tgcatttcgg ctgccgggtt ggccatgcg gccatgttgt agatggagcc tgtgtctcct 6000
gccggggtta ggtatttggg gtggttgtgg gttttgcagt cgtgcgggag tgagcagcgg 6060
aaacgcattt ttcttatttc ggctgggccg ccccaaacgg ggtacatgta tgggatgggtg 6120
atgcactggt tgtagttttc gtggcctggg atggggtcat tgtccgatgta tccaaggtgg 6180
tggtagcggg ctgtttcttc gctgatgcct cttgctgaga gcaggtcgag tatgttttcg 6240
aggtgggttt cgtagcgggc tgaggctttc tggattcggc ggcgttccgc aatgttgtat 6300
gggcgtatgc tgtcgtacat ttgggttttc ttcttctaat cgttgttgta gcttggcagg 6360
tccgcctccg acaccgcatg tgtggcagta ccagacgccc ttgtcgaggt tgatgctcat 6420
ggagggctgt tggtcgtcgt ggaacgggca gagtatgtgt tgctcgttcc tggacggatt 6480
gtaccgtatc tgataatggt cgaggaggcg gcaggtgtca gaggtgtggg aggagctcgt 6540
tgagggttga taccacatag gcttcactcc atggcttgtt gcgctgtttc atcactacga 6600
gtccgatggt ggaattgttt tgtttgtttc ggtgtgtttc gtagttgcgt gcctcccggc 6660
tggcttgttt cacgaattgg gctaggtgtg gttgcccggc tttcgcctcg ataatgtagg 6720
ttttatggcc ggttgtgagg atgaggtcgc cttcgtcttc gcggccgttg aggtggaggc 6780
gttcgatatt gtgtccggtg tcgcgtagct ggtggaggag tcttgtttcc cattcggctg 6840
cggcccgccg gttgcgtgcc tgctgtgtgg ccatagtttt ttagagtcct ttgtgtgttg 6900
tggtcatgtt ccaggctgt ttttcggcga gtggcccgaa gaatgtgtat tcggggtatg 6960
ctctgagtcg ttcgtatcgg gtgccgtcgg ggctggattt gcctgtgcgc tgtttgagta 7020
cggcgatgcg tgcctctgcc ggtatcgata gcccgttgcc gttatcctcg ccaccataca 7080
atgagactcc gaggatgagt tgtggttttt cggagaggcc gttttttgatt tctcgccgtg 7140
ctggcgggtg ttcgatgtcg gttccggttt tgtcggttgc gtggtgtgtg acaataatgg 7200
tggagccagt atccctgccc aatgctgtga tccattgcat ggcttcttgc tgtgcctggt 7260
agtcggattc gcagtcttga atgtccatca ggttgtcgat aacaatgagt ggtgggaagg 7320
tgttccacat ttccatgtag gcttgtaact ccatgtgat gtctgccat gtgatgggtg 7380
actgaatgat gaatgtgatg tgttggccgt ggtggatgct gtctcgatag tattctggcc 7440
cgtagtcgtc gatgtttttgt tgtatttgtt gggtggtgtg ttgtgtgttg agggagatga 7500
ttcgtgtgga ggcctcccag ggtgtcatgt ccctgatat gtagagggcg ggctggttga 7560
gcatcgctgt gatgaacatg gctagccctg atttttgcct gccggaccgc cccgcgatca 7620
tcaccaagtc gccctatgg atgtgcaaat cttggttatc atatagtggt gcgagttgtg 7680
gtatgcgggg tagttcggct gcggtttggg aggctctctc gaaggatcgt tgtagagaga 7740
gcatcgggac cttaatctat ctgtctgttg gttgtgtggc tggtcagatg gagtcgatat 7800
cgatatcagc atcagcagag gctgaagtgt catctagatg accattatcg cgcttgtcta 7860
cgtattcgag aaccttatcg tagatggcgt cgtccaatgt tttgagcacg accgcgttga 7920
aaccgttttt ggtgcgcacg gtggctagtt tgaaggcctg ctcctcgcca aggtatgcct 7980
ctagttcgcg gatcatggag tgtgggcggt cgttattgcc gcgggctttc tcaataatag 8040
cgttggggat ggtttctggg gtgccgttgt tgagatcgtc tagggtgtgg aagatggtga 8100
catcagcgta gatgcggtct gcgacctgtc accgtagcc ttcagtgttg tgctggacgt 8160
cgtgcacttt gaaggcgatg gccgtggcgt cctggttttcg ggagggggttg aagaaggtgc 8220
tgttgctgtt gttgcggtag tttgcgagtc ccataactat tgtttccttt tactgttgtg 8280
tctgttttttg ttggcttata ttggtttatc gggtgaggct gtttcgctta gtgcggaaag 8340
cgtcggaaac atcactgtta ctggtgatga tcttcttgta ctgttttaga aggtctgcta 8400
gctgtgcctt gcttgttgca ttgttgattt tgttgatgac gatggtgttt tctttggatg 8460
cgatttttgtt gacgtagtct tttggctgcct ggttgtatcg gtcttggagg atgattgatg 8520
```

-continued

```
cgctcgctac gagtgttgct agatcccagt ctttggacac gtcatcgttt ttgagtccgc   8580
ctagcaggtc gatgatggcc tgttttgtct gctctgctgt gtctcctcgg atgaccgccc   8640
atggtgcagc atagtctcca ccatatttga gtgtgatcgt gagtcgatca ttgtcgatct   8700
tgtctttatc tgtcatttgg tgtccttttc tttattgtct gtttctggtg gctgtacggt   8760
ggattctacc gggtatctgt acgagttttt gccgttgacg gcccagcagg cgtctcgtac   8820
ggggcatcct ttacagagtg ttgtgacgtg ggggacgaag atgccttcgc tgattccttt   8880
cattgcttga ctgtacatgg atgatacatg ccggtaggtg ttgttgtcaa ggtcgtagag   8940
ttcggtggat gtgccttgtg tcggggactt gtcgtcgttg cggctggtgg ctggcgtcca   9000
aaacatgcct ttcgtgacat ggatgtcgtg ttggttgagc atgtaccggt atgtgtgcag   9060
ctgcatactg tcggcgggta ggcgtccggt tttgaggtcg aggataagg tttcgccggt   9120
gtcggtgtcg gtgaaaacac ggtcgatgta gccgactatt tttgtgtcat cgtcgaggat   9180
ggttctacc gggtattcga tgcctggttt accgtccagg attgcggtga tgtattctgg   9240
gtggttgcgc ctccatgttt tccagcggtc acaaaggtg gggccgtaaa ccatccacca   9300
gtcgtagtct ttcttgtgtg gtccgcctga ctcgcacatg tttttgcata ttctgccgga   9360
gggtttgatt tctgtgcctt cggattcggc gagggctacc tgggtgtcga aaatgttttt   9420
gaaggatgag agtttgtctg gcagtgcagg gtattcggcg ggattgtaca ggtgtaggtc   9480
gtattgttcg gtgatgtggt gtatggcgct tccggcgatg gtggcgtacc aggtgtggtg   9540
ttgggcgtga tagccgtggg ataggcgcca tttttctccg cattcggccc actgggtagg   9600
tgaactgtag gagatgtgtc ctgggtggct gatggttttc gggtattgtg ctagaggcat   9660
tacttgtcgc ttgtgttcca tgtgttgcgg gtgtcttggc cggcgtggtg ttgctggtag   9720
gcgaggagtg cgaggcagtg ccaggctgcg tgtgctagat ggggtagccc ggattcgtgg   9780
tcgaggttgt tgccttgctg ccatgatagt agagggcgtc gacactgttg   9840
ctccacgggt atcctccggt ccagttgttg tcgccatatt tggtggcacc gtatccggct   9900
acttcgccta gggcgtgaag ggatgctggg tcgatgaggg agagcctgca gagtttcaat   9960
tcttttcggg caccgctgtt ggggtcggtg tacatgcggg tgggctcatc catggggtgt  10020
gtgctcctta agggtgggtt actgttgtt gttgtggcgt agggcgggag cgagaataat  10080
gatggcgagg gttcggcta tcagtatggg tgttgtgatc atttggtgtc tcggggattg  10140
ttggtgagtg ttgaggcacc caggagggtg gcgagggcgc atgcggcaat aatggcgagg  10200
gctgccttgt gtggggtgcc ggttgcgtac atccatgtga tgatgcacc ttggatccag  10260
gctaggctgg tgaagaaggt ttcgtagctg tgcagctcaa tgttgttgtt gggtgtgttc  10320
atgcttgctc ctgaagaatg gtgttgatgg ttttataaat gttgtacagg tcggtttcga  10380
tagataacag ttggttgatt tggtggtcga gatcaatgtc tgggttgagt gtgttgatgc  10440
gggaggcaat atcggtggct gtgcgtagtg tgccgccggt gtggtgaata atgtgtgccg  10500
tgtcggcgag tccggtggtg acggcgtagt gggataggag aggcatacg gggatgctcc  10560
ttggcgggtt actgttgcgg gttgatgttg aggtcggtga cgtgcggtga gttttctgtt  10620
ccggtgacga ggcagtggac ggtgacgggt agtttggatg ctcccggctg cgggacggtg  10680
gcgccgtaga cgatgctgaa tgtgtctta ccgatggttt tgtggagttg gaggtcgatg  10740
tcggggttgc cgttccagtt gacaccttgc gctgcggcct gttgttcggc tttgtggttg  10800
caggtgtgtg ctgccgtgat catggtgagt ccggtgcggg tttcttcacc ccttgcttgg  10860
gcttgcttgt gggctttggc ctgctcggct tgtagggatc gggtggcggc tgcctgccgt  10920
gccgctttct cggctttgcg ctgttgggta gtcttggggg tccatgtggt gttggctgtg  10980
gttgcctgtg gggctggctg tgaggtgagt ggcgggttgt cgtctggtgc tggcatgaat  11040
gaggcgcgg caatgatggc ggctgtgatg cctgcgatgg tgtagccgtt tttcttgttc  11100
atgtttttgtg tcccctttcc ggggtgttgt tcgttgctga catggttaat actttcagcg  11160
gctgggccca ctgtcaaggc tgcgctcagt ttgtgtgagc gtttggtgtg tggctagggg  11220
ttttgtcatg taagcgtgac atgtcactac cttgcgtcca gtatccatgg cggttgcgag  11280
ccatcccttt ggcgagcatc tcgtccacag tgaggcacct ggggcgattg gggccttcct  11340
tgaccccgtg atcgcctatg cggtgcatgt ccccggcata agtgccatta aatgtttcgt  11400
ggcagactgt gcagtgttct ggtcggtatc cgatgattgt gctatcgcac ttgtggcatg  11460
tccattgcat gattggtcct tcttcgtgt tttaagcttg tgctctgagg attagagcga  11520
ctttcagccc ttgggggtag gattatatag gtcaggtatt tctaggcgat tctaggctca  11580
ttgtgtgtgg ttgggggtttt atcgggcgca tagggttagc aggtggccca cattggtgcg  11640
gctcacattc cagtagagtt gcgtggcttc cttactggtg agcggcttcc actcgtcatg  11700
gctgaacacg gtgccatcgg atgcgatgaa cgtgttgggg cgtagcttgt gaagctcggc  11760
ttccacatgc tgccggtagg cttcgcggag gctctcaaaa tccatgtggt cgcaggagag  11820
gttttcgagg cgtgtcaggt cgaaaggctc cgggcagtcg tagctggctg gagtgtagag  11880
ctgggtgaag tggtcggcga tcttctgcat ggcgggttcc tttctggtgt gtggatggtt  11940
tttatcgtgt ggatgcgaca aggatggcgt ctacgtcgat catgtcgatc atgtcgttga  12000
gttcctcggc ctcattctcg gagaggtggc gccagtcggg tggccgtat acggcgccgt  12060
cgagggtgac agtccacagg ggccggatga gtcgtatgc ttcttcgact ttggcgtgga  12120
acatgcggcg caccatatcc agatcgatgt cgtctgaatg gttccggtg aggctgtgga  12180
ggctgagcgt gtcgatttct gtctgcctgt agaggctggt gaatgatggt gtgatgagtg  12240
tgccatccat gagtgtgctc ctttctaggg gttgttgtgg tttctagagt gtgtgggctg  12300
tgaccccaca gtcaaggcta cgctcatttg gattgagcgt ttcatatggg tgtggcagg  12360
aatctacacc ctcatactgt gtgagatgta tcacatcccc ctggcttggt gtgcacccct  12420
caagactact ctgccgacct ggcgtggagg gtgtagccca gaaatgccgt ttaaagcttc  12480
aggggtacgc ctaggagcgc cttacagggt ggggctagga tatttatacc cccagcatat  12540
tctgatcgat tctagacgac tcccagagcc cgatacgtca tcaaccatct cgacatagac  12600
catcagcccc tatcctggtt agctaagcct caactatgtg gacagtgtgg gacactgtgg  12660
gggaagaagg acacggtaca agaaagaggg gggagcatca gccttaaagc cttaagatct  12720
tagcgcttag caccgatggt cttagcagtt agcaccgagc ccttgagggg gctcggcatc  12780
agcctcatcg ggctcagctc atcaggcaca gccctgaaaa gggtacacgc catcagggaa  12840
ggcttgagag tacgaggagc cctagcgacg agtactcgaa agcctgaggg aacaccctca  12900
gtactgatga gcctagcgta ttcggaaagg acgcaagagt aaagtgtgac agctatccgg  12960
gagtgaaacc cgttccgact aggggttca gccttaacca ccctcaaagg ttacaagact  13020
ctaagaaaat ttaagaaact tcttaggaag aaagttgtgt tcatatcccc ctaaaaacac  13080
ccaaaatagt cctcaaaccc gcctatagag ccaaacagtc aagtttgact cgtctagacg  13140
gcgtatgata ggctggacag gtagccagct ggacgcaagg ccagaaagtg ctgacgcact  13200
tcccgacctc gcttaccatc agtctaccaa acactttaaa gcttcaaggc ttagcgctaa  13260
```

```
gcccttaaga tcttaacgct tagcaccgag ccccccctcaa gggctcgaca tcagtcttaa    13320
agtcttaaac actttaagta actttaaagc ttcaaggctt agcccttaag gatctaagtt    13380
actataaaag ctttaaacac ttaaagtaac tataaagctt taagagctta acatttaagg    13440
atataaaataa acattaaagc tttaaagtct taaagtaaat atataaccttt aacacttaag    13500
ttaagtataa aaccttaaag gcttagcact taaggataa aacttaacat cagtgtttaa    13560
gacttaaaga gttaaagtaa ctattaagac ttaaaggctt ataagcttta atactttaag    13620
tagctataag actttaaaaa cctgaagtac ttaaagttaa ccatcagtct taaactttaa    13680
tattataagt attaaagctt ataagttata aaagttttta gaagagttaa agggttaact    13740
tcttaacttc tcttctctct ttggttcttt ctctcttctc ttcttttctt catcagggga    13800
gaagaggaac cttaaccgt caacgctgat ggacttttca ccgtgtgact cgtgtgcttc    13860
tggtcgcaag ctcccatcgc acactcccca cactctttca cccgtgcccc tttacggctt    13920
agcgtgttcg tcggaaggcg tacgcgtgt cacgcttaaa cccttaacac caggtaagac    13980
ttaaagtgca tattataagt agaagacttt aaaacctata aggtgttccc gcttagcccg    14040
tgttccttta acgctaggcg ctcagccgta agatgtgaaa cgtgaaccac catccaccc    14100
cattttttctt ccgtgtcctt ctcctttttga caccgctggg gggcgatgtg atatttctca    14160
catgccaggg ggtagtggag aaaacaacca ccccggaacg tttaagacac ccctcaaac    14220
gaacaaaaca gggcctagaa tcgatcagca gggcaccggt agggtattcc taccccccaga    14280
cgattcaagg ccattacagg agcaatgaga ggctcacagg ggccatggga gattgggggg    14340
cgtgatggca cacaccaacc gcacagccag ccaagcccac cggcgctggc gggcaaggct    14400
catcacccaa gcccgacaac aaggccaaac cgaatgccca ctctgcggag tcaccatcac    14460
ctggaacacc cacgacctgc caaccagccc cgaagccgac cacatcacac ccgtcagccg    14520
gggaggactc aacaccctcg acaacgggca aatcatctgc agaacatgca acagaagcaa    14580
aggcaacaga acacaaccaa acatcaaatt ccaacaacaa accacaaaaa cattgattcc    14640
atggtgaaaa acccgccaac cccaccgg cacacccctc gcacacccgt gcaagacctc    14700
gtacggctta gtgaaatacc tccctttgt tgttttatcg ttttgtcgac ttttgttgtg    14760
gtgggtgtg tggtgcagcc tgagcttcct gatagtcgtg attggtgcgg ggagacgcgt    14820
cggtggtggt gtgtgtgggg cgaggatccg cgtgccgggt ttgtgtctga tgaggagtgg    14880
ttgtttctca tggatgctgc ggtgattcat gatgtggtgt ggcgtgaggg tcgcgcggat    14940
ttggtggctt cgttgcgtgc tcatgtgaag gcttttatgg gtatgttgga taggtattcg    15000
gttgatgtgg cgtctggtgg ccgtggtggg ggttctgcgg tagcgatgat tgaccggtat    15060
aggaagcgta ggggggcttg agtaggtgtc tggtgttgtt gggtctcagg ttcctcgtca    15120
ccgggtggct gtgcgtatt cggtgtctgc tggcggggat gctggggagc ttggtagggc    15180
ttatgggttg acgcctgatc cgtggcagca gcaggtgttg gatgattggc ttgctgtggg    15240
tggtaatggc aggcttgctt cgggtgtgtg tggggtgttt gttccgcggc agaatggcaa    15300
gaatgctatt ttggagattg tggagttgtt taaggcgact attcagggtc gccgtattt    15360
gcatacggct cacgagttga agtcggctcg taaggcgttt atgcggttgc ggtcgttttt    15420
tgagaatgag cggcagtttc ctgacttgta tcgtatggtg aagtcgattc gtgcgacgaa    15480
tggccaggag gctattgtgt tgcatcatcc ggattgtgcc acgtttgaga agaagtgtgg    15540
ttgtccgggt tgggggtcgg ttgagtttgt ggctcgtagc cgggggttctg ctcgcgggtt    15600
tacggttgat gatttggtgt gtgatgagcc tcaggagttg tcggatgagc agttggaggc    15660
tttgcttcct accgtgagcg ctgccccgtc tggtgatcct cagcagattt ttttgggtac    15720
gccgccgggg ccgttggctg acgggtctgt ggtgttgcgt cttcgcgggc aggctttgtc    15780
gggtgtaaa cggtttgcgt ggacggagtt ttcgattcgt gacgagtctg atccggatga    15840
tgtgtcgcgg cagtggcgga agttggcggg tgacactaat ccggcgttgg ggcgccgcct    15900
gaatttcggg acagtctcgg atgagcatga gtcgatgtct gctgccgggt ttgctcggga    15960
gcggcttggc tggtgggatc gtggccagtc tgcttcgtct gtgattccgg cggataagtg    16020
ggttcagtcg gctgtggttg aggcggctct ggttggcggg aaggttttg gtgtctcgtt    16080
ttctcgctcg ggggatcgtg tcgcgttggc tggtgctggt aaaacggatt ctggtgtgca    16140
tgttgaggtt attgatggcc tgtctgggac gattgttgat ggtgtgggcc agctggctga    16200
ttggttggcg ttgcgttggg gtgacactga aaaggttatg gttgcaggggt ctggtgcggt    16260
gttgttgcag aaggctttga cggatcgtgg tgttccgggtc cgtggcgtga ttgtggctga    16320
tactggggtg tatgtggagg cgtgtcaagc cttcctggag ggtgtcaggt ctgggagcgt    16380
gtctcatcct cgtgccgatt cgaggcgtga catgttggat attgctgtga ggtcggctgt    16440
gcagaagaag aagggttctg cgtgggggttg gggttcctcg tttaaggatg ttctgaggtt    16500
tcctttggag gctgtgtctt tggcgtatct tggtgcgaag atggcgaaag cgaagcggcg    16560
tgaacggtct ggtaggaagc gggtgtctgt ggtatgaact cggatgagtt ggctctgatt    16620
gagggcatgt acgatcgtat tcaagggttg tcttcgtggc attgccgtat tgagggctac    16680
tatgagggct ctaatcgggt gcgtgatttg ggggttgcta ttccttcgga gttgcagcgg    16740
gtgcagacgg tggtgtcatg gcctgggatt gcggtggatg ctttggagga gcgtctggat    16800
tggccttggct ggactaatgg tgacggctac ggttttgatg gtgtgtatgc tgcgaatcgg    16860
cttgctacgg cgtcgtgtga tgttcacctt gatgcactga tttttgggtt gtcgttttgtg    16920
gcgatcattc cccaagagga tgggtcggtg ttggttcgtc ctcagtcgcc gaagaattgt    16980
actggccggt tttctgccga tgggtcttgt ttggatgctg gccttgtggt gcagcagacg    17040
tgtgatcctg aggttcttga ggcggagttg ttgcttcctg atgtgattgt tcaggtggag    17100
cggcggggtt cgcgtgagtg ggttgagacg ggccgtatcg agaatgtgtt gggtgcggtt    17160
ccgttggtgc ctgttgtgaa tcgtcgccgt acttctagga ttgatggccg ttcggagatt    17220
acgaggtcta ttagggctta cacgatgag gctgttcgca cactgtgggg gcagtctgtg    17280
aatcgtgatt tttatgcgta tcctcagcgt tgggtgactg gcgtgagcgc ggatgagttt    17340
tcgcagccgg gttgggttct gtcgatgct tctgtgtgga ctgtggataa ggatgatgat    17400
ggtgacactc cgaatgtggg gtcgtttcct gtgaattctc ctacaccgta ttctgatcag    17460
atgcgtttgt tggcgcagtt gactgcgggt gaggcggctg ttccgaaacg ctattcgggg    17520
tttatcactt ctaacccgcc ttctggggag cttttggctg cggaggagtc tcggcttgtg    17580
aagcgtgctg aacgcaggca gacgtcgttt ggtcagggct ggctgtcggt tggttttcctg    17640
gctgcccggg cgttggattc gagtgttgat gaggccgctt ttttgatg tgttggtttg    17700
cgttggcgtg atgcgtcgac gccgactcgg gcgctacgg ctgatgctgt gacgaagctt    17760
gtgggtgctg gtatttgcc tgctgattct cggacggtgt tggagatgtt gggtttggat    17820
gatgtgcagg ttgaggctgt gatgcgtcat cgtgccgagt cttcggatcc gttggcggca    17880
ctggctgggg ctatttcccg tcaaactaac gaggtttgat aggcgatggc ttcgggtgct    17940
gtgtcgaggc ttgctgcgac tgagtatcag cgtgaggctg tcaggtttgc tgggaagtat    18000
```

```
gcgggctatt atgccgagtt gggtcgtttg tggcgtgccg gcaggatgag tgacacgcag    18060
tatgtgcgtt tgtgtgtgga gttggagcgt gccggccatg acggttcagc agctatggcg    18120
ggcaaattcg tttcagattt tcgccggttg aatggtgtcg atcctggttt gatcgtgtat    18180
gacgagtttg atgctgcggc ggctttggct aggtcgtttt cgactatgaa gattatgaat    18240
agtgacccgg ataggggcgaa tgatacgatt gatgcgatcg ctgcgggtgt taatcgggct    18300
gttatgaatg ctggtcgtga cacggttgag tggtcggcgg gtgcgcaggg taggtcgtgg    18360
cgtcgggtga ctgatggtga tccgtgtgct ttttgtgcca tgttggctac gaggtcggat    18420
tatacgacta aagagcgggc gcttactact ggtcatacgc ggcgtcataa gcgtgccggt    18480
aggcgtccgt ttggttcgaa gtatcatgat cattgtggtt gtacggtggt tgaggttgtt    18540
ggtccttggg aaccgaatag ggctgatgcc gagtatcaga ggacgtatga gaaggctcgt    18600
gagtgggttg atgatcatgg gttgcagcag tcgtctggca atattttgaa ggctatgcgt    18660
actgttggtg gcatgagata atttgatgtg gtttccggtt gtgtgccgcc ggttatcggt    18720
gcacagggtt gtctcccgca cggggtcaa caatgttgtg ttgttttccg caaggagtgt    18780
agggttaggc tatggccgat cagagtattg aggaacagaa tgttgacaat gatgttgtgg    18840
agtccggaaa ggataaccggc attgttgata cagtaaaaga cgatggcggg caggaggtag    18900
ccgacaatca gttgaagaat gaaggcgagg gtaaatcgcc ggggactgat tggaaggcgg    18960
aggcccgtaa gtgggagtct cgtgctaaaa gtaatttcgc cgagttggag aagcttcgta    19020
catcgagtga cgattctgga tctactattg atgagcttcg ccgcaagaat gaggaactcg    19080
aagaccggat taacgggttt gttcttgagg gtgtgaagcg cgaggtggct gccgagtgtg    19140
gcctgtcggg tgatgcgatc gcttttcttc acggtagcga taaggagtcg cttgccgagt    19200
ctgctaaggc tttgaagggt ttgatcgacc atagtagtgg tggtggcgcg ggtgtgcgcc    19260
gtcttgcggg gagtgcccc gttgatgatg ttaaacgacg tggtgacgg ccgttttgtgg    19320
atgctcttgt caataattct aggagatgat ttatcatggc tgacgatttt ctttctgcag    19380
ggaagcttga gcttcctggt tctatgattg gtgcggttcg tgaccgtgct atcgattctg    19440
gtgttcttgc taaactgtca ccggagcagc cgactatttt cgggcctgtt aagggcgccg    19500
tttttagtgg tgttccgcgc gctaagattg ttggcgaggg cgatgttaag cctttccgcta    19560
gcgttgatgt ttctgcgttt actgcgcagc ctatcaaggt tgtgactcag cagccgtgtct    19620
cggacgagtt tatgtgggct gacgccgatt accgtctggg tgtgcttcag gatctgattt    19680
ccccggccct gggtgcttct attggtcgcg ccgttgatct tattgctttc catggtattg    19740
atcctgctac gggtaagcct gctgcggctg tcaaggtgtc gctggataag acgaataaga    19800
cggttgatgc caccgattcc gctacggctg atcttgttaa ggctgttggt ctgattgctg    19860
gtgctggttt gcaggttcct aacggtgttg ctttggatcc ggcgttctcg tttgctctgt    19920
caactgaggt gtatccgaag ggttcgccgc ttgccggtca gccaatgtat cctgccgccg    19980
ggttcgccgg cctggataat tggcgcggcc taaatgttgg ttcttcttcg actgtttctg    20040
gtgccccgga gatgtcgcct gcttctggtg ttaaggctat tgttggtgat ttctctcgtg    20100
tccattgggg gttccagcgt aacttcccga ttgagctgat cgagtatggt gacccggatc    20160
agacggggcg tgacttgaag ggccataatg aggttatggt tcgtgccgag gctgtgctgt    20220
atgttgcgat tgagtcgctt gattcgtttg ctgtcgtgaa ggagaaggct gccccgaagc    20280
ctaatccgcc ggccggtaac tgattcattt gttgcgataa tgtttatgct gtgtgcaggg    20340
ggtggtgttg atgggtatca tttttgaagcc tgaggatatt gagcctttcg ccgatattcc    20400
tagagagaag cttgaggcga tgattgccga tgtggaggct gtggctgtca gtgtcgcccc    20460
ctgtatcgct aaaccggatt tcaaatatag ggatgccgct aaggctattc tgcgtagggc    20520
tttgttgcgc tggaatgata ctggcgtgtc gggtcaggtg cagtatgagt ctgcgggccc    20580
gtttgctcag actacacggt cgaatactcc tacgaatttg ttgtggcctt ctgagattgc    20640
cgcgttgaag aagttgtgtg agggtgatag tggggctggt aaggcgttca ctattacacc    20700
gaccatgagg agtagtgtga atcattctga ggtgtgttcc acggtgtggg gtgagggttg    20760
ctcgtcggga tcgaatatta acggctatgc tggcccgttg tgggagatat gatatgaccg    20820
gttttcctta cggtgaaacg gttgtgatgc ttcagccgac tgttcgtgtc gatgatcttg    20880
gtgacaaggt ggaggattgg tctaagcctg tcgagactgt gtaccataac gtggccatct    20940
atgcttccgt ttcgcaggag gatgaggccg cggggcgtga ctcggattat gagcattgga    21000
cactgctgtt caagcagcct gtcaaggctg ctggttatcg gtgtcgttgg cgtattcggg    21060
gtgttgtgtg ggaggctgac gggtctccta tggtgtggca tcatccgatg tctggctggg    21120
atgctggtac gcaggttaat gtgaagcgta agaagggctg atgggttgtg gcacgtgatg    21180
ttgatgtgaa gctgaacttg ccgggtattc gtgaggtgtt gaagtcttct ggggtgcagg    21240
gcatgttggc tgagcgtggt gagcgtgtca agcgtgcggc ctcgcgaat gtgggcggta    21300
acgcttacga tagggcccag tatcgtgccg ggttgtcgtc tgaggtgcag gttcaccgtg    21360
ttgaggctgt ggcgcgtatt ggcaccacct ataaaggtgg taaaaggatt gaggctaagc    21420
atggcacgtt ggcgaggtcg attggggctg cgtcgtgatc gtttacggtg atcctcgaat    21480
atgggctaaa cgtgtgttgg cggatgatgg ttggctgtct gatgtaccgt gcacgggtac    21540
tgtgccggat acatttgagg gtgatctgat ttggttggcg ttggatgggg gcccggagtt    21600
gcatgttcgt gagcgtgttt ttttgcgtgt gaatgtgttt tcggatacgc cggatcgtgc    21660
tatgtctttg gctcgccggg ttgaggctgt gctggctgat ggtgtggatg gtgatccggt    21720
ggtgttttgc aggcgttcga ctgggcctga tttgctggtg gatggtgcac gttttgatgt    21780
gtattcgctt tttgagctga tatgtaggcc tgcggatgtc gaataagctt attgttttg    21840
ttttaatgta attgtttgat atttaatggg ggttgtgatg gctgctacac gtaaagcgtc    21900
taatgttcgt tcagcggtta ctggcgacgt ttatattggt gacgcgcacg cgggtgattc    21960
tattaagggt gtggaggcgg ttccttccgg gcttacagct ttggggtatc tgtctgatga    22020
cgggtttaag attaagcctg agcgtaaaac ggatgatttg aaggcttggc agaatgcgga    22080
tgttgctgtc actgtggcta tcgagtcgtc tatcgagatt tctttccagc tgattgagtc    22140
gaagaaggag gttatcgaac tgttttggca gtcgaaggtt actgccggat ctgattcggg    22200
ttcgttcgat atttctcctg gtgccacaac aggtgttcac gccctgttga tggatattgt    22260
tgatggcgat caggttattc gctactattt ccctgaggtt gagctcattg atcgtgacga    22320
gattaagggc aagaatggcg aagtgtacgg gtatggtgtg acgttgaagg cgtatcctgc    22380
ccagattaat aagactggta atgcggttgc gggtcggggg tggatgacgg ctttaaaagc    22440
tgatactcct ccgactcctc cgccggcccc ggttcctccg aagcctcagc cggatccgaa    22500
tccgccgtcc ggtaactgat acacgatttt agggggattgt taatagatga gtgacactgg    22560
tttcacgttg aagattggtg atcgtagctg ggtgttggcg gatgcggagg agacggctca    22620
ggctgttcct gcccgcgttt tccgtcgtgc cgccaggatt gcccagtcgg gggagtctgc    22680
ggatttcgcc caggttgagg tgatgttttc tatgttggag gctgccgccc cagctgacgc    22740
```

```
ggtggaggcc ctggaggggc ttcctatggt tcgtgtggcg gaggttttcc gtgagtggat    22800
ggaatacaag cctgacggta agggtgcctc gctgggggaa tagtttggct ccacggcctg    22860
attgatgatt atcgtggggc catcgaatac gatttccgca ccaagtttgg tgtttctgtt    22920
tatagtgttg gtgcccgca gatgtgttgg ggtgaggctg tccggctggc tggcgtgttg    22980
tgtaccgata cgtctagcca gttggcggcc caccttaatg gttggcagcg cccgtttgag    23040
tggtgcgagt gggctgtgtt ggacatgttg gatcattaca ggtctgctaa tagtgagggg    23100
cagccggagc ctgtggcgag gccgactgat gagcgtcggg caaggtttac gtctgggcag    23160
gtggacgata ttttggcgcg tgttcgtgcc ggtggcgggg tgtctcgcga gattgatatt    23220
atggggtgaa tagtgtatgt ctggtgagat tgcttccgca tatgtgtcgt tgtatacgaa    23280
gatgcctggc cttaaaagtg atgttggtaa acagttgtcg ggtgttatgc ctgctgaggg    23340
gcagcgttcg ggtagcctgt ttgctaaagg catgaagttg gcgcttggtg gtgcggcgat    23400
gatgggtgcc atcaatgttg ctaagaaggg cctcaagtct atctatgatg tgactattgg    23460
tggcggtatt gctcgcgcta tggctattga tgaggctcag gctaaactga ctggtttggg    23520
tcacacgtct tctgatacgt cttcgattat gaattcgaat attgaggctg tgactggtac    23580
gtcgtatgcg ttgggggatg cggcgtctac ggcggcggcg ttgtctgctt cgggtgtgaa    23640
gtctggcggt cagatgacgg atgtgttgaa gactgtcgcg gatgtgtctt atatttcggg    23700
taagtcgttt caggatacgg gcgctatttt tacgtctgtg atggctcgcg gtaagttgca    23760
gggcgatgac atgttgcagc ttacgatggc tggtgttcct gtgctgtctt tgcttgccag    23820
gcagacgggt aaaacctcgg ctgaggtttc gcagatggtg tcgaaggggc agattgattt    23880
tgccacgttt gcggctgcga tgaagcttgg catgggtggt gctgcgcagg cgtctggtaa    23940
gacgtttgag ggcgctatga agaatgttaa gggcgctttg ggctatttgg gtgctacggc    24000
tatggcgccg tttcttaacg gcctgcggca gatttttgct gcgttgaatc cggttattaa    24060
gtctatcacg gattctgtga agccgatgtt tgctgccgtc gatgctggta tccagcggat    24120
gatgccgtct attttggcgt ggattaaccg tatgccggct atgatcacga gaatgaatgc    24180
acagatgcgc gccaaggtgg agcagttgaa gggcattttt gcgagaatgc atttgcctgt    24240
tcctaaagtg aatttgggtg ccatgtttgc tggcggcacc gcagtgtttg gtattgttgc    24300
tgcgggtgtg gggaagcttg ttgcaggggt tgctccgttg gcgagttgcgt tgaagaatgc    24360
gttgccgtcg tttggtgctt tgaggggtgc cgccggggg cttggtggcg tgtttcgcgc    24420
cctgggtggc cctgtcggga ttgtgatcgg cttgtttgcg gcaatgtttg ccacgaacgc    24480
ccagttccgt gccgctgtta tgcagctggt ggctgtgtt ggtcaggcgt tgggccagat    24540
tatggcagct gtgcagccgc tgtttggttt ggttgctggc gtggttgcca ggttggcgcc    24600
ggtgttcggc cagattatcg gtatgggtgc tggtttggct gcccggctgg tgcctgttat    24660
tggtatgctt attgcccggc tggttcctgt tatcacccag attattggta tggtaaccca    24720
ggttgctgcc atgttgttgc ctatgctgat gccggttatt caggctgttg ttgctgtgat    24780
acggcaggtt attggtgtca ttatgcagtt gatacctgct ttgatgccgg ttgtgcagca    24840
gattttgggt gctgtcatgt ctgtttttgcc gccgattgtt ggtttgatac ggtcgctgat    24900
accggtgatc atgtcgatta tgcgtgtggt ggtgcaggtt gttggtgctg tgctacaggt    24960
ggtggcccgt attattccgg ttgttatgcc gatttatgtt tcggtgattg gattcattgc    25020
caagatttat gctgcggtta tcgttttga ggctaaggtt attggcgcta ttcttcgtac    25080
tattacgtgg attgtgaatc attcagtgtc tggcgtgagg tctatgggca cggccatcca    25140
gaatggctgg aatcatatta aatcgtttac gtctgcgttt attaacggtt taagtcgat    25200
catttctggc ggcgtgaacg cggttgtggg gttttttacg cggcttggtt tgtcggttgc    25260
ttcccatgtg aggtccggtt ttaacgctgc gaggggtgct gtttcttccg ccatgaatgc    25320
tattcggagt gttgtgtctt cggtggcgtc tgctgttggc gggttttttca gttcgatggc    25380
gtctcgtgtt cggaatggtg ctgtgcgcgg gtttaatggt gcccggagtg cggcttcttc    25440
tgctatgcat gctatgggt ccgctgtgtc tagtggtgtg catggtgtgc tgggtttttt    25500
ccggaatttg cctgacaata ttcggcgtgc gcttggtaat ggggtcccc tgttggtgtc    25560
ggctggccgt gatgtggtgt ccggtttagg taatggtatc aagaatgctt tgagtggcct    25620
gttggatacg gtgcgtaata tgggttctca ggttgctaat gcggcgaagt cggtgttggg    25680
tattcattcc ccgtctcggg tgtttcgtga cgaggttggc cggcaggttg ttgccggttt    25740
ggctgagggt attactggta atgctggttt ggcgttggat gcgatgtgcg gtgtggctgg    25800
gaggctgcct gatgcggttg atgcccggtt tggtgtgcga tcgtctgtgg gttcgtttac    25860
cccgtatggc aggtatcagc gcatgaatga taagagtgtt gtggtgaatg tgaatgggcc    25920
tacttatggg gatcctgccg agtttgcgaa gcggattgag cggcagcagc gtgacgcttt    25980
gaacgcgttg gcttacgtgt gattttgggg gtgtggtgca tgtttattcc gacccgtct    26040
gatcgttctg gtttgactgt gacttggtct atgttgccgt tgattggtaa tgatccggag    26100
cgtgtgcttc atttgacgga ttatacgggg tcgtctccga taatgttgtt gaatgattcg    26160
ttgcgcggtt tgggtgttcc tgaggtggag catttttctc aaactcatgt tggggtgcat    26220
ggctcggagt ggcgcgggtt taatgtgaag cctcgcgagg tgacgctacc ggtgttggtg    26280
tcgggtgttg gcccggatcc ggtgggcggt tttcgtgacg gtttttttgaa ggcgtatgac    26340
gagttgtggt ctgctttcc tcctggcgag gtgggggagt tgtctgtgaa gactcctgcc    26400
ggtcgtgagc gtgtgttgaa gtgccggttt gattcggtgg atgacacgtt tacggtggat    26460
ccggtgaaca ggggttatgc gcgttatctg ttgcatttga cggcttatga cccgttttgg    26520
tatggggatg agcagaagtt tcgtttcagt aacgctggtt tgcaggattg gttgggtggc    26580
ggccctgtcg acggtaaggg taccgcgttt ccggtggtgt tgacgcctgg tgttggttcg    26640
ggttgggata atctgtctaa taagggtgat gtgcctgcgt ggcctgtgat tcgtgttgag    26700
gggccgttgt cgtcgtggtc tgtgcagatt gatggtttgc gtgtgtcctc ggattggccg    26760
gtggaggagt atgattggat cactattgat acggatcctc gtaagcagtc tgcgtgttg    26820
gacgggtttg aggatgtgat ggatcgtttg aaggagtggg agtttgcgcc tatcccgcct    26880
ggcggttctc ggagtgtgaa tattgagatg gttggtttgg gtgccattgt tgtgtcggtg    26940
cagtacaggt ttttgagggc ttggtgaata gttgatggct ggttttgttc cgcatgtaac    27000
attgtttaca ccgattatc gccgtgtggc gcctatcaat tttttgagt cgttgaagtt    27060
gtcgttgaag tggaatggtt tgtccacttt ggagttggtg gtgtctggtg atcattctag    27120
gcttgacagg ttgactaggc ggtgtgtgcg gcttgtggtt gattatggtg gtggccagat    27180
ttttcctgg cctgtgcgtc gggtgcatgg tgtgggtccg tggcgttctt cgcgtgtgac    27240
tatcacgtgt gaggatgata ttcgtctgtt gtggcgtatg ttgatgtggc ctgtgaatta    27300
tcgtcctggt atggttggta tggagtgcg tgcggatcgg gattatgccc attattcggg    27360
tgcggcgag tcggtggcta agccggtgtt gggggataat gcttggcgtt ttccgtctgg    27420
tttgtttatg aacgatgatg agagtcgtgg ccgctatatt aaggattttc aggtgcggtt    27480
```

```
tcacgtgttt gccgataagt tgttgccggt gttgtcgtgg gctcggatga ctgtcacggt  27540
gaaccagttt gagaatgcga agtttgatca gcgtggtttg gtgtttgatt gtgtgcctgc  27600
tgtgacccgg aaacatgtgt tgactgccga gtcgggttcg attgtgtcgt gggagtatgt  27660
gcgtgacgcc ccgaaggcga catctgtggt ggttggtggc cgtggcgagg gtaaggatcg  27720
gctgttttgt gaggatgttg attcggcggc cgaggatgat tggtttgatc gtgtcgaggt  27780
gtttaaggat gcccgtaaca cggattccga gaaggtgtct ctcttcgatg aggctgagcg  27840
ggtgttgtcc gagtcggggg ctacgtcggg gtttaagatt gagttggctg agtcggatgt  27900
gttgcggttt ggtcccggca atctgatgcc tggggatttg atctatgtgg atgtgggttc  27960
tgggcctatt gcggagattg tgcggcagat tgatgtggag tgtgtatcgc ctggtgatgt  28020
ttggacgaag gtgactccgg ttgcggggga ttatgaggat aatccgtccg ccctgttggc  28080
tcgccgtgtg gctggtttgg ctgcgggtgt gcgggatttg caaaagtttt agtaagtgat  28140
tggggtttgt tgtgggtatt gtgtgtaaag ggtttgatgg tgtgttgacc gagtatgatt  28200
gggctcaaat gtctggtctg atgggtaata tgccgtctgt gaaggggcct gacgattttc  28260
gtgtcggcac gacgattcag ggttctacgg tgttgtgtga gatcctgccg gggcaggctt  28320
gggctcacgg ggtgatgtgc acgtcgaata tgttgagac ggtgacgggt cagcttccgg  28380
gcccgggtga gactcgatac gactatgtgg tgtttgtctcg ggattggcag gagaatacgg  28440
ccaagttgga gattgttccc ggtgggcgtg cggagcgtgc cagggatgtg ttgagggctg  28500
agcctggcgt gtttcatcag cagctactgg cgactttggt gttgtcgtct aacgggtgc  28560
agcagcagtt ggataggcgt gctgtggcgg ctagggttgc gtttggggag tctgctgcgt  28620
gtgatcctac ccctgtggag ggtgaccgtg tgatggttcc ttcggggct gtgtgggcta  28680
accatgccgg cgagtggatg ttgttgtctc ccaggattga gacgggttcg aagtcgatca  28740
tgtttggtgg ttctgctgtg tatgcttaca cgatcccgtt tgagcgccag ttcagtagtc  28800
cgcctgttgt ggtggcgtct atggctacgg cggctgggg cacggcacag attgatgtga  28860
aagcctacaa tgtgactgcc caaaatttta gtttggcgtt tattacgaat gatggttcga  28920
agccgaatgg tgtgcctgcg gtggcgaatt ggattgctgt cggcgtgtga ctgcacgggt  28980
gttgtgcgg atggtgtgat gttgggggc gtgtggtgtcg tggtttactc ctgcactggt  29040
ggcctctatt tgtaccgcgt tggccacggt tttgggttct gttcaggctg tcacatcccg  29100
gtctaggaag cgtttacgca ggctgtcggc tcaggtggat gcgatggaag agtatacgtg  29160
gggtgtgcgg cgcgaggtgc gaaggtttaa cgccgggctt cctgatgatg tggagccgat  29220
gcatcttcct gatttgcccg agttttttgaa agatactgtt gatgtggag gtgagtaggg  29280
ttgagggagt tggaggagga gaagcggcag cgccgcaatt tgagaaggc ttcactggtg  29340
ttgttgtttt tgtcgcttgt gttgttggcg gtggttgctg cgggtgcttt gcgtttcggg  29400
gctgtatcct ctgagcggga ttcggagcag gcgagggccc agtcgaatgg tacggctgcc  29460
aggggttttgg ctgcccgtgt gaagcaggcg tgtgcttcgg gtggggtgga gtctgtgcgt  29520
cttcaccgtt ctggttttgtg tgtggatgct gtgcgtgtgtc agcagcgtgt tcagggtggg  29580
ccgggtcctg ccggtgagcg cggcccgcaa ggcccttcag gtcctgccgg ccgggatggt  29640
gttaatggtt cggctgggct ggttggccct gttggtccgc aaggttctcc gggttttgaat  29700
ggtgtgaaag gtcctgacgg cttgcctggc gctaacggtt cggatggccg tgatggtgtt  29760
ccaggtcg                                                           29768
```

SEQ ID NO: 69        moltype = DNA  length = 29238
FEATURE               Location/Qualifiers
misc_feature        1..29238
                      note = PAC1
source               1..29238
                      mol_type = other DNA
                      organism = synthetic construct
SEQUENCE: 69

```
tagcgtacag ggtgtgccag gtcccgccgg tgagcgcggc ccgcaagggc cggctggtgc   60
tgatggtcgg gatggtgtta atggttcgac tgggctggtt ggcccgtgtgg gtccgcaggg  120
ttctccggc ttgaatggtg tggctggccc ggacgggttg cctgtgcga acggatcgga   180
tggccatgat ggtgttccag gtcgtgcagg tgctgacggt gtgaacggcg ctgatgtcg   240
ggatggttcg gccggtgagc gcggtgatgt gggcccttca ggtcctgccg gcccgcaagg   300
tgcacagggt gaacgggtc ctattgggcc tcagggtccg cagggttctg ccggtgctga   360
cggcacgaat ggtaaagacg gtaaagatgg gcgctcggtt gtgtctgtgt actgttccga   420
gggccgcctg gttgtgaaat atagtgacgg tgtggcttct acaatatcga gctcggtggc   480
ctgccagggt gtgaaccgt cgcctatagt gactatatca tcccacaagt aaaaaagaaa   540
agggaagggt gttactagtg ttgattgtgg tgttaggtgg tgtgtggtga gatacattcc   600
tgccgcgcat cattctgccg gctcgaatag tccggtgaat aggttgtga ttcatgcgaa   660
gtgcccggat gtgggggtttc cgtctgcctc gcgtaaaggg cgggcggtgt ctacagcaaa   720
ctatttcgcg tccccatcgt cgggtggttc ggcgcattat gtttgcgata ttagtgagac   780
ggtgcagtgc ttgtcggagt ctacgattgg gtggcatgcc ccgccgaatc cgcatagttt   840
gggtatcgag atttgcgcgg atgggggttc gcacgcctcg ttccgtgtgc cggggcatgc   900
ttacactcgg gagcagtggc ttgatcctag ggtgtggcct gcggtggaga aggctgccat   960
cctgtgtaga cgtttgtgtg acaaatataa tgttccgaag aggaagctta gtgcagccga  1020
tttgaaggct ggtaggcggg gcatctgcgg gcatactgat gtgacggatg cgtggcacca  1080
gtcggatcat gacgatcctg ggccgtggtt tccgtgggac aggtttatgg ccgtcgtcaa  1140
cggcaaagat gagagtgggg agttaacggt ggctgatgtg aaagccttgc atgatcagat  1200
taaacaattg tctgcccagc ttactggttc ggtgaataag ctgcaccatg atgttggtgt  1260
ggttcaggtt cagaatggtg atttgggtaa gcgtgttgac gccttgtcgt gggtgaagaa  1320
tccggtgacg gggaagctgt ggcgcacaaa ggatgctttg tggagtgtct ggtattacgt  1380
gctggagtgt cgcagccgca tcagtaggct ggagtctact gtcaacgatt taagaagtg  1440
atctatggtg ggtaaacagt tttggttggg cttgtttgag cgtgccctga aaacttttat  1500
tcaaacgttt gttgctgtgt gttgggtgac acttatactg cggagtcgtt  1560
tcgcggtttg ccgtgggagt ctgctctgat tacggccggg gttgctgcaa tactgtcggt  1620
tgctacctcg tttggtagcc cgtcgtttgt ggctggcaaa cctaaaacta cggttgtgga  1680
tgcgggtttg gttccaccgg atgatggggg cttggttgag ccgcacatgg tggatgtgtc  1740
ggatcctggc atgatcgagc ctgcagatga tgcggatctt ggtgtaggct atgtgccgaa  1800
acacgctgcc gagtcggagg ttggcacggt agagtctact gttgcataat tgaatatgtg  1860
```

-continued

```
tgtgccccag cggtgctgcc acgatcgtgt ggtggttgcc gctggggcac tattttttgta  1920
tattgcggtg tggctatgat tcgttgctgt cgatggtgtc ttcgagcatc tgatacaggt  1980
ggaggcaggt agagatagtt tcgctggcct ggtctagaac gttccggccg ataacatttt  2040
tgtgattgtc gcggtggcgg atgatagccc acatgatctc gtcggctgcc gcttgcaata  2100
gttttgactg gtatgcgatt ccggcgagcc agtctatggc ttccgggctt gccggtgtgt  2160
cgtctggaat gccacaggtg ttgctgttgt ttgtggggta tcctgcactg tcgcaaaacc  2220
acaggatttc gctgcactcg tctagcgtgt cctggtcgat agcaagatcg tcgaggctga  2280
cttcgttgac ggtaaggttc acgttgtcga gggagatggg tacaccgtac tggttttcga  2340
cactgtcaac aatgttttcc agctgttgca tgttggtggg ctgttgttgg acgatacggt  2400
gtatcgctgt gttgagggtg gtgtaggtga tattgtgt gttgttcatg gtttttattcc  2460
atctctgtgc tgtcgtcttg gtcgtatcga ctgtttgcgt agcctgtgag ggtgatgagt  2520
gtttggtctg cccattgttt cactgtttgc cgggtgacac ccaatcgttg ggcggctgtg  2580
gcgtaggttt ggtcgtatcc gtatacttct cggaatgctg ccagccgtgc taaatgtttt  2640
cgctgtttgg atggctggca ggtgagggtg tagtcgtcga tggctagctg tagatcgatc  2700
atggcgacaa tgttgttgcc gtggtgttgt ggcgcggttg gtgggggtgg cattcccggc  2760
tccacggagg gtttccatgg gccgccgttc caaatccatt gggcggcctg aataatatct  2820
gcggtggtgt aggtcctgtt catgtgtcat cccctgaaca ggttgtcgaa gtcgtctgtg  2880
ttgctggtgt tggtggtatc gaatccgtcc acgcagtggc agtagtcgta catgagtttg  2940
ataatgtgtt ggtggtctcc caaataggtg ttgccgctga tgctgtaggt ggctgtgccg  3000
tctttgctga tggtgtattt ggcggtgatg gtttcggggt tttctgtgtt tgtgatgatg  3060
gctgtggtgg tggcgcctac ggtttgtagc ctggtggttt gggttccgtc gtcgagggtg  3120
gtagtaacca tagttggggt tctccttaaa tactggtttg gttgtcggct agatgaataa  3180
tatcggataa aggtttcggc tggtctaggt gttgtatggt tttgttggcg agccgtttga  3240
ctaccctgta gcacattttg atgtagtgtt tgttgtctag gttgtggtat tgttcccgta  3300
ccgcaatata tagtagggag tcttggtaca ggtcgtctgc gttgattgcg gggtagtgtg  3360
tggctatttt tgtgcatgcc cggttgagtg tgcgtagatg atggtctgtg gcccatcccc  3420
acgatgctgt ggtggccagg tctgatttgg tgggtcgtct gctcatggcg ctatttcatc  3480
tcgctatctg atagttgttt ggtgttttgt tgttgatagt gtagcacact agtccgggat  3540
ggccggtggt gcctgtgcgg tgccggaacc atgtggattc tccttccatg gatgggcatt  3600
ggataagggt gcgttgtcct tgctcggaga ttctaggtg gtgccggtgc ggccgccatga  3660
gaatattaga tgtggtgccg ttgtggaatt cttggccgcg ccaccattcg tattgtttgc  3720
cggttttcca ttggtgcccg tgtgcgtgca ggatttgtgt gccggctact tcgacggtgg  3780
tggtcatttc gtcccgtgcg gggaagtgga agtgaaggtt gggatattgg ttgtcgagct  3840
ggtaggcttc tgcgatggcg cggcagcagt ccacgtcgaa ggagtcatcg taggtggtga  3900
cgcctttacc gaaacgcacg gcttcaccgt ggttgcccgg gatggatgtg atggtcacat  3960
ttttgcagtg gtcgaacatg tggacgagtt gcatcatggc catgcgagtc aaccggatttt  4020
gttccgtcaa gggtgtttgt gtgcgccagg cgttgttgcc tccttgtgac acgtatcctt  4080
cgatcatgtc gccgaggaat gcgatgtgga ctcgttgcgg ctgtccggct tgctgccagt  4140
agtgttttgc gactatgagg gagtgcaaat agtcgtctgc gaagtgtgat gtttcccgc  4200
cggggatgcc tttgccgatt tgaaagtctc ccgcccctac cacgaacgca acattgctgt  4260
agtcggtgtg tgtgtcttgg ttgggtttgg ggggtgtcca ttcggctagt ttatcgacga  4320
gttcgtcgac cggatagggg tcggttgcgg gttggtggtc gatgattttt tgtatggatc  4380
ggccggtttc tccgttgggg agtgtccatt cggagatgcg tgtgcgcgt acggtgccgt  4440
ttgcgagatc atcgcggatg gtgtctgctt cgttgtcgtg gttggctagc tgtgtgagga  4500
gccggtctat attgtctatc atcgggtatc ctcctcttgt ggggtggtgt tggcttgttt  4560
gcggcgatag tcttttataa cggtggcgga gatgggtat cctgcctggg tgagctgttt  4620
tgctagccat gaggcgggga tagacctgtc ggcgaggacg ttgcctttt tagcccgta  4680
gcgttgaata agggtttcag ttttggttgc catgatgtcc tagggggttgt gtggtgggct  4740
gccatcctgt gcggcagtcg ccgtcgtgtc ctggtttgcg ggtgcaccac gatacggttc  4800
cgtctgtgtg gttgagtgtt ttaccgcaca tgacgtcacg taggtgctcg ggaaactcat  4860
cgttgttgtt gtccccgtgc atgtcgatca agtgttggt tttagtaacc atcatgcctg  4920
ctatgtgtga aagagtgtgc aaatactatg caggtgtcat ggatgtttat gcgggtatgt  4980
ttttcatcac cttgctgaac gttacttggt tactgtacat catctgagtg atttcctgat  5040
cagtcttatc ggggtgctgc tttcgcaggt tcgcccactg gcaggcgttg tcggtctcct  5100
gctgtaaacg tgtcaggtgc tgctcgttga tgatgtgttt ccacattgtc catgacacgt  5160
cgagcctgcg gagcatgttc atggctggca cgttgaagga gttgaggaag agtatttctt  5220
cggtgtagta ctgttttttcg tattggtccc atcgcttcg gtgcctgttg ggctggtttt  5280
tggggtaggc ttcccggcag attttgtgta accgtttggc catgtcgtcg ggtagtttaa  5340
tgtcgggggtt ggcgcggatc atggatcgca tcccgtcata ggtagtgccc caggtgtgca  5400
tgatgtggag tgggtcttca ccatcggccc attttttcggc gatgatgggg aggcggatgc  5460
gcctcctggc ggctttactg gtgttgcgcc ggtggggat ggggcatgtg tcgaggggat  5520
ccatgatatt ttagtgtacc tttccgtgtt gtggttgttt gtctggtttt attgtagcac  5580
tgtgttgagg gcttgtgtca accctgtttt gccggttttc aggtatgtgt ctgtgacatc  5640
ccccaggggg aggggcacgt gggtggcttg ggggagtgct gcctggaggg tttgggccat  5700
ctggtggcct gcctggtctg ggtcggacca gatgtagatg tggtcgtagc cttcgaagaa  5760
tttggtccag aaggtttgcc acgaggttgc gccgggtagg gcgacggctg gccatccgca  5820
ttgttcgagg atcatggagt cgaattcgcc ttcgcaaatg tgcatttcgg ctgccggggt  5880
ggccatggcg gccatgttgt agatggagcc tgtgtctcct gccggggtga ggtatttggg  5940
gtggttgtg gttttgcagt cgtgtgggag tgagcagcgg aaacgcattt ttcgtatttc  6000
ggctggccgc ccccaaactg ggtacatgta tgggatggtg atgcactggt tgtagttttc  6060
gtggcctggt atggggtcat tgttgatgta tccaaggtgg tggtagcgag ctgtttcttc  6120
gctgatgcct cttgccgaga ggaggtcgag tatgttttcg aggtgggttt cgtagcgggc  6180
tgaggctttc tggattcggc ggcgttccgc aatgttgtat gggcgtatgc tgtcgtacat  6240
tcgggttttc tttctctaat tgttgttgta gtttggcagg tccgcctccg ataccgcatg  6300
tgtggcagta ccagacgccc ttgtcgaggt tgatgctcat ggagggctgg ggtcgtcgt  6360
ggaacgggca gaggatgtgt tgctcgtttt tggacgggtt gtaccgtatc tggtaggtgt  6420
cgaggaggcg gcaggtgtca gaggtgtggg aggagctcgt tgagggttga taccacatag  6480
gcttcgctcc atggcttgtt gcgctgtttc atcactacga gtccgatggt ggactgactt  6540
tcgcggtttc ggtgggtttc gtagttgcgt gcctcccggc tggcttgttt cacgaattcg  6600
```

```
gctaggtggg gctggccggc tttcgcctct atcacatagg ttttgtggcc ggttgtgagg  6660
ataaggtcgc cttcgtcttc acggccgttg aggtggaggc gttctatatc atggccggtg  6720
tcgcgtagtt ggtggaggag tcgtgtttcc cattctgcgc cggccctgcg gtttcttgat  6780
tgttgtgtcg acatgatagt cctttgtgtg ttgtggtcat attccagggc tgttttcgg    6840
cgagggcc gaagaaggtg tattcggggt aggctcgtga ccgctcgtat cgggtgccgt     6900
cggggctgga tttgcctgtg cgctgtttga ggacggcgat gcgtgcctct gccgggatcg  6960
atagcccgtt gccgttatcc tcgccaccat acaatgagac tccgaggatg agttgtggtt  7020
tttcggagag gccgttttg atttctcgcc gggcgggcgg gtgttcgatg tcggagccgg   7080
ttttgtcggt tgcgtggtgt gtgacaataa tggtggagcc agtatcgcgg ccgagggctg  7140
tgatccattg catggcttct tgctgggcct gatagtcact ctcgcagtct tggatgtcca  7200
tcaggttgtc gataacgatg atgagtggga aggtgttcca catttccatg taggcttgca  7260
gttccatggt gatatcggtc caggtgatgg gtgactggaa tgagaatgtg atgtgttggc  7320
cgtggtggat gctgtctcga tagtattctg gcccgtaatc gtcgatgttt tgttgtatct  7380
gggcggtggt gtgttgggtg ttgagtgaga tgattcgtgt ggaggcctcc caggtgtcca  7440
tgtcccctga tatgtagagg gctgctggt tgagcatcgc tgtgatgaac atggctagcc   7500
ctgattttg gctgccggac cgccccgcga tcatgacgag atcccctttg tggatgtgca   7560
tatcctggtt gcggtagagg ggttctagtt gtggtatgcg gggcagctcg gctgcggttt  7620
gggaggccct ctcgaaggat cgttggagag agagcatcgg gacctatct atctatcggt   7680
tacgatttgt atgaatattg gcggttagat ggagtcgatg tctacatcat cactaccagt  7740
ggtgttgggc tgactgtctc gctggtcaac gtaggctgct acaaggtcgt agatggcgtc  7800
gtccaatggt ttgagcacga ccgcgttgaa gccgttttg gtgcgcacgg tggcgagttt   7860
gaaggcttgc tcttcgccaa ggtaggtttc gaggtcggag atcatggagt gtgggcggtc  7920
gttgctgccg cgtactttt cgatgatggc gttgggatg gtttctgggg tgctgttgtt    7980
gaggtcgtct agggtgtgga agatggtgac atcagcgtag atgcgatcgg cggtctgtcc  8040
accgtagcct tcagtgttgt gctcgacgtc gtggactttg aaggcgatgg cggtggcgtc  8100
ctggtttcgg gaggggttga agaaggtcgt gttgctgttg tttcggtagtt ttgcgagtcc  8160
cattgttgtt tccttactα tttttgttgg tttgtgtcgg ttttttatcgg gtgaggctgt  8220
ttcgtttgct gcggaacgcc tcggatacgt cagtgttgct ggtgatgatc ttcttgtact  8280
gtttcagaag gtcggctagc tgtgcttgc ttgttgcatt gttgattttg tcaatgatgg    8340
tgttgtttcc ttcactggca atgttgtcta cgtagtcttt ggcggcctgg ttgtatcggt  8400
cttggaggat gatggatgcg gaggcgatca gtgttgccag gtcccagttc cttgccgcca  8460
aactgttttt gagtccgcct agcaagtcga tgatagtctt ctttacttcg tcggcggtgt  8520
ctccacggat gactgtccat ggggcggcgt agtctccgcc gtatttgagt gtgatggtga  8580
tgcgatcatc agtgctgttg gtgttatcgt tcactggtgc tccttgcttt cttctgttgg  8640
ggctgtgatg gtggtttctg tagggtacct gtaggcgtct ttcccgttga cggcccagca  8700
ggcgtccttg acggggcatc ctttgcagag tgctgtgacg tggggtacga agatgccttg  8760
actgattcct ttcattgctt gactgtacat ggatgataca tgccggtagg tgttgttgtc  8820
aaggtcgtac agttcggtgg atgtgccttg tgtcgggac ttgtcgtcgt tgcggctggt    8880
ggcgggtgtc caaaacatgc cttcgtcac atgaatgctg tgttgggcga gcatgtaccg   8940
gtatgtgtgc agctgcatac tgtcggcggg taggcggccg gttttgaggt cgaggatgaa  9000
ggtttcgccg gtgtcggtat ctgtgaaaac acggtcgatg tagccgacaa tctgggtgcc  9060
gtcggggagg gtggtttcta ccgggtattc gatgcctggc tggccgtcaa taacagcggt  9120
gatgtattct gggtggttgc gcctccatgt tttccagcgg tctacaaagg tggggccgta  9180
aaccatccac cagtcgtagt ctttttttgtg tggtccgccc gactcgcaca tgttttttca  9240
tattctgccg gagggtttga tttctgtgcc ttcggattcg gcgagggcta cttgggtgtc  9300
gaaaatgttt ttgaaggatg cgagtttgtc tggcagtgca gggtattcgg cgggattgta  9360
caggtatagg tcgtattgtt cggtgatgtg atgtatggcg cttccggcga tggtggcgta  9420
ccaggtgtgg tgttgggcgt ggtagccgtg ggataggcgc catttttctc cgcattcggc  9480
ccactgggtg agtgaactgt aggagatgtg gcctggatgg ttgatggttt tcggatattg  9540
tgctagggc attactggtc gccttttgtgt gtgttccatg ggttgcgggt gtcttggccg  9600
gcgtggtgtt gctggtaggc gaggagtgcg aggcagtgcc aggcagcatg ggctagatgg  9660
ggtagcccgg attcataatc gaggttgttg ccttgctgcc atgatagtag gtgcctgtag  9720
agggcgtcga cgctgtggct ccacgggtag ccgccggtcc agttgttgtc gccgtatttg  9780
gtggcaccgt agcctgccac ggagccgagg gcgtgcaagg ctgtagggtc gatgagggat  9840
agcctgcaaa gtttcaattc ttttttggca ccgctgttgg ggtcggtgta catgcgggtt  9900
ggcttatcca tggggtgtg ctccttaggg gtgggttact ggttgggggtt gtgggcgagt   9960
gctacggcga gaataatgat ggcgagggtt tcagcaataa gtatgggtgt tgtgatcatt 10020
tgctgtctcg gggattgttg gtgagtgtgg aggcgcctag gagggtggcg agggcgcatg 10080
cggcaataat ggcgagggct gccttgtgtg gggtgccggt tgcgtacatc catgtgatga 10140
tggcgccttg gatccaggcg aggctgtga agaacgtttc gtagctgtgt agctcaatgt   10200
tgttgggtgt gttcatgctt gctcctgaag aatggtgttg atggttttat aaatgttgta 10260
caggtcggtt tcgatagata acagttggtg gatttcgtgg tcgagatcaa tgtctgggtt 10320
gagggtgttg atgcgggagg caatatcggt ggctgtgcgt agtgtgccgc cggtgtggtg 10380
aataatgtgt gccgtgtcgg cgatccggt ggtgacagcg tagtgggaga ggagaggcat   10440
agctgggggt gctccttggc gggttactgt tgcgggttga tgttgaggtc ggtgacgtgc  10500
ggtgagcttt ctgttccggt gacgaggcag tggacggtga cgggtagttt ggatgctccc 10560
ggctggcgta cggtggcgcc gtaggcgatg gagaaggtgt ctttgccaat aattttgtgg  10620
agttggaggt cgatgtcggg gttgccgttc catttgacac cgtgtgcggc ggcctgttgt  10680
tcggctttgc ggttgcaggt gtgtcgtgcc tgtatcatgg tggtccggt gccggtttct    10740
tcccccttg cttgggcttg ccggtggttt ttggcctgct cggctcgcag tgactgttct   10800
gcggctgcct ggcgggcttt cttttcggct ttgcgctgtt ggacggtttt gggggtccac  10860
gcggtgttgg ctgtggtggc ctgtggggct ggctgtgagg caagtggcgg attgtcgtct  10920
ggggctggca tgaatgaggc ggcggcaatg atggcgactg tggcgccggc gatggtgtag 10980
cctttttct tgttcatgac tgtttgtcccc tttccgggt gttgttcgtt gctgacatga   11040
tcaatacttc cagcgaatga acctcgtgtc aaggctgcgc tcaacgattg tgagcgattc 11100
gtgtgtggct aggggtttta tcggctgtac agggtgagga ggtggcctac gttgatgcgg 11160
gtcacattcc agtagagttg cgtggcttca ccccggtga gtggcttcca ctcgttgtgg   11220
ctgaacacgg tgccgtcggt ggcgatgaat gtgttgggc gtagcttgtg gagttcggct   11280
tccacgctct gccggtaggc ttcggcgagg ccctcaaaat ccatgtggtc gcaggagagg 11340
```

```
ttttcgaggc gtgtcaggtc gaagggtgtg ggacagtcgt agctggcggg gctgtagagc   11400
tgggtgaagt ggttggcgat cttctgcatc atgattcctt ttctggtgat ggtgtgttga   11460
tggttttatc gtgtggcttc ggcgatgatg gcgtccacat cgattgtgtc gatcatgtcg   11520
tggagttcct cagcctcatc cgcggtgagt ggctgccagt cctggggtcc gtatatggca   11580
ccgtcgaggg tgacagtcca caggggccgg atgagtcgta cggcttcttc gactttggca   11640
cggtgcaggc ggcagatgat agacgtgtgg gtgttgccta tgtcacatcc tgccaggtgt   11700
gtggggtgga gtgggttgat ttctgtctgc ccgtagaggt tggtgaagga tggtgtgatg   11760
agtgtgccat ccatgagggt gtgctccttt cggtggtgta tgggttgttg tggtttctag   11820
agtgtgtagg ttgcgatccc atagtcaagg ctgcactcat tcggattgag cgtttcatgg   11880
gatgtggcag gggatgtggc gtatctcact taagccttta tggcctctct cagtgcctca   11940
aatcctctga gggtaggatt atgcagggtt gaccctgctg atcgattcta ggggccttct   12000
agggcgtctc aggggtatgt ctgggttatg gcgggtgtgg cagatgatct agcgagtcaa   12060
ggtgccgagc tgagacataa gatctatcat ctaggtgtgt gagatgcatc acatcctcct   12120
ggcgtggtgt acacccttaa ggctactcgg tcgatctggc gtggagggtg tagtaaagaa   12180
atgccgttta aagccttcgc acggcgccta ggagcgcctt acggggtggg ggctaggtat   12240
ttatacccc agcacattct gatcgattct agacgcctcc aggatcctga tacacgatca   12300
gctatccaga cgcagatcac cagtcccat cctggttagc taagcctcaa ctatgtggac   12360
agtgtgggat actgtggggg aagaaggaca cggtaaaaag aagagggggg agcatcagcc   12420
ttcacacctt caagccttaa ggttttagcg cttagcaccg atggtcttag cagttagcac   12480
cgagcccct cacgggctcg gcatcagccc gaacaggcac agccctgaaa ggagtacacg   12540
ccatcaggga aggcttgaga gtacgaggag ccctagcgac gagtactcga aagcctgagg   12600
gaacaccctc agcactgatg ggcctagcgt gttcggaaag gacacaagag tgaagtgtga   12660
cagctatccg ggagtgaaac ccgttctgac taggggtttc agccttaacc acctgtaaag   12720
gttacaagac tctaagaaaa tttaaggaaa agtttaggtt taattttggg accttttacta   12780
ccaaaaacac ccgtttacac ccctcaaacc cgccctataga gccaaatcca ccagtttgac   12840
tcatccagg tggggtatga taggctggac aggtagccac ctggacgcaa ggccgaaatc   12900
cgctgacgcg gcttttcaccc ttacatccat cagtctacca aagacttaaa gacctaaggg   12960
cttagcgcta aggtgctgat agcttagcac cgagcccctc aagggctcgg catcagtctt   13020
aaagctttaa acactttaag taaacttaag agcttagcac ttaaagttaa ttaataacct   13080
taaaggctta cacacttagc actgagccct ttaaggctca gcatcagtat aaagatctta   13140
acacctaagt taagtataaa accttaaagg cttagcactt aaggatataa acttaacatc   13200
agtgtttaag actttaaaac ttaaaataac tattaagact taaagactta taagctttaa   13260
acacttaaag taactataag actttaaaga ccttaagtat ttaaagttaa ccatcagtct   13320
taaactttaa tattataacc tataagtctt aaagcttata ggtataataa tataatataa   13380
gttataaaag ttttagaaga gctaagggg taacttcttt acttctctac tctctttggt   13440
actttctctc ttctcttctt ttcttcatca ggggagaaga ggaaccttta accgtcaacg   13500
ctgatggact tttcaccgtg tgactcgtgt gcttctggtc gcacgctccc atcgcacact   13560
ccccacactc tgacacccgt gccccttttca ggcttgacgt gttcggctga aggcgtacgg   13620
cgtgtcacgc ttaaacccttt aacaccaggt aagacttaaa gtgtatatta taagtagaag   13680
actttaaaac cttaaggtgt tcccgcttag cctgtgtcct ttagcgctag gcgccaagcg   13740
ctaagctgtg aaacgcgaac acccatccac ccccattttt cttccgtgtc cttcttcttt   13800
tgacaccgct gggggggcgat gtgatatttc tcacatgcca ggggtagtg gagaaaacaa   13860
acacccggc acaaacagaa caccccctca acgaacaaa caccccccca gaatcgatca   13920
gcagggcaag ggcaaggtat tcatacccccc aacacctttc aggccgttac aggagcaatg   13980
agaggctcac aggggcaagg ggagatcagg ggacgcgatg gcacacacca accgcaccgc   14040
atcatcagcc caccggcgtt ggcggcaacg actcatcacc caagcccaac aacaaggcca   14100
aaccgaatgc ccactctgcg gagcccagat agcctgacgc acccatgacc taccaaccag   14160
ccccgaagcc gaccacatca cacccgtcag cagaggagga ctcaacaccc tcgacaacgg   14220
gcaaatcatc tgcagaacat gcaacagaag caaaggcaat cgcagcgaac caaacatcaa   14280
attccaacaa caaaccacaa aaacattgat tccatggtga aaaacctgtc aacccccacc   14340
ggggacaacc cctgcacagg cgtgcaagac ctcgtacggc ttagtgaaat acctcccttt   14400
tgtggatttg tctgttttgtc gacttttttgt gttggtggtg agtgttgtgc agcctgagct   14460
tcctgatggt cgtgattggt gtggggagac gcgtcgttgg tggcgtgtgt ggggtgagga   14520
ttcgcgtgcc gggttggtgt ctgatgagga gtggctgttt ctcatggatg ctgcggtgat   14580
tcatgatgtg gttggcgtg agggtcgcgc ggatttggtg gcttcgcttc gtgctcatgt   14640
gaaggcgttt atgggcatgc tggaggctca ttctgggagt gctggcacta ctgtgggtgg   14700
tggggttct gcggtggcga tgattgaccg gtataggaag cgcaaggggg cctgattagg   14760
tgtctggtgt tgtgggttct caggttcctc gtcaccgtgt ggctgcggcg tatcaggtga   14820
ctgccggcaa tgatgctggt gctcttgggg ctgcgtatgg gttgactccg gatccgtggc   14880
agcagcaggt gttggatgat tggctggctg tcggtggtaa tggcaggctt gctgcgggtg   14940
tgtgtgggt gtttgtgcct cgccagaacg gcaaaaacgc gatccttgag gttgttgagc   15000
tttttaagat ggtggttcag ggtcggcgta ttttgcatac ggctcacgag ttgaagtcgg   15060
ctcgtaaggc gtttatgcgg ttgagatcgt ttttgagaa tgagcgccgc tatccggatt   15120
tggctcgtat ggtgaaggcg attcgggcga cgaatgtcgatc attttgcatc   15180
atcctgattg cagtgtgggt ggtaagaagt gtggctgccc tggttggggt tcggttgagt   15240
ttgtggctcg tagccgggggt tcggctgcgc ggttacggt tgatgatttg gtgtgtgatg   15300
aggctcagga gttgtcggat gagcagttgg aggctttgct tcctacggtg tctgcggctc   15360
cttcgggtga tccgcagcag attttcccttg gtaccccgc ggggcctttg gctgatggtt   15420
ctgtggtgtt gcgtttgcgt gggcaggctt tgtcgggtgg taaaaggttt gcgtggacgg   15480
agttttcgat tcctgacgag tctgatccgg atgatgtgtc gcggcagtgg cggaagttgg   15540
cgggtgacac taatccagcc ttgggtaggc gtctgaattt tgggactgtg tcggatgagc   15600
atgaatcgat gtctgctgcc gggtttgctc gggagcggct tggctggtgg atcgtggcc   15660
agtctgctac gtctgttgtt ccggcggata agtgggctca gtctgctgtg gatgaggcgg   15720
ctctggttgg cggcaaggtg tttggtgtct tttttctcgg cgtcggaggc gctcaagctt   15780
tggcgggtgc cggccggact gatgctgggg ttcatgttga ggttattgat gggctgtcgg   15840
ggacgattgt tgatggtgtg ggccggttgg ctgactggtt ggcggttcgt tggggtgata   15900
ctgaccggat catggttgcc gggtctgtg cggtgttgtt gcagaaggcg ttgacgatc   15960
gtggtgttcc gggccgtggc gtgtggtggt tg ctgatactgg cacctatgtg gaggcgtctc   16020
aggcgttttt ggaggggtgt gaggtctggga atgtttctca tcctcgtgct gattctgcc   16080
```

```
gtgacatgtt ggatattgct gtgaggtcgg cggttcagaa gaagaagggt tctgcgtggg    16140
gttggggttc ctcgtttaag gatggttctg aggttccttt ggaggctgtg tctttggcgt    16200
atcttggtgt gaagatggcg aaggctaggc ggcgtgagag gtctggtagg aagcgggtgt    16260
ctgtggtatg aactcggatg agttggcttt gattgagggc atgtacgatc gtatccaaag    16320
gttgtcttcg tggcattgtc gtattgaggg ctactatgag ggttctagcc gggtgcgtga    16380
tttgggggtg gctattcctc cggagttgca gcgtgtgcag acggtggtgt cgtggcctga    16440
tatagctgtg gatgctttgg aggagcgtct ggattggctt ggctggacta atggtgacgg    16500
ctacggcctg gatggtgtgt atgctgcgaa tcggcttgct acggcgtcgt gtgatgtgca    16560
tttgatgcg ctgattttttg gtttgtcgtt tgtggctgtt atccctcagg gggatgggtc    16620
ggtgttggtt cgtccgcagt caccaaagaa ttgtactgge cggttttcgg ctgacgggtc    16680
tcgtttggat gctggccttg tggtgcagca gacgtgtgat cctgaggttg ttgaggcgga    16740
gttgttgctg cctgatgtga ttgttcaggt ggagcggcgt gggtctcgtg agtgggttga    16800
gacgggccgt atcgtaaata gtcttggtgc ggttccgttg gtgccgattg tgaatcgtcg    16860
ccgtacgtct aggattgatg gccgttcgga gatcactcgg tcgattaggg cttacacgga    16920
tgaggctgtg cgcacactgt tgggcagtc tgtgaatcgt gacttctatg cctaccctca    16980
gcgttgggtg actggcgtgt cggctgacga gttttcgcag cctggctggg tcctgtcgat    17040
ggcttctgtg tgggctgttg ataaggatga tgacggtgac accccgaatg tggggtcgtt    17100
tcctgtgaat tcgcctacac cgtattcaga tcagatgcgg ctgttggcgc agttgactgc    17160
gggtgaggct gcggttcctg aacgctatt cgggtttatc acgtctaacc cacctagtgg    17220
ggaggctttg gctgcggagg agtctcggct tgtgaagcgt gctgaacgca ggcagacgtc    17280
gtttggtcag ggctggttgt cggttggttt cctggctgcc agggcgcttg attcgagtgt    17340
tgatgaggcc gcgttttcg ggtggtggg tttgaggtgg cgtgatgctt cgacgccgac    17400
tcgggcggct acggcggatg ctgtgacgaa gcttgttggt gccggtattt tgcccgcgga    17460
ttctcggacg tgttggaga tgttgggggct tgatgatgtg caggttgagg ctgtgatgcg    17520
gcatcgtgcc gagtcgtcgg atccgttggc tgcgcttgct gggctatat cgcgtcaaac    17580
taacgaggtt tgataggcga tggcttcggg ggttgcgtcg aggttgcgtc ctgccgggta    17640
tcagcggcag gcgattcgtt ttgccggaaa gtatgcgggc tattatgccg agttggggcg    17700
tttgtggcat tccgggaaga tgacagatgc gcagtatgtg cgtttgtgtg tggagttgga    17760
gcgtgccggc catgacggtt ccgcggcgct ggcgggcaag ttcgtgtcgg attttcggaa    17820
gcttaacggt gtggatcctg gtttgatcgt gtatgacgag tttgatgctg ccgccgcttt    17880
ggctaggtcg ttttcgacta tgaagattat gaatagtaac ccggataggg cgaatgatac    17940
gattgatgct atgcggcgg gtgttaatcg ggctgtcatg aatgctggcc gtgacacggt    18000
tgagtggtct gctggcgcgc agggtaggtc gtggcgcagg gtgactgatg gtgatccgtg    18060
cgcgttttgt gccatgttgg ctacgaggtc ggattatacg accaaagagc gggcgcttac    18120
tactgtcat acgcggcgtc ataagctgc cggttggtt cgaagtatca    18180
tgatcattgt gggtgtacgg tggttgaggt tgttgggcgt tgggagccaa ataggctga    18240
tgccgagtat cagaggacgt atgagaaggc ccgtgagtgg gttgatgatc atggtttgca    18300
gcagtcgcct ggcaatattt tgaaggctat gcgtactgtt ggcggcatga gataatttga    18360
tgtggtttcc ggttgtcgc cgccggttat cggtgcacag ggttgtctcc cgcacggggg    18420
tcaacaatgt tgtgttgttt tccgcaagga gtgtaaggtt aggctatggc cgatcagagt    18480
gttgaggaac agaatgtcga caatgatgct gttgagcccg gaaagggtgg agacattgtt    18540
gatgttgtga aggatgggcg ggctgccggc gatgatcatg ccggtgatgt ttccgtgaag    18600
ggtgaggctt ctgggtcttc gggcacggat tggaaggctg aggctcgtaa gtggggagtct    18660
cgtgctaaaa gtaatttcgc cgagttggag aagcttcgta catcgagtga cgattctgga    18720
tctactattg atgagcttcg ccgcaagaat gaggaactcg aagacaggat caacgggttt    18780
gttcttgagg gtgtgaagcg tgaggtggct gccgagtgtg gcctgtcggg tgatgcggtc    18840
gcttttcttgc acggtagcga tcgtgaagca ctggtggagt ctgctaaggc tttgaagggt    18900
ttgattgacc atagtagtgg tggcgcgggt gtgcgccgtc ttgcggggag tgccccgtt    18960
gatgatgtta aacgacgtga gggtgtcgcg tttgtggatg ctcttgtcaa taattctagg    19020
agatgatttg tgatgctga cgatttttctt tctgcaggga agcttgagct tcctggttct    19080
atgattgggtg cggttcgtga ccgtgctatc gattctggtg ttttggcgaa gctttcgccg    19140
gagcagccga ctatttttgg ccctgttaag ggtgccgtgt ttagtggtgt tcctcgcgcc    19200
aagattgttg gtgaggtga ggttaagcc tctgcgtctg ttgatgttc ggcgtttact    19260
gcgcagccta tcaaggttgt gactcagcag cgtgtctcgg acgagtttat gtgggctgat    19320
gctgattacc gctctgggtgt tttgcaggat ctgattcgc ctgctcttgg cgcttcgatt    19380
ggtcgcgctg ttgatctgat tgctttccac ggtattgatc cggctacggg taagcctgct    19440
gcggctgtca gtcttcgct ggataagacg aagaatattg ttgatgcaac cgatagtgct    19500
acggctgatc tgattaaggc ggttgggctg attgctggtg ccggttttgca ggttcctaac    19560
ggggttgctt tggatccggc gttctgtttt gccctgtcta ctgaggtgta tccgaagggg    19620
tctccgcttg ccggccagcc tatgtatcct gccgccgggt tcgccggttt ggataattga    19680
cgtggcttga atgtttggtgc ttcttcgact gtttctggcg ccccggagat gtcgcctgcc    19740
tctggtgtta aggctattgt tggtgatttc tctcgtgttc attgggggtt ccagcgtaac    19800
ttcccgatcg agcttatcga gtatggtgac ccggatcaga ctgggcgtga cctgaagggc    19860
cataatgagg ttatggttcg cgccgaggcg gtgctgttag tggctatcga gtcgcttgat    19920
tcgtttgctg ttgtgaagga gaaggctgcc ccgaagccta atcctccggc cgagaactga    19980
tttattgttg cggtgatgtg tcaatgtgca ggggtgtgg ttgatgggta tcattttgaa    20040
gcctgaggat attgagcctt tcgccgatat tcctagagag aagcttgagg cgatgattgc    20100
cgatgtggag gctgtggctg tcagtgtcgc ccctgtatc gctaaaccgg atttcaaata    20160
caaggatgcc gctaaggcta ttctgcgcag ggctttgttg cgctggaatg ataccgggtg    20220
ttctggtcag gtgcagtatg agtctgcggg tcctttcgct cagactacac ggtctaatac    20280
tcccacgaat ttgttgtggc cttctgagat tgccgcgttg aagaagctgt gtgagggtga    20340
tggtggggct ggtaaagcgt tcactatcac tccaactatt aattgtcgat atgcacattc    20400
tgaggtgtgt tccacggtgt ggggtgaggg ttgctcgtgc gggtcgaata ttaacggcta    20460
cgctgccct ttgtgggaga tatgatatga ccagtttcc ttatggtgaa acgattgtga    20520
tgcttcagcc gactgttcgt gtcgatgatc ttggtgacaa ggtggaagac tggtctaagc    20580
ctgtcgagac tgtgttccat aacgtggcca tctatgcttc gttgtcgcag gaggatgagg    20640
ccgcggggcg tgactcggat tatgagcatt ggtcgatgct tttcaagcag cctattgtgg    20700
gtgctgatta tcgttgcagg tggcgtatcc ggggtgttgt gtgggaggct gacgggtctc    20760
ctatcgtgtg gcatcatccg atgtctggct gggatgcggg cacgcaggtt aatgtgaagc    20820
```

```
gcaagaaggg ctgataggtt gtggctcagg atgtgaatgt gaagctgaac ttgccgggta   20880
ttcgtgaggt gttgaagtct tctggggtgc agtctatgtt ggctgagcgt ggcgaaaggg   20940
ttaggcgtgc ggcctcggcg aatgttggcg gtaacgcttt cgatagggcc caatacagta   21000
atggtttgtc gtcggaggtg caggttcacc gggttgaggc tgtggcgagg attggtacca   21060
cctataaggg tggtaaaagg attgaggcga agcatggcac gttggcggga tcgattgggg   21120
ctgcgtcgtg atcgtttacg gtgatccgcg cgtgtgggct aaacgcgtac tcaaggatga   21180
tggctggctg tctgatatac catgtacccg gacagtgccg gatagctttg agggtgacct   21240
tatttggttg gctcttgatg gtgggcccaca gttgcatgtg cgtgagcagg ttttttttgcg  21300
cgtgaatgtg ttttcggata cgccgaatcg tgctatgtcg ttggcgcgtc gtgttgaggc   21360
tgtgctggct gatggtgtgg acggtgaccc tgtggtgtac tgtaaacggt ctactggccc   21420
tgatttgctg gttgacggtg cacgtttga tgtgtattcg cttttttgagc tgatatgtag    21480
gcctgcggag tctgaataag cttattgttt ttgttttaat gtaattgttt gatatttaat   21540
gggggttgtg atggctgcaa cacgtaaagc gtctaatgtt cgctctgctg ttacgggtga   21600
cgtttatatt ggtgccgctc atgctggtga cgctattgat ggtgtgaaga cggttcctga   21660
cggtcttacc gctttagggt acctgtctga tgacggggttt aagattaagc ctgagcgtaa  21720
aacgatgat ttgaaggctt ggcagaatgc ggatgttgtt cgcacggttg ctactgagtc   21780
gtctatcgag atttcttttc agctgatcga gtctaagaag gaggttatcg aactgttttg   21840
gcagtcgaag gttactgccg gatccgattc gggttcgttt gatatttctc ccggtgccac   21900
gacgggtgtt cacgccctgt tgatggatat tgtggatggc gatcaggtta tccgttacta   21960
tttccctgag gttgagcttg tcgatcgtga cgagattaag ggtaagaatg gcgaggtgta   22020
cgggtatggt gtgacgttga aggcgtatcc tgcccagatt aataagaagg gtgatgcggt   22080
gtctgtcgg gggtggatga gcctttaaa agctgatact cctccggttc cgccttctcc    22140
gaagcctcag ccggatccga atccgccgtc cgataattga tacacgagtt tgagggattg   22200
ttgatagatg agtgacacag gttacacgtt gaagatcggt gaccgtagtt gggtgttggc    22260
ggatgcggag gagacggctc aggctgttcc tgcccgcgtg tttcgtcgtg cagctaagat   22320
tgcccagtcg ggggagtctg cggatttcgc ccaggttgag gtgatgtttt ctatgttgga   22380
ggctgccgcc ccggctgacg cggtggaggc tctggagggg cttcctatgg ttcgtgttgc   22440
cgagattttc cgccagtgga tggagtgaaa gcctgaaggt aagggtgcct ctttggggga   22500
atagtttggc tccacggcct gattgatgag tatcgtgggg ccatcgaata tgattggcgc   22560
acaaggtttg gtgtgtgcat atacgatata ggtggtctcg caatggggtg gggtgaggct   22620
gtccggctgg ctgcgtgtt gtgtaccgat acgtctagcc agttggcggc ccacctgaat   22680
ggttggcagc gcccgtttga gtggtgcgag tgggctgtgt tggacatgct ggatcattac   22740
aggtctgcta atagtgaggg gcagccgag cctgtggcga ggcctacgga tgagcgtagg    22800
gcccggttta cgtctgggca ggtggacgat attttggcgc gtgttcgtgc cggtggcggg    22860
gtgtctcgcg agattaatat ttgggggtga atagtgtatg tctggtgaga ttgcttccgc   22920
atatgtgtcg ttgtatacga agatgccggg tttgaaatca gatgttggta aacagctttc    22980
tggggtgatg ccgctgagg gtcagcgttc gggtagcttg tttgctaaag gcatgaagct    23040
ggctttgggt ggcgccgcaa tggtgggcgc cattaatgtt gctaagaagg gcctcaagtc    23100
gatttatgat gtgactattg gtggcggtat tgctcgcgat tggctgtattg atgaggctca  23160
ggctaagttg actggtttgg gtcatacgtc ttctcgatacg tcttcgatta tgaattcggc   23220
tattgaggct gtgactggta cgtcgtatgc gttggggggat gcggcttcta ctgcggcggc    23280
gttgtctgct tcgggtgtga agtctggcgg gcagatgacg gatgtgttga agactgtcgc    23340
cgatgtgtct tatatttcgg gtaagtcgtt tcaggatacg ggcgctatt ttacgtctgt    23400
gatggctcgc ggtaagttgc agggcgatga catgttgcag cttactatgg cgggtgttcc    23460
tgtcctgtct ttgcttgcca ggcagacggg taaaacgtct gctgaggtgt cgcagatggt   23520
gtcgaagggg cagattgatt ttgccacgtt tgcggctgcg atgaagcttg gcatgggtgg    23580
tgctgcgcag gcgtctgta agacgtttga gggcgctatg aagaatgtta agggtgcct    23640
gggctatctt ggtgctacgg ctatggcgcc gtttcttaac ggtttgcggc agattttgt     23700
tgcgttgaat ccggttatca agtcggtgac ggattctgtg aagccgatgt ttgctgccgt    23760
cgatgctggt attcagcgta tgatgccgtc tattttggcg tggattaacc gtatgccggg    23820
catgatcact cgaatgaatg cacagatgcg cgccaaggtg gagcagttga agatattt    23880
tgcaaggttg catttgcctg ttcctaaagt gaatttgggt gccatgtttg cgggtggcac    23940
agccgtgttc ggtattgtgg ctgccggtgt ggggaagctt gttgcagggt ttgccccgtt    24000
ggcggtgtcg ttgaagaatc tgttgccgtc gtttggtgct ttgaagggtg ccgctggtgg    24060
gcttggcggc cgtgtttcgcg ccctgggtgg ccctgttgt attgtgatcg gcttgtttgc    24120
ggccatgttt gctacgaacg cccgttccg tgccgctgtt atgcagcttg tggctgtggt    24180
tggcaggcg ttgggccaga ttatggccgc tgtgcagccg ctgttgggtt tggttgctgg    24240
gctggtggca cggttggctc ccgttttttgg ccagattgtt ggtttggtgg ctggtttggc    24300
tgcgcagctt gttccttttga ttagtatgct ggttgccga ctagttccctg tgatcaccca    24360
gattattggt gcagtcacgc aggtggcggc catgttggc ccggcgttga tgccggtgct    24420
tcaggcgatt gttgctgatga tacggcaggt tgttggtgtt gtgatgcaac tggtgcctgt    24480
tttgatgcct gtgattcagc agattttggg tgctgtcatg tctgtgctgc cgcctatcat    24540
cggcctgatc cggtcgttga taccagtcat catgtccgttt atgcgtgtgg tggttcaggt    24600
tgttgcggtt gtgatacagg tggtggcccg tattcttgct gttgtgcctc cgtgtggtt    24660
tgctgtggtg ggttttgttg cccgtattgt tggtgctgtc gtgtcggctg tgcccgtgt    24720
gattgcggct gtggcccgtg tgatcggatg ggtgtgtgcc cattttgtgt ctggttttgc    24780
acgcatgggt tcgttattc aggctggctg gaatcatatt agagcgttta cgtcggcgtt    24840
tatgagcggt ttcaagtcga tcatttctgg cggcgtgaac gctgttgtgg ggttttttac    24900
gcggcttggt tcttcggttg cttcccatgt gaggtcggt tttaacgcgt ctcgtggcgc    24960
tgtttcttct gcgatgaatg ctatccggag tgttgtgtct tcggtggcgt ctgctgttgg    25020
cgggttttttc agttcgatgg cgtcaggagt tcgtagtggt gctgtgcgcg gtttaatgg    25080
tgcccggagt gcggcttctt ctgctatgca tgctatgggg tccgctgtat ctagcgggt    25140
gcatggtgtg ctgggtttttt tccggaattt gcctggtaat attcggcgtg cgcttggtaa    25200
tatgggggtcc ttgttggtgt ctgcggggcg tgatgtgtg tctggtttgg gtaatggtat    25260
ccggaatgtg atgagtggct tgttggatac ggtgcgtaat atgggttctc aggttgcgaa    25320
tgcggcgaag tcggtgttgg gtattcattc accgtctagg gtgtttcgtg accaggttgg    25380
ccggcaggtt gttgccggtt tggctgaggg gatcacaggg aatgctggtt tggcgttgga    25440
tgcgatgtcg ggtgtggctg gaaggctgcc ggatgctgtt gatgccccggt ttggtgtgcg    25500
atcgtctgtg ggctcgtttta ccccgtacga ccggtatcgg cgtgcgagcg agaagagtgt    25560
```

-continued

```
tgtggtgaat gtgaatgggc ctacttatgg ggatccgaac gagtttgcga agcggattga 25620
gcggcagcag cgtgacgctt tgaacgcgtt ggcttacatg tgatcgaggg ggtgttgtgc 25680
atgtttattc ctgacccgtc tgatcgttct ggtttgactg ttacctggtc tatgttgccg 25740
ttgattggta atgatccgga gcgtgtgctt catttgacgg attatacggg tgcgtcgcct 25800
gtcatgttgt tgaatgattc gttgcgcggt ttgggtgttc ctgaggttga gcattttct 25860
caaactcatg ttggggtgca cggctcggag tggcgcgggt ttaatgtgaa gcctcgcgag 25920
gtgacattac ctgtcctggt gtcgggtgtg gatccggatc cggtgggcgg gtttcgtgac 25980
ggtttcatga aagcctatga cgagttgtgg tcggcgtttc ccccgggcgg ggtggggag 26040
ttgtctgtga agactcctgc tggtcgtgag cgtgtgttga agtgccggtt tgattcggtg 26100
gatgatacgt ttacggttga tccggtgaat cgtggctatg ctcgctatct gttgcatttg 26160
acagcttatg acccgttttg gtatgggggat gagcagaggt ttcgttttag taacgcgaag 26220
ttgcaggatt ggttgggtgg cggccctgtc ggtaaggatg gcacggcgtt tcctgtggtg 26280
ttgacgcctg gtgttggttc gggttgggat aatctgtcga ataagggtga tgtgcctgcg 26340
tggcctgtga ttcgtgttga ggggccttttg gagtcgtggt ctgtgcagat tgatggtttg 26400
cgtgtgtctt cggattatcc tgttgaggag tatgattgga tcactattga tacgatcct 26460
cgtaagcagt ctgcgttgtt ggatgggttt gaggatgtga tggatcgttt gacagagtgg 26520
gagtttgcgc ctatcccgcc tggcggttct cggagtgtga atattgagat ggttggtttg 26580
ggtgccattg ttgtgtcggt gcagtacagg ttttttgaggg cttggtgaat agttgatggc 26640
tggtcttgtc ccgcatgtaa cgttgtttac gccggattat cgtcgtgtgg cgcctatcaa 26700
tttttttgag tcgttgaagt tgtcgttgaa gtggaatggt tgtctacgc tggagttggt 26760
ggtgtctggg gatcattcta ggcttgacgg gttgactagg ccgggtgcgc ggctggttgt 26820
tgattatggt ggtggccaga ttttttctgg gcctgtgcgt aaggttcatg gtgtgggtcc 26880
gtggcgttct tcgcgggtga ctatcacgtg tgaggatgat atccgcctgt tgtggcgtat 26940
gctaatgtgg cctgtgaatt atcgtcccgg catggttggt tcggagtggc gtgccgacag 27000
ggattatgct cactattcgg gtgcggcgga gtcggtggct aagcaggtgt tggggataa 27060
tgcttggcgt tttccgcctg gttttgttat gaacgatgat gagagtccgtg gccgctatat 27120
taaggatttt caggcccggt tccatgtgtt tgccgataag ttgttgccgtg tgttgtcgtg 27180
ggctcggatg actgtttcgg tgaaccagtt tgagaatgcg cagtttgatc agcggggttt 27240
gctgtttgat tgtgtgcctg ctgtgacccg gaagcatgtg ttgactgccg agtctggttc 27300
gattgtgtcg tgggagtatg tgcgtgacgc cccgaagcgt acgtctgtgg tggttggtgg 27360
ccgcggcgag ggcaaagatc ggctgttttg tgaggatgtt gattcgatgg ccgaggggga 27420
ttggttttgat cgtgtcgagg tgtttaagga tgcccgtaac acggattctg aacatgtgca 27480
tctcatcgat gaggctgagc aggtgctgtc cgagttaggg gccacgtcgg ggtttaagat 27540
cgagttggct gagtcggatg tgttgcggtt tgggccaggc aatctgatgc cgggtgatct 27600
tatctatgtg gatgtgggtt ctggcctat tgccgagagt tgcggcagga ttgatgctga 27660
gtgtgattcg cctggtgatg gttggacgaa ggtgactcct gttgcggggg attatgagga 27720
taatccgtcg gcgttgttgg ctcgccgtgt ggctggtttg gctgcgggtg tgcgggattt 27780
gcaaaagttt tagtaagtga ttgggttttg ttgtgggtat tgtgtgtaaa gggtttgatg 27840
gtgtgttgac cgagtatgat tgggctcaaa tgtctgctgt gatgggtaat atgccgctcg 27900
tgaagggccc ggatgatttt cgtgtcggta cgacggttca gggtgccaca gtgttggtgta 27960
gtgttttgcc ggggcaggcg tgggctcacg gggtgatgtg cacgtcgaat agtgttgaga 28020
cggtgacggg gcagcttccg ggccctggcg agactagata cgactatgtt gtcctgtctc 28080
gggattggga gcagaacacg gccaagttgg agattgttcc tgggggcgt gcggagccgtg 28140
ccagggatgt gttgcgcgcc gagcctggcg tgtttcatca gcaactgttg gcgactttgt 28200
tggtgtcgtc taacgggttg cagcagcagt tggataggcg tgctatagcg gctagggtgg 28260
cgtttggcga gtctgctgcg tgtgatccta ccccctgtgga gggtgaccgg gtgatggttc 28320
cttcgggggc tgtgtgggct aatcatgcta acgagtggat gctactgtct ccgaggattg 28380
agacgggttc taagtcgatc atgtttggcg ggtctgctgt gtatgcttac acgatcccgt 28440
ttgcccgccc gtttagtagt ccgcctgttg tggtggcgtc tatggctacg gcggctgggg 28500
gcacgcagca gattgatgtg aaagcctaca atgtgactgc caaggatttt ggtttagcgt 28560
ttattacgaa tgacgggtct aagccttctg gtgtgcctgc ggtagctaac tggattgctg 28620
tcggcgtgta atgcgctgct tgtgtgtgcg ggatatgttg tggtggttgt agtggtaggg 28680
ggctgtagtg tcatggtttta cacccacact tgtagcctct atttgtaccg ctatcgctac 28740
tgtccttggt tcgattcagg cggttactta caggtcgaag aagaggctta ggcagttgtc 28800
tgcacaggtt gatgcgatgg aagaatacac atggaatatt cgccatattg ttcatcgcta 28860
taacgcgaat ttgcctgaga atgttgagcc tgtaaaaatg cctgatttgc ccgagttttt 28920
gaaggatact gttgatagtg gtgggggggtg aattgtgagg gagttggagg aagagaaacg 28980
gcagcgccgc aattttgaga aggcttcact ggtgttgttg tttttgtcgc ttgtgttgtt 29040
ggctgtggtt gctgtgggtg ctttgcgttt cggggctgta tcctctgagc gggattcgga 29100
gcaggctagg gcccagtcga atggtacggc cgctaagggg ttggctgcga gtgtaaggcg 29160
ggcgtgcgtc tctggtgggc aggagtcggt gcgtcttcac cagtctggct tgtgtgtgga 29220
tgctcagcgt gttgagcg                                                29238
```

SEQ ID NO: 70      moltype = DNA  length = 29699
FEATURE            Location/Qualifiers
misc_feature      1..29699
                    note = PAC9
source             1..29699
                    mol_type = other DNA
                    organism = synthetic construct
SEQUENCE: 70

```
tgatggtcgg gatggttcgg ccggtgagcg cggtgatgtg ggcccttcag gtcctgccgg  60
cccgcaaggt gcacagggtg aacgggtgag cgcggcccc gccggtgcga acggatccga 120
tggtaaagac ggtaaggatg gtgctgatgg ccgtgatggc cgttcggtga tatcggtgta 180
ctgttccggg ggccgcctgg ttgtgaaata tagtgacggt acggcctcta ccgtgtcggg 240
ttctgcggcc tgcgagagtg tgaaaccatc acctgtggtt actgtatcat cccataggtg 300
aacaagaaga gggaagggtg ttactagtgt tgattgtggt gtttggggt ggtgtgtggt 360
gagatacatt ccagcggcgc atcactctgc cggttcgaat agtccggtga acagggttgt 420
gattcatgca acatgcccgg atgtgggggtt tccgtccgct tcgcgtaagg gtcgggctgt 480
```

-continued

```
gtctacagcg aactatttcg cttccccatc atcggggggt tcggcgcatt atgtttgtga   540
tattggggag acggtgcagt gcctgtcaga ggggactata gggtggcatg ccccgccgaa   600
tccgcattct ttgggtatag agatttgcgc ggatggggt tcgcatgcct cgttccgtgt   660
accgggcat gcttacacga gggagcagtg gcttgatccg caggtgtggc ccgcagtgga   720
gagggccgct atcctgtgtc ggcagttgtg tgacaagcat ggtgttccga aaaggaaact   780
gtctgtggcc gatttgaagg ccggtaaacg gggtgtgtgc gggcatgtgg atgttacgga   840
tgcgtggcat cagtcggatc atgacgatcc ggggccgtgg tttccgtggg acaaatttat   900
ggctgtggtg aatggccacg gcggcggttc aagtagtgag gagttgagta tggctgatgt   960
acaagcgtta cataatcaga ttaaacagtt gtcggcacag gtggcccagt cggtgaataa  1020
gctgcatcac gatgttggtg tggttcaggt tcagaatggt gatttgggta aacgtgttga  1080
tgccctgtcg tgggtgaaga atccggtgac cgggaagctg tggcgcacca aagacgccct  1140
gtggagcatc tggtattacg tgttggagtg tcgcagccgc atagacaggc ttgagtctgc  1200
tgttaatggt ttgaaaaagt gatggtggtt tgttgtgggt aaacagtttt ggttgggctt  1260
gtttgagcgt gccctgaaaa cttttattca aacgtttgtt gctgtgcttg gggtgacggc  1320
gggtgttact tatactgcgg agtcgtttcg cggtttgccg tgggagtctg ccctgataac  1380
agcaacggtt gctgcggtgc tgtctgttgc tacatcgttt ggtagcccgt catttgtggc  1440
cggcaaacct aaaaccacgg ttgtggatgc tgggcttgtt ccacccgacg atgggggcat  1500
ggttgagccg cactcggttg atgtgtcgga tcctggcatg atcgagccga cagatgatgt  1560
ggatggtttt gctggctatg tgccgaagcg tgcagccgag tcggaggtta gcacggtgga  1620
gtctactgtt gcataattga acatagatgt gtgcccagc ggtgctgcca cgatcgtgtg  1680
gtggttgccg ctggggcact ctttttgtgt ctataggagt tttacaggtt gtcgtctagt  1740
gtgtcttcga gcatctggtc caggtagagg caggcggaga tagtatcgtt ggcctggtct  1800
agaacgttct ggccgataac attttttatga ttgtcgcggt ggctgatgat agaccgcatg  1860
atatcgtcgg ccgccgcctg caatagtttg gcctggtatg cgattcctgc gagccagtct  1920
agtgcttcct ggcttgccag tgtgtcgtct ggaatgccac gggtgttgct gttgtttgtg  1980
gggtgtcctg cactgtcgca gcaccacaag atttcgctgc actcgtctag cgtgtcctgg  2040
tcgatagcaa gatcgtcgag gctgacttct ttgacggtaa ggttcacatt gtcgagggag  2100
atgggtacac cgtattggtt ttcgacactg tcaacaatgt tttccaactg ttgcatgttg  2160
gtgggctgtt gttggatgat acggtgtact actgttttga tggcggtgta ggggatattg  2220
tgtgtgttgt tcatggtttt tatcccaccc ctgtgttgtc gtcgttattg tctggatagt  2280
atctactgtt tgcgtagcct gtgagggtga tgagtgtttg gtctgcccac tgtttcactg  2340
tctgccgggt gacacccaat cgttgggcgg ctgtggcgta ggtttgatca tacccgtata  2400
cttcacggaa tgcggctagc ctggctaggt gttttcgctg tttggagggt tcacatgata  2460
gggtgtagtc gtcgatggcg agctgtagat cgatcatggt ggcaatgttg ttgccgtgat  2520
gctgggggc ggttggtggg ggtggcattc ctggctccac actgggtttc catgggccgc  2580
cgttccagat ccattgggcg gcttggatga tgtcggcgag ggtgtaggtt cggttcatgt  2640
gtcaccccct gaacaggtcg ttgctggtgc tggtgttggt ggtgtcgaat cgtccgacgc  2700
agtggcagta gtcgtacatg agtttgataa tgtgttggtg gtctcccaaa taggtgtttc  2760
cgctgatact gtaggtggct gtgccgtctt tactgatggt gtatttggcg gtgatggttt  2820
cggggttttc ggtgtcggtg atgattgctg tggtggtggt gcctactgtt tgtagcacgg  2880
tggtttgggt tccgtcgtcg atagtggttt taaccatggt gtgtgttctc cctttttaga  2940
tgctggtttg gttgtcggct agatgaatga tgtcgggtaa gggtttcggc tggtctaggt  3000
gttgtatggt tttgttggct agccgtttgg ctaccctgta acacattttg gtgtagtgtt  3060
tgttgtctag gttgtggtat tgttcccgca ccgcaatata tagtagagag tcttggtaca  3120
ggtcgtctgc actgattgcg gggtagtgtg cggctgtttt ggtgcatgcc cggttgagtg  3180
tgcgtagatg atggtctgtg gcccacaccc acgatgcggt ggtggctagg tcggcttttg  3240
ttggtcgtct gctcatggca tttctttcat cgggctatct gtagttgtt tggtgtttttg  3300
ttgttgatag tgtagcacac gagtccgggg tttccggtgg tgccagtctt gtgccggtac  3360
catgtggatt cgccttccat ggatgggcat tggatgaagg tgcgttgtcc ttgttcggag  3420
atttctaggt ggtgccggtg cccggccatg aggatgtggg atgtggtgcc gttgtggaat  3480
tcttggccgc gccaccaatc atagtgtttg ccggtgcgcc attggtgtcc ggttgcgggg  3540
aggatttgtg tgccggccac gtcgacggtg gtggtcattt cgtcccgttg ggggaagtgg  3600
aagtgaaggt tggggtattg gttgttgagc tggtaagctt ctgcgatggc gcggcagcag  3660
tccacgtcaa aggagtcgtc gtaggtggtg actcctttgc cgaagcgcac ggcttcgccg  3720
tggttgccgg ggatggatgt gatggtcaca tttttgcagt ggtcgaacat gtggacgagt  3780
tgcatcatgg ccatgcgggt gagcctgatt tgttcggtga ggggtgtttg tgtgcgccag  3840
gcgttgttgc ctccttgtga cacgtatcct tcgatcatgt cgccgaggaa tgcgatgtgg  3900
actcgttcgg gtttgcctgc ctgttgccag tagtgttttg cgactatgag ggagtgcaaa  3960
tagtcgtctg cgaatcggct ggtttctccg ccggggatgc ctttgccgat ttggaagtcg  4020
cctgccccga taacgaaggc tgtctcgtca ctgctttggg tgtcttgttc gggtttgggt  4080
ggctgccatt cggctagttt gttgacgagt tcgtcgacgg ggtagggg tc ggttgcgggt  4140
tggtggtcga tgattttttg tatggatcgg cctgtttctc cgttggggag tgtccattcg  4200
gagatgcgtg tgcggcgtac agtaccgttg gctagattgt cgtcgatggt gtcgatggcg  4260
ttgtcgtggt tggctagctg tgtgagtagc cggtctatct tgtctatcac tggttttcct  4320
cctctggcgg ggtggtgttg gcttgtttgc ggcggtagtc ttttataacg gtggcggaga  4380
tggggtatcc tgcctgggtg agctgttttg ctagccacga ggcgggtata gacctgtcgg  4440
cgaggacgtc tgcagcctgt tgccgtagc gttgaataag ggtttcagtt ttggttgcca  4500
tgatgtccta tcggttgtgt ggcgggctgc catcctgtgc ggcagtcgcc gtcgtggcct  4560
gtttgcgtg tgcaccacga tacggttccg tctgtgtggt tgagtgtttt gccgcacatg  4620
acgttttgta gatgctcggg cagggcgccg tcacccgtct tgctggtttg tgtgtcgaag  4680
agtgttttct ggttggtgaa atgctctgac acggtgccgt tgtgtacggg tagtatccat  4740
gttttccatt gttgttgtag ccgggtgttc cagtggaatt gtttggccgc gttcgtggct  4800
tgtttgatgg ttttgtagta gccgacgagg atgcgctggt gttcactgtc gggtgggttt  4860
tggcctgcc agtattgtgc cgcgacggca tacctgtgaa ggcgtccgag ggcgtccagg  4920
cagtattcga taatgtgttg tagtacacta tcgggaatgt ctcgtacttg gttttcgtcg  4980
agccacgcgc cgacaatgat gttgcgtatg cgtgttttgt ctttggtggt gggtttgaac  5040
gagatactca ccatgctggc ctgtcgtctt gcatgaaatc gttaaggat gattcgcttg  5100
tgcggcgtgc ctgggtgatt tgctggtcag tccagtcggg gtgttgctgt ttcagatagt  5160
accagcggca ggcatcatat gtttcgttct gcaagcgggt gagatggttt tcggtgatga  5220
```

```
tttgtttcca cattgtccac gaaacgtcga gcctgcggag catgtccatg gccggcacat  5280
taaacgagtc aaggaagagt atttcgtggg tgtagtagtt tttctcgtag gcgtaccatc  5340
cgcttcggtg cctgtggggc tggtttttgg ggtaggcttc ccggcatact ttgtgtaaac  5400
gtttggccat gtcgtcgggt agttcaatgt cggggttggc gcggatcatg gatcgcatcc  5460
cgtcgtaggt ggtgcccag gtgtgcatga tgtgtagtgg gttgtctcca tcggcccatt  5520
tttctgcaca gatggcgagg cggatgcgcc tcctggctgt ttggctggtg ttgcgccggt  5580
tggggattgg gcacgtgtcg aggggatcca ttatgtttta gtgtaccttt ctggtttcgt  5640
gttgttgacg tgttttactg tagcacagtg tctagtgctt gtgtcaaccc tgttttccg   5700
gcctgcaggt aggtgtctgt gacatctccg accgtgaggg gcacatgggt ggcttggggg  5760
agtgctgcct ggatggtttg tgccatctgg tcgcctgcgg ggtctggtc tgaccagatg   5820
tagatgtggt cgtagccttc gaagaatttg gtccagaagt tttgccacga ggttgcgccg  5880
ggtagggcta cggccggcca tccgcattgt tcgaggatca tggagtcgaa ttcgccttcg  5940
caaatgtgca tttcggctgc cgggttggcc atggcggcca tgttgtagat ggagcctgtg  6000
tccccggctg gggtcaagta tttggggtgg ttgtggtttt tgcagtcgtg tgggagtgag  6060
cagcggaaac gcattttcg tatttcggct ggccgctccc aaacggggta catgtatggg   6120
atggtgatgc actggttgta gttttcgtgg cctggtatgg ggtcattgtc gatgtatcca  6180
aggtggtggt agcgggctgt ttcttcgctg atgcctcttg ctgagagcag gtcgagtatg  6240
ttttcgaggt gggtttcgta gcgggctgag gctttctgga ttcggcggcg ttccgcaatg  6300
ttgtaggggt gtatgctgtc gtacattcgg gttttcttct tctagtcgtt gttgtagttt  6360
gtggagtcct cctccgacac cgcatgtgtg gcagtaccag acgcccttgt cgaggttgat  6420
gctcatggag ggctggtggt cgtcgtggag cgggcagagt atgtgttgct cgttttttga  6480
cgggttgtag cgtatctggt agatgtcgga gatgcggcgg gtgtcagagg tgtgggagga  6540
gctcgttgag ggttgatacc acataggctt cgctccaggg tttgttgcgt tgtttcatca  6600
ctacgagtcc gatggtggaa ttgttttcgc ggtttcggtg tgtttcgtag ttgcgtgcct  6660
cccggctggc ttgtttcacg aattcggcta ggtggggctg gccggctttc gcctcgataa  6720
tgtaggtttt gttgctggtt gtgaggatga ggtcgccttc gtcttcgcgg ccgttgaggt  6780
ggaggcgttc gatatcgtgt ccggtgtcgc gtagctggtg caataatcgt gtttcccatt  6840
cggctccggc ccgccggttg cgtgcctgct gtgtggccat agttttttaga gtcctttgtg  6900
tgttgtggtc atgttccagg gctgtttttc ggcgaggggc ccgaagaatg tgtattcggg  6960
gtaggctcgt agtcgttcat atcgggtgcc gtcgggggctg gatttgccgg tgcgctgttt  7020
caatactgcg atgcgtgcct cggccggtat cgtgagaccg ttgccgttat cctcgccacc  7080
atacaatgag actcccaata tgagtgtggg tttttcggag aggccgtttt tgatttctcg  7140
ccgtgccggg gggtgttcga tgtcggttcc ggttttgtcg gtggcgtggt gtgtgacaat  7200
aatggtggat ccggtgtcgc ggcctaatgc tgtgatccat tgcatggctt cttgctgtgc  7260
ctgatagtca ctctcgcagt cttggatgtc catcaggttg tcgataacaa tgagtggcgg  7320
gaaggtgttc cacatttcca tgtaggcttg cagctccatg gtgatgtctg tccatgtgat  7380
gggtgactga aatgagaatg tgatgtgttg gccgtggtgg atgctgtctc gatagtattc  7440
tggtccgtag tcgtcgatgt tttgttgtat ctgtgtggtg gtgtgttggg tgttgagtga  7500
gatgattcgt gtggaggcct cccagggtgt catgtcccct gatatgtgaa gggcgggctg  7560
gttgagcatg gcggtgatga acatggctag cccggatttt tggctgcctg agcgccccgc  7620
aatcatgacg agatcccctt tgtggatgtg catgtcctgg ttgcggtaga ggggttctag  7680
ttgtggtatg cggggcagct cggctgcggt ttgggaggct ctctcgaagg atcgttggag  7740
agagagcatc gggaccttat ctatctatcg gttgggtgtg tttgggtgtt cagatggagt  7800
cgatgtcgat gtcagcatcg gcgggggctg tggtgtcgtc tagctggccg ttatcgcgct  7860
tgtctacgta ttcggcaacc ttatcgtaga tggcgtcatc gaggggggtgg tgtcgtctag  7920
ctggccgtta tcgcgcttgt ctacgtattc ggcaaccttat cgtagatgg cgtcatcgag  7980
gggtttgagc acgaccgcat tgaacccgtt tttggtggtg gcagtttgaaggc          8040
ctgctcctcg ccaaggtagg cttcgaggtc gcggatcatg gaatgtgggc ggtcgttgtt  8100
gccgcgcgct ttctcaataa tagcgttggg aatgattctc ggggtgccgt tgttgagatc  8160
gtctagggtg tggaagattg tgacatcagc gtagatgcga tcggctgtct gtccaccgta  8220
gccttcgtg ttgtgttcta cgtcgcggat tttgaaggcg atggcggttg gtcctggtt   8280
tcggggaggggg ttgaagaagg tgctgttgct gttgttgcgg tagttggcga gtcccatggt  8340
tgtttccttt actgtttgtg ttggtttgtg tcggttttat cgggtgaggc tgtttcgttt  8400
gctgcggaaa gcctcggaca cgtcactgtt actggtgatg attttcttgt actgtttcag  8460
aaggtcggct agctgtgcct tgcttgttgc atttgttgatt ttgtcgatga taatctcgtt  8520
ttcgtttgat gcgatgttgt ctacgtagtc tttggctgcc tggttgtagc ggtcttggag  8580
gatgatggat gcgcttgcta cgagtgttgc tagatcccag tctttggaca cgtcaccgtt  8640
tttgaggccg cctagcagat caataatgga ttgtttgatg tcttctgcgg tgtctccgcg  8700
gatgactgtc catggggctg cgtagtctcc accgtatttg agtgtagtag ttagctttcc  8760
gctgtctgtg gtgtcgtcgt cggtcacgtg ttttcctttt cgttgttttc ggcttctggt  8820
ggctgtacgt tggtttctac cgggtatctg tacgagtttt tccgttgac ggcccagcag   8880
gcgtccttga cggggcatcc tttgcagagt gctgtgacgt ggggtacgaa gatgccttgg  8940
ctgattcctt tcattgcttg actgtacatg gatgatacat gccggtaggt gttgttgtca  9000
agatcaatga gttcggtgga tgtgccctgc tcaaccgatt gctcgtctcc cttggtgtta  9060
gcggtgtcc aaaacattcc tttcgtcaca tggatgccat gttgttgag catgtaacgg    9120
taggtgtgca gctgcatact gtcggcgggt aggcgtccgg ttttgaggtc caaaatgaag  9180
gtttcacccg tattcgtatc tgtgaatacc cggtcgatgt agccaacgat ctgggtgccg  9240
tcggggaggg tggtttctac cgggtattcg atgcccggct cgccgtcaat aacagcgtaa  9300
gcatattctg ggtggttgcg cctccatgtt ttccaccggt ccacaaaggt gggggccgtaa  9360
atcatccacc aattgtagtc tttcttgtgt gtcccgcccg actcgcacat gtttttgcat  9420
attctgccgg agggtttgat ttctgtgcct tcggattcgg cgaggggcgac ttgggtgtcg  9480
aaaatgttt tgaaggatga gagttttgtct ggcagtgcag ggtattcggc gggattgtac  9540
aggtgtaggt cgtattgttc ggtgatgtgg tgtatgcgc ttccggcgat ggtggcatac   9600
caggtgtgt gttgggcgtg gtagccgtgg gataggcgcc attttttcacc gcattcggcc  9660
cactgtgaca gtgatgagta ggagatgtgg cctggatggt caatggtgga cggttttgt   9720
gctaggggca ttacttgtcg cttttgtggg tgttccatgg gtttcgggtg tcttggccgg  9780
cattgtgttg ctggtatgcg aggagtgcga gcagtgcca ggcagcatgg gccagatggg   9840
gtagcccgga ttcatcatcg aggttgttgc cttgctgcca tgataacagg tgccggtaga  9900
gggcgtcaac actgtggctc cacgcgatagc cgccggtcca gttgttgtcg ccgtatttgg  9960
```

```
tggcgccgta tccggccaca gagccgaggg cgtgtaaggc tgtagggtcg atgagggata  10020
gcctgcaaag tttcaattct ttcttggcgc cagtatcagg gtcggtgtac atgctggtgg  10080
gctcatccat ggtgtgtgtg ctccttaagt atggggttac tggttggggt tgtgggcgag  10140
tgctacggcg agaataatga tggcgagggt ttcagcgatc agtatgggtg ttgtgatcat  10200
ttgtggtcgc ggggattgtt ggtgagggtt gaggcgccca ggaggatgat gagggcgcat  10260
gcggcgatga tggcgagggc tgccttgtgt ggggtgccgg tggcgtacat ccatgtgatg  10320
atgccgcctt ggatccaggc gaggctggtg aagaacgttt cgtagctgtg tagctcaatg  10380
ttgttgttgg gtgtgttcat gcttgctcct gaagaatggt gttgatggtt gtgtaaatgt  10440
tgtacaggtc ggtttcgata gataacagtt ggtggatttg gtggtcgaga tcaatgtcgg  10500
ggttgagggt gttgatgcgg gaggcgatgt cggtgagtgt gcgtagtgtg ccgccggtgt  10560
ggtgaatgat gtgtgccgtg tcggcgagtc cggtggtgac agtgtagtgg gagaggagag  10620
gcatagctgg gggtgctcct tgacgggggtt actgttgcgg gttgatgttg aggtcggtga  10680
cgttggggtg gtcttctgtt ccggtgacga ggcagtggac ggtgactggg agtttggatg  10740
cgccgggctg tttcgcggtt gcgccgtaga cgatggagaa ggtgtctttg ccaataattt  10800
tgtggagttg gaggtcgatg tcgggggttgc cgttccattt gacgccttgt gtggcggcct  10860
gttgttcggc tttgcggttg caggtgtgtg ctgcggtgat catggtgagt ccggtggcgg  10920
tttcttcacc ccttgcttgg gcttgcttgt gggttttctg ctgttcggct cgcagtgact  10980
gttctgctgc tgcctgccgt gcttttcttt cggctttcgc tgttgggta gtcttggggg  11040
tccattcggt gttggctgtg gtggcttgcg gtgcgggttg tgatgcgagt ggcggattgt  11100
cgtctggggc tggcatgaag gatgctgcgg cgatgatggc ggctgtgatt ccggcgatgg  11160
tgtagccgtt tttcttgttc atgattttgt gttcccttt ccggggtgtt gttcgttgct  11220
gacatgatta atactttcag cggctgggcc cactgtcaag gctgcgctca acgattgtga  11280
gcgatacttg tgtggctagg ggttttgtcc ttgaggtggg agatgtcttt ccttgcgtc  11340
cagtatccat ggcggttgcg agtcatccct tggcgagca tctcgtccac ggtgagacac  11400
ctgcgacgat ctggaccctc cttgactccc tgatcgcctg tgcggtgcat gtcaccggca  11460
caagtaccat taaatgtctc gtggcagatt gtgcaatgct ctggtcggta tccgatgatt  11520
gtgctatcgc acttgtggca tgtccattgc atgattggtc cttctttcgt gttttaagct  11580
tgtactctga ggattagagc gactttcagc ccttgggggg tatgattata taggtcaggt  11640
atttctaggc gattctaggc tcattgtgtg tggctggggg ttatcgggca cagggtgta  11700
ggagttggcc aacattgatg cgggtcacat tccagtagag ttgcgtggt tccccaccgg  11760
tgagtggctt ccactcgtca tggctgaaca cggtgccgtc ggttgcgatg aatgtgttgg  11820
ggcgtagctt gtgaagctca gtctctacac gctgccggta ggcttcggcg aggccctcga  11880
aatccatgtg gtcgcagggg aggttttcga ggcgtgtcag gtcgaagggt gtggggcagt  11940
cgtagctggc ggggctgtag agctgggtga aatggttggc gatcttctgc atgacggtt  12000
cctttctcg tatggtgagt tgatagtttt atcgggtgga tgcgacaagg atggcgtcta  12060
catcgatcat gtcgatgaga tcgtggagtt cctcggcctc attctcggag aggtggcgcc  12120
agccatagtc gccgtatacg gcgccgtcga gggtgacagt ccacaggggc cggatgagtc  12180
gtatggcttc ttgtacttta gcgtggtaca tgcgcgcac catatccaga tcgatgtcgt  12240
ctgaatggtt tccagtgagg ctgagaggc tgagcggctg gatttctgtc tgcctgtaga  12300
gggatgtgaa tgatggtgtg atgagtgtgc catccatgag agtgtgctcc tttcggtggt  12360
ggaggggttg ttgtggtttc tagagtgtgt aggctgcgac ccatagtcaa ggctgcgctc  12420
attcggattg agcgtttcat atgggtgtgg catgaatct acaccccat actgtgtgag  12480
ataggccaca tcctcctggc ttggtgtgaa ccctcgaagc tactctgcct atctggcgtg  12540
gagggtgtag cccagaaata ccgtttaaag ccttcatacg gcgcctagga gcgccttaca  12600
gggtgggggc taggtattta tacccccaag caattctgat cgattctaga cgcctcccag  12660
gagcccgata cacgatccgc tatccagaca cagatccatca gccctatcc tggttagcta  12720
agcctcaact atgtggacag tgttgattac tgtgggtaa gaaggacacg gtaaagaaa  12780
gagggggag catcggcttt caagccttaa ggtcttagca gttagcaccg agccctcaa  12840
gggctcgtcg tcagcccatc aggcacggcc ctgaacgggg tacacgccat cagggaaggc  12900
ttgagagtac gaggagcctt agcgacgagt actcgaaagc ctgagggaac accctcagca  12960
ctgatgggtc tagcgtgttc ggaaaggaca caggagtaaa gcgtgacagc tgtccgggag  13020
tgaaacccgt tctgactagg ggtttcagcc ttaaccaccc tcaaaggtta caagactcta  13080
agaaaattta aggaaaagtt taggtttaat ttttggacct ttactaccaa aaacacccgt  13140
ttacacccct caaacccgcc tatagagcca aatccaccag tttgactcat cccaggtggc  13200
atatgatagg ctgacaggt agccagctgg acgcaaggcc gaaatccgct gacgcggctt  13260
tcaccttac atccatcagt ctaccaaaga cttaaagacc taagggctta gcgctaaggt  13320
gctgatagct tagcaccgag cccttgaggg gctcggcatc agccctaaag ccttaaacac  13380
ttaaagtaca tataaaactt taaaagctta acacttaagg ttataaataa acattaaagc  13440
tttaaagtct taaagtacat atataaaacctt aacacctaag ttaagtataa aaccttaaag  13500
gcttagcact gaaggatata aacttcacat cagtttttaa gactttaaaa cttaaaataa  13560
ctattaagac ttaaagactt ataagtttta aacacttaaa gtaactataa gactttaaag  13620
accttaagta cttaaagtta accatcagtc ttaaacttta atattataac ctataagtct  13680
taaagcttat aagttataaa agttttagaa gagctaagag gttaacttct ttacttctct  13740
tctctctttg gttctttctc tcttctcttc tttcttcat cagggggagaa gaggaacctt  13800
ttaccatcag cgccgatgga ctgtcaccgt gtgactcgtg taccaccggt cgcacgctcc  13860
cggtttcaca ctccccacac tctgacaccc gtgtcccttt caggcttagc gtgttcggct  13920
gaaggcgtac ggcgtgtcgc gccaacaccc ttaacaccag gtaagactta aagtgtatat  13980
tatatgtaga agactttaaa acctataagg tgttcccgct tagcctgtgt cctacaccgc  14040
taggcgccaa gcgttaagtc ttgaaacgcg aacacacac caccccatt tttctttcgt  14100
gtccttctct tttgacaccg ctgggggcg atgtgatctt tctcactacc catggggta  14160
gtggagaaca cacccacccc accatcaaca gaacaccccc tcaaacgaac aaaacagggc  14220
ctagaatcga tcggcagggc aagggcaagg tattcatacc cccaacacat tccaggccgt  14280
cagagaggca aataagaccc gtacagggct agtcgaggat cggagacgtg atggcacaca  14340
ccaatcgac cgcatccgcc gcacaccgac actggcggca acgactcatc acccaagccc  14400
gacagcaagg ccaaaccgaa tgcccactct gcggagcaac catcacctgg gacacctacc  14460
agctgccaac tagccccgaa gccgaccaca tcacacccgt cagcagggga ggactcaaca  14520
ccctcgacaa cgggcaaatc atctgcagaa catgcaacag aagcaaggc aacagaacac  14580
aaccaaacat caaattccaa caacaaacca caaaaaacct tgttccatgg tgacaaaacc  14640
cgccaacccc caccggggac acccctgca cacccgtgca agacctcgta cggcttagtg  14700
```

-continued

```
aaatacctcc cttttgtgga tttgtctgtt tgtcgacttt ttgtgttggt ggtgagtgtt   14760
gtgcagcctg agcttcctga gggacacgag tggtgtgggg agacgcgtcg ttggtggcgt   14820
gtgtggggtg aggatagccg cgcgcagtac gtgtctgatg aggagtggct gtttcttatg   14880
gatgctgcgg tgattcatga ttgtgtgtgg cgtgagggtc gcgcggattt ggtggcttcg   14940
cttcgtgctc atgtgaaggc ttttatgggt atgttgagtc gttattcggt tgatgtggcg   15000
tctggtggcc gtggtggggg ttctgcggtg gcgatgattg accggtatag gaagcgtagg   15060
ggggcctgat taggtgtctg gtgttgttgg gtctcaggtt cctcgtcatc gtgtggctgc   15120
ggcgtattcg gtgtctgctg gcggtgatgc tggggagttg ggtcgtgcgt atgggttgac   15180
gcctgatccg tggcagcagc aggtgttgga tgattggctg gctgtgggtg gtaatgcag   15240
gcttgcttcg ggtgtgtgtg gggtgtttgt gcctcgccag aatggcaaga atgctatttt   15300
ggaggtgtg gagttgttta aggcgactat tcagggtcgc cgtattttgc atacggctca   15360
cgagttgaag tcggctcgta aggcgtttat gcggttgagg tcgttttttg agaatgagcg   15420
gcagtttcct gacttgtatc gtatggtgaa gtcgattcgt gcgacgaatg gccaggaggc   15480
tattgtgttg catcatccgg attgtgccac gtttgagcgt aagtgtggt gtccgggttg   15540
gggttcggtt gagtttgtgg cccgttctcg tggttctgct cgcgggttta cggttgatga   15600
tttggtgtgt gatgaggctc aggagttgtc ggatgagcag ttggaggcgt tgcttcctac   15660
ggtgtctgcg gctccttcgg gtgatcctca gcagattttc ttgggtacgc cgcctgggcc   15720
gttggctgac gggtctgtgg tgttgcgttt gcgcgggcag gctttgtcgg gtggtaaaag   15780
gtttgcgtgg acgagttttt ctatcccgga tgagtctgat ccggatgatg tgtcgcggca   15840
gtggcggaag cttgctggtg agacgaatcc tgcgctgggt aggcgtctga atttcgggac   15900
ggtgagcgat gagcatgagt cgatgtctgc tgccgggttt gctcgggagc ggcttggctg   15960
gtgggatcgt ggccagtctg cttcttcggt gattccggcg gataagtggg ttcagtcggc   16020
tgtggatgag gcggctctgg ttggcggaa agtgtttggt gtctcgtttt ctcgttcggg   16080
ggatcgtgtc gctttggctg gtgctggccg gactgatgct ggtgttcatg ttgaggtgat   16140
tgatgggctg tcgggacga ttgttgatgg tgtgggccgg ttggctgact ggttggcggt   16200
tcgttggggt gatactgacc ggatcatggt tgccggtct ggtgcggtgt tgttgcagaa   16260
ggcgttgacg gatcgtggtg ttccggggccg tggcgtgatt gtgcgctgata ctggggtgta   16320
tgtggaggcg tgtcaggcgt ttttggaggg tgtcaggtcg ggtgtggttt ctcatcctcg   16380
tgccgattcg aggcgtgaca tgttggatat tgctgtgagg tcggctgtgc agaagaagaa   16440
gggttctgcg taggggttggg gttcctcgtt taaggatggt tctgaggttc cttttggaggc   16500
tgtgtctttg gcgtatcttg gtgcgaagat ggcgaaggct aggcggcgtg aacggtctgg   16560
taggaagcgg gtgtctgtgg tatgaattcg gatgagttgg ctctgattga gggcatgtac   16620
gatcgtatcc gaaggttgtc ttcgtggcat tgccgtattg agggctacta tgagggctct   16680
agccgggtgc gtgatttggg ggttgctatt cctccggagt tgcacgcgtgt gcagacggtg   16740
gtgtcggtggc ctggtattgc ggtggatgct ttggaggagc gtctggattg gcttggctgg   16800
actaatggtg acggctacgg tctgatggt gtgtatgctg cgaatcggct tgctacggcg   16860
tcgtgtgatg tgcatttgga tgcgctgatt ttgggttgt cgtttgtggc tgttattccc   16920
cagggtgatg ggtcggtgtt ggttcgtccg cagtcgccga agaattgcac gggccggttt   16980
tcggctgacg ggtctcgtct ggatgctggc ctgtgatgc agcagacgtg tgatcctgag   17040
gttgttgagg ctgagctttt gttgcctgat gtgattgttc aggtggagcg gcgaggtagc   17100
cgtgagtggg ttgagacggg ccgtataccg aatgtgcttg ggctgttcc gttggtgcct   17160
gttgtgaatc gtcgccgtac gtctaggatt gatgggcgtt cggagatcac tcggtcgatt   17220
agggcttaca cggatgagc tgttcgcaca ctgttggggc agtctgtgaa tcgtgacttt   17280
tatgcctatc ctcagcgttg ggtgacgggt gtgtcggctg acgagttttc gcagcctggc   17340
tgggtcctgt cgatggcttc tgtgtgggct gtggataagg atgacgacgg tgacactccg   17400
aatgtggggt cgtttcctgt gaattctcct acaccgtatt cggatcagat gcgtttgttg   17460
gctcagctga cggcgggtga ggctcggctt ccggagcgct atttcgggtt tatcacgtct   17520
aacccgcctt ctgggggaggc tttggctgcg gaggagtcga ggcttgtgaa gcgtgccgag   17580
cggcgtcaga cgtcgtttgg tcagggctgg ctgtcggttg gtttcctggc tgccagggcg   17640
cttgattcga gtgttgatga ggccgcgttt ttcggcgatg tgggtttgcg ttggcgtgac   17700
gcttcaaccc cgactcgggc ggctacggct gatgctgtga cgaagcttgt gggtgccgag   17760
attcttccgg cggattctcg tacggtgttg gagatgctgg ggcttgatga tgtgcaggtt   17820
gaggctgtga tgcgtcatcg tgccgagtct tcggatccgt tggcggcact ggctggggct   17880
atatcgcgtc aaactagcga ggtttgatag gcgatggctt cgggtgttgc gtcaaggttg   17940
gctgctgccg ggtatcagcg tgaggcggtc aggtttgccg ggaagtatgc gggctattat   18000
gccgagcttg gtcgtttgtg gcattccggg aagatgacag atgcgcagta tgtgcgtttg   18060
tgtgtggagt tggagcgtgc cggccatgac ggttcagcgg cgttggcggg taagttcgtg   18120
tcggatttc ggaagcttaa cggtgtggat cctggtttga tcgtgtatga cgagtttgat   18180
gctgccgccg cgttggctag gtcgtttttcg actattaaga tgatgaatag tgacccggat   18240
agggctaagg atacggttga tgcgatgcg gcgggtgtta atcgggctgt catgaatgct   18300
ggccgtgaca cggttgagtg gtctgcgggt gcgcagggta ggtcgtggcg ccgggtgacg   18360
gatggtgatc cgtgcgcgtt ttgtgccatg ttggctacga ggtcggatta tacgaccaaa   18420
gagcgggcgc ttactactgg tcatactcgg cgtcataagc gtggcggtag gcgtccgttt   18480
ggttcgaagt atcatgatca ttgtggttgt acggtggttg aggttgttgg cccttgggag   18540
ccaaataggg ctgatgccgc atatcagagg acgtatgaga aggctcgtga gtgggttgat   18600
gatcatgggt tgcagcagtc gcctggcaat attttgaagg ctatgcgtac tgttggtggc   18660
atgagataat ttgatgtggt ttccggttgt gtgccgccgg ttatcggtgc acagggttgt   18720
ctcccgcacg ggggtcaaca atgttgtgtt gttttccgca aggagtagg ggtaggcta   18780
tggccgatca aaagttgaa gaacagaatg ttgacaatga tgctgttgag cccggaaagg   18840
gtggagacgt tgttgatgtt gtgaaggatg ggcaggctgc cggcgatgat catgccggtg   18900
atgtttccgt gaaggaggag tcttcttctg cgacggattg gaaggctgag gctcgtaagt   18960
gggagtctcg tgctaaaagt aatttcgccg agttggagaa gcttcgcgcc tcggatggtg   19020
atgcgggtc tgtgattgat gagcttcgcc gcaagaatga ggaactcgaa gaccggatta   19080
tttggttgt tcttgagggt gtgaagcgcg aggtggctgc cgggtcggag cctgggaggg   19140
atgctgtcgc tttttgcac ggtggcgatc gtgaagcact ggtggagtct gctaaggctt   19200
tgaagggttt gatcgaccat agtagtggtg gcgcggggtgt gcgccgtctt gcgggagtgg   19260
cccccgttga tgatgttaaa cgacgtgagg gtgtcgcgtt tgtggatgct cttgtcaata   19320
attctaggag atgatttgtg atggctgacg atttttcttc tgcagggaag cttgagcttc   19380
ctggttctat gattggtgcg gttcgtgacc gtgctatcga ttctggtgtt ttggcgaagc   19440
```

```
tttcgccgga gcagccgact attttttggcc ctgttaaggg tgccgtgttt agtggtgttc   19500
ctcgcgctaa gattgttggt gagggcgagg ttaagccttc cgcgtctgtt gatgtttcgg   19560
cgtttactgc gcagcctatc aaggttgtga ctcagcagcg tgtctcggac gagtttatgt   19620
gggctgatgc tgattaccgt ctgggtgttt tgcaggatct gatttcccg gctcttggtg    19680
cttcgattgg tcgcgccgtg gatctgattg cttttccatg tattgatcct gccactggta   19740
aagcggctgc cgctgtgcat acttcgctgc ataagacgac gcatattgtt gatgccacgg   19800
attctgctac ggctgatctt gttaaggctg tcggcctgat tgctggtgct ggtttgcagg   19860
ttcctaacgg ggttgctttg gatcccgcgt tctcgtttgc cctgtctact gaggtgtatc   19920
cgaaggggtc tccgcttgcc ggccagccta tgtatcctgc cgcgggttt gccggtttgg   19980
ataattggcg cggcctgaat gttggtgctt cttcgactgt ttctggcgcc ccggagatgt   20040
cgcctgactc gggtgttaag gctattgtgg gtgatttctc tcgtgttcat tggggttcc    20100
agcgtaactt cccgatcgag cttatcgagt atggcgatcc ggatcagact ggccgcgatt   20160
tgaagggcca taatgaggtt atggttcgtg ccgaggctgt gctgtatgtg gctatcgagt   20220
cgcttgattc gtttgctgtt gtgaaggaga aggctgcccc gaagcctaat ccgccggccg   20280
agaactgatt tattgttgcg gtgatgtgtc aatgtgcagg gggtggtgtt gatgggtatc   20340
attttgaagc tgaggatat tgagcctttc gccgatattc ctagagagaa gcttgaggcg    20400
atgattgccg atgtggaggc tgtggctgtc agtgtcgccc cctgtatcgc taaaccggat   20460
ttcaaataca aggatgccgc taaggctatt ctgcgcaggg cttttgttgcg ctggaatgat   20520
actggcgtgt cgggtcaggt gcagtacgag tctgcgggtc ctttcgctca gactacacgg   20580
tctagtactc ccacgaattt gttgtggcct tctgagattg tcgcgttgaa gaagctgtgt   20640
gagggtgatg gtggggctgg taaagcgttc actattacac cgaccatgag gagtagtgtg   20700
aatcattctg aggtgtgttc cacggtgtgg ggtgagggtt gctcgtgcgg gtcgaatatt   20760
aacggctacg ctgcccctt gtgggagata tgatatgacc agttttcctt atggtgaaac    20820
ggttgtgatg cttcaaccga ctgttcgtgt cgatgatctt ggcgacaagg tggaagactg   20880
gtctaagcct gtcgagactg tgtaccataa cgtggccata tatgcttccg tttcgcagga   20940
ggatgaggct gcggggcgtg actcggatta tgagcattgg tcgatgctgt tcaagcagcc   21000
tgttgtgggc gctgattatc gttgtaggtg gcgtattcgg ggtgttgtgt gggaggctga   21060
cgggtctcct atggtgtggc atcacccat gtccggttgg gatgctggta cgcaggttaa    21120
tgtgaagcgt aagaagggct gatgggtagt ggctcaggat gtgaatgtga agctgaactt   21180
gccgggtatt cgtgaggtgt tgaagtcttc tggagtgcat ggcatgttgg ctgagcgtgg   21240
cgagcgtgtc aagcgtgccg cagcggcgaa tgtgggtggt aacgcgtttg ataggcccca   21300
ataccgtaat ggtttgtcgt cggaggtgca ggttcaccgt gttgaggctg tggcgaggat   21360
tggcaccacc tataagggtg ggaagcgtat tgaggcgaag catggcacgt tggcgaggtc   21420
gattggggct gcgtcgtgat cgtttacggt gatccgcgtg tgtgggctaa acgcgtgctc   21480
aaggatgatg gctggctgtc tgggataccg tgtacgggga cggtgcctga ggatttcagc   21540
ggtgacctga tctggttggc gttggatggt ggcccacagt tgcatgttcg tgagcgtgtt   21600
tttttgcgcg tgaacgtgtt ttcggatacg ccggatcgtg ctatgtcgtt ggcgcgtcgt   21660
gtcgaggctg tgctggctga tagtgtggac ggtgaccctg tggtgtactg taaacggtct   21720
actggccctg atttgctggt tgatgtgca cgttttgatg tgtattcgct ttttgagctg    21780
atatgtaggc ctgcggagtc tgaataagct tattgttttt gttttaatgt aattgtttga   21840
tatttaatgg gggttatgat ggctgcaaca cgtaaagcgt ctaatgttcg ctcagcggtt   21900
actggcgacg tttatattgg tgacgcgcac gcgggtgata ctattaaggg tgtggaggcg   21960
gttccttccg gtcttaccgc tttaggtgat ctgtctgata acggtttaa gattaagcct   22020
gagcgtaaaa cggatgattt gaaggcttgg cagaatgcgg atgttgttcg cactgtggct   22080
acggagtctt ctatcgagat ttcttttccag ctgatcgaat ccaaaaaaga ggttatcgaa   22140
ctgttttggc agtcgaaggt tactgccgga tccgattcgg gttctttga tatttctcct    22200
ggtgccacga cgggtgttca cgctctgttg atggatattg ttgatggtga tcaggttatt   22260
cgctactatt tccctgaggt tgagctcatt gatcgtgacg agatcaaggg taagaatggt   22320
gaagtgtacg ggtatggtgt gacgttgaag gcgtatcctg cccagattgg taagactggt   22380
aatgcggtgt ctggtcgggg gtggatgacg gctttaaaag ctgatactcc tccttctccg   22440
aagcctcagc cggatccgaa tccgccggcc gagaactgat acacgatttt aggggattgg   22500
tgatagatga gtgacactgg tttcacgttg aagattggtg atcgtagctg ggtgttggcg   22560
gatgctgagg agacgcgcga ggctgttcct gcccgcgttt tccgtcgtgc cgccaggatt   22620
gcccagtcgg gggagtctgc ggatttcgcc caggttgagg tgatgttttc tatgttggag   22680
gctgccgccc cggctgacgc tgtggaggcc ctggagggc ttcctatggt tcgtgtggcg    22740
gaggttttcc gtgagtggat ggaatataag cctgacggta agggtgcctc gctggggaa    22800
tagtttggct ccacgcctg attgatgatt atcgcggggc catcgaatac gatttccgca   22860
ctaaatttgg tgtttctgtt tatagtgttg gtgcccgca gatgtgttgg ggtgaggctg    22920
tccggctggc tggcgtgttg tgtactgata cgtctagcca gttggcggcc cacctgaatg   22980
gttggcagcg cccgtttgag tggtgtgagt gggctgtgtt ggacatgttg gatcattaca   23040
ggtctgctaa tagtgagggg cagccggagc ctgtggcgag gccgacggat gagcgtaggg   23100
cccgtttac gtctgggcag gtggacgata ttttggcgcg tgttcgtgcc ggtgggcggg   23160
tgtctccgcga gattaatatt atgggttgaa tagtgtatgt ctggtgagat tgcttccgcg   23220
tatgtgtcgt tgtatacgaa gatgcctggc cttaaaagtg atgttggtaa acagctttct   23280
ggggtgatgc ctgcggaggg tcagcgttcg ggtagcttgt ttgctagcgg gatgaagttg   23340
gcgcttggtg gtgcggcgat gatgggtgcc atcaatgttg ctaagaaggg cctcaagtct   23400
atctatgatg tgactattgg tggcggtatt gctaggcga tggctattga tgaggctcag   23460
gctaaactga ctggtttggg tcatacgtcg tctgacacgt cttcgattat gaattcggct   23520
attgaggctg ttactggtac gtcgtacgcg ttgggggatg gtcgctacga ctgcggaggtc   23580
ttgtctgctt cgggtgtgaa gtctggcggg cagatgacgg atgtgttgaa gactgtcgcc   23640
gatgtgtctt atatttcggg taagtcgttt caggatacgg gcgctatttt tacgtccgtg   23700
atggctcgcg gtaagttgca gggcgatgac atgttcagc ttactatggc gggtgttcct    23760
gtgctgtctt tgcttgccag gcagacgggt aaaacgtctg ctgaggtgtc gcagatggtg   23820
gcggcgagatt gatttt tgccacgttt gccgctgcg tgaagcttgg catggtgtgg    23880
gctgcgcagg cgtctggtaa gacgtttgag ggcgctatga agaatgttaa gggtgccctg   23940
ggttatttgg gtgctacggc tatgcgccg tttcttaacg ggttgcggca gattttttgtt   24000
gcgttgaatc cggttattaa gtctatcacg gattctgtga agcctatgtt tgcgtcggtg   24060
gatcagggga ttcagcgggt gatgccgtct attttggcgt ggattaaccg tatgccgggc   24120
atgattacga gaatgaatgc acagatgcgc gccaaggttg agcagttgaa gggcgttttt   24180
```

```
gcgaggctgc atttgcctgt tcctaaggtg aattttggtg ccatgtttgc tggcggcacc   24240
gcagtgttcg gtattgttgc tgcgggtgtt gggaagcttg ttgcggggtt tgccccgttg   24300
gcggtgtctt tgaagaatct gttgccgtcg tttggtgctt tgaggggtgc cgctgggggg   24360
cttggtggcg tgtttcgcgc cctgggtggc cctgttggta ttgtgatcgg gctgtttgct   24420
gccatgtttg ctacgaacgc ccagttccgt gccgctgtta tgcagcttgt ggggtttgtt   24480
ggccgggctt tggggcagat tatggtcgct gtgcagccac tgttcggat tgttgctggg   24540
gtggttgcca ggttggcgcc agtgttcggc cagattatcg gtatggttgc tggtttggct   24600
gcccggctgg tgcctgttat tggtatgctt attgcccggc tggttcctgt tatcacccag   24660
attattggta tggtaaccca ggttgctgcc atgttgttgc tcatgctgat gccggttatt   24720
caggctgttg ttgctgtgat acggcaggtt attggtgtga tcatgcagtt gatacctgt   24780
ttgatgccgg ttgtgcagca gattttgggt gctgtcatgt ctgtttgcc gccgattgtt   24840
ggtttgatac ggtcgctgat accggtgatc atgtcgatta tgcgtgtggt ggtgcaggtt   24900
gttggtgccg tgttgcaggt ggtggcccgt attattccgg ttgttatgcc gatttatgtt   24960
tcggtgattg gattcattgc caagatttat gctgcggtta tcgtttttga ggctaaggtt   25020
attggcgcta ttcttcgtac tattacgtgg attgtgaatc attcagtgtc tggcgtgagg   25080
tctatgggca cggccatcca gaatggctgg aatcatatca aatcgtttac gtcggcgttt   25140
attaacggtt tcaagtcgat cattctgcc ggtgttgccg cggttgtggg gtttttttacg   25200
cggcttggtt tgtccggttgc ttctcatgtt ccggtctgggt ttaacgcggc ccgtggcgct   25260
gtttcggctg cgatgaatgc tattcggagt gttgtgtctt cggtggcgtc tgctgttggc   25320
gggttttcg ggtcgatggc gtctagggtt cgtagtggtg ctgtgcgcgg gtttaatggt   25380
gccggagtg cggcttcttc tgctatgcat gctatgggct cggctgtgtc tagtggtgtg   25440
catggtgtgc taggattttt ccggaatttg cctggcaata ttcggcatgt tctcggcaat   25500
atggggttct tgttggtgtc ggctggccgt gatgtggtgt ctggtttggg taacggtatt   25560
aagaatgcta tgagtggcct gttggatacg gtgcgtaaca tgggttctca ggttgctaat   25620
gcggctaagt ctgtgtgggg tattcattcc ccgtctcgag tgtttcgtga ccaggttggc   25680
cggcaggttg ttgccggttt ggccgagggg atcaccggga atgcgggttt ggcgttggat   25740
gcgatgtcgg gtgtggctgg acggctgcct gatgcggttg atgcccggtt tggtgtgcga   25800
tcatcggtgg gctcgtttac cccgtatgac aggtatcggc ggatgggcga aagagtgtt   25860
gtggtgaatg tgaatgggcc tacttatggt gatcctaacg agtttgcgaa gcggattgag   25920
cggcagcagc gtgacgcttt gaacgcgttg cttacgtgt gattgggggt gttgtgcgta   25980
tttattcctg acccgtctga tcgtgccggt ttgactgtta cctggtctat gttgccgttg   26040
attggtaatg atccggagcg tgtgcttcat ttgacggatt atacgggtgc gtctcctgtc   26100
atgttgttga atgattcgtt gcgcggtttg ggtgttcctg aggtggagca tttttctcaa   26160
actcatgttg gggtgcacgg ctcggagtgg cgcgggttta atgtgaagcc tcgcgaggtg   26220
acattacctg tcctggtgtc gggtgttggt gtggatccgg ttggcggggtt tcgtgacggt   26280
ttttttgaagg cgtatgacga gttgtggtct gcttttcctc cgggcgagga ggggagttg   26340
tctgtgaaga ccccgtctgg ccgtgagcgt gtgctaaaat gccggtttga ttcggtggat   26400
gacacgttta ctgtggatcc ggtgaacagg ggttatgcgc gctatctgtt gcatttgaca   26460
gcttatgacc cgtttttggta tgggatgag cagaagtttc gttttagtaa tgcgaagttg   26520
caggattggt taggtggcgg ccctgtcggc aagaagggta ccgcttttcc ggtggtgttg   26580
acgcctggtg ttggttcggg ttgggataat ctgtctaata ggggtgatgt gcctgcgtgg   26640
cctgtgattc gtgtggaggg cccgttggag tcgtggtctg tgcagattga tggtttgcgt   26700
gtgtcttcgg attacccggt ggaggagttt gattggatca ctattgatac ggatcctgc   26760
aaacagtctg cattgttgaa cgggtttgag gatgtgatgg atcgtttgac agagtgggag   26820
tttgcccta tcccgcctgg cggttctaag agtgtgaata ttgagatggt tggtttgggt   26880
gccattgttg tgtcggtgca gtacaggttt ttgagggctt ggtgaatagt tgatggctgg   26940
tcttgttccg catgtaacat tgtttacacc tgattatcgc cgtgtggcgc ctatcaattt   27000
ttttgagtcg ttgaagttgt cgttaaagtg gaatggtttg tccactttgg agttggtggt   27060
gtctggtgat cattctaggc ttgacgggtt gactaggccg ggtgcacggc tggttgttga   27120
ttatggtggt ggcagatttt tttctgggcc tgtgcgtcgg gttcatggtg tgggtccgtg   27180
gcgttcttcc catgtgacta tcacgtgtga ggatgatatt cgtctgttgt gccgtatgtt   27240
gatgtggcct gtggattatc gtcctgtttt ggttggtatg gagtggcgtg ctgaccggga   27300
ttatgcccac tattcgggtg cggctgagtc ggtggctaag caggtgttgg gggataatgc   27360
ttggcgtttt ccgcctggtt tgtttatgaa cgatgatgag agtcgtggac ggttcattaa   27420
ggattttcag gtgcggtttc acgtgttgc cgataagttg tgtcgtgggc   27480
tcggatgact gtcacggtga accagtttga gaatgcgaag tttgatcagc gtggtttggt   27540
gtttgattgt gtgcctgctg tgacgcgtaa gcatgtgttg actgccgagt ctggttcgat   27600
tgtgtcgtgg gagtatgtgc gtgacgcccc gaaggcgaca tcggtggtgg ttggtggccg   27660
cggcgagggc aaagatcggc tgttttgtga ggatgttgat tcgatggccg aggatgactg   27720
gtttgatcgt gtcgaggtgt ttaaggatgc ccgtaacacg gattctgagc atgtgcatct   27780
cattgatgag gctgagcagg tgttgtccga gttgggggcc acgtcggggt ttaagatcga   27840
gttggctgag tcggatgtgt tgcggttttgg gcccggcaat ctgatgcccg gggatttgat   27900
ctatgtggat gtgggttctg gccctatcgc agagattgtg cggcagattg atgtggagtg   27960
tgagtcgccg ggtgacgggt ggacgaaggt gactcctgtt gcaggggatt atgagaataa   28020
tccgtcggcc ctgttggcgc ggcgtgttgc tggttggct gcgggtgtgc gggatttgca   28080
aaaattctag aaaagattag gggtttgttg tgggtattgt gtgtaaaggg tttgatggtg   28140
tgttaccgga gtatgattgg gctcaaatgt ctggtctgat gggtaatatg ccgtccgtga   28200
aagggccgga cgatttcgt gtcggcacta ctgttcaggg tgccacagtg ttgtgtgagg   28260
tcctgccggg gcaggcttgg gccccacggg tgatgtgcac cggaataagt gttgagacgg   28320
tgaccggcca gcttccggc ccgggtgaga cccgatacga ctatgtgtg ttgtctcggg   28380
attgggaggc gaatacggcc aagttggaga ttgttcctgg ggggctgccg gagcgtgccc   28440
gtgacgtgtt gagggccgag cctggcgtgt accatcagca gttgttggct actttggtgg   28500
tgtcgtctaa cggggttgcag cagcagctgg ataggcgtgc tatagcggct agggtggcgt   28560
ttggcgagtc tgctgcgtgt gatcctaccc cagtggaggg tgaccgttgg atggttcctc   28620
ctggggctgt gtgggctaat catgccggcg agtggatgct gttgtccccc aggattgaga   28680
cgggttctaa gtcgatcatg tttggcgggt ctgctgtgta tgcttacacg attccgtttg   28740
agcggccgtt tagtagtgcg cctgttgtgg tggcgtctat ggctacgcg gctgggggca   28800
cgcagcagat caatgtgaaa gcctacaatg tgactgtcca aaatttagt ttggcgttta   28860
ttacgaatga tggttcgaag ccgaatggtg tgcctgcggc ggctaattgg attgctgtcg   28920
```

```
gcgtgtgact gtacaggtgt tgtggcggat ggtgtgatgt tggggggctg tggtgtcgtg   28980
gtttactcct gcactggtgg cctctatttg taccgcgttg gccacggttt tgggttctgt   29040
tcaggctgtc acatcccggt ctaggcgcg tttacgcagg ctgtctgcgc aggtggatgc   29100
gatgaagag tatacgtggg gtgtgcgcg cgaggtgcga aggtttaacg ccgggcttcc   29160
tgatgatgtg gagccgatgc atcttcctga tgtgcccgag tttttgaagg atactgttga   29220
tggtggaggt gagtagggtt gagggagttg gaggaggaga agcggcagcg ccgcaatttt   29280
gagaaggctt ccctgatact gttatttttg tcgcttgtgt tgttggcggt ggttgccggg   29340
ggtgctttgc ggtacgggtc tgtggcttct caaagggatt cggagcaggc gagggcccag   29400
tcgaatggta cagccgctaa agggttggct gcccgtgtga agcagcgtg tacccagggt   29460
ggcgtggagt ctgtgaagct gcacaggtct ggtttgtgtg tggatgctgt gcgtgttgag   29520
cagcgtgttc agggtgtgca gggtcctgcc ggtgagcgtg gcccgcaagg gcccgctggt   29580
gttgatggcc gggatggtag caatggttct gctgggctgg ttggccctgt tgggccgcag   29640
ggttcccctg gtttgaatgg tgttccaggt cgtgcaggtg tcgatggtgt gaacggcgc    29699

SEQ ID NO: 71           moltype = DNA   length = 29596
FEATURE                 Location/Qualifiers
misc_feature            1..29596
                        note = PAC2
source                  1..29596
                        mol_type = other DNA
                        organism = synthetic construct
SEQUENCE: 71
ctggtttgaa tggtgtgaaa ggtcctgacg ggttgcctgg cgctaacggt tcggatggcc   60
gtgatggtgt tccaggtcgt gcaggtgtcg atggtgtgaa cggcgctgat ggtcgggatg   120
gttcggccgg tgagcgcggt gatgtgggcc cttcaggtcc tgccgcccg caaggtgcac    180
agggtgaacg gggtgagcgc ggccccgccg gtgcgaacgg atccgatgt aaagacggta    240
aggatggtgc tgatgccgt gatgggcgtt cggtgatatc ggtgtactgt tccggggggcc   300
gcctggttgt gaaatatagt gacggtacgg cctctaccgt gtcgggttct gcggcctgcg   360
agagtgtgaa accatcacct gtggttactg tatcatccca taggtgaaca agaagaggga   420
agggtgttac tagtgttgat tgtggtgttt ggggtggtg tgtggtgaga tacattccag   480
cggcgcatca ctctgccggt tcgaatagtc cggtgaacga ggttgtgatt catgcaacat   540
gcccggatgt ggggtttccg tccgcttcgc gtaagggtcg ggctgtgtct acagcgaact   600
atttcgcttc cccatcatcg gggggttcgg cgcattatgt ttgtgatatt ggggagacgg   660
tgcagtgcct gtcagagggg actataggg ggcatgcccc gccgaatccg cattctttgg   720
gtatagagat ttgcgcggat gggggttcgc atgcctcgtt ccgtgtaccg gggcatgctt   780
acacgaggga gcagtggctt gatccgcagg tgtggcccgc agtggagagg gccgctatcc   840
tgtgtcggca gttgtgtgac aagcatgtg ttccgaaaag gaaactgtct gtggccgatt    900
tgaaggccgg taaacggggt gtgtgcgggc atgtggatgt tacggatgcg tggcatcagt   960
cggatcatga cgatccgggg ccgtgtttc cgtgggacaa atttatggct gtggtgaatg   1020
gccacgcgg cggttcaagt agtgaggagt tgagtatggc tgatgtacaa gcgttacata   1080
atcagattaa acagttgtcg gcacaggtgg cccagtcggt gaataagctg catcacgatg   1140
ttggtgtggt tcaggttcag aatggtgatt tgggtaaacg tgttgatgcc ctgtcgtggg   1200
tgaagaatcc ggtgaccggg aagctgtggc gcaccaaga cgccctgtgg agcatctgtt   1260
attacgtgtt ggagtgtcgc agccgcatag acaggcttga gtctgctgtt aatggtttga   1320
aaaagtgatg gtgtttgtt gtgggtaaac agttttggtt gggcttgtt gagcgtgccc   1380
tgaaaacttt tattcaaacg tttgttgctg tgcttggggt gacggcgggt gttacttata   1440
ctgcgagtc gtttcgcggt ttgccgtggg agtctgccct gataacagca acggttgctg   1500
cggtgctgtc tgttgctaca tcgtttggta gcccgtcatt tgtggccggc aaacctaaaa   1560
ccacggttgt ggatgctggg cttgttccac ccgacgatgg gggcatggtt gagccgcact   1620
cggtggatgt gtcggatcct ggcatgatcg agccgacaga tgatgtggat ggttttgctg   1680
gctatgtgcc gaagcgtgca gccgagtcgg aggttagcac ggtggagtct actgttgcat   1740
aattgaacat agatgtgtgc cccagcggtg ctgccacgat cgtgtggtgg ttgccgctgg   1800
ggcacacttt ttgtgtctat aggagtttta caggttgtcg tctagtgtgt cttcgagcat   1860
ctggtccagg tagaggcagg cggagatagt atcgttggcc tggtctagaa cgttctggcc   1920
gataacattt ttatgattgt cgcggttggct gatgatagac tgcatgatat cgtcggccgc   1980
cgcctgcaat agtttggcct ggtatgcgat tcctgcgagc cagtctagtg cttcctggct   2040
tgccagtgtg tcgtctggaa tgccacgggt gttgctgttg tttgtggggt gtcctgcact   2100
gtcgcagcac cacaagattt cgctgcactc gtctagcgtg tcctggtcga tagcaagatc   2160
gtcgaggctg acttctttga cggtaaggtt cacattgtcg agggagatgg gtacaccgta   2220
ttggttttcg acactgtcaa caatgttttc caactgttgc atgttggtgg gctgttgttg   2280
gatgatacgg tgtactactg ttttgatggc ggtgtagggg atattgtgtg tgttgttcat   2340
ggttttatc ccaccctgt gttgtcgtcg ttattgtctg gatagtatct actgtttgcg   2400
tagcctgtga gggtgatgag tgtttggtct gcccactgtt tcactgtctg ccgggtgaca   2460
cccaatcgtt gggcgctgt ggcgtaggtt tgatcatcac cgtataccctc acggaatgcg   2520
gctagcctgg ctaggtgttt tcgctgtttt gagggttcac atgataggt gtagtcgtcg   2580
atggcgagct gtagatcgat catggtggca atgttgttgc cgtgatgctg gggggcggtt   2640
ggtgggggtg gcattcctgg ctccacactg gtttccatg gccgccgtt ccagatccat   2700
tgggcggctt ggatgatgtc ggcggtggtg taggttcggt tcatgtgtca cccccctgaac  2760
aggtcgttgc tggtgctggt gttggtggtg tcgaatcgtc cgacgcagtg gcagtagtcg   2820
tacatgagtt tgataatgtg ttggtggtct cccaaatagg tgtttccgct gatactgtag   2880
gtggctgtgc cgtctttact gatggtgtat ttggcggtga tggtttcggg gttttcggtg   2940
tcggtgatga ttgctgtggt ggtggtgcct actgtttgta gcacggtggt ttgggttccg   3000
tcgtcgatag tggttttaac catggtgtgt gttctccctt tttagatgct ggtttggttg   3060
tcggctagat gaatgatgtc gggtaagggt ttcggctagt tgttgtatgg tttttg      3120
ttggctagcc gttttgctac cctgtaacac attttggtgt agtgtttgtt gtctaggttg   3180
tggtattgtt cccgcaccgc aatatatagt agagagtctt ggtacaggtc gtctgcactg   3240
attgcggggt agtgtgcggc tgttttggtg catgcccggt tgagtgtgcg tagatgatgg   3300
tctgtggccc acacccacga tgcggtgtg gctaggtcgg cttttgttgg tcgtctgctc   3360
atggcatttc tttcatcggg ctatctggta gttgtttggt gttttgttgt tgatagtgta   3420
```

```
gcacacgagt ccggggtttc cggtggtgcc agtcttgtgc cggtaccatg tggattcgcc    3480
ttccatggat gggcattgga tgaaggtgcg ttgtccttgt tcggagattt ctaggtggtg    3540
ccggtgcccg gccatgagga tgtgggatgt ggtgccgttg tggaattctt ggccgcgcca    3600
ccaatcatag tgtttgccgg tgcgccattg gtgtccgtgg gcgtgcagga tttgtgtgcc    3660
ggccacgtcg acggtggtgg tcatttcgtc ccgttgggtg aagtggaagt gaaggttggg    3720
gtattggttg ttgagctggt aagcttctgc gatggcgcgg cagcagtcca cgtcgaagga    3780
gtcgtcgtag gtggtgactc cttttgccgaa gcgcacggct tcgccgtggt tgccggggat    3840
ggatgtgatg gtcacatttt tgcagtggtc gaacatgtgg acgagttgca tcatggccat    3900
gcgggtgagc ctgatttgtt cggtgagggg tgtttgtgtg cgccaggcgt tgttgcctcc    3960
ttgtgacacg tatccttcga tcatgtcgcc gaggaatgca atgtggactc gttcgggttt    4020
gcctgcctgt tgccagtagt gttttgcgac tatgagggag tgcaaatagt cgtctgcgaa    4080
tcggctggtt tctccgccgg ggatgccttt gccgatttgg aagtcgcctg ccccgataac    4140
gaaggctgtc tcgtcactgc tttgggtgtc ttgttcgggt ttgggtggct gccattcggc    4200
tagtttgttg acgagttcgt cgacgggta ggggtcggtt gcgggttggt ggtcgatgat    4260
tttttgtatg gatcggcctg tttctccgtt ggggagtgtc cattcggaga tgcgtgtgcg    4320
gcgtacagta ccgttggcta gattgtcgtc gatggtgtcg atggcgttgt cgtggttggc    4380
tagctgtgtg agtagccggt ctatattgtc tatcactggt tttcctcctc tggcggggtg    4440
gtgttggctt gtttgcgggcg gtagtctttt ataacggttg cggagatggg gtatcctgcc    4500
tgggtgagct gttttgctag ccacgaggcg ggtatagacc tgtcggcgag gacgtctgca    4560
gccttgttgc cgtagcgttg aataagggtt tcagttttgg ttgccatgat gtcctatcgg    4620
ttgtgtggcg ggctgccatc ctgtgcgca gtcgccgtcg tggcctggtt tgcgtgtgca    4680
ccacgatacg gttccgtctg tgtggttgag tgttttgccg cacatgacgt tttgtagatg    4740
ctcgggcagg gcgccgtcac cctggttgct ggtttgtgtg tcgaagagtg ttttctggtt    4800
ggtgaaatgc tctgacacgg tgccgttgtg tacgggtagt atccatgttt tccattgttg    4860
ttgtagccgg gtgttccagt ggaattgttt ggccgcgttc gtggcttgtt tgatggtttt    4920
gtagtagccg acgaggatgc gctggtgttc actgtcggt ggggttttgg ctcgccagta    4980
ttgtgccgcg acggcatacc tgttgttgtc tgtgaaggcg tcccagcagt attcgataat    5040
gtgttgtagt acactatcgg gaatgtctcg tacttggttt tcgtcgagcc acgcgtcgac    5100
aatgatgttg cgtatggcgt gtttgtcttt ggtggtgggt ttgaacgaga tactcaccat    5160
gctggcctgt cgtcttgcat gaaatcgtta aaggatgatt cgcttgtgcg gcgtgcctgc    5220
gtgatttgct ggtcagtcca gtcggggtgt gctgtttca gatagtacca gcggcaggca    5280
tcatatgttt cgttctgcaa gcgggtgaga tggttttcgg tgatgatttg tttccacatt    5340
gtccacgaga cgtcgagcct gcggagcatg tccatggccg gcacattaaa cgagtcaagg    5400
aagagtattt cgtgggtgta gtagttttc tcgtaggcgt accatccgct tcggtgcctg    5460
tggggctgtt ttttgggga ggcttccgg catactttgt gtaaacgttt ggccatgtcg    5520
tcgggtagtt caatgtcggg gttggcgcgg atcatggatc gcatcccgtc gtaggtggtg    5580
ccccaggtgt gcatgatgtg tagtgggttg tctccatcgg cccatttttc tgcacagatg    5640
gcgaggcgga tgcgcctcct ggctgtttgg ctggtgttgc gccggttggg gattgggcac    5700
gtgtcgaggg gatccattat gttttagtgt acctttctgg tttcgtgttg ttgacgtgtt    5760
ttactgtagc acagtgtcta gtgcttgtgt caaccctgtt tttccggcct gcaggtaggt    5820
gtctgtgaca tctccgaccg tgaggggcac atgggtggct tggggagtg ctgcctggat    5880
ggtttgtgcc atctggtcgc ctgcggggtc tgggtctgac cagatgtaga tgtggtcgta    5940
gccttgcaag aatttggtcc agaagttttg ccacgaggtt gcgccgggta gggctacggc    6000
cggccatccg cattgttcga ggatcatgga gtcgaattcg ccttcgcaaa tgtgcatttc    6060
ggctgccggg ttgccatgg cggccatgtt gtagatggag cctgtgtccc cggctggggt    6120
caagtatttg gggtggttgt gggttttgca gtcgtgtggg agtgagcagc ggaaacgcat    6180
ttttcgtatt tcggctggcc gctcccaaac ggggtacatg tatgggatgg tgatgcactg    6240
gttgtagttt tcgtggcctg gtatgggtc attgtcgatg tatccaaggt ggtggtagcg    6300
ggctgtttct tcgctgatgc ctcttgctga gagcaggtcg agtatgtttt cgaggtgggt    6360
ttcgtagcgg gctgaggctt tctggattcg gcggcgttcc gcaatgttgt agggttgtat    6420
gctgtcgtac attcggggttt tcttcttcta gtcgttgttg tagtttgtgg agtcctcctc    6480
cgacaccgca tgtgtggcag taccagacgc ccttgtcgag gttgatgctc atggagggct    6540
ggtggtcgtc gtgagcgggg cagagtatgt gttgctcgtt tttggacggg ttgtagcgta    6600
tctggtagat gtcgaggatg cggcgggtgt cagaggtgtg ggaggagctc gttgagggtt    6660
gataccacat aggcttcgct ccagggtttg ttgcgttgtt tcatcactac gagtccgatg    6720
gtggaattgt tttcgcggtt tcggtgtgtt tcgtagttgc gtgcctcccg gctggcttgt    6780
ttcacgaatt cggctaggtg gggctggccg gctttcgcct cgataatgta ggttttgttg    6840
ctggttgtga ggatgaggtc gccttcgtct tcgcggccgt tgaggtggag gcgttcgata    6900
tcgtgtccgg tgtcgcgtag ctggtgcaat aatcgtgttg cccattcggc tccggcccgc    6960
cggttgcgtg cctgctgct ggccatagtt tttagagtcc tttgtgtgtt gtggtcatgt    7020
tccagggctg ttttttcggcg aggggcccga agaatgtgta ttcggggtag gctcgtagtc    7080
gttcatatcg ggtgccgtcg gggctggatt tgccggtgcg ctgtttcaat actgcgatgc    7140
gtgcctcggc cggtatcgtg agaccgttgc cgttatcctc gccaccatac aatgagactc    7200
ccaatatgag ttgtggtttt tcggagaggc cgttttgat ttctcgccgt gccgggggat    7260
gttcgatgtc ggttccggtt ttgtcggtgg cgtggtgtgt gacaataatg gtggatccgg    7320
tgtcgcggcc taatgctgtg atccattgca tggcttcttg ctgtgcctga tagtcactct    7380
cgcagtcttg gatgtccatc aggttgtcga taacaatgag tggcgggaag gtgttccaca    7440
tttccatgta ggcttgcagc tccatggtga tgtctgtcca tgtgatgggt gactggaatg    7500
agaatgtgat gtgttggccg tggtggatgc tgtctcgata gtattctgat ccgtagtcgt    7560
cgatgttttg ttgtatctgt gtggtggtgt gttgggtgtt gagtgagatg attcgtgtgg    7620
aggcctccca gggtgtcatg tcccctgata tgtagagggc gggctggttg agcatggcgg    7680
tgatgaacat ggctagcccg gattttggc tgcctgagcg ccccgcaatc atgacgagat    7740
cccctttgtg gatgtgcatg tcctggttgc ggtagagggg ttctagttgt ggtatgcggg    7800
gcagctcggc tgcgggttgg gaggctctct gcaaggatcg ttggagagag agcatcggga    7860
ccttatctat ctatcggttg ggtgtgtttt ggtggtcaga tggagtcgat gtcgatgtca    7920
gcatcggcgg gggttgagca cgaccgcatt gaacccgttt ttggtgcgca cggtggcgag    7980
tttgaaggcc tgctcctcgc caaggtaggc ttcgaggtcg cggatcatgg aatgtgggcg    8040
gtcgttgttg ccgcgcgctt tctcaataat agcgttggga atgatttctg gggtgccgtt    8100
gttgagatcg tctagggtgt ggaagattgt gacatcagcg tagatgcgat cggctgtctg    8160
```

```
tccaccgtag ccttcggtgt tgtgttctac gtcgcggatt ttgaaggcga tggcggtggc   8220
gtcctggttt cgggaggggt tgaagaaggt gctgttgctg ttgttgcggt agttggcgag   8280
tcccatggtt gtttccttta ctgtttgtgt tggtttgtgt cggttttatc gggtgaggct   8340
gtttcgtttg ctgcgaaaag cctcggacac gtcactgtta ctggtgatga ttttcttgta   8400
ctgtttcaga aggtcggcta gctgtgcctt gcttgttgca ttgttgattt tgtcgatgat   8460
aatctcgttt tcgtttgatg cgatgttgtc tacgtagtct ttggctgcct ggttgtagcg   8520
gtcttggagg atgatggatg cgcttgctac gagtgttgct agatcccagt ctttggacac   8580
gtcaccgttt ttgaggccgc ctagcagatc aataatggat tgtttgatgt cttctgcggt   8640
gtctccgcgg atgactgtcc atggggctgc gtagtctcca ccgtatttga gtgtgatagt   8700
tagcttttccg ctgtctgtgg tgtgctcgtc ggtcacgtgt tttccttttc gttgttttcg   8760
gcttctggtg gctgtacggt ggtttctacc gggtatctgt acgagttttt cccgttgacg   8820
gcccagcagg cgtccttgac ggggcatcct ttgcagagtg ctgtgacgtg gggtacgaag   8880
atgccttggc tgattccttt cattgcttga ctgtacatgg atgatacatg ccggtaggtg   8940
ttgttgtcaa gatcaatgag ttcggtggat gtgccctgct caaccgattg ctcgtctcca   9000
ttggtggtag cgggtgtcca aaacattcct ttcgtcacat ggatgccgtg ttggttgagc   9060
atgtaacggt aggtgtgcag ctgcatactg tcggcgggta ggcgtccggt tttgaggtcc   9120
aaaatgaagg tttcacccgt attcgtatct gtgaataccc ggtcgatgta gccaacgatc   9180
tgggtgccgt cggggagggt ggtttctacc gggtattcga tgcccggctc gccgtcaata   9240
acagcggtag catattctgg gtggttgcgc ctccatgttt tccaccggtc cacaaaggtg   9300
gggccgtaaa tcatccacca attgtagtct ttcttgtgtg tcccgcccga ctcgcacatg   9360
tttttgcata ttctgccgga gggtttgatt tctgtgcctt cggattcggc gagggcgact   9420
tgggtgtcga aaatgttttt gaaggatgag agtttgtcgg gcagtgcagg gtattcgacg   9480
ggattgtaca ggtgtaggtc gtattgttcg gtgatgtggt gtatggcgct tccggcgatg   9540
gtggcatacc aggtgtggtg ttgggcgtgg tagccgtggg ataggcgcca ttttcaccg   9600
cattcggccc actgtgacag tgatgagtag gagatgtggc ctggatggtc aatggtggac   9660
ggtttttgtg ctaggggcat tacttgtcgc tttttgtggt gttccatggg tttcgggtgt   9720
cttggccggc attgtgttgc tggtatgcga ggagtgcgag gcagtgccag gcagcatggg   9780
ccagatgggg tagcccggat tcatcatcga ggttgttgcc ttgctgccat gataacaggt   9840
gccggtagag ggcgtcaaca ctgtggctcc acggatagcc gccggtccag ttgttgtcgc   9900
cgtattttggt ggcgccgtat ccggccacag agccgaggcc gtgtaaggct gtagggtcga   9960
tgagggatag cctgcaaagt ttcaattctt tcttggcgcc agtatcaggg tcggtgtaca  10020
tgctggtggg ctcatccatg gtgtgtgtgc tccttaagta tggggttact ggttggggtt  10080
gtgggcgagt gctacggcaa gaataatgat ggcgaggggt tcagcgatca gtatgggtgt  10140
tgtgatcatt tgtggtcgcg gggattgttg gtgagggttg aggcgcccag gaggatagtg  10200
agggcgcatg cggcgatgat ggcgagggct gccttgtcg gggtgccggt ggctacatc   10260
catgtgatga tgccgccttg gatccaggcg aggctggtga agaacgtttc gtagctgtgt  10320
agctcaatgt tgttgttggg tgtgttcatg cttgctcctg aagaatggtg ttgatggttg  10380
tgtaaatgtt gtacaggtcg gtttcgatag ataacagttg gtggatttgg tggtcgagat  10440
caatgtcggg gttgagggtg ttgatgcggg aggcgatgtc ggtggctgtg cgtagtgtga  10500
cgccggtgtg gtgaatgatg tgtgccgtgt cggcgagtcc ggtggtgaca gtgtagtggg  10560
agaggagagg catagctggg ggtgctcctt gacggggtta ctgttgcggg ttgatgttga  10620
ggtcggtgac gttggggtgg tcttctgttc cggtgacaag gcagtggacg gtgactggga  10680
gtttggatgc gccgggctgt ttcgcggttg cgccgtagac gatggagaag gtgtctttgt  10740
caataattt gtggagttgg aggtcgatgt cggggttgcc gttccatttg acgccttgtg  10800
tggcggcctg ttgttcggct ttgcggttgc aggtgtgtgc tgcggtgatc atggtgagtc  10860
cggtggcggt ttcttcaccc cttgcttggg cttgcttgtg ggttttctgc tgttcggctc  10920
gcagtgactg ttctgctgct gcctgccgtg ctttcttttc gctttgtc tgttgggtag  10980
tcttgggggt ccattcggtg ttggctgtgg tggcttgcgg tgcgggttgt gatgcgagtg  11040
gcggattgtc gtctggggct ggcatgaagg atgctgcggc gatgatggcg gctgtgattc  11100
cggcgatggt gtagccgttt ttcttgttca tgattttgtg ttcccctttc cggggtgttg  11160
ttcgttgctg acatgattaa tactttcagc ggctgggccc actgtcaagg ctgcgctcaa  11220
cgattgtgag cgatacttgt gtggctaggg gttttgtcct tgaggtggga gatgtctttc  11280
ccttgcgtcc agtatccatg gcggttgcga gtcatcccctt tggcgagcat ctcgtccacg  11340
gtgagacacc tgccgacgatc tggaccctcc ttgactccct gatcgcctgt gcggtgcatg  11400
tcaccggcac aagtaccatt aaatgtctcg tggcggatgg tgtgatgctc tggtcggtat  11460
ccgatgattg tgctatcgca cttgtggcat gtccattgca tgattggtcc ttctttcgtg  11520
ttttaagctt gtactctgag gattagagcg actttcagcc cttgggggt atgattatat  11580
aggtcaggta tttctaggcg attctaggct cattgtgtgt ggctgggggt tatcgggcac  11640
acagggtgag gagttggcca acattgatgc gggtcacatt ccagtagagt tgcgtggctt  11700
ccccaccggt gagtggcttc cactcgtcat ggctgaacac ggtcgcgtcg gttgcgatga  11760
atgtgttggg gcgtagcttg tgaagctcag tctctacacg ctgccggtag gcttcggcga  11820
ggccctcgaa atccatgtgg tcgcagggga ggttttcgag gcgtgtcagg tcgaggggtg  11880
tggggcagtc gtagctggcg gggctgtaga gctgggtgaa atggttggcg atcttctgca  11940
tgacgggttc ctttttcgt atggtgagtt gatagtttta tcgggtgagt gcgacaaagga  12000
tggcgtctac atcgatcatg tcgatgagat cgtggagttc ctcggcctca ttctcggaga  12060
ggtggcgcca gccatagtcg ccgtatacgc cgccgtcgag ggtgacagtc cacaggggcc  12120
ggatgagtcg tatggcttct tgtactttag cgtggtacat gcggcgcacc atatccagat  12180
cgatgtcgtc tgaatggttt ccggtgaggc tgtagaggct gagcgggtcg atttctgtct  12240
gctgtagag ggatgtgaat gatggtgtga tgagtgtgac atccatgaga tgtgctcct  12300
ttcggtggtg gagggttgt tgtggtttct agagtgtgta ggctgcgacc catagtcaag  12360
gctgcgctca ttcggattga gcgtttcata tgggtgtggc atggaatcta caccccata  12420
ctgtgtgaga taggccacat cctcctggct tggtgtgaac cctcgagact actctgccta  12480
tctggcgtgg agggtgtagc ccagaaatac cgttttaaagc cttcatacgg cgcctaggag  12540
cgccttacag ggtggggggct aattgtttat acccccaagc aattctgatc gattctagac  12600
ggcctcccagg agcccgatac acgatccgct atccagacac agatcatcag cccctatcct  12660
ggttagctaa gcctcaacta tgtggacagt gttgattact gtggggtaag aaggacacgg  12720
taaaagaaag aggggggagc atcggccttc aagccttaag gtcttagcag ttagcaccga  12780
gcccctcaag ggctcgtcgt cagcccatca ggcacggccc tgaacggggt acacgccatc  12840
agggaaggct tgagagtacg aggagcctta gcgacgagta ctcgaaagcc tgagggaaca  12900
```

```
ccctcagcac tgatgggtct agcgtgttcg gaaaggacac aggagtaaag cgtgacagct    12960
gtccgggagt gaaacccgtt ctgactaggg gtttcagcct taaccaccct caaaggttac    13020
aagactctaa gaaaatttaa ggaaaagttt aggtttaatt tttggacctt tactaccaaa    13080
aacacccgtt tacaccccctc aaacccgcct atagagccaa atccaccagt ttgactcatc   13140
ccaggtggca tatgataggc tggacaggta gccagctgga cgcaaggccg aaatccgctg    13200
acgcggcttt caccctaca tccatcagtc taccaaagac ttaaagacct aagggcttag     13260
cgctaaggtg ctgatagctt agcaccgagc ccttgagggg ctcggcatca gccctaaagc    13320
cttaaacact taaagtacat ataaaacttt aaaagcttaa cacttaaggt tataaataaa    13380
cattaaagct ttaaagtctt aaagtacata tataaccttta acacctaagt taagtataaa  13440
acctttaaagg cttagcactg aaggatataa acttcacatc agttttttaag actttaaaac 13500
ttaaaataac tattaagact taaagactta taagttttaa acacttaaag taactataag   13560
actttaaaga ccttaagtac ttaaagttaa ccatcagtct taaactttaa tattataacc   13620
tataagtctt aaagcttata agttataaaa gttttagaag agctaagagg ttaactttct   13680
tacttctctt ctctctttgg ttctttctct cttctcttct tttcttcatc aggggagaag   13740
aggaaccttt taccatcagc gccgatggac tgtcaccgtg tgactcgtgt accaccggtc   13800
gcacgctccc ggtttcacac tccccacact ctgacacccg tgtcccttttc aggcttagcg   13860
tgttcggctg aaggcgtacg gcgtgtcgcg ccaacaccct taacaccagg taagacttaa    13920
agtgtatatt atatgtagaa gactttaaaa cctataaggt gttcccgctt agcctgtgtc    13980
ctacaccgct aggcgccaag cgttaagtct tgaaacgcga acacacaccc acccccattt    14040
ttctttcgtg tccttctctt ttgacaccgc tggggggcga tgtgatcttt ctcactaccc    14100
ccatgggtag tggagaacac acccacccca ccatcaacag aacacccct caaacgaaca     14160
aaacaggtga tagaatcgat cggcagggca agggcaaggt attcataccc ccaacacatt   14220
ccaggccgtc agagaggcaa ataagacccg tacaggcgta gtcgaggatc ggagacgtga   14280
tggcacacac caatcgcacc gcatccgccg cacaccgaca ctggcggcaa cgactcatca    14340
cccaagcccg acagcaaggc caaaccgaat gcccactctg cggagcaacc atcacctggg    14400
acacctacca gctgccaact agccccgaag ccgaccaact cacaccccgt cagcagggag    14460
gactcaacac cctcgacaac gggcaaatca tctgcagaac atgcaacaga agcaaaggca    14520
acagaacaca accaaacatc aaattccaac aacaaaccac aaaaaaacctt gttccatggt   14580
gacaaaaccc gccaaccccc accggggaca cccctgcac acccgtgcaa gacctcgtac     14640
ggcttagtga aatacctccc tttttgtggat ttgtctgttt gtcgactttt tgtgttggtg   14700
gtgagtgttg tgcagcctga gcttcctgag ggacacgagt ggtgtgggga gacgcgtcgt    14760
tggtggcgtg tgtggggtga ggatagccgc gcgcagtacg tgtctgatga ggagtggctg    14820
tttcttatgg atgctgcggt gattcatgat tgtgtgtggc gtgagggtcg cgcggatttg    14880
gtggcttcgc ttcgtgctca tgtgaaggct tttatgggta tgttggatcg ttattcggtt   14940
gatgtggcgt ctggtggccg tggtgggggt tctgcggtgg cgatgattga ccggtatagg    15000
aagcgtaggg gggcctgatt aggtgtctgg tgttgttggg tctcaggttc ctcgtcatcg    15060
tgtggctgcg gcgtattcgg tgtctgctgg cggtgatgct ggggagttgg gtcgtgcgta    15120
tgggttgacg cctgatccgt ggcagcagca ggtgttggat gattggctag ctgtgggtgg    15180
taatggcagg cttgcttcgg tgtgtgtggg ggtgtttgtg cctcgccaga atggcaagaa    15240
tgctatttttg gaggttgtgg agttgtttaa ggcgactatt cagggtcgcc gtattttgca   15300
tacggctcac gagttgaagt cggctcgtaa ggcgtttatg cggttgaggt cgttttttga    15360
gaatgagcgg cagtttcctg acttgtatcg tatggtgaag tcgattcgtg cgacgaatgg    15420
ccaggaggct attgtgttgc atcatccgga ttgtgccacg tttgagcgta agtgtggttg    15480
tccgggttgg ggttcggttg agtttgtggc ccgttctcgt ggttctgctc gcggttttac    15540
ggttgatgat ttggtgtgtg atgaggctca ggagttgtcg gatgagcagt tggaggcgtt    15600
gcttcctacg gtgtctgcgg ctccttcggg tgatcctcag cagatttttct tgggtacgcc   15660
gcctggccgg ttggctgacg ggtctgtggt gttgcgtttg cgcggcgcagg ctttgtcggg  15720
tggtaaaagg tttgcgtgga cggagttttc tatcccggat gagtctgatc cggatgatgt    15780
gtcgcggcag tggcggaagc ttgctggtga gacgaatcct gcgctgggta ggcgtctgaa    15840
tttcgggacg gtgagcgatg agcatgagtc gatgtctgct gccgggtttg ctcgggagcg    15900
gcttggctgg tgggatcgtg gccagtctgc ttcttcggtg attccggcgg ataagtcggt    15960
tcagtcggct gtggatgagg cggctctggt tggcggaaaa gtgtttggtg tctcgttttc    16020
tcgttcgggg gatcgtgtcg cttttggctgg tgctggccgg actgatgctg tgttcatgt    16080
tgaggtgatt gatgggctgt cggggacgat tgttgatggt gtgggccggt tggctgactg    16140
gttgcggtt cgttggggtg atactgaccg gatcatggtt gccgggtctg gtgcggtgtt     16200
gttgcagaag gcgttgacgg atcgtggtgt tccgggccgt ggcgtgattg tggctgatac    16260
tggggtgtat gtggaggcgt gtcaggcgtt tttggagggt gtcaggtcgg gtgtggtttc    16320
tcatcctcgt gccgattcga ggcgtgacat gttggatatt gctgtgaggt cggctgtgca    16380
gaagaagaag ggttctgcgt ggggttgggg ttcctcgttt aaggatggtt ctggaggttcc   16440
tttggaggct gtgtctttgg cgtatcttgg tgcgaagatg gcgaaggcta ggcgcgctga    16500
acggtctggt aggaagcggg tgtctgtggt atgaattcgg atgagttggc tctgattgag    16560
ggcatgtacg atcgtatccg aaggttgtct tcgtggcatt gccgtattga gggctactat    16620
gagggctcta gccgggtgcg tgatttgggg gttgctattc ctccggagtt gcagcgtgtg    16680
cagacggtgg tgtcgtgcc tggtattgcg gtggatgctt tggaggaggcg tctggattgg   16740
cttggctgga ctaatggtga cggctacggt ctgatggtgt tgtatgctgc gaatcggctt    16800
gctacggcgt cgtgtgatgt gcatttggat gcgctgattt tgggttgtc gtttgtggct   16860
gttattcccc agggtgatgg gtcggtgttg gttcgtccgc agtcgccgaa gaattgcacg   16920
ggccggtttt cggctgacgg gtctcgtctg gatgctggcc ttgtggtgca gcagacgtgt    16980
gatcctgagg ttgttgaggc tgagcttttg ttgcctgatg tgattgttca ggtggagcgg    17040
cgaggtagcc gtgagtgggt tgagacgggc cgtataccga atgtgcttgg ggctgttccg    17100
ttggtgcctg ttgtgaatcg tcgccgtacg tctaggattg atgggcgttc ggagatcact    17160
cggtcgatta gggcttacac ggatgaggct gttcgcacac tgttgggca gtctgtgaat    17220
cgtgactttt atgcctatcc tcagcgttgg gtgacgggt gtcggctga cgagttttcg    17280
cagcctggct gggtcctgtc gatggcttct gtgtgggctg tggataagga tacgacggt    17340
gacactccga atgtgggctc gtttcctgtg aattctccta caccgtattc ggatcagatg    17400
cgtttgttgg ctcagctgac ggcggtgag gctgcggttc cggagcgcta tttcgggtttt   17460
atcacgtcta acccgccttc tggggaggct ttggctgcgg aggagtcgag gcttgtgaag   17520
cgtgccgagc ggcgtcagac gtcgtttggt cagggctggc tgtcggttgg tttcctggct    17580
gccagggcgc ttgattcgag tgttgatgag gccgcgtttt tcgcgatgt gggtttgcgt     17640
```

```
tggcgtgacg cttcaacccc gactcgggcg gctacggctg atgctgtgac gaagcttgtg   17700
ggtgccggta ttcttccggc ggattctcgt acggtgttgg agatgctggg gcttgatgat   17760
gtgcaggttg aggctgtgat gcgtcatcgt gccgagtctt cggatccgtt ggcggcactg   17820
gctgggcta tatcgcgtca aactagcgag gtttgatagg cgatggcttc gggtgttgcg   17880
tcaaggttgg ctgctgccgg gtatcaagcg gaggcggtca ggtttgccgg gaagtatgcg   17940
ggctattatg ccgagcttgg tcgtttgtgt cattccggga agatgacaga tgcgcagtat   18000
gtgcgtttgt gtgtggagtt ggagcgtgcc ggccatgacg gttcagcggc gttggcgggt   18060
aagttcgtgt cggattttcg gaagcttaac ggtgtggatc ctggtttgat cgtgtatgac   18120
gagtttgatg ctgccgccgc gttggctagg tcgttttcga ctattaagat gatgaatagt   18180
gacccggata gggctaagga tacggttgat gcgatggcgg cgggtgttaa tcgggctgtc   18240
atgaatgctg gccgtgacac ggttgagtgg tctgcgggtg cgcagggtag gtcgtggcgc   18300
cgggtgacgg atggtgatcc gtgcgcgttt tgtgccatgt tggctacgag gtcggattat   18360
acgaccaaag agcgggcgct tactactggt catactcggc gtcataagcg tggcggtagg   18420
cgtccgtttg gttcgaagta tcatgatcat tgtggttgta cggtggttga ggttgttgc    18480
ccttgggagc caaatagggc tgatgccgca tatcagagga cgtatgagaa ggctcgtgag   18540
tgggttgatg atcatgggtt gcagcagtcg cctggcaata ttttgaaggc tatgcgtact   18600
gttggtggca tgagataatt tgatgtggtt tccggttgtg tgccgccggt tatcggtgca   18660
cagggttgtc tcccgcacgg gggtcaacaa tgttgtgttg ttttccgcaa ggagtatagg   18720
gttaggctat ggccgatcaa aaagttgaag aacagaatgt tgacaatgat gctgttgagc   18780
ccggaaaggg tggagacgtt gttgatgttg tgaaggatgt gcaggctgcc ggcgatgatc   18840
atgccggtga tgtttccgtg aaggaggagt cttcttctgg cacggattgg aaggctgagg   18900
ctcgtaagtg ggagtccgt gctaaaagta atttcgccga gttggagaag cttcgcgcct   18960
cggatggtga tgcggggtct gtgattgatg agcttcgccg caagaatgag gaactcgaag   19020
accggattaa tgggtttgtt cttgagggtg tgaagcgcga ggtggctgcc gagtgtggcc   19080
tgtcgggtga tgctgtcgct tttttgcacg gtggcgatcg tgaagcactg gtggagtctg   19140
ctaaggcttt gaagggtttg atcgaccata gtagtggtgg cgcgggtgtg cgccgtcttg   19200
cggggagtgc ccccgttgat gatgttaaac gacgtgaggg tgtcgcgttt gtggatgctc   19260
ttgtcaataa ttctaggaga tgatttgtga tggctgacga ttttcttttct gcagggaagc   19320
ttgagcttcc tggttctatg attggtgcgg ttcgtgaccg tgctatcgat tctggtgttt   19380
tggcgaagct ttcgccggag cagccgacta ttttgccc tgttaagggt gccgtgttta   19440
gtggtgttcc tcgcgctaag attgttggtg agggcgaggt taagccttcc gcgtctgttg   19500
atgtttcggc gtttactgcg cagcctatca aggttgtgac tcagcagcgt gtctcggacg   19560
agtttatgtg ggctgatgct gattaccgtc tgggtgtttt gcaggatctg atttccccgg   19620
ctcttggtgc ttcgattggt cgcgccgtgg atctgattgc tttccatggt attgatcctg   19680
ccactggtaa agcggctgcc gctgtgcata cttcgctgta taagacgacg catattcgtg   19740
atgccacgga ttctgctacg gctgatcttg ttaaggctgt cggcctgatt gctggtgctg   19800
gttttgcaggt tcctaacggg gttgctttgg atcccgcgtt ctcgtttgcc ctgtctactg   19860
aggtgtatcc gaaggggtct ccgcttgccg gccagcctat gtatcctgcc gccgggtttg   19920
ccggtttgga taattggcgc ggcctgaatg ttggtgcttc ttcgactgtt tctgcgcgcc   19980
cggagatgtc gcctgactcg ggtgttaagg ctattgtggg tgatttctct cgtgttcatt   20040
gggggttccg cgctaacttc ccgatcgagc ttatcgagta tggcgatccg gatcagactg   20100
gccgcgattt gaagggccat aatgaggtta tggttcgtgc cgaggctgtg ctgtatgtgg   20160
ctatcgagtc gccttgattcg tttgctgttg tgaaggagaa ggtgcccccg aagcctaatc   20220
cgccggccga gaactgattt attgttgcgg tgatgtgtca atgtgcaggg ggtggtgttg   20280
atgggtatca ttttgaagcc tgaggatatt gagccttcg ccgatattcc tagagagaag   20340
cttgaggcga tgattgccga tgtggaggct gtggctgtca gtgtcgcccc ctgtatcgct   20400
aaaccggatt tcaaatacaa ggatgccgct aaggctattc tgcgcaggc tttgttgcgc   20460
tggaatgata ctggcgtgtc gggtcaggtg cagtacgagt ctgcgggtcc tttcgctcag   20520
actacacggt ctagtactcc cacgaatttg ttgtggcctt ctgagattgt cgccgttgaag   20580
aagctgtgtg agggtgatgg tggggctggt aaagcgttca ctattacacc gaccatgagg   20640
agtagtgtga atcattctga ggtgtgttcc acggtgtgga gtgaggggttg ctcgtgcgagg   20700
tcgaatatta acggctacgc tggccccttg tgggagatat gatatgacca gttttccttca   20760
tggtgaaacg gttgtgatgc ttcaaccgac tgttcgtgtc gatgatcttg gcgacaaggt   20820
ggaagactgg tctaagcctg tcgagactgt gtaccataac gtggccatat atgcttccgt   20880
ttcgcaggag gatgaggctg cggggcgtga ctcggattat ggacagttgt cgatgctgtt   20940
caagcagcct gttgtgggcg ctgattatcg ttgtaggtgg cgtattcggg tgtgtgtgt    21000
ggaggctgac gggtctccta tggtgtggca tcacccatg tccggttggg atgctggtac    21060
gcaggttaat gtgaagcgta agaagggctg atgggtagtg gctcaggatg tgaatgtgaa   21120
gctgaacttg ccgggtattc gtgaggtgtt gaagtcttct ggagtgcatg gcatgttggc   21180
tgagcgtggc gagcgtgtca agcgtgccgc agcggcgaat gtgggtggta acgcgtttga   21240
tagggcccaa taccgtaatg gtttgtcgtc ggaggtgcag gttcaccgtg ttgaggctgt   21300
ggcgaggatt ggcaccacct ataagggtgg aagcgtatt gaggcgaagc atggcacgtt    21360
ggcgaggtcg attggggctg cgtcgtgatc gtttacggtg atccgcgtgt gtgggctaaa   21420
cgcgtgctca aggatgatgg ctggctgtct gggataccgt gtacggggca ggtgcctgag   21480
gatttcagcg gtgacctgat ctggttggcg ttggatggtg gcccacagtt gcatgttcgt   21540
gagcgtgttt ttttgcgcgt gaacgtgttt tcggatacgc cggatcgtgc tatgtcgttg   21600
gcgcgtcgtc tcgaggctgt gctggctgat agtgtggacg tgaccctgt ggtgtactgt    21660
aaacggtcta ctgcccctga tttgctggtt gatggtgcac gttttgatgt gtattcgctt   21720
tttgagctga tatgtaggcc tgcggagtct gaataagctt attgttttg ttttaatgta   21780
attgtttgat atttaatggg ggttatgatg gctgcaacac gtaaagcgtc taatgttcgc   21840
tcagcggtta ctggcgacgt ttatattggt gacgcgcacg cgggtgatac tattaagggt   21900
gtggaggcgg ttccttccgg gcttaccgct ttagggtatc tgtctgatga cgggtttaag   21960
attaagcctg agcgtaaaac ggatgatttg aaggcttggc agaatgcgga tgttgttcgc   22020
actgtggca cggagtcttc tatcgagatt tctttccagc gaatc caaaaaagag         22080
gttatcgaac tgttttggca gtcgaaggtt actgccggat ccgattcggg ttcttttgat   22140
attctcctg gtgccacgac gggtgttcac gctctgttga tggatattgt tgatggtgat    22200
caggttattc gctactattt ccctgaggtt gagctcattg atcgtgacga gatcaagggt   22260
aagaatggta agtgtacgg gtatggtgtg acgttgaagg cgtatcctgc ccagattggt    22320
aagactggta atgcggtgtc tggtcgggg tggatgacgg ctttaaaagc tgatactcct   22380
```

```
ccttctccga agcctcagcc ggatccgaat ccgccggccg agaactgata cacgatttta  22440
ggggattgtt gatagatgag tgacactggt ttcacgttga agattggtga tcgtagctgg  22500
gtgttggcgg atgctgagga gacggcgcag gctgttcctg cccgcgtttt ccgtcgtgcc  22560
gccaggattg cccagtcggg ggagtctgcg gatttcgccc aggttgaggt gatgttttct  22620
atgttggagg ctgccgcccc ggctgacgct gtggaggccc ttggaggggt tcctatggtt  22680
cgtgtggcgg aggttttccg tgagtggatg gaatataagc ctgacggtaa gggtgcctcg  22740
ctgggggaat agtttggctc cacggcctga ttgatgatta tcgtgggcc atcgaatacg  22800
atttccgcac taaatttggt gtttctgttt atagtgttgg tggcccgcag atgtgttggg  22860
gtgaggctgt ccggctggct ggcgtgttgt gtactgatac gtctagccag ttggcggccc  22920
acctgaatgg ttggcagcgc ccgtttgagt ggtgtgagtg ggctgtgttg gacatgttgg  22980
atcattacag gtctgctaat agtgaggggc agccggagcc tgtggcgagg ccgacggatg  23040
agcgtagggc ccgtttacg tctgggcagg tggacgatat tttggcgcgt gttcgtgccg  23100
gtggcggggt gtctcgcgag attaatatta tggggtgaat agtgtatgtc tggtgagatt  23160
gcttccgcgt atgtgtcgtt gtatacgaag gcctagcc ttaaaagtga tgttggtaaa  23220
cagctttctg gggtgatgcc tgcggagggt cagcgttcgg gtagcttgtt tgctagcggg  23280
atgaagttgg cgcttggtgg tgcggcgatg atgggtgcca tcaatgttgc taagaagggc  23340
ctcaagtcta tctatgatgt gactattggt ggcggtattg ctagggcgat ggctattgat  23400
gaggctcagg ctaaactgac tggttttgggt catacgtcgt ctgacacgtc ttcgattatg  23460
aattcggcta ttgaggctgt tactggtacg tcgtacgcgt tggggatgc ggcgtctacg  23520
gctgcgcgt tgtctgcttc gggtgtgaag tctggcgggc agatgacgga tgtgttgaag  23580
actgtcgccg atgtgtctta tatttcgggt aagtcgtttc aggatacggg cgctattttt  23640
acgtccgtga tggctcgcgg taagttgcag ggcgatgaca tgttgcagct tactatggcg  23700
ggtgttcctg tgctgtcttt gcttgccagg cagacgggta aaacgtctgc tgaggtgtcg  23760
cagatggtgt cgaaggggca gattgatttt gccacgtttg cggctgcgat gaagcttggc  23820
atgggtggtg ctgcgcaggc gtctggtaag acgtttgagg gcgctatgaa gaatgttaag  23880
ggtgccctgg gttatttggg tgctacggct atggcgcgt ttcttaacgg gttgcggcag  23940
atttttgttg cgttgaatcc ggttattaag tctatcacgg attctgtgaa gccgtatgttt  24000
gcgtcggtgg atcaggggat tcagcgggtg atgccgtcta ttttggcgtg gattaaccgt  24060
atgccgggca tgattacgag aatgaatgca cagatgcgcg ccaaggttga gcagttgaag  24120
ggcgttttttg cgaggctgca tttgcctgtt cctaaggtga attttggtgc catgtttgct  24180
ggcggcaccg cagtgttcgg tattgttgct gcgggtgttg ggaagcttgt tgccgggttt  24240
gccccgttgg cggtgtcttt gaagaatctg ttgccgtcgt ttggtgcttt gagggttgcc  24300
gctgggggc ttggtggcgt gttttcgcgcc ctgggtggcc ctgttggtat tgtgatcggg  24360
ctgtttgctg ccatgtttgc tacgaacgcc cagttccgtg ccgctgttat gcagcttggc  24420
ggggttgttg gccggggctt gggggcagatt atggtcgctg tgcagccact gttcggatt  24480
gttgctggcg tggttgccag gttggcgcca gtgttcggcc agattatcgg tatggttgct  24540
ggtttggctg cccggctggt gcctgttatt ggtatgctta ttgcccggct ggttcctgtt  24600
atcacccaga ttattggtat ggtaacccag gttgctgcca tgttgttgcc tatgctgatg  24660
ccggttattc aggctgttgt tgctgtgata cggcaggtta ttggtgat catgcagttg  24720
atacctgttt tgatgccggt tgtgcagcag attttggggtg ctgtcatgtc tgtttttgccg  24780
ccgattgttg gtttgatacg gtcgctgata ccggtgatca tgtcgattat gcgtgtggtg  24840
gtgcaggttg ttggtgccgt gttgcaggtg gtgggcccgta ttattccggt tgttatgccg  24900
attttatgtt cggtgattgg attcattgcc aagatttatg ctgcggttat cgttttttgag  24960
gctaaggtta ttggcgctat tcttcgtact attacgtgga ttgtgaatca ttcagtgtct  25020
ggcgtgaggt ctatgggcac ggccatccag aatggctgga atcatatcaa atcgtttacg  25080
tcggcgttta ttaacggttt caagtcgatc atttctgccg gtgttgccgc ggtgtgggg  25140
ttttttacgc ggcttggttt gtcggttgct tctcatgttc ggtctggtt taacggctc  25200
cgtggcgctg tttcgctgcg gatgaatgct attcggagtg ttgtgtcttc ggtggcgtct  25260
gctgttggcg ggtttttcgg gtcgatggcg tctagggttc gtagtggtgc tgtgcgcggg  25320
tttaatggtg cccggagtgc ggcttcttct gctatgcatg ctatgggctc ggctgtgtct  25380
agtggtgtgc atggtgtgct agggttttttc cggaatttgc ctggcaatat tcggcatgct  25440
ctcggcaata tggggttctt gttggtgtcg gctggccgtg atgtggtgtc tggtttgggt  25500
aacggtatta agaatgctat gagtggcctg ttggatacgg tgcgtaacat gggttctcag  25560
gttgctaatg cggctaagtc tgtgttgggt attcattccc cgtctcgagt gtttcgtgac  25620
caggttggcc ggcaggttgt tgccggtttg gccgagggga tcaccgggaa tgcgggtttg  25680
gcgttggatg cgatgtcggg tgtggctgga cggctgcctg atgcggttga tgcccgtttt  25740
ggtgtgcgat catccgtggg ctcgtttacc ccgtatgaca ggtatcggcg gatgggcgag  25800
aagagtgttg tggtgaatgt gaatgggcct acttatggtg atcctaacga gtttgcgaag  25860
cggattggac ggcagcagcg tgacgctttg aacgcgttgg cttacgtgtg gttggggggtg  25920
ttgtgcatgt ttattcctga cccgtctgat cgtgccggtt tgactgttac ctggtctatg  25980
ttgccgttga ttggtaatga tccggagcgt gtgcttcatt tgacggatta tacgggtgcg  26040
tctcctgtca tgttgttgaa tgattcgttg cgcggtttgg gtgttcctga ggtggagcat  26100
ttttctcaaa ctcatgttgg ggtgcacggc tcggagtggc gcgggtttaa tgtgaagcct  26160
cgcgagggta cattacctgt cctggtgtcg gtgttggtg ggatccggt tggcgggttc  26220
cgtgacggtt ttttgaaggc gtatgacgag ttgtggtctg cttttcctcc gggcgaggag  26280
ggggagttgt ctgtgaagac cccgtctggc cgtgagcgtg tgctaaaatg ccggtttgat  26340
tcggtggatg acacgtttac tgtggatccg gtgaacaggg gttatgcgcg ctatctgttg  26400
catttgacag cttatgaccc gttttggtat ggggatgagc agaagttcg ttttagtaat  26460
gcgaagttgc aggattggtt aggtggcggc ccgtcgtgca agaagggtac cgcttttccg  26520
gtggtgttga cgcctggtgt tggttcgggt tgggataatc tgtctaatag gggtgatgtg  26580
cctgcgtggc ctgtgattcg tgtggagggc ccgttggagt cgtggtctgt gcagattgat  26640
ggtttgcgtg tgtcttcgga ttacccggtg gaggagtttg attggatcac tattgatacg  26700
gatcctcgca aacagtctgc attgttgaac gggttgaggg atgtgatgga tcgttttgaca  26760
gagttggtgc ttgcccctat cccgcctggc ggttctaaga gtgtgaatat tgagatggtt  26820
ggtttggggt ccattgttgt gtcggtgcag tacaggttt tgagggcttg gtgaatagtt  26880
gatgctggt cttgttccgc atgtaacatt gtttacacct gattatcgcc gtgtggcgcc  26940
tatcaatttt tttgagtcgt tgaagttgtc gttaaagtgg aatggtttgt ccactttgga  27000
gttggtggtg tctggtgatc attctaggct tgacgggttg actaggccgg gtgcacggct  27060
ggttgttgat tatggtggtg gccagatttt ttctgggcct gtgcgtcggg ttcatggtgt  27120
```

```
gggtccgtgg cgttcttccc atgtgactat cacgtgtgag gatgatattc gtctgttgtg  27180
gcgtatgttg atgtggcctg tggattatcg tcctggtttg gttggtatgg agtggcgtgc  27240
tgaccgggat tatgcccact attcgggtgc ggctgagtcg gtggctaagc aggtgttggg  27300
ggataatgct tggcgttttc cgcctggttt gtttatgaac gatgatgaga gtcgtggacg  27360
gttcattaag gattttcagg tgcggtttca cgtgtttgcc gataagttgt tgccggtgtt  27420
gtcgtgggct cggatgactg tcacggtgaa ccagtttgag aatgcgaagt ttgatcagcg  27480
tggtttggtg tttgattgtg tgcctgctgt gacgcgtaag catgtgttga ctgccgagtc  27540
tggttcgatt gtgtcgtggg agtatgtgcg tgacgcccg aaggcgacat cggtggtggt  27600
tggtggccgc ggcgagggca aagatcggct gttttgtgag gatgttgatt cgatggccga  27660
ggatgactgg tttgatcgtg tcgaggtgtt taaggatgcc cgtaacacgg attctgagca  27720
tgtgcatctc attgatgagg ctgagcaggt gttgtccgag ttgggggcca cgtcggggtt  27780
taagatcgag ttggctgagt cggatgtgtt gcggtttggg cccggcaatc tgatgcccgg  27840
ggatttgatc tatgtggatg tgggttctgg ccctatcgca gagattgtgc ggcagattga  27900
tgtggagtgt gagtcgccgg gtgacgggtg gacgaaggtg actcctgttg caggggatta  27960
tgagaataat ccgtcggccc tgttggcgcg gcgtgttgct ggtttggctg cgggtgtgcg  28020
ggatttgcaa aaattctaga aaagattagg ggtttgttgt gggtattgtg tgtaaagggt  28080
ttgatggtgt gttgaccgag tatgattggg ctcaaatgtc tggtctgatg ggtaatatgc  28140
cgtccgtgaa agggccggac gattcgtg tcggcactac tgttcagggt gccacagtgt  28200
tgtgtgaggt cctgccgggg caggcttggg cccacggggt gatgtgcacg tcgaatagtg  28260
ttgagacggt gaccggccag cttccgggcc cgggtgagac ccgatacgac tatgtggtgt  28320
tgtctcggga ttgggaggcg aatacggcca agttggagat tgttcctggg gggcgtgcgg  28380
agcgtgcccg tgacgtgttg agggccgagc ctggcgtgca ccatcagcag ttgttggcta  28440
ctttggtggg tcgtctaac gggttgcagc agcagctgga taggcgtgct atagcggcta  28500
gggtggcgtt tggcgagtct gctgcgtgtg atcctacccc agtggagggt gaccgtgtga  28560
tggttccctc tggggctgtg tgggctaatc atgccggcga gtggatgctg ttgtccccca  28620
ggattgagac gggttctaag tcgatcatgt ttggcgtgct tgctgtgtat gcttacacga  28680
ttccgtttga gcggccgttt agtagtgcgc ctgttgtggt ggcgtctatg gctacggcgg  28740
ctgggggcac gcagcagatc aatgtgaaag cctacaatgt gactgtccaa aattttagtt  28800
tggcgtttat tacgaatgat ggttcgaagc cgaatggtgt gcctgcggcg gctaattgga  28860
ttgctgtcgg cgtgtgactg tacaggtgtt gtggcggatg gtgtgatgtt gggggcgtg  28920
ggtgtcgtgg tttactcctg cactggtggc ctctatttgt accgcgttgg ccacggtttt  28980
gggttctgtt caggctgtca catcccggtc taggcggcgt ttacgcaggc tgtctgcgca  29040
ggtggatgcg atggaagagt atacgtgggg tgtgcggcgc gaggtgcgaa ggtttaacgc  29100
cgggcttcct gatgatgtgg agccgatgca tcttcctgat gtgcccgagt ttttgaagga  29160
tactgttgat ggtggaggtg agtagggttg agggagagaa gcggcagcgc  29220
cgcaattttg agaaggcttc cctgatactg ttgtttttgt cgcttgtgtt gttggcggtg  29280
gttgccgggg gtgctttgcg gtacgggtct gtggcttctc aaagggattc ggagcaggcg  29340
agggcccagt cgaatggtac agccgctaaa gggttggctg cccgtgtgaa gcaggcgtgt  29400
acccagggtg gcgtggagtc tgtgaagctg cacaggtctg gtttgtgt ggatgctgtg  29460
cgtgttgagc agcgtgttca gggtgtgcag ggtcctgccg gtgagcgtgg cccgcaaggg  29520
cccgctggtg ttgatggccg ggatggtagc aatggttctg ctgggctggt tggccctgtt  29580
gggccgcagg gttccc                                                 29596

SEQ ID NO: 72           moltype = DNA   length = 29124
FEATURE                 Location/Qualifiers
misc_feature            1..29124
                        note = PAC10
source                  1..29124
                        mol_type = other DNA
                        organism = synthetic construct
SEQUENCE: 72
gggtttagcc agccgtgtgc ggcaggcgtg tgcttcgggt ggggtggagt ctgcgcggct  60
tcaccggtct ggtttgtgtg tggatgctgt gcgtgttgag cgtagcgtgc agggtgtgcc  120
gggtcctgcc ggtgtacggg gcccgcaagg ccctgcaggt gctgacggca gggatggtgt  180
taatggttcg gctgggctgg ttggccctgt tggtccgcaa ggttcccctg gcttgaatgg  240
tgtgaaaggt cctgacgggt tgcctggtgc gaatggatcg gatggccatg atggtgttcc  300
aggtcgtgca ggtgctgacg gtatgaacgg cgttgacggc agggatggtg ttaatggttc  360
ggctggtgag cgcggtgatg tgggcccttc aggtcctgcc ggcccgcaag gtgcacaggg  420
tgaacggggt gagcgcggcc ccgccggtac gaacggatac gatggtaagg atggtaaggg  480
tggccgttct gttgtgtccg tgtactgttc cggggggcagc ctggttgtga aatatagtga  540
cggtgtggtt tctaccgtat cggactcggc ggcctgccag ggtgtgaaac cgtcgcctat  600
agtgactata tcatcccaca aatagaaagg agtggctgtg atggtagtgt ttggtggtgt  660
gtggtgaggt ttattcctgc ggcgcatcac tcaagcggtt cgaatagtcc ggtgaatagg  720
gttgtgattc atgcgacatg cccggatgtg gggtttccgt ctgcctcgcg taagggcggt  780
gcggtgtcta cagcaaacta ttttgcttcc ccgtcttcgg gtgtgttcggc gcattatgtg  840
tgtgatattg gggagacggt gcagtgcttg tctgagtcta cgattgggtg gcatgccccg  900
ccgaatccgc atagttttggg tatagagatt tgcgcggatg ggggttcgca cgcctcattc  960
cgggtgccgg ggcatgctta cactcgtgag cagtggctgg atcctagggt gtggcctgcg  1020
gtggagaagg ctgccatcct ctgtgacgtt ttgtgtgaca aatataatgt tccgaaaagg  1080
aagcttagtg cagccgattt gaaggctggt aaacgtggtg tttgcgggca tgtggatgtt  1140
acggatgcgt ggcatcagtc ggatcatgat gatcctgggc cgtggtttcc gtgggacagg  1200
tttatgccgc tcgtcaacgg cggcagtgga gatagtgggg agttaactgt ggctgatgtg  1260
aaagccttgc atgatcagat taaacaattg tctgctcagc ttactggttc ggtgaataag  1320
ctgcaccacg atgtgggtgt ggttcaggtt cagaatggtg atttgggtaa acgtgttgat  1380
gccctgtcgt gggtgaagaa tccggtgacg gggaagctgg ggcgcgccaa ggatgctttg  1440
tggagtgtct ggtattacgt gctggagtgt cgtagccgta ttgacaggct tgagtcgact  1500
gttaatggtt tgaaaagtg atggtggtgt gttgtgggta aacagttttg gttgggcctg  1560
ttggagcgtg ccctgaaaac tttttattcaa acgtttgttg ctgtgcttgg ggtgacggcg  1620
ggtgtcacgt atactgcgga gtcgtttcgc ggtttgccgt gggagtctgc actgattacg  1680
```

```
gctacggttg ctgctgtgtt gtcggtggct acttcgtttg gtagcccgtc gtttgtggcc    1740
ggcaagccta aaaccacggt tgtggatgcg ggtttggttc caccggatga tgggggcttg    1800
gttgagccgc atatggttga tgtgtcggat cctggcatga tcgagcctgc agatgatgcg    1860
gatcttggtg taggctatgt gccgaaacac gctgccgagt cggaggttgg gacggtagag    1920
tctactgttg cataattgaa catagatgcg tgccccacgg gtgctgccac gatcgtgtgg    1980
tggttgccgc tggggcacta tttctgttta tgcggtgtgg ctatgattcg ttgcggtcga    2040
tggtgtcttc gagcatctga tacaggtgga ggcaggtaga gatcgtatcg ctggcctggt    2100
ctagaacgtt ccgccgata acgttttgt ggttgtcgcg gtggcggatg atagcccaca     2160
tgatctcgtc ggcctccgct tgtaatagtt ttgcctggta tgcgattccg gcgagccagt    2220
ctagtgcttc ctggcttgca taggggctct ggtcctcgct gttgtcacgg gtgttgctgt    2280
tgtttgtggg gtgtcctgca ctgtcgcata accacaggat ttcgctgcac tcgtctagcg    2340
tgtcctggtc gatagcgaga tcgtcgaggc tgacttcgtt gacggtaagg ttcacgttgt    2400
cgagtgagat gggtacaccg tactggtttt cgacactgtc aacaatgttt tccagctgtt    2460
gcatgttggt gggctgttgt tggacgatac ggtgtatcgc tgtgttgagg gtgtgggtagg   2520
tgatattgtg tgtgttgttc atggttttat cccatccctg tgctgtcgtc gttttcgtct    2580
ggatagtatc tactgtttgc gtagcctgtt agggtgatga gtgtttggtc tgcccactgt    2640
ttcacgtttt gtccttgtcac cccgagtcgt tgggctgcca ccgaataggt ttgatcatac    2700
ccgtatactt ctctgaatgc tgccagccgt gccaaatgtt ttcgctgttt ggatggctgga   2760
caggtgaggg tgtagtcgtc gatggctagc tgcaaatcga tcatggtgac aatgttgttg    2820
ccgtggtgtt gtggcgcggt tggtggtggt ggcattcctg gttcgacact cggtttccat    2880
gggcctccgt tccagatcca ttgggcggct tggatgatgt cggcggtggt gtaggttcgg    2940
ttcactggta atccttaaac aagtcgttca tgttgctggt gttgctggtg ttgctggtga    3000
cgaatcgtcc cacacagtgg cagtagtcgt acatgagttt aataatgtgt tggtggtctc    3060
ccaaataggt gttgccgctg atgctgtagg tggctgtgcc gtctttactg atggtgtatt    3120
tggcggtgat ggtttcgggg ttttcggtgt cggtgatgat ggctgtggtg gtggtgccta    3180
cggtttgtag cacggtggtt tgggttccgt cgtcgatggt gttttaacc atgagggggtt    3240
ctccttttaa atgcttgttt ggttgtcggc tagatgaata atatcggata aaggtttcgg    3300
ctggtctagg tgttgtatgg ttttgttggc tagccgtttg gctaccctgt agcacatttt    3360
ggtatagtgt ttgttgtcta ggttgtggta ttgttcccgc accgcaatat atagtaggga    3420
gtcttgatag aggtcgtctg cactgattgc ggggtagtgt gtggctgttt tggtgcatcg    3480
ccggttgagt gtgcgtagat gatggttttgt ggcccatccc cacgatgcgg tggtggctat   3540
gtctgctttt gttggtcgtc tgctcatggc atctctttca tctggctatc tggtagttgt    3600
ttggtgtttt gttgttgata gtgtagcaca cgagtccggg gtttccggtg gcgcctgtgc    3660
ggtgccggaa ccatgtggat tcgccttcca tggatgggca ttggatgaag gtgcgttggc    3720
cttgctcgga gatttctagg tggtgccggt gcccggccat gaggatgtgg gatgtgggtgg   3780
cgttgtggaa ttcttggccg cgccaccatt cgtagtgttg gttgttgcgc cattggtggc    3840
cgtgggcgtg caggatttgt gtgccggcca ccccaacggt ggtggtcatt tcgtcccggc    3900
tggggaagtg gaagtgaaga ttggggtagt tgttgttgag ctggtaggct tctgcgatgg    3960
cccggcagca gtccacgtcg aaggagtcgt cgtaggtggt gactcctttg gccaagcgta    4020
cggcttctcc gtggttgccg gggattgagg tgatgctgac gttttggcag tggtcgaaca    4080
tgtggatgag ttgcatcatg gccatgcggg tgagcctgat ttgttccgtc aagggtgttt    4140
gggtgcgcca ggcgttgttg cctccttgtg acacgtatcc ttcgatcatg tcgccgagga    4200
aggcgatgtg gactcgttgc ggctgtcctg cctgttgcca gtagtgtttt gctgctgtga    4260
gggagtgcaa atagtcgtcg gcgaagtgtg ctgtttctcc gttggggatg cctttgccga    4320
tttgaagtc tcccgcccct accacgaacg caaccttgtt gttgctgcgg gtgtgggtgt     4380
ctggttttgg gggtgtccat tcggctagtt tatcaacgag ttcgtccacg gggtaggggt    4440
ctgttgcggg ttggtggtcg atgattttt gtatggatcg gcctgtttct ccgttgggga    4500
gtgtccattc ggagatgcgt gtgcggcgta cggtgccgtt ggctagattg tcgcagatgg    4560
tgtctgcttc gctatcgtgg ttggctagct gtgtgaggag ccggtctata ttgtctatca    4620
ctggttttc tcctcttgcg gggtggtgtt ggcttgtttg cggcgatagt ctttaataac    4680
ggtggcggag atggggtatc ctgcctgggt gagctgtttt gctagccatg aggcgggagt    4740
ggttttgtcg gcgagcacgt ctgcagcttt gttgccgtag cgttgaataa gggtttcagt    4800
tttggttgcc atgatgtggt tttgtcgcg agcacgtctg cagcttttgtt gccgtagcgt    4860
tgaataaggg tttcagtttt ggttgccatg atgtcctagg ggttgtgtgg tgggctgcca    4920
tcctgtgcgg cagtcgccgt cgtgtcctgg tttgcgtgtg caccacgata cgttgccggc    4980
attgtggatg atggcacggc cgcatatgac gtcacgtaga tgctcgggaa acttgtcgtt    5040
gttgtttccg ttcgtgtcga tcaagtgttg ggttttagta accatcatgt ctccatatgt    5100
tgaaagagtg tgcaaatact atgcaggtgt catggatgtt tatgcgggta tggttttcat    5160
caccttgctg aatgtgactt ggttactgta catcatctgg gtgatttcct gatcggtctt    5220
gtcggggtgc tgctttcgca ggttcgccca ttggcaggcg ttgtcggtct cttgctggag    5280
ccgggtcagg tgctgctcgt tgatgatgtg tttccacatt gtccacgaca cgtcgagcct    5340
gcggagcatg ttcatggctg gcacgttaaa cgagtcgagg aagagtattt cttcggtgta    5400
gtactgtttt tcgtattggt cccatccgct tcggtgcctg ttgggctggt ttttgggggta   5460
ggcttcccgg catactttgt gtaaccgttt ggccatgtcg tcgggtagtt taatgtcggg    5520
gttggcgcgg atcatggatc gcatcccatc gtaggtggtg ccccagcggt gcatgatgct    5580
gagtgggtct tcaccatcgg cccatttttt tgcacagatg gcgaggcgta tgcgcctcct    5640
ggcggctttt ctggtgtcgc ggcggccggg gatgggcac gtgtcgagag gatccatgat    5700
gttttatatg cctttctttg tttggtttgc ttgtgtggtt ttattgtagc actgtgtcta    5760
gtgcttgtgt caaccctgtt tttccggcct gcaggtaggt gtctgtgaca tcgcccaggg    5820
tgaggggcac gtgtatggct tgggggagtg ctgcctggag ggtttgtgcc atctggtggc    5880
ctgccttgtc tgggtcggac cagatgtaga tgtggtcgta gccttcgaag aatttggtcc    5940
aaaagttttg ccacgaggtt gcgccgggta gggcgacggc cgaccatccg cattgttcga    6000
ggatcatgga gtcgaattca ccttcgcaaa tgtgcatttc tgctgccggg ttggccatgg    6060
cggccatgtt gtagatggag cctgtgtcac cggccggggt taggtatttg gggtggtttgt   6120
gggttttgca gtcgtgcggg agtgagcagc ggaaacgcat ttttcttatt tcggctggcc    6180
gccccaaac gggtacatg tatgggatgg tgatgcactg gttgtagttt tcgtggccgg     6240
gtatgggtc attgtcgatg tatccaaggt ggtggttgcg ggctgtttct tcgctgatgc    6300
ctcttgctga gagcaggtcg agtatgtttt cgaggtgggt ttcgtagagg gccgaggctt    6360
tctggattcg gcggcgttcc gcaatgttgt atgggcgtat gctgtcgtac attcggggttt   6420
```

```
tctttctcta gttgttgttt cagttgggcg agtccgcctc cgataccgca tgtgtggcag   6480
taccagacgc ccttgtcgag gttgatgctc atgcagggct ggtggtcgtc gtggaatggg   6540
cagaggatgt gttgctcgtt cctgatggg ttgtaacgga tgcggtaggt gtcgaggagg    6600
cggcaggtgt cagaggtgtg ggaggagctc gttgagggtt gataccacat aggcttcgct   6660
ccaggggttg ttgcgctgtt tcatcactac gagtccgatg gtggactggc tttctcggtt   6720
tcggtgggtt tcgtagttgc gtgcctccag gctggcttgt ttcacgaatt cggctaggtg   6780
gggctgcccg gctttcgcct cgataatgta ggttttatgg ccggttgtga ggatgaggtc   6840
gccttcatcc tctttaccgt tgaggtggag gcgttctata tcatagccgg tgtcgcgtag   6900
ctggtggagg agtcttgttt cccattcggc cccggcccgc cggttgcgtg cctgctgtgt   6960
aaccatcata gtcctttgtg tgttgtggtc atgttccagg gatgttttc ggcgagtggc    7020
ccgaagaatg tgtattcggg gtaggctcgt agccgctcat attttgttcc gtctgggctg   7080
gatttgccgg tgcgctgttt caacactgcg atgcgcgcct cggctggtat cgtgagcccg   7140
ttgccgttat cctcgccacc ataaagtgag actcccaata tgagttgtgg tttttcggag   7200
aggccgtttt taatttcccg tctagctggc gggtgttcga tgtcggagcc ggttttgctg   7260
gttgcgtggt gtgtgacaat aatggtggag ccagtatccc tgcccaatgc tgtgatccat   7320
tgcatggctt cttgctgtgc ctggtagtcg gattcgcagt cttgaatgtc catcaggttg   7380
tcgataacaa tgagtggtgg gaaagtgttc cacatttcca tgtaggcttg tagctccatg   7440
gtgatgtcgg tccaggtgat gggtgactgg aatgagaagg tgatgtgttg gccgtggtgg   7500
atgctgtctc gatagtattc tggcccgtag tcgtcgatgt tgtgttgtat ctgtgtggtg   7560
gtgtgttggg tgttgagtga gatgattcgt gtggaggcct cccagggtgt catgtcccct   7620
gatatgtaga gggcgggctg gttgagcatg gcggtgatga acatggctag cccggatttt   7680
tggctgccgg agcgccccgc gatcatgacc aaatccccct tgtggatgtg catgtcctgg   7740
ttgcggtaga ggggttctag ttggggtatg cggggcagct cggctgcggt ttgggaggct   7800
ctcgcaaagg atctttggag agagagcatc ggagccttta tctatcgatc ggttggatgt   7860
gttgtggtgg tcagatggag tcgatgtcta catcatcact atcagtggtg ttgggctggc   7920
tgtctcgccg atcaacgtag gctgctacaa ggtcgtagat ggcgtcgtcc aatggtttga   7980
gcacgaccgc gttgaacccg ttttagtgc gcacctgatc gagtttgaag gcctgctcct    8040
cgccaagata tgcctctaaa tcgcggatca tggagtgtgg gcggtcgttg ttgcctcgca   8100
cttttttcgat aatggcgttg gggatggttt ctgggggtgcc gttgttgagg tcgtctaggg   8160
tgtggaagat ggtgacatca gcgtagatac gatcggcgac ctgtccaccg tagcccttcag   8220
tgttgtgctg aacgtcgtgg acttttgaagg cgatgcggt ggcgtcctgg tttcgggagg    8280
ggttgaagaa ggtgctgttg ctgttgttgc ggtagtttgc gagtcccatt attgtttcct   8340
ttactgttttt gttggtttgt gtcggttttt atcgggtgag gctgtttcgt ttgctgcgga   8400
aagcctcgga aacgtcactg ttactagtga tgatcttttt gtactgtttc agtagatcgg   8460
ctagctgtgc tttgcttgtt gcattgttga ttttgtcgat gatgctgttg tttccttctg   8520
aggcgatgtt gtctacgtag tctttggcgg cctggttgta tcggtcttgg aggatgatgg   8580
atgctgtggc gatcagtgtt gccaggtccc agttccttgc cgcggagctg tttttgagtc   8640
cgcctaacag gtcgatgatg gctttcttta cctggtcgg ggtgtctcct cggatgacgg    8700
tccatgggc ggcgtagtct ccgccgtatt tgagggtgac ggtgaatcgg tcgtcgtctg    8760
tgttgtcggt cactggtgct ccttgtcttc ttgtgttggg gctgtgatgg tggtttctat   8820
agggtacctg taggcgtctt tcccgttgac ggcccagcag gcgtctctga cggggcatcc   8880
tttacagagt gctgtgacgt gtgggacgaa gatgccttgg ctgattcctt tcattgcttg   8940
actgtacatg gatgatacat gccggtaggt gttgttgtca aggtcgtaca gttcggtcgg   9000
cgttccctgc ttggcggact gttttgtcgt tttggttgat gcgggtgtcc aaaacatgcc   9060
ttttgtcaca tcgttgccgt gttgggcgag catgtaccgg taggtgtgca gctgcatgct   9120
gtctgctggt aggcggccgg ttttgaggtc gaggatgaag gtttcgccgg tgtcggtgtc   9180
ggtgaagata cggtcgatgt agccaacgat ctgggtgccg tcctgaggg tggttttctac    9240
cgggtattcg atgcctggct ggccgtctag gactgctgtg tggtattgcg gattgttttgt   9300
gcgcagtgt ttccaccggt cgacgaaggt ttgcccgtaa accatccacc agtcgtagtc    9360
tttttttgtgt ggcccgcccg actcgcacat gttttttgcac accctgccgg agggtttaat   9420
ctccataccc tctgatcgg tgagggcgac ttgggtgtgc aaaatgtttt tgaaggatga    9480
gagtttgtct ggcagtgcag ggtattcggc ggggttgtat aggtgtaggt cgtattgttc   9540
ggtgatgtgg tgtatggcgc ttccggcgat ggtggcgtac caggtgtggt gttgggcgtg   9600
gtagccgtgg gataggcgcc attttctcc gcattcggcc cactgtgaca gtgatgagta    9660
ggagatgcgg cctggatggt ggatggtttt cggatattgt gctagaggca ttacttgtcg   9720
cttttgttcc atgggttgcg ggtgtctacc ccggcattgt gttgctggta tgcgaggagt   9780
gctaggcagt gccaggcagc atgtgccagg tgggtagcc cggattcata atcgaggttg    9840
tttccttgct gccaggatag cacatggcgg tagagggcgt caacgctgtg gctccacgga   9900
tagccgccgg tccagttgtt gtcgccgtat ttggtggcac cgtagcctgc aacctcgccg   9960
agggcgtgta aggctgcggg gtcgatgagg gagagcctgc aaagtttgag ttctttcttg  10020
gcgccagtat cagggtcggt gtacatgcgg gtgggctcat ccatgggtg tgtgctcctt   10080
aagggtgggt tactggttgg ggttgtggc gagtgctact gcgagaataa tgatggcgag  10140
ggtttctgcg atgaggatgg gtgttgtgat catttgttgt ctcggggatt gctggtgagt  10200
gtggaggcgc ctaggaggt ggtgaggcg catgcgggca tgatgcgagg ggctgccttg   10260
tgtggggtgc cggtggcgta catccatgtg atgatggcgc cttggatcca ggcgaggctg  10320
gtgaagaacg tttcgtagct gtgtagctcg ctgttgttgc tggtgatgtc attcatggta  10380
gttttctgct ttgtgtgcga tggttgtgta catgtcgttg agtgtggttt cgatggtgat   10440
gagagtgttg atttcttggt tgaggtcgat gttgctttg agggtgtcga tgcgggcggc    10500
gatgtcggtg gcggtgcgta ggcttactgc tgcaccgtag atgatgtggc acatgctggt   10560
gaggccgacc ttggcgatat agtgtggacat gagaggcatg atgggtgtgt cgtctttctg   10620
gtcagcgtga cgggttgatg gacatgtctt ctacctgtgg ccttgtcttcg gtgcctgata    10680
cttggcaaaa gactttcacg tgcgccttgg atgctccggg ttgcttggcg gtggcaccgt    10740
aggcgatagt aaaggcgtct ttgtgggcgc cgatgacttt gtgtaggaag aggtcgatgt    10800
cggggtttcc gttccatttg acaccgttttt ctgcggctcc ctgggtgggt ttctggttgg   10860
aggcgtgtgc tgccgtaatc atggtgagtc cggtggcggt ttcttcaccc cttgcttggg    10920
cttgcttgtg ggttttttgct tgttcggctt gtagggagcg gactcgggct gcctgccgtg   10980
cttttctttc ggctttgcgc tgctgggtag tcttgggggt ccattcggtg ttggctgtgg   11040
tggcctgtgg ggctggctgt gaggcgagtg gcggattgtc gtctgggct ggcatgaatg    11100
aggcggcggc aatgatggcg gctgtgattc cggcgatggt gtagccgttt tcttgttca   11160
```

```
tgactgttgt cccctttccg gggtgttgtt cgttgctgac atgattaatc atggtgtgga  11220
cggttcccca tgtcaaggct gcgctcaacg attgtgagcg tttggtgtgt ggctaggggt  11280
tttatcgggc acacagggtg agtagatggc caacattgat gcggctcaca ttccagtaga  11340
gttgtgtggc ttcaccgccg gtgagcggct tccactcgtt gtggctgaac acggtgccat  11400
cggatgcgat gaatgtgtcg gggcgtagct tgtgaagctc ggcttccacg ctctgccggt  11460
aggtttcggc gaggccctca aaatccatgt ggtcgcagga gaggttttcg aggcgtgtca  11520
ggtcgaaggg tgtggggcag tcgtagctgg cggggggtgta gagctgggtg aagtggttgg  11580
cgatcttctg catgatgatg tccttttggt tgctgataac cttgttgagg gtttatcggg  11640
tggatgtgat aaggatggcg tccacgtcga tcatgtcgat gagatcgtgg agttcctcgg  11700
cctcgttttc ggtgagtggc tgccagttgt tgtcgccgta cacggcgccg tcgagggtga  11760
cagtccacag tggccggatg aggcgtacgg cttcttgtac tttagcgtgg tacatgcggc  11820
gcaccatatc cagatccatg tcgtctgaat ggtttccgat gaggttgtgg aggctgagcg  11880
ggtcgatttc tgtctgcctg tagagggatg tgaaggatgg ggtgatgagt gtgccatcca  11940
tgggtgatgt tccttttctgg attgtcttgg ttggttgttg tggttttctag agtgtgcggg  12000
ttgcaaccgg gagtcaaggc tgcgctcatt cggattgagt gtttcatgct ggagtgtcgg  12060
gtgtgacaga tgtcacttaa gcctttattg cctctctcgg cgtctcacat catctgggggg  12120
taagattatg cagggttgac cctgctgatc gattctaggg cccttctagg gcgtctcagg  12180
ggtacgtctg ggtgatagcg ggtgtggcag atgatctagc gagtcaaggt accgagctta  12240
gacgtaagat ctatcatcta ggcgtgtgag atgtatcaca tcctcctggc tgggtgtgca  12300
ccctcaaggc tactctgccg atctggcgtg gagggtgtag cccagaaatg ccgtttaaag  12360
ccttcacatg gcgcctagaa gcgccttgca gggtgggggc taggtattta tacccccaac  12420
acattctgat cgattctaga cgcctatagg agcctgatac acgatcaacc atctcggcat  12480
agatcatcag cccctatcct agttagctaa gcctgaacta tgtggacagt gtaggatgct  12540
aagagggaag aaggacacgg taaaagaaag aggggggggc atcaaccttc acgcccgagg  12600
tacttaagtt aaccttaggg tcttagcacc gagcccctca agggctcggc atcagcatca  12660
tcgggatcag ccgatccggc acagccttag caagtacaca ccatcaggga aggcttgaga  12720
gtacgaggag ccctagcgac gagtactcga aagcctgagg gaacaccctc agcactgatg  12780
ggcctagcgt gttcggaaag tacacagggg tacagtgtga gagctgttcg ggagctaaac  12840
cccttccggc tagggcaaac accagtccta gactatccca caccctcatc tgttaacctt  12900
ccgttcatta aacgttaagg aaactttag gtttgatttt tggaccttaa ccaccaaaaa  12960
caccccattta caccccctcaa acccgccaat agagccaaac gccggtgttg agggtatctc  13020
tacctagtgt gataggctgg acaggtagcc agctggacgc aaggccagaa agtgctgacg  13080
cacttcccga cctcgcttac catcagtcta ccaaacactt aaaagcttaa cagctaagcg  13140
ctaagcccctt aagacctcaa cgcttagcac cgagccccctg aggggctcgg catcagtctt  13200
aggtacttaa agtaactttta aaccttaaag gcttagcact taaggatata aacttaacat  13260
cagtgtttaa gactttaata ctttaagtaa ctataagacc ttaaagcttt aaacacttaa  13320
agttaaccat cagtcttaaa ctttaatatt ataacttata agctttaata cttatattat  13380
attataaacct ataagtctta aagcttttag gttataaaag ttttagaaga gctaagaggt  13440
taacttctttt acttctctac tcttctttggt tcttctctct ttctcttcatca  13500
ggggagaaga ggaatctttta ccatcagcgc cgatgaccttt tcaccgtgtg gatcgtgtgc  13560
ttctggtcgc aagctcccat cgcacactcc ccacactctt acaccgtgt ccctttcggg  13620
cttggcgtgt tcgctaaag gcgtacgcg tgtcacgcta acacccttaa caccgggtaa  13680
gacttaaagt gtatattata tgtagaagac tttaaaacct ataaggtgtt cccgcttagc  13740
ccgtgtccta caccgctagg cgccaagcgc taagccttga aacgcgaaca cacacccacc  13800
ccctttttttc ttccgtgtcc ttctcttttg acaccgctgg ggggcgatgt gatctttctc  13860
acacccatgg gggtagtgga gaaaacaaac accccgcac aaacagaaca cccccctcaaa  13920
cgaacaaaac agccccccag aatcgaccag cagggcaagg gtagagtatc catacccca  13980
acggtttccca ggccgttaca gaggcaaata agacccgtac agggctaggc gaggaacaga  14040
cacatcatgg cacgcaccaa ccgcacagcc gccacggcac accgacgctg gcggcaacga  14100
ctcatcaccc aagcccaaca gcaaggccaa accacctgcc cactctgcgg agtcaccatc  14160
acctgggaca cccaccagct accaaccagc cccgaagccg accacatcac acccgtcagc  14220
cggggaggac tcaacaccct agacaacggg caaatcatct gcagaacatg caacagaagc  14280
aaaggcaatc gcagcgaacc aaacatcaaa ttccaacaac aaaccacaaa aaaccttgtt  14340
tcatggtaga aaacctgcca gcccccaccg gggacacccc ctgcacaggc gtgcaagacc  14400
tcgtacggct tagtgaaata cctcccttt gtggatttgt ctgtttgtcg acttttttgtg  14460
ttggtggtga gtgttgtgca gcctgagctt cctgatagtc gtgattggtg tgggagacg  14520
cgtcgttggt ggcgtgtgtg gggtgaggat agccgtgcat cgtacgtgtc tgatgaggag  14580
tggttgtttc tccttgatgc ggctgtgatt catgatgtgg tgtggcgtga gggtcgcgcg  14640
gatttggtgg cttcgcttcg tgctcatgtg aaggcttta tgggtatgtt ggatcggtat  14700
tcggttgatg tggtgtctgg tggccgtgcc ggtggttctg cggtggcgat gattgatcgg  14760
tataggaagc gtaaagggggc ctaatgtcga gtgttgttgg ttctcaggtt cctcgtcatc  14820
gtgtggctgc ggcgtattcg gtgtctgctc gtggtgatgc tggggagttg ggtcgtgcgt  14880
atgggttgac gcctgatccg tggcagcagc aggtgttgga tgattggctg gctgtcggta  14940
gcaatggcag gcttgcttcg ggtgtgtgtg gggtgtttgt gcctcgccag aatggcaaga  15000
atgctatttt ggaggttgtg gagttgttta aggcgactat tcagggtcgc cgtattttgc  15060
atacggctca cgagttgaag tcggctcgta aggcgtttat gcggttgagg tcgtttttttg  15120
agaatgagcg gcagtttcct gacttgtatc gtatggtgaa gtcgattcgg gcgacgaatg  15180
gtcaggaggc tattgtgttg catcacccgg attgtccgac ttttgagaag aagtgtggct  15240
gcagcggttg gggttcggtt gagtttgtgg cccgttctcg cgcgggtta  15300
cggttgatga tttggtgtgt gatgaggctc aggagttgtc ggatgagcag ttggaggcgt  15360
tgcttcctac ggtaagtgct gccccgtctg tgatccgca gcagatttttc cttggtacgc  15420
cgcctgggcc gttggctgat ggttctgtgg tgttgcgttt gcgtgggcag gcgcttggtg  15480
gcggtaaaag gtttgcgtgg acggagtttt cgattcctga cgagtctgat ccggatgatg  15540
tgtcgcggca gtgcggaag ttggcggggg atacgaatcc ggcgttgggg cgtcgcctga  15600
attttgggac cgtaagcgat gagcatgagt cgatgtctgc tgccggtttt gtctcgggag  15660
ggcttggctg gtgggatcgt ggccagtctg ctgtgtctgt ggttcctgct gataagtggg  15720
ctcagtctgc ggtggatgag gcgagtctgg ttggcgggaa agtgtttggt gtctcgtttt  15780
ctcgttctgg ggatcgggtt gctttggcgg gtgccggcaa gactgatgct ggggttcatg  15840
ttgaggttat tgatgggctg tcgggaacga ttgttgatgg tgtgggccgg ttggcggact  15900
```

-continued

```
ggttggcggt tcgttggggt gatactgacc ggatcatggt tgccgggtct ggtgcggtgt    15960
tgttgcagaa ggcgttgacg gatcgtggta ttccggggccg tggcgtggtg gttgctgata    16020
ctggcgttta tgtggaggct tgtcaggcgt ttccttgagggg tgtcaggtcg ggtgtgatca    16080
gtcatcctcg tgctgattct cgccgtgaca tgttggatat tgctgtgagg tcggctgtgc    16140
agaagcgtaa ggggtctgcg tggggttggg gttcctcgtt taaggatggt tctgaggttc    16200
ctttggaggc tgtgtctttg gcgttttttg gggctaaacg tgttcgtcgt ggccgtcggg    16260
agcgtagtgg taggaagcgg gtgtctgtgg tatgaactcg gatgagtcgg ctctgattga    16320
gggcatgtac gatcgtatcc aaaggttgtc ttcgtggcat tgtcgtattg agggctacta    16380
tgagggctct aatcgggtgc gtgatttggg ggtggctatt cctccggagt tgcagcgtgt    16440
gcagacggtg gtgtcgtggc ctggtatagc tgtggatgct ttggaggagc gtctgattg    16500
gcttggctgg atgaatggtg acggctacgg cctggatggt gtgtatgctg cgaatcggct    16560
tgctacggcg tcgtgtgatg tgcatttgga tgcgctgatt tttgggttgt cgtttgttgc    16620
gataattcct catggtgatg gtacggtgtc ggttcgtccg cagtcaccaa agaattgtac    16680
gggcaagttt tcggctgacg ggtctcgttt ggatgctggt ttggtggtgc agcagacgtg    16740
tgatcctgag gttgttgagg ctgagcttt gcttcctcgt gtgattgttc aggtggagcg    16800
gcgtggttcg cgtgaatggg ttgaggtgga tcgtataccg aatgtgttgg gtgcggttcc    16860
gttggtgcct attgtgaatc gtcgccgtac ttctaggatt gatggccgtt cggagattac    16920
gaggtctatt agggcttaca cggatgaggc tgtgcgcaca ctgttgggc agtctgtgaa    16980
tcgtgatttt tatgcgtatc ctcagcgttg ggtgactggc gtgagcgcgg atgagttttc    17040
gcagcctggc tgggtcctgt cgatggcttc tgtgtgggct gtggataagg atgatgacgg    17100
tgacactccg aatgtgggggt cgtttcctgt caatagtcct acaccgtatt cggatcagat    17160
gagactgttg gcgcagttga ctgcgggtga ggcgctcgtt ccggaacgct atttcgggtt    17220
tatcacgtct aacccaccta gtggggaggc tttggctgcc gaggaatctc ggcttgtgaa    17280
gcgtgctgag cggcgtcaaa cgtcgtttgg tcagggttgg ctgtcggttg gttttttggc    17340
tgccaaggcg ttgattctc gtgttgatga ggccgatttt ttggtgatg ttggtttgcg    17400
ttggcgtgat gcttcgacgc ctacccggggc ggctacagct gatgctgtga cgaagctgtt    17460
tggtgccggt attttgcctg ctgattctcg tacggtgttg gagatgttgg ggcttgatga    17520
tgtgcaggtt gaggctgtga tgcgtcatcg tgctgagtcg tctgacccgt tggcggtgct    17580
tgctggggct atatcgcgtc aaactaacga ggtatgatag gcgatggctt cggggggttga    17640
ggcgaggctt gcgcgactg agtatcagcg tgaggcggtc aggttgctg ggaagtatgc    17700
gggctattat tctgagcttg gtcgtttgtg gcgtgccggc aggatgagtg acacgcagta    17760
tgtgcgtttg tgtgtggagt tggagcgtgc cggccatgat ggttcggcat cgttggctgc    17820
caggtttgtg tcggatttc gccggttgaa tggtgtggat ccgggtttga ttgtgtatga    17880
cgagtttgat gctgcggcgg ctttggctag gtctatttcg accacgaaga ttcttgagag    17940
tgacccggat agggcgaatg acacgattga tgcgatggcg gcgggttttg atcgggctgt    18000
tatgaatgct ggtcgtgaca cggttgagtg gtctgcgggt gcgcagggta ggtcgtggcg    18060
tcgtgtgacg gatggtgatc cgtgtgcttt ttgtgccatg ttggctacga ggtcggatta    18120
tacgacaaaa gagagggcac ttactactgg acatactcgg cgtcataagc gtggtggtaa    18180
gcgtccgttt ggttcgaagt atcatgatca ttgtggttgt acggtggttg aggttgttgg    18240
cccttgggaa ccaaataggg ctgatgccga gtatcagagg acgtatgaga aggcccgtga    18300
gtgggttgat gatcatgggt tgcagcagtc gcctggcaat attttgaagg ctatgcgtac    18360
tgttggcggc atgagataat ttgatgtggt ttccggttgt gcgccgccgg ttattggtgc    18420
acagggttgt ctcccgcacg ggggtcaaca atgttgtgtt gttttccgca ggagtgtag    18480
ggttaggcta tggccgatca gagtgttgag gaacagaatg ttgacaatga tgttgtggag    18540
tccgaaaagg ataacggcat tgttgataca gtaaaagacg atgcggaca ggaggtggcc    18600
gacaatcagt tgaagaatga aggcgagggt aaatcgccgg ggactgattg gaaggcgag    18660
gcccgtaagt gggagtctcg tgctaaaagt aatttcgctg agttggagaa gcttcgcgcc    18720
tcggatggtg atgcggggtc tgtgattgat gatcttcgcc gcaagaatga ggaactcgaa    18780
gaccggatta acgggtttgt tcttgagggt gtgaagcgcg aggtggcttc agagtgtggc    18840
ctgtcggtg atgctgtcgc tttcttgcac ggtagcgatc gtgaagcgct ggtggagtct    18900
gcgaaagctt tgaagggttt gatcgaccat agtagtggtg gcgcgggtgt gcgccgtgth    18960
gcggggagtg ccccgttga tgatgttaaa cgacgtgagg gtgtcgcgtt tgtggatgct    19020
cttgtcaata attctaggag atgatttgtg atggctgacg attttctttc tgcagggaag    19080
cttgagcttc ctggttctat gattggtgcg gttcgtgacc gtgctatcga ttctggtgtt    19140
ttggcgaagc tttcgccgga gcagccgact atttttggcc ctgttaaggg tgccgtgttt    19200
agtggtgttc ctcgcgctaa gattgttggt gagggcgagg ttaagccttc cgcgtctgtt    19260
gatgtttcgg cgtttactgc gcagcctatc aaggttgtga ctcagcagcg tgtctcggac    19320
gagtttatgt gggctgatgc tgattaccgt ctgggtgttt tgcaggatct gatttccccg    19380
gctcttggtg cttcgattgg tcgcgccgtg gatctgattg cttcccatgg tattgatcct    19440
gccactggta aagcggctgc cgctgtgcat acttcgctag ataagacgaa gcatattgtt    19500
gatgccacgg attctgctac gaccgatctg gtcaaggctg tcggtcttat cgctggtgct    19560
ggtttgcagg ttcctaaccg ggttgctttg gatccgcgt tctcgtttgc tttgtctact    19620
gaggtgtatc ctaagggttc gcctcttgct ggccagccga tgtatcctgc cgccgggttt    19680
gccggtttgg ataattggcg tggcttgaat gttggttctt cttcgactgc ttctcgccga    19740
ccggagatgt cgcctgcctc tggtgttaag gctattgtgg gtgatttctc tcgtgttcat    19800
tggggtttcc agcgtaactt cccgatcgag cttatcgagt atggtgaccc ggatcagact    19860
gggcgtgacc tgaagggcca taatgaggtt atggttcgtg ctgaggctgt gctgtatgtg    19920
gctatcgagt cgcttgattc gtttgctgtt gtgaaggaga aggctgcccc gaagcctaat    19980
ccgccgggcg agaactgatt tattgttgcg tgatgtgtc aatgtgcagg gggtggtgtt    20040
gatgggtatc attttgaagc ctgaggatat tgagcctttc gccgatattc ctagagagaa    20100
gcttgaggcg atgattgccg atgtggaggc tgtggctgtc agtgtcgccc cctgtatcgc    20160
taaaccggat ttcaaataca aggatgctgc taaggctatt ctgcgtaggg cttttgttgcg    20220
ctggaatgat actggcgtgt cgggtcaggt gcagtatgag tctgcgggtc ctttcgctca    20280
gactacacgg tctagtactc ccacgaattt gttgtggcct tctgagattg ccgcgttgaa    20340
gaagctgtgt gagggtgatg gtgggctgg taaagcgttc actattacac cgaccatgag    20400
gagtagggta aatcattctg aggtgtgttc cacggtgtgg ggtagggggt gctcgtgtgg    20460
gtcgaatatt aacggctacg ctggccctt tggggagata tgatatgacc agttttcctt    20520
atggtgaaac ggttgtgatg cttcaaccga ctgttcgtgt cgatgatctt ggtgacaagg    20580
ttgaggattg ggggcatctt gtagaaacag tgtaccataa cgtggccatc tatgcttccg    20640
```

```
tttcgcagga ggatgaggcc gcggggcgtg actctgacta tgagcattgg tcgatgcttt   20700
tcaagcagtc tgttgttggt gctgattatc gttgcaggtg gcgtatccgg ggtgttgtgt   20760
gggaggctga cgggtctcct atggtgtggc atcatccgat gtctggctgg gatgcgggca   20820
cgcagatcaa tgtgaagcgt aagaagggct gatgggtagt ggctcaggat gtgaatgtga   20880
agctgaactt gccgggtatt cgtgaggtgt tgaagtcttc tggggtgcag gctatgttgg   20940
ctgagcgtgg cgagcgtgtc aagcgtgcgg cctcggcgaa tgtgggcggg aacgctttcg   21000
ataaggccca ataccgtaat ggtttgtcgt cggaggtgca ggttcaccgt gttgaggctg   21060
tcgctcgtat aggcaccaca tataagggtg ggaagcgtat tgaggcgaag catggcacgc   21120
tggctcgttc gattggggct gcgtcgtgat cgtctacgat gaccccagga agtgggctaa   21180
acgcgtgctc aaggatgatg gctgctgtc tgatataccc tgtgtggga cggtgcccga   21240
tgattttatg ggtgacctgg tttggttggc gttggatggt ggcccgcagt tgcatgttcg   21300
tgagcgtgtt ttttgcgcg tgaatgtgtt ttctgatacg cctgatcggg ctatgtcttt   21360
ggcgcgtcgt gttgaggctg tgctggctga cggggttgat ggtgatccgg tggtgtactg   21420
taaacggtct actggtcctg attttgctgg tgatggtgca cgttttgatg tgtattcgat   21480
gttcgagctg atatgtaggc ctgtcgaatc cgagtaaacg tatttgtttt tgttttaatg   21540
taattgtttg atatttaatg gggggttgtga tggctgcaac acgtaaagcg tctaatgttc   21600
gttcagcggt tactggcgac gtttatattg gtgacgcgca cgcgggtgat actattaagg   21660
gtgtggaggc ggttccttcc gggcttacag ctttagggta tctgtcggat gacgggttta   21720
agattaagcc tgagcgtaaa acggatgatt tgaaggcttg gcagaatgcg gatgttgttc   21780
gcacggttgc taccgagtct tctatcgaga ttttcttttca gctgatcgag tctaagaagg   21840
aggttatcga actgttttgg cagtcgaagg ttactgccgg agccgattcg ggttcgttcg   21900
atatttctcc tggtgccacc actggcgtgc acgctttact gatggatatt gttgatgggg   21960
atcaggttat tcgctactat ttccctgagg ttgagcttat cgatcgtgac gagattaagg   22020
gtaagaatgg cgaagtgtac gggtatggtg tgacgttgaa ggcttaccct gctcagatta   22080
ataagactgg taatgcggtg tcgggtcgag ggtggatgac ggctttaaaa gctgatactc   22140
cccttctcc gaagcctcag ccggatccga atccgccgtc tgagaactga tacacgattt   22200
tagggattgt tgatagatga gtgacacagg ttacacgttg aagattggtg accgtagctg   22260
ggtgttggcg gatgcggagg agacggctca ggctgttcct gctcgcgttt ttcgtcgtgc   22320
agctaagatt gcccagtctg gggagtctgc ggatttcgct caggttgagg tgatgttttc   22380
tatgtttggag gctgcagccc cggctgacgc ggtggaggcc ctggagggcc ttcctatggt   22440
tcgtgttgcc gagattttcc gccagtggat ggagtggaag cctgaaggta agggtgcctc   22500
ttttggggaa tagtttggct ccacggcctg attgatgagt atcgtggggc catcgaatat   22560
gattggcgca caaggtttgg tgtgtgcata tacgatatag gtggtcctgc gatggggtgg   22620
ggtgaggctg tccggctggc tggcgtggttg tgtggtgata cgtcgagcca gttggcggcc   22680
cacctgaatg gttggcagcg cccgtttgag tggtgcgagt gtgttgtgtt ggacatgctg   22740
gatcattaca ggtctgctaa tagtgagggg cagccggagc ctgtggcgag gcctacggat   22800
gagcgtaggg gccggtttac gtctgggcag gtggatgata ttttggcgcg tgttcgtgct   22860
ggtggcgggg tgtctcgcga gattaatatt atggggtgaa tagtgtatgt ctggtgagat   22920
tgcttccgca tatgtgtctt tgtatacgaa gatgcctggt ttgaaggcgg atgttggtaa   22980
acagcttct ggtgtgatgc ctgctgaggg tcagcgttcg ggtagtcttt ttgctaaggg   23040
catgaagttg gcgcttggtg gtgccgcaat ggtgggtgcc atcaatgttg ctaagaaggg   23100
cctcaagtcg atttatgatg tgactattgg tggtggtatt gctagggcga tggctattga   23160
tgaggctcag gctaaactga ctggtttggg tcatacggtc tctgacacgt cttcgattat   23220
gaattcggct attgaggctg tgactggtac gtcgtatgcg ttgggtgatg cggcttctac   23280
tgcggcggcg ttgtctgctt cgggtgtgaa gtctggcggg cagatgacgg atgtgttgaa   23340
gactgtcgcc gatgtgtctt atatttcggg taagtcgttt caggatacgg gcgctatttt   23400
tacgtctgtg atggcccgcg gtaagttgca gggcgatgac atgttgcagc ttacgatggc   23460
gggtgttcct gtgttgtctt tgcttgccag gcagacgggt aaaacgtcgg ctgaggtgtc   23520
gcagatggtg tcgaaggggc agattgattt tgccacgttt gcgctgcga tgaagcttgg   23580
catgggtggt gctgcgcagg cgtctggtaa gacgtttgag ggcgctatga agaatgtgaa   23640
gggcgccctg ggttatttgg gtgctacggc tatggccccg tttcttaatg ggttgcggga   23700
gattttgtt gcgttgaatc cggttatcaa gtcggtgacg gattctgtga agccgatgtt   23760
tgctgccgtc gatgctggta ttcagcgtat gatgccgtct atttttggcgt ggattaatcg   23820
tatgccgggc atgatcactc gaatgaatgc acagatgcgc gccaaggttg agcagttgaa   23880
gggcattttt gcgagaatgc atttgcctgt tcctaaagtg aatttgggtg ccatgtttgc   23940
tggcggcacc gcagtgtttg tgttgttgc tgccggtgta gggaagcttg ttgcagggtt   24000
tgccccgttg gcggtgtcgt tgaagaatct gttgccgtcg tttggtgctt tgaagggtgt   24060
cgctggcggg cttggtggcg tgtttcgcgc cctgggtggc cctgttggta ttgtgatcgg   24120
cttgtttgct gccatgtttg ctacgaacgc ccagttccgt ggcgcggtga tgcagctgat   24180
ggggtttgtt ggccaggctt tggggcagat tatggccgct gtgcagcctg tgttttgttt   24240
ggttgccggt ttggtggccc ggttggcgcc agtgtttgcc cagattatcg gtttggttgc   24300
aggtttggct gcccagctta tgccggtgat tagtatgctt gttgcccggc tggttcctgt   24360
gatcacccag attattggtg cggtgacaca ggttgctgca atgttgttgc ctgcgttgat   24420
gccggtgttg caggcgtgtt tggctgtgat tcggcaggtt gttggcgtga tcatcgagtt   24480
ggtgcctgtt ttgatgcctg tgattcaaca gattttgggt gctgtcatgt ctgtgctgcc   24540
acccattatt ggtcttatcc ggtcgttgat gcctgtgatt gcggcggtta tgcgtgtggt   24600
ggtgcaggtt gttgcggttg tgatacaggt ggtggcccgt attcttgcgg ttgtggctcc   24660
gatggtggcg gctgtggtag ggtttgtggc ccgtattgtt ggtgtgtcg tgtcggctgt   24720
tgcccgtgtt attgctgctg ttgcccgtgt catcgggtgg attgtggccc attttggtgc   24780
tggtttggca cgtatgggtt cggtggttca ggctggctgg aatcggatta gggcgtttac   24840
gtcagcgttt attaacggtt tcaagtcggt gatttctggc ggcgtgaacg cggttgtggg   24900
gttttttgcc cggctgggtt cttctgttgc ttctcatgtg aggtctggtt ttaacgcggc   24960
ccgtggcgct gtttcttctg cgatgaatgc tatccggagt gtggtgtctt cggtggcgtc   25020
tgctggc ggggttttca gttcgatggc gctcagggt cgtagtggtg ctgtgcggtg   25080
gtttaatggt gcccgagtg cggcatcttc tgctatgcat gctatgggt ccgctgtgtc   25140
taacggtgtg catggtgtgc tgggtttttt ccggaatttg cctggcaata ttcggcgtgc   25200
gcttggtaat atgggtgccc tgttggtgtc ggctggccgt gatgtggtgt ctggtttggg   25260
taatggtatc cggaatgcta tgagtggcct gttggatacg gtgcgtaata tgggttctca   25320
ggttgctaat gcggcgaagt cggtgttggg tattcattcc ccgtctcggg tgtttcgtga   25380
```

```
ccaggttggc cgtcaggttg ttgctggttt ggctgagggt attactggta atgctggttt  25440
ggcgttggat gcgatgtcgg gtgtggcgga acggctgcct gatgcggttg atgcccggtt  25500
tggtgtgcga tcgtctgtgg gctcgtttac cccgtatggc aggtatcagc gtatgaatga  25560
taagagtgtt gtggtgaatg tgaatgggcc tacttatggt gatcctaacg agtttgcgaa  25620
gcggattgag cggcagcagc gtgacgcgtt gaatgcgttg gcttacgtgt gattggggat  25680
gttgtgcatg tttattcctg acccgtctga tcgttcgggt ttgactgtga catggtcgat  25740
ggatccgctg tttggtgggg ggcgtgtgct tcatttgacg gattatacgg gtgcgtctcc  25800
tgctatgttg ttgaatgatt cgttgcgcgg tttgggtgtt cccgaggttg agcattttc  25860
tcaaacacat gttggggtgc acggctcgga gtggcgcggg tttaatgtga agcctcgcga  25920
ggtgacgcta ccggtgttgg tgtcgggtgt tgactcggat ccggatggcg ggtttcgtga  25980
cggttttttg aaagcctatg gcgagttgtg gtctgctttt cctcctgcg aggaggggga  26040
gttgtcggtg aagactcctg caggtcgtga gcgtgtgttg aagtgtcggt ttgattcggt  26100
ggatgacacg tttacggttg atcctgtgaa tcgtggctat gcgcgttatg tgattcattt  26160
gacagcttat gacccgtttt ggtatgggga ggagcagaag tttcgtttta gtaacgcgaa  26220
gttgcaggat tggttgggtg gcggccctgt cggcaaggat ggcacggcgt ttcctgtggt  26280
gttgacgcct ggtgttggtt ctggttggga taatctgtct aataagggtg atgtgcctgt  26340
gtggcctgtg attcgtgttg aggggccttt ggagtcgtgg tctgtgcaga ttgatggttt  26400
gcgtgtgtct tcggattatc tcgtcgagga gtttgattgg atcactattg atacggatcc  26460
tcgtaaacag tctgcgttgt tgaatggggtt tgaggatgtg atggatcgtt tgacagagtg  26520
ggagtttgcc ccgattccgc ctggcggttc gaagagtgtg aatattgaga tggttggttt  26580
gggtgccatt gttgtgtcgg tgcagtacag gttttgagg gcttggtgaa tagttgatgg  26640
ctggtctggt tccgcagata acattgttta cgccggatta tcgccgggtt gcgcctatca  26700
atttttttga gtcgttgaag ttgtcgttga agtggaatgg tttgtcgacg ctggagttgg  26760
tggtgtcggg ggatcattct aggcttgacg ggttgactag gccgggtgca cggctggtgg  26820
ttgattatgg tggtggccag atttttctg ggcctgtgcg tcgggtgcat ggtgtgggtc  26880
cgtggcgttc ttcgcgggtg actatcacgt gtgaggatga tattcgcctg ttgtggcgta  26940
tgttgatgtg gcctgtgaat tatcgtcctg gtttggttgg tatggagtgg cgtgccgaca  27000
gggattatgc tcactattct ggtgcggcgg agtcggttgc taagcaggtg ttgggggata  27060
atgcttggcg ttttccgcct ggtttgttta tgaacgatga tgagagtcgt ggccgctata  27120
ttaaggattt tcaggtgcgg tttcacgtgt ttgccgataa gttgttgccg gtgttgtcgt  27180
gggctcggat gactgtttcg gtgaaccagt ttgagaatgc gaagtttgat cagcggggtt  27240
tgctgtttga ttgtgtgcct gctgtgacgc gtagtcatgt gttgactgcc gagtctgggt  27300
ctattgtgtc gtgggagtat gtgcgtgacg ccccgaaggc tacttcggtg gtggttggtg  27360
gccgtggcga gggtaaggat cggctgtttt gtgaggatgt tgattcgatg gccgagggggg  27420
attgggttga tcgtgtagag gtgtttaagg atgcccgtaa cacggattct gaacatgtgc  27480
atctcatcga tgaggctgag caggtgctgt ccgagttagg ggccacgtcg ggggtttaaga  27540
tcgagttggc tgagtcggat gtgttgcggt ttgggcagg ccgcctgatg cccggggatt  27600
tgatctatgt ggatgtgggc tcggggccta ttgcggagat tgttcggcag attgatgtgg  27660
agtgtgattc gcctggtgat ggttggacga aggtgacacc gttgcgggg gattatgagg  27720
ataatccgtc ggcactgttg gctcgccgtg tggctggttt ggctgccggt gtgcgggatt  27780
tgcaaaaatt ttagtaagtg attgggggttt gttgtgggta ttgtgtgtaa agggtttgat  27840
ggtgtgttga ccgagtatga ttgggctcaa atgtctggtc tgatgggtaa tatgccgtct  27900
gtgaaagggc cggacgattt tcgtgtcggc acgacgattc agggtgccac agtgttgtg  27960
gaggtcctgc cggggcaggc ttgggctcac ggggtgatgt gcacgtcgaa tagtgttgag  28020
acggtcgacgg ggcagctgcc tggtcctggt gagaccgct acgactatgt ggtgttgtcg  28080
cgggattggg agcagaacac agccaagttg gagattgttc agggtggccg tgcggagcgt  28140
gcccgggatg tgttgcgtgc cgagccctggc gtgtttcatc agcagctact ggcgactttg  28200
gtgttgtcgt ctaacgggtt gcagcagcag ctggataggc gtgctgttgc ggctagggtt  28260
gcgtttggcg agtctgcggc ttgcgatccc acccctgtgg agggtgaccg tataatggtg  28320
ccttcgggggg ctgtgtgggc taaccatgcc ggcgagtgga tgctgttgtc acccagaatt  28380
gagacgggtt cgaagtcgat catgtttggt ggttctgctg tgtatgctta cacgatcccg  28440
tttgagcgcc agttcagtag tccgcctatt gtggtggcgt ctatggctac ggccgctggg  28500
ggcacgcagc agatcgatgt gaaagcctac aatgtgactg cccaaaattt tagttttggcg  28560
tttattacga atgatggttc gaagccgaat ggtgtgcctg cggttgcgaa ttggattgct  28620
gtcggagtgt gactgcacgg gtgttgtggc ggatggtggg atgttggggg gctgtagtgt  28680
cgtggtttac tcctgcactg gtggcctcta tctgtaccgc gttggccacg gttttgggtt  28740
ctgttcaggc tgtcacatcc cggtctagga agcgttacg caggctgtcg gctcaggtgg  28800
atgcgatgga agagtatacg tgggggtgtgc ggcgcgaggt gcgaaggttt aacgccgggc  28860
ttcctgacga tgtggagccg atgcatcttc ctgatttgcc cgagttttg aaagatactg  28920
ttgatggtgg aggtgagtag ggttgaggga gttggaggaa gagaaacggc agcgccgcaa  28980
ttttgagaaa gcttcactgt tgctgttgtt tttgtcgctt gtactgttgg cggtggttgc  29040
tgcgggtgct ttgcgtttcg gggctgtatc ctctgagcgg gattcggagc aggcgagggc  29100
ccagtcgaat ggtacggctg ccag                                         29124

SEQ ID NO: 73        moltype = DNA   length = 30016
FEATURE              Location/Qualifiers
misc_feature         1..30016
                     note = PAC22
source               1..30016
                     mol_type = other DNA
                     organism = synthetic construct
SEQUENCE: 73
gcgcagggtg agcgtggccc cgccggtgtg aacggatccg atggtaaaga cggtaaagat   60
ggtaaggatg gcgctgatgg gcgttcggtg atatcggtgt actgttccgg gggccgcctg  120
gttgtgaaat atagtgacgg tacagcctcc accgtgtcgg ttctgcggc ctgtgagagt   180
gtgaaaccgt cacctgtggt taccgtatca tcccacaaat agaatatgaa gagggaaggg  240
tgttactagt gttgattgtg gtgtttgtg gtggtgtgtt gtgagataca ttccagcggc  300
gcatcactcg gccggttcga atagtccggt gaacagggtt gtgattcatg cgacatgccc  360
ggatgtgggg tttccgtctg cttcgcgtaa ggggcgggcg gtgtctacgg cgaactattt  420
```

```
tgcttcccca tcgtctggtg gttcggcgca ttatgtgtgt gatgttgggg agactgtgca    480
gtgcctgtcg gagtctacga ttggttggca tgcccgccg  aatccgcatt ctttgggtat    540
agagatttgc gcggatggcg gttcgcacgc ctcgtttcgt gtgccagggc atgcttacac    600
tcgtgagcag tggcttgatc cgcaggtgtg gcccgcggtg gagagggcgg ctgtcctgtg    660
tcggcagttg tgtgacaagc atggtgttcc gaaaagaaaa ctgtctgtgg ccgatttgaa    720
ggccggtaaa cggggcatct gcgggcacac tgatgtgacg gatgcgtggc atcagtcgga    780
tcatgacgat ccggggccgt ggtttccgtg ggacaaattt atggctgtgg tgaatggcca    840
cggctgcggt tcaagtagtg aggagttaac ggtggctgat gtgaaagcgt tacatgatca    900
gattaaacaa ttgtctgccc agcttactgg ttccggtgaat aagctgcatc acgatgttgg    960
tgtggttcag gttcagaatg gtgacctggc gcgccgcgtg gaggctttgt cgtgggtgaa   1020
gaatccggtg acggggaagc tgtggcgcag caaggatgcc ctgtggagtg tctggtatta   1080
cgtgttggag tgtcgtagcc gtattgacag gcttgagtct gctgtcaacg atttgaaaaa   1140
gtgatggtgg tttgttgtgg gtaaacagtt tggttgggc  ctgctggagc gggcgttgaa   1200
gacttttgtg caaacgtttg ttgctgtgtt gggggtgacg gcgggtgtca cgtatactgg   1260
ggagtcgttt cgtggtttgc cgtgggagtc ggcgctgatt acgcgtacgg ttgctgcggt   1320
tttgtcggtt gctacctcgt ttggtagccc gtcgtttgtg gctggtaagc caagcaagcc   1380
tcaggtggat gcgggtttgg ttgagcctca catggtggat gtgtcggatc ctggcatgat   1440
cgagccgacg gatgatgctg atcttggtgt gggctatgtg ccgaaacacg ctgccgagtc   1500
ggaggttggc acggtagagt cgactgttgc ataagtgaat atagatgtgt gccccagcgg   1560
tgctgccacg gttgtgtggt ggttgccgct ggggcactat ttttgtgtct atagtatttt   1620
atgattcgtt gctgtcgatg gtgtcttcga gcatctggta caggtggagg caggtgcaga   1680
tggtttcgct ggcctggtct agaacgggtt c ggccgataac gttttttgtgg ttgtcgcggt   1740
ggcggatgat agcccacatg atctcgtcgg ctgccgcctg taatagtttt gcctggtatg   1800
cgattccggc gagccagtct agtgcttcct ggcttgcgta ggggctctgg tcctcgctgt   1860
tgccgcgggt gttgctgttg tttgtggggt gtccttcact gtcgcatagc cataggattt   1920
cgctgcactc gtctagcgtg tcttggtcga tagcgagatc gcgaggctg  acattgttga   1980
cggtaaggtt cacgttgtcg atggagatgg gtacaccgta ctggttttca acactgtcaa   2040
caatgttttg tagttgttgc atgttggtgg gctgttgttg gacgatgcgg tgtatcgctg   2100
tgttgagggt ggtgtaagtg atgttgtgtg tgttgttcat ggttttatg  ccattccttc   2160
gttatcgtct ggcatgtagt atgtgcgtgt tgcgtactcg gtgagggtga tgagtgtttg   2220
gtctgcccac tgtttcacgg tttgccgggt gactccgagt agttgggcgg ctgtggcgta   2280
ggtttggtcg tatccgtata cttcccggaa tgctgccaac ctagctaaat gttttcgctg   2340
tttggagggt tcacaggcga gggtgtagtc gtcgatggcg agtgtagat  cgatcatggt   2400
aacaaggttg ttgccgtgat gctgggggc  ggttggtggg ggtggcatgc ccggctccac   2460
actgggtttc catggtccgc cgttccagat ccattgtgcg gcttgatga  tcggccggt    2520
agtgtaggtt cggttcatgt gtcaccccct gaacaggtcg ttggtgttgc tggtgcgggt   2580
ggtgtcgaat cgtccgacgc agtggcagta gtcgtacatg agtttgataa tgtgttggtg   2640
gtctcccaaa taggtgttgc cgctgatgct gtaggtggct gtgccgtctt tgctgatggt   2700
gtatttggcg gtgatggttt cggggtttttc ggtgtcggtg atgattgctg tggtggtggt   2760
gcctactgtt tggagcacgg tggtttgggt tccgtcgtcg atgctggttt taaccatggt   2820
gtgtgttctc cccttttgtgt tagttgctgg ttttggttgtc ggctagatga atgatgtcgg   2880
gtaagggttt cggctggtct aggtgttgtg tggttttgtt ggctaaacgt ttggctaccc   2940
tgtagcacat tttggtgtag tgttttgttgt cgaggttgtg gtattgttcc cgcaccgcaa   3000
tatatagcag ggagtcttgg tataggtcgt ctgcactgat tgcggggtag tgtgcggctg   3060
ttttggtgca tgcccggttg agtgtgcgta gatgatggtt tgtggcccac acccacgatg   3120
cggtggtggc taggtcggct tttgttggtc gtcggctcat ggcatctctt tcatctggct   3180
atctggtagt tgttttggtgt tttgttgttg atagtgtagc acacgagtcc ggggttgccg   3240
gtggtgcctg ttttgtgccg gaaccatgtg gattctcctt ccatggaggg gcattggatg   3300
aaggtgcgtt gtccttgctc ggagatttct aggtggtgcc ggtgcccggc catgagaatg   3360
tgggatgtgg tgccgttgtg gaattcttgt ccgcgccacc attcgtagtg tttgccggtg   3420
cgccattggt ggccgtgggc gtgcagtatc cgtgtgcctg ccacatcaac ggtggtggtg   3480
atttcgtcgc gttgggggaa gtggaagtgt aggttggggt attggttgtt gagctgtag    3540
gcttctgcga tggcgcggca gcagtccacg tcgaaggagt cgtcgtaggt ggtgactcct   3600
ttgccgaagc gtacgcttc  tccgtggttg ccggggatgg atgtgatggt gacgttttg    3660
cagtggtcga attggtggat gagttgcatc atggccatgc gtgtcaaccg gatttgttcc   3720
gtcaaggggg tttgtgtgcg ccaggcgttg ttgccgcctt gtgacacgta tccttcgatc   3780
atgtcgccga ggaatgcgat gtggactcgt tgccggttttc cggcttgttg ccagtagtgt   3840
ttagctgatg tgagggtgtg taggtagtcg tcggcgaagt gtgatgtttc tcctccgggg   3900
atgcctttgc cgatttggaa gtctcctgcc ccgatgacga aggccgcggt gctgtagtcg   3960
gtgcgggtgt cttgttcggg ttttgggggt gtccattcgg ctagcttgtc gacgagttcg   4020
tctaccgggt aggggttggt tgcgggttgg tggtcaataa ttttttgtat ggatcggcct   4080
gtttctccgt tcggtaaggt ccattcggag atgcgtgtgc ggcgcacggt gccgttggct   4140
agattgtcgt cgatggtgtc gatggcgttg tcgtggttgg cgactgtgt  gaggagccgg   4200
tctatgttgt ctatcatcgg gtatcctcct cttctgtttg tggtgggtg  gcttgtttgc   4260
ggcggtagtc tttgatgacg gtgcggagga tggggggta  tcctcctctt ctgtttgtgt   4320
tgtggtggct tgtttgcggc ggtagtcttt gatgacggtg gcgagatgg  ggtatccggc   4380
ttcagtgagc attcgggcta gctgtgtggc gggatcgtc  ttgtcggcga ggacgtctgc   4440
agccttatca ccgtagcgtt ggatgagggt ttcagttttg gttgccatgg tgtcctatcg   4500
gttgtgtggt gggctgccat cctgtgcggc agtcgccgtc tggtcctgt  ttgcgtgtcg   4560
accacgatac ggttccgtct gtgtggttga gtgttttgcc gcacatgacg ttttgtagat   4620
gctcgggcag tgcgccgtta ctctggttgc tggtttgtgt gtcgaagagt gttttctggt   4680
tggtgaaatg ctcggatacg gtgccgttgt ggactgggag tatccatgtt ttccattgtt   4740
gttgcatccg ggtgttccag tggaattgtt tagccgcgtt ttctgcctgt ttggcggttt   4800
gtagtagcc  tacaatgatt cgctggtggt tgttgtctgg ctggtgtggc cctttccagt   4860
attgtgccgc cacggcgtag cggttgctgg ctgtgaagcg ctcccagcag tattcaataa   4920
tgtgttgcag tacactatcg ggaatgtctt tgtcttggtt ttcgttaagc cattcttcaa   4980
caatgatgtc gcgtatggcg cgtttgtctt tagtggtggg tttgaacgag atgctcacga   5040
tagcaccggc tggtcgtctt gcatgaactg gttgaaggtc ttgttcccgg cgtgttggc    5100
ttgtgtgatt tgctggtcgg tccagtctgg gtgttgctgt ttcagatagt gccagtggca   5160
```

```
cgcattgtag gtttcgtctt gtagccgtgt gagatggttt tcggtgatga tttgtttcca   5220
catagtccac gagacgtcga gcctgttgag gatttcgagg gctgggatgt tgaattggtt   5280
gaggaacagg atttcgtggg tgtagtattc cttctcgtag gcgtcccatc cgcttcggtg   5340
cctgttgggc tggttttttgg ggtaggcttc ccggcagatt ttgtgcaaat gtttggccat   5400
gtcgtcgggt agtttaatgt caggggttggc gcggatcatg gatcgcatcc catcataggt   5460
ggtgccccag gtgtgcatga tgtaggtggg gtcttcacca tcagtccatt tttctgcaca   5520
gatggcgagg cggatacgcc tcctggcggc ttggctggtg ttgcgccggt tggggattgg   5580
gcacgtgtcg aggggatcca tgatgctttt tatgcctttc tttgtttggg ttgtttgtct   5640
agttttactg tagcacagtg tctagtgctt gtgtcaaccc tgttttttccg gcctgcaggt   5700
aggtgtctgt gacgtcgccg agggtgaggg gcacatgggt ggcttggggg agtgctgcct   5760
ggagggtgtg ggccatctgg tcgcctgctt tgtctgggtc tgaccatatg tagatgtggt   5820
cgtagccttc aaaaaatttg gtccaaaagt tttgccacga ggtggcgccg ggtagggcga   5880
cggccgacca tccgcattgt tcgaggatca tggagtcgaa ttcgccttcg caaatgtgca   5940
tttcggctgc ctggttggcc atgcggcca tgttgtagat ggagccgtgt tccccctgccg   6000
gtgtcaagta tttggggtgg ttgtgggttt tgcaatcatg ggggagtgag cagcggaaac   6060
gcattttttcg tatttcggct ggcccttccc agacggggta catgtagggg atggtgatgc   6120
actggttgta gttttcgtgg cctgggatgg ggtcattgtc gatgtatcca aggtggtggt   6180
agcgggctgt ttcttcgctg attcctcttg ccgagagcag gtcgagtatg ttttcgaggt   6240
gggtttcgta tagggccgag gctttctgga ttcggcggcg ttccgcaatg ttgtaggggc   6300
gtatgctgtc gtacattcgg gttttcttcc tctaatcgtt gtttcagttt gtggagtcca   6360
cctccgatac cgcatgtgtg gcagtaccag acgcccttgt cgaggttgat gctcatggag   6420
ggctggtggt cgtcgtggaa cggggcagag atgtgttgct cgttcctgga cggggttgtag   6480
cgtatctggt gggcgtcgag gaggcggcag gtgtcagagg tgtgggagga gctcgttgag   6540
ggttgatacc acataggctt cgctccaggg tttgttgcgc tgtttcatga tgacgagtcc   6600
gatggtggac tggttttctc ggtttcggtg ggtttcatag ttgcgtgcct cccggctggc   6660
ttgtttcacg aattcggcga gatgtggttt cccggcttttc gcctcgataa tgtaggtttt   6720
gtggccggtt gtgaggatga ggtcgccttc gtcttcgcgg ccgttgaggt ggaggcgttc   6780
gatatcatgt ccgatgtcgc gtagctggtg gaggagtctt gtttcccatt cggcccagc   6840
tcgcctattc ctgattgct gtgtagccat catagtcctt tgtgtgttgg ggtcatgttc   6900
cagggctgtt tttctactag gggtccgaag aatgtgtatt cggggtcgag tcgtagtcgt   6960
tcgtatcggg tgccgtctgg gctgatttg ccgttctct gtttgagtac ggcgatgcgc   7020
gcctcggcgg ggatggtgag cccgttgccg ttgtcttcgc caccgtagag tgagactccc   7080
aggattagtt gtgggttttc ggagaggccg ttttttgattt cccgcctagc tgggggggtgt   7140
tcgatgtcgg tgccggtttt gtcggttgcg tggtgggtga caataatggt ggagccagtg   7200
tcgcggccta gtgctgtgat ccattgcatg gcttcttgct gtgcctgata gtcacttcg   7260
cagtcttgga tgtccatcag gttgtcgatg acgatgatgg gtggtgaaggt gttccacatt   7320
tccatgtagg cttggagttc catggtgatg tctgtccatg tgatgggtga ctggaatgag   7380
aatgtgatgt gtccgccgtg gtggatgctg tctcgatagt atttctgggcc gtagttgtcg   7440
atgttgtgtt gtatctgttg ggtggtgttgtgt tgggtgttta gtgagatgat tcgtgtggag   7500
gcctcccagg gtgtcatgtc ccctgatatg tagagggctg gctggttgag catcgcggtg   7560
atgaacattg ctagccctga tttttggctg ccggaccgcc ccgcgatcat gactaggtcc   7620
cctttgtgga tgtgcatgtc ctggttgtca tacaagggtg ctagttgggg tatgcgggggc   7680
agttcggcgg cggtttggga ggccctctcg aaggatcttt ggagagagag catcggaggc   7740
ttaatctatc tgtctgttgg ttgggtgttg gtgtcagat ggagtcgatg tcgatgtcag   7800
catcggcggg ggctgtggtg tcgtctagct ggccggtgtc gcgcttgtct acgtattcgg   7860
caaccttatc gtagatggcg tcgtccaatg gtttgaggac gaccgcgttg aacccgtttt   7920
tggtcgcaac ggtggcgagt tgaaggcct gctcttcgtc gagataggct tctaggtcgc   7980
ggatcatgga gtgtgggcgg tcgttgttgc ctcgcgcttt tcgatgata gcgttgggga   8040
tagtttctgg ggtgccattg ttgagatcct ggagtgtgtg gaagatggtg acatcggcgt   8100
aaaatacggtc ggcgacctgt ccgccgtagc cttcggtgtt gtgctggacg tcgcggattt   8160
tgaaggcgat ggcggtggcg tcctggtttc gggaggggtt gaagaaggtg ctgttcgtgt   8220
tgttgcggta gttggcgagt cccattgttg tttccttttac tatttgtgtt ggttttttgtt   8280
gtcttatatt ggtttatcgg gtgaggctgc ttcgtttact gcggaacgcc tcagacacgt   8340
cactgttact ggtgatgatc ttcttgtact gtttgaggag gtctgctagt tgtgtcttgc   8400
tggtggcttt gttgatccgg tcgatgatga tgtcgttttc ctggttgggg atttttgttga   8460
cgtagtcttt ggcggcttta tcgtatcgat cttgaagcag gattgctgcg ctagcgatca   8520
aggtggctaa atcccagtct ttggatacgg tttcgtcttt caatcctcct agcaggtcaa   8580
tgatggattg tttgatgtct tctgcggtgt ctccgcggat gactgtccat ggggcggcat   8640
agtctccacc gtatttgagt gtgatagtta gttttccgtt gtcgtggtg tgctcgtcgg   8700
tcacgtgttt tccttttcgt tactgtcggt ttgggggtggc tgtacggtgg tttctatcgg   8760
gtatctgtac gagttttttgc cgttgacggc ccagcaggcg tccttgacgg ggcatcctttt   8820
gcagagtgct gtgacgtggg gtacgaagat gccttggctg attccttttca ttgcttgact   8880
gtacatggat gatacatgcc ggtaggtgtt gttgtcaagg tcgtagagtt cggttgctgt   8940
gccctgtcg actgattgct cgtctcccctt ggtggtggcg tgtccaaa acatgcctgt   9000
cgtcacatgg atgccgtgtt ggtgagcat gtaccggtat gtgtgcagct gcatactgtc   9060
ggcgggtagg cggccggttt tgaggtcgag gatgaaggtt tcgccggtgt tggtgtcggt   9120
gaatacccgt tcaatatatc cgacaatctg ggtgccgtct tggagggtgg tttctaccgg   9180
gtattcgatg cctggctggc cgtcaataac agcggtagcg tattctgggt ggttgcgcct   9240
ccatgttttc caccggttcca caaaggtggg gccgtatatc atccaccaat tgtagtcttt   9300
cttgttgggg cccccgcttt cgcacatgtt tttgcacact cggccggagg gtttgatgtt   9360
tgtgccttcg gattcggcga gggcgatttg ggtgtcgaaa atgtttgtga aggatgcgag   9420
tttgtctggt agtgcagggt attcggcggg attgtacagg tgtaagtcgt attgttcggt   9480
gatgtggtgt atggcgcttc cggcgatggt ggcgtaccag gtgtggtgtt gggtgtggta   9540
gccgtgggat aggcgccatt tttctccgca ttccggcagtg aactgtagga   9600
gatgtggcct ggatggtgga tggttttcgg gtattgtgct aggggcatta cttgtcgcct   9660
ttgtgggtgt tccatgggtt gcgggtgtct accccggcat cgttgctgtg gtaggcgagg   9720
agtgccaagc agtgccaggc agcatgtgcc agatgcggca aatgtgattc gtggtcgagg   9780
ttgtttcctt gctgccatga tagcaggtgc ctgtagaggg cgtcgacact gtggctccac   9840
gggtagccgc cggtccagtt gttgtcgccg tatttggtgg caccgtagcc tgccacttcg   9900
```

```
ccgagggcgt gcaaggcggt agggtcgatg agggatagcc tgcaaagttt caattcttto   9960
ttggcacccg tatcagggtc ggtgtacatg ctggttggct catccatggt gtgtgtgctc  10020
cttacgtgtg gggttactgg ttggggttgt gggcgagtgc tacggcgaga ataatgatgg  10080
cgagggtttc tgcgatcagt attggtgttg tgatcatttg ctgtcgcggg gattgttggt  10140
gagggtggat gcgcctagca gggtggtgag ggcgcatgcg gcgatgatgg cgagggcggc  10200
tttgtggctg gtgccggtgg cgtacatcca tgtgatgatg gcgccctgta tccatgccag  10260
tgtggtgaag aacgtttcgt agctgtgcag ctcgatactg ttgggtgtgt tcatgcttgc  10320
tcctgaagaa tggtgttgat ggttgtgtaa atgttgtaca ggtcggcttc gatggtttgt  10380
agctgtttga tttggtggtc gaggtcaatg tttgggttga gggtgttgat gcgggatgcg  10440
atgtcggtgg ctgtgccgtag tgtgccgccg gtgtggtgaa tgatgtgtgc cgtgtcggcg  10500
agtccggtgg tgacagcgta gcgggagagg agaggcatga ctggggggtg ctccttgacg  10560
gggttactgt tgcgggttga tgttgaggtc ggtgacgtgc ggtgagcttt ctgttcctgt  10620
gacgaggcag tggacggtga cggggagttt ggatgctccc ggctggcgga cggtggcgcc  10680
gtagacgatg ctgaacgtgt ctttgccaat aattttgtgg agttggaggt cgatgtcggg  10740
gttgccgttc catttgacac cctgtgctgc agctgcctgt tcagccttgt cattgcaggc  10800
gtgtgccgcg gtgatcatgg tgagacctgt ggaggtttct tcaccccgtg tttgggcttg  10860
ccggtggggcg cgctgctgtt cggcttggag ggagcggact gctgcagcct gcttggcggc  10920
tttctcggct ttgcgctgtt ggacggtttc aggtgtccat tcggtgttgg ctgtggtggc  10980
ttgtggggct ggctgtgagg cgagtggcgg attatcatcg ggtgccggga ggaaggatgc  11040
tgcggcgatg atggcgatgg tggcgccggc gatggtgtag cctgtttttct tgttcatgat  11100
tttgtgttcc ccttttccggg gtgttgttcg ttgctgacat gatcaatact ttcagcggct  11160
ggaccctgtg tcaaggtgtc gctcagtatt cttgagcgaa tgtggtttga ctgggggtga  11220
tggcttcttt cgcccaatag gatgtgccac cgctggtcca gtatccgagt ttgttgcgct  11280
gcatgccctt ggcttccatc tcatccacgg tgaggcacct cgcgcgattg gggccttcct  11340
tgaccccgtg gtcgcctacc cggtgcatgt cgcctgaggt ggtactcgtg aatgtttcgt  11400
ggcagattgt gcagtgctct ggtcgatatc cgatgattgt gctatcgcac ttgtcggcgt  11460
tccattgcat gattgctcct attttcatt ataagacttc ctgtagtgcc attttagcgc  11520
cttgcgggtc ttgggggtac aactatatag gtcaggtatt tctaggcgat tctaggctca  11580
ttgtgtgcga ctggtggtta tcgggcgcac agagtgagca ggtggccaac attgatgcgg  11640
gtcacattcc agtagagttg cgtggcttcc tcactggtga ccggcttcca ctcgttgtgg  11700
ctgaacacgg tgccatcgga tgctatgaac gtgttgggc gtagcttgtg gagttcagtc  11760
tctacatgcc gacggtaggt ttcggcgagg ccctcgaaat cgaggtggtc gcaggagagg  11820
ttttcgaggc gtgtcaggtc gaaaggctca gggcagtcgt agctggcggg gctgtagagc  11880
tgggtgaagt ggttggcaat cttctgcatc atgattcctt ttctggtgat ggtgtgttga  11940
tggttttatc gggtggatgc tttgaggatg gcgtctacat cgatcatgtc gatcatgtcg  12000
ttgagttcct cggcctcatt ctcggagagg tggcgccagc cgggtggccc gtataggggcg  12060
ccgtcgaggg tgacagtcca cagggccggg atgagtcgta tggcttcttc gactttggcg  12120
tggtacatgc ggcgcaccat atccagatcg atgtcgtctg aatggtttcc ggtgaggctg  12180
tggaggctga gtgggtcgat ttctgtctgc ccgtagaggc tggtgaatga tggtgtgatg  12240
agtgtgccat ccatgagggt gctccccttct gaactgtttg ggttggttgt tgtggtttct  12300
agagtgtgta ggttgcaacc ccatagtcaa ggctacgctc attcggattg agcgtttcat  12360
gctggagtgt gtcgggtgtg acagatgtca ctgaatcctt gatggcctct ctcagcgcct  12420
gaaatatgtc cggggtggga ttatgcaggg ttgaccctgc tgatcgattc taggccccct  12480
acagggcgtc tcaggggtat gtctgggtga tagcaggttc ggtagatgat ctagcgagtc  12540
aaggtgccaa gctgagacag aagatctacc atctaggtgt gtgagatgta tcacactcgc  12600
ctggcttagt gtgcaccctc aagaccacct agtcgatctg gcgtgagggg tgcagcccag  12660
aaataccgtt taaagccttc gcgcgggagcc taggagcgcc ttacagggtg ggggctaggt  12720
attcataccc ccaagcaatt ctgatcgatt ctagacgcct ccaggggccc gatacacgat  12780
cagtagtcca gacacagatc atcaacccct atcctggtta gctaagcctc aactatgtgg  12840
acagtgtggg atgctaagag ggaagaagga cacggtaaaa gaaagagggg ggagcatcag  12900
ccttcaagcc tgaaggtctt agcgcttagc accgagcccc ctcaagggct gggcatcagc  12960
ccgaacaggc tcagctcatc aggcacagcc ctgaaaaggg tacacgccat cagggaaggc  13020
ttgagagtac gaggagccct agcgacgagt actcgaaagc ctgaggaaac accctcagca  13080
ctgatgggcc tagcgtgttc ggaaaggaca caagagtaaa gtgtgacagc tgtccggag  13140
tgaaaccgt tccggctagg ggtttcagcc ttaaccaccc tcaaaggtta caagactcta  13200
agaaaattta agaaaactct taggaagaaa gttgtgttca tatccccccta aaaacaccca  13260
aaatagccct caaacccgcc tatagagcca aaaccaccag tttgactcat cccaggtggg  13320
gtatgatagg ctggacaggt agccagctgg acgcgaggcc agaaagtgct gacgcacttc  13380
ccgacctcgc ttaccatcag tctaccaaac actttaaagc ttcaaggctt agcgctaagc  13440
ccttaagacc ttaacactga acaccgagcc ccctcaaggg ctcggcatca gccttaaagc  13500
cttaaacact ttaagtaact ttaaaacctt aacagcttaa cacttaaggt tataaaataaa  13560
cattaaagct ttaaagtctt aaagtaaata tataaccttta acacttaagt taagtataaa  13620
acttaaaaag ctaagcactt aaagatataa acttaacatc agtgtttaag acttaaagag  13680
ttaaagtaac tattaagact taaaggctta taagcttaaa acacttaaaag taactataag  13740
actttaaaaa ccttaagtac ttaaagttaa ccatcagtct taaactttaa tactataacc  13800
tataagtctt aaagcttata ggtataataa tataatataa gtattaaagc ttataagtta  13860
taaaagttt agaagagtta aagggttaac ttctttactt ctcttctctc tttggttctt  13920
tctctcttct cttcttttct tcatcagggg agaagaggaa cctttaaccg tcaacgctga  13980
tggactttca accgtgtgac tcgtgtacca ccggtcgcac ccgcgaacgc gctcccgatg  14040
cacatgctac ctgtgtccct ttcaggctta gcgtgttcgg ctgaaggcgt acggcgtgtc  14100
acgcttaaac ccttaacacc aggtaagact taaagtgtat attataagta gaagacttta  14160
aaacctttaa ggtgttcccg ctgagcctgt gttcttcacc gctaggcgct aagcgctaag  14220
ccttgaaacg cgaacaccca tccacccttt tcttttaccg tgtccttctt cttttgacac  14280
gcgctggggg cgatgtgatc ttttttcacat gccaggggt aggagaagaa aacaaccacc  14340
ccggcacaaa cagaacaccc ccctaaacga acaaaacagg gcccaggatc gaacagcagg  14400
gcaccggtag agtattccta cccccagaca attccaggcc gttacaggag caatgagagg  14460
ctcacagggg ccataggaga tcaggggacg tgatggcaca caccaaccgc acagccagcc  14520
aagcccaccg gcgctggcgg caacgactca tcacccaagc caaacagcaa ggccaaaccg  14580
aatgcccact ctgcggagcc accatcaccct ggggcacaca tgacctgcca accagcccg  14640
```

```
aagccgacca catcacaccc gtcagcaggg gaggactcaa caccctcgac aacgggcaaa   14700
tcatctgcag aacatgcaac agaagcaaag gcaatcgcag cgaaccaaac attcaattcc   14760
aacaacaaac cacaaaaacg ttgatcccat ggtgaaaaaa cagccaaccc ccacgggaac   14820
cacccctgc acaccgtgc aagacctcgt acggcttagt gaaatacctc ccttttgtgg    14880
ttttgtctgt ctgtcgactt ttttgtgttgg tggtgagtgt tgtgcagcct gagcttcctg  14940
atagtcgtgg atggtgtggg gagacgcgtc gttggtggcg tgtgtggggt gaggatagtc   15000
gcgcgcagta cgtgtctgat gaggagtggc tgtttctcat ggatgctgcg gtgattcatg   15060
attgtgtgtg gcgtgagggt cgcgcggatt tggtggcttc gcttcgtgct catgtgaagg   15120
cttttatggg catgttggat cggtattcgg ttgatgtggt gtctggtggc cgtggtgggg   15180
gttctgctgt ggcgatgatt gaccggtatc ggaagcgtaa aggggcctaa tgtcgagcgt   15240
tgttggttct caggttcctc gtcaccgggt ggctgcggct tattcggtgt ctgctgcgg    15300
tgatgcgggt gagcttggta gggcttacgg gttgacgcct gatccgtggc agcagcaggt   15360
gttggatgat tggctggctg tgggtggtaa tggcaggctt gcttcgggtg tgtgtggggt   15420
gtttgtgcct cgccagaatg gcaagaatgc tattttggag attgtggagt tgtttaaggc   15480
gactattcag ggtcgccgta ttttgcatac ggctcacgag ttgaagtcgg ctcgtaaggc   15540
gtttatgcgg ttgaggtcgt ttttttgagaa tgagcggcag tttcctgact tgtatcgtat  15600
ggtgaagtcg attcgggcga cgaatggcca ggaggctatt gtgttgcatc atccggattg   15660
tgccacgttt gagaagaagt gtggcgtcc gggttgggt tcggttgagt ttgtggcccg     15720
tagccggggt tcggctcgcg ggtttactgt tgatgatttg gtgtgtgatg aggctcagga   15780
gttgtcggat gagcagttgg aggctttgct tcctacagtg agcgctgccc cgtctggtga   15840
tccgcagcag attttccttg gcacgccgcc tgggccgttg gctgacgggt ctgtggtgtt   15900
gcgtcttcgc ggacaggcgc ttggtggcgg taagcggatt ggtggacgg agttttcgat    15960
tcctgacgag tctgatccgg atgatgtgtc gcggcagtgg cggaagcttg ctggtgacac   16020
taatccggcg ttgggtcgtc gtctgaattt tgggactgtg tcggatgagc atgagtcgat   16080
gtctgctgcc ggttttgctc gggagcggct tggctggtgg gatcgtggcc agtctgcttc   16140
gtcggtgatt ccggcggata agtgggttca gtctgctggc ggtgaggcga gtcttgttgg   16200
cggtaaagtg tttggtgtct cgttttctcg ctcgggggat cgtgtcgcgt tggcgggtgc   16260
tggccggact gatgctgggg ttcatgttga ggttattgat ggcctgtctg gcacgattgt   16320
tgatggtgtg ggccagctgg ctgactggtt ggcgttgcgt tgggtgaca ctgaaaagat    16380
tatggttgcc ggtcggggtg cggtgttgtt gcagaaggcg ttgacggatc gtggtgttcc   16440
gggccgtggc gtgattgtgg ccgatactgg ggtgtatgtg gaggcgtgtc aagccttcct   16500
ggagggtgtc aggtcgggtg tgatcagtca ccctagggct gattcgaggc gtgacatgtt   16560
ggatattgct gtgaggtcgg ctgtgcagaa gaagaaggt tctgcgtggg gttggggttc    16620
ctcgtttaag gatggttctg aggttccttt ggaggctgtg tctttggcgt atcttggtgc   16680
gaagatggcg aaagcgaagc ggcgtgaacg gtctggtagg aagcgggtgt ctgtggtatg   16740
aactcggatg agttggctct gattgagggc atgtttgatc gtatccgaag gttgtccttcg  16800
tggcattgtc gtattgaggg ctactatgag ggttctgccc gggtgcgtga tttgggggtg   16860
gctattcctc cggagttgca gcgtgtgcag acggtggtgt cgtggcctgg gattgcggtg   16920
gatgctttgg aggagcgtct ggattggctt ggctggacga atggtgacgg ctacggcctg   16980
gatggtgtgt atgctgcgaa tcggcttgct acggcgtcgt gtgatgtcca ccttgatgcg   17040
ctgattttg ggttgtcgtt tgttgcgatc attccccaag aggatgggtc ggtgttggtt    17100
cgtccgcagt cgccgaagaa ttgtacgggc cggttttctg ccgatgggtc tcgtttggat   17160
gctggccttg tggtgcagca gacgtgtgat cctgaggttg ttgaggcgga gttgttgctt   17220
cctgatgtga ttgttcaggt ggagcggcga ggtagccgtg agtgggttga gacgggccgt   17280
atcgagaatg tgttgggtgc ggttccgttg gtgcctgttg tgaatcgtcg ccgtacttcg   17340
aggattgatg gccgttcgga gatcactcgg tcgattcgtc cttacacgga tgaggctgtt   17400
cgcacactgt tggggcagtc tgtgaatcgt gatttttatg ctcatccgca aaggtgggtt   17460
acgggtgtgt cggctgacga gttttcgcag cctggctggg ttctgtcgat ggcttctgtg   17520
tgggctgttg ataaggatga tgacggcgat accccgaatg tggggtcgtt tcctgtgaat   17580
tctcctacac cgtattcgga tcagatgcgt ttgttggcgc agttgactgc gggtgaggcg   17640
gctgttccgg aacgctattt cgggtttatc acgtctaacc cgccttcggg tgaggcttg    17700
gctgcggagg agtctcggct tgtgaagcgt gctgagcgga ggcagacgtc gtttggtcag   17760
ggctggttgt cggttggttt cttggctgcc agggcgttgg attcgagtgt tgatgaggcc   17820
gcgttttttg tgatgtgggg tttgcgttgg cgtgatgctt cgacgccgac tcgggcggct   17880
acggcggatg ctgtgacgaa gcttgtgggt gtcggtattt tgccggcgga ttctcggacg   17940
gtgttggaga tgttggggct tgatgatgtg caggttgagg ctgtgatgcg gcatcgtgcc   18000
gagtcgtcgg atccgttggc ggcgctggct gggctatttt ctcgtcaaac taacgaggtt   18060
tgataggcga tggcttcggg ggttgtgtcg aggcttgctg cgactgagta tcagcgtgag   18120
gcggtcaggt ttgccgggaa gtatgcgggc tattatgccg agctgggtcg tttgtggcat   18180
tccgggaaga tgacagatgc gcagtatgtg cgtttgtgtg tggagtttgga gcgtgccggc   18240
catgacggtt ccgcggcgtt ggcgggcaaa ttcgtgtccg attttcgccg gttgaatggt   18300
gtggatccgg gtttgatcgt gtatgacgag tttgatgctg cggcggcgtt ggctaggtcg   18360
ttttcgacta tgaagattct taagagtgac ccggataggc gaatgatac gattggtgcg    18420
atggctgcgg gttttgatcg ggctgtgatg aatgctgcgc tgacacggt tgagtgtcgt    18480
gcgggtgtgc agggtaggtc gtggcgcagg gtgactgatg tgatccgtg tgcttttgt    18540
gccatgttgg ctacgaggtc ggattatacg actaaagagc gggcgcttac tacgggtcat   18600
actcggcgtg ataagcgtgc cggtaggcgt ccgtttggtt cgaagtatca tgatcattgt   18660
ggttgtacgg tggttgaggt tgttggccct tgggagccga ataggctga tgccgcatat    18720
cagaggacgt atgagaaggc tcgtgagtgg gttgatgatc atggtttgga gcagtcgcct   18780
ggcaatattt tgaaggctat gcgtactgtt ggcgatatga gatgatggtt ccggttgtg    18840
tgccgccggt tattggtgca cagggttgtc tcccgcacgg gggtcaacaa tgttgtgttg   18900
ttttccgcaa ggagtgtagg ttaggctatg ccgatcaga gtgttgaaga acagaatgtt    18960
gacaatgatg ctgttgagcc cggaaagggt ggagacgttg ttgatgttgt gaaggatggg   19020
caggctgccg gcgatgatca tgccggtgat gtttccggta aggaggagtc ttcttcctgag  19080
acggattgga aggctgaggc ccgtaagtgg gagtctcgtg ctaaaagtaa ttttgccgag   19140
ttggagaagc ttcgcgcctc ggatggtgat gcggggtctg tgattgatga gcttcgccgc   19200
aagaatgagg aactcgaaga ccggattaat gggtttgttc ttgagggtgt gaagcgtgag   19260
gtggctgccg agtgtggcct gtcgggtgat gcggtcgctt tcttgcacgg tggcgatcgt   19320
gaagcactgg tggagtctgc taaggctttg aagggtttga tcgaccagag tggtggtggc   19380
```

```
gcgggtgtgc gccgtcttgc ggggagtgcc cccgttgatg atgttaaacg acgtgagggt   19440
gtcgcgtttg tggatgctct tgtcaataat tctaggagat gatttataat ggctgacgat   19500
tttctttctg cagggaagct tgagcttcct ggttctatga ttggtgcggt tcgtgaccgt   19560
gctatcgatt ctggtgtttt ggcgaagctt tcgccggagc agccgactat tttcggcccg   19620
gtgaagggtg ccgtgtttag tggtgttcct cgcgcgaaga ttgttggtga gggcgaggtt   19680
aagccttccg cgtctgttga tgtttcggcg tttactgcgc agcctatcaa ggttgtgact   19740
cagcagcgtg tgagcgacga gtttatgtgg gctgacgcgg attaccgtct gggtgttttg   19800
caggatctga tttcgcctgc tctgggtgcc tcgattggtc gcgccgtgga tttgattgct   19860
ttccacggta ttgatcctgc cactggtaag cctgccgcgg ctgtcaaggt gtcgctggat   19920
aagacgaagc atattgttga tgccacggat tccgctacga ctgatcttgt gaaggctgtc   19980
ggcctgatcg ctggtgctgg tttgcaggtt cctagcgggg ttgctttgga tccggcgttc   20040
tcgtttgctc tgtctactga ggtgtatccg aaggggctc cgcttgccgg tcagccgatg   20100
tatcctgccg ccgggtttgc cggtttggat aattggcgtg ggctgaatgt tggtgcttct   20160
tcgactgttt cgggtgcccc ggagatgtcg cctgcctctg gtgttaaggc tattgttggt   20220
gatttctctc gtgttcattg gggggttccag cgtaacttcc cgatcgagct gatcgagtat   20280
ggtgacccgg atcagactgg gcgtgatctg aagggccata atgaggttat ggttcgtgcc   20340
gaggctgtgc tgtatgtggc tatcgagtcg cttgattcgt ttgctgttgt gaaggagaag   20400
gctgcaccga ctcctcctcc ggctggtaac tgatacaaga taagcgaatg tgtactatgt   20460
gcagggggtg tgttgatgg gtatcattt gaagcctgag gatattgagc ctttcgctga   20520
tattcctaga gagaagcttg aggcgatgat cgctgatgtg gaggctgtgg ctgtcagtgt   20580
cgcccccctgt atcgctaaac cggatttcaa atacaaggat gccgctaagg ctattctgcg   20640
cagggctttg ttgcgctgga atgataccgg ggtttcgggt caggtgcagt atgagtctgc   20700
gggcccgttt gctcagacta cacggtctaa tactcccacg aatttgttgt ggccttccga   20760
gattgctgcg ttgaagaagt tgtgtgaggg tgatggtggg gctggtaaag cgttcactat   20820
cacacccact attaatagta gatatgcaca ttctgaggtg tgttccacgg tgtgggtgga   20880
gggttgctcg tgcgggtcga atattaacgg ctacgcgtcg cctttgtggg agatatgata   20940
tgaccagttt tccttatggt gaaacggttg tgatgcttca gccgactgtt cgtgtcgatg   21000
atcttggcga caaggtggaa gactggtcta agcctgtcga gactgtgtac cataacgtgg   21060
ccatttatgt ctctgtttcg caggaggatg aggctgccgg ccgtgactct gattatgagc   21120
attggtcgat gcttttcaag cagcctgttg tgggtgccga ttatcgttgc cggtggcgta   21180
ttcggggtgt tgtgtgggag gctgacgggt ctcctatcgt gtggcatcac cccatgtccg   21240
gttgggatgc tggtacgcag gttaatgtga agcgtaagaa gggctgatgg gttgtggctc   21300
aggatgtgaa tgtgaagctg aacttgccgg gtattcgtga ggtgttgaag tcttctgggg   21360
tgcagtcgat gttggctgag cgtggcgagc gtgtcaagcg tgcggcctcg gcgaatgtgg   21420
gcggtaatgc ttttgataag gcccaatacc gtagcggttt gtcgtcggag gtgcaggttc   21480
accgtgttga ggctgtggcc cgtattggca ccacctataa gggtggaag cgtattgagg   21540
cgaagcatgg cacgctggcc cggtcgattg gggctgcgtc gtgatcgttt atggtgatcc   21600
gcgtgtgtgg gctaaacgtg tgctcaagga tgatggctgg ctgtccgata taccttgtgt   21660
gggacggtg cctgaggatt ttagcggtga cttgatttgg ttggctcttg atggtggccc   21720
gcagttgcat gttcgtgagc gtgttttttt gcgtgtgaat gtgttttctg atatgccgga   21780
tcgtgctatg tcgttagcta ggcgtgttga ggctgtgctg gctgatggtg tggacggtga   21840
cccggtggtg ttttgtcggc gttctactgg ccctgatttg ctggttgatg gtgcacgttt   21900
tgatgtgtat tcgcttttg agctggtgtg tcggcctgtc gaatccgaat aagcgtatcg   21960
ttgttttta gtttgattgt tttgtagttt gattgttttt tgggggttat gatggctgaa   22020
acacgtaaag cgtctaatgt tcgctctgct gttactggcg acgtttatat tggtaaagcg   22080
cacgcgggtg attctattaa gggtgtggag gcggttcctt ccgggcttac agctttaggg   22140
tatctgtctg atgacgggtt taagattaag cctgagcgta aaacgatga tttgaaggct   22200
tggcagaatg cggatgttgt tcgcactgta gctacggagt cgtctatcga gatttctttc   22260
cagctgatcg agtctaagaa agaggttatc gaactgtttt ggcagtcgaa ggttactgcc   22320
ggatccgatt cgggttcgtt cgatatttca ccaggcgcca ccactggcgt gcatgcttta   22380
ctgatgata ttgttgatgg tgatcaggtt attcgctact atttccctga tgtcgagttg   22440
atcgatcgtg acgagattaa gggcaagaat ggcgaggtgt atgggtatgg tgtgacgttg   22500
aaggcgtatc ctgccagat taataagact ggtgatgcgg tgtctggtcg ggggtggatg   22560
acggctttaa aagctgatac tcctccgact cctcctccag ccccgttcc tccgaagcct   22620
cagccgatc cgaatccgcc gtccgataac tgatacacga ttttaggggga ttgttgatag   22680
atgagtgaca ctggttacac gttgaagatt ggtgaccgta gctgggtgtt ggcggatgcc   22740
gaggagacgg ctcaggctgt tcctgcccgc gtgtttcgcc gtgccgccag gattgcccag   22800
tcgggtgagt ctgcggattt cgcccaggtt gaggtgatgt tttcgatgtt ggaggctgcc   22860
gcaccggctg acgcggtgga tgctttggag gggcttccta tggttcgtgt tgccgagatt   22920
ttccgcgagt ggatggaata taagcctgac ggtaaggtg cctcgctggg ggaatagttt   22980
ggctccacgg cctgattgat gattatcgtg gggccatcga atacgatttc cgcaccaagt   23040
ttggtgtttc tgtttatagt gttggtgcc cgcagatgtg ttggggtgag gctgtccggc   23100
tggctggcgt gttgtgtacc gatacgtcta gccagttggc ggcccatctg aatggttggc   23160
agcgcccgtt tgagtggtgt gagtgggctg tgttggacat gttggatcat tacaggtctg   23220
ctaatagtga ggggcagccg gagcctgtgg tgaggccgac ggatgagcgt agggcccggt   23280
ttacgtctgg gcaggtggac gatatttggg cgcgtgttcg tgctggtggc ggggtgtctc   23340
gcgagattaa tattatgggg tgaatagtgt atgtctggtg agattgcttc cgcgtatgtg   23400
tcgttgtata cgaagatgcc tggccttaaa agtgatgttg gtaaacagct ttctggggtg   23460
atgcctgcag agggtcagcg ttcggtagc ttgtttgctg gcgggatgaa gttgcgcgtt   23520
ggtggtgcgg cgatgatggg tgccatcaat gttgctaaga agggcctcaa gtcgatttat   23580
gatgtgacta ttggtggcgg tatagctagg gctatgctta ttgatgaggc tcaggctaaa   23640
ctgactggtt tgggtcatac gtcgtctgac acgtcttcga ttatgaattc ggctattgag   23700
gctgtgactg gtacgtcgta tgcgtttggg gatgcggcgt ctacgcggc ggcgttgtct   23760
gcttcgggtg tgaagtctgg cgggcagatg acggatgtgt tgaagactgt gccgatgtg   23820
tcttatattt cgggtaagtc gtttcaggat acgggtgcta tttttacgtc tgtgatggct   23880
cgcggtaagt tgcagggcga tgacatgttg cagcttacga tggcgggtgt tcctgtgctg   23940
tctttgcttt ccaggcagac tggtaaaacg tctgctgagg tgtcgcagat ggtgtcgaag   24000
gggcagattg attttaacac gtttgcggct gcgatgaagc ttggcatggg tggtgctgcg   24060
caggcgtctg gtaagacgtt tgagggcgct atgaagaatg ttaaggggtg cctgggttat   24120
```

```
cttggtgcta cggctatggc gccgtttctt aacgggttgc ggcagatttt tgttgcgttg   24180
aatccggtta tcaagtcggt gacggattct gtgaagcccc tgtttgcatc ggtggatcag   24240
gggattcagc ggatgatgcc gtctattttg gcgtggatta accggatgcc gggcatgatc   24300
actcgaatga atgcacagat gcgcgccaag gtggagcagt tgaagggcgt ttttgcgagg   24360
ctgcatttgc ctgtccctaa agtgaatttg ggtgccatgc ttgctggcgg caccgcagtg   24420
tttggtattg ttgccgccgg tgtgggaag cttgttgcag ggtttgcccc gttggcggtg   24480
tcgttgaaga atttgttgcc gtcttttggt gctttgaggg gtgccgctgg ggggcttggt   24540
ggcgtgtttc gcgccttggg tggccctgtt ggtattgtga tcggcttgtt tgctgccatg   24600
tttgctacga atgcccagtt ccgtgccgct gttatgcagc ttgtggggt tgttggccgg   24660
gctttgggc agattatggt cgccttgcag ccactgttcg ggattgttgc tggcgtggtt   24720
gccaggttgg ctcccgtttt tggccagatt attggtatgg ttgctggttt ggcggcccgg   24780
ctggtgcctg ttattggtat gcttattgcc aggctggttc ctgttatcac ccagattatt   24840
ggtatggtaa cccaggttgc tgccatgttg ttgcctatgc tgatgccggt tattcaggct   24900
gttgttgctg tgatacggca ggttattggt gtggtcatgc agttgatacc tgttttgatg   24960
ccggttgtgc agcagatttt gggtgctgtc atgtctgttt tgccgccgat tgttggtttg   25020
atacggtcgc tgataccggt gatcatgtcg attatgcgtg tggtggtgca ggttgttggt   25080
gccgtgctac aggtggtggc ccgtattatt ccggttatta tgccgattta tgtttcggtg   25140
attggattca ttgccaagat ttatgctgcg gttatcttt tgaggctaa ggttattggc   25200
gctattcttc gtactattac gtggattgtg aatcattcag tgtctggcgt gaggtctatg   25260
ggcacggcca tccagaatgg ctggaatcat atcaaatcgt ttacgtctgc gtttattaac   25320
ggtttcaagt cgatcatttc tgccggtgtt gccgcgttg tggggttttt tacgcggctt   25380
ggtttgtcgg ttgcctccca tgtgaggtct ggtttttaatg gcgcccgtgg agctgtttct   25440
tccgctatgg gtgcgattcg gagtgttgtg tcttcggtgg cgtctgctgt tggcgggttt   25500
ttcgggtcga tggcttctcg ggtccggaat ggtgctgtgc gcgggtttaa cggggccagg   25560
agtgcggctt cttctgctat gcatgctatg gggtccgcgg tgtctaacgg tgtgcatagt   25620
gtgctgggt tttcccggaa tctgcccagc aatattaggg ggccttggtg tagtatgggg   25680
tctttgttgg tgtctgctgg ccgtgatgtg gtggccggtt tgggtaacgg tattaagaat   25740
gctttgagtg gcctgttgga tacggtgcgt aatatgggtt ctcaggttgc gaacgcggcg   25800
aagtctgtgt tgggtattca ttctccgtct cgggtgtttc gtgacgaggt tggccgtcag   25860
gttgttgccg gtttggctga gggtattact gggaagtgc gtttggcgtt ggatgctatg   25920
tcgggtgtgg ctggtcggct gccggatgtt gtggatgccc ggtttggtgt gcgatcgtct   25980
gtgggctcgt ttaccccgta tgaccggtat cggagtgcga gcgagaagag tgttgtggtg   26040
aatgtgaatg ggcctactta tggtgatcct aatgagtttg cgaagcggat tgagcggcag   26100
cagcgtgacg cttgtgaacgc gttggcttac gtgtgattgg gggtgttgtg catgtttatt   26160
cctgaccctt ctgatcgtgc cggtttgact gttacttggt ctatgttgcc gttgattgtt   26220
aatgatcctg agcgtgtgct tcatttgacg gattatacgg gtgcgtctcc tgtcatgttg   26280
ttgaatgatt cgttgcgtgg ccttggtgtt cctgaggttg agcattttc tcaaactcat   26340
gttggggtgc atggctcgga gtggcgcggg tttaatgtga agcctcgcga ggtgacgttg   26400
ccggttgtgg tgtcgggtgt cgacgaggat ccggtgggcg ggtttcgtga cggttttttg   26460
aaagcctatg atgcgttgtg gtctgctttt cctcccggcg aggaggggga actgtccggtg   26520
aagactcctg ccggcaaaga gcgtgtgttg aagtgccggt ttgattcggc tgatgacacg   26580
tttacgtggg atccggtgaa caggggttat gcccgctatc tgttcatttt gacagcttat   26640
gacccgtttt ggtatgggga tgagcaaaag tttcgtttca gtaacgcgaa gttgcaggat   26700
tggttgggtg gcgccctgt cggcaagaag ggtaccgcgt ttcctgtggt gttaacaccg   26760
ggtgtgggct ctgctggga taacctgtct aacaggggtg atgtgccggc gtggcctgtg   26820
attcgtgttg agggcccct ggagtcgtgg tctgtgcaga ttgatggttt gcgtgtgtct   26880
tcggactatc cggtggagga gtatgattga attactattg atacggatcc tcgtaagcag   26940
tctgcgttgt tggacgggtt tgaggatgtg atggatcgtt tgacggagtg ggagtttgct   27000
cctattcctc cgggtggttc gaagagtgtg aatattgaga tggttggttt gggtgccatt   27060
gttgtgtcgg tgcagtacag gttttttgagg gcttggtgaa tggttgatgg ctggtcttgt   27120
tccgcatgtc acattgttta cacctgatta tcgccgggta gccccatca attttttgg   27180
gtcgctaaaa ctgtcgttga agtggaatgg tttgtccact ttggagttgg tggtgtcgag   27240
ggatcattcc aggcttgacg ggttgacgaa gcctggggct cggctggttg ttgattatgg   27300
tggtggccaa atttttttctg ggcctgtgcg taaagtgcat ggtgtgggtc cttggcgttc   27360
ttcccgtgtg actatcacgt gtgaggatga tatccgcctg ttgtgcgta tgctgatgtg   27420
gcctgtgaat tatcgtcctg gtttggtggg ttcggagtgg cgtgcggacc gggattatgc   27480
ccactattcg ggtgcggctg agtcggttgc taagcaggtg ttgggggata atgcttggcg   27540
ttttccgcct ggtttgtttt tgaacgatga tgagagtcgt ggccgctata ttaaggattt   27600
tcaggccgg tttcacttgt ttgccgataa actgttgccg gtgttgtcgt gggctcggat   27660
gactgtcacg gtgaaccagt ttgaggatgc gaagtttga cagcgtggtt tgctgttgta   27720
ttgtgttccg gctgtgactc gtgagcatgt gttgactgcc gagtcgggtt cgattgtgtc   27780
gtgggagtat gtgcgtgacg caccgaaggc tacgtcggtg gttgtgggtg gccgcggcga   27840
gggccgggac aggctgtttt tgaggatgt tgattcggcg gccgaggagg actggtttga   27900
tcgtgtagag gtgttttaagg atgcccgtaa cacggattct gagaaggtgt ctctcgttga   27960
tgaggctgag caggtgctgc aagagtcggg ggcacgtcg gggtttaaga tcgagttggc   28020
cgagtcggat gtgttacggt ttgggcccgg caatctgatg cccggtgatc ttatctatgt   28080
ggatgtgggc tcgggcccta ttgcgggagat tgttcggcag attgatgtgg agtgcgattc   28140
gccgggtgac gggtggacga aggtgactcc tgttgctggg gattatgagg ataatccgtc   28200
ggcgctgttg gctcgccgtg ggctgcggtt tgctgcggt tacaaaaatt   28260
ctaattgttg ggggttttgtt gtgggtattg tgtgtaaagg gtttgatggt gtgttgaccg   28320
agtatgattg ggctcaaatg tctggtctga tgggtaatat gccgtccgtt catgcccggg   28380
atgattttcg tgtcggcacg acgattcagg gttccacggt gtttgtgtgag gtcctgccgg   28440
ggcaggcttg ggctcacggg gtgatgtgca cgtcgaatgc tgttgagacg gtgacaggtc   28500
agcttccggg ccccgggtgag acccgctatg actatgtggt gttgtcgcgg gattgggagc   28560
agaatacggc gaagtggagg attgttcctg gtgggcgtgt tgagcgtgct agggatgtgt   28620
tgcgtgcgga gcctgcgctg ttccatcagc agttgttggc tactttggtg gtgtcgtcta   28680
acgggttgca gcagcagctt gacaggcgtg ctatagctgc ccgtgtggcg tttgggagt   28740
ctgctgcgtg tgaccctacc cctgtggagg gtgaccgtgt gatggttcct tcgggggctg   28800
tgtgggctaa ccatgctaac gagtggatgc tcctgtctcc tcgggttgag acgggttcta   28860
```

```
agcagatcca gtttggcggg tctgctgtgt atgcttacac gatcccgttt gcccggccgt  28920
ttagtagccc gcctatcgtg gtggcgtcta tggctacggc ggctgggggc acgacacaga  28980
ttgatgtgaa agcctacaat attactagca aggattttag tttggcgttt attacgaatg  29040
atggttcgaa gccgaatggt gtgcctgcgg cggctaattg gattgctgtc ggcgtgtaat  29100
gtacggcttg cgtgtgcggg acgtgttgtg gtggttgtga tggtaggggg ctgtagtgtc  29160
atggtttaca cctacgcttg tggcctctct ttgtaccgct atcgctactg ttcttggttc  29220
gattcaggcg gctatgtaca ggtcgaagaa gaggcttagg cagttgtctg cgcaggttga  29280
tgcgatggaa gagtacacgt ggaatattcg ccatattgtt caccgctata acgcgaattt  29340
gccggatgat gttgagcgg tgaagatgcc tgatttgccc gagtttttga aggatactgt  29400
tgatgtggt gggggtgaa ttgtgaggga gttagaggag gagaagcggc agcgccgctc  29460
gtttgagaag gcttccctga tattgttgtt cttgtcgctt gtcctgttgg cggtggttgc  29520
cgggggtgct ttacgtttcg gggctgtatc ctctgagcgg gattcggagc aggctaaagc  29580
ccagtctaat ggtacagccg ccaggggttt ggctgcccgt gtgtggcagg tgtgtgcttc  29640
tggtggatgg gagtctgtgc ggcttcacca gtctggtttg tgtggatgt ctgtgcgtgt  29700
tgagcggagt gtgcagggtg ttccgggtcc ggctggtgtg cgtggcccgc aggggccggc  29760
tggtgttgat ggccgggatg gtagcaatgg ttctgctggg ctggttgggc ctgttggtcc  29820
gcagggttcc cctggcttga atggcgtgaa gggtcctgac gggctgcccg gcagtgacgg  29880
ccaggatggc cgtgatggtg ttccgggccg tgcaggagtg gacggtgtga acggatccga  29940
tggcaaggat ggtcgtgatg gttcggctgg tgagcgcggc gatgtgggc cttcgggtcc  30000
tgccggaccc cctggc                                                 30016

SEQ ID NO: 74           moltype = DNA   length = 29913
FEATURE                 Location/Qualifiers
misc_feature            1..29913
                        note = PAC13
source                  1..29913
                        mol_type = other DNA
                        organism = synthetic construct
SEQUENCE: 74
tgagcgtggc cccgccggtg tgaatggatc cgatggtaaa gatggtaagg atggccgctc    60
ggtggtgtct gtgtactgtt ctgatggtcg cctggttgtg aaatatagtg acggtgtggc   120
ttctaccata tcgggttcgg tggcctgcca gggtgtgaaa ccgtcgccta tagtgactat   180
atcatcccaa aaatagaaag gagtggctgt gatggtagtt tttggtggtg gtgtgtggtg   240
agatacattc ctgcagcgca tcactcggcc ggttcgatca gtccggtgaa cagggttgtg   300
attcatgcga catgcccgga tgtggggttt ccgtccgcct cgcgtaaggg tcgggcggtg   360
tctacagcaa actattttgc ttccccatcg tcgggtggtt ctgctcatta tgtttgcgat   420
attagtgaga cagtgcaatg tttgagtgag tctacgattg gttggcatgc cccgccgaat   480
ccgcattctt tgggtataga gatttgcggc gatgggggtt cgcacgcctc gttccgtgtg   540
ccggggcatg cttacacgag ggagcagtgg ctggatccta gggtgtggcc tgcggtggag   600
aaggctgcca tcctgtgtag acgtttgtgt gacaaatata atgttccgaa aaggaaactg   660
tcggctgccg atttgaaggc cggtaaacgt ggtgtttgcg ggcatgtgga tgttacggat   720
gcgtggcatc agtcggatca tgacgatccg gggccgtggt ttccgtggga caaatttatg   780
gctgtggtga atgccacgg cggcggttca agtagtgagg agttgagtat ggctgatgta   840
caagcgttac atgatcagat taaacagttg tcggcacagg tggcccagtc ggtgaataag   900
ctgcatcacg atgttggtgt ggttcaggtt cagaatggtg atttgggtaa gcgtgttgat   960
gccttgtcgt gggtgaagaa tcctgtgacg gggaagctgt ggcgcactaa ggatgctttg  1020
tggagtgtct ggtattacgt gttggattgt cgtagccgta ttgacaggct cgatctgct  1080
gtcaacgatg tgaaaaagtg atggtggttt gtggtgggta aacagttttg gttgggcctg  1140
ctggagcggg cgttaaagac ttttgtgcaa acgtttgtgg ctgtgttggg ggtgacggcg  1200
ggtgtcacgt atacggcgga gtcgtttcgt ggtttgccgt gggaatcggc cctgatcaca  1260
gccggggttg ctgcggtttt gtcggttgct acctcgtttg gtagcccgtc gtttgtgcg  1320
ggcaaacctg gcaagcagcc cctggtggat gaggggtttgg ttccaccgga tgatcctgga  1380
atagtggagt ctcactcggt ggatgtgtcg gatcctggca tgatcgagcc gacggatgat  1440
gcggatcttg tgtaggctat gtgccgaaa catgctgccg agtcggaggt tggcatgata  1500
gagtctactg ttgcataagt gaatatagat gtgtgcccca gcggtgctgc cacggttgtg  1560
tggtggttgc cgctggggca ctcttttat gttctatagt attctatgat tcgttgctgt  1620
cgatggtgtc ttcgagcatc tggtacaggt ggaggcaggt agagatagtt tcgctggcct  1680
ggtcgagaac ggttcggccg ataacgtttt tgtgattgtc gcggtggcgg atgatagccc  1740
acatgatctc ctcggccgcc gcctgcaata gtttggcctg gtatgcgatc ccggcgagcc  1800
agtctagtgc ttccgggctt gcatgggggc tctgttgccg cggtgttgc  1860
tgttgtttgt ggggtgtcct gcactgtcgc ataaccacag gatttcgctg cactcgtcta  1920
gcgtgtcctg gtcgatagcg agatcgtcga ggctgacatt ttgacggta aggttcacgt  1980
tgtcgaggga gatgggtaca ccgtactggt tttcgacact gtcaacaatg ttttgtagtt  2040
gttgcatgtt ggtgggctgt tgttggacga tgcggtgtat cgctgtgttg agggtggtgt  2100
aggtgatgtt gtgtgtgttg tccatgggttt ttatgccatt ccttcgttat cgtctggcat  2160
gtagtatgtg ctgtttgcgt actcggttaa cgtcatcagt gtttggtctg cccactgttt  2220
cacagtctgc cttgtcactc cgagtcgttg ggcggcagac gcatatgttt ggtcataccc  2280
gtacttcc ctgaatgctg ccaaccgtgc caaatgtttt cgctgtttgg atggctggca  2340
ggtgagggtg tagtcgtcga tggctagctg tagatcgatc atggtaacga tgttgttgcc  2400
gtggtgttgt ggcgcggttg gtggggtggg catgcctggc tccacactgg gtttccatgg  2460
tccgccgttc cagatccatt gggcggcttg aataatgtcg gcgtagtat aggttcggct  2520
cacttggtca cccccctgaac aggtcgttgc tggtggtggt gtcgaatcgt ccgacgcagt  2580
ggcagtagtc gtacatgagt ttaataatgt gttggtggtc tcccaaatag gtgtttccgc  2640
tgatactgta ggtgctgtg ccgtctttac tgatggtgta tttggcggtg atggtttcgg  2700
ggttttcggt gtcggtcgatg atggctgtgg tggtggcacc tactgtttgg agcacggttg  2760
tttgggttcc gtcgtcgatg gtggttttaa ccatgaggtg ttctcccttt gtgttagttg  2820
ctggtttggt tgtcggctag atgaatgatg tcgggtaagg gttcggctg gtcgaggtgt  2880
tgtatggttt tgttggctag ccgttgggct acctgtaac acattttggt gtagtgtttg  2940
ttgtctaggt tgtggtattg ttcccgcacc gcaatatata gcaggagtc ttggtatagg  3000
```

-continued

```
tcgtctgcac tgattgcggg gtagtgtgcg gctactttgg tacatgcccg gttgagtgtg   3060
cgtagatgat ggtctgtggc ccacacccaa gatgcgtgg tggctaggtc ggcttttgtt    3120
ggtcgtctac tcatggcatc tctttcatct ggctatctgg tagttgtttg gtgttttgtt   3180
gttgatagta tagcacacga gcccggggtt tccggtggtg cccgtcttgt gccggtacca   3240
tgtggattcg ccttccatgg atgggcattg gatgaagtg cgttgtcctt gctcggagat    3300
ttctaggtgg tgccggtgcc ctgccatgag aatatgggat gtggtgccgt tgtgaattc    3360
ttggccgcgc caccaatcat agtgtttgcc ggtcgccat tggtggccgt gggcgtgcag    3420
tatccgtgtg cctgccacat caacggtggt ggtcatttcg tctcggctgg ggaaatggaa   3480
gtgtaggttg gggtattggt tgttgagctg gtaggcttct gcgatggcgc ggcagcagtc   3540
tacgtcgaag gagtcgtcgt aggtggtgac gcctttgccg aagcgtacgg cttctccgtg   3600
gttgccgggg atggatgtga tggtgacgtt tttgcagtgg tcgaattggt ggatgagttg   3660
catcatggcc atgcgggtga gcctgatttg ttctgtcagg ggtgtttggg tgcgccaggc   3720
gttgttgcct ccttgtgaca cgtatccttc gatcatgtcg ccgaggaagg cgatgtggac   3780
tcgttcgcgt ttgcctgcct gttgccagta gtgttttgcg actatgaggg agcgtaggta   3840
gttgtcggcg aagtgtgctg tttctcctcc ggggatgcct ttgccgattt ggaagtctcc   3900
cgccccgatg acgaaggccg cggtgctgta gtcggtgtgg gtgtcttgtt cgggttttgg   3960
gggtgtccat tcggctagtt tatcaacgag ttcgtctacc gggtagggt tggttgctgg    4020
ttggtggtca ataattttt gtatggatcg gccggtttct ccgttcggta aggtccattc    4080
ggagatgcgt gtgcggcgca cggtgccgtt ggctagattg tcgtcgatgg tgtcgatggc   4140
gttgtcgtgg ttggctagct gtgtgagtag ccggtctatg ttgtctatca ctgggtatcc   4200
tcctcgtgtg tggtggtggc ttgtttgcgg cggtagtctt tgataacggt ggcggagatg   4260
gggtatccgg cttgggtgag ttgttttgct agccacgagg ggggatggt tttgtcggcg    4320
agcacgtctg cagccttatc accgtagcgt tggatcaatg tttcagtttt ggttgccatg   4380
atgtcctatc ggctgtgtgg cgggctgcca tcctgtgcgg cagtcgccgt cgtgtcctgg   4440
tttgcgggtg caccacgata cggttccgtc tgtgtggtgt agtgttttgc cgcacaggac   4500
gttttggaga tgctccggca gctggtcatt ctggttgctg gtttgtgtgt cgaagagtgt   4560
tttctggttg gtgaaatgct cggacacggt gccattatgc acgggtagta tccatgtttt   4620
ccattgttgt tgcatccggg tgttccagtg gaattgtttg gcagctgtct cggcttgttt   4680
ggcggttttg tagtagccga ctagtatgcg ctggtgttca ctgtcgggcg ggttttggcc   4740
tcgccagtat tgtgccgcaa ccgcgtacct gttgttgtcg gtgaagcgct gccagcagta   4800
ttcgatgatg tgttgcagta cactatcggg aattttttgt gtttggtttt cgttgagcca   4860
ttcggcttcg atgatgccgt gtatggcgcg ttttgtcttg gtggtgggtt tgaacgagat   4920
gctcacgata gtaccggctg atcgtcttgc atgaactggt tgaaggtgtt gttcccggcg   4980
tgttgggctt gtgtgatttg ctggtcggtc cagtctgggt gttgctgttt cagatagtgc   5040
cagtggcacg cattgtaggt ttcgtcttgt agccgtgtga gatggttttc ggtgatgatt   5100
tgtttccaca tagtccatga cacgtcgagc ctgttgagga tttctatggc tgggatgttg   5160
aattggtcga ggaagaggat ttcgtgggtg tagtagtttt tctcgtaggc gtcccatccg   5220
cttcggtgcc tgttgggctg gtttttgggg taggcttccc ggcatacttt gtgtaaccgt   5280
ttggccatgt cgtcgggtag tttaatgtcg gggttggcgc ggatcatgga tcgcatccca   5340
tcataggtgg tgccccaggt gtgcatgatg taggtggggt cttcaccatc ggcccatttt   5400
tctgcacaga tggcgaggcg gatgcgcctc ctggctgttt ggctgatgtt cgccggttg    5460
gggatggggc acgtgtcgag gggatccatg atgtttttta tgcctttctt ggtttcgtgt   5520
tgttgacggg ttttactgta gcacagtgtc tagtgcttgt gtcaaccctg ttttttccggg   5580
ctgcaggtag gtgtctgtga catcccccag ggtgaggggc acgtgggtgg cttggggggag   5640
tgctgcctgg agggtttgtg ccatctgtc gcctgctttg tctgggtcgg accagatgta    5700
gatgtggtcg tagccttcga agaatttggt ccaaaagttt tgccacgagg tggcgccggg   5760
tagtgctacg gccgaccatc cgcattgttc gaggatcagg gagtcgaatt cgccttcgca   5820
aatgtgcatt tcggctgccg ggttggccat ggcggccatg ttgtagatgg agcctgtgtc   5880
ccctgccggg gtcaaatatt tggggtggtt gtgggttttg cagtcgtgcg ggagtgagca   5940
gcggaaacgc attttttcgta tttcggctgg ctgtccccaa acgggtaca tgtatgggat    6000
ggtgatgcac tggttgtagt tttcgtggcc tgggatgggg tcattgtga tgtatccaag    6060
gtggtggtag cgggctgttt cttcgctgat gcctcttgcc gagagcaggt cgagtatgtt   6120
ttcgaggtgg gtttcgtagc gggctgaggc tttctggatt cggcggcgtt ccgcaatgtt   6180
gtaggggcgt atgctgtcgt acattcgggt ttttttttctc tagtcgttgt tgtagtttgg   6240
cgagtcctcc tccgataccg catgtgtgcc agtaccagac gcccttgtcg aggttgatgc   6300
tcatggaggg ctggtggtcg tcgtggaacg ggcagaggat gtgttgctca ttcctagacg   6360
gattgtaccg tatctggtag gtgtcgagga ggcggcaggt gtcagaggtg tgggaggagc   6420
tcgttgaggg ttgataccac ataggcttcg ctccatggct tgttgcgttg tttcatgacg   6480
acgagtccga tggtggactg gttttcgcgg tttcggtgtg tttcgtagtt gcgtgcctcc   6540
cggctggctt gtttcacgaa ttgggctagg tgggggttgtc ctgctttcgc ctcgataagt   6600
taggttttat ggccggttgt gaggatgagg tcgccttcgt cctctttacc gttgaggtgg   6660
aggcgttcta tatcatggcc ggtgtcgcgt agctggtgca ataatcgtgt ttcccattct   6720
gcgcctgccc tgcggttgcg tgactgttgt gtcgacatga tagtccttg tgtgttgtgg    6780
tcatgttcca tggctgtttt tcggcgagtg gcccgaagaa tgtgtattcc gggtatgccc   6840
tgagccgctc atattttgtt ccgtctgggc tggatttgcc tgtgcgctgt ttcaacactg   6900
agatgcgtgc ctcggcgggg atcgtgagcc cgttgccgtt atcctcgcca ccataaagtg   6960
agactcccaa tatgagttgt ggttttcgg agaggccgtt tttgatttcc cgcctagccg    7020
ggggggtgttc gatgtcggtg ccggttttgt cggtggcgtg gtgggtgaca atgatggtgg   7080
agccagtatc tctacctaat gctgtgatcc attgcatggc ttcctgctgg gcctggtagt   7140
cgctctcgca gtcttggatg tccatcaggt tgtcgataac gatgatgggt gggaaggtgt   7200
tccacatttc catgtaggct tgcagttcca tggtgatgtc tgtccatgtg atgggtgact   7260
ggaatgaaga tgtgatgtgt tggccgtggt ggatgctgtc tcgatagtat tctgccccgt   7320
agtcgtcgat gttttgttgt atctgtgtgg tggtgtgttg ggtgttgagt gagatgattc   7380
gcgtgagacg ctcccagggt gtcatgtccc ctgatatgta gagggcgggc tggttgacta   7440
tggcggtgat gaacattgct agcccggatt tttggctgcc ggaccgcccc gcgatcatga   7500
ctaggtcccc tttgtggatg tgcatggtcca ggttgtcata caagggtgct agttgtggta   7560
tgcgggggcag ttcggcggct gtttgggagg ctctctcgaa ggatcgttgg agagagagca   7620
tcggagcctt aatctatctg tctatcggtt ggatgatgtt ttggtggtca gatggagtcg   7680
atgtcgatgt cagcatcagc aggggctgtg gtgtcgtcta gctgaccgtt atcgcgtttg   7740
```

```
tctacgtatt cggcaacctt atcgtagatg gcgtcatcga gggtttgag cacgaccgcg   7800
ttgaagccgt tttttggtgcg cacggtggcg agtttgaagg cctgctcctc gccaaggtag   7860
gcttcgaggt cgcggatcat ggagtgtggg cggtcgttgt tgccgcgggc tttctcaatg   7920
atagcgttgg ggatggtttc tggggtgccg ttgttgagat cctcgagggt gtggaagata   7980
gtcacatcag cgtaaatacg atcggcggtc tgtccaccgt agccttcggt gttgtgttcc   8040
acgtcgcgga ttttgaaggc gatggcggtg gcgtcctgct tcgggagggg gttgaagaag   8100
gtgctgttgc tgttgttgcg gtagtttgcg agtccattgt ttgtttcctt tactgtttgt   8160
gttgttttgt ttgttggttt gtgtcggttt ttatcgggtg aggctgtttc gtttgctgcg   8220
gaaagcctca gacacgtcac tgttactagt gatggtcttc ttgtactgtt tgaggaggtc   8280
ggctagctgt gccttgcttg ttgcattgtt gattttgtcg atgacgatgc tgttttcttt   8340
ggatgcgatg ttgtccacgt agtctttggc ggcctggttg tatcggtctt ggaggatgat   8400
ggatgctgtg gcgatcaggg ttgccaggtc ccagttcctt gccgcggagc tgttttttgag   8460
tccgcctagc aggtcgatga tagtcttctt tacctggtcg gcggtgtctc cgcggatgac   8520
ggtccatggg gcggcgtagt cgcctccgta tttgagtgtg acggtgaatc gtcgtcgtc   8580
tgtgttgtcg gtcactggtg ctccttgcct tcttttgttg gggctgtgat ggtggtttct   8640
atagggtacc tgtaggcgtc tttcccgtta acagcccagc aggcgtcctt gacggggcat   8700
cctttacaga gtgctgtgac gtggggtacg aagatgcctt gactgattcc tttcattgct   8760
tgactgtaca tggatgatac atgccggtag tgttgttgt caagatcgta cagttcgggg   8820
gatgtgccct gttcgaccga ttgctcgtcc cccttggtgg tggcgggtgt ccaaaacatg   8880
cctttcgtca catcgttgcc gtgttgggcg agcatgtacc ggtaggtgtg cagctgcata   8940
ctgtcggcgg gtaggcgtcc tgttttgagg tcgagaatga aggtttcgcc agtgtcggtg   9000
tcggtgaaaa cgcggtcgat gtagccaacg atctgggtgc cgtcctggag ggtgtttct   9060
accgggtatt cgatgcctgg ctggccgtct aggattgcgg tgatgtattc tgggtggttg   9120
cgcctccatg ttttccagcg gtccacaaag gtggggccgt acatcatcca ccagtcgtag   9180
tcttcttgt gtgcccgcc cgactcgcac atgtttttgc atattctgcc ggagggttg    9240
attctgtgc cttcggattc ggcgagggc acttgggtgt cgaaaatgtt ttgaaggat   9300
gagagtttgt ttggtagtgc agggtattcg gtggggttgt acaggtgtag gtcgtattgt   9360
tcggtgatgt ggtgtatggc gcttccgggcg atggtggcat accaggtgtg gtgttgggca   9420
tggtagccgt gggataggcg ccattttca ccacattcgg cccactgtga cagtgatgag    9480
taggagatgt ggcctgatg gtggatggtt ttcgggtatt gtgctagggg cattactggt   9540
cgcctttgtg ggtgttccat gggtttcggg tgtcttggcc ggcattgtgt tgctggtagg   9600
cgaggagtgc gaggcagtgc caggcagcat gggctagatg gggtagcccg gattcgtggt   9660
cgaggttgtt gccttgctgc catgatagta ggtgcctgta gagggcgtcg acgctgtggc   9720
tccacgggta tccgccggtc cagttgttgt cgccgtattt ggtggcaccg tagcctgcgg   9780
cttcgccgag ggcgtgtaag gctgcgggt cgatgagggga gagtcggcat agtttgagtt   9840
ctttttttggc gcctgtgtct gggttggtgt acatgcgggt gggcttatcc atgggtgtg   9900
tgctccttag gggtggggta ctggttgggg ttgtgggcga gtgctacggc gaggatgatg   9960
atggcgaggg tttctgcgat gatgatgggt gttgtgatca tttggtgtct cggggattgt   10020
tggtgaggct tgaggcgcct aggaggggtgg tgagggcga tgcgcggtg atggcgaggg   10080
ctgccttgtg tggggtgccg gttgcgtaca tccatgtgat gatggcgcct tggatccatg   10140
ccagtgtggt gaagaatgtt tcgtagctgt gtagctcgct tttgttgctg gtgatgtcat   10200
tcatggtagt ttttctgcttt gtgtgcgatg gttgtgtaca tgtcgttgag tgtggtttcg   10260
atggtgatga gagtgttgat ttcttggttg aggtcgatgt tgtctttgag ggtgttgttg   10320
cgggcggcga tgtcggtggc ggtgcgtagg cttactgctg caccgtggat gatgtggcat   10380
atgtcggtga ggccgacttt ggcgatgtag tgtgacatga gaggcatagc ggggatgctc   10440
cttggcgggt tactgttgcg ggttgatgtt gaggtcggtg acgttgggt ggtcttctgt   10500
tccggtgacg aggcagtgga cggtgactgg gagtttgaat ggtcggcat gtttcgcggt   10560
tgcgccgtag acgatggaga aggtgtcttt accaataatt ttgtggagtt ggaggtcgat   10620
gtcgggggttg ccgttccagt tgacaccgtg tgctgcggcc tgctgttcgg ctttgcggtt   10680
gcaggtgtgt gctgcggtga tcatggtgag accctgtgag gtttcttcac cccttgcttg   10740
ggcttgccgg tgggttttct gctgttcggc tcgcagtgac tgttctgcgg cggcctggcg   10800
tgctttcttt tcggctttgc gctgttggat agtcttgggt gtccattcgg tgttggctgt   10860
ggtggcttgc ggtgcgggct gtgatgcgag tggcggattg tcgtcgggtg ctggcaggaa   10920
ggatgctgcg gcgatgatgg cggctgtgat tccggcgatg gtgtagcctg ttttcttgtt   10980
catggcttttg tgttcccctt tccggggtgt tgttcgttgc tgacatgatt aatactttca   11040
gcggctgggc ccactgtcaa ggctgcgctc agtttgcgtg agcgatactt gtgtggctag   11100
gggtgatggc ttcttttcgcc caataggatg tgccaccgct ggtccagtat ccgagtttgt   11160
tgcgctgcat gcccttggcg tccatctcgt cgatcgtgag gcacctgcga cgactggggc   11220
ctgtcttgac tccatggtcg cctacccggt gcatctcgcc tgaggtggta ctcgtgaatg   11280
tttcgtggca gattgtgcag tgctctggct tgtatccgat gatggtgcta tcgcacttgt   11340
ggcatgtcca ttgcatgatt gctcctattt tccattataa gacttcctgt agtgccattt   11400
tagcgccttg cgagtcttgg gggtacaact atataggtcg ggtatttcta ggcgattcta   11460
ggctcgttgt gtgtggttgg gggtttatcg ggcgcacagg gtgagcaggc ttccgatgtt   11520
gatgcgtatc acattccagt agagttgtgt ggcttcaccg tgggcaggtg gcttccactc   11580
gtcatggctg aacacggtgc catcggatgc gatgaacgtg ttgggcgta gcttgtggag   11640
ttcagtctct acacgctgcc ggtaggcttc ggcgaggccc tcaaaatcca tgtggtcgca   11700
ggagaggttt tcgaagcgtg tcaagtcgat gggtgtgggg cagtcgtcgt tggtgggggt   11760
gtagagctgg gtgaagtggt tggcgatcct ctgcatgacg ggttcctttt ctcgtgtgat   11820
gggttgatag tttatcgggg ttgcggcggc aataatggca tccacgtcga tcatgtcgat   11880
catgtcgttg agttcctcgg cctcattctc ggagaggtgg cgccagccat agtcgccgta   11940
tacggcgccg tcgagggtga cagtccacag gggccggatg agtcgtacgg cttcttcgac   12000
tttggcgtgg tacatgcggc gcaccatatc cagatcgatg tcgtctgaat ggtttccggt   12060
gaggctgtgg aagctgagcg ggtcgatttc tgtctgcctg tcgaggctgg tgaatgatgg   12120
tgtgatgagt gtgcatccta taggtgtgt gctccttttg ggtgtgggaggg ggttgttgtg   12180
gtttctagag tgtgtaggtt gcgacccac agtcaaggtg gcgctcattc ggattgagcg   12240
tttcatggaa ggtgacggat gtcactgaag ccttgatggc ctctctcatc gcctgaaatc   12300
ttctagaggt aggattatgc agggtttacc ctgctgatcg attctagggg ccttctaggg   12360
cgtctcaggg gtgtatctgg gtgatagcag gtccggtaga tctatcttgg ctttcatgac   12420
gggggtcgag gtgccagatc tggtcatgga atccacaccc tcatactgtg tgagatgtat   12480
```

```
cacatcctcc tggcttggtg tgccctctcg aggctactct gccgatctgg cgtgaagggt   12540
gtagcccaga aatgccgttt aaagcctccc tatggcgcct aggagcgcct tacagagtgg   12600
gggctaggta ttcataccccc caagcaattc tgatcgattc tagacgcctc ccagagcctg   12660
atacacgatc aaccatctcg gcatagacca gcagccccta tcctggttag ctaagcctca   12720
actatgtgga cagtgtggga tactaagggg gaagaaggac acggtaaaag aaagagggg    12780
agcatcagcc ttagggtctt agcacttagc gcttagcacc gagcccctca agggctcggc   12840
atcagcccga cagcccgagc aggctcagcc gatcaggcac agccctgaaa ggggtacacg   12900
ccatcaggga aggcttgaga gtacgaggag ccctagcgac gagtactcga aagcctgagg   12960
gaacacccat cagcactgat gggcctagcg tgttcggaaa ggacacaaga gtacagtgga   13020
acagctgttc gggagtgaaa cctgttctga ctaggggttt cagccttaac cacccctcaaa  13080
ggttacaaga ctctaagaaa atttaaggaa aagtttaggt ttaattttg gacctttact    13140
accaaaaaca cccgtttaca cccctcaaac ccgcctatag agccaaaacc accagtttga   13200
ctcatcccag gtggggtatg ataggctgga caggtagcca gctggacgca aggccgaaat   13260
ccgctgacgc ggcttacc cttacatcca tcagtctacc aaagacttaa aagcttaaca   13320
gctaagcgct aagcccttaa gaccttaaca cttagcaccg agccctcaa gggctcggca   13380
tcagtcttaa agccttaaac acttaaagtt ataaataaac attaaagctt taaagtctta   13440
aagtaaatat ataaccttaa cagttaaacg tttaaagctt taaacttaa cacctaagtt   13500
aagtataaaa ccttaaaggc ttagcactta aggatataaa cttaacatca gtgtttaaga   13560
ctttaagact ttaaaactta aaataactat taatacttaa aagcttataa gtattaaaca   13620
cttaaagtaa ctataagact ttaaaaacct taagtactta aagttaacca tcagtcttaa   13680
actttaatat tataacctat aagtcttaaa gcttataggt gtaataatat aatataagta   13740
ttaaagctta taagttataa aagtttttaga agagttaaag ggttaacttc tttacttctc   13800
tactctcttt ggtactttct ctcttctctt cttttcttca tcaggggaga agaggaacct   13860
ttaccatcag cgccgatgga cttttcgccg tgtgtctcgt gtaccaccgg tcgcacgctc   13920
ccggtttgta cactcccccac actctgacac ctgtgtccct ttacggcttg gcgtgttcgg   13980
ctgaaggcgt acggcgtgtc acgctcacac ccttaacacc aggtaagact taaagtgtat   14040
attataagta gaagacttta aaacctgtaa ggtgttcccg cttagcccgt gtccttccac   14100
gctaggcgcc aagcgctaag ctgtgaaacg cgaacacaca cccacccccct tttttctttc   14160
gtgtccttct cttttgaca cagctggggg gcgatgtgat ctttttcaca tgccaggggg   14220
tagtggagaa aacaagcacc ccggaatgtt caagacaccc cctcaaacga acaaaacgcc   14280
ccccataatc gatgagcagg gcaagggcaa ggtattcata cccccaacgg ttcccaggct   14340
gttagagagg caaataagac ccctgcaagg gtaggcgagg aacagacaca tcatggcacg   14400
caccaaccgc accgcatcat cagcccaccg ccgctggcgg gcaagactca tcacccaagc   14460
acgcaagcaa ggcaaaccg aatgcccact ctgcggagcc accatcacct ggaacacaca   14520
tgacctgcca accagccccg aagccgacca catcacaccc gtcagcaggg gaggactcaa   14580
cacctcgac aacgggcaaa tcatctgcag aacatgcaac agaagcaaag gcaatcgcag   14640
cgaaccaaac atccaattcc aacaacaaac cacaaaaacg ctgatcccat ggtgaaaaaa   14700
ctgtcaaccc ccaccgggac cccccctgca cacccgtgca agacctcgta cggcttagtg   14760
aaatacctcc cttttgtggt tttgtctgtt tgtcgacttt ttgtgttggt ggtgagtgtt   14820
gtgcagcctg agcttcctgg tggtcgtgag tggtgtgggg agacgcgtcg ttggtggcgt   14880
gtgtggggtg aggatagccg cgcatcgtat gtgtctgatg aggagtggtt gtttcttatg   14940
gatgctgcgg tgattcatga ttgtgtgtgg cgtgagggca gggcggattt ggtggcttcg   15000
cttcgtctca atgtgaaggc gtttatgggc atgttggatc gttattcggt tgatgtgctg   15060
tctggtggcc gtggtggggg ttctgcggtg gcgatgattg accggtatag gaagcgcagg   15120
gggggcttgag taggtgtctg gtgttgtggg ttctcaggtt cctcgtcatc gtgtggctgc   15180
ggcgtattcg gtgtctgctg ggggtgatgc tgggggagttg ggtcgtgcgt atgggttgac   15240
gcctgatccg tggcagcagc agtgttgga tgattggct gctgtgggtg gtaatggtag   15300
gcttgcttcg ggtgtgtgtg gggtgtttgt tccgcggcag aatggcaaga atgctatttt   15360
ggagattgtg gagttgttta aggcgactat tcagggtcgt cgtattttgc atacggctca   15420
cgagttgaag tcggctcgta aggcgtttat gcggttgagg tcgttttttg agaatgagcg   15480
gcagttttcct gatttgtatc gtatggtgaa gtcgattcgt gcgacgaatg gccaggaggc   15540
tattgtgttg catcatccgg attgtgccac gtttgagcgt aagtgtggtt gtccggggttg   15600
gggttcggtt gagtttgtgg ctcgtagccg gggttctgct cgcggggttta cggttgatga   15660
tttggtgtgt gatgaggctc aggagttgtc ggatgagcag ttggaggctt tgcttcctac   15720
ggtgagcgct gccccgtctg gtgatccgca gcagattttt ttgggtacgc cgcctggccc   15780
gttggctgac gggtctgtgg tgttgcgttt gcgcgggcaa gccctcggtg gggggaaacg   15840
tatcgcgtgg actgagtttt cgattcctga cgagtctgat ccgatgatg tgtcgcggca   15900
gtggcggaag cttgctggtg atactaatcc ggcgttgggg cgtcgtctga attttgggac   15960
cgtaagcgat gagcatgagt cgatgtctgc tgccggtttt gctcgggagc ggcttggctg   16020
gtggatccgt ggccagtctg ctgcgtctgt gataccggct gataagtggg ctcattctgc   16080
ggtggatgag gcgcctcgg ttggcggaa ggttttttggt gtctcgtttt ctcgttcggg   16140
ggatcgtgtc gcgttggcgg gtgctggccg gactgatgct ggtgtgcatg ttgaggtgat   16200
tgatggcctg tcggggacga ttgttgatgg tgtgggccag ttggctgatt ggttggcgtt   16260
gcgttggggt gacactgaaa agatcatggt tgccggtct ggtgcggtgt tgttgcagaa   16320
ggcgttgacg gatcgtggtg ttccgggtcg tggcgtgatt gtgcctgata ctggggtgta   16380
tgtggaggcg tgtcaggctt ttctggaggg tgttcgttcg ggtgtgatca gtcatccgcg   16440
tgccgattcg aggcgtgaca tgttggatat tgctgtgagg tcggctgtgc agaagaagaa   16500
gggttctgcg tgggggttggg gttcctcgtt taaggatggt tctgaggttc ctttggaggc   16560
tgtgtctttg gcgtatcttg gtgcgaagat ggcgaaggct gggcgcgtg aacggtctgg   16620
taggaagcgg gtgtctgtgg tatgaactcg gatgagttgg ctctgattga gggcatgtac   16680
gatcgtattc aaaggttgtc ttcgtggcat tgtcgcattg agggctacta tgagggttct   16740
gccccgggtgc gtgatttggg ggttgctatt cctccggagt tgcagcgtgt gcagacggtg   16800
gtgtcgtggc ctggtattgc tgtggatgct tggaggagc gtctggattg gcttggctgg   16860
actaatggta acggctacgg cctgatggt gtgtatgtgc cgaatcgtgt atcaaccgcg   16920
tcatgcgacg tccaccttga tgcactgatt tttgggttgt cgtttgttgc gatcattccc   16980
caggggggatg gttcggtgtc tgttcgtccg cagtcgccca agaattgtac tggccggttt   17040
tcggctgacg ggtctcgttt ggatgcgggt ttggtggttc agcagacgtg tgatcctgag   17100
gtggttgagg ctgagttgtt gcttcctgat gtgattgttc aggtggagcg gcgtgggtct   17160
cgtgagtggg ttgagacggg ccgtatcgag aatagtcttg gtgcggttcc gttggtgcct   17220
```

```
attgtgaatc gtcgccgtac ttctaggatt gatggccgtt cggagattac gaggtctatt   17280
agggcttaca cggatgaggc tgtgcgcaca ttgttgggcc agtctgtgaa tcgtgacttc   17340
tacgcctacc cgcaaaggtg ggttacgggt gtgtcggctg acgagttttc gcagcctggc   17400
tgggtcctgt cgatggcttc tgtgtgggct gtggataagg atgatgacgg cgacacaccg   17460
aatgtgggat cgtttcctgt gaattctcct acaccgtatt cggatcagat gcgtttgttg   17520
gcgcagttga ctgcgggtga ggcggctgtt ccggaacgct atttcgggtt tatcacgtct   17580
aacccgcctt ctggggaggc tttggctgcg gaggagtctc ggcttgtgaa gcgtgctgaa   17640
cgccggcaga cgtcgtttgg tcagggctgg ttgtcggttg gttttttggc tgcccgggcg   17700
ttggattcga gtgttgatga ggctgcgttt tttggtgatg tgggtttgcg ttggcgtgat   17760
gcttcgacgc cgactcgggc ggctacggcg gatgctgtga cgaagcttgt tggtgccggt   17820
attttgcccg cggattctcg gacggtgttg gagatgttgg gtttggatga tgtgcaggtt   17880
gaggctgtga tgcgtcatcg tgctgagtct tcggatccgt tggcggcgct ggctggggct   17940
atatcgcgtc aaactaacga ggtttgatag gcgatggctt cgggtgctat gtcgaggctt   18000
gctgcgactg agtatcagcg tgaggcggtc aggtttgctg ggaagtatgc gggctattat   18060
gccgagcttg gtcgtttgtg gcattccggg aagatgacag atgcgcagta tgtgcgtttg   18120
tgtgtggagt tggagcgtgc cggccatgat ggttcggcat cgttggcggg caggtttgtg   18180
tcggattttc gccggttgaa tggtgtggat cctggtttga ttgtgtatga cgagtttgat   18240
gctgccgccg cgttggctag gtcgttttcg actattaaga ttcttaagag tgatccggat   18300
agggtgaatg acacgattga tgcgatggct gcgggtgtta atcgggctgt catgaatgct   18360
ggccgtgaca cggttgagtg gtctgcgggt gcgcagggta ggtcgtggcg cagggtgacg   18420
gatggtgatc cgtgcgcgtt ttgtgccatg ttggctacga ggtcggatta tacgaccaaa   18480
gaaagggcac tcactactgg tcatacgcgg cgtcataagc ggtggtaa cgtccgttt   18540
ggttcgaagt atcatgatca ttgtgggtgt acggtggttg aggttgttgg cccttgggaa   18600
ccaaataggg ctgatgccgc atatcagagg acgtacgaga aggcccgtga gtgggttgat   18660
gatcatgggt tgcagcagtc gcctggcaat attttgaagg ctatgcgtac tgttggcgac   18720
atgagatgat ggtttccggt tgtgtgccgc cggttatcgg tgcacaggt tgtctcccgc   18780
acggggtca acaatgttgt gttgttttcc gcaaggagta taggttaggc tatgccgat   18840
cagagttgttg aagaacagaa tgtcgacaat gatgctgttg agcccggaaa gggcgaggac   18900
attgttgctg ttgtgaagga tgggcaggct gccggcgatg atcatgccgg tgatgtttcc   18960
gtgaaggaga agtcttcttc tggcacggat tggaaggctg aggcccgtaa gtgggagtct   19020
cgtgctaaaa gtaatttcgc cgagttggag aagcttcgcg cctcggatgg tgatgcggga   19080
tctactattg atgagcttcg ccgcaagaat gaggaactcg aagacaggat caacgggttt   19140
gttcttgagg gtgtgaagcg cgaggtggct gccgagtgtg gcctgtcggg tgatgcggtc   19200
gctttcttgc acggcgacga tcgtgaagca ctggtggagt ctgcaagggt tttgaagggt   19260
ttgatcgacc atagcagtgg tggcgcgggt gtgcgccgtc ttgcggggag tgcccccgtt   19320
gatgatgtta aacgacgtga gggtgtcgcg tttgtggatg ctcttgtcaa taattctagg   19380
agatgatttg tgatggctga cgattttctt tctgcaggga agcttgagct tcctggttct   19440
atgattggtg cggttcgtga ccgtgctatc gattctggtg ttttggcgaa gctgtcgccg   19500
gagcagccga ctattttcgg cccggtgaag ggtgccgtgt ttagtggtgt tcctcgccgt   19560
aagattgttg gtgagggtga ggttaagcct tccgcgtctg ttgatgtttc ggcgtttact   19620
gcgcagccta tcaaggttgt gactcagcag cgtgtctcgg acgagtttat gtgggctgac   19680
gctgattacc gtttgggtgt tttgcaggat ctgatttccc ctgctcttgg tgcttcgatt   19740
ggtcgcgctg tggatctgat tgctttccat ggtattgatc ctgctacggg taagcctgct   19800
gcggctgtca aggtgtcgct ggataagact tcgaagacgg ttgatgcaac cgattccgct   19860
acggctgatc ttgttaaggc tgtcggcctg attgctgggg ctggtttgca ggttcctaat   19920
ggtgttgctt tggatccggc gttctcgttt gctctgtcga ctgaggtgta tccgaagggg   19980
tctccgcttg ccggtcagcc gatgtatcct gcggccgggt ttgccggttt ggataattgg   20040
cgtgggctga atgttggtgc ttcttcgact gtttctggtg ccccggagat gtcgcctgcc   20100
tctggtgtta aggctattgt tggtgatttc tctcgtgttc attggggttt ccagcgtaac   20160
ttcccgatcg agcttatcga gtatggtgac ccggatcaga ctgggcgtga cctgaagggc   20220
cataacgagg ttatggttcg tgccgaggct gtgctgtcag tggctatcga gtcgcttgat   20280
tcgtttgctg ttgtgaagga gaaggctgcc ccgaagccta atccgccggc cgagaactga   20340
tttattgttg cggtgatgtg tcaatgtgca ggggtggtg ttgatgggta tcattttgaa   20400
gcctgaggat attgagcctt tcgccgatat ccctgagggg aagcttgagg cgatgattgc   20460
tgatgtggag gctgtggctg tcagtgtcgc ccctgtatc gctaaaccgg atttcaaata   20520
caaggatgcc gctaaggcta ttctgcgtag ggctttgttg cgctggaatg ataccggggt   20580
ttcgggtcag gtgcagtatg agtctgcggg cccgttttgct cagactacac ggtcgaatac   20640
tcctacgaat ttgttgtggc cttctgagat tgctgcgttg aagaagttgt gtgaggggaa   20700
tggtgggggct ggtaaaagcgt tcactatcac cccaacgatt aatggtcgat atgcacattc   20760
tgaggtgtgt tccacggtgt gggtgaggg ttgctcgtgc ggatctgata ttaacggcta   20820
cgctggcccct ttgtgggaga tatgatatga ccggttttcc ttacggtgaa acggttgtga   20880
tgcttcagcc gactgttcgt gtcgatgatc ttggtgacaa ggtggaagac tggtctaagc   20940
ctgtcgagac tgtgtactat aacgtggcca tctatgcttc cgtttcgcag gaggatgagg   21000
ccgcgggaca tgactctgac tatgagcatt ggtcgatgct tttcaagcag cctgttgtgg   21060
gtgccggtta tcgttgccgg tggcgtattc gtgtgtttgt gtgggaggct gacgggtctc   21120
ctatcgtgtg gcatcacccc atgtccggtt gggatgctgg cacgcaggtt aatgtgaagc   21180
gtaagaaggg ctgataggtt gtggctcagg atgtgaatgt gaagctgaac ttgtctggta   21240
ttcgtgaggt gttgaagtct tctggggtgc agggcatgtt ggctgagcgt ggcgagaggg   21300
tgaggcgtga ggcctcggcg aatgtgggcg gtaatgcttt cgataggccc cagtatcgtg   21360
ccgggttgtc gtcggaggtg caggttcacc gtgttgaggc tgtggcccgt attggcacca   21420
cctataaggg tgggaagcgt attgaggcga agcatgcac gctggcccgg tcgattgggg   21480
cggcgtcgtg atcgtctacg gtgacccag gaaatgggct aaacgcgtgc tcaaggatga   21540
tggctggctg tctgatatac cctgtgtggg gacggtgcct gatgatttca gcggtgatct   21600
gatttggttg gctcttgatg gtggcccgca gttcgatgct ctgagcgtg ttttttcgag   21660
ggtgaatgtg ttttctgata tgccggatcg tgctatgtcg ttggcgcgtc gtgttgaggc   21720
tgtgctggct gatggtgtgg acggtgaccc tgtgggtac tgtaggcgtt ctactggccc   21780
tgatttgctg gttgatggtg cacgtttga tgtgtattcg cttttttgagc ttatatgtag   21840
gcctgcgag tctgaataag cttattgttt ttgttttaat gtaattgttt gatatttaat   21900
gggggttatg atggctgcaa cacgtaaagc gtctaatgtt cgctctgctg ttactggcga   21960
```

```
cgtttatatt ggtgacgcgc acgcgggtga tactattaag ggtgtggagg cggttccttc   22020
cgggcttaca gctttagggt atctgtcgga tgacgggttt aagattaagc ctgagcgtaa   22080
aacggatgat ttgaaggctt ggcagaatgc ggatgttgtt cgcacggttg ctaccgagtc   22140
gtctatcgag atttcttttc agctgatcga gtctaagaag gaggttatcg agctgttttg   22200
gcagtcgaag gttactgctg gcgccgattc gggttcgttt gatatttcct caggcgccac   22260
cactggcgtg cacgctttac tgatggatat tgttgatggg gatcaggtta ttcgctacta   22320
tttccctgag gttgagttga tcgatcgtga cgagattaag ggtaagaatg gcgaggtgta   22380
tgggtatggt gtgacgttga aggcgtatcc tgcccagatt aataagaagg gtgatgcggt   22440
gtctggtcgg gggtggatga cggctttaaa agctgatact cctccgacgc ctcctccggt   22500
cccggttcct ccgaagcctc agccggatcc gaatcctccg gctggtaact gatacacgat   22560
tttagggatt gttgatagat gagtgacacg ggtttcacgt tgaagattgg tgaccgtagc   22620
tgggtgttgg cggatgcgga ggagacggcg caggctgttc ctgcccgtgt ttttcgccgt   22680
gccgccagga ttgcccagtc gggggagtct gcggatttcg cccaggttga ggtgatgttt   22740
tctatgttgg aggctgccgc cccggctgat gctgtggagg ccttggaggg gcttcctatg   22800
gttcgtgtgg cggaggtttt ccgtcagtgg atgaataca agcctgacgg taagggtgcc   22860
tcgctggggg aatagtttgg ctccacggcc tgattgatga ttatcgtggg gccatcgaat   22920
atgattggag gacccggttc ggttgctcgg tttatgatgt tggtggcccg gtgatgtgtt   22980
ggggtgaggc tgtccggctg gctggcgtgt tgtgtaccga tacgtctagc cagttggcgg   23040
cccacctgaa tggttggcag cgcccgtttg agtggtgtga gtgggcgtg ttggacatgt    23100
tggatcatta caggtctgct aatagtgagg ggcagccgga gcctgtggcg aggcctacgg   23160
atgagcgtag ggcccggttt acgtctgggc aggtggacga tattttggcg cgtgttcgtg   23220
ccggtgcgg tgtgtctcgc gagattaata ttatgggtg aatagtgtat gtctggtgag    23280
attgcttccg catatgtgtc gttgtatacg aagatgcctg gtttgaaggc tgatgttggt   23340
aaacatttgt cgggtgtgat gcctgctgag ggtcagcgtt ctggtagcct gtttgctaag   23400
ggcatgaagt tggctcttgg tggtgcgcg atgatgggcg ctatcaatgt tgctaagaag    23460
ggcctcaagt ctatcatga tgtgactatt ggtggcgta ttgctagggc gatggctatt    23520
gatgaggctc aggctaagtt gactggtttg ggtcatacgc cttctgatac gtcttcgatt   23580
atgaattcgg ctattgaggc tgtgactggt acgtcgtatg cgttgggtga tgcggcgtct   23640
acggctgcgg cgttgtctgc ttcgggtgtg aagtctggcg ggcagatgac ggatgtgttg   23700
aagactgtcg ccgatgtgtc ttatatttcg ggtaagtcgt ttcaggatac gggtgctatt   23760
tttacgtcgg ttatggcgcg cggtaagttg cagggcgatg acatgttgca gcttacgatg   23820
gcgggtgttc ctgtgctgtc tttgcttgcc aggcagactg gtaaaacgtc tgctgaggtg   23880
tcgcagatgt tgtcgaaggg gcagattgat tttaacacgt ttgcggctgc gatgaagctt   23940
ggcatggggt gtgctgcgca ggcgtctggt aagacgtctt agggcgctat gaagaatgtt   24000
aagggcgccc tgggttattt gggtgctacg gctatggccc cgttttttgaa cggtctgcgg   24060
cagattttg ttgcgttgaa tccggttatc aagtctatca cggattctgt gaagcccctg   24120
tttgcgtcgg tggatcaggg gattcagcgg gtgatgccgt ctatttttggc gtggattaat   24180
cgtatgccgg ctatgatcac gagaatgaat gcacagatgc gcgccaaggt ggagcagttg   24240
aagggcgttt ttgcgaggct gcatttgcct gttcctaagg tgaatttggg tgccatgttt   24300
gctggcggca ccgcggtgtt tggtattgtt gctgcgggtg ttgggaagct tgttgcgggg   24360
tttgcccgt tggcggtgtc gttgaagaat ctgttgccgt cgtttggtgc tttgaggggt   24420
gccgccgggg ggcttggtgg cgtgtttcgc gccctgggtg gccctgttgg tattgtgatc   24480
ggcttgtttg ctgccatgtt tgctacgaat gcccagttcc gtgccgctgt tatgcagctt   24540
gtgggggttg ttggccgggc tttggggcag atcatggtcg ctattcagcc actgttcggg   24600
attgttgctg gcgtggttgc caggttggcg ccagtgttcg gccagattat cggtatggtt   24660
gctggttttg ctgcccaatt ggtgcctgtt attggtatgc ttattgcccg gctggttcct   24720
gttatcaccc agattattgg tatggtaacc caggttgctg cgatgatttt gcctatgctg   24780
atgccggtta ttcaggctgt tgttgctgtg atacggcagg ttattggtgt gatcatgcag   24840
ttggtgcctg ttttgatgcc ggttgtgcag cagattttgg gtgctgtcat gtctgttttg   24900
ccgccgattg ttggtttgat acggtcgctg ataccggtga tcatgtcgat tatgcgtgtg   24960
gtggtgcagg ttgttggtgc cgtgctacag gtggtggccc gtattattcc ggttgttatg   25020
ccgatttatg tttcggtgat tggattcatt gccaagattt atgctgcggt tatcgttttt   25080
gaggctaagg ttattggcgc tattcttcgt actattacgt ggattgtgaa tcattcggtg   25140
tctggcgtga ggtctatggg cacagccatc cagaatggct ggaatcatat caaatcgttt   25200
acgtctgcgt ttattaacgg tttcaagtcg atcatttcg gcggcgttgc cgcggtttgtg   25260
gggttttta cgcggcttgg tttgtcggtt gcctcccatg tgaggtccgg ttttaacgcg   25320
gctcgtggcg ctgtttcttc tgcgatgggt gctatccgga gtgttgtgtc ttcggtggcg   25380
tctgctgttg gcgggttttt cgggtcgatg gcttctcggg ttcgtagtgg tgctgtgcgc   25440
gggtttaatg gcgcccggag tgcggcttct tctgctatgc atgctatggg gtccgcggtg   25500
tctaacggcg tgcatgtgt gctaggggttt tccggaatc tgccgggcaa tattcggcg    25560
gctctcggta atatgggtc cttgttggtg tctgctggcc gtgatggt gtctggtttg    25620
ggtaatggta tccggaatgc tatgagtggc ctgttggata cggtgcgtaa tatgggttct   25680
caggttgcta atgcggcgaa gtcggtgttg ggtattcatt cgccgtcgag ggtgtttcgt   25740
gacgaggttg gccgtcaggt tgttgctggt ttggctgagg gtattactgg taatgctgct   25800
ttggcgttgg atgcgatgtc gggtgttgct tcgcagcttc cggatgctgt tgatgcccgg   25860
tttggtgtgc gatcgtctgt gggctcgttt accccgtacg accggtatcg gcgtgcgagc   25920
gagaagagtg ttgtggtgaa tgttaacggg ccgacgtatg gggatccgaa cgagtttgcg   25980
aagcggattg agcggcagca gcgtgacgct ttgaacgcgt tggcttacgt gtgataggg    26040
ggtgtatttg atgttttattc ctgacccgtc tgatcgtgcc ggtttgactg tgacctgtc    26100
tatgttgccg ttgattggtg atgctccgga gcgtgtgctt catttgacgg attatacggg   26160
gtcgtctccg gtgatgttgt tgaatgattc gttgcgcgt ttgggtgttc ctgaggttga   26220
gcattttct cagactcatg ttggggtgca cggctcggag tggcgcgggt ttaatgtgaa   26280
gcctcgcgag gtgactttgc cggtgttggt gtcgggtgtt gaccctgatc cggtgggcgg   26340
gtttcgtgac ggttttttga aagcctatga tgagttgtgg tctgcgtttc ctcctggcag   26400
ggtgggggag ttgtcggtga agaccccgtc tggtcgtgag cgtgtgctgc ggtgccggtt   26460
tgattcggtg gatgacactt ttacggtgga tccggtgaac aggggttatg cgcgttatct   26520
gttgcatttg acggctatg acccgttttg gtatgggat gagcaaaagt ttcgttttag     26580
taacgcgaag ttgcaggatt ggttgggtgg cggccctgtt aataagaagg gtaccgcgtt   26640
tcctgtggtg ttaacaccgg gtgtgggctc gggctgggat aacctgtcta ataagggtga   26700
```

```
tgtgcctgcg tggcctgtga ttcgtgttga gggtccttttg gagtcgtggt ctgtgcagat   26760
tgatggtttg cgtgtgtctt cggattggcc tgtcgaggag tatgattgga tcactattga   26820
tacggatcct cgtaagcagt ctgcgttgtt ggacgggttt gaggatgtga tggatcgttt   26880
gacgagtgga gagtttgcgc ctattcctcc tggcggttct cggagtgtga atattgagat   26940
ggttggtttg ggtgccattg ttgtgtcggt gcagtacagg tttttgaggg cttggtgaat   27000
agttgatggc tggtcttgtt ccgcatgtaa cattgtttac gccggattat cgccgtgtgg   27060
cgcctatcaa ttttttttgag tcgttgaaac tgtcgttgaa gtggaatggt ttgtccactt   27120
tggagttggt ggtgtcgggg gatcattcta ggcttgacgg gttgacgagg ccgggtgcgc   27180
ggctggttgt tgattatggt ggtggccaga ttttttctgg gcctgtgcgt agggtgcatg   27240
gtgtgggtcc gtggcggtct tcccgtgtga ctatcacgtg tgaggatgat attcgtctgt   27300
tgtggcgtat gttgatgtgg cctgtgaatt atcgtcctgg tttgtgggt atggagtggc    27360
gtgcggatag ggattatgct cactattcgg gtgcggcgga gtcggtggct aagcaggtgt   27420
tggggataa tgcttggcgt tttcctcctg gtttgtttat gaacgatgat gagagtcgtg    27480
gccgctatat taaggatttt caggtgcggt ttcacgtgtt tgccgataaa ttgttgccgg   27540
tgttgtcgtg ggctcggatg actgtcacgg tgaaccagtt tgagaatgcg aagtttgatc   27600
agcgtggttt ggtgtttgat tgtgtgccgg ctgtgacccg gaagcatgtg ttgactgccg   27660
agtcgggttc gattgtgtcg tgggagtatg tgcgtgacgc cccgaaggct acttcggtgg   27720
tggttggtgg ccgcggcgag gcaaggatc ggctgttttg cgaggatgtt gattcgatgg    27780
ccgaggatga gtggtttgat cgtgtcgagg tgtttaagga tgcccgtaac acggattcag   27840
agcatgtgca tcttattgat gaggctgagc aggtgttgtc cgagttaggg gctacgtcgg   27900
ggtttaagat cgagttggct gagtcggatg tgttgcgttt tgggccaggc aatctgatgc   27960
cgggtgattt gatctatgtg gatgtgggct cggggcctat tgccggagatt gtgcggcaga   28020
ttgatgtgga gtgtgattcg cctggtgatg ggtggacgaa ggtgacacct gttgcggggg   28080
attatgagga taatccgtcg gccctgttgg cgcggcgtgt tgccggtttg gctgcgggtg   28140
tgcgggattt gcaaaaattc tagaaaagat gaggggtttg ttgtgggtat tgtgtgtaaa   28200
gggtttgatg gtgtgttgac cgagtatgat tgggctcaaa tgtctggtct gatgggtaat   28260
atgccgtctg tgaagggccc ggatgatttt cgtgtgggca cgactgttca gggtgccaca   28320
gtgttgtgtg aggttttgcc ggggcaggct tgggctcacg gggtgatgtg cacgttgaat   28380
agtgttgaga cggtgacagg gcagctgccg ggccctgggg gggcccgcta cgactatgtg   28440
gtcctgtctc ggggattgca ggagaatacg gccaagttgg agattgttcc tggggggcgg   28500
gcggagcgtg cccgtgacgt gttgagggct gagcctggcc tgtttcatca gcagttgttg   28560
gcgactttgg tgttgtcgtc tgacgggttg cagcagcagc tggataggag ggctatagcg   28620
gctagggttg cgtttggcga gtctgctgcg tgtgacccga ccccggtgga gggtgaccgt   28680
gtgatggttc cttcggggggc tgtgtgggct aatcatgcta acgagtggat gttgttgtct   28740
ccgaggattg agacgggttc gaagtcgatc atgtttggcg gttctgctgt gtatgcttac   28800
acgatcccgt ttgatcgcca gtttgctagt ccgccggttg tggtggcgtc tatggctacg   28860
gcggctgggg gcacggcaca gattgatgtg aaagcctaca atattactgc caaagatttt   28920
agtttggcgt ttattacgaa tgatggttcg aagccgaatg tgtgcctgc ggttgcgaat    28980
tggattgctg tcggcgtgtg accgggttgt tgttgtgcgg gatggtgtga tgttgggggg   29040
ctgtggtgtc gtggtttact cctgcactgg tggcctctat ttgtaccgcg ttggccacgg   29100
ttttgggttc tgttcaggcg gtcacgtcta aatctcggag gcgtttgcgg cggctgtcgg   29160
cgcaggtgga tgcgatggaa gagtatacgt ggggtgtgcg gcgtgaggtt cgccggttta   29220
acgctgggct tccggatggg gtggagccga tgcatcttcc tgatgtgcct gagttttga    29280
aggatactgt tgatggtgga ggtgagtagg gttgagggag ttggaggagg agaagcggca   29340
gcgccgcaat tttgagaagg cttcactggt gttgttgttt ttgtcgcttg tgttgttggc   29400
ggtggttgct gtgggtgctt tgcgtttcgg ggcggtatcc tctgagcggg attcggagca   29460
ggcgagggcc cagtcgaatg gtacacgggc tcggggttta gccagcagtg tgaagcaggc   29520
gtgtgcttcg agtggggtgg agtcggtgcg gcttcaccgg tctggtttgt gtgtggatgc   29580
tgtgcgtgtt gagcggagtg tgcagggtgt gccgggtcct gccggtgagc gcggcccgca   29640
aggccctgca ggggttgacg gccggatgg tgttaatggt tcgctgggc tggttggccc    29700
tgttgctcca cagggttctc ctggtttgaa tggtgtgaag ggtcctgacg ggttgcctgg   29760
tgtgaatgga tcgatggcc atgatggtgt tccaggtcgt gcaggtgctg acggtgtgaa   29820
cggcgctgat ggtcggatgg gttcgggcgg tgagcgcggc gatgtgggcc cttcaggtcc   29880
tgtcggaccc cctggtgcgc agggtgaacg ggg                                 29913

SEQ ID NO: 75        moltype = DNA   length = 29562
FEATURE              Location/Qualifiers
misc_feature         1..29562
                     note = PAC263
source               1..29562
                     mol_type = other DNA
                     organism = synthetic construct
SEQUENCE: 75
aatggtgtga agggtcctga cgggttgcct ggcgttaacg gttcggatgg ccgtgatggt   60
gttccgggtc gtgcaggtgc tgacggtgtg aacggcgttg acggccggga tggtgttaat   120
ggttcggctg gtgagcgcgg cgaacagggc ccttcaggtc ctgccggccc ccaaggcgaa   180
cggggtgagc gcggccccgc cggtgctaac ggatccgatg gtaaagatgg taaagatggt   240
aaagatggcc gttctgtggt gtctgtgtac tgttctgatg gtcgcctggt tgtgaaatat   300
agtgacggtg tggcttccac gatatcgatc tcggtagcct gcagggtgt gaaaccgtcc    360
cctatagtga ctatatcatc ccacaaataa aagaggaagg gtgttactgt gattgtcatg   420
ttttgggtg tgtgtggtg aggtttattc ctgcggcgca tcattcttcc ggttcgaata    480
gtccggtgaa taggggttgtg attcacgcga catgcccgga tgtgggggttt ccgtccgcgt   540
cccgtaaagg gcgggcggtg tccacggcaa actatttcgc gtcccatcg gcgggtgggt    600
gggggttttccg tccgcgtccc gtaaagggcg acggcaaact atttcgctgt                660
cccatcggcg gtggttcgg cgcattatgt gtgtgatatt tcggagactg tgcagtgctt     720
gtcggagtct acgattgggt ggcatgcccc gccgaatccg catagtttgg gtatagagat   780
ttgcgcggat gggggttcgc atgcctcgtt ccgggtgcca ggccatgctt acacgaggga    840
gcagtggctt gatccgcggg tgtgcccgc ggttgagaag gcggctgtcc tgtgccgcg     900
tttgtgtgac aaatataatg ttccgaagag gaaactgtct gtggccgatt tgaaggccgg   960
```

```
taaacggggt gtgtgtggcc atgtggatgt gacggatgcg tggcatcagt cggatcatga  1020
cgatccgggg ccgtggtttc cgtgggacaa gtttatggcc gtagtcaacg gcaaagatga  1080
gagtggggag ttaactgtgg ctgatgtgaa agccttgcat gatcagatta aacaattgtc  1140
tgctcagctt agtggttcgg tgaataagct gcatcacgat gttggtgtgg ttcaggttca  1200
gaatggtgat ttgggtaaac gtgttgatgc ctttgtcgtgg gtgaagaatc ctgtgacggg  1260
gaagctgtgg cgcagcaagg atgctttgtg gagtgtctgg tattacgtgt tggagtgtcg  1320
tagccgtctt gacaggctcg agtctgctgt caacgatttg aaaaagtgat ggtggtttgt  1380
tgtgggtaaa cagttttggt taggtgtgct ggagcgggcg gctaagactt ttgtgcaaac  1440
gtttgttgcg gtgttgggg tgacggcggg tgtcacctat acggcggagt cgtttcgcgg  1500
tttgccgtgg gagtctgccc tgatcacggc tacggtggct gcggtgctgt cggttgctac  1560
atcgtttggt agcccagcgt ttgtggccgg taaacctaaa accacgcctg tggatgcggt  1620
tttgttcca ccgatgatg gggcttggt tgagccgcac tcggtggatg tgtcggatcc  1680
tggcatgatt gagcctgcag atgatgtgga tcttggtgta ggctatgagc ctcggcgtgc  1740
tgccgagtcg gaggttggca cggtagagtc tactgttgca taagtgaata tatgtgtgtg  1800
ccccagcggt gctgccacga tcgtgtggtg gttgccgctg gggcactatt tttgtatatt  1860
gcggtgtggc tatgattcgt tgctgtcgat ggtgtcttcg agcatctgat acaggtggag  1920
gcaggtagag atcgtttcgc tggcctggtc gagaacgttc cggccgataa cgtttttgtg  1980
gttgtcgcgg tggcggatga tagaccacat gatctcgtcg gctgccgcct gcaatagttt  2040
tgcctgatat gcgatcccgg cgagccagtc tagtgcttcc tggcttgcat aggggctctg  2100
gtcctcgctg ttgccgcggg tgttgctgtt gtttgtgggg tgtcctgcac tgtcgcagaa  2160
ccataggatt tcgctgcact cgtctagcgt gtcttggtcg atagcgagat cgtcgaggct  2220
gacattgttg acggtaaggt tcacgttgtc gagggagatg ggtacaccgt actggttttc  2280
gacactgtca acaatgtttt gcagctggtt catgttggtg ggctgttgtt ggatgattcg  2340
gtgtaccgct gttttgaggg cggtgtaggg gatattggtt atgttgttca tggttttatc  2400
ccatccctgc gctgtcgtct tggtagtatc gactgtttgc gtaacctgtg agggtgatga  2460
gtgtttgtc tgcccactgt ttcacggttt gccgggtgac tccgagtcgt tggctgcca  2520
ccgaataggt ttggtcatac ccgtatactt ccctgaaggc tgccaggcgt gctagccgtt  2580
tccgctgttt ggatgctgg caggtgaggg tgtagtcgtc tatcgctaat tgtaggtcga  2640
tcatggtgac gatgttgttg ccgtggtgtt ggggggcggt tggtgggggt ggcatgcctg  2700
gctccacact gggtttccat gggcctccgt tccagatcca ttgggcggct tggatgatgt  2760
cggcggtggt gtaggttcgg ttcactggtc atcccctgaa taggttgtcg aggttgtctg  2820
ggttgctgg gttggtggtg tcgaatcgtc ccacacagtg gcagtagtcg tacatgagtt  2880
taataatgtg ttggtggtct cccaaatagg tgtttccgct gatactgtag gtggctgtgc  2940
cgtctttact aatagtgtat ttggcggtga tggtttcggg tgtttctgtg ttggtgatga  3000
ttgctgtgt ggtggcgcct acggtttgta gcctgctgg ttgggttccg tcgtcgagga  3060
tggtagtaac catgagggtt gtcctttagt tgctggtttg gttgtcggct agatgaatga  3120
tatcgggtaa aggtttcggc tggtcgaggt gttgtatggt tttgttggct agccgtttgg  3180
ctaccctgta gcacattttg gtgtagtgtt tgttgtctag gttgtggtat tgttcccgca  3240
ccgcaatata tagtagggag tcttgtatat ggtcgtctgc actgattgcg ggtagtagtg  3300
tggctgtttt ggtgcatgcc cggttgagtg tgcgtagatg atggtctgtg gcccacaccc  3360
acgatgcggt ggtggctagg tcggcttttg ttggtcgtct gctcatggca ctattacctg  3420
gctatctggt agttgtttgg tgttttgttg ttgatagtgt agcacacgag tccggggttg  3480
ccggtggtgc ctgtgcggtg cctataccag acggattcgt cttccatgga tgggcattgg  3540
atgaaggtgc gttgtccttg ctcggagatt tcgaggtggt gccggtgtcc ggccatgagg  3600
atgtgggatg tggtgccgtt gtggaattct tggccgcgcc accattcgta gtgttggttg  3660
ttgcgccatt ggtgtccgtg ggcgtgcagt atttgtgtgc cggccacatc aacggtggtg  3720
gtcatttcgt ctcgtctggg gaagtggaag tgaaggttgg ggtagtttgtt ggtgagttgg  3780
taggcttcgg cgatggcgcg gcagcagtct acatcgaagg agtcgtcgta ggtggtgact  3840
cctttgccga atcgtacggc ttcaccgtgg ttgccgggga tggaggtgat ggtgacgttg  3900
gcgcagtggt cgaacatgtg gacgagttgc atcatggcca tgcgggtgag cctgatttgt  3960
tccgtcaagg gtgtttgtgt gcgccacgcg ttagagccgc cttgtgacac gtatccttcg  4020
atcatgtcgc cgaggaatgc gatgtggacc cgttgcggct ggcctgcctg ttgccagtag  4080
tgttttgcga ctatgaggga gtgcaaatag tcgtcggcga agtgtgctgt ttctccgccg  4140
gggatgcctt tgccgatttg gaagtcgcct gccccgatga cgaaggccgc agtgctgtag  4200
tcggtgtggg tgtcttgttc gggttttggg ggctgccatt cggctagctt gtcgacgagt  4260
tcgtctatag ggtaggggtt tgttgcggtg tggtggtcga tgattttttg tatggatcgt  4320
cctgtttctc cgttgggag tgtccattcg gagatgcgtg tgcggcgtac ggtgccgttg  4380
gctaggttgt cgtcgatggt gtcgatgcg ttgtcgtggt tggctagttg tgtgagtagc  4440
cggtctatat tgtctatcac tgggtatcct cctcttcctc gtgtgtggtg gtggcttgtt  4500
tgcggcggta gtcttttaatg acggtggcgg agatgggtta tcctgcctgg gtgagcattt  4560
gggctagctg tgtggcgggg atagacctgt cggcgagcac gtctgcagcc ttgcggccgt  4620
agcgttggat gagggtttca gttttggttg ccatgatgtc ccatcggttg tgtggtgggc  4680
tgccatcctg tgcggcagtc gccgtcgtgt cctggtttgc gtgtgcacca cgatacggtt  4740
ccgtctgtgt ggttgagtgt tttaccgcac atgacgtttt gtagatgctc cggcagcgtcg  4800
ctattgctat cgtcttgctc gtctagcaaa gttttttgtt gggtgaaaaa ctcggacacg  4860
gtgccgttgt ggactgggag tatccatgtt ttccattgtt gttgtagccg ggtgttccag  4920
tggaattgtt ttgctgcgtt cgtggcttgt ttgatggttt tgaagtagcc tacaatgatc  4980
cgttgatggt cactatcggg ccttgtgtggc cctttccaat attgggcagc tacagcgtac  5040
ctgttgttgt ctgtgaagcg cccccagcag tattccacca tgtgtgatag tacccttgtcg  5100
ggcatgtctc gtacttggtt ttcgtcgagc catgcgtcga caataatgtt gcgtatggct  5160
cgcttgtctt tggtggtggg tttgaatgcg atgctcacaa tgcgggcctg tcgtcttgca  5220
tgaactggtt gaaggtgttg ttcccggcgt gttgggcttg tgtgatttgc tggtcggtcc  5280
agtcggggtg ttgctgtttc agatagtgcc agtggcacgc attgtaggtt tcgtcttgga  5340
gccgtgtgag atggttttcg gtgatgattt gttttccacat ggcccatgac acgtcgaggt  5400
ggttgaggat ttcgagggct gggatggtga attggttcag gaagaggatt tcatgggtgt  5460
agtagttttt ctcgtaggcg tcccatccgc ttccggtgcc ttgtgggctgg ttttttgggt  5520
aggcttcccg gcagatttg tgtaaccgtt tggccatgtc tttgggtagt ttaatgtcgg  5580
ggttggcgcg gatcatggat cgcatcccat cataggtggt gccccaggtg tgcatgatgc  5640
ggagtgggtc ttcaccatcg gcccattttt ctgcacagat ggcgaggcgt atgcgtctcc  5700
```

```
tggcggcttt actggtgtcg cggcggccgg ggatggggca ggtgtcgagg ggatccatga    5760
tgttttagtg tacctttccg tgttgtggtt gtttgtctgg ttttattgta gcactgtgtt    5820
gagggcttgt gtcaaccctg tttttccgac ctgaaggtag gtgtctgtga catccccag    5880
ggtgaggggc acatgggtgg cttggggag tgccgtctgg aaggtttggg ccatctggtc    5940
tcctgctttg tctgggtcgg accagatgta gatgtggtcg tagccttcga agaatttggt    6000
ccaaaagttt tgccacgagg ttgcgccggg tagggcgacg gccgaccatc cgcattgttc    6060
gaggatcatg gagtcgaatt cgccttcgca aatgtgtatt tcggctgccg ggttggccat    6120
ggcggccatg ttgtagatgg agcctgtgtc tcctgccggg gttaggtatt tggggtggtt    6180
gtgggttttg cagtcgtgct ggagtgagca gcggaaacgc attttttctta tttcggctgg    6240
cccttcccaa acggggtaca tgtatgggat ggtgatgcac tggttgtagt tttcgttggcc    6300
tgggatgggg tcattgtcga tgtatccaag gtggtggtag cgggctgttt cttcgctgat    6360
gcctcttgct gagaggaggt cgagtatgtt tcgaggtgg gtttcgtaga gggccgaggc    6420
tttctggatt cggcggcgtt ccgcaatgtt gtatgggcgt atgctgtcgt acattcgggt    6480
tttcttcttc taattgttgt tgtagttttgt cgaggcctcc tccgataccg catgtgtggc    6540
agtaccagac gcccttgtcg aggttgatgc tcatggaggg ctggtggtcg tcgtggaacg    6600
ggcagaggat gtgttgctcg ttcttggacg ggttgtaccg tatgtggtag gtgtcgagga    6660
ggcggcgggt gtcagaggtg tgggaggagc tcgttgaggg ttgataccac ataggcttcg    6720
ctccagggtt tgttgcgctg tttcatcact acgagtccga tagtggactg gttttcgcgg    6780
tttcggtggg tttcgtagtt gcgtgcctcc cggctggctt gtttcacgaa ttcggcgagg    6840
tggggctgcc cggctttggc ttcgataatg taggttttgt tgccggtggt gaggatgagg    6900
tcgccttcat ccctctttacc gttgaggtgg aggcgttcta tatcatggcc ggtgtcgcgt    6960
agctggtgga ggagtcgtgt ttcccattcg gctccggctc ggcggtttct tgattgttgt    7020
gtcgacatga tagtcctttg tggtgttcgg tcatgttcca tggctgtttt tcggcgagtg    7080
gcccgaagaa tgtgtattcg gggtaggctc tgagtctttc gtatcgggtt ccgtctgggc    7140
tggatttgcc tgtgcgctgt ttgagtacag cgatgcgtgc ctctgccggt atcgataggc    7200
cgttgccgtt gtcttcgcca ccatacaggg agactcccaa tatgagttgt ggttttttcgg    7260
agaggccgtt tttgatttcc cgcctagccg ggggtgttc gatgtcgag ccggttttgt    7320
cggttgcgtg gtgtgtgaca ataatggtgg agcccgtgtc cctacctaat gctgtgatcc    7380
attgcatggc ttcttgctgg gcctgatagt cactctcgca gtcttgtatg tccatcaggt    7440
tgtcgataac gatgatgggt gggaaggtgt tccacatttc catgtaggct tgcagttcca    7500
tggtgatgtc tgtccatgtg atgggtgact ggaatgagaa tgtgatgtgt ccgccgtgtg    7560
ggatgctgtc tcgatagtat tctggcccgt agtcgtcgat gttgtgttgt atctgggcgg    7620
tggtgtgttg ggtgttgagt gagatgattc gtgtggaggc ctccagggg gtcatgtccc    7680
ctgatatgta gagggctggc tggttgagca ttgctgtgat gaacatggct agcccggatt    7740
tttggctgcc ggagcgcccc gcgatcatga cgagatcccc ttttgtggatg tgcatgtcca    7800
ggttgcggta gagggttct agctggggga tgcggggcag ctcggctgcg gtttgggagg    7860
ctctctcgaa ggatcgttgg agagagagca tcgggacctt atctatctgt ctatcggttg    7920
gatgatgttt tggtggtcag atggagtcga tgtcgatgtc agcatcagca ggggctgtgg    7980
tgtcgctcag ctggccgtta tcgcgctttgt ctacgtattc ggcaaccta tcgtagatgg    8040
cgtcgtcgag gggtttgagc acgaccgcgt tgaagccgtt ttggtgcgt acggtcgcga    8100
gtttgaaggc ttgttcttcg ccaaggtagg cttcgaggtc gcggatcatg gagtgtgggc    8160
ggtcgttgct gccgcgtact ttttcgatga tggcgttggg gatggtttct gggtgccgt    8220
tgttgaggtc gtctagggtg tggaagatgg tgacatcagc gtagatgcga tcggcggtct    8280
gtccaccgta gccttcggtg ttgtgttcta cgtcgtggat tttgaaggcg atggcggtgg    8340
cgtcctggtt tcgggagggg ttgaagaagg tgctgttgct gttgtttcgg tagtttgcga    8400
gtcccattgt tgtatccttt actgttttgt tggtttgtgt aggttttatc gggtgaggct    8460
gtttcgtttg ctgcggaaag cctcggaaac gtcactgtta ctggtgatga tcttttttgta    8520
ctgtttgaga aggtcggcta gctgtgcttt gctggttgca ttgttgattt tgtcgatgat    8580
ggtgttgttt ccttctgagg cgatgttgtc tacgtagtct ttggcggcct ggttgtagcg    8640
atcttggagg atgatggatg ctgtggcgat cagtgttgcc aggtcccagt tccgtgccgc    8700
cgaactgttt ttgagtccgc ctaacaggtc gatgatgcct tgttttgtct gctctgccgt    8760
gtctcctcgg atgaccgccc atggtgcagc atagtctcca ccgtatttga tgtgtgatcgt    8820
gagtcgatca ttgtcgatct tgtctttatc ggtcatttgg tgtccttttc tttattgtct    8880
gtttctggtg gctgtacggt agattctacc gggtacctgt aggcgtcttt cccgttgacg    8940
gcccagcagg cgtcttgtac ggggcagcct ttacagagtg ttgtgacgtg tgggacgaag    9000
atgcctgcgc tgattccttt cattgcttga ctgtacatgg atgatacatg ccggtaggtg    9060
ttgttgtcaa ggtcgtacag ttcggtggat gtgccttgtg tcgggacttt gtcgtcgttg    9120
cggctggtgg ccgcgtcca aaacatgcct tttgttacat cgttgccgtg ttggttgagc    9180
atgtaccggt aggtgtgcag ctgcatactg tcggcgggta ggcgtccggt tttgagatcg    9240
aggatgaagg tttcgccggt gtcggtgtcg gtgaagatac ggtcgatgta gccaacgatc    9300
tgggtgccgt cggggagggt ggtttctacc gggtattcga tgcctggttt accgtccagg    9360
attgcggtga tgtattctgg gtggttgcgt ctccatgttt tccagcggtc cacaaaggtg    9420
gggccgtaca tcatccacca attgtagtct tttttgtgtg gcccgcccga ttcgcacatg    9480
tttttgcata ttctgccgga gggtttgatt tctgtgcctt cggattcggc gagggctact    9540
tgtgtggcga aaatgttttt gaaggatgcg agtttgcctg gtagcgcagg gtattcggcg    9600
gggttgtata ggtgtaggtc gtattgttcg gtgatgtggt gtatgcgcct tccggcgatg    9660
gtggcgtacc aggtgtggtg ttgggtgtgg tatccgtgtt ggagacgcca ttttttcgccg    9720
cattcggccc attgtgacag tgatgagtag gagatgtggc ctggatggtt gatggttttc    9780
gggtattgtg ctagaggcat tacttgtcgc ttttgttcca tgggttttcgg gtgtcttggc    9840
cggcatcgtg ttgctggtat gcgaggagtc cgaggcagtg ccaggcagca tgggctagat    9900
gcggtagccc ggattcataa tcgaggttgt tgccttgctg ccatgataac aggtgccggt    9960
agagggcatc aacgctgtgg ctccacgggt atcctccggt ccagttgttg tcgccgtatt   10020
tggtggcacc gtagcctgct acgtcgccga gagcgtgaag ggatgctggg tcgatgaggg   10080
gtcgca aagtttgagt tctttttcggg caccgctggt tcggttg tacatgcggg   10140
ttggctcatc catgagatat gtgctcctta agcgtgggtt actggttagg gttgtgggcg   10200
agtgctacgg cgagaataat gatgcgaggg gtttcagcga tgatgatggg tgttgtgatc   10260
atttgctgtc tcggggattg ttggtgagtg ttgatgcgcc taggagggtg gtgagggcgc   10320
atgcggcaat gatggcgagg gctgccttgt gtggggtgcc ggttgcgtac atccatgtga   10380
tgatgccgcc ttggatccag gctaggctgg tgaagaacgt ttcgtagctg tgtagctcaa   10440
```

```
tgttgttgtt gggtgtgttc atgcttgctc ctgaagaatg gtgttgatgg ttttataaat   10500
gttgtacagg tcggcttcga tggtttgtag ctgtttgatt tggtggtcga gattaatgtc   10560
tgggttgagg gtgttgatgc gggaggcaat atctgtggct gtgcgtagtg ttccgccggt   10620
gtggtgaata atgtgtgccg tgtcggcgag tccggtgatg acagcgtagt gggataggag   10680
aggcatagct gggggggtgct ccttggcggg ttactgttgc gggttgatgt tgaggtcggt   10740
gacgtgcggg tggtcttctg ttccggtgac gaggcagtgg acggtgacgg gtagtttgga   10800
tgcgccggga tgtttcgcgg ttgcgccgta gacgatggag aaggtgtctt taccaataat   10860
tttgtggagt tggaggtcga tgtcgggggtt gccgttccag ttgaggccgt gtgcggcggc   10920
ctgttgttcg gctttgcggt tgcaggtgtg tgctgccgtg atcatggtga gtccggtggc   10980
ggtttcttca cccgtgttt gggcttgctt gtgggctttc tgctgttctg cttgtaggga   11040
gcggactgcg gctgcctgct tggctgtttt ctcggctttg cgctgttgga cggttttggg   11100
ggtccattcg gtgttggctg tggtggcttg tggggctggt tgtgaggcga gtggcggatt   11160
gtcgtcgggt gctgggagga aagagcatgc ggcgatgatg gcggctgtga ttccggccgat   11220
ggtgtagccg tttttcttgt tcatggctgt tgtccccttt ccggggtgtt gttcgttgct   11280
gacatgatca atacttccag cgaatggacc tcgtgtcaag actcgctca aatgttctga   11340
gcgatccttg tgtggctagg ggttttatcg ggcgcatagg gtgagtaggt ggcctacgtt   11400
gatgcggctc acattccagt agagttgtgt ggcttcaccg ccggtgagcg gcttccactc   11460
gtcgtggctg aacacggtgc catcggatgc gatgaacgtg tcggggcgta gcttgtgaag   11520
ttcggcttcc acgctctgcc ggtaggtttc ggcgaggccc tcaaaatcca tgtggtcgca   11580
ggagaggttt tcgaggcgtg tcaggtcgaa gggtgtgggg cagtcgtagc tggcgggggt   11640
gtagagctgg gtgaagtggt cggcgatctt ctgcatgacg ggttccttt ctcgtgtggt   11700
gggttgatgg tttttatcgt gtggcttcgg cgatgatgc gtctacatag atcatgtcga   11760
tgagatcgtg gagttcctcg gcctcattct cggagaggtg gcgccagtcg ggtggcccat   11820
atactgcgcc gtcgagggtg acagtccaca gtggccggat gagtcgtatg gcttcttgta   11880
ctttagcgtg gtacatgcgg cgcaccatat cgagatcgat gtcgtctgaa tggtttccgg   11940
tgaggctgtg gaggctaagc gggtcgattt ctgtctgcct gtagagggat gtgaaggatg   12000
gtgtgatgag tgtgccatcc atgatgggt tgctcctttc ggtggtgtag ggggttgttgt   12060
ggttttttatg gtgtgagggt tgtgatccat agtcaaggct gcgctcaatc ggattgagcg   12120
tttcatggag tgtgtcgggt gtgacagatg tcactgaagc ctttattgcc tctctcagcg   12180
tctcaaatct tctaggggta gaaatatact agggcagccc tataaatgca ttctaggccc   12240
ctttctgtga ctctgagggg catatgtgag tggagggtgg tatgacaggt ggcatggact   12300
tggaggaagg tgtccagtcg ggagcgctcg atgatccggc tgcacgggtg tctgaaggc   12360
ttatggtctg cgtgagatat gtcacatcac ctagactcta ggaacactac ccacacctgt   12420
agagtctatt ctgcagatgg caccagagcc aagaatgcct ctctaaggca cgtaaaggcc   12480
cctctgaggc tcttacaccc tcaactctag gtatttgtac ccccagcata ttctgatcga   12540
ttctagggcc ctttttgagg cttacgcgag aacagcaccc aaagactagc ccatcaaccc   12600
ttactctggt tagctaagcc tgcactatgt ggacagtgtg ggatgctaag agggaagaag   12660
gacacggtaa aagaaaaaag ggggagtacc agccttcacg cctttcaagcc ttaaggtctt   12720
agcactaagc acttagcacc gagcccctc aagggctcagg catcagcccg agcaggctca   12780
gccctgaaag gggtacacgc catcagggaa ggcttgagag tacgaggagc cttagcgacg   12840
agtactcgaa agcctgagga aacaccatca gcactgatgg gcctagcgcg ttcggaaagg   12900
acacaagagt aaagtgtgac agctatccgg gagtgaaacc cgttctggct aggggtttca   12960
gccttaacca cctgtaaagg ttacaagact ctaagaaaat ttaagaaact tcttaggaag   13020
aaagttgtgt tgatgtcacc ccaaaaacac ctaaaatagc cctcaaaccc gcctatagag   13080
ccaaacagtc aagtttgact cgtcttgacg gcgtatgcta ggctggacag gtagccagct   13140
ggacgcaagg ccagaaagtg ctgacgcact tcccgacctt gcttaccatc agtctaccaa   13200
agacttaaaa gtttaacagc taagcgctaa gcccttaaga cctaaaacgct tagcaccgag   13260
cccctcaag ggctcggcat cagtcctaag agcttagccc ttaaggatct aaggttacta   13320
taaagctta aacactttaa gtaaacttaa gagcttagca cttaaagtta attaataacc   13380
ttaaaggctt acacacttag cactgagccc ttcaaggctc agcatcagta taagacctt   13440
aacacctaag ttaagtataa aactttaaag gcttagcgct taaggatata aacttaacat   13500
cagtgtttaa gacttaaaga gttaaacact taaagtaact ataatacttt aaaaatctta   13560
agtacttaaa gttaaccatc agtcttaaac tttaatatta taacctataa gtattaaagc   13620
ttataagtta taaaagtttt agaagagcta aggggttaac ttctttactt ctcttctctc   13680
tttggttctt tctctcttct ctccttttct tcatcagggg agaagaggaa ccttaccat   13740
cagcgccgat gggcttttca tcgtgtgact cgtgtgcttc tggtcgcaag ctcccatcg   13800
acactcccca cactcttaca cccgtgcccc tttcaggctt agcgtgttcg gctgaaggcg   13860
tacggcgtgt cacgctcaca cccttaacac cgggtgagac ttaaagtgta tattatatgt   13920
agaagacttt aaaacctata gagtgtttct gctgagcctg tgtcctacac cgctaggcgc   13980
caagcgctaa gccttgaaac gcgaacacac acccaccccc tttttctctt cgtgtccttc   14040
tcttttgaca ccgctgggg gcgatgtgat cttttctcaca tgccaggggg tagtggagaa   14100
aacaaacacc ccggcacaaa cagaacaccc cctcaaacga acaaaacagc ccccaggatc   14160
gactagcagg gcaagggtag agtattcata cccccagacg attccaggcc gttagagagg   14220
caatgagg ctcacagggg tcatgggaga tcggggaacg cgatggcaca caccaaccgc   14280
acagccagcc aagccaccg acgctggcgg caacgactca tcacccaagc ccgacaacaa   14340
ggccaaaccg aatgccact ctgcggagca accatcacct gggacacaca ccagctgcca   14400
accagccccg aagccgacca catcacaccc gtcagcaggg gaggactcaa caccctcgac   14460
aacgggcaaa tcatctgcag aacatgcaac agaagcaaag gcaatcgcag cgaaccaaac   14520
atcaaattcc aacaacaaac cacaaaaaca cttgtttcat ggtgacaaac cgccaaccc   14580
ccaccgggca caccccctgc acacccgtgc aagacctcgt acgcttagt gaaatacctc   14640
cctttttgtgg atttgtctgt ttgtcgactt tttgtgttgg tggtgagtgt ggtgcagcct   14700
gagcttcctg atggtcgtga gtggtgtggg gagacgcgtc gttggtggcg tgtgtggggt   14760
gaggatagtc gcgcgcagta cgtgtctgat gaggagtggc tgtttctcat ggatgctgcg   14820
gtgattcatg atttgtgtg gcgtgagggt gcgcgagatt tggtggcttc gcttcgtgct   14880
catgtgaagg ctttttatggg tatgttggat cggtattcgg ttgatggtggc tctggtggc   14940
cgtggtggg gttctgcggt ggcgatgatt accggtata ggaagcgcaa gggggcctga   15000
ttaggtgtct ggtgttgttg ggtctcaggt tcctcgtcat cgtgtggctg cggcgtattc   15060
ggtgtctgct ggcggtgatg cgggtgagct tggtagggcg tatgggttga cgcctgatcc   15120
gtggcagcag caggtgttgg atgattggct ggctgtcggt ggtaatggca ggcttgcttc   15180
```

```
gggtgtgtgt ggtgtgtttg tgcctcgcca gaatggcaag aatgcgatcc ttgaggttgt    15240
ggagttgttt aaggcgacta ttcagggtcg ccgtattttg catacggctc acgagttgaa    15300
gtcggctcgt aaggcgttta tgcggttgag gtcgtttttt gagaatgagc ggcagtttcc    15360
tgacttgtat cgtatggtga agtcgattcg tgcgacgaat ggtcaggagg ctattgtgtt    15420
gcatcatccg gattgtgcca cttttgagaa gaagtgtgac tgtccggatc gggttcggt    15480
tgagtttgtg gcccgttctc gtggttctgc tcgcgggttt acggttgatg atttggtgtg    15540
tgatgaggct caggagttgt cggatgagca gttggaggct ttgcttccta cggtgagcgc    15600
tgccccgtct ggtgatccgc agcagatttt cctgggtacg ccgcctgggc cgttggcgga    15660
cgggtctgtg gtgttgcgtt tgcgtggtca ggctttgtcg ggtggtaaaa ggttgcgtg    15720
gacggagttt tcgattcctg acgagtctga tccggatgat gtgtcgcggc agtggcggtga   15780
gttggcgggg gatacgaatc ctgcgttggg tcgtcgcctg aatttcggga ccgtaagcga    15840
tgagcatgag tcgatgtctg ctgccggttt tgctcgggag cggcttggct ggtgggatcg    15900
tggccagtct gctacgtcgg tgattccggc tgataagtgg gctcagtcgg ctgtggatga    15960
ggcgagtctg gttggcggga aagtgtttgg tgtctcgttt tctcgttctg gggatcgggt    16020
tgctttggct ggtgccggcc ggactgatgc tggggttcat gttgaggtta ttgatgggat    16080
gtctggcacg attgttgatg gtgtgggccg gttggctgac tggttggcgg ttcgttgggg    16140
tgatactgac cggatcatgg ttgccgggtc tggtgcggtg ttgttgcaga aggcgttgac    16200
ggatcgtggt attccggggcc gtggcgtggt ggttgccgat actggcgtgt atgtggaggc    16260
gtgtcaagcc ttcctggaag gtgtaaggtc tgggaatgtt tctcatcctc gtgctgattc    16320
tcgccgtgac atgttggata ttgctgtgag gtcggctgtg cagaagcgta aggggtctgc    16380
gtggggttgg ggttcctcgt ttaaggatgg cagtgaggtg cctttggagg ctgtgtcttt    16440
ggcgtatctt ggtgcgaaga tggcgaaagc gaagccgtcg gaacggtctg atgtggaagcg   16500
ggtgtctgtg gtatgaactc ggatgagttg gctctaattg agggcatgta cgatcgtatc    16560
caaaggttgt cttcgtggca ttgtcgcatt gagggctact atgagggctc gaatcgggtg    16620
cgtgaccttg gtgtggctat tccgccgag ttgcagcgtg tgcagactgt ggtgtcgtgg     16680
cctggtatag ccgtggatgc tttggaggag cgtctggagg ggcttggctg gactaatgat    16740
gacggctacg gcctggatgg tgtgtatgct gcgaatcggc ttgctacggc gtcgtgtgat    16800
gtgcatttgg atgcactaat ttttgggttg tcgtttgttg cgattattcc tcatggtgat    16860
gggtcggttt tggttcgtcc gcagtcacca aagaattgca caggtaagtt ttcggctgac    16920
ggttctcgtc tggaggctgg cctttgtggtg cagcagacgt gtgatcctga ggtggtttgag  16980
gctgagctt tgttgcctga tgtgattgtt caggtgaggc ggcggggttc gcgtgaatgg     17040
gtcgagacgg gccgtattga gaatgtgttg ggtgcggttc cgttggtgcc tattgtgaat    17100
cgtcgtcgta cttctaggat tgatggccgt tctgagatta cgaggtctat tagggcttac    17160
acggatgagg ctgttcgcac actgttgggg cagtctgtga atcgtgattt ttatgcgtat    17220
cctcaacgtt gggtgactgg cgtgtcggct gacgagtttt cgcagccggg ttgggtcctg    17280
tcgatggctt ctgtgtgggc tgtggataag gatgatgacg tgacactcc gaatgtgggg     17340
tcgtttcctg tcaattcgcc tacaccgtat tcggatcaga tgagactgtt ggcgcagttg    17400
actgcgggtg aggcggctgt tccggaacgc tatttcgggt ttatcacgtc taacccacct    17460
agtggggagg ctttggctgc cgaggaatct cggcttgtga agcgtgctga acgcaggcag    17520
acgtcgtttg gtcagggctg gttgtcggtt ggttttttgg ctgccaaggc gttggattct    17580
cgtgttgatg aggccgattt ttttggtgat gttggtttgc gttggcgtga tgcttcaacc    17640
ccgactcggg cggctacggc tgatgctgtg acgaagcttg ttggtgccgg tattttgcct    17700
gctgattctc gtacggttgt ggagatgctg gggcttgatg gtgcaggt tgaggctgtg      17760
atgcgtcatc gtgccgaatc tgcggatccg ttggcggcac tggctggggc tatatcgcgt    17820
caaactaacg aggcatgata ggcgatggct tcgggtgcta tgtcgaggct tgctgcgact    17880
gagtatcagc gtgaggcggt caggtttgct gggaagtatg cgggctatta tgccgagctg    17940
ggtcgtttgt ggcgtgccgg gaagatgaca gacgcgcagt atgtgcgttt gtgtgtggag    18000
ttggagcgtg ccggccatga tggttcggca tcgttggctg ccaggtttgt gtcggatttt    18060
cgccggttga atggtgtgga tccgggtttg attgtgtatg acgagtttga tgctgccgcc    18120
gcgttggcta ggtcgttttc gactatgaag attcttgaga gtgacccgga tagggcgaat    18180
gacacgattg atgcgatgc tgcgggtgtt aatcgggctg tcatgaatgc tggccgtgac     18240
acggttgagt ggtctgcggg tgcgcagggt aggtcgtggc gtaggggttac tgatggtgat   18300
ccgtgtgctt tttgtgccat gttggctacg aggtcggatt atacgacaaa gaaagggca    18360
ctcactaccg gtcatacgcg gcgtcataag cgtggtggta agcgtccgtt tggttcgaag    18420
tatcatgatc atttgtgtttg tacggtggtt gaggttgttg gcccttggga gccaaatagg    18480
gctgatgtcg agtatcagag gacgtatgag aaggccgtg agtgggttga tgatcatggg     18540
ttgcagcagt cgcctggcaa tatttttgaag gctatgcgta ctgttggcga tatgagataa    18600
tttgatgtgg tttccggttg tgcgccgccg gttattggtg cacagggttg tctcccgcac    18660
gggggtcaac aatgttgtgt tgttttccgc aaggagtgta gggttaggc atggccgatc     18720
agagtgttga ggaacagaat gttgacaatg atgttgtgga gtccggaaag gataacgca     18780
ttgttgatac agtaaaagac gatggcgggc aggaggtagc cgacaatcag ttgaagaatg    18840
aaggcgaggg taaatcgccg gggactgatt ggaaggcgga ggcccgtaag tgggagtctc    18900
gtgctaaaag taatttcgcc gagttggaga agcttcgcgc ctcggatggt gattctggat    18960
ctactattgc tgagcttcgc cgcaagaatg aggaactcga acacaggatc aacgggttg     19020
ttcttgaggg tgtgaagcgc gagatggctt cagagtatgg ttttgtccagt gatgcgatcg    19080
ttttcttgtc gggtggcgat aaggagtcgc ttgccgagtc tgcgaaagct tgaagggtt     19140
tgatcgacca tagtagtggt ggcgcgggtg tgcgccgtct tgcggggagt gccccgttg     19200
atgatgttaa acgacgtgag ggtgtcgcgt ttgtggatgc tcttgtcaat aattctagga    19260
gatgatttgt gatggttgac gattttcttt ctgcagggaa ggtggagctt cctggttcta    19320
tgattggtgc ggttcgtgac cgtgctatcg attctggtgt tttggcgaag cttttcgccgg   19380
agcagccgac tattttttggc cctgttaagg gtgccgtgtt tagtggtgtt cctcgtgcta    19440
agattgttgg tgagggcgag gttaagcctt ccgctagcgt tgatgtttcg gcgtttactg    19500
cgcagcctat caaggttgtg actcagcagc gtgtctcgga cgagtttatg tgggctgatg    19560
ctgattaccg tctgggtgtt ttgcaggatc tgatttcccc ggctcttggt gcttcgattg    19620
gtcgcgcctc ggatctgatt gctttccatg gtattgatcc tgccactggt aaagcggctg    19680
ccgctgtgca tacttcgctg gataagacga agcatattgt tgatgccacg gattctgcta    19740
cgaccgatct ggtcaaggct gtcggtctta tcgctggtgc tggtttgcag ttcctaacg     19800
gggttgcttt ggatccggcg ttctcgtttg ccctgtctac tgaggtgtat ccgaaggggt    19860
ctccgcttgc cggccagcct atgtatcctg ccgccgggtt tgctggtttg gataattggc    19920
```

```
gtggcttgaa tgttggttct tcttcgactg tttctggcgc cccggagatg tcgcctgcct  19980
ctggtgttaa ggctattgtt ggtgattct cgcgtgttca ttggggtttc cagcgtaact   20040
tcccgatcga gcttatcgag tatggtgacc cggatcagac tgggcgtgac ctgaagggcc   20100
ataatgaggt tatggttcgt gccgaggctg tgctgtatgt ggctatcgag tcgcttgatt   20160
cgtttgctgt tgtgaaggag aaggctgccc cgaagcctaa tccgccggcc gagaactgat   20220
ttattgttgc ggtgatgtgt caatgtgcag ggggtggtgt tgatgggtat cattttgaag   20280
cctgaggata ttgagccttt tgccgatatt cctagagaga agcttgaggc gatgattgcc   20340
gatgtggagg ctgtggctgt cagtgtcgcc ccctgtatcg ctaaaccgga tttcaaatac   20400
aaggatgccg ctaaggctat tctgcgcagg gctttgttgc gctggaatga tactggcgtg   20460
tcgggtcagg tgcagtatga gtctgcgggt cctttcgctc agactacacg gtctagtact   20520
cccacgaatt tgttgtggcc ttctgagatt gccgcgttga agaagctgtg tgagggtgat   20580
ggtggggctg gtaaagcgtt cactattaca ccgaccatga ggagtagtgt gaatcattct   20640
gaggtgtgtt ccacgtgtgt gggtgagggt tgctcatgcg ggtcgaatat taacggctac   20700
gctggccctt tgtgggagat atgatatgac cagtttcct tatggtgaaa cggttgtgat   20760
gcttcaaccg actgttcgtg tcgatgatct tggtgacaag gttgaggatt ggggcatcc    20820
tgtagaaacc gtgtaccata acgtggccat ctatgcttcc gtttcgcagg aggatgaggc   20880
cgcggggcgt gactctgact atgagcattg gtcgatgctt tcaagcagt ctgttgttgg    20940
tgctgattat cgttgccggt ggcgtattcg gggtgttgtg tgggggctg acgggtctcc    21000
tatggtgtgg catcaccca tgtccggttg ggatgcgggc acgcagatca atgtgaagcc    21060
caagaagggc tgatagattg tggctcagga tgtgaatgtg aagctgaact tgccgggtat   21120
tcgtgaggtg ttgaagtctt ctgggtgcca ggctatgttg gctgagcgtg gcgagcgtgt   21180
caagcgtgcg gcctcggcga atgtgggcgg taacgctttc gataaggccc aataccgtaa   21240
tggtttgtcg tcgaggtgc aggttcaccg tgttgaggct gtcgctcgta taggtaccac    21300
atataagggt gggaagcgta ttgaggcgaa gcatggcacg ctggctaggt cgattgggc    21360
ggcgtcgtga tcatctacga tgaccccagg aagtgggcta aacgcgtgct caaggatgat   21420
ggctggctgt ctgggatacc atgcaccggg acagtgcccg atgattttac gggtgacctg   21480
atttggttgg cgttggatgg tggcccacag ttgcatgcttc gcgagcaagt ttttttgcgc   21540
gtgaatgtgt tttctgatac gccggatcgt gctatgtcgc tagccaggcg ggtgaggct    21600
gtccttgcgg atgggttga tggcaaccct gtggtgtact gtaaacgtc tactggtcct    21660
gatttgctgg ttgattggtgc acgttttgat gtgtattcgc tgttcgagct gatatgtagg   21720
cctgtcgagt ctgagtaaac gtatttgttt ttgttttaat gtaattgttt gatatttaat   21780
gggggttgtg atgctgcaa cacgtaaagc gtcaatgtt cgttcagcgg ttactggcga     21840
cgtttatatt ggtgacgcgc acgcgggtga tactattaag ggtgtggagg cggttcctga   21900
cggtcttacc gctttagggt atctgtcgga tgacgggttt aagattaagc ctgagcgtac   21960
aacgcgatgat ttgaaggctt ggcagaatgc ggatgttgtt cgcacggttg ctaccgagtc   22020
ttctatcgag atttctttcc agctgatcga gtctaagaag gaggttatcg agctgttttg   22080
gcagtcgaag gttactgccg gatccgattc aggttcgttc gatatttctc cgggtgccac   22140
gacgggtgtt cacgccctgt tgatggatat tgtggatggt gatcaggtta ttcgctacta   22200
tttccctgga gttgagttga tcgatcgtga cgagatcaag gccaagaatg gcgaggtgta   22260
cgggtatggt gtgacgttga aggcgtatcc tgcccagatt aataagaagg gcgatgcggt   22320
gtcgggtcgg gggtggatga cggctttaaa agctgatact cctccggttc cgccttctcc   22380
gaagccgaag ccggatccta atccgccgtc tgagaactga tacacgattt taggggattg   22440
ttgatagatg agtgacacgg gttacacgtt gaagattggt gaccgtagct gggtgttggc   22500
ggatgcggag gagacggctc aagctgtgcc tgcccgcgtg tttcgccgtg cagctaagat   22560
tgcccagtcg ggggagtctg cggatttcgc ccaggttgag gtgatgtttt ctatgttgga   22620
ggctgccgcc ccagtggatg ctgtggaggc cctgaggggg cttcctatgg ttcgtgtggc   22680
cgagattttc cgtgagtgga tggaatataa gcctgacggt aagggtgcct cgctgggga    22740
atagtttggc tccacggcct gattgatgat tatcgtgggg ccatcgaata tgattgagg    22800
acccggttcg gttgctcggt ttatgatgtt ggtggcccga taatgtgttg gggtgaggct   22860
gttcggctgg ctggcgtgtt gtgtaccgat acgtctagcc agttggcggc ccacctgaat   22920
ggttggcagc gccgtttga ttggtctgag tgggcgtgt tggacatgtt ggatcattac     22980
aggtctgcta atagtgaggg gcagccggag cctgtggcga ggcctacgga tgagcgtagg   23040
gcccggttta cgtttgggca ggtggacgat attttggcgc gtgttcgtgc cggtggcggg   23100
gtgtctcgcg agattaatat tatggggtga atagtgtatg tctggtgaga ttgcttccgc   23160
atatgtcg ttgtatacga agatgcctgg tttgaaggct gatgttggta aacagttgtc     23220
gggtgttatg cctgctgagg gtcagcgttc gggtagtctt tttgctaagg gtatgaagtt   23280
ggcgcttggt ggtgccgcaa tggtgggtgc catcaatgtt gctaagaagg gcctcaagtc   23340
gatttatgat gtgactattg gtggcggtat tgctcgcgct atggctattg atgaggctca   23400
ggctaagttg actggtttgg gtcatcagtc gtctgacacg tcttcgatta tgaattcggc   23460
tattgaggct gtgactggta cgtcgtatgc gttgggggat gcggcttcta ctgcggcgtg   23520
gttgtctgct tcgggtgtga agtctggcgg gcagatgacg gatgtgttga agactgtcgc   23580
cgatgtgtct tatatttcgg gtaagtcgtt tcaggatacg ggcgcatttt ttacgtctgt   23640
gatggcccgc ggtaagttgc agggtgatga catgttgcag cttacgatgg cgggtgttcc   23700
tgtactgtct ttgcttgcca ggcagacggg taaaacgtcg gctgaggtgc tgcagatgtt   23760
gtcgaagggg cagattgatt ttgccacgtt tgccggctgcg atgaagcttg catgggtgg   23820
tgctgcgcag gcgtctggta agacgtttga gggcgctatg aagaatgtta agggcgcttt   23880
gggctatctt ggtgctacgg ctatggcgcc gtttcttaac gggttgcggc agattttgt    23940
tgccttgaat ccggttatca agtctatcac ggattctgtg aagccgatgt ttgctgccgt   24000
cgatgctgat attcagcgta tgatgccgtc tattttgcgg tggattaacc gtatgccggg   24060
catgatcact cgaatgaatg cacagatgcg cgccaaggtg gagcagttga agggcatttt   24120
tgcaaggttg catttgcctg tccctaaagt gaatttgggt gccatgtttg ctggcggcac   24180
cgcagtgttt ggtattgttg ctgccggtgt ggggaagctt gtcgcggggt ttgccccgtt   24240
ggcggtgtcg gtgaagaatc tactgccgtc gtttggtgct ttgaagggtg ccgccggcgg   24300
gcttgctggc gtgtttcgcg ccctgggtgg ccctgtcggg attgtgatcg gcttgtttgc   24360
tgccatgttt gctacgaacg cccagttccg tgccgctgtt atgcagcttg tgctgtggt    24420
tggtcaagcc ctgggcggaga ttatggccgc tgtgcagcct gtgtttggtt tggttgcggg   24480
tctggtggcc cggttggcgc cagtgtttgc ccagattatt ggtttggttg ccgggctggc   24540
tgcccagttg atgcctgtga ttggtatgct tgttgcccgg ctggttcctg tgatcaccca   24600
gattattggt gcggtgacgc aggtggcggc catgttgctg ccggcgttga tgccggtgtt   24660
```

```
gcaggctgtt gttgctgtga tacggcaggt tgttggcgtg atcatgcagt tggtgccggt   24720
gttgatgccg gtgattcagc agattttggg tgcggtcatg tctgtgctgc cgccgattat   24780
tggtttgatc cggtcgttga tgcctgtgat tgcggcggtt atgcgtgtgg tggtgcaggt   24840
tgtttcggtt gtgatacagg tggtggcccg tattcttgct gttgtggctc cgatggtggc   24900
tgccgtggta gggtttgttg cccgtattgt tggtgctgtc gtgtcggctg ttgcccgtgt   24960
tattgctgct gttgcccgtg ttatcggtg gattgttgct cattttgtgt cgggtttgc   25020
gcgtatgggt tcggttattc aggctggctg gaatcatatt agggcgttta cgtctgcgtt   25080
tattaacggt tttaagtcgg tgatttctgg cggcgtgaac gctgttgtgg ggttttttac   25140
gcggcttggt ttgtcggttg cttctcatgt tcggtctggt tttaacgcgg ctcgtggtcg   25200
tgtttcttct gcgatgaatg ctattcggag tgttgtgtct tcggtggcgt ctgctgttgg   25260
cgggttttc agttcgatgg cgtctagggt tcgtagtggt gttgtgcgcg ggtttaatgg   25320
ggccaggaat gcggcatctt ccgctatgca tgctatgggg tccgctgtgt ctagcggcgt   25380
gcatagtgtg ctagggtttt tccggaatct gcctggcaat attcggcatg ctctcggtaa   25440
tatgggggtct ttgttggtgt ctgctggccg tgatgtggtg gccggtttgg gtaacggtat   25500
taagaatgct ttgagtggcc tgttggatac ggtgcgtaat atgggttctc aggttgctaa   25560
tgctgcgaag tcggtcgttgg gtattcattc cccgtcgagg gtgtttcgtg acgaggttgg   25620
ccgtcaggtt gttgccggtt tggctgaggg tattactggt aatgcgggtt tggcgttgga   25680
tgccgatgtct ggtgtggctg gtcggctgcc tgatgtggta gatgcccggt ttggtgtgcg   25740
atcgtctgtg ggctcgttta ccccgtacga ccggtatcgg cgtgcgagtg agaagagtgt   25800
tgtggtgaat gttaacgggc ccacgtatgg tgatcctaac gagtttgcga agcggattga   25860
gcgtcagcag cgtgacgctt tgaacgcttt ggcttacgtg tgatagggg tgtggttcat   25920
gtttcttcct gacccgtctg atcgttctgg tttgactgtt acctggtcta tggatccgct   25980
gtttggcgat gagcgtgtgc ttcatttgac ggattatacg gggtcgtctc cggtgatgtt   26040
gttgaatgat tcgttgcgcg gtttgggtgt tcctgaggtg gagcattttt ctcaaactca   26100
tgttggggtg catggctcgg agtggcgcgg gtttaatgtg aagcctcgcg aggtgacgct   26160
gcctgtcctg gtgtcgggtg ttggtgtgga tcctgtgggc gttttcgtg acggttttt   26220
gaaagcctat gacgcgttgt ggtctgcttt tcctcccggg gaggagggtg aactgtcggt   26280
gaagactcct gccggcaaag agcgtgtgct gaagtgccgg tttgattcgg ctgatgacac   26340
gtttacggtg gatccggtga acaggggtta tgcgcgttat ctgttgcatt tgacggctta   26400
tgacccgttt tggtatgggg atgagcagaa gtttcgtttc agtaacgcga agttgcagga   26460
ttggttgggt ggcggccctg tcggcaagaa gggtacagcg tttcctgtgg tgttgacgcc   26520
tggtgttggt tcgggttggg ataacttgtc taataggggt gatgtgccgg cgtggcctgt   26580
gattcgtgtg gagggccccc tggagtcgtg gtctgtgcag attgatggtt tgcgtgtgtc   26640
ttcggattgg cctgtcgagg agtatgattg gatcactatt gatacggatc ctcgtaaaca   26700
gtctgccgttg ttgaacgggt ttgaaggatgt gatggatcgt tgaaggagt gggagtttgc   26760
gcctatcccg cctggcggtt ctaagagtgt gaatattgag atggttggtt tgggtgccat   26820
tgttgtgtcg gtgcagtaca ggttttttgag ggcttggtga atagttgatg ctggtcttg   26880
ttccgcggat aacattgttt acaccggatt atcaccgtgt ggcgcctatc aatttttttg   26940
aatcgttgaa actgtcgttg aagtggaatg gtttgtccac tttggagttg gtggtgtctg   27000
gtgatcattc taggcttgac gggttgacta agccgggtgac acggctggtt gttgattatg   27060
gtggtggcca gatttttttct gggcctgtgc gtaaggttca tggtgtgggt ccgtggcgtt   27120
cttcgcgggt gactatcacg tgtgaagatg atattcgtct gttgtggcgt atgttgatgt   27180
ggcctgctgaa ttatcgtcct ggtatggttg gtatggagtg gcgtgccgac agggattag   27240
cccactattc gggtgcggct gagtcggtgg ctaagcaggt gttgggggat aatgcttggc   27300
gttttccgcc tgatatattt atggtggatg ataaagagtcg tggccgctat attaaggatt   27360
ttcaggcgcg gtttcacgtg tttgccgata agttgttgcc ggtgttgtcg tgggctcgga   27420
tgactgtcac ggtgaaccag tttgagatg cgaagcagga tcagcgggat ttgctgtttg   27480
attgtgtgcc tgccgtgacc cgtaagcatg tgttgactgc cgagtctggg tctattgtgt   27540
cgtgggagta tgtgagggat gccccgaagg cgacatctgt ggtggttggt ggccgcggcg   27600
agggtaagga tcggctgttt tgtgaggatg ttgattcggc ggccgaggat gactggtttg   27660
atcgtgtcga ggtgttttaag gatgcccgta acacggattc tgaacggtg catcttattg   27720
atgaggcgga gcaggtgctg caggagtctg gggccacgtc ggggtttaag atcgagttgg   27780
ccgagtcgga tgtgttgcgg tttgggccag gcaatctgat gccgggtgat ttgatctatg   27840
tggatgtggg ctcgggctct atcgcggaga ttgttcggca gattgatgtg gagtgtgatt   27900
cgccgggtga tggttggacg aaaagtgactc ctgttgcggg ggattatgag gataatccgt   27960
cagcattgtt ggctcgccgt gttgccggtt tggctgcggg tgtgcgggat ttgcaaaagt   28020
tttagaagga ttgggggttg ttgtgggtat tgtgtgtaaa gggtttgatg gtgtgttgac   28080
cgagtatgat tgggctcaaa tgtctggtct gatgggtaat atgccgtcgg tgaaagggcc   28140
ggatgatttt cgtgtcggta cgactattca gggtgccaca gtgttgtgtg aggtcctgcc   28200
ggggcaggct tgggctcacg gggtgatgtg cacgtcgaat agtgttgaga cggtgacggg   28260
gccgcttccg ggcctggcg agacccgata cgactatgtg gtgttgtctc gggattggga   28320
gcagaatacg gccaagttgg agattgtttc tgggggcgt gcggagcgtg ccagggatgt   28380
gttgcgtgcc gagcctggcg tgtttcatca gcagttgttg gcgactttgg tgttgtcgtc   28440
taacgggttg cagcagcagt tggatagcg tgctataggcg gtaggggttg cgtttggcga   28500
gtctgctgcg tgtgatccta ccccggtgga gggtgaccgg gtgatggttc cttcggggc   28560
tgtgtgggtc aatcatgcta acgagtggat gctactgtct ccgaggattg agacgggttc   28620
taagcagatc cagtttggcg gtctgccgt gtatgcttac acgatcccgt ttgatcgcca   28680
gttcactagt gcgcctgtcg tggtggcgtc tatggctacg gcggctgggg gcacggcaca   28740
gatcgatgtg aaagcctaca atgttactgc caaggatttt cggttggcgt ttatcacgaa   28800
tgacgggtct aagccgaatg tgtgtgcctgc ggtggctaac tggattgctg tcggcgtgtg   28860
actgtacagg tgttgtggcg gatggtgtga tgttgggggg ctgtggtgtc gtggtttact   28920
cctgcactgt tggcctctat ctgtacgcg ttggccacgg ttttgggttc tgttcaggct   28980
gtcacatccc ggtctaggaa gcgtttacgg aggctgtctg cgcaggtgga tgcgatggaa   29040
gagtatacgt gggggctgtcg acgcgaggtt cgaaggttta acgcgggct tcctgacgag   29100
gtggagccta tgcatcttcc tgatttgccc gagtttttga aagatactgt tgatgctggt   29160
gggggggtgaa ttgtgaggga gttggaggaa gaaaaaaggc agcgccgctc gtttgagaag   29220
gcttccctga tactgttgtt cctgtcgctt tgctgttgg cggtggttgc tgcgggtgct   29280
ttacggtacg ggtctgtggc ttcccagcgg gattcggagc aggcgagggc ccagtctaat   29340
ggtacagccg ctaaaggggtt ggccagccgt gtgaagcggg tgtgtgcttc gggtgggcag   29400
```

-continued

```
gagtcggtgc ggcttcacca gtctggcttg tgtgtggatg ctcggcgtgt tgagcggagt      29460
gtgcagggtg tgccgggtcc tgcaggtgct gatggccggg atggtgttaa tggttcggct      29520
gggctggttg gccctgttgg tccgcagggt tctcctggtt tg                        29562

SEQ ID NO: 76           moltype = DNA  length = 83
FEATURE                 Location/Qualifiers
misc_feature            1..83
                        note = Cos PAC7 83bp
source                  1..83
                        mol_type = other DNA
                        organism = synthetic construct
SEQUENCE: 76
aaaacccgcc aaccccccacc gggcacaccc cctgcacacc cgtgcaagac ctcgtacggc      60
ttagtgaaat acctcccttt tgt                                               83

SEQ ID NO: 77           moltype = DNA  length = 816
FEATURE                 Location/Qualifiers
misc_feature            1..816
                        note = endolysin gene
source                  1..816
                        mol_type = other DNA
                        organism = synthetic construct
SEQUENCE: 77
gtgaataggg ttgtgattca tgcgacgtgc ccggatgtgg ggtttccgtc cgcctcgcgt      60
aaaggacggg ctgtgtccac ggcaaactat ttcgcttccc catcgtctgg tggttcggcg     120
cattatgtgt gtgatattgg ggagacggtg caatgcttgt cggagtctac gattgggtgg     180
catgccccgc cgaatccgca tagtttgggt atagagattt gcgcggatgg gggttcgcac     240
gcctcgttcc gggtgccggg gcatgcttac actcgtgagc agtggctgga tcctcgcgtg     300
tggcctgcgg ttgagcgtgc cgccatcctg tgtagacgtt tgtgtgacaa gcatggtgtt     360
ccgaaaagga aactgtctgt ggccgatttg aaggccggta aacggggtgt ttgcgggcat     420
gtggatgtta cggatgcgtg gcatcagtcg gatcatgacg atccggggcc gtggtttccg     480
tgggacaaat ttatgctgt ggttaatggc cacggcggcg gttcaagtag tgaggagttg      540
agtatgcgct atgtacaagc gttacataat cagattaaac agttgtcggc acaggtggcc     600
cagtcggtga ataagctgca tcacgatgtt ggtgtggttc aggttcagaa tggtgatttg     660
ggtaaacgtg ttgatgcctt gtcgtgggtg aagaatcctg tgacggggaa gctgtggcgc     720
actaaggatg ctttgtggag tgtctggtat tacgtgttgg agtgtcgtag ccgtcttgac     780
aggctcgagt ctgctgtcaa cgatttgaaa aagtga                                816

SEQ ID NO: 78           moltype = DNA  length = 249
FEATURE                 Location/Qualifiers
misc_feature            1..249
                        note = PAC7-m28-gp45 plaque n:1 from alignment figure 18
source                  1..249
                        mol_type = other DNA
                        organism = synthetic construct
SEQUENCE: 78
tagtggagaa aacaaccacc ccggaacgtt taagcacccc cctcaaacga acaaaacagg      60
gcctagaatc gatcagcagg gcaccggtag ggtattccta ccccccagacg attcaaggcc    120
aaaccgaatg cccactctgc ggagtcacca tcacctggaa cacccacgac ctgccaacca    180
gccccgaagc cgaccacatc acaccccgtca gccggggagg actcaacacc ctcgacaacg    240
ggcaaatca                                                              249

SEQ ID NO: 79           moltype = DNA  length = 20
FEATURE                 Location/Qualifiers
misc_feature            1..20
                        note = endolysin target
source                  1..20
                        mol_type = other DNA
                        organism = synthetic construct
SEQUENCE: 79
atgcgacgtg cccggatgtg                                                   20

SEQ ID NO: 80           moltype = DNA  length = 20
FEATURE                 Location/Qualifiers
misc_feature            1..20
                        note = Cos target
source                  1..20
                        mol_type = other DNA
                        organism = synthetic construct
SEQUENCE: 80
aaaacccgcc aaccccccacc                                                  20

SEQ ID NO: 81           moltype = DNA  length = 1673
FEATURE                 Location/Qualifiers
misc_feature            1..1673
                        note = editing template endolysin
source                  1..1673
                        mol_type = other DNA
                        organism = synthetic construct
```

```
SEQUENCE: 81
tcacctgtca agacggctac gacactccaa cacgtaatac cagacactcc acaaagcatc    60
cttagtgcgc cacagcttcc ccgtcacagg attcttcacc cacgacaagg catcaacacg   120
tttacccaaa tcaccattct gaacctgaac cacaccaaca tcgtgatgca gcttattcac   180
cgactgggcc acctgtgccg acaactgttt aatctgatta tgtaacgctt gtacatcagc   240
catactcaac tcctcactac ttgaaccgcc gccgtggcca ttaaccacag ccataaattt   300
gtcccacgga aaccacggcc ccggatcgtc atgatccgac tgatgccacg catccgtaac   360
atccacatgc ccgcaaacac cccgtttacc ggccttcaaa tcggcacacag acagtttcct   420
tttcggaaca ccatgcttgt cacacaaacg tctacacagg atggcggcac gctcaaccgc   480
aggccacacg cgaggatcca gccactgctc acgagtgtaa gcatgccccg gcacccggaa   540
cgaggcgtgc gaaccccccat ccgcgcaaat ctctataccc aaactatgcg gattcggcgg   600
ggcatgccac ccaatcgtag actccgacaa gcattgcacc gtctcccaa tatcacacac   660
ataatgcgcg gaaccaccag acgatgggga agcgaaatag tttgccgtgg acacagcccg   720
tcctttacgc gaggcggacg gaaatcccac atccggcacg gtcgcatgaa tcaaccct    780
attcaccgga ctattcgagc cggcagaatg atgcgccgca ggaatatatc tcacaacaca   840
ccaccaccaa acaccaccat cacagccact ccttttctatt tgtgggatga tatagtcact   900
agaggcgacg gtttcacacc ctggcaggcc gccgaaccg atatcgtgga agccacaccg   960
tcactatatt tcacaaccag gcggccccccg gaacagtaca cagacaccac cgagcgccca  1020
tccttaccat catggccatc cgatccattc gcaccggcgg gaccacgctc accccgttca  1080
ccctgtgcac cttgcgggcc ggcaggacct gaagggcctt gcgggccgcg ctcaccggca  1140
gaaccatccc gaccatcagc gccgtcaacg ccgttcacac cgtcagcacc tgcacgacct  1200
ggaacaccat cacggccatc cgaaccgtta gcgccaggca agccgtcagg acctttcaca  1260
ccattcaaac ccggagaacc ttgcggacca acagggccaa ccagcccagc cgaaccatta  1320
acaccatccc ggccggcagg acctgaaggg ccttgcgggc cgcgctcacc ggcaggaccc  1380
ggcacaccct gaacacgctg ctcaacacgc acagcatcca cacacaaacc agaacggtga  1440
agacgcacag actccacccc acccgaagca cacgcctgct tcacacgggc agccaaaccc  1500
ctggcagccg taccattcga ctgggccctc gcctgctccg aatcccgctc agaggataca  1560
gccccgaaac gcaaagcacc cgcagcaacc accgccaaca acacaagcga caaaaacaac  1620
aacaccagtg aagccttctc aaaattgcgg cgctgccgct tctcctcctc caa          1673

SEQ ID NO: 82           moltype = DNA  length = 1908
FEATURE                 Location/Qualifiers
misc_feature            1..1908
                        note = editing template cos
source                  1..1908
                        mol_type = other DNA
                        organism = synthetic construct
SEQUENCE: 82
acgagccaca aactcaaccg aaccccaacc cggacaacca cacttcttct caaacgtggc    60
acaatccgga tgatgcaaca caatagcctc ctggccattc gtcgcacgaa tcgacttcac   120
catacgatac aagtcaggaa actgccgctc attctcaaaa aacgaccgca accgcataaa   180
cgccttacga gccgacttca actcgtgagc cgtatgcaaa atacggcgac cctgaatagt   240
cgccttaaac aactccacaa tctccaaaat agcattcttg ccattctgcc gcggaacaaa   300
caccccacac acacccgaag caagcctgcc attaccaccc acagcaagcc aatcatccaa   360
cacctgctgc tgccacggat caggcgtcaa cccataagcc ctaccaagct ccccagcatc   420
cccgccagca gacaccgaat acgccacagc cacccggtga cgaggaacct gagacccaac   480
aacaccagac acctactcaa gcccccctac gcttcctata ccggtcaatc atcgctaccg   540
cagaaccccc accacggcca ccagacgcca catcaaccga atacctatcc aacataccca   600
taaaagcctt cacatgagca cgcaacgaag ccaccaaatc cgcgcgaccc tcacgccaca   660
ccacatcatg aatcaccgca gcatccatga gaaacaacca ctcctcatca gacacaaacc   720
cggcacgagg atcctcgccc cacacacacc accaccgacg cgtctcccca caccaatcac   780
gactatcagg aagctcaggc tgcaccacac acaccaccaa acaaaaagtc gacaaaacga   840
taaaacaaca aaagggaggt atttcactaa gccgtacgag gtcttgcacg ggtgtgcagg   900
gggtgtgtcc ggtgggggtt ggcgggtttt tcaccatgga atcaatgttt ttgtggtttg   960
ttgttggaat ttgatgtttg gttgtgttct gttgccttgg cttctgttgc atgttcttga  1020
gatgatttgc ccgttgtcga gggtgttgag tcctccccgg ctgacgggtg tgatgtggtc  1080
ggcttcgggg ctggttggca ggtcgtgggt gttccaggtg atggtgactc cgcagagtgg  1140
gcattcggtt tggccttgtt gtcgggcttg ggtgatgagc cttgcccgcc agcgccggtg  1200
ggcttggctg gctgtgcggt tggtgtgtgc catcacgccc cccaatctcc catggccctt  1260
gtgagcctct cattgctcct gtaatggcct tgaatcgtct gggggtagga ataccctacc  1320
ggtgccctgc tgatcgattc taggcccgtgt tttgttcgtt tgaggggggtg tcttaaacgt  1380
tccggggtgg ttgttttctc cactacccccc tggcatgtga gaaatatcac atcgcccccc  1440
agcggtgtca aaaggagaag gacacggaag aaaaatgggg gtggatgggt gttcacgttt  1500
cacatcttag cgctgagcgc ctagcgttaa aggaacgcgg aacaccttat  1560
aggttttaaa gtcttctact tataatatgc actttaagtc ttacctggtg ttaagggttt  1620
aagcgtgaca cgccgtacgc cttccgacga acacgctaag ccgtaaaggg gcacgggtga  1680
aagagtgtgg ggagtgtgcg atgggagctt gcgaccagaa gcacacgagt cacacggtga  1740
aaagtccatc agcgttgacg gttaaaggtt cctcttctcc cctgatgaag aaaagaagag  1800
aagagagaaa gaaccaaaga gagaagagaa gtaaagaagt taacccttta actcttctaa  1860
aaactttat aacttataag cttaatact tataatatta agtttaa                 1908

SEQ ID NO: 83           moltype = DNA  length = 1705
FEATURE                 Location/Qualifiers
misc_feature            1..1705
                        note = editing template endonuclease
source                  1..1705
                        mol_type = other DNA
                        organism = synthetic construct
SEQUENCE: 83
```

```
                                              -continued
actataaaag ctttaaacac ttaaagtaac tataaagctt taagagctta acatttaagg    60
atataaataa acattaaagc tttaaagtct taaagtaaat atataacctt aacacttaag   120
ttaagtataa aaccttaaag gcttagcact taaggatata aacttaacat cagtgtttaa   180
gacttaaaga gttaaagtaa ctattaagac ttaaaggctt ataagcttta atactttaag   240
tagctataag actttaaaaa cctgaagtac ttaaagttaa ccatcagtct taaactttaa   300
tattataagt attaaagctt ataagttata aaagttttta gaagagttaa agggttaact   360
tctttacttc tcttctctct ttggttcttt ctctcttctc ttcttttctt catcagggga   420
gaagaggaac ctttaaccgt caacgctgat ggacttttca ccgtgtgact cgtgtgcttc   480
tggtcgcaag ctcccatcgc acactcccca cactcttttca cccgtgcccc tttacggctt   540
agcgtgttcg tcggaaggcg tacggcgtgt cacgcttaaa cccttaacac caggtaagac   600
ttaaagtgca tattataagt agaagacttt aaaacctata aggtgttccc gcttagcccg   660
tgttccttta acgctaggcg ctcagcgcta agatgtgaaa cgtgaacacc catccacccc   720
cattttttctt ccgtgtcctt ctcctttga caccgctggg gggcgatgtg atatttctca   780
catgccaggg ggtagtggag aaaacaacca ccccggaacg tttaagacac cccctcaaac   840
gaacaaaaca gggcctagaa tcgatcagca gggcaccggt agggtattcc taccccccaga   900
cgattcaagg ccattacagg agcaatgaga ggctcacagg ggccatggga gattgggggg   960
cgtgatggca cacaccaacc gcacagccag ccaagcccac cgtcgctggc gggcaaggct  1020
catcacccaa gcccgacaac aaggccaaac cgaatgccca ctctgcggag tcaccatcac  1080
ctggaacacc cacgacctgc caaccagccc cgaagccgac cacatcacac ccgtcagccg  1140
gggaggactc aacaccctcg acaacgggca aatcatctgc agaacatgca acagaagcaa  1200
aggcaacaga acacaaccaa acatcaaatt ccaacaacaa accacaaaaa cattgattcc  1260
atggtgaaaa acccgccaac ccccaccggg cacaccccgt gcaagacctc  1320
gtacggctta gtgaaatacc tcccttttgt tgttttatcg ttttgtcgac tttttgtttg  1380
gtggtgtgtg tggtgcagcc tgagcttcct gatagtcgtg attggtgtgg ggagacgcgt  1440
cggtggtggt gtgtgtgggg cgaggatccg cgtgccgggt ttgtgtctga tgaggagtgg  1500
ttgtttctca tggatgctgc ggtgattcat gatgtgggt ggcgtgaggg tcgccgcgtt  1560
ttggtggctt cgttgcgtgc tcatgtgaag gcttttatgg gtatgttgga taggtattcg  1620
gttgatgtgg cgtctggtgg ccgtggtggg ggttctgcgg tagcgatgat tgaccggtat  1680
aggaagcgta gggggggcttg agtag                                       1705

SEQ ID NO: 84          moltype = DNA  length = 420
FEATURE                Location/Qualifiers
misc_feature           1..420
                       note = UnaG cds
source                 1..420
                       mol_type = other DNA
                       organism = synthetic construct
SEQUENCE: 84
atggtggaga agttcgtcgg tacatggaag atcgccgact cgcacaactt tggcagtac    60
ctgaaggcca ttggtgctcc caaggagctg tcggacggcg gcgatgccac caccccgacc   120
ctgtacatct cgcagaagga cggcgataag atgacggtga agattgaaaa cggcccgccc   180
accttcctcg atactcaagt gaagttcaag ttgggtgagg agttcgatga attcccgtcg   240
gaccgtcgta agggcgtcaa gagcgtcgtc aatctcgtcg aagaagct ggtctacgtt     300
cagaagtggg acggcaagga gactacctac gtgcgtgaga tcaaggacgg taagctggtg   360
gtgaccctca ccatgggaga tgtcgtcgcc gtccgcagct accggcgcgc caccgagtga   420

SEQ ID NO: 85          moltype = DNA  length = 249
FEATURE                Location/Qualifiers
misc_feature           1..249
                       note = PAC7-m28-gp45 plaque n:2 from alignment figure 18
source                 1..249
                       mol_type = other DNA
                       organism = synthetic construct
SEQUENCE: 85
tagtggagaa aacaaccacc ccggaacgtt taagacaccc cctcaaacga acaaaacagg    60
gcctagaatc gatcagcagg gcaccggtag ggtattccta cccccagacg attcaaggcc   120
aaaccgaatg cccactctgc ggagtcacca tcacctggaa cacccacgac ctgccaacca   180
gccccgaagc cgaccacatc acacccgtca gccggggagg actcaacacc ctcgacaacg   240
ggcaaatca                                                          249

SEQ ID NO: 86          moltype = DNA  length = 300
FEATURE                Location/Qualifiers
misc_feature           1..300
                       note = Cos PAC7 pIC400
source                 1..300
                       mol_type = other DNA
                       organism = synthetic construct
SEQUENCE: 86
aggcaacaga acacaaccaa acatcaaatt ccaacaacaa accacaaaaa cattgattcc    60
atggtgaaaa acccgccaac ccccaccggg cacaccccct gcacaccgt gcaagacctc   120
gtacggctta gtgaaatacc tcccttttgt tgttttatcg ttttgtcgac tttttgtttg   180
gtggtgtgtg tggtgcagcc tgagcttcct gatagtcgtg attggtgtgg ggagacgcgt   240
cggtggtggt gtgtgtgggg cgaggatccg cgtgccgggt ttgtgtctga tgaggagtgg   300

SEQ ID NO: 87          moltype = DNA  length = 300
FEATURE                Location/Qualifiers
misc_feature           1..300
                       note = Cos PAC7 pIC401
source                 1..300
```

```
                        mol_type = other DNA
                        organism = synthetic construct
SEQUENCE: 87
gaccacatca cacccgtcag ccggggagga ctcaacaccc tcgacaacgg gcaaatcatc    60
tgcagaacat gcaacagaag caaaggcaac agaacacaac caaacatcaa attccaacaa   120
caaaccacaa aaacattgat tccatggtga aaaaccegcc aaccccecace gggcacaccec   180
cctgcacacc cgtgcaagac ctcgtacggc ttagtgaaat acctcccttt tgttgtttta   240
tcgttttgtc gacttttgt ttggtggtgt gtgtggtgca gcctgagctt cctgatagtc    300

SEQ ID NO: 88           moltype = DNA   length = 217
FEATURE                 Location/Qualifiers
misc_feature            1..217
                        note = Cos PAC7 pIC402
source                  1..217
                        mol_type = other DNA
                        organism = synthetic construct
SEQUENCE: 88
aggcaacaga acacaaccaa acatcaaatt ccaacaacaa accacaaaaa cattgattcc    60
atggtgaaaa accegccaac ccccaccggg cacacceect gcacaccegt gcaagacctc   120
gtacggctta gtgaaatacc tccettttgt tgtttatcg ttttgtcgac ttttgtttg   180
gtggtgtgtg tggtgcagcc tgagcttcct gatagtc                            217

SEQ ID NO: 89           moltype = DNA   length = 150
FEATURE                 Location/Qualifiers
misc_feature            1..150
                        note = Cos PAC7 pIC403
source                  1..150
                        mol_type = other DNA
                        organism = synthetic construct
SEQUENCE: 89
aaaaccegee aaccccacce gggcacacce cctgcacacc egtgcaagac ctcgtacggc    60
ttagtgaaat acctcccttt tgttgtttta tcgttttgtc gacttttgt ttggtggtgt   120
gtgtggtgca gcctgagctt cctgatagtc                                    150

SEQ ID NO: 90           moltype = DNA   length = 150
FEATURE                 Location/Qualifiers
misc_feature            1..150
                        note = Cos PAC7 pIC404
source                  1..150
                        mol_type = other DNA
                        organism = synthetic construct
SEQUENCE: 90
aggcaacaga acacaaccaa acatcaaatt ccaacaacaa accacaaaaa cattgattcc    60
atggtgaaaa accegccaac ccccaccggg cacacceect gcacaccegt gcaagacctc   120
gtacggctta gtgaaatacc tcccttttgt                                    150

SEQ ID NO: 91           moltype = DNA   length = 35
FEATURE                 Location/Qualifiers
misc_feature            1..35
                        note = AD1541 primer
source                  1..35
                        mol_type = other DNA
                        organism = synthetic construct
SEQUENCE: 91
gttccagctc ttccgaggac cacatcacac ccgtc                               35

SEQ ID NO: 92           moltype = DNA   length = 35
FEATURE                 Location/Qualifiers
misc_feature            1..35
                        note = AD1542 primer
source                  1..35
                        mol_type = other DNA
                        organism = synthetic construct
SEQUENCE: 92
gttccagctc ttcctgccca ctcctcatca gacac                               35

SEQ ID NO: 93           moltype = DNA   length = 38
FEATURE                 Location/Qualifiers
misc_feature            1..38
                        note = IC511 primer
source                  1..38
                        mol_type = other DNA
                        organism = synthetic construct
SEQUENCE: 93
gttccagctc ttccgagagg caacagaaca caaccaaa                            38

SEQ ID NO: 94           moltype = DNA   length = 37
FEATURE                 Location/Qualifiers
misc_feature            1..37
```

```
                        note = IC512 primer
source                  1..37
                        mol_type = other DNA
                        organism = synthetic construct
SEQUENCE: 94
gttccagctc ttcctgcgac tatcaggaag ctcaggc                              37

SEQ ID NO: 95           moltype = DNA  length = 37
FEATURE                 Location/Qualifiers
misc_feature            1..37
                        note = IC513 primer
source                  1..37
                        mol_type = other DNA
                        organism = synthetic construct
SEQUENCE: 95
gttccagctc ttccgagaaa acccgccaac ccccacc                              37

SEQ ID NO: 96           moltype = DNA  length = 38
FEATURE                 Location/Qualifiers
misc_feature            1..38
                        note = IC514 primer
source                  1..38
                        mol_type = other DNA
                        organism = synthetic construct
SEQUENCE: 96
gttccagctc ttcctgcaca aagggaggt atttcact                              38

SEQ ID NO: 97           moltype = DNA  length = 21
FEATURE                 Location/Qualifiers
misc_feature            1..21
                        note = AD1261 primer
source                  1..21
                        mol_type = other DNA
                        organism = synthetic construct
SEQUENCE: 97
cagcggcgct gctaagaact t                                               21

SEQ ID NO: 98           moltype = DNA  length = 20
FEATURE                 Location/Qualifiers
misc_feature            1..20
                        note = AD1262 primer
source                  1..20
                        mol_type = other DNA
                        organism = synthetic construct
SEQUENCE: 98
ccggctggca aatgaggcat                                                 20

SEQ ID NO: 99           moltype = DNA  length = 25
FEATURE                 Location/Qualifiers
misc_feature            1..25
                        note = IC208 primer
source                  1..25
                        mol_type = other DNA
                        organism = synthetic construct
SEQUENCE: 99
gcttccttag cttgcgaaat ctcga                                           25

SEQ ID NO: 100          moltype = DNA  length = 26
FEATURE                 Location/Qualifiers
misc_feature            1..26
                        note = IC310 primer
source                  1..26
                        mol_type = other DNA
                        organism = synthetic construct
SEQUENCE: 100
gttcggctaa acccaaaagt aaaaac                                          26

SEQ ID NO: 101          moltype = DNA  length = 25
FEATURE                 Location/Qualifiers
misc_feature            1..25
                        note = IC443 primer
source                  1..25
                        mol_type = other DNA
                        organism = synthetic construct
SEQUENCE: 101
ccagggtgtg aaaccgtcgc ctcta                                           25

SEQ ID NO: 102          moltype = DNA  length = 25
FEATURE                 Location/Qualifiers
```

```
misc_feature           1..25
                       note = IC444 primer
source                 1..25
                       mol_type = other DNA
                       organism = synthetic construct
SEQUENCE: 102
cgcaaacacc ccgtttaccg gcctt                                           25

SEQ ID NO: 103         moltype = DNA  length = 25
FEATURE                Location/Qualifiers
misc_feature           1..25
                       note = IC446 primer
source                 1..25
                       mol_type = other DNA
                       organism = synthetic construct
SEQUENCE: 103
agggtattcc taccccagga cgatt                                           25

SEQ ID NO: 104         moltype = DNA  length = 22
FEATURE                Location/Qualifiers
misc_feature           1..22
                       note = AD1289 primer
source                 1..22
                       mol_type = other DNA
                       organism = synthetic construct
SEQUENCE: 104
ccaatcatcc aacacctgct gc                                              22

SEQ ID NO: 105         moltype = DNA  length = 29768
FEATURE                Location/Qualifiers
misc_feature           1..29768
                       note = PAC7_1.1
source                 1..29768
                       mol_type = other DNA
                       organism = synthetic construct
SEQUENCE: 105
tcgtacgggct tagtgaaata cctcccttt gttgttttat cgttttgtcg acttttttgtt    60
tggtggtgtg tgtggtgcag cctgagcttc ctgatagtcg tgattggtgt ggggagacgc    120
gtcggtggtg gtgtgtgtgg ggcgaggatc cgcgtgcgg gtttgtgtct gatgaggagt    180
ggttgttct catggatgct gcggtgattc atgatgtggt gtggcgtgag ggtcgcgcgg    240
atttggtggc ttcgttgcgt gctcatgtga aggcttttat gggtatgttg ataggtatt    300
cggttgatgt ggcgtctggt ggcgtggtg ggggttctgc ggtagcgatg attgaccggt    360
ataggaagcg taggggggct tgagtaggtg tctggtgttg ttgggtctca ggttcctcgt    420
caccgggtgg ctgtggcgta ttcggtgtct gctggcgggg atgctgggga gcttggtagg    480
gcttatgggt tgacgcctga tccgtggcag cagcaggtgt tggatgattg gcttgctgtg    540
ggtggtaatg gcaggcttgc ttcgggtgtg tgtggggtgt ttgttccgcg gcagaatggc    600
aagaatgcta ttttggagat tgtggagttg tttaaggcga ctattcaggg tcgccgtatt    660
ttgcatacgg ctcacgagtt gaagtcggct cgtaaggcgt ttatgcggtt gcggtcgttt    720
tttgagaatg agcggcagtt tcctgactttg tatcgtatgg tgaagtcgat tcgtgcgacg    780
aatgccagg aggctattgt gttgcatcat ccggattgtg ccacgtttga agaagtgt       840
ggttgtcgg gttgggttc ggttgagttt gtggctcgta gccggggttc tgctcgcgg     900
tttacggttg atgattttggt gtgtgatgag gctcaggagt tgtcggatga gcagttggag    960
gcttttgcttc ctaccgtgag cgctgcccg tctggtgatc ctcagcagat tttttttggggt   1020
acgccgccgg ggccgttggc tgacgggtct gtggtgttgc gtcttcgcgg gcaggctttg   1080
tcgggtggta aacggtttgc gtggacggag ttttcgattc ctgacgagtc tgatccggat   1140
gatgtgtcgc ggcagtggcg gaagttggcg ggtgacacta atccggcgtt ggggcgccgc   1200
ctgaatttcg ggacagtctc ggatgagcat gagtcgatgt ctgctgccgg gtttgctcgg   1260
gagcggcttg gctggtggga tcgtggccag tctgcttcgt ctgtgattcc ggcggataag   1320
tgggttcagt cggctgtggt tgaggcggct ctggttggcg ggaaggtttt tggtgtctg   1380
ttttctcgct cgggggatcg tgtcgcgttg gctggtgcg gtaaaacgga ttctggttcg   1440
catgttgagg ttattgatgg cctgtctggg acgattgttg atggtgtggg ccagctggct   1500
gattggttgg cgttgcgttg gggtgacact gaaaaggtta tggttgcagg gtctggtgcg   1560
gtgttgttgc agaaggcttt gacgatcgt ggtgttccgg tcgtggcgt gattgtggct   1620
gatactgggt tgtatgtgga ggcgtgtcaa gccttcctgg agggtgtcag gtctgggagt   1680
gtgtctcatc ctcgtgccga ttcgaggcgt gacatgttgg atattgctgt gaggtcggct   1740
gtgcagaaga agaagggttc tgcgtggggt tggggttcct cgtttaaggga tggttctgag   1800
gttcctttgg aggctgtgtc tttggcgtat cttggtgcga agatggcgaa agcgaagcgg   1860
cgtgaacggt ctggtaggaa gcgggtgtct gtggtatgaa ctcgatgag ttggctctga   1920
ttgagggcat gtacgatcgt attcaagggt tgtcttcgtg gcattgccgt attgaggggct   1980
actatgaggg ctctaatcgg gtgcgtgatt tggggggttgc tattcttcg gagttgcagc   2040
gggtgcagac ggtggtgtca tggcctggga ttgggttgga tgctttggag gagcgtctgg   2100
attggcttgg ctggactaat ggtgacggct acggtttgga tggtgtgtat gctgcgaatc   2160
ggcttgctac ggcgtcgtgt gatgttcacc ttgatgcact gatttttggg ttgtcgtttg   2220
tggcgatcat tccccaagag gatgggtcg tgttggttg tcctcagtcg ccgaagaatt   2280
gtactggcag gttttctgcc gatgggctctt gtttggatgc tggccttgtg gtgcagcaga   2340
cgtgtgatcc tgaggttgtt gaggcggagt tgtttgcttcc tgatgtgatt gttcaggtgg   2400
agcggcgggg ttcgcgtgag tgggttgaga cgggccgtat cgagaatgtg ttgggtgcgg   2460
ttccgttggt gcctgttgtg aatcgtcgcc gtacttctag gattgatggc cgttcggaga   2520
ttacgaggtc tattagggct tacacggatg aggctgttcc cacactgttg gggcagtctg   2580
```

```
tgaatcgtga tttttatgcg tatcctcagc gttgggtgac tggcgtgagc gcggatgagt   2640
tttcgcagcc gggttgggtt ctgtcgatgg cttctgtgtg ggctgtggat aaggatgatg   2700
atggtgacac tccgaatgtg gggtcgtttc ctgtgaattc tcctacaccg tattctgatc   2760
agatgcgttt gttggcgcag ttgactgcgg gtgaggcggc tgttccggaa cgctatttcg   2820
ggtttatcac ttctaacccg ccttctgggg aggctttggc tgcggaggag tctcggcttg   2880
tgaagcgtgc tgaacgcagg cagacgtcgt ttggtcaggg ctggctgtcg gttggtttcc   2940
tggctgcccg ggcgttggat tcgagtgttg ataggccgc gtttttttggt gatgttggtt   3000
tgcgttggcg tgatgcgtcg acgccgactc gggcggctac ggctgatgct gtgacgaagc   3060
ttgtgggtgc tggtattttg cctgctgatt ctcggacggt gttggagatg ttgggtttgg   3120
atgatgtgca ggttgaggct gtgatgcgtc atcgtgccga gtcttcggat ccgttggcgg   3180
cactggctgg ggctatttcc cgtcaaacta acgaggtttg ataggcgatg gcttcgggtg   3240
ctgtgtcgag gcttgctgcg actgagtatc agcgtgaggc tgtcaggttt gctgggaagt   3300
atgcgggcta ttatgccgag ttgggtcgtt tgtggcgtgc cggcaggatg agtgacacgc   3360
agtatgtgcg tttgtgtgtg gagttggagc gtgccggcca tgacggttca gcagctatgg   3420
cgggcaaatt cgtttcagat tttcgccggt tgaatggtgt cgatcctggt ttgatcgtgt   3480
atgacgagtt tgatgctgcg gcggctttgg ctaggtcgtt ttcgactatg aagattatga   3540
atagtgaccc ggatagggcg aatgatacga ttgatgcgat ggctgcgggt gttaatcggg   3600
ctgttatgaa tgctggtcgt gacacggttg agtggtcggc gggtgcgcag ggtaggtcgt   3660
ggcgtcgggt gactgatggt gatccgtgtg cttttttgtgc catgttggct acgaggtcgg   3720
attatacgac taaagagcgg gcgcttacta ctggtcatac gcggcgtcat aagcgtgccg   3780
gtaggcgtcc gtttggttcg aagtatcatg atcattgtg ttgtacggtg gttgaggttg   3840
ttggtccttg ggaaccgaat agggcgatg ccgagtacta gaggacgtat gagaaggctc   3900
gtgagtgggt tgatgatcat gggttgcagc agtcgtctgg caatattttg aaggctatgc   3960
gtactgttgg tggcatgaga taatttgatg tggtttccgg ttgtgtgccg ccggttatcg   4020
gtgcacaggg ttgtctcccg cacgggggtc aacaatgttg tgttgttttc cgcaaggagt   4080
gtaggggttag gctatggccg atcagagtat tgaggaacaa aatgttgaca atgatgttgt   4140
ggagtccgga aaggataacg gcattgttga tacagtaaaa gacgatgcg ggcaggaggt   4200
agccgacaat cagttgaaga atgaaggcga gggtaaatcg ccggggactg attggaaggc   4260
ggaggcccgt aagtgggagt ctcgtgctaa aagtaatttc gccgagttgg agaagcttcg   4320
tacatcgagt gacgattctg gatctactat tgatgagct cgccgcaaga gtaggaact   4380
cgaagaccgg attaacgggt ttgttcttga gggtgtgaag cgcgaggtgg ctgccgagtg   4440
tggcctgtcg ggtgatgcga tcgctttttct tcacggtagc gataaggagt cgcttgccga   4500
gtctgctaag gctttgaagg gtttgatcga ccatagtagt ggtggtggcg cgggtgtgcg   4560
ccgtcttgcg gggagtgccc ccgttgatga tgttaaacga cgtgaggtg tcgcgtttgt   4620
ggatgctctt gtcaataatt ctaggagatg atttatcatg gctgacgatt ttctttctgc   4680
agggaagctt gagcttcctg gttctatgat tggtgcggtt cgtgaccgtg ctatcgattc   4740
tggtgttctt gctaaactgt caccggagca gccgactatt ttcgggcctg ttaagggcgc   4800
cgtttttagt ggtgttccgc gcgctaagat tgttggcgag ggcgatgtta agccttccgc   4860
tagcgttgat gtttctgcgt ttactgcgca gcctatcaag gttgactc agcagcgtgt   4920
ctcggacgag tttatgtggg ctgacgccga ttaccgtctg ggtgtgcttc aggatctgat   4980
ttccccggcc ctgggtgctt ctattggtcg cgccgttgat cttattgctt ccatggtat   5040
tgatcctgct acgggtaagc ctgctgcggc tgtcaaggtc tcgctggata agacgaataa   5100
gacggttgat gccaccgatt ccgctacggc tgatcttgtt aaggctgttg gtctgattgc   5160
tggtgctggt ttgcaggttc ctaacgtgt tgctttggat ccggcgttct cgtttgctct   5220
gtcaactgag gtgtatccga agggttcgcc gcttgccggt cagccaatgt atcctgccgc   5280
cgggttcgcc ggcctggata attggcgcgg cctaaatgtt ggttcttctt cgactgtttc   5340
tggtgccccg gagatgtcgc tgcttctgg tgttaaggct attgttggtg attttctctg   5400
tgtccattgg gggttccagc gtaacttccc gattgagctg atcgagtatg gtgacccgga   5460
tcagacgggg cgtgacttga agggccataa tgaggttatg gttcgtgccg aggctgtgct   5520
gtatgttgcg attgagtcgc ttgattcgtt tgctgtcgtg aaggagaagg ctgccccgaa   5580
gcctaatccg ccggccggta actgattcat ttgttgcgat aatgttttatg ctgtgtgcag   5640
ggggtggtgt tgatgggtat cattttgaag cctgaggata ttgagccttt cgccgatatt   5700
cctagagaga agcttgaggc gatgattgcc gatgtggagg ctgtggctgt cagtgtcgcc   5760
ccctgtatcg ctaaaccgga tttcaaatat agggatgccg ctaaggctat tctgcgtagg   5820
gctttgttgc gctggaatga tactggcgtg tcgggtcagg tgcagtatga gtctgcgggc   5880
ccgtttgctc agactacacg gtcgaatact cctacgaatt tgttgtggcc ttctgagatt   5940
gccgcgttga agaagttgtg tgagggtgat agtgggggctg gtaaggcgtt cactattaca   6000
ccgaccatga ggagtagtgt gaatcattct gaggtgtgtt ccacggtgtg gggtgagggt   6060
tgctcgtgcg ggtcgaatat taacggctat gctggcccgt tgtggagat atgatatgac   6120
cggttttcct tacggtgaaa cggttgtgat gcttcagccg actgtcgtg tcgatgatct   6180
tggtgacaag gtgagggatt ggtctaagcc tgtcgagact gtgtaccata acgtggccat   6240
ctatgcttcc gttcgcagg aggatgaggc gcgggggcgt gactcggatt atgagcattg   6300
gacactgctg ttcaagcagc ctgtcaaggc tgctggttat cggtgtcgtt ggcgtattcg   6360
gggtgttgtg tgggaggctg acgggtctcc tatggtgtgg catcatccga tgtctggctg   6420
ggatgctggt acgcaggtta atgtgaagcg taagaagggc tgatgggttg tggcacgtga   6480
tgttgatgtg aagctgaact tgccgggtat tcgtgaggtg ttgaagtctt ctgggggtgca   6540
gggcatgttg gctgagcgtg gtgagcgtgt caagcgtgcg gcctcggcga atgtgggcgg   6600
taacgcttac gataggcc agtatcgtgc cgggttgtcg tctgaggtgc aggttcaccg   6660
tgttgaggct gtggcgcgta ttggccaccac ctataaggt ggtaaaagga ttgaggcgg   6720
gcatggcacg ttggcgaggt cgattgggc tgcgtcgtga tcgtttacgg tgatcctcga   6780
atatgggcta aacgtgtgtt ggcggatgat ggttggctgt ctgatgtacc gtgcacgggt   6840
actgtgccgg atacatttga gggtgatctg atttggttgg cgttgatgg tggcccggag   6900
ttgcatgttc gtgagcgtgt tttttgcgt gtgaatgtgt ttcggatac gccggatcgt   6960
gctatgtctt tggctcgccg ggttgaggct gtgctggctg atgtggga tggtgatccg   7020
gtggtgtttt gcaggcgttc gactgggcct gatttgctgg tggatggtgc acgtttgat   7080
gtgtattcgc tttttgagct gatatgtagg cctgcggagt ctgaataagc ttattgtttt   7140
tgtttttaatg taattgtttg atatttaatg ggggttgtga tggctgctac acgtaaagcg   7200
tctaatgttc gttcagcggt tactggcgac gtttatattg gtgacgcgca cgcgggtgat   7260
tctattaagg gtgtggaggc ggttccttcc gggcttacag ctttgggga tctgtctgat   7320
```

```
gacgggttta agattaagcc tgagcgtaaa acgatgatt  tgaaggcttg gcagaatgcg  7380
gatgttgttc gcactgtggc tacgagtcg  tctatcgaga tttctttcca gctgattgag  7440
tcgaagaagg aggttatcga actgttttgg cagtcgaagg ttactgccgg atctgattcg  7500
ggttcgttcg atatttctcc tggtgccaca acaggtgttc acgccctgtt gatggatatt  7560
gttgatggcg atcaggttat tcgctactat ttccctgagg ttgagctcat tgatcgtgac  7620
gagattaagg gcaagaatgg cgaagtgtac gggtatggtg tgacgttgaa ggcgtatcct  7680
gcccagatta ataagactgg taatgcggtg tcgggtcggg ggtggatgac ggcttttaaaa 7740
gctgatactc ctccgactcc tccgccggcc ccggttcctc cgaagcctca gccggatccg  7800
aatccgccgt ccggtaactg atacacgatt ttaggggatt gttaatagat gagtgacact  7860
ggtttcacgt tgaagattgg tgatcgtagc tgggtgttgg cggatgcgga ggagacggct  7920
caggctgttc ctgcccgcgt tttcgtcgt  gccgccagga ttgcccagtc gggggagtct  7980
gcggatttcg cccaggttga ggtgatgttt tctatgttgg aggctgccgc cccagctgac  8040
gcggtggagg ccctggaggg gcttcctatg gttcgtgtg  cggaggtttt ccgtgagtgg  8100
atggaataca agcctgacgg taagggtgcc tcgctgggg  aatagtttgg ctccacgcg   8160
tgattgatga ttatcgtggg gccatcgaat acgatttccg caccaagttt ggtgtttctg  8220
tttatagtgt tggtggcccg cagatgtgtt ggggtgaggc tgtccggctg gctggcgtgt  8280
tgtgtaccga tacgtctagc cagttggcgg cccaccttaa tggttggcag cgcccgtttg  8340
agtggtgcga gtgggctgtt ttggacatgt tggatcatta caggtctgct aatagtgagg  8400
ggcagccgga gcctgtggcg aggccgactg atgagcgtcg ggcaaggttt acgtctggcc  8460
aggtggacga tattttggcg cgtgttcgtg ccggtggcgg ggtgtctcgc gagattgata  8520
ttatggggtg aatagtgtat gtctggtgag attgcttccg catatgtgtc gttgtatacg  8580
aagatgcctg gccttaaaag tgatgttggt aaacagttgt cgggtgttat gcctgctgag  8640
gggcagcgtt cgggtagcct gtttgctaaa ggcatgaagt tggcgcttgg tggtgcggca  8700
atgatgggtg ccatcaatgt tgctaagaag ggcctcaagt ctatctatga tgtgactatt  8760
ggtggcggta ttgctcgcgc tatggctatt gatgaggctc aggctaaact gactggtttg  8820
ggtcacacgt cttctgatac gtcttcgatt atgaattcgt ctattgaggc tggactgtcg  8880
acgtcgtatg cgttgggga  tgcgcgtct  acggcggcgg cgttgtctgc ttcgggtgtg  8940
aagtctggcg gtcagatgac ggatgtgttg aagactgtcg cggatgtgtc ttatatttcg  9000
ggtaagtcgt tcaggatac  gggcgctatt tttacgtctg tgatggctcg cggtaagttg  9060
cagggcgatg acatgttgca gcttacgatg gctggttgtc ctgtgctgtc tttgcttgcc  9120
aggcagacgg gtaaaacctc ggctgaggtt tcgcagatgg tgtcgaaggg gcagattgat  9180
tttgccacgt ttgcggctgc gatgaagctt ggcatgggtg tgctgcgca  ggcgtctggt  9240
aagacgtttg agggcgctat gaagaatgtt aagggcgctt tgggctattt gggtgctacg  9300
gctatggcgc cgtttcttaa cggcctgcgg cagattttt  tgcgttgaa  tccggttatt  9360
aagtctatca cggattctgt gaagccgatg tttgctgccg tcgatgctgg tatccagcgg  9420
atgatgccgt ctatttggc  gtggattaac cgtatgccgg ctatgatcac gagaatgaat  9480
gcacagatgc gcgccaaggt ggagcagttg aagggcattt tgcgagaat  gcatttgcct  9540
gttcctaaag tgaatttggg tgccatgttt gctggcggca ccgcagtgtt tggtattgtt  9600
gctgcgggtg tggggaagct tgttgcaggg tttgctccgt tggcggttgc gttgaagaat  9660
ctgttgccgt cgtttggtgc tttgaggggt gccgccgggg gcttggtgg  cgtgtttcgc  9720
gccctgggtg gccctgtcgg gattgtgatc ggcttgtttg cggcaatgtt tgccacgaac  9780
gcccagttcc gtgccgctgt tatgcagctg gtggctgtgg ttggtcaggc gttgggccag  9840
attatggcag ctgtgcagcc gctgtttggt ttggttgctg caggttgggt ttgaatattat  9900
ccggtgttcg gccagattat cggtatggtt gctggtttgg ctgcccggct ggtgcctgtt  9960
attggtatgc ttattgcccg gctggttcct gttatcaccc agattattgg tatggtaacc  10020
caggttgctg ccatgttgtt gccatgctg  atgccggtta ttcaggctgt tgttgctgtg  10080
atacggcagg ttattggtgt cattatgcag ttgataccta ttttgatgcc ggttgtgcag  10140
cagattttgg gtgctgtcat gtctgttttg ccgccgattg ttggtttgat acggtcgctg  10200
ataccggtga tcatgtcgat tatgcgtgtg tgggtgcagg ttgttggtgc tgtgctacag  10260
gtggtggccc gtattattcc ggttgttatg ccgatttatg tttcggtgat tggattcatt  10320
gccaagattt atgctgcggt tatcgtttt  gaggctaagg ttattggcgc tattcttcgt  10380
actattacgt ggattgtgaa tcattcagtg tctggcgtga ggtctatggg cacggccatc  10440
cagaatggct ggaatcatat taaatcgttt acgtctgcgt ttattaacgg ttttaagtcg  10500
atcatttctg gcggcgtgaa cgcggttgtg gggttttta  cgcggcttgg tttgtcggtt  10560
gcttcccatg tgaggtccgg ttttaacgct gcgaggggtg ctgtttcttc cgccatgaat  10620
gctattcgga gtgttgtgtc ttcggttggc gctgctgttg gcgggttttt cagttcgatg  10680
gcgtctcgtg ttcggaatgg tgctgtgcgc gggtttaatg gtgcccggag tcggcttct   10740
tctgctatgc atgctatggg gtccgctgtg tctagtggta tgcatggtgt gctgggtttt  10800
ttccggaatt tgcctgacaa tattcggcgt gcgcttggta atatggggtc cctgttggtg  10860
tcggctggcc gtgatgtggt gtccggttta ggtaataccg tcaagaatgc tttgagtggc  10920
ctgttggata cggtgcgtaa tatgggttct caggttgcta atgcggcgaa gtcggtgttg  10980
ggtattcatt ccccgtctcg ggtgtttcgt gacgaggttg gccggcaggt tgttgccggt  11040
ttggctgagg gtattactgg taatgctggt ttggcgttgg atgcgatgtc gggtgtggct  11100
gggaggctgc ctgatgcggt tgatgcccgg tttggtgtgc gatcgtctgt gggttcgttt  11160
accccgtatg gcaggtatca gcgcatgaat gataagagtg ttgtggtgaa tgtgaatggg  11220
cctacttatg gggatcctgc cgagtttgcg aagcggattg agcggcagca gcgtgacgct  11280
ttgaacgcgt tggcttacgt gtgattttgg gggtgtggtg catgtttatt cctgacccgt  11340
ctgatcgttc tggtttgact gtgacttggt ctatgttgcc gttgattggt aatgatccgg  11400
agcgtgtgct tcatttgacg gattatacgg ggtcgtctcc gataatgttg ttgaatgttt  11460
cgttgcgcgg tttgggtgtt cctgaggtgg agcattttc  tcaaactcat gttgggggtgc  11520
atggctcgga gtggcgcggg tttaatgtga agcctcgcga ggtgacgcta ccggtgttgg  11580
tgtcgggtgt tggcccggat ccggtgggcg gttttcgtga cggttttttg aaggcgtatg  11640
acgagttgtg gtctgctttt cctcctggcg aggtggggga gttgtctgtg aagactcctg  11700
ccggtcgtgg gtcgttgttg aagtgccggt tgattcggt  ggatgacacg tttacggtgg  11760
atccggtgaa caggggttat gcgcgttatc tgttgcattt gacggcttat gacccgtttt  11820
ggtatgggga tgagcagaag tttcgtttca gtaacgctaa gttgcaggat tggttgggtg  11880
gcggccctgt cgacgtaag  ggtaccgcgt ttccggtggt gttgacgcct ggtgttggtt  11940
cgggttggga taatctgtct aataagggtg atgtgcctgc gtggcctgtg attcgtgttg  12000
agggggccgtt gtcgtcgtgg tctgtgcaga ttgatggttt gcgtgtgtcc tcggattggc  12060
```

```
cggtggagga gtatgattgg atcactattg atacggatcc tcgtaagcag tctgcgttgt   12120
tggacgggtt tgaggatgtg atggatcgtt tgaaggagtg ggagtttgcg cctatcccgc   12180
ctggcggttc tcggagtgtg aatattgaga tggttggttt gggtgccatt gttgtgtcgg   12240
tgcagtacag gttttttgagg gcttggtgaa tagttgatgg ctggttttgt tccgcatgta   12300
acattgttta caccggatta tcgccgtgtg gcgcctatca attttttttga gtcgttgaag   12360
ttgtcgttga agtggaatgg tttgtccact ttggagttcg tggtgtctgg tgatcattct   12420
aggcttgacg ggttgactag gccgggtgcg cggcttgtgg ttgattatgg tggtggccag   12480
atttttttctg ggcctgtgcg tcgggtgcat ggtgtgggtc cgtggcgttc ttcgcgtgtg   12540
actatcacgt gtgaggatga tattcgtctg ttgtggcgta tgttgatgtg gcctgtgaat   12600
tatcgtcctg gtatggttgg tatggagtgg cgtgcggatc gggattatgc ccattattcg   12660
ggtgcggcgg agtcggtggc taagcgggtg ttggggata atgcttggcg tttttccgtct   12720
ggtttgttta tgaacgatga tgagagtcgt ggccgctata ttaaggattt tcaggtgcgg   12780
tttcacgtgt ttgccgataa gttgttgccg gtgttgtcgt gggctcggat gactgtcacg   12840
gtgaaccagt ttgagaatgc gaagtttgat cagcgtggtt tggtgtttga ttgtgtgcct   12900
gctgtgaccc ggaaacatgt gttgactgcc gagtcgggtt cgattgtgtc gtgggagtat   12960
gtgcgtgacg ccccgaaggc gacatctgtg gtggttggtg gccgtggcga gggtaaggat   13020
cggctgtttt gtgaggatgt tgattcggcg gccgaggatg attggtttga tcgtgtcgag   13080
gtgtttaagg atgcccgtaa cacggattcc gagaaggtgt ctctcttcga tgaggctgag   13140
cgggtgttgt ccgagtcggg ggctacgtcg gggtttaaga ttgagttggc tgagtcggat   13200
gtgttgcggt ttggtcccgg caatctgatg cctgggggatt tgatctatgt ggatgtgggt   13260
tctgggccta ttgcggagat tgtgcggcag attgatgtgg agtgtgtatc gcctggtgat   13320
ggttggacga aggtgactcc ggttgcgggg gattatgagg ataatccgtc ggcccctgttg   13380
gctcgccgtg tggctggttt ggctgcgggt gtgcggggatt tgcaaaagtt ttagtaagtg   13440
attgggggttt gttgtgggta ttgtgtgtaa agggtttgat ggtgtgttga ccgagtatga   13500
ttgggctcaa atgtctggtc tgatgggtaa tatgccgtct tgtgaagggc ctgacgattt   13560
tcgtcgtcggc acgacgattc agggttctac ggtgttgtgt gagatcctgc cggggcaggc   13620
ttgggctcac ggggtgatgt gcacgtcgaa tagtgttgga acggtgacgg gtcagcttcc   13680
gggcccgggt gagactcgat acgactatgt ggtgttgtct cggattggc aggagaaatac   13740
ggccaagttg gagattgttc ccggtgggcg tgcggagcgt gccagggatg tgttgagggc   13800
tgagcctggc gtgtttcatc agcagctact ggcgactttg gtgttgtcgt ctaacgggtt   13860
gcagcagcag ttggatagggc gtgctgtggc ggctaggggt gcgtttgggg agtctgctgc   13920
gtgtgatcct accccgtgg agggtgaccg tgtgatggtt ccttcgggggg ctgtgtgggc   13980
taaccatgcc ggcgagtgga tgttgttgtc tcccaggatt gagacgggtt cgaagtcgat   14040
catgtttggt ggttctgctg tgtatgctta cacgatcccg tttgagcgcc agttcagtag   14100
tccgcctgtt gtggtggcgt ctatgcgtac ggcggctggg ggcacggcac agattgatgt   14160
gaaagcctac aatgtgactg cccaaaattt tagtttggcg tttattacga atgatggttc   14220
gaagccgaat ggtgtgcctg cggtggcgaa ttggattgct gtcggcgtgt gactgcacgg   14280
gtgttgtggc ggatggtgtg atgttgggggg gctgtgtgt cgtggtttac tcctgcactg   14340
gtggcctcta tttgtaccgc gttggccacg gttttcaggc tcgttcaggc tgtcacatcc   14400
cggtctagga agcgtttacg caggctgtcg gctcaggtgc atgcgatgga agagtatacg   14460
tggggtgtgc ggcgcgaggt gcgaaggttt aacgccgggc ttcctgatga tgtggagccg   14520
atgcatcttc ctgatttgcc cgagttttttg aaagatactg ttgatggtgg aggtgagtag   14580
ggttgaggag gttggaggag gagaagcggc agcgccgcaa ttttgagaag gcttcactgg   14640
tgttgttgtt tttgtcgctt gtgttgttgg cggtggttgc tgcgggtgct ttgcgtttcg   14700
gggctgtatc ctctgagcgg gattcggagc aggcgagggc ccagtcgaat ggtacggctg   14760
ccaggggttt ggctgcccgt gtgaagcagg cgtgtgcttc gggtgggggtg gagtctgtgc   14820
gtcttcaccg ttctggtttg tgtgtggatg ctgtgcgtgt tgagcagcgt gttcagggtg   14880
tgccgggtcc tgccggtgag cgcggcccgc aaggcccttc aggtcctgcc ggccgggatg   14940
gtgttaatgg ttcggctggg ctggttggcc ctgttggtcc gcaaggttct ccgggtttga   15000
atggtgtgaa aggtcctgac ggcttgcctg gcgctaacgg ttcggatggc cgtgatggtg   15060
ttccaggtcg tgcaggtgct gacggtgtga acggcgctgt ggtcgggatg   15120
gttctgccgg tgagcgcggc ccgcaaggcc cttcaggtcc tgccggcccg caaggtgcac   15180
agggtgaacg gggtgagcgt ggtcccgccg gtgcgaatgg atcggatggc catgatggta   15240
aggatgggc ctcggtggtg tctgtgtact gttccggggg ccgcctggtt gtgaaatata   15300
gtgacggtgt ggcttccacg atatcggggtt cggcggcctg ccagggtgg aaaccgtcgc   15360
ctctagtgac tatatcatcc cacaaataga aaggagtgc tgtgatggtg gtgtttggtg   15420
gtggtgtgtt gtgagatata ttcctgcggc gcatcattct gccggctcga atagtccggt   15480
gaatagggtt gtgattcatg cgacgtgccc ggatgtgggg tttccgtccg cctcgcgtaa   15540
aggacgggct gtgtccacgg caaactattt cgcttcccca tcgtctggtg gttcggcgca   15600
ttatgtgt gatattgggg agacggtgca atgcttgtcg gagtctacga ttgggtggca   15660
tgccccgccg aatccgcata gtttgggtat agagatttgc gcggatgggg gttcgcacgc   15720
ctcgttccgg gtgccgggc atgcttacac tcgtgagcag tggctggatc ctcgcgtgtg   15780
gcctgcggtt gagcgtgccg ccatcctgtg tagacgtttg tgtgacaagc atggtgttcc   15840
gaaaaggaaa ctgtctgtgg ccgatttgaa ggccggtaag tgcgggcatg   15900
ggatgttacg gatgcgtggc atcagtcgga tcatgacgat ccggggccgt ggtttccgtg   15960
ggacaaattt atggctgtgg ttaatggcca cggcggcgt tcaagtagtg aggagttgag   16020
tatgctgat gtacaagcgt tacataatca gattaaacag ttgtcggcac aggtggccca   16080
gtcggtgaat aagctgcatc acgatgttgg tgtggttcag gttcagaatg gtgatttggg   16140
taaacgtgtt gatgccttgt cgtgggtgaa gaatcctgtt ggaggaagc tgtggcgcac   16200
taaggatgct ttgtggagtg tctggtatta cgtgttggag tgtcgtagcc gtcttgacag   16260
gctcgagtct gctgtcaacg atttttgaaaaa gtgatggtgg tttgttgtgg gtaaacagtt   16320
ttggttaggt ttgctggagc gtgccctgaa aactttgtt caaacgtttg ttgccgtgtt   16380
gggggttact gcgggtgtca cctatactgc ggagtcgttt cgtggtttgc cgtgggaatc   16440
ggatgatc acggcaacgg ttgctgctgt cctgtcggtt gctacctcgt ttggtagccc   16500
gtcgtttgtg gccggcaagc ccggcaagca gccccaggtg gatgcgggtt tggttccacc   16560
ggatgatggg ggcttggttg agccgcatat ggtggatgtg tcggatcctg gcatgatcga   16620
gccgacggat gatgcggatc ttgccggcta tgagcctcgg cgtgcagccg agtcggaggt   16680
tggcacggta gagtctactg ttgcataatt gaatatagat gtgtgcccca gcggtgctgc   16740
cacgattgtg tggtggcggc tgctgggggca ctattttttgt atatgcggtg tggctatgat   16800
```

```
tcgttgctgt cgatggtgtc ttcgagcatc tgatacaggt ggaggcaggt agagatagtt   16860
tcgctggcct gatcgagaac gttccggccg ataacgtttt tgtggttgtc gcggtggcgg   16920
atgatagccc acatgatctc gtcggctgcc gcctgtaata gtttggcctg gtatgcgatt   16980
ccggcgagcg agtctagtgc ttcctggctt gtataggggc tctggtcctc gctgttgccg   17040
cgggtgttgc tgttgtttgt ggggtgtcct gcactgtcgc atagccacag gatttcgctg   17100
cactcgtcta gcgtgtcttg gtcgatagcg agatcgtcga ggctgacatt gttgacggta   17160
aggttcacgt tgtcgaggga gatgggtaca ccgtactggt tttcgacact gtcaacaatg   17220
ttttccagct gttgcatgtt ggtgggctgt tgttggacga tacggtgtat cgctgtgttg   17280
agggtggtgt aggtgatgtt gtgtgtgttg tccatggttt ttatgccatt ccttcgttat   17340
cgtctggcat gtagtatgtg ctgtttgcgt actcggttaa cgtcatcagt gtttggtctg   17400
cccactgttt cacggtttgc cgggtgactc cgagtcgttg ggcggctgtg gcgtaggttt   17460
gatcataccc gtatacttcc cggaatgctg ccaacctagc taggtgtttc ctctgtttgg   17520
atggttcaca ggtgagggtg tagtcgtcga tggctagctg tagatcgatc atggagacga   17580
tgttccgcc gtggtgttgt ggcgcggttg gtggggggtg cattcctggc tccacggagg   17640
gtttccaggg gccgccgttc cagatccatt gggcagcttg gatgatgtcg gcggtggtgt   17700
aggttcggtt cactggtcac ccctgaaca ggtcgttggt gttgttggtg tcgaatcgtc   17760
cgacgcagtg gcagtagtcg tacatgagtt taataatgtg ttggtggtct cccaaatagg   17820
tgtttccgct gatgctgtat gtggctgtgc cgtctttcgc gatggtgtat ttggcggtga   17880
tggtttcggg gttttcggtg tcggtgatga ttgctgtggt ggtggcgcct actgtttgga   17940
gtatggtggt ttgggttccg tcgtcgatgg tggttttaac catggtgtgt gttttcccttt  18000
ttgttagttg cttgtttggt tgtcggctag atgaataata tcgggtaaag gtttcggctg   18060
gtctaggtgt tgtatggttt tgttggctag ccgtttggct accctgtaac acattttggt   18120
gtagtgtttg ttgtctaggt tgtggtattg ttcccgcacc gcaatatata gcagggagtc   18180
ttggtacagg tcgtctgcac tgattgcggg gtagtgtgcg gctgttttgg tgcatgcccg   18240
gttgagtgtg cgaagatgat ggtctgtggc ccacacccac gatgcggtgg tggccaggtc   18300
ggcttttgtt ggtcgtctgc tcatggcact atttcatctc gctatctgat agttgtttgg   18360
tgttttgttg tggatagtgt agcacactag tcctgggtgg ccggtggtgc ctgtgcggtg   18420
acggaaccat gtggattcgc cttccatgga tgggcattgg atgaaggtgc gttgtccttg   18480
ctcggagatt tctaggtggt gccggtgccc ggccatgaga atattagata cggtgccgtt   18540
gtggaattct tggccgcgcc accaatcata gtgtttaccg gtgcgccatt ggtgcccgtg   18600
ggcgtgcagt atccgtgtgc ctgccacatc aacggtggtg gtcatttcgt ctcggctggg   18660
gaagtggaag tgtaggttgg ggtattggtt attgagctgg taggcttctg cgatggcccg   18720
gcagcagtcc acgtcgaatg agtcatcgta ggtggtgact cctttaccga agcgcacggc   18780
ttcaccatgg ttgccgggga tggatgtgat ggtcacattt ttgcagtggt cgaattggtg   18840
gatgagttgc atcatggcca tgcgggtgag cctgatttgt tcggtgaggg gtgtttgttg   18900
tcgccaggcg ttgttgcctc cttgtgacac gtatccttcg atcatgtcgc cgaggaaggc   18960
gatgtggact cgttcgggtt tgcctgcttg ttgccagcag tgttttgcga ctatgaggga   19020
gtgtaggtag ttgtcggcga agtgtgctgt ttctccgccg gggatgcctt tgccgatttg   19080
gaagtctcct gccccgatga cgaaggctgc ggtgctgtga tcggtgtggg tgtcttgttc   19140
gggttttggg ggtgtccatt cggctagttt atcgacgagt tcgtctaccg ggtagggggtt  19200
tgttgcgggt tggtggtcga tgattttttg tatggatcgg cctgtttctc cgttggggag   19260
tgtccattcg gagatgcgtg tgcggcgcac ggtgccgttg gctagattgt cgtcgatggt   19320
gtcgatggcg ttgtcgtgct tggctagctg tgtgagtagc cggtcaatat tgtctatcac   19380
tgggtatcct cctcttgcgg ggtggtgctg cgttgtttgc ggcgatagtc tttaataacg   19440
gtggcggaga tggggtatcc tgcctgggtg agctgttttg ctagccatga ggcggggata   19500
gacctgtcgg cgagcacgtc ggcggctttg ttgccgtagc gttgaataag ggtttcagtt   19560
ttggttgcca tgatgtccta tcggttgtgt ggtgggctgc catcctgtgc ggcagtcgcc   19620
gtcgtgtcct ggtttgcgtg tgcaccacga tacggttccg tctgtgtggt tgagtgtttt   19680
accgcacatg acgtttcgga gatgctccgg cagctggtca tcctggttgc tggttttgtgt  19740
gtcgaagagt gttttctggt tggtgaaatg ttctgacacg gtgccgttat gcacgggtag   19800
tatccatgtt ttccattgtt gttgtagcct ggtgttccaa tggaatttgtt tggccgcgtt   19860
ttcggcctgt tttaaggttt tgtggtagcc gactagtatg cgttgatgct gctggtctgt   19920
aggggtttggg cctcgccagt attgtgccgc cacggcgtag cggttgctgt ctgtgaaggc   19980
gtcccagcag tattcgataa tgtgttgcaa catactgtct ggcaggctgt cagggttgat   20040
gttgatgttt tgggtgataa tgtcacggat ggcttgccgg tttttgttgg tgggtttgaa   20100
cgagatgctc acgatagtac cggctggtcg tcttgcatga actggttgaa ggtgttgttc   20160
ccggcgtgtt gggcttgtgt tatttggttgg tcgtccagt ctgggtgttg ctgtttcaga   20220
tagtgccagt ggcacgcatt gtaggtttcg tcttgtagcc gtgtgagatg gttttcggtg   20280
atgatttgtt tccacatggc ccatgacacg tcgagccggt cgaggattc gagggctggg   20340
atgttgaatt ggttcaggaa gaggatttcg tgggtgtagt agttttctc gtaggcgtcc   20400
catccgcttc ggtgcctgtt gggctggttt ttggggtagg cttcccggca tactttgtgt   20460
aaacgcttgg ccatgtcgtc gggtagttta atgtcggggt tggcgcggat catggatcgc   20520
atcccatcat aggtggtgcc ccaggtgtgc atgatgtagg tggggtcttc tccgtcggcc   20580
cattttctg cacagatggc gaggcggata cgcctcctgg cagcttggct ggtggtcgcc   20640
cggttgggga ttgggcacgt gtcgagggga tccatgatgt tttagtgtac ctttctggtt   20700
tcgtgttgtt gacaggtttt actgtagcac agtgtctagt gcgtgtgtca accctgtttt   20760
tccggcttga aggtaggtgt ctgtgacatc ccctagggtg aggggcacgt gcacagcttg   20820
ggggagtgcc ggcctggaggg tttgggcact ctggtcgcct gcggggtctg ggtctgacca   20880
gatgtagatg tggtcgtagc cttcaaaaaa tttggtccaa aaaatttgcc acgaggttgg   20940
gccgggtagg gcgacggccg accatccgca ttgttcgagg atcatggagt cgaattcgcc   21000
ttcgcaaatg tgcatttcgg ctgccgggtt ggccatggcg gccatgttgt agatggagcc   21060
tgtgtctcct gccggggtta ggtatttggg gtggttgtgg gttttgcagt cgtgcgggag   21120
tgagcagcgg aaacgcattt ttcttatttc ggctgggccg ccccaaacgg ggtacatgta   21180
ggtggtggtg atgcactggt tgtagttttc gtggcctggg atggggtcat tggtgatga   21240
tccaaggtgg tggtagcggg ctgttttctt gctgatgcct cttgctgaga gcaggtcgag   21300
tatgttttcg aggtgggttt cgtagcgggc tgaggcttc tggattcggc ggcgttccgc   21360
aatgttgtat gggcgtatgc tgtcgtacat ttggggttttc ttcttctaat cgttgttgta   21420
gcttggcgag tccgcctccg acaccgcatg tgtggcagta ccagacgccc ttgtcgaggt   21480
tgatgctcat ggagggctgg tggtcgtcgt ggaacgggca gagtatgtgt tgctcgttcc   21540
```

```
tggacggatt gtaccgtatc tgataatggt cgaggaggcg gcaggtgtca gaggtgtggg   21600
aggagctcgt tgagggttga taccacatag gcttcactcc atggcttgtt gcgctgtttc   21660
atcactacga gtccgatggt ggaattgttt tgtttgtttc ggtgtgtttc gtagttgcgt   21720
gcctccggc tggcttgttt cacgaattgg gctaggtgtg gttgcccggc tttcgcctcg   21780
ataatgtagg ttttatggcc ggttgtgagg atgaggtcgc cttcgtcttc gcggccgttg   21840
aggtggaggc gttcgatatt gtgtccggtg tcgcgtagct ggtcgtaggag tcttgtttcc   21900
cattcggctc cggcccgccg gttgcgtgcc tgctgtgtgg ccatagtttt ttagagtcct   21960
ttgtgtgttg tggtcatgtt ccagggctgt ttttcggcga gtggcccgaa gaatgtgtat   22020
tcggggtatg ctctgagtcg ttcgtatcgg gtgccgtcgg ggctggattt gcctgtcgcgc  22080
tgtttgagta cggcgatacg tgcctctgcc ggtatcgata gcccgttgcc gttatcctcg   22140
ccaccataca atgagactcc gaggatgagt tgtggttttt cggagaggcc gtttttgatt   22200
tctcgccgtg ctggcgggtg ttcgatgtcg gttccggttt tgtcgttgc gtggtgtgtg    22260
acaataatgg tggagccagt atccctgccc aatgctgtga tccattgcat ggcttcttgc   22320
tgtgcctggt agtcggattc gcagtcttga atgtccatca ggttgtcgaa aacaatgagt   22380
ggtgggaagg tgttccacat ttccatgtag gcttgtaact ccatggtgat gtctgtccat   22440
gtgatgggtg actggaatga gaatgtgatg tgttggccgt ggtggatgct gtctcgatag   22500
tattctggcc cgtagtcgtc gatgtttgt tgtatttgtt gggtggtgtg ttgtgtgttg    22560
agggagatga ttcgtgtgga ggcctcccag ggtgtcatgt cccctgatat gtagagggcg   22620
ggctggttga gcatcgctgt gatgaacatg gctagccctg attttttggct gccggaccgc  22680
cccgcgatca tcaccaagtc gcccttatgg atgtgcaaat cttggttatc atatagtggt   22740
gcgagttgtg gtatgcgggg tagttcggct gcggtttggg aggctctctc gaaggatcgt   22800
tgtagagaga gcatcgggac cttaatctat ctgtctgttg gttgtgtgc tggtcagatg    22860
gagtcgatat cgatatcagc atcagcagag gctgaagtgt catctagctg accattatcg   22920
cgcttgtcta cgtattcggc aaccttatcg tagatgcgt cgtccaatgt tttgagcacg    22980
accgcgttga aaccgttttt ggtgcgcacg gtggctagtt gaaggcctg ctcctcgcca    23040
aggtatgcct ctagttcgcg gatcatgag tgtgggcgt cgttattgcc gcgggctttc     23100
tcaataatag cgttggggat ggtttctggg gtgccgttgt tgagatcgtc tagggtgtgg   23160
aagatggtga catcagcgta gatgcggtct gcgacctgtc caccgtagcc ttcagtgttg   23220
tgctggacgt cgtgcacttt gaaggcgatg gccgtgggcgt cctggtttcg ggaggggttg   23280
aagaaggtgc tgttgctgtt gttgcggtag tttgcgaatc ccataactat tgtttccttt   23340
tactgttgtg tctgtttttg ttggcttata ttggtttatc gggtgaggct gtttcgctta   23400
gtgcggaaag cgtcggaaac atcactgtta ctggtgatga tcttcttgta ctgttttaga   23460
aggtctgcta gctgtgcctt gcttgttgca ttgttgattt tgttgatgac gatggtgttt   23520
tctttggatg cgattttgtt gacgtagtct ttggctgcct ggttgtatcg gtcttggagg   23580
atgattgatg cgctcgctac gagtgttgct agatcccagt ctttggacac gtcatcgttt   23640
ttgagtccgc ctagcaggtc gatgatggcc tgttttgtct gctctgctgt gtctcctcgg   23700
atgaccgccc atggtgcagc atagtctcca ccatatttga gtgtgatcgt gagtcgatca   23760
ttgtcgatct tgtctcttatc tgtcatttgg tgtccttttc tttattgtct gtttctggtg   23820
gctgtacggt ggattctacc gggtatctgt acgagtttgt gccgttgacg gcccagcagg   23880
cgtctcgtac ggggcatcct ttacagagtg ttgtgacgtg ggggacgaag atgccttcgc   23940
tgattccttt cattgcttga ctgtacatgg atgatacatg ccgtaggtg ttgttgtcaa     24000
ggtcgtagag ttcggtggat gtgccttgtg tcgggggactt gtcgtcgttg cggctggtgg   24060
ctggcgtcca aaacatgcct ttcgtgacat ggatgtcgtg ttggttgagc atgtaccggt   24120
atgtgtgcag ctgcatactg tcggcgggta ggcgtccggt tttgaggtcg aggatgaagg   24180
tttcgccggt gtcggtgtcg gtgaaaaacac ggtcgatgta gccgactatt tttgtgtcat   24240
cgtcgaggat ggtttctacc gggtattcga tgcctggttt accgtccagg attgcggtga   24300
tgtattctgg gtggttgcgc ctccatgttt tccagcagtt cacaaaggtg gggccgtaaa   24360
ccatccacca gtcgtagtct ttcttgtgtg gtccgcctga ctcgcacatg tttttgcata   24420
ttctgccgga gggtttgatt tctgtgcctt cggattcggc gagggctacc tgggtgtcga   24480
aaatgttttt gaaggatgag agtttgtctg gcagtcagg gtattcggcg ggattgtaca    24540
ggtgtaggtc gtattgttcg gtgatgtggt gtatggcgct tccggcgatg gtggcgtacc   24600
aggtggtg ttgggcgtga tagccgtggg ataggcgcca tttttctccg cattcggccc     24660
actgggtgag tgaactgtag gagatgtgtc ctgggtggct gatggttttc gggtattgtg   24720
ctagaggcat tacttgtcgc ttgtgttcca tgtgttgcgg gtgtcttggc cggcgtggtg   24780
ttgctggtag gcgaggagtg cgaggcagtg ccaggctgcg tgtgctagat ggggtagcc     24840
ggattcgtgg tcgaggttgt tgccttgctg ccatgatagt agatgcctgt agagggcgtc   24900
gacactgtgg ctccacgggt atccccggt ccagttgttg tcgccatatt tggtggcacc    24960
gtatccggct acttcgccta gggcgtgaag ggatgctggg tcgatgaggg agagcctgca   25020
gagtttcaat tcttttcggg caccgctgtt ggggtcggtg tacatgcggg tgggctcatc   25080
catggggtgt gtgctcctta aggggtggtt actggttgtt gttgtgggtc aggcggcgg    25140
cgagaataat gatggcgagg gtttcggcta tcagtatggg tgttgtgatc atttggtgtc   25200
tcggggattg ttggtgagtg ttgaggcacc caggagggtg gcgagggcgc atgcggcaat   25260
aatggcgagg gctgccttgt gtggggtgcc ggttgcgtac atccatgtga tgatggcacc   25320
ttggatccag gctagctgg tgaagaaggt ttcgtacgtg gcagctcaa tgttgtttgtt    25380
gggtgtgttc atgcttgctc ctgaagaatg gtgttgatgg ttttataaat gttgtacagg   25440
tcggtttcga tagataacag ttggttgatt tggtggtcga gatcaatgtc tgggtgagt    25500
gtgttgatgc gggaggcaat atcggtggct gtgcgtagtg tgccgccggt gtggtgaata   25560
atgtgtgccg tgtcggcgag tccggtggtg acggcgtagt gggataggag aggcatagcg   25620
gggatgctcc ttggcgggtt actgttgcgg gttgatgttg aggtcggtga cgtgcggtga   25680
gttttctgtt ccggtgacga ggcagtggac ggtgacgggt agtttggatg ctcccggctg   25740
gcggacggtg gcgccgtaga cgatgctgaa tgtgtctttta ccgatggttt tgtggagttg   25800
gaggtcgatg tcggggttgc cgttccagtt gacaccttgc gctgcggcct gttgttcggc   25860
tttgtggttg caggtgtgtg ctgccgtgat catggtgagt ccggtggcgg tttcttcacc   25920
cctgcttgg gcttgcttgt gggctttggc ctgcctgct tgtagggatc gggtggcgg     25980
tgcctgccgt gccgcttct cggctttgcg ctgttgggta gtcttggggg tccatggt     26040
gttggctgtg gttgcctgtg gggctggctg tgaggtgagt ggcggggttgt cgtctggtgc   26100
tggcatgaat gaggcggcgg caatgatggc ggctgtgatg cctgcgatgg tgtagccgtt   26160
tttcttgttc atgtttgtgt tccccttttcc gggggttgtt tcgttgctga catggttaat   26220
actttcagcg gctgggccca ctgtcaaggc tgcgctcagt ttgtgtgagc gtttggtgtg   26280
```

-continued

```
tggctagggg ttttgtcatg taagcgtgac atgtcactac cttgcgtcca gtatccatgg   26340
cggttgcgag ccatccctt ggcgagcatc tcgtccacag tgaggcacct gcggcgattg   26400
gggcctccct tgaccccgtg atcgcctatg cggtgcatgt ccccggcata agtgccatta   26460
aatgtttcgt ggcagactgt gcagtgttct ggtcggtatc cgatgattgt gctatcgcac   26520
ttgtggcatg tccattgcat gattggtcct tctttcgttg tttaagcttg tgctctgagg   26580
attagagcga ctttcagccc ttgggggtag gattatatag gtcaggtatt tctaggcgat   26640
tctaggctca ttgtgtgtgg ttgggggtttt atcgggcgca tagggttagc aggtggccca   26700
cattggtgcg gctcacattc cagtagagtt gcgtggcttc cttactggtg agcggcttcc   26760
actcgtcatg gctgaacacg tgccatcggg atgcgatgaa cgtgttgggg cgtagcttgt   26820
gaagctcggc ttccacatgc tgccgtagg cttcggcgag gctctcaaaa tccatgtgct   26880
cgcaggagag gttttcgagg cgtgtcaggt cgaaaggctc cgggcagtcg tagctggctg   26940
gagtgtagag ctgggtgaag tggtcggcga tcttctgcat ggcgggttcc tttctggtgt   27000
gtggatggtt tttatcgtgt ggatgcgaca aggatgcgct ctacgtcgat catgtcgatc   27060
atgtcgttga gttcctcggc ctcattctcg gagaggtggc gccagtcgtg tggcccgtat   27120
acggcgccgt cgagggtgac agtccacagg ggccggatga gtcgtatggc ttcttcgact   27180
ttggcgtggt acatgcggcg caccatatcc agatcgatgt cgtctgaatg gtttccggtg   27240
aggctgtgga ggctgagcgg gtcgatttct gtctgcctgt agaggctggt gaatgatggt   27300
gtgatgagtg tgccatccat gagtgtgctc cttctcaggg gttgttgtgg tttctagagt   27360
gtgtgggctg tgaccccaca gtcaaggcta cgctcatttg gattgagcgt ttcatatggg   27420
tgtggcatgg aatctacacc ctcatactgt gtgagatgta tcacatcccc ctggcttggt   27480
gtgcacccct caagactact ctgccgacct ggcgtggagg gtgtagccca gaaatgccgt   27540
ttaaagcttc aggggtacgc ctaggagcgc cttacagggt ggggggctagg tatttatacc   27600
cccagcatat tctgatcgat tctagacgac tcccagagcc cgatacacga tcaaccatct   27660
cgacatagac catcagcccc tatcctggtt agctaagcct caactatgtg gacagtgtgg   27720
gacactgtgg gggaagaagg acacggtaca agaaagaggg gggagcatca gccttaaagc   27780
cttaagatct tagcgcttag caccgatggt cttagcagtt agcaccgagc ccttgaggggg   27840
gctcggcatc agcctcatcg ggctcagctc atcaggcaca gccctgaaaa gggtacacgc   27900
catcagggaa ggcttgagag tacgaggagc cctagcgacg agtactcgaa agcctgaggg   27960
aacaccctca gtactgatga gcctagcgta ttcggaaagg acgcaagagt aaagtgtgac   28020
agctatccgg gagtgaaacc cgttccgact aggggttca gccttaacca ccctcaaagg   28080
ttacaagact ctaagaaaat ttaagaaact tcttaggaag aaagttgtgt tcatatcccc   28140
ctaaaaacac ccaaaatagt cctcaaaccc gcctatagag ccaaacagtc aagtttgact   28200
cgtctagacg gcgtatgata ggctggacag gtagccagct ggacgcaagg ccagaaagtg   28260
ctgacgcact tcccgacctc gcttaccatc agtctaccaa acactttaag gcttcaaggc   28320
ttagcgctaa gcccttaaga tcttaacgct tagcaccgag ccccccctcaa gggctcgaca   28380
tcagtcttaa agtcttaaac actttaagta acttttaaagc ttcaaggctt agcccttaag   28440
gatctaagtt actataaaag ctttaaacac ttaaagtaac tataaagctt taagagctta   28500
acatttaagg atataaataa acattaaagc tttaagtct taagtaaat ataaaccctt   28560
aacacttaag ttaagtataa aaccttaaag gcttagcact taaggatata aacttaacat   28620
cagtgttaaa gacttaaaga gttaagtaaa ctattaagac ttaaggcctt ataagcttta   28680
atactttaag tagctataag actttaaaaaa cctgaagtac ttaaagttaa ccatcagtct   28740
taaacttttaa tattataagt attaaagctt ataagttata aaagttttta gaagagttaa   28800
agggttaact tctttacttc tctttctctc ttggttcttt ctctcttctc ttctttttctt   28860
catcagggga gaagaggaac ctttaaccgt caacgctgat ggactttca ccgtgtgact   28920
cgtgtgcttc tggtcgcaag ctcccatcgc acactcccca cactcttcca cccgtgcccc   28980
tttacgcttt agcgtgttcg tcggaaggcg tacgcgtgt cacgcttaaa cccttaacac   29040
caggtaagac ttaaagtgca tattataagt agaagacttt aaaaacctata aggtgttccc   29100
gcttagcccg tgttccttta acgctaggcg ctcagcgcta agatgtgaaa cgtgaacacc   29160
catccacccc cattttttctt ccgtgtcctt ctccttttga caccgctggg gggcgatgtg   29220
atatttctca catgccaggg ggtagtggag aaaacaacca ccccgggaacg tttaagcacac   29280
cccctcaaac gaacaaaaaca ggggcctagaa tcgatcagaa gggcaccggt agggtattcc   29340
taccccccaga cgattcaagg ccatacagg agcaatgaga ggctcacagg ggccatggga   29400
gattgggggg cgtgatggca cacaccaacc gcacagccag ccaagcccac cggcgctggc   29460
gggcaaggct catcacccaa gcccgacaac aaggccaaac cgaatgccca ctctgcggag   29520
tcaccatcac ctggaacacc cacgacctgc caaccagccc cgaagccgac cacatcacac   29580
ccgtcagccg gggaggactc aacaccctcg acaacgggca aatcatctgc agaacatgca   29640
acagaagcaa aggcaacaga acacaaccaa acatcaaatt ccaacaacaa accacaaaaa   29700
cattgattcc atggtgaaaaa acccgccaac ccccaccggg cacaccccct gcacacccgt   29760
gcaagacc                                                           29768
```

```
SEQ ID NO: 106        moltype = DNA   length = 23
FEATURE               Location/Qualifiers
misc_feature          1..23
                      note = primer IC290
source                1..23
                      mol_type = other DNA
                      organism = synthetic construct
SEQUENCE: 106
gatggagacc accaacacat tat                                             23

SEQ ID NO: 107        moltype = DNA   length = 303
FEATURE               Location/Qualifiers
misc_feature          1..303
                      note = PAC7 endonuclease
source                1..303
                      mol_type = other DNA
                      organism = synthetic construct
SEQUENCE: 107
atggcacaca ccaaccgcac agccagccaa gcccaccggc gctggcgggc aaggctcatc   60
```

```
acccaagccc gacaacaagg ccaaaccgaa tgcccactct gcggagtcac catcaccctgg    120
aacacccacg acctgccaac cagccccgaa gccgaccaca tcacacccgt cagccgggga    180
ggactcaaca ccctcgacaa cgggcaaatc atctgcagaa catgcaacag aagcaaaggc    240
aacagaacac aaccaaacat caaattccaa caacaaacca caaaaacatt gattccatgg    300
tga                                                                   303

SEQ ID NO: 108             moltype = DNA   length = 20
FEATURE                    Location/Qualifiers
misc_feature               1..20
                           note = sgRNA target in PAC7 wt endonuclease region
source                     1..20
                           mol_type = other DNA
                           organism = synthetic construct
SEQUENCE: 108
gccattacag gagcaatgag                                                 20

SEQ ID NO: 109             moltype = DNA   length = 22
FEATURE                    Location/Qualifiers
misc_feature               1..22
                           note = primer AL97
source                     1..22
                           mol_type = other DNA
                           organism = synthetic construct
SEQUENCE: 109
ggtcttgcac gggtgtgcag gg                                              22

SEQ ID NO: 110             moltype = DNA   length = 30
FEATURE                    Location/Qualifiers
misc_feature               1..30
                           note = primer IC619
source                     1..30
                           mol_type = other DNA
                           organism = synthetic construct
SEQUENCE: 110
aggcttataa gctttaatac tttaagtagc                                      30

SEQ ID NO: 111             moltype = DNA   length = 21
FEATURE                    Location/Qualifiers
misc_feature               1..21
                           note = primer AL219
source                     1..21
                           mol_type = other DNA
                           organism = synthetic construct
SEQUENCE: 111
acaaacaccc cacacacacc c                                               21

SEQ ID NO: 112             moltype = DNA   length = 2999
FEATURE                    Location/Qualifiers
misc_feature               1..2999
                           note = template for homologous recombination to introduce
                           908bp in locus1
source                     1..2999
                           mol_type = other DNA
                           organism = synthetic construct
SEQUENCE: 112
gggtttccgt ccgcctcgcg taaaggacgg gctgtgtcca cggcaaacta tttcgcttcc    60
ccatcgtctg gtggttcggc gcattatgtg tgtgatattg gggagacggt gcaatgcttg    120
tcggagtcta cgattgggtg gcatgccccg ccgaatccgc atagtttggg tatagagatt    180
tgcgcggatg ggggttcgca cgcctcgttc cgggtgccgg ggcatgcctta cactcgtgag    240
cagtggctgg atcctcgcgt gtggcctgcg gttgagcgtg ccgccatcct gtgtagacgt    300
ttgtgtgaca agcatggtgt tccgaaaagg aaactgtctg tggccgattt gaaggccggt    360
aaacggggtg tttgcgggca tgtggatgtt acgatgcgt ggcatcagtc ggatcatgac    420
gatccggggc cgtggtttcc gtgggacaaa tttatgctt tggttaatgg ccacggcggc    480
ggttcaagta gtgaggagtt gagtatggct gatgtacaa cgttacataa tcagattaaa    540
cagttgtcgg cacaggtggc ccagtcggtg aataagctgc atcacgatgt tggtgtggtt    600
caggttcaga atggtgattt gggtaaacgt gttgatgcct tgtcgtgggt gaagaatcct    660
gtgacgggga agctgtggcg cactaaggat gctttgtgga gtgtctggta ttacgtgttg    720
gagtgtcgta gccgtcttga caggctcgag tctgctgtca acgatttgaa aaagtgatgg    780
tggtttgttg tgggtaaaca gttttggtta gttttgctgg agcgtgtctct gaaaacttgt    840
gttcaaacgt ttgttgccgt gttggggggtt actgcgggtg tcacctatac tgcggagtcg    900
tttcgtggtt tgccgtggga atccgcgctg atcacggcaa cggttgctgc tgtcctgtcg    960
gttgctacct cgtttggtag cccgtcgttt gtggccggca agcccggcaa gcagcccag    1020
gtggatgcgg gtttggttcc accggatgat ggggggcttgg ttgagccgca tatggtggat    1080
gtgtcggatc ctggcatgat cgagccgacg gatgatgcgg atcttgccgg ctatgagcct    1140
cggcgtgcag ccgagtcgga ggttggcacg ctagagtcta ctgttgcata attgaatata    1200
gatgtgtgcc ccagcggtgc tgccacgatt gtgtggtggc ggctgctggg gcactatttt    1260
tgtatatgcg gtgtggtcat catcagagcc aggcagggtc ggcgaggagg gtttgcagtt    1320
cgtcagtcag acgggcggtg tggaacccgt cggccgccgc gtggtggatc tggaccgaaa    1380
gtggcagcag gaggcgagcg tcacgctctg tgtaacggcg gagagtgaag atcggtgcca    1440
```

```
ggtgatccca accgtcacgg atatcaagag tgaatccggt gaaggaggcc cacggcaggg   1500
aggacacatc gaaagcgtta gggggggggt ttccctgcgg gaagaagtcg gtggcgcggg   1560
agtgctcggc cagcaacggg gcagcggtat cgtggaaggt gccgaagtct gggtcgtacg   1620
gagcccacac acaggcgaag gtctctcgtt ccggattgaa aacggtgaag gctgggtgga   1680
cgaccggcca gacagcgggg tcgccggagg ccgtcaggca catacggaac tcctcgtgtc   1740
ggttgacgac ggtggccaaa gcccacacct gggccaagta cgatttgcgc ggggagcggc   1800
gcagggcggc cgcgaaggcg gtcacgtcca cctcgacggt catggcgtaa gtgcagggca   1860
cgcgacgacg gtagtggtcg aagtgctgcc ggcgcggcca cgtgtccagg tcgattgggg   1920
ccggggtcgg gatcggggcg tccatctcag taggtccctt tctgtccgtt gcgcggcgtc   1980
cccgacgctc ttactgcagg agactcttcc aaggccgcgg ccgttctgac ggcaactggg   2040
agagaatatc aactctgccc attaggcgcg aatcctgatg cgagatgaga tattgccgac   2100
cgaggagaag cccccaaaga aattccacgc tcagcgggct caactgacgc cccaagagaa   2160
ccggaccgc ccaggccgca ccccctatga ttcgttgctg tcgatggtgt cttcgagcat   2220
ctgatacagg tggaggcagg tagagatagt ttcgctgagc tgatcgagaa cgttccggcc   2280
gataacgttt ttgtggttgt cgcggtggcg gatgatagcc cacatgatct cgtcggctgc   2340
cgcctgtaat agtttggcct ggtatgcgat tccggcgagc cagtctagtg cttcctggct   2400
tgtatagggg ctctggtcct cgctgttgcc gcgggtgttg ctgttgtttg tggggtgtcc   2460
tgcactgtcg catagccaca ggatttcgct gcactcgtct agcgtgtctt ggtcgatagc   2520
gagatcgtcg aggctgacat tgttgacggt aaggttcacg ttgtcgaggg agatgggtac   2580
accgtactgg ttttcgacac tgtcaacaat gttttccagc tgttgcatgt tggtgggctg   2640
ttgttggacg atacggtgta tcgctgtgtt gagggtggtg taggtgatgt tgtgtgtgtt   2700
gtccatggtt tttatgccat tccttcgtta tcgtctggca tgtagtatgt gctgtttgcg   2760
tactcggtta acgtcatcag tgtttggtct gcccactgtt tcacggtttg ccgggtgact   2820
ccgagtcgtt gggcggctgt ggcgtaggtt tgatcatacc cgtatacttc ccggaatgct   2880
gccaacctag ctaggtgttt cctctgtttg gatggttcac aggtgagggt gtagtcgtcg   2940
atggctagct gtagatcgat catggagacg atgttgttgc cgtggtgttg tggcgcggt    2999

SEQ ID NO: 113         moltype = DNA  length = 383
FEATURE                Location/Qualifiers
misc_feature           1..383
                       note = PAC7 wt from alignment figure 18
source                 1..383
                       mol_type = other DNA
                       organism = synthetic construct
SEQUENCE: 113
tagtggagaa aacaaccacc ccggaacgtt taagacaccc cctcaaacga acaaaacagg    60
gcctagaatc gatcagcagg gcaccggtag ggtattccta cccccagacg attcaaggcc   120
attacaggag caatgagagg ctcacagggg ccatgggaga ttgggggggcg tgatggcaca   180
caccaaccgc acagccagcc aagcccaccg gcgctgaagg gcaaggctca tcacccaagc   240
ccgacaacaa ggccaaaccg aatgcccact ctgcggagtc accatcacct ggaacaccca   300
cgacctgcca accagccccg aagccgacca catcacaccc gtcagccggg gaggactcaa   360
caccctcgac aacgggcaaa tca                                          383

SEQ ID NO: 114         moltype = DNA  length = 249
FEATURE                Location/Qualifiers
misc_feature           1..249
                       note = PAC7-m28-gp45 plaque n:3 from alignment figure 18
source                 1..249
                       mol_type = other DNA
                       organism = synthetic construct
SEQUENCE: 114
tagtggagaa aacaaccacc ccggaacgtt taagacaccc cctcaaacga acaaaacagg    60
gcctagaatc gatcagcagg gcaccggtag ggtattccta cccccagacg attcaaggcc   120
aaaccgaatg cccactctgc ggagtcacca tcacctggaa cacccacgac ctgccaacca   180
gccccgaagc cgaccacatc acaccgtca gccggggagg actcaacacc ctcgacaacg   240
ggcaaatca                                                          249
```